(12) United States Patent
Brestel et al.

(10) Patent No.: US 7,088,435 B2
(45) Date of Patent: Aug. 8, 2006

(54) CONTROLLED SUBSTANCE DETECTION AND IDENTIFICATION SYSTEM

(75) Inventors: Mordechai Brestel, Rehovot (IL); Michael Gaft, Rishon-Lezion (IL); Uzi Sharon, Tel-Aviv (IL)

(73) Assignee: Laser Detect Systems Ltd., Rishon Lezion (IL)

( * ) Notice: Subject to any disclaimer, the term of this patent is extended or adjusted under 35 U.S.C. 154(b) by 356 days.

(21) Appl. No.: 10/428,398

(22) Filed: May 2, 2003

(65) Prior Publication Data

US 2004/0051867 A1    Mar. 18, 2004

(30) Foreign Application Priority Data

Sep. 12, 2002    (IL)    ..................... 151745

(51) Int. Cl.
G01N 21/00    (2006.01)
G01J 3/44    (2006.01)

(52) U.S. Cl. .................. 356/72; 356/301; 356/318; 356/73

(58) Field of Classification Search ................. 356/73, 356/72, 71, 301, 318, 317
See application file for complete search history.

(56) References Cited

U.S. PATENT DOCUMENTS

| | | | |
|---|---|---|---|
| 3,941,478 A * | 3/1976 | Dougherty et al. .......... 356/30 |
| 5,383,200 A | 1/1995 | Barrett et al. ................. 372/25 |
| 5,609,744 A | 3/1997 | Zenharusern et al. ....... 204/606 |
| 5,638,166 A | 6/1997 | Funsten et al. ............... 356/36 |
| 5,697,373 A | 12/1997 | Kortum et al. ............. 128/664 |
| 5,728,584 A | 3/1998 | Sausa et al. ................. 436/106 |
| 5,759,859 A | 6/1998 | Sausa ......................... 436/106 |
| 5,760,898 A | 6/1998 | Haley et al. ................ 356/318 |
| 5,812,261 A | 9/1998 | Nelson et al. ............... 356/318 |
| 5,826,214 A | 10/1998 | Lieb et al. ..................... 702/24 |
| 5,847,825 A | 12/1998 | Alexander ................... 356/318 |
| 5,866,430 A | 2/1999 | Grow |
| 5,906,946 A | 5/1999 | Sausa et al. ................. 436/116 |
| 5,912,466 A | 6/1999 | Funsten et al. ............. 250/372 |
| 6,002,471 A | 12/1999 | Quake .......................... 356/73 |
| 6,002,478 A | 12/1999 | Zhu .......................... 356/316 |
| 6,008,896 A * | 12/1999 | Sabsabi et al. ............. 356/318 |
| 6,069,695 A | 5/2000 | Rohr et al. .................. 356/318 |
| 6,081,330 A | 6/2000 | Nelson et al. ............... 356/318 |
| 6,147,754 A | 11/2000 | Theriault et al. ........... 356/318 |
| 6,154,708 A | 11/2000 | Koashi ........................ 702/40 |
| 6,157,037 A | 12/2000 | Danielson ................ 250/458.1 |
| 6,160,255 A | 12/2000 | Sausa .................... 250/227.24 |

(Continued)

FOREIGN PATENT DOCUMENTS

WO    WO 00/23958    4/2000

(Continued)

OTHER PUBLICATIONS

Chithambo et al, A pulsed light-emitting-diode system for stimulation of luminescence, Feb. 2000, Meas. Sci. Technol., 11 (2000), pp. 418-424.*

(Continued)

*Primary Examiner*—Layla G. Lauchman
(74) *Attorney, Agent, or Firm*—Ladas and Parry LLP

(57) ABSTRACT

A system for detecting controlled substances on an object including at least one laser for illuminating at least part of an object with laser energy and either a second harmonic detector or a luminescence controlled substance detector, or both. Additionally, a system also including a Raman scattering controlled substance detector is disclosed.

33 Claims, 139 Drawing Sheets

U.S. PATENT DOCUMENTS

| | | | |
|---|---|---|---|
| 6,268,125 B1 | 7/2001 | Perkins | 435/5 |
| 6,278,518 B1 | 8/2001 | Schrof et al. | 356/318 |
| 6,411,388 B1* | 6/2002 | Downer et al. | 356/453 |
| 6,441,901 B1* | 8/2002 | McFarland et al. | 356/364 |
| 6,777,684 B1* | 8/2004 | Volkov et al. | 250/341.1 |
| 2004/0043502 A1* | 3/2004 | Song et al. | 436/172 |

FOREIGN PATENT DOCUMENTS

| | | |
|---|---|---|
| WO | WO 01/40773 | 6/2001 |

OTHER PUBLICATIONS

Jehuda Yinon, "Forensic and Environmental Detection of Explosives", John Wiley & Sons Ltd. (1999).

L. Smilowitz, et al, Abstracts, Jun. 2001 SHOCK 01 Session L2-DE.

C. Cheng et al, J. of Forensic Sciences, 1995, 40 pp. 31-37.

K. Horton et al, Abstracts, Lunar and Planetary Science XXXII (2001).

Brochure: InPhotote™ Portable Raman Spectrometer, 2000.

T. Arusi-Parpar, et al, "Photodissociation followed by laser-induced fluorescence at atmospheric pressure and 24 C : a unique scheme for remote detection of explosives", Dec. 2001, Applied Optics, vol. 40, No. 36, pp. 6677-6681.

G. Mizutani, et al, "Detection of starch granules in a living plant by optical second harmonic microscopy", Journal of Luminscence 87-89 (2000) 824-826.

N.G.Paulter, "Guide to the technologies of concealed weapon and contraband imaging and detection", NIG Guide 602-00. Feb. 2001.

J.I.Steinfeld, et al, "Explosives Detection: A Challenge for Physical Chemistry", Annu. Rev. Phys. Chem. 1998, 49:203-32.

C.Bruschini, Comercial Systems for the Direct of Explosives (for Explosives Tasks), ExploStudy, Final Report, Feb. 17, 2001.

L.V.Haley, et al, "Laser Based Explosives Detection", pp. 207-217, 2000.

* cited by examiner

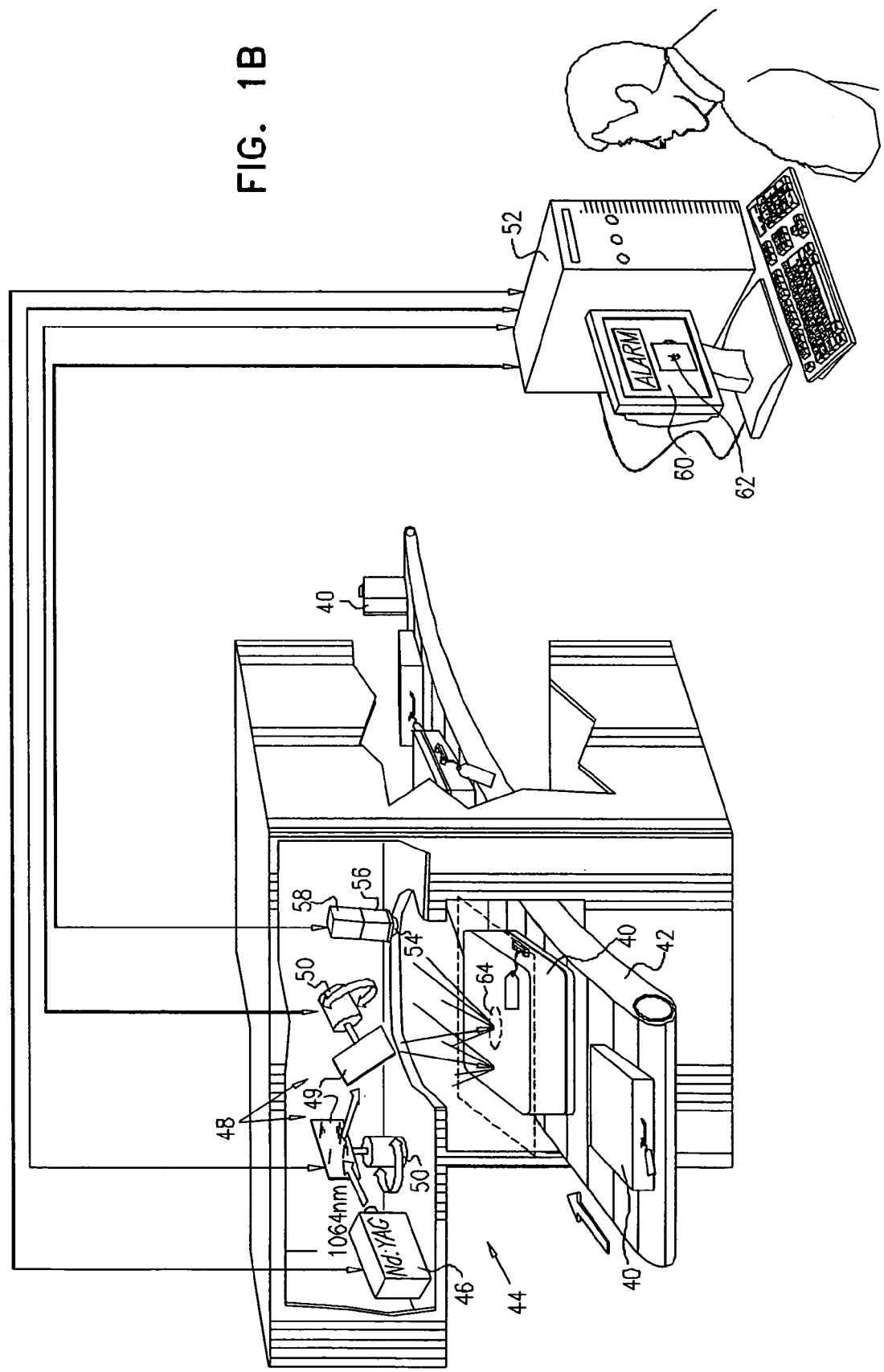

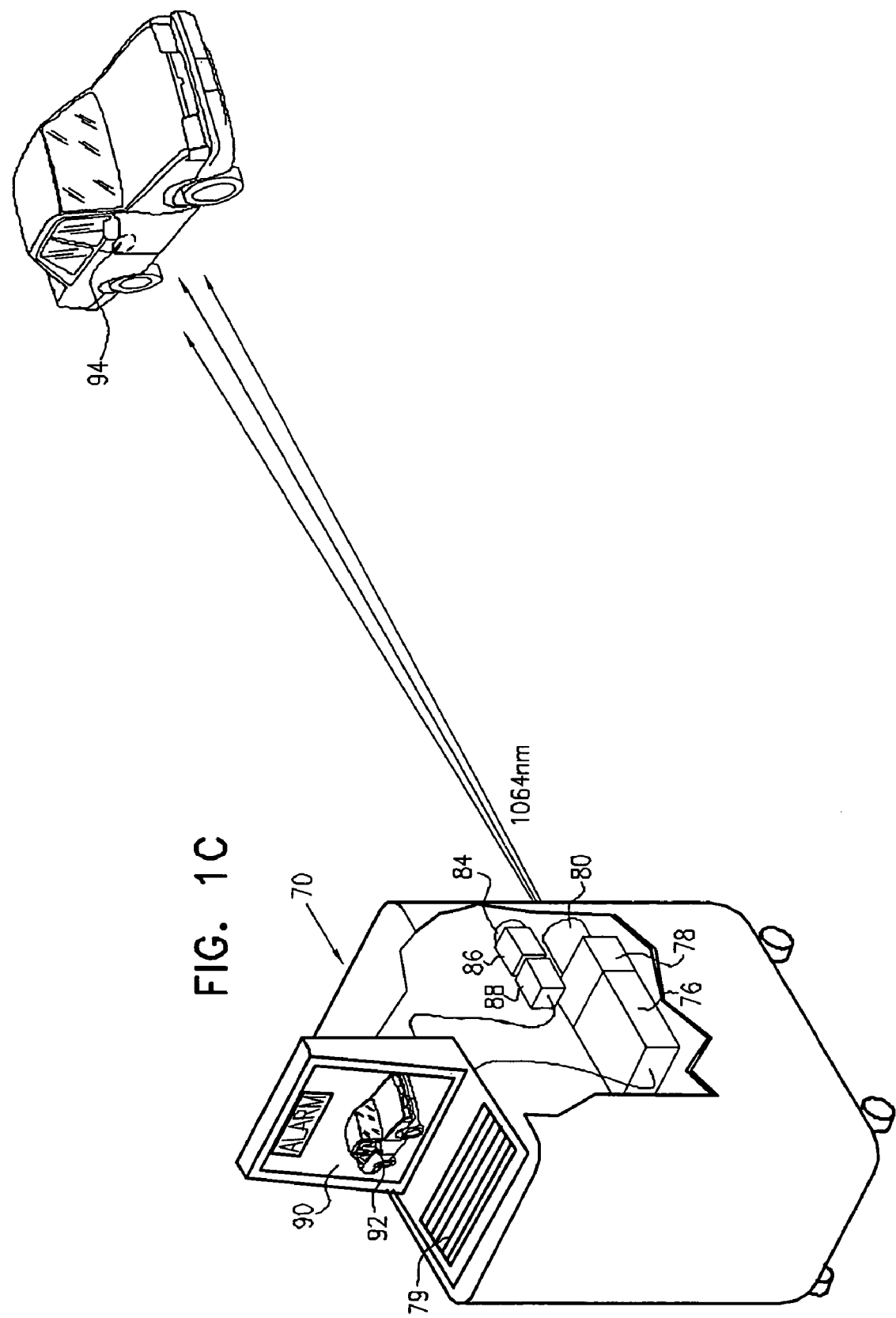

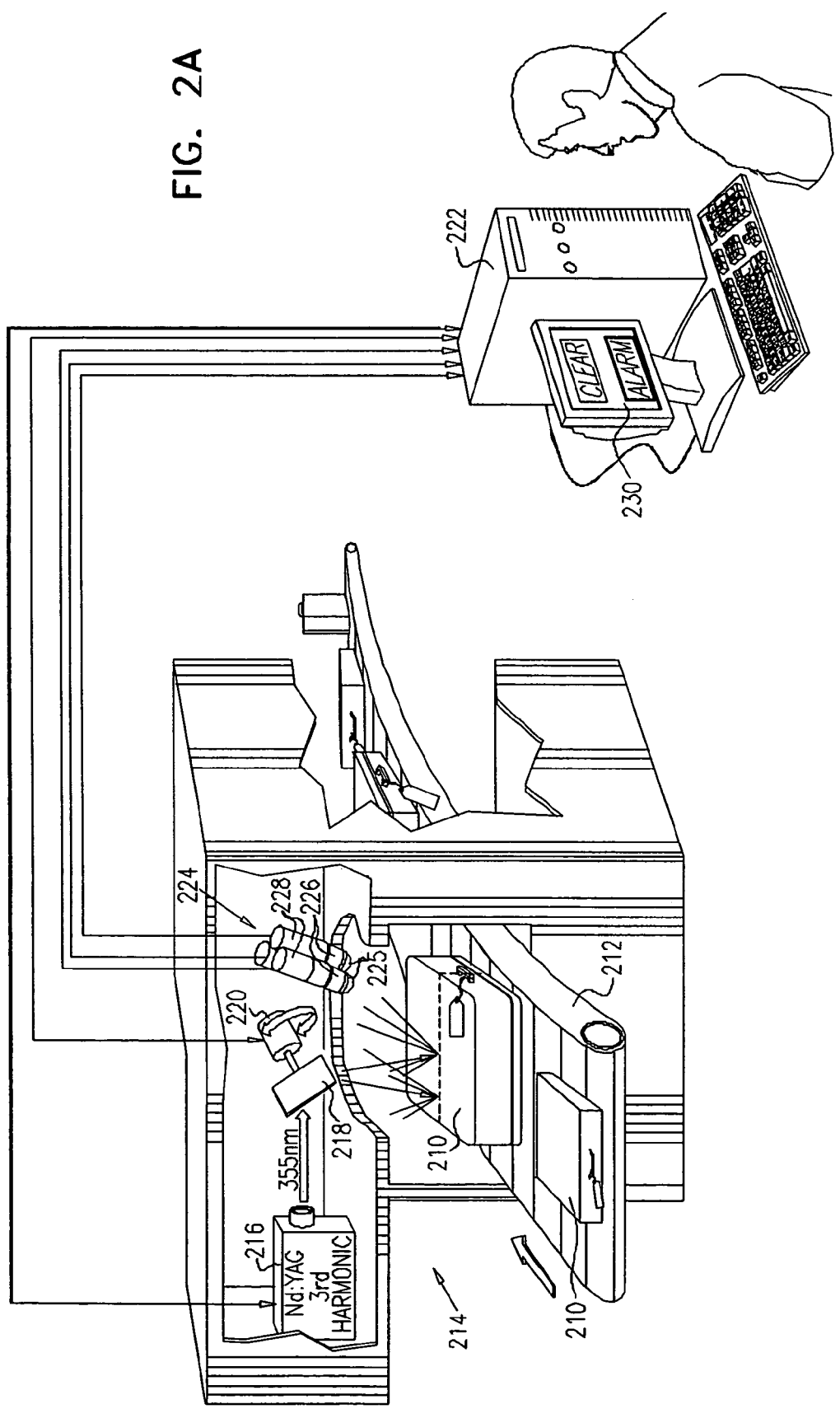

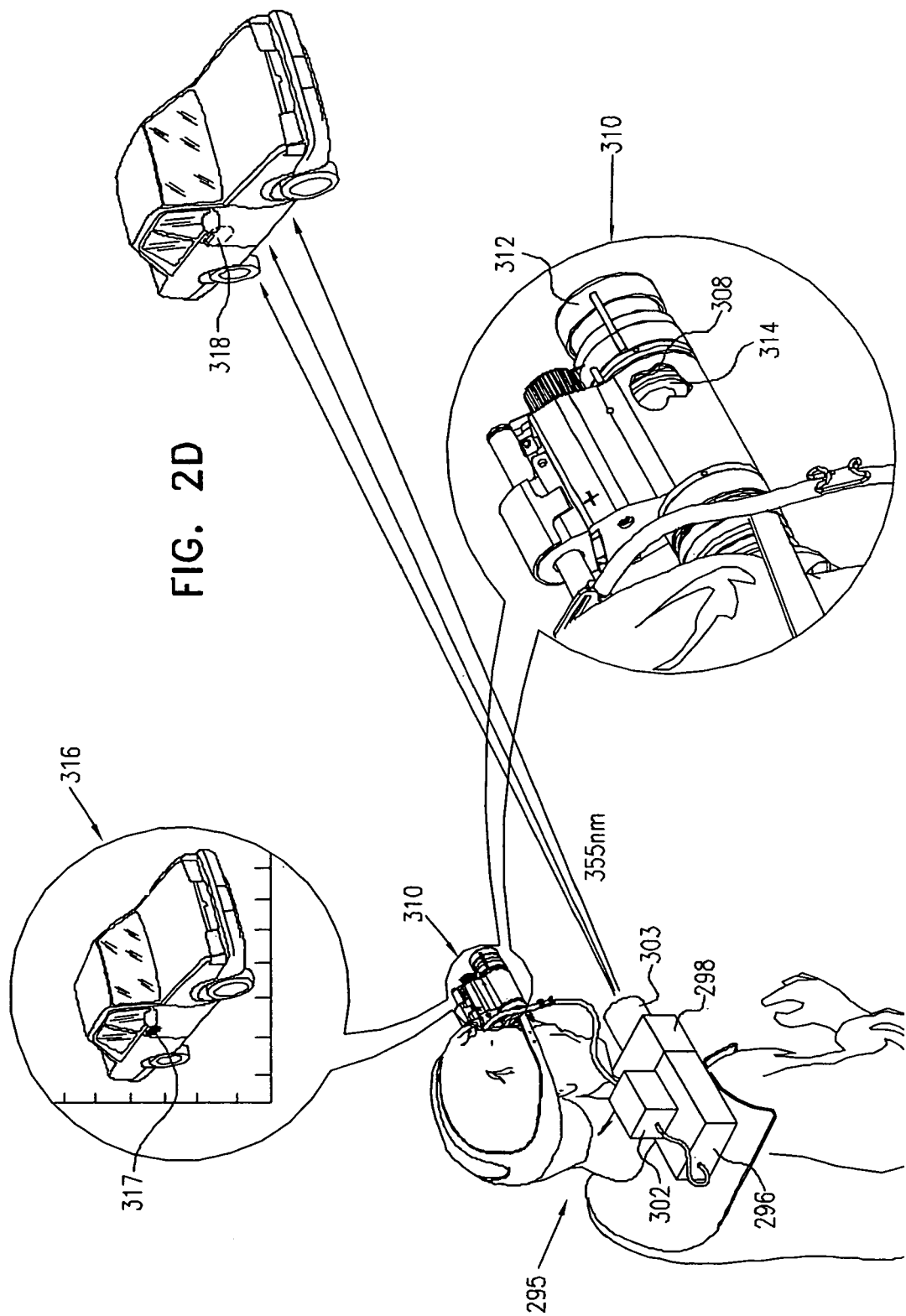

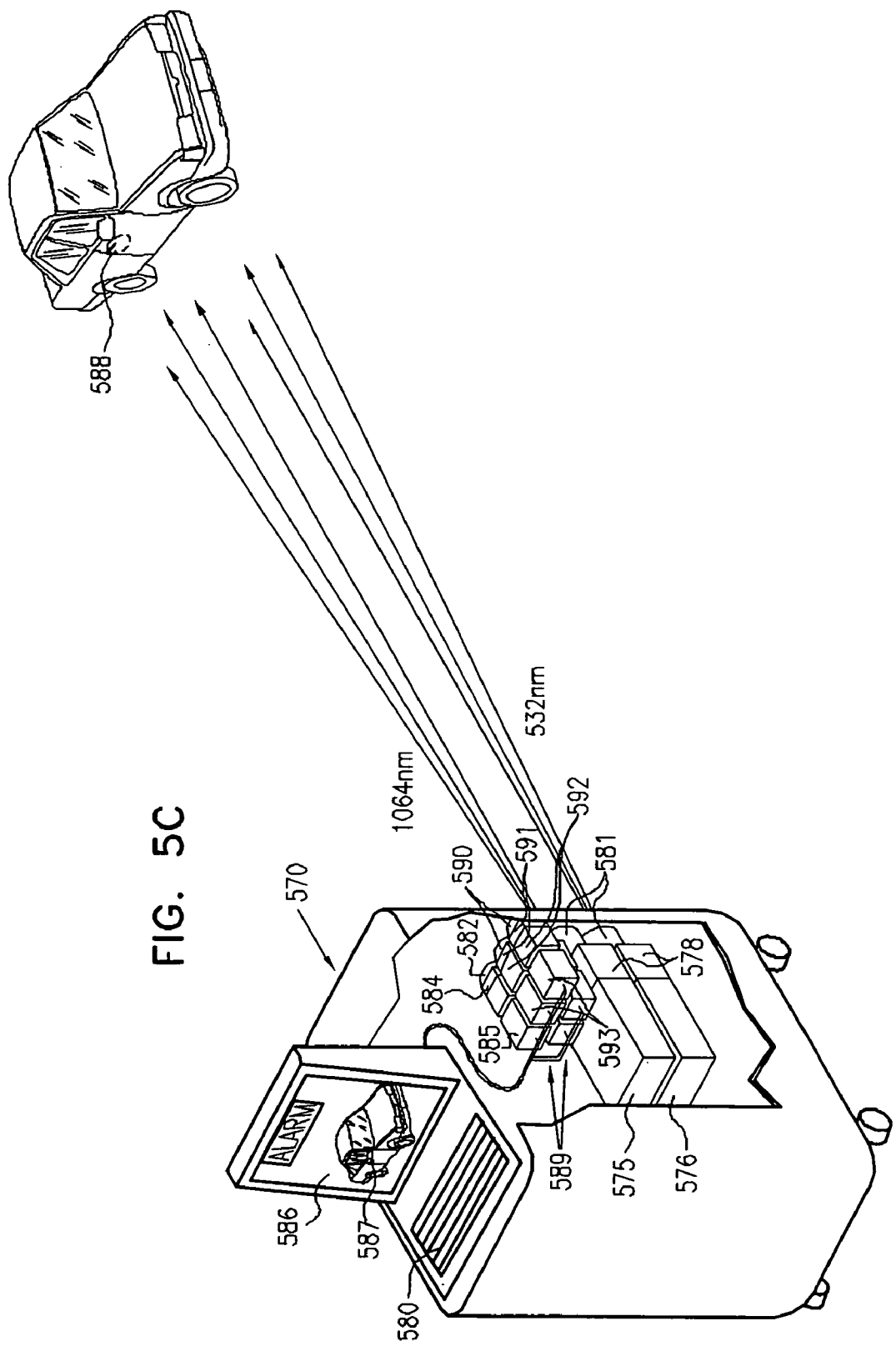

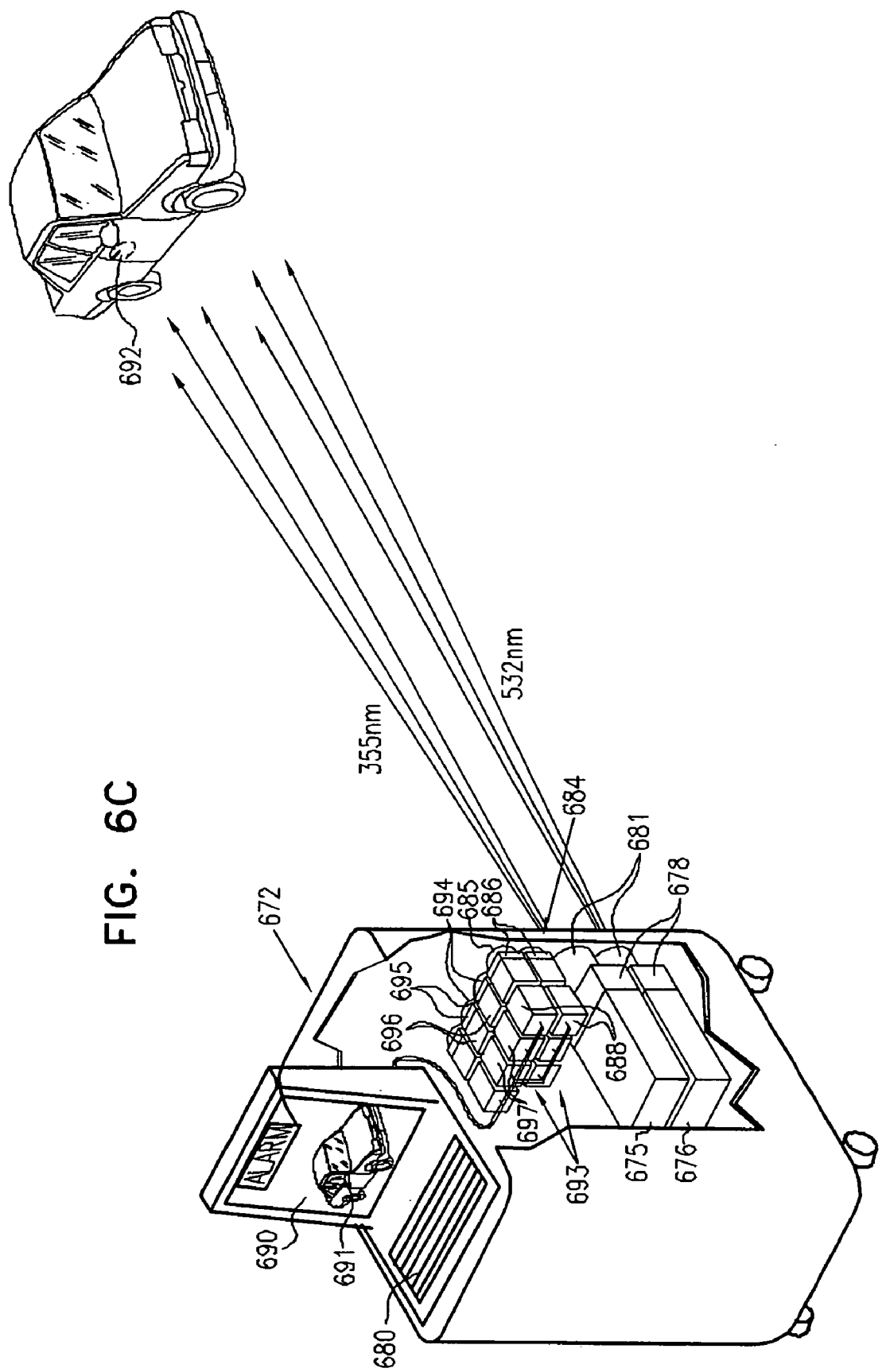

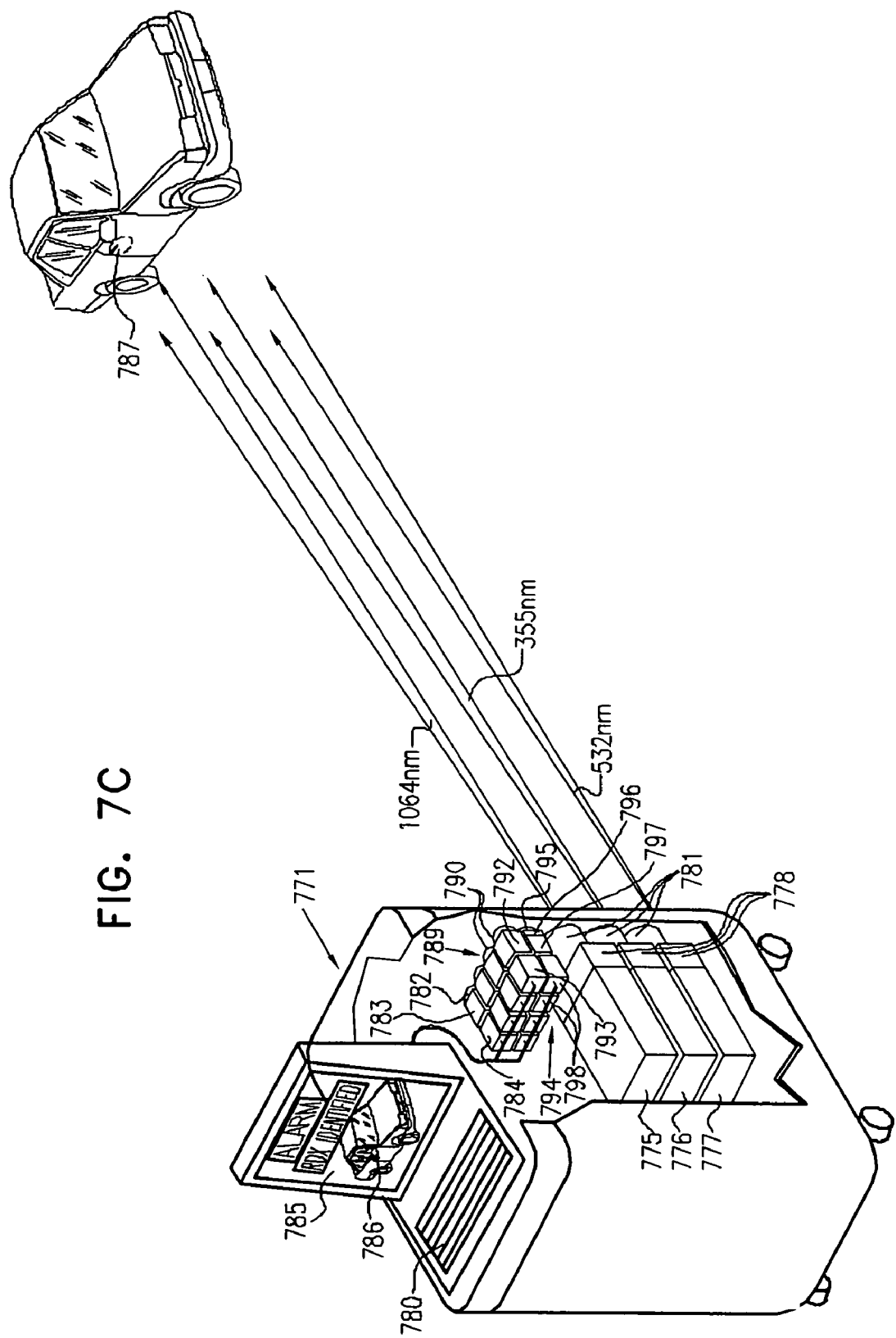

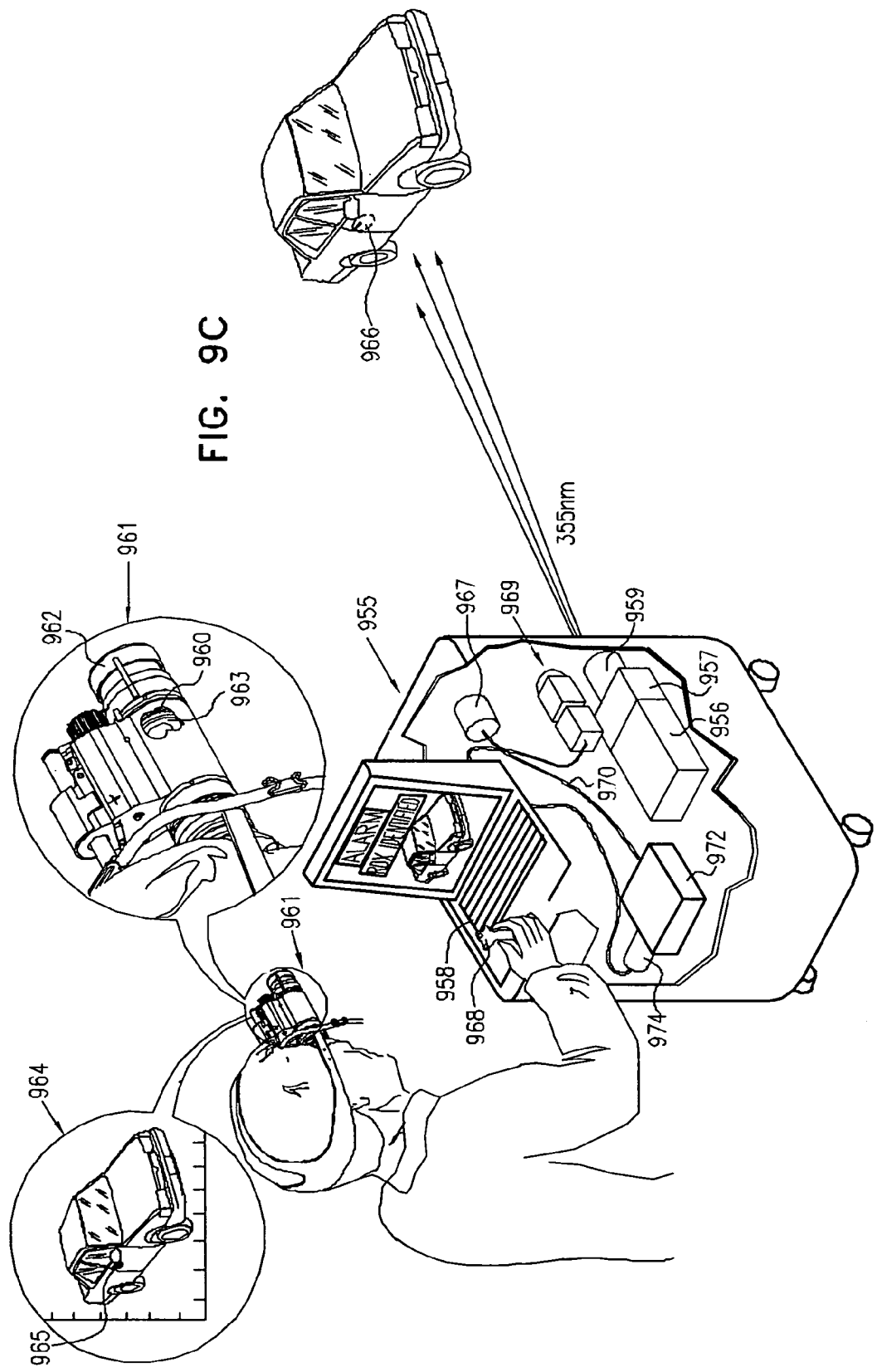

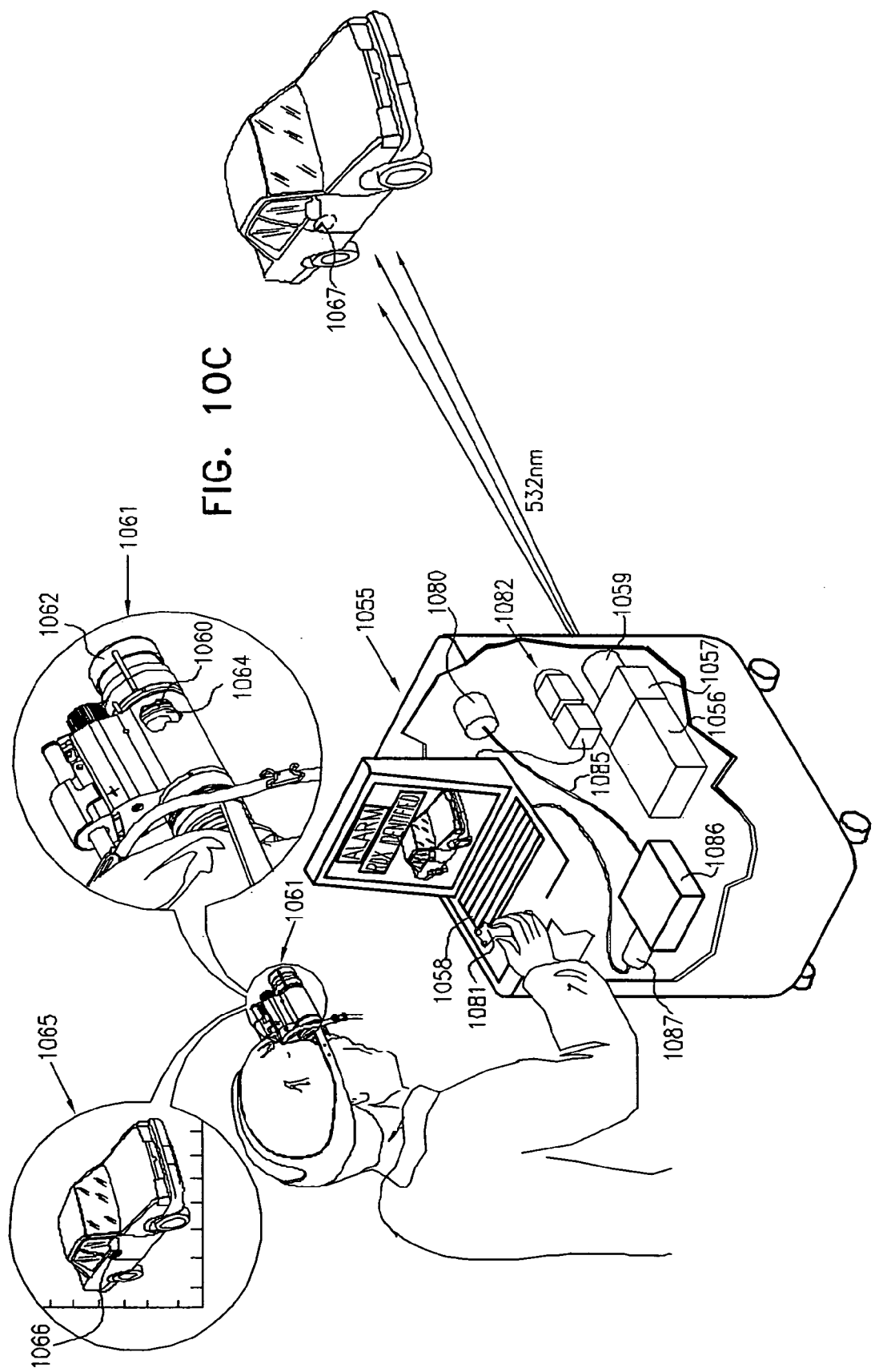

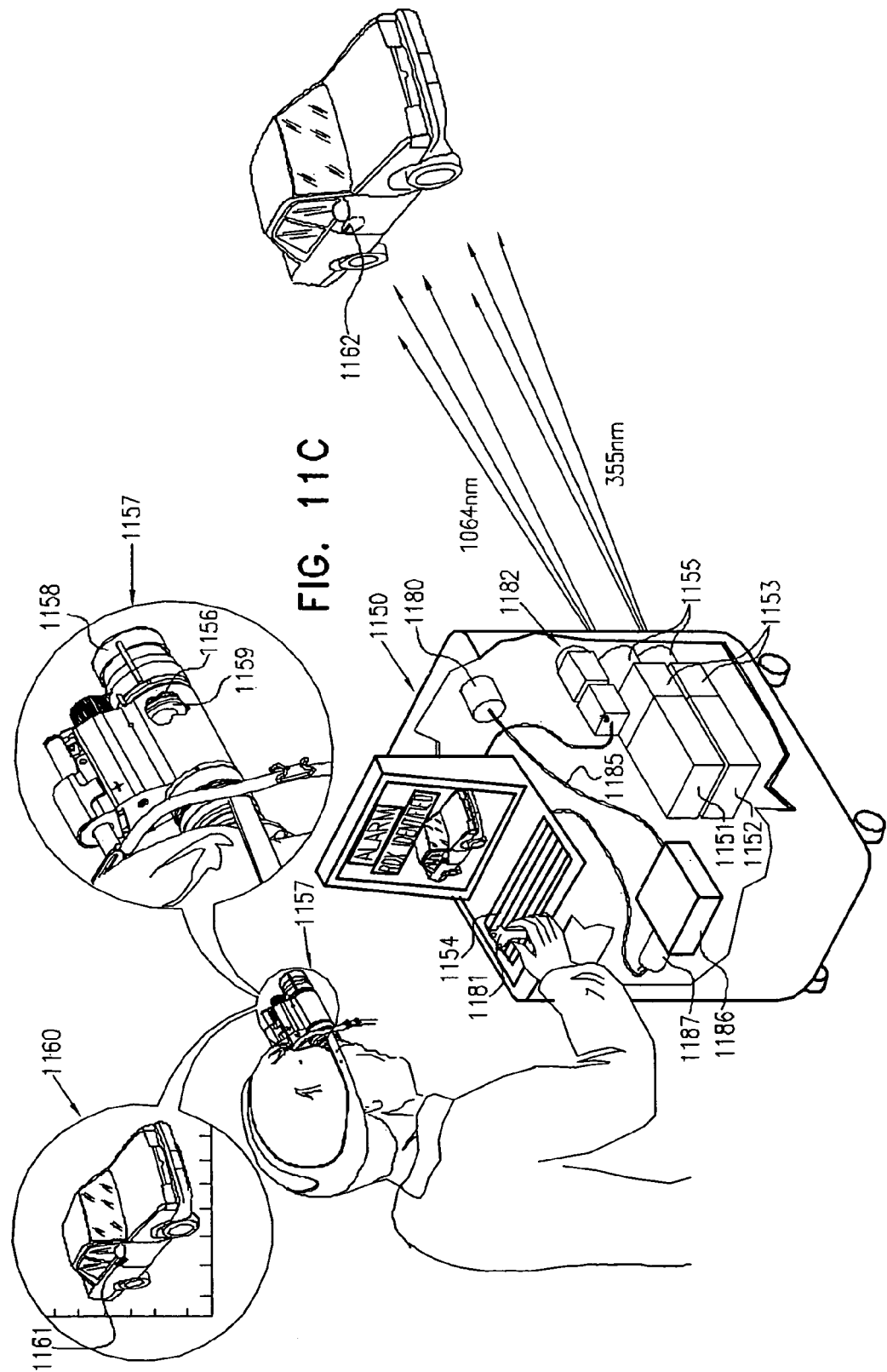

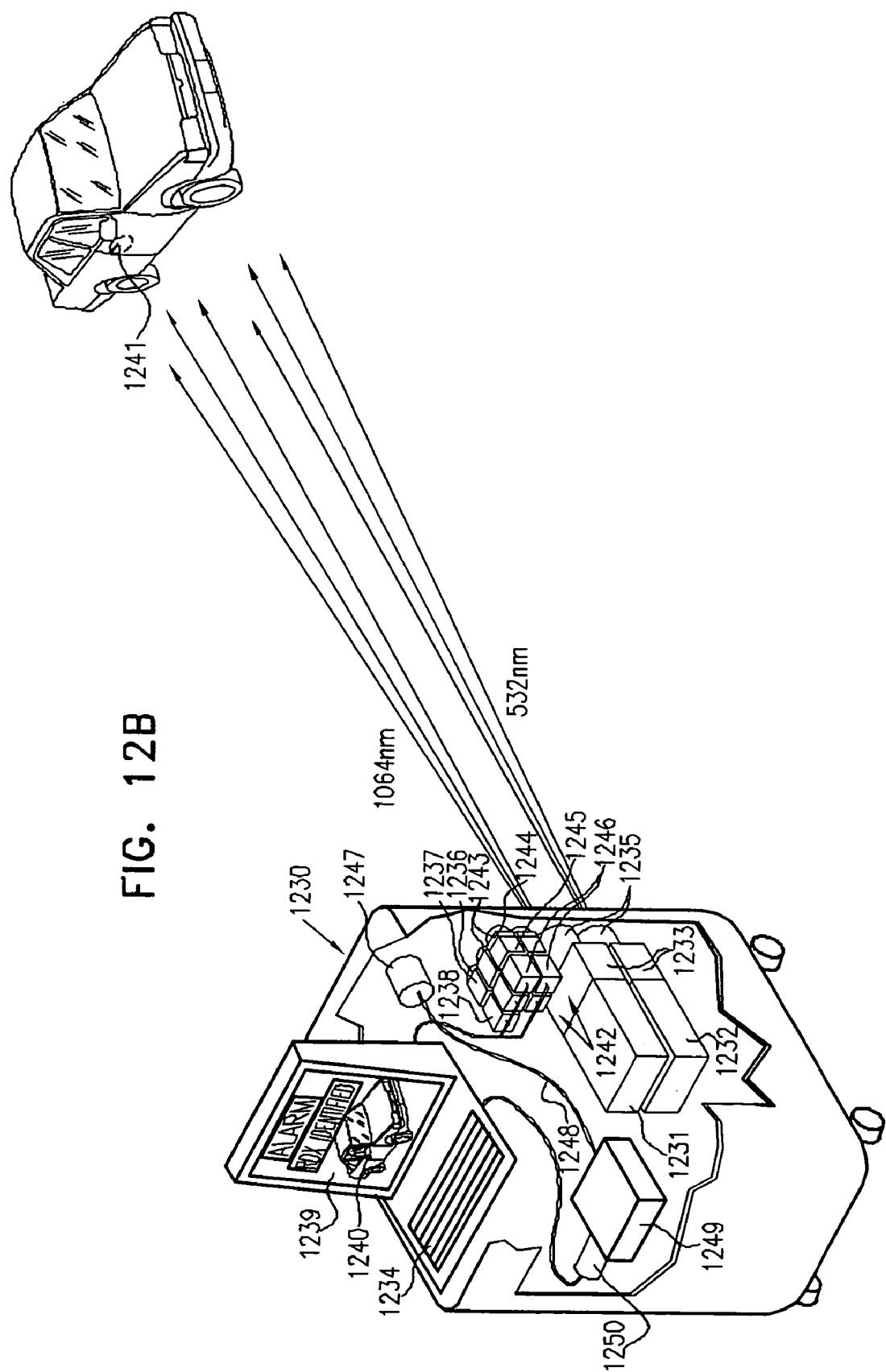

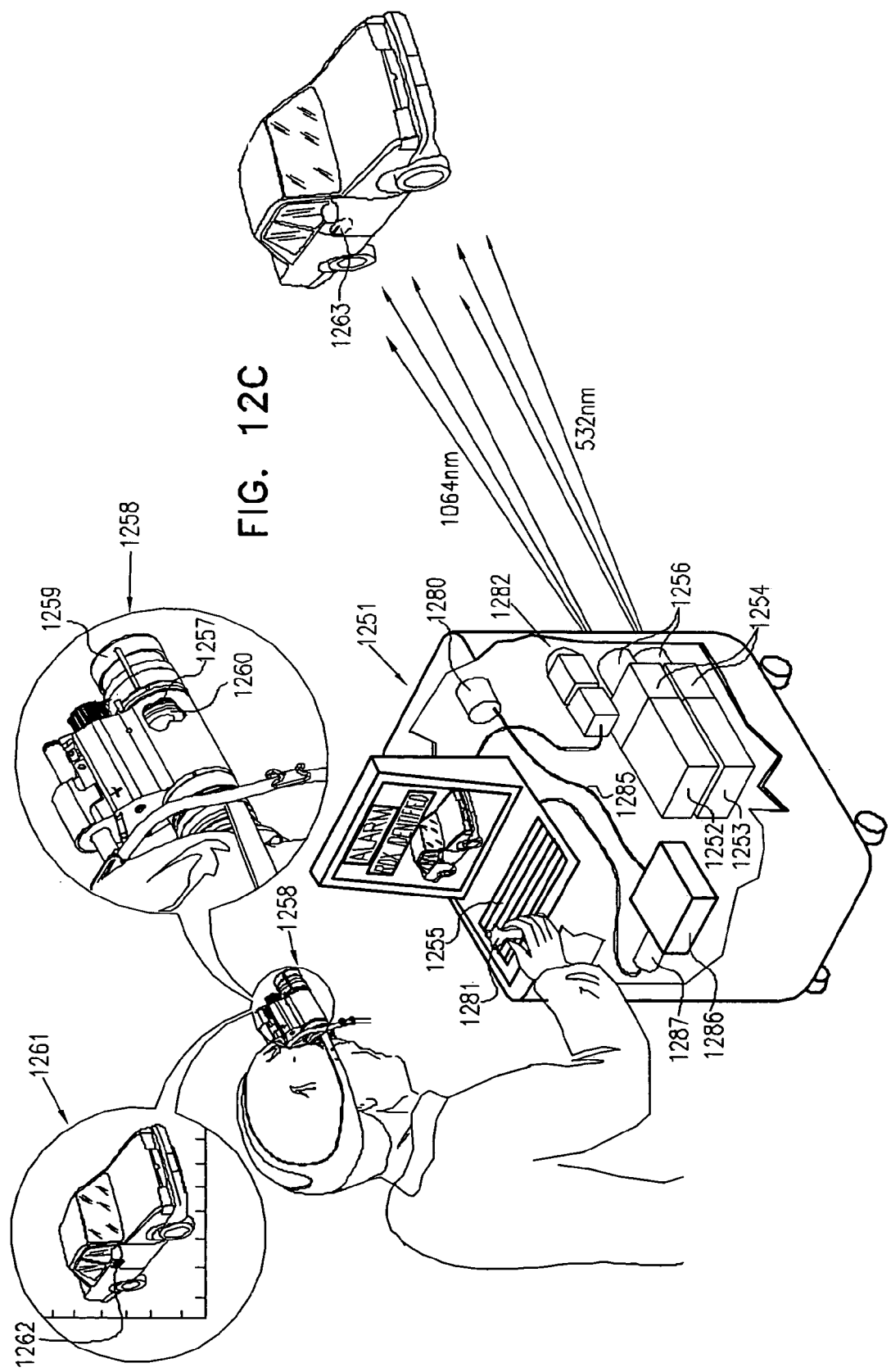

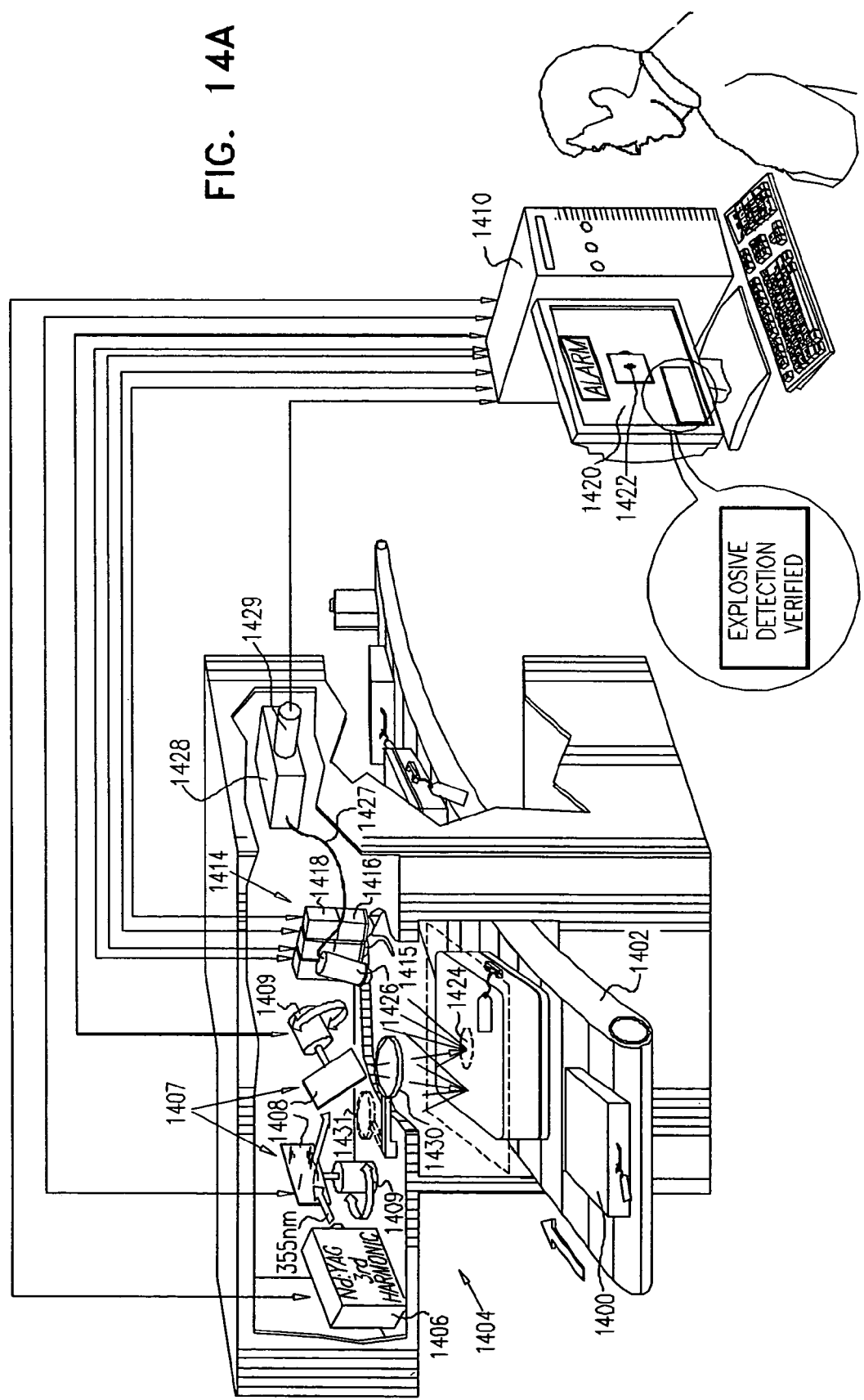

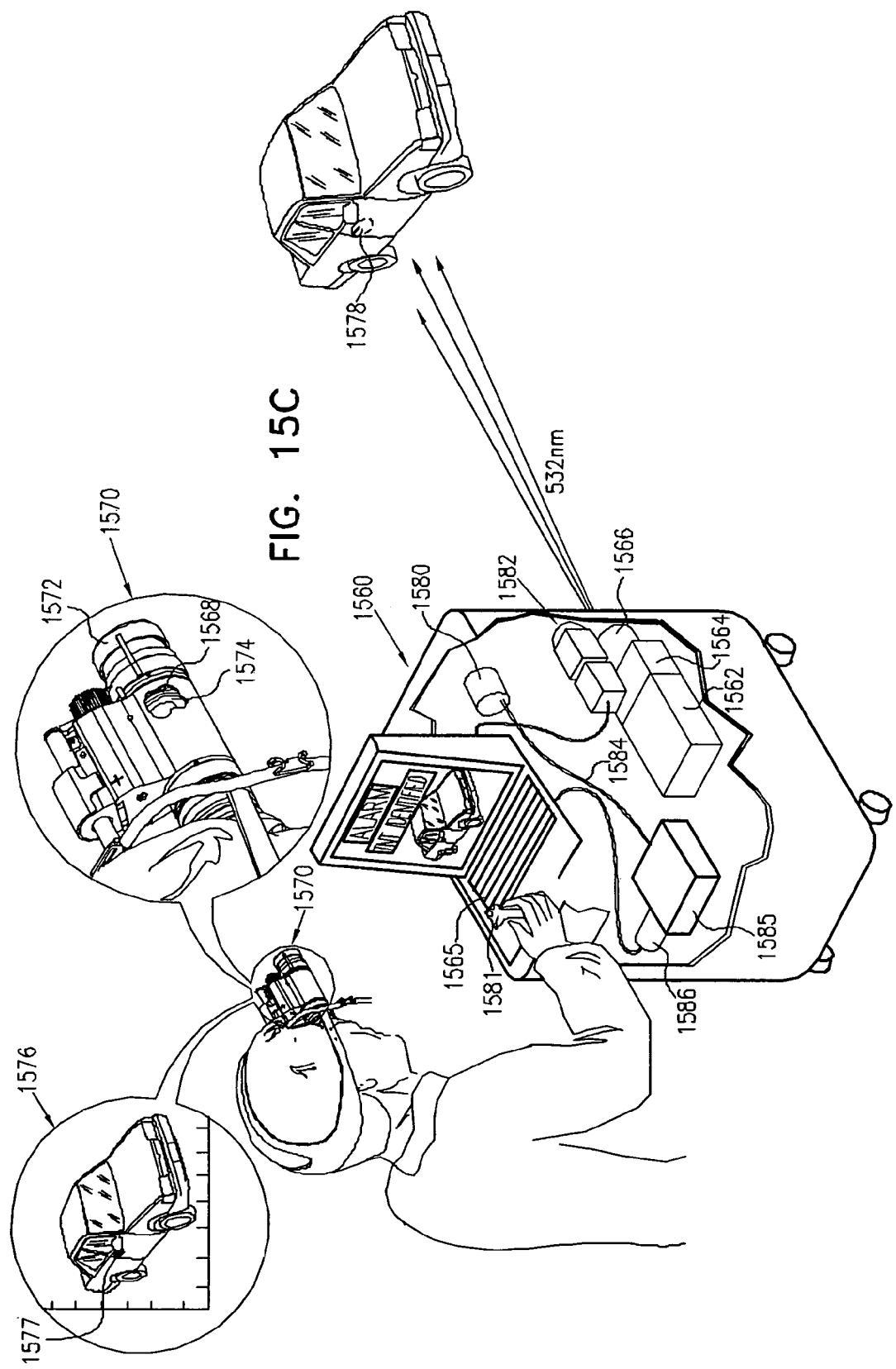

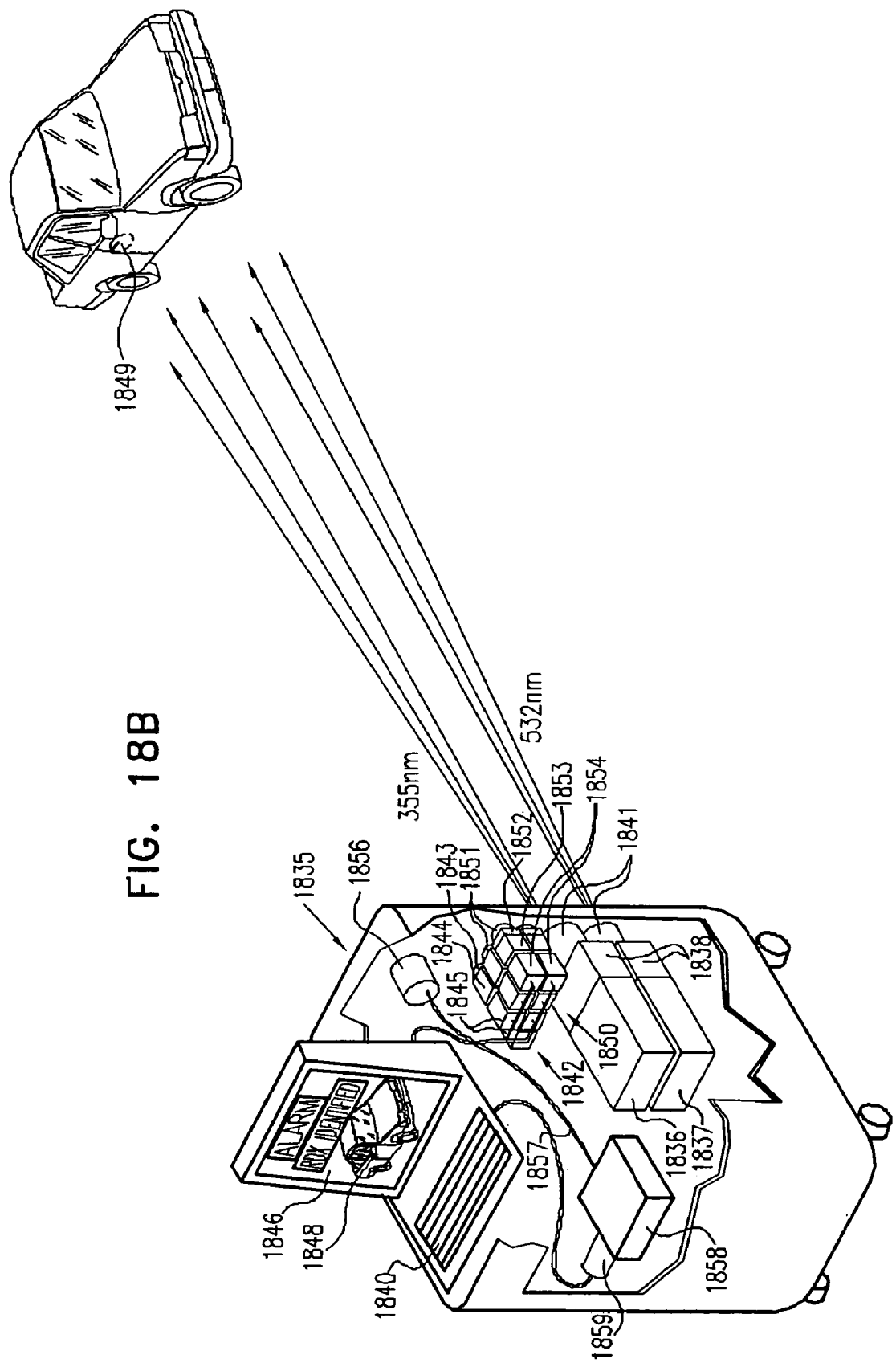

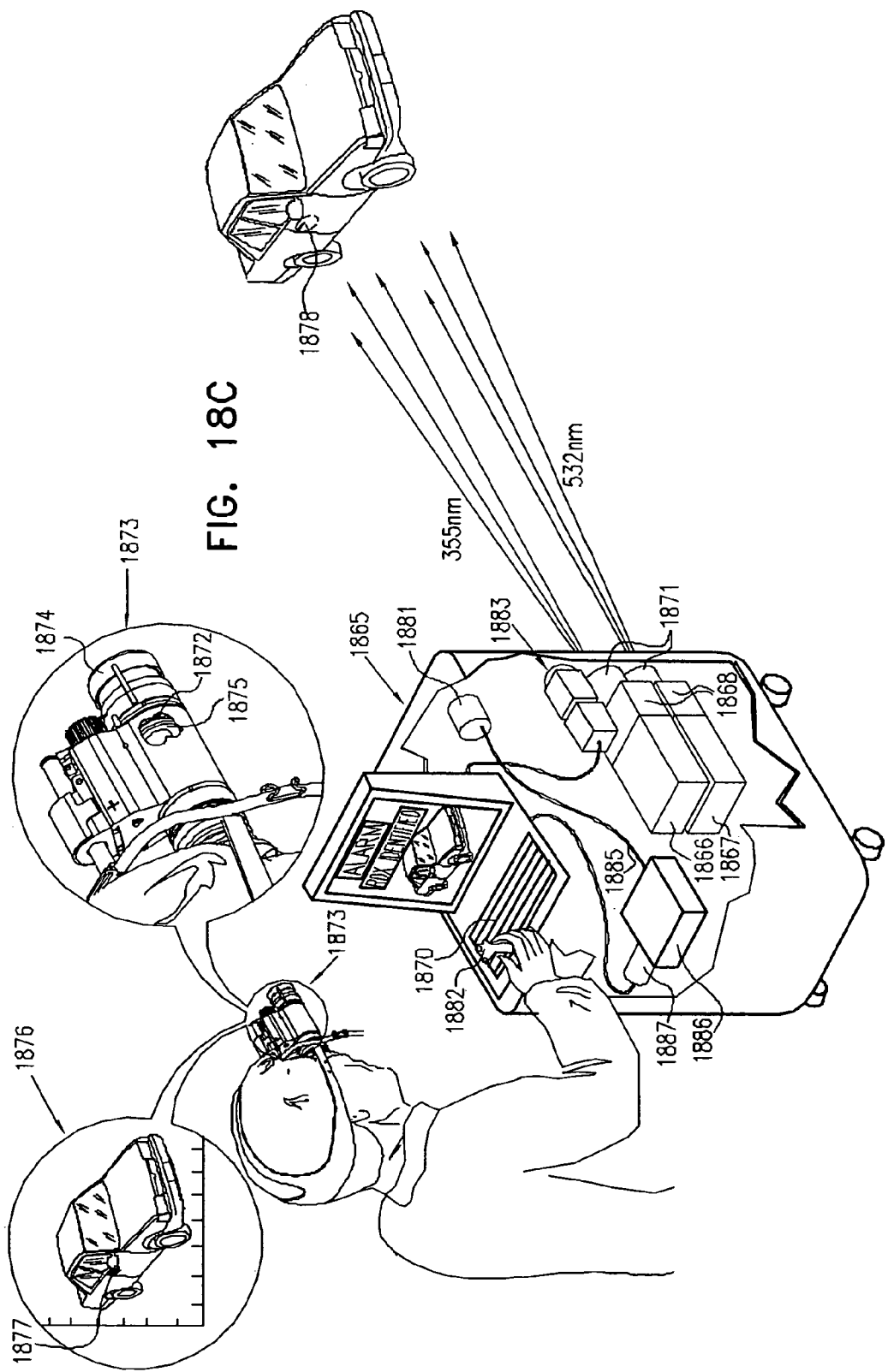

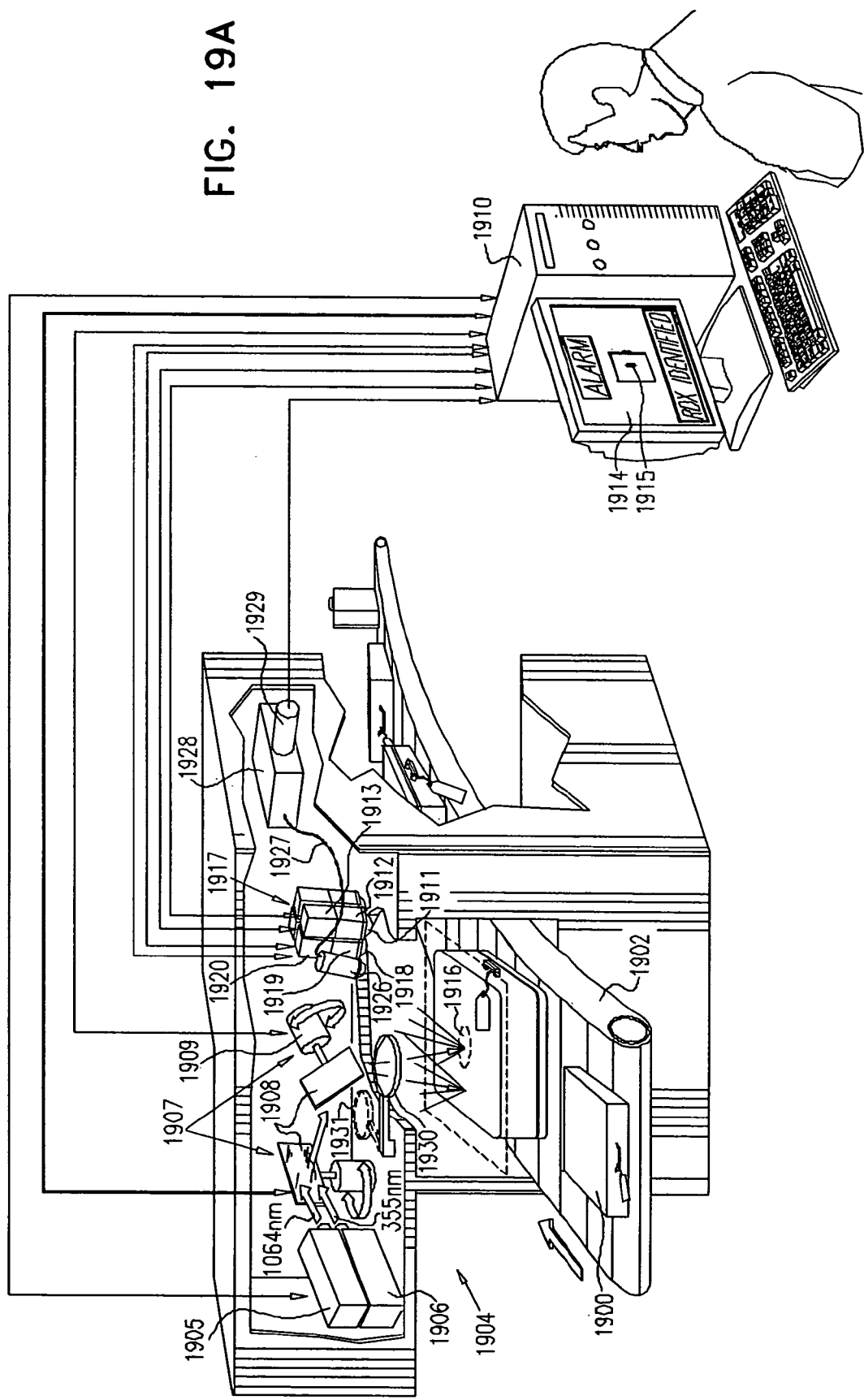

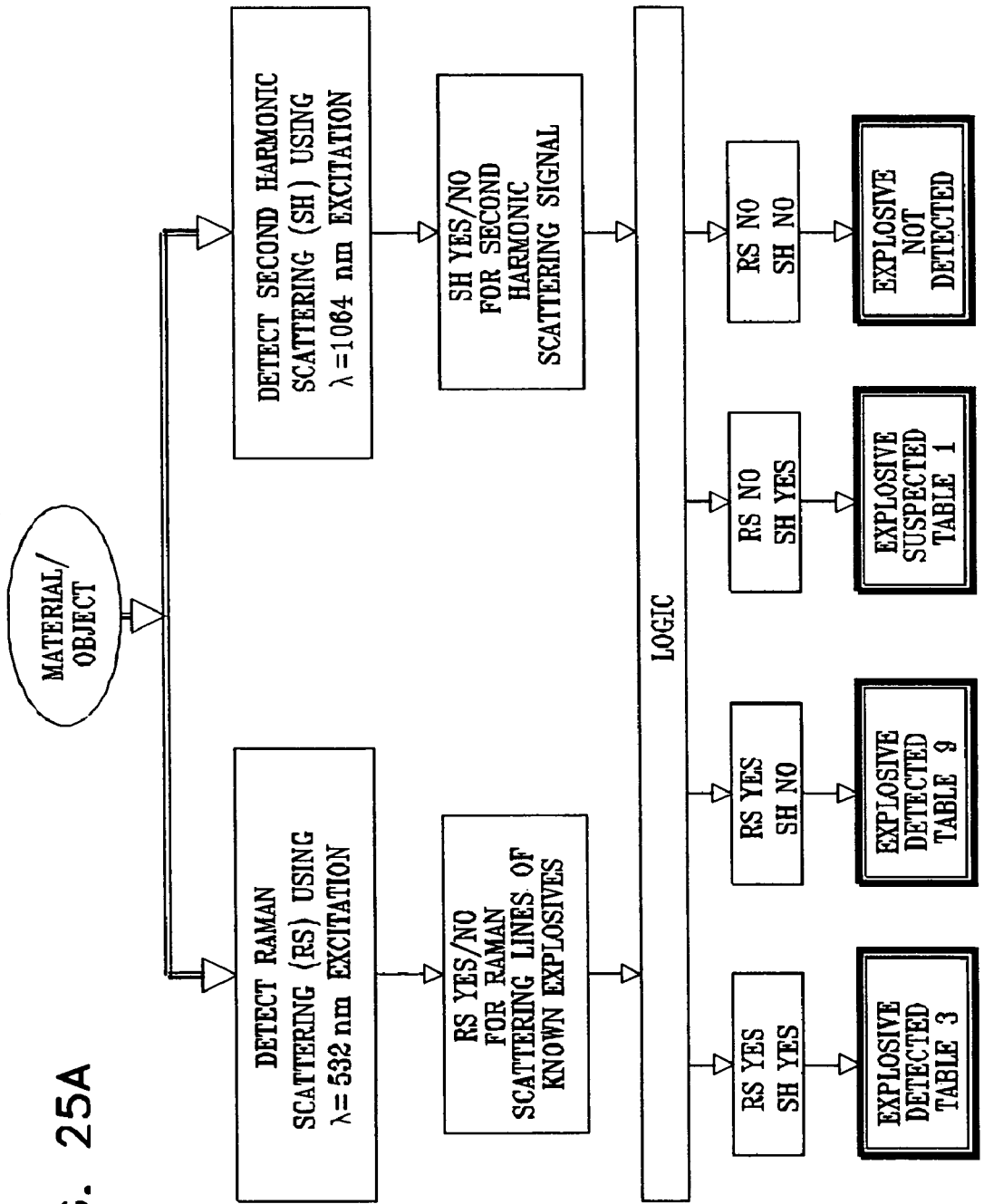

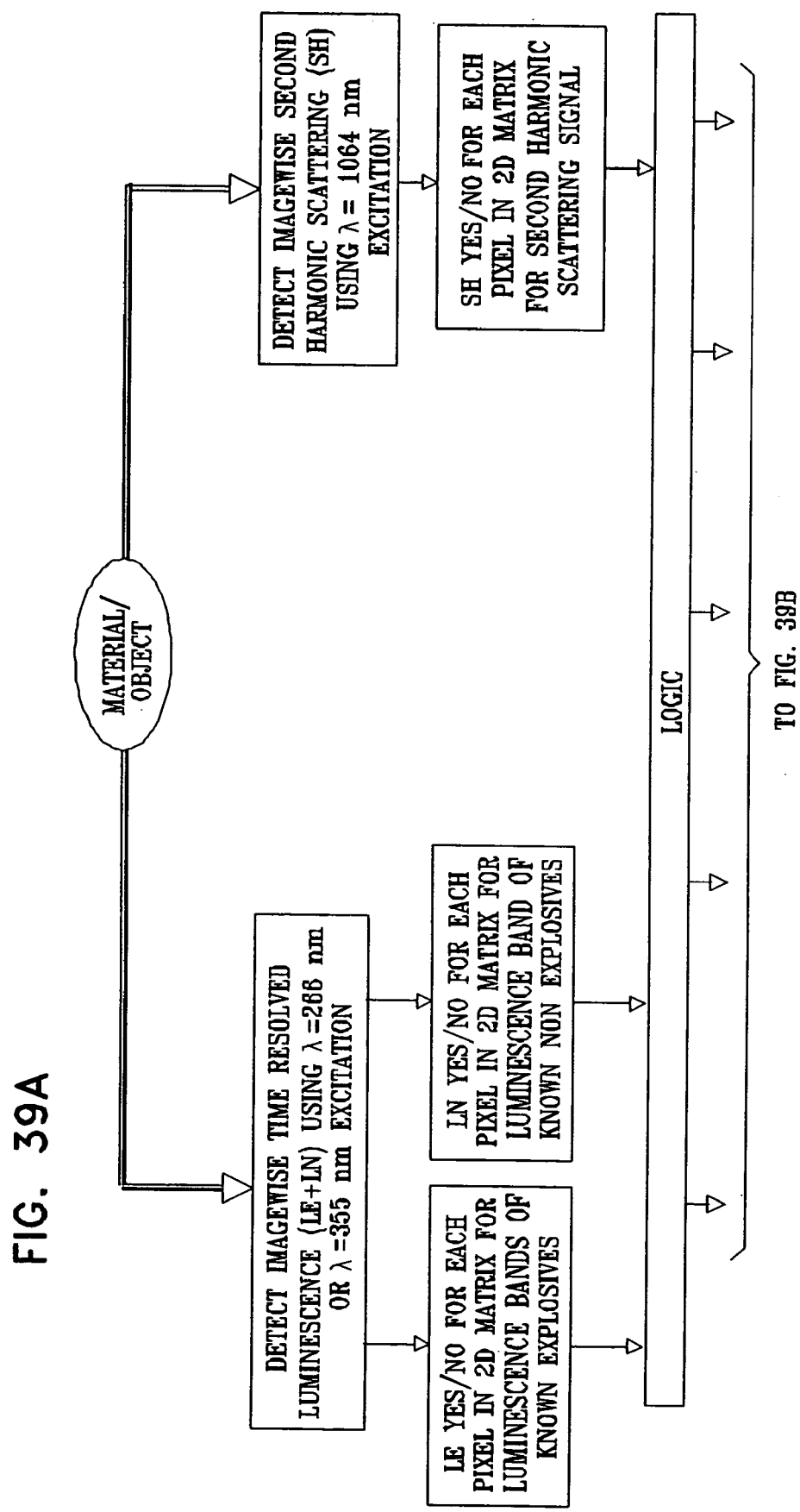

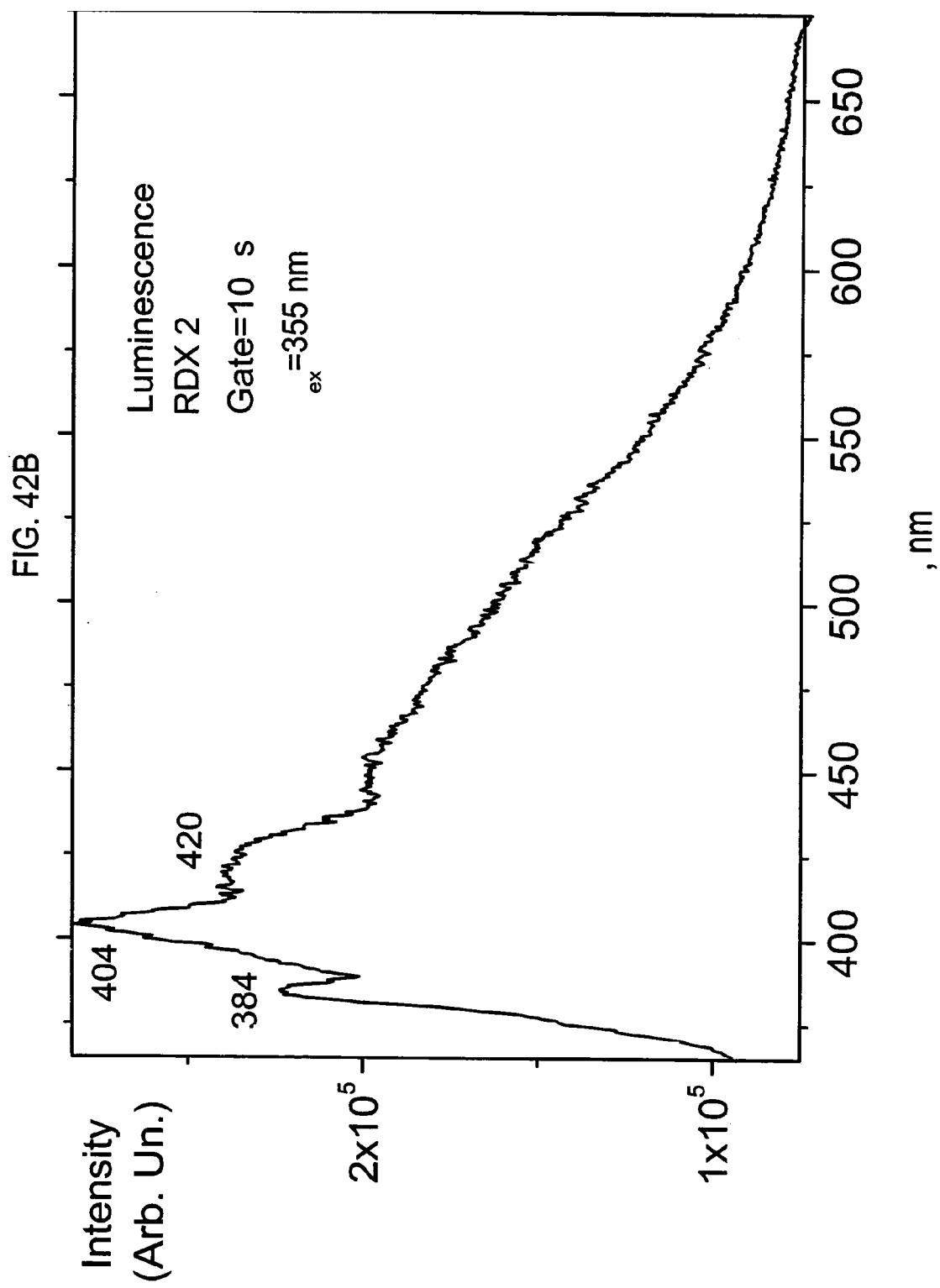

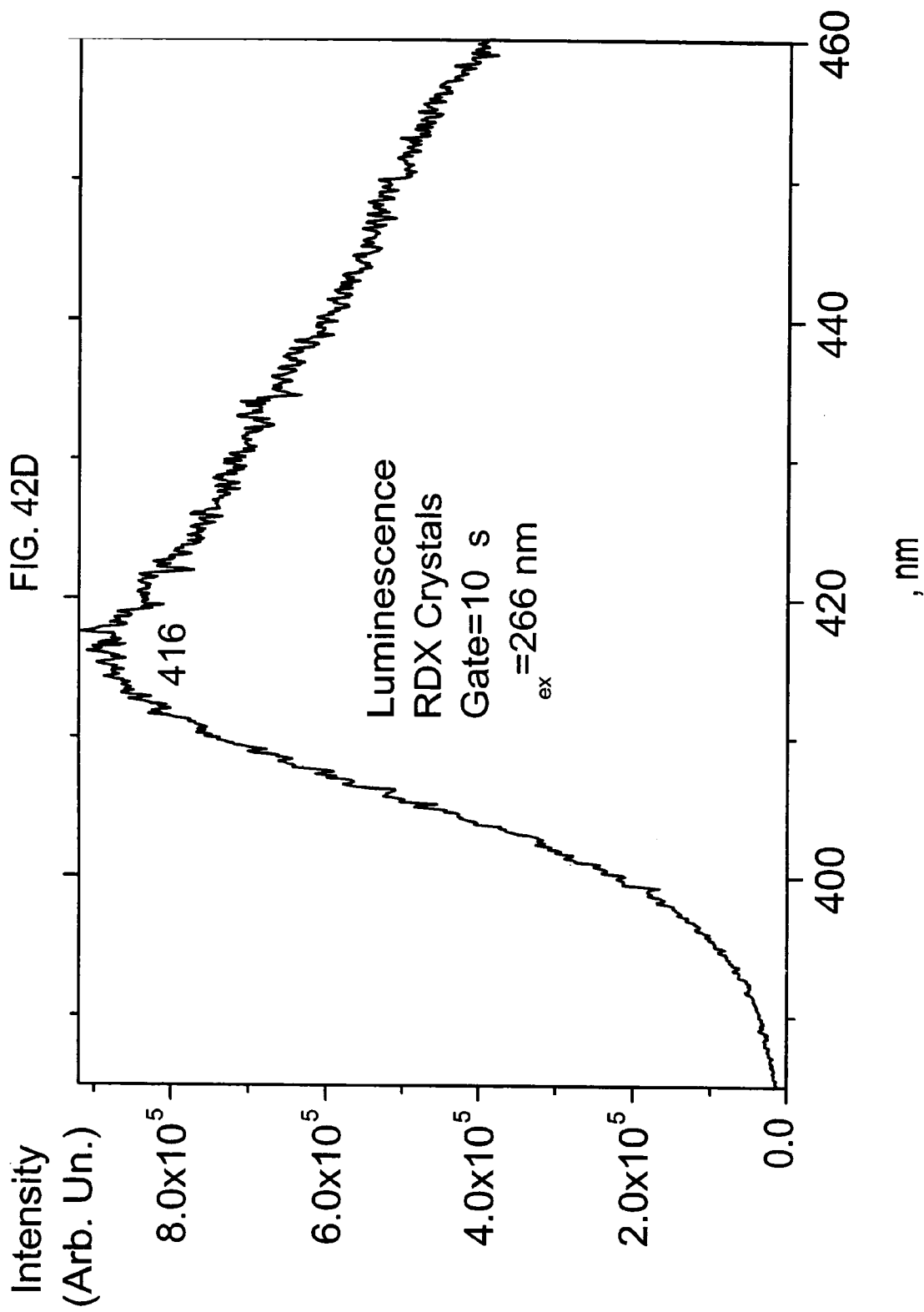

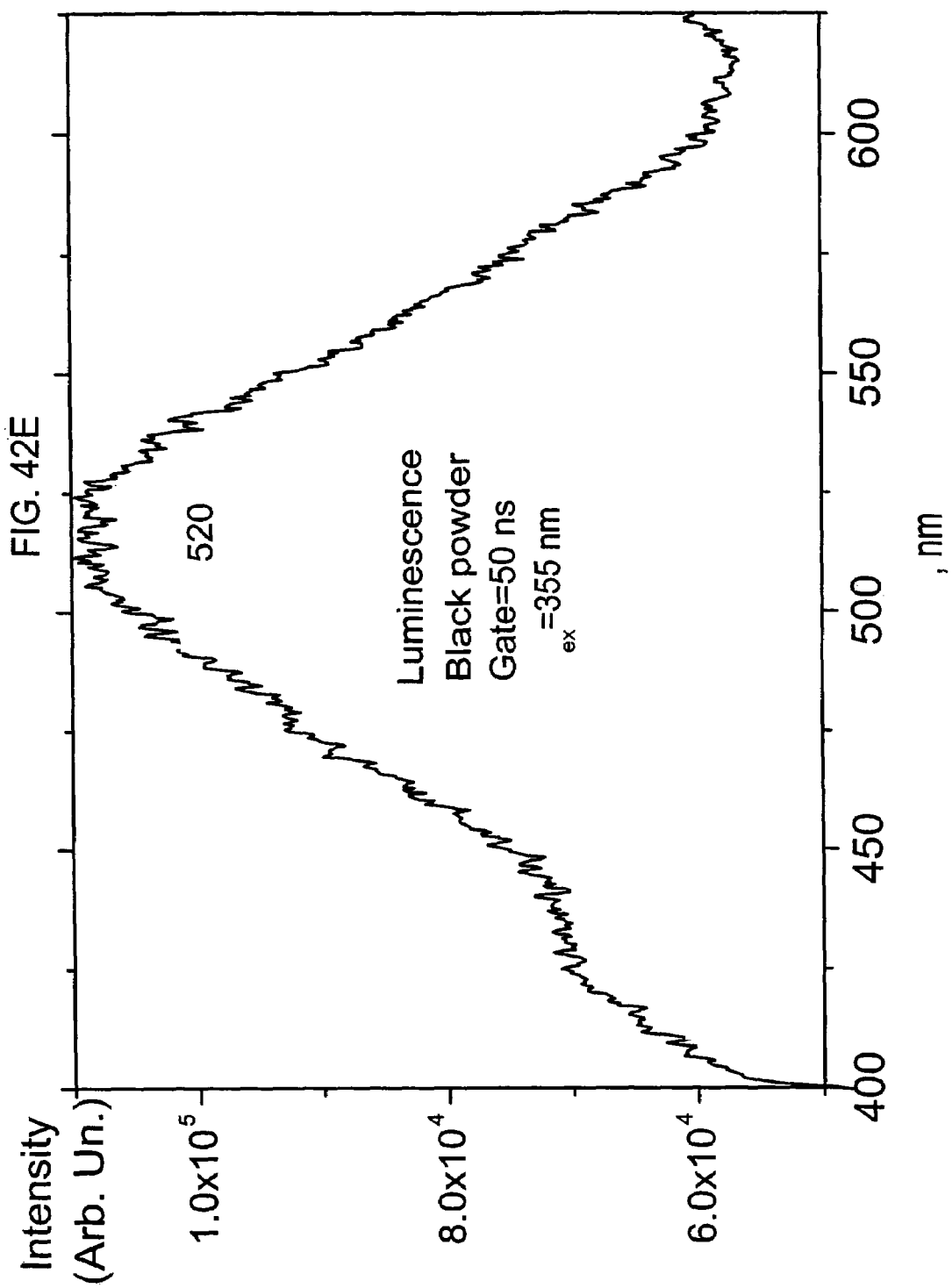

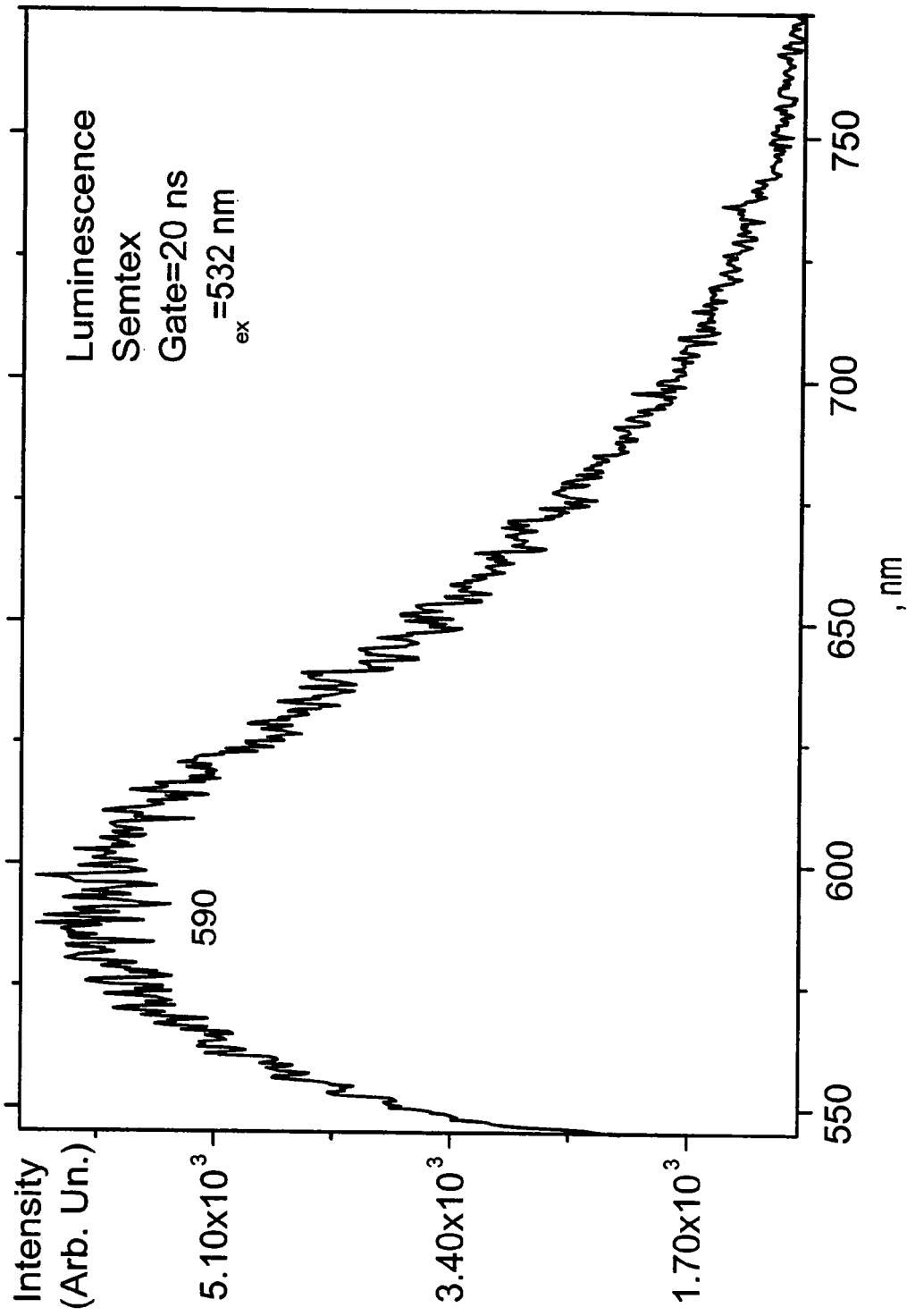

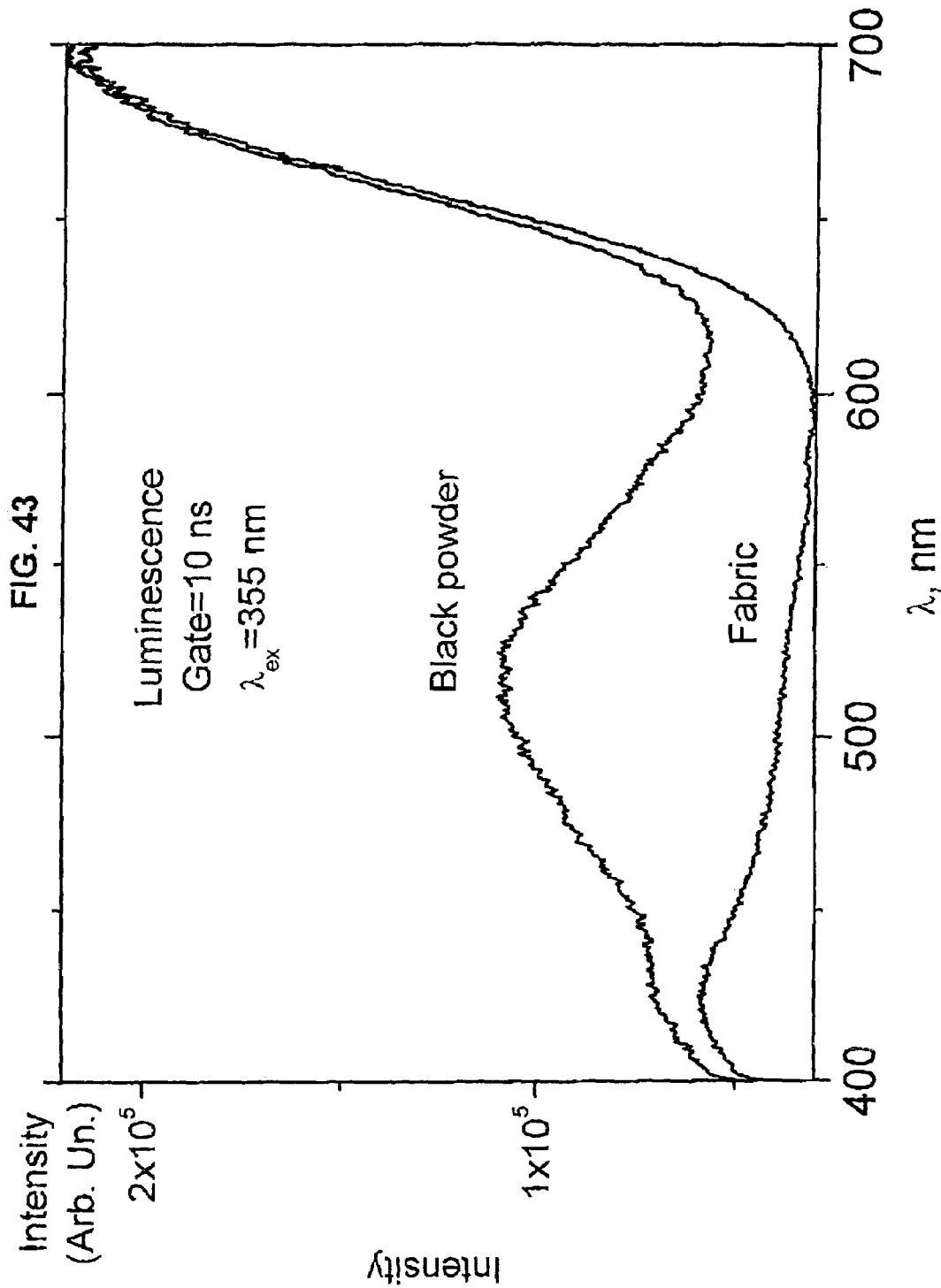

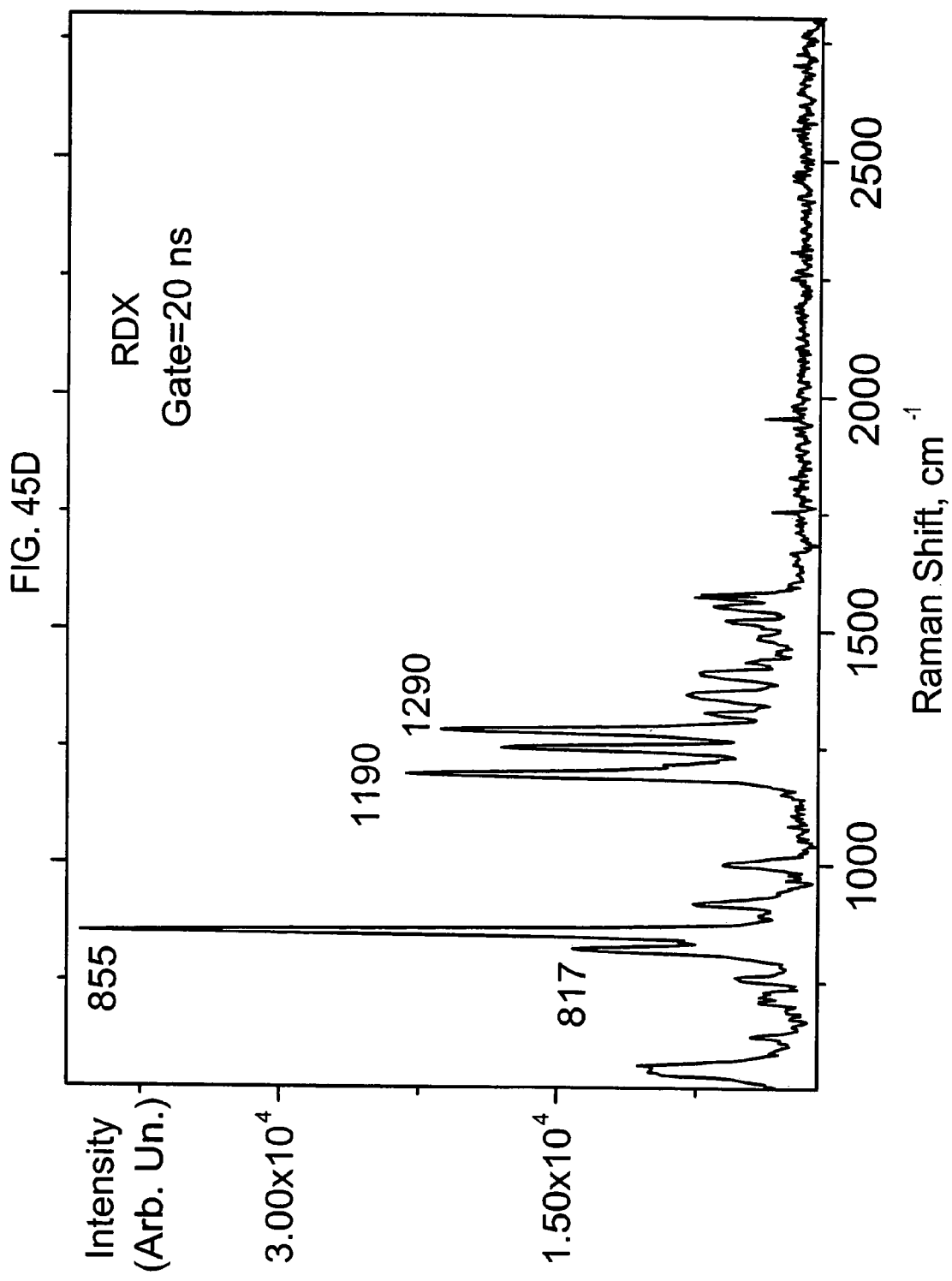

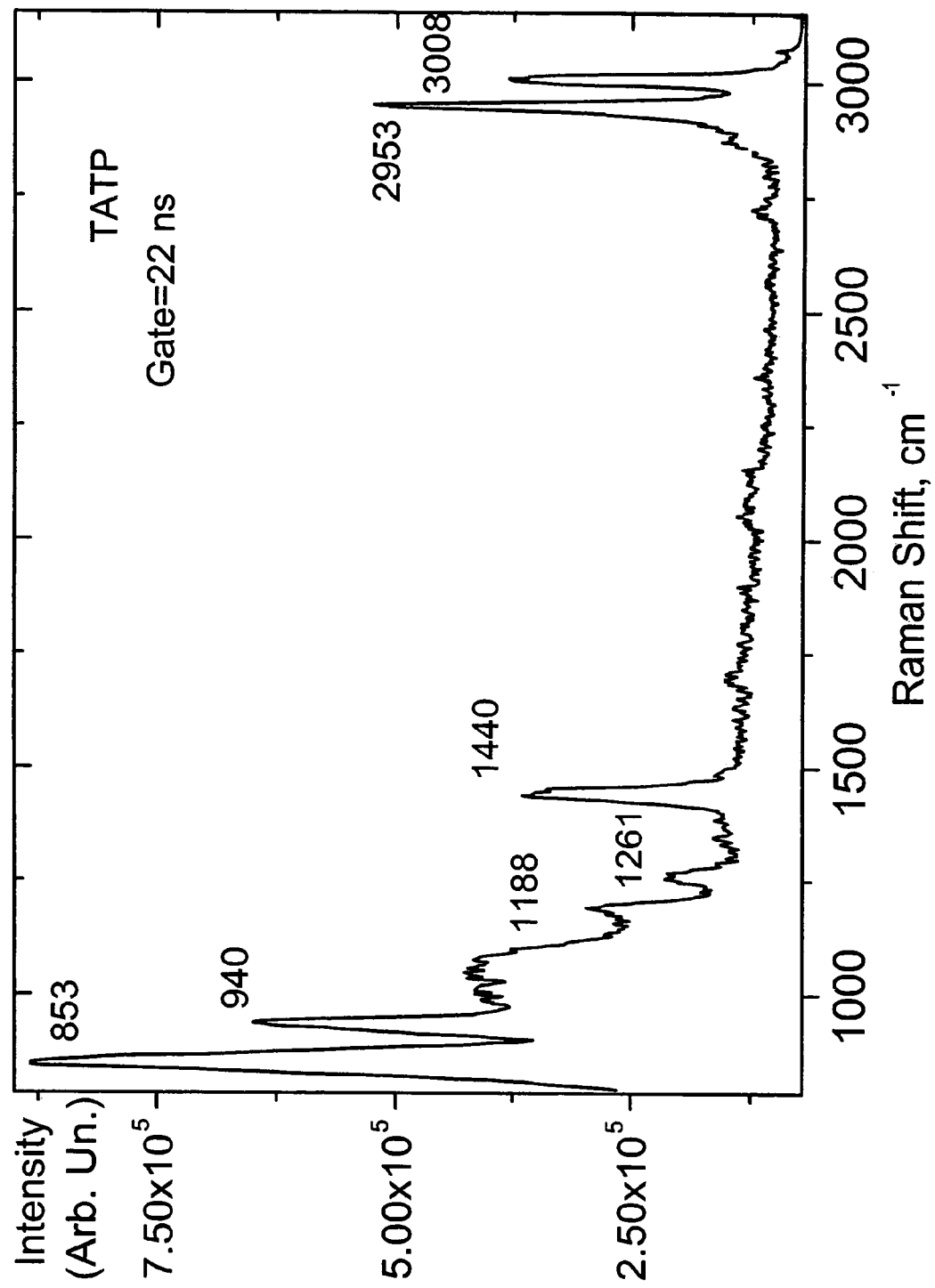

Raman Shift, cm$^{-1}$

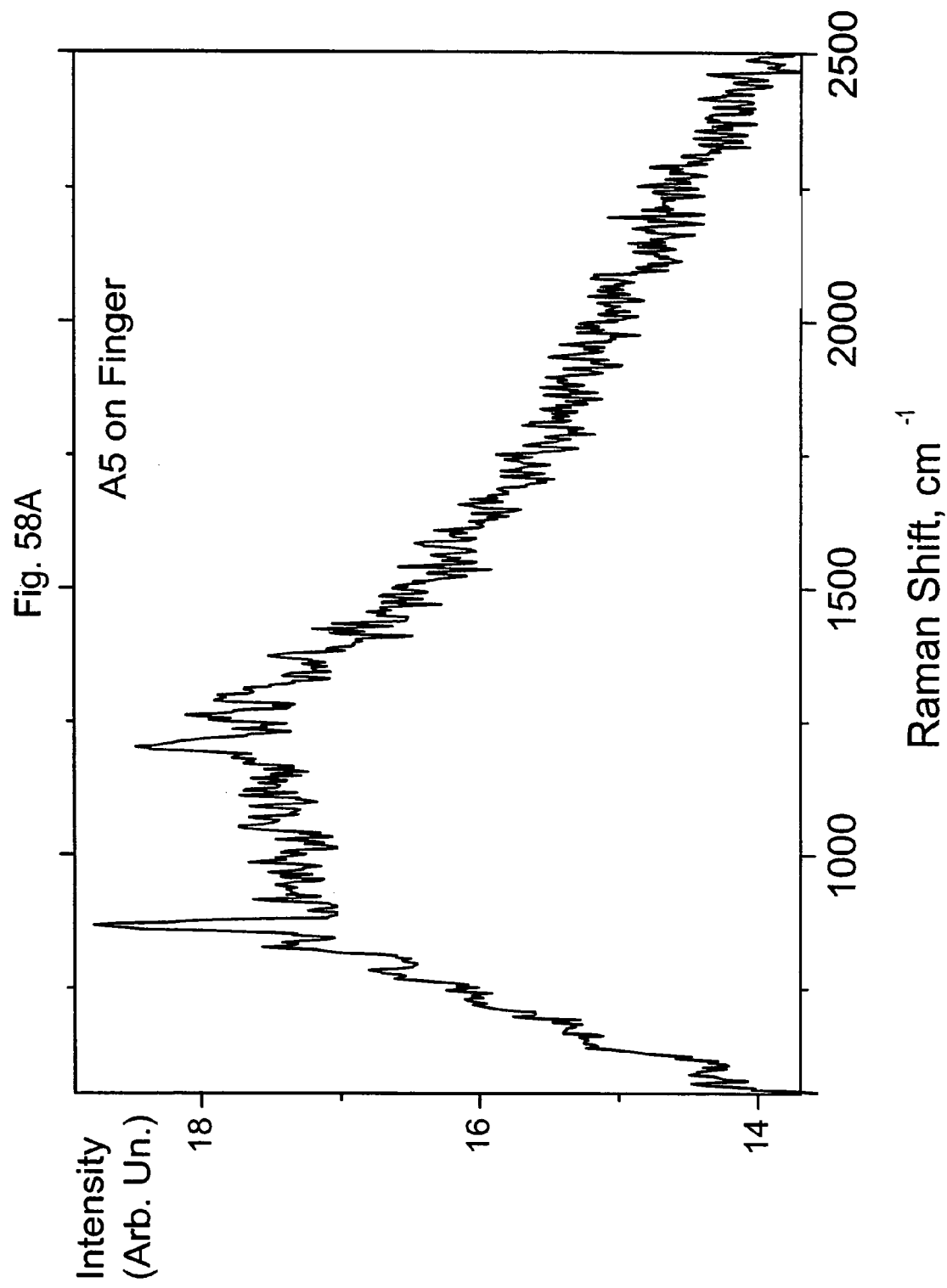

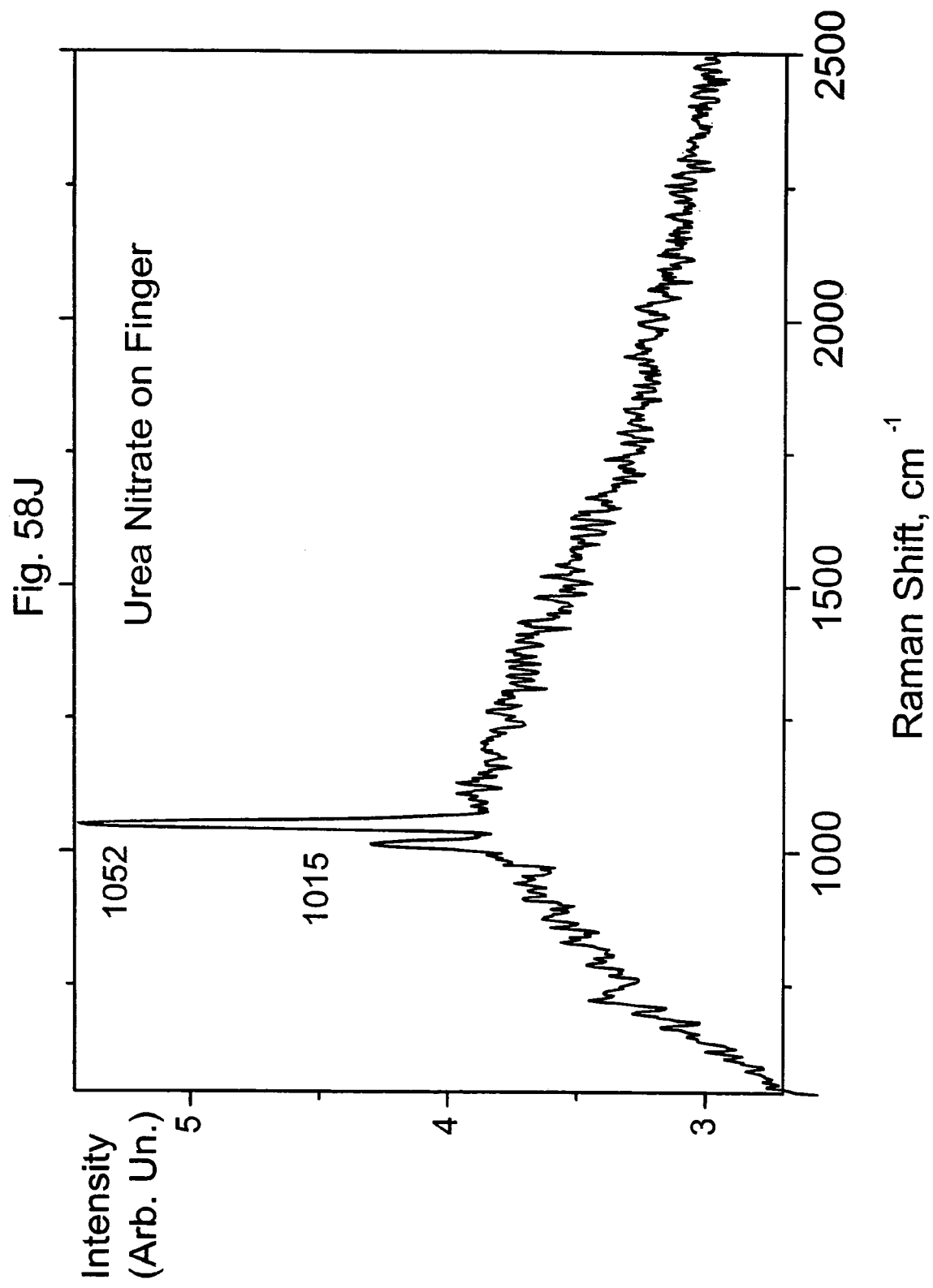

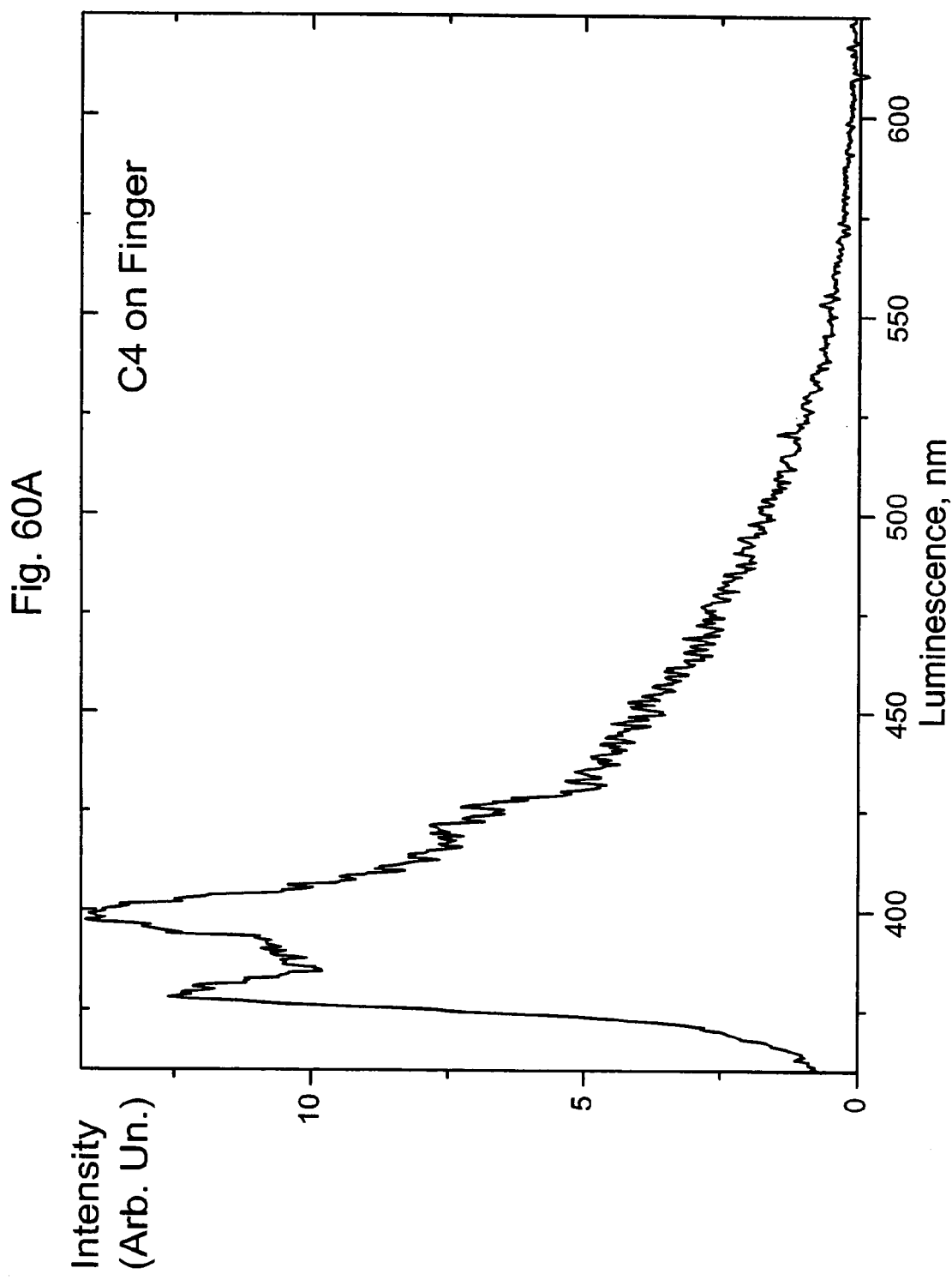

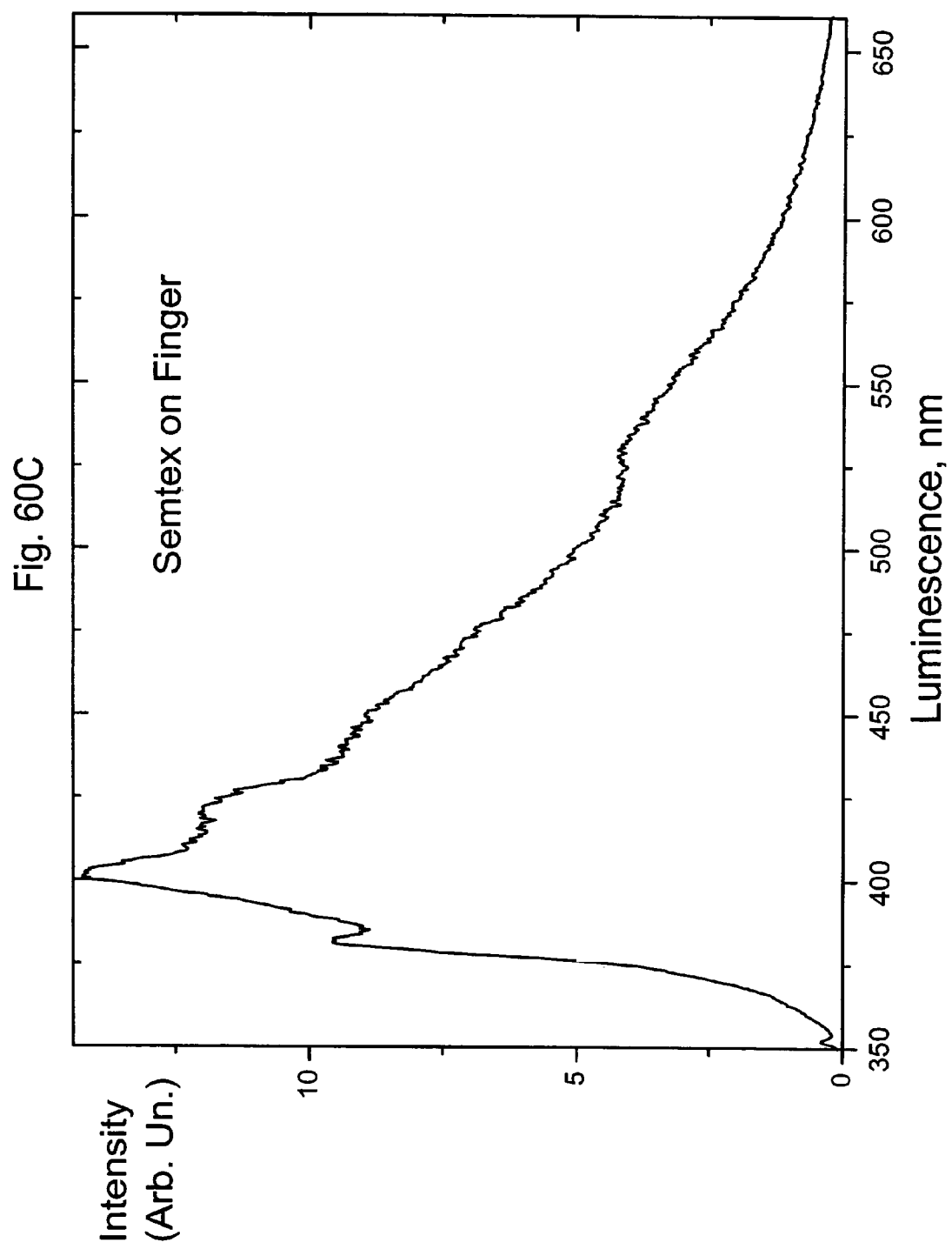

CONTROLLED SUBSTANCE DETECTION AND IDENTIFICATION SYSTEM

FIELD OF THE INVENTION

The present invention relates to detection and identification of explosives and other controlled substances.

BACKGROUND OF THE INVENTION

Detection and identification of explosives are important in forensic, security screening, environmental pollution and a variety of other applications. A variety of analytical tools and methods, including mass-spectrometry, gas chromatography and ion mobility spectrometry, are used in the laboratory for detection and identification of explosives. These methods have also been applied in airport security screening systems. Since conventional X-Ray and CT systems are not analytic systems, complementary analytical methods are used to verify suspected explosives that are detected. Systems based on these methods perform detection or identification utilizing material sampling. Conventional sampling methods include vapor detection systems, such as sniffers, which use vacuum pumping, and pad swiping systems, which detect traces of contaminants on a body surface. However, even the most sensitive methods are limited by sampling, since the system can fail to detect an explosive because the sampling is not done efficiently enough.

Explosive detection methods and systems are described, inter-alia, in "Forensic and Environmental Detection of Explosives", Jehuda Yinon, John Wiley & Sons Ltd. (1999); and in a review by Jeffrey I. Steinfeld and Jody Wormhoudt, Ann. Rev. Phys. Chem. (1998), v49, 203–232. Steinfeld and Wormhoudt mention the stickiness of explosive particulates as an important physical-chemical property. This property of explosive particulates enables traces of explosives to be detected on materials that have come in contact with explosives.

A method for detection of traces of explosives is described by Haley et al in U.S. Pat. No. 5,760,895. This patent describes performing detection without sampling by applying laser radiation, causing micro-denotation of explosive particulates that are found on a suitcase surface. The explosive is detected by measuring the characteristic emission of the explosive micro-detonation. Another method, described by Funsten et al in U.S. Pat. Nos. 5,638,166 and 5,912,466, uses sampling to detect micro-detonation emission caused by heating resulting in deflagration.

The following U.S. Patents and articles are believed to be representative of the prior art: U.S. Pat. Nos. 6,160,255; 5,912,466; 5,906,946; 5,826,214; 5,760,895; 5,728,584; 5,697,373 and 5,638,166.

Arusi-Parpar et al Applied Optics, 2001 V40, No. 336, pp 6677–6681;

G. Mizutani et al, J. of Luminescence, 2000, 87–89, pp 824–826;

L. Smilowitz et al, Abstracts, June, 2001 SHOCK 01, Session L2-DE;

C. Cheng et al, J. of Forensic Sciences, 1995, 40 pp 31–37;

K. Horton et al, Abstracts, Lunar and Planetary Science XXXII (2001).

SUMMARY OF THE INVENTION

The present invention seeks to provide improved apparatus and methodologies for detection and identification of explosives and other controlled substances.

There is thus provided in accordance with a preferred embodiment of the present invention a system for detecting controlled substances on an object including at least one laser for illuminating at least part of an object with laser energy at a first wavelength and a second harmonic controlled substance detector for detecting laser energy scattered from the object to detect scattered laser energy having a second wavelength which is a second harmonic of the first wavelength, wherein detection of scattered laser energy having a second wavelength which is a second harmonic of the first wavelength indicates that one or more controlled substances may be present on the object.

In accordance with another preferred embodiment of the present invention the system also includes at least one additional controlled substance detector including at least one of a luminescence controlled substance detector for detecting luminescence produced by impingement of the laser energy, wherein detection of luminescence indicates that one or more controlled substances may be present on the object, and a Raman scattering controlled substance detector, for detecting Raman scattering produced by impingement of the laser energy. Preferably, the system also includes logic operative in response to outputs of the second harmonic detector and the at least one additional controlled substance detector to provide an enhanced output indication of a possibility that one or more controlled substances may be present.

There is also provided in accordance with another preferred embodiment of the present invention a system for detecting controlled substances on an object including a laser for illuminating at least part of an object with laser energy and a luminescence controlled substance detector for detecting luminescence produced by impingement of the laser energy, wherein detection of luminescence indicates that one or more controlled substances may be present on the object.

In accordance with yet another preferred embodiment of the present invention the system also includes a Raman scattering controlled substance detector for detecting Raman scattering produced by impingement of the laser energy. Preferably, the system also includes logic operative in response to outputs of the luminescence controlled substance detector and Raman scattering controlled substance detector to provide an enhanced output indication of a possibility that one or more controlled substances may be present.

There is further provided in accordance with yet another preferred embodiment of the present invention a system for detecting controlled substances on an object including at least one laser for illuminating at least part of an object with laser energy and a time-resolved controlled substance detector for detecting Raman scattering produced by impingement of the laser energy, wherein time-resolved detection of Raman scattering indicates that one or more controlled substances may be present on the object.

Preferably, the second harmonic controlled substance detector is a time-resolved detector. Additionally or alternatively, the luminescence controlled substance detector is a time-resolved detector. Alternatively or additionally, the Raman scattering controlled substance detector is a time-resolved detector.

In accordance with another preferred embodiment of the present invention the system is an imagewise system. Alternatively, the system is a non-imagewise system.

In accordance with yet another preferred embodiment of the present invention the system also includes a controlled substance detection verifier. Preferably, the controlled substance detection verifier employs time-resolved laser induced breakdown spectroscopy verification.

In accordance with still another preferred embodiment of the present invention the system also includes a controlled substance identifier. Preferably, the explosives identifier employs at least one of time-resolved luminescence and time-resolved Raman scattering. Additionally, the explosives identifier also employs time-resolved laser induced breakdown spectroscopy for enhanced identification.

In accordance with another preferred embodiment of the present invention the system also includes a scanning mechanism for directing at least one laser beam from the at least one laser to the object.

There is also provided in accordance with still another preferred embodiment of the present invention a method for detecting controlled substances on an object including illuminating at least part of an object with laser energy at a first wavelength and detecting scattered laser energy from the object having a second wavelength which is a second harmonic of the first wavelength, wherein the detecting indicates that one or more controlled substances may be present on the object.

In accordance with another preferred embodiment of the present invention the detecting also includes detecting at least one of luminescence produced by impingement of the laser energy, wherein the detecting luminescence indicates that one or more controlled substances may be present on the object, and Raman scattering produced by impingement of the laser energy. Additionally, the method also includes providing an enhanced output indication of a possibility that one or more controlled substances may be present in response to the detecting scattered laser energy having a second wavelength which is a second harmonic of the first wavelength and the detecting at least one of luminescence produced and Raman scattering produced.

There is further provided in accordance with still another preferred embodiment of the present invention a method for detecting controlled substances on an object including illuminating at least part of an object with laser energy and detecting luminescence produced by impingement of the laser energy, wherein the detecting luminescence indicates that one or more controlled substances may be present on the object.

In accordance with another preferred embodiment of the present invention the method also includes detecting Raman scattering produced by impingement of the laser energy. Additionally, the method also includes providing an enhanced output indication of a possibility that one or more controlled substances may be present in response to the detecting luminescence and the detecting Raman scattering.

There is yet further provided in accordance with another preferred embodiment of the present invention a method for detecting controlled substances on an object including illuminating at least part of an object with laser energy and detecting in a time-resolved manner Raman scattering produced by impingement of the laser energy, wherein time-resolved detecting of Raman scattering indicates that one or more controlled substances may be present on the object.

In accordance with another preferred embodiment of the present invention the detecting scattered laser energy having a second wavelength which is a second harmonic includes detecting in a time-resolved manner. Additionally or alternatively, the detecting of luminescence includes detecting in a time-resolved manner. Additionally or alternatively, the detecting of Raman scattering includes detecting in a time-resolved manner.

Preferably, the method also includes displaying an image of the object on a display and visually indicating at least one location of the controlled substance on the display. Additionally or alternatively, the method also includes verifying the presence of the controlled substances on the object. Preferably, the verifying includes employing time-resolved laser induced breakdown spectroscopy verification.

In accordance with yet another preferred embodiment of the present invention, the method also includes identifying the controlled substances. Preferably, the identifying includes employing at least one of time-resolved luminescence identification and time-resolved Raman scattering identification. Additionally, the identifying includes employing time-resolved laser induced breakdown spectroscopy for enhanced identification.

BRIEF DESCRIPTION OF THE DRAWINGS

The present invention will be understood and appreciated more fully from the following detailed description, taken in conjunction with the drawings in which:

FIG. 1B is a simplified pictorial illustration of an imagewise system for detecting explosives on objects constructed and operative in accordance with a preferred embodiment of the present invention and employing laser induced second harmonic detection;

FIG. 1C is a simplified pictorial illustration of an imagewise system for detecting explosives constructed and operative in accordance with another preferred embodiment of the present invention and employing laser induced second harmonic detection;

FIG. 2A is a simplified pictorial illustration of a non-imagewise system for detecting explosives on objects constructed and operative in accordance with a preferred embodiment of the present invention and employing time-resolved luminescence detection;

FIG. 2D is a simplified pictorial illustration of an imagewise system for detecting explosives constructed and operative in accordance with yet another preferred embodiment of the present invention and employing laser induced time-resolved luminescence detection;

FIG. 5C is a simplified pictorial illustration of an imagewise system for detecting explosives constructed and operative in accordance with another preferred embodiment of the present invention and employing laser induced second harmonic and time-resolved Raman scattering detection;

FIG. 6C is a simplified pictorial illustration of an imagewise system for detecting explosives constructed and operative in accordance with another preferred embodiment of the present invention and employing laser induced time-resolved luminescence and time-resolved Raman scattering detection;

FIG. 7C is a simplified pictorial illustration of an imagewise system for detecting explosives constructed and operative in accordance with another preferred embodiment of the present invention and employing laser induced second harmonic, time-resolved luminescence and time-resolved Raman scattering detection;

FIGS. 9A, 9B and 9C are simplified pictorial illustrations of imagewise systems for detecting and identifying explosives on objects constructed and operative in accordance with preferred embodiments of the present invention and employing time-resolved luminescence detection and identification;

FIGS. 10A, 10B and 10C are simplified pictorial illustrations of imagewise systems for detecting and identifying explosives on objects constructed and operative in accordance with preferred embodiments of the present invention and employing time-resolved Raman scattering detection and identification;

FIGS. 11A, 11B and 11C are simplified pictorial illustrations of an imagewise system for detecting and identifying explosives on objects constructed and operative in accordance with preferred embodiments of the present invention and employing second harmonic and time-resolved luminescence detection and time-resolved luminescence identification;

FIGS. 12A, 12B and 12C are simplified pictorial illustrations of imagewise systems for detecting and identifying explosives on objects constructed and operative in accordance with preferred embodiments of the present invention and employing second harmonic and time-resolved Raman scattering detection and time-resolved Raman scattering identification;

FIGS. 14A, 14B and 14C are simplified pictorial illustrations of dual mode systems for detecting and identifying explosives constructed and operative in accordance with preferred embodiments of the present invention and employing time-resolved luminescence detection and employing time-resolved luminescence and time-resolved laser induced breakdown spectroscopy for enhanced identification;

FIGS. 15A, 15B and 15C are simplified pictorial illustrations of dual mode systems for detecting and identifying explosives constructed and operative in accordance with preferred embodiments of the present invention and employing time-resolved Raman scattering detection and employing time-resolved Raman scattering and time-resolved laser induced breakdown spectroscopy for enhanced identification;

FIGS. 18A, 18B and 18C are simplified pictorial illustrations of triple mode systems for detecting and identifying explosives constructed and operative in accordance with a preferred embodiment of the present invention and employing time-resolved luminescence and time-resolved Raman scattering detection and employing time-resolved luminescence, time-resolved Raman scattering and time-resolved laser induced breakdown spectroscopy for enhanced identification;

FIGS. 19A, 19B and 19C are simplified pictorial illustrations of triple mode systems for detecting and identifying explosives constructed and operative in accordance with preferred embodiments of the present invention and employing second harmonic and time-resolved luminescence detection and employing time-resolved luminescence and time-resolved laser induced breakdown spectroscopy for enhanced identification;

FIG. 25A is a simplified flowchart illustrating operation of the embodiment of FIG. 5A;

FIGS. 39A and 39B, taken together, are a simplified flowchart illustrating operation of the embodiments of FIGS. 19A–19C;

FIGS. 42A, 42B, 42C, 42D, 42E, 42F, 42G and 42H are graphs showing luminescence spectra of various explosives;

FIG. 43 is a graph showing a comparison of luminescence spectra of an explosive and a background material;

FIGS. 45A, 45B, 45C, 45D, 45E, 45F and 45G are graphs showing Raman spectra of various explosives;

FIGS. 58A, 58B, 58C, 58D, 58E, 58F, 58G, 58H, 58I, 58J and 59 are graphs showing time-resolved Raman spectra of various explosives against the background of a human hand;

FIGS. 60A, 60B, 60C and 61 are graphs showing time-resolved luminescence spectra of various explosives against the background of a human hand.

DETAILED DESCRIPTION OF PREFERRED EMBODIMENTS

Figure 1A:
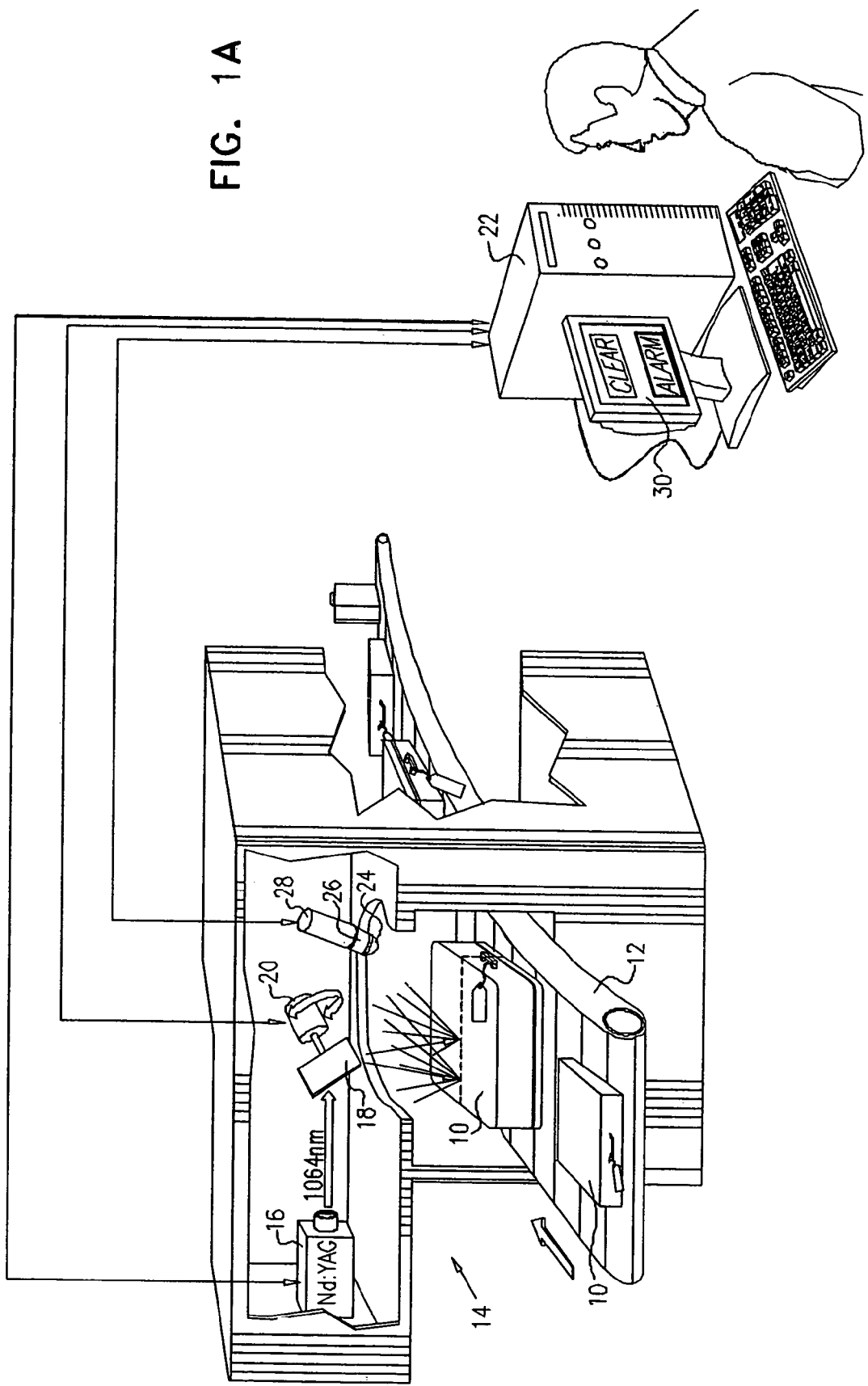
FIG. 1A is a simplified pictorial illustration of a non-imagewise system for detecting explosives on objects constructed and operative in accordance with a preferred embodiment of the present invention and employing laser induced second harmonic detection.

The present invention preferably uses at least one laser or other light source for in-situ explosive detection without sampling and a fast screening detection technology combined with fast laser induced spectroscopic identification tools for detection verification. The present invention is thus suitable for use in airport security screening systems, and operates in a fashion similar to X-Ray screening systems. In another embodiment, the present invention preferably uses at least one laser or other light source for in-situ detection of controlled substances, such as explosives or drugs, without sampling, utilizing a fast screening detection technology. The present invention utilizes multiple spectral analysis tools to achieve high throughput identification and detection of explosives and other controlled substances. This high throughput is suitable for a conveyer driven luggage security screening system as well as personal screening systems with detection accuracy rates comparable to that found in a high-accuracy laboratory testing environment. This high-accuracy testing results in reduced False-Negative and False-Positive Detection Rates and reduces interference from other materials.

The following spectroscopic tools are utilized in the present invention:

Second Harmonic Scattering (SH) of excitation wavelengths;

Laser Induced Luminescence (LE);

Raman Scattering (RS);

Laser Induced Breakdown Spectroscopy (LIBS); and

Excitation spectra of the above, namely: sensitivity of measured spectral signals to excitation wavelength.

Additionally, the present invention preferably utilizes Time-resolved Laser-induced Spectroscopic measurements of the above.

Introduction to Laser Induced Spectroscopy

Luminescence by Fluorescence and Phosphorescence:

Several physical and chemical processes may occur when material is irradiated using a laser or light source. When a molecule of the material being irradiated absorbs a photon, the molecule is excited to an electronic state above the ground electronic state. The typical lifetime of organic molecules in the lowest excited state is about $10^{-9}$ to $10^{-7}$ sec. There are several spectroscopic phenomena that can be measured, including:

Emission of fluorescence from the electronic excited state to the electronic ground state;

Intersystem crossing to a triplet state causing emission of phosphorescence from the electronic triplet state to the electronic ground state; and Internal conversion from the electronic excited state to high excited vibrational states in the electronic ground state causing, inter alia, IR fluorescence emission.

The terms laser induced luminescence and luminescence, when used throughout the description of the present invention, refer to measuring one or more of these three spectroscopic phenomena. These emissions of fluorescence and phosphorescence, which are produced by the energy differences between molecular electronic states, are measured as luminescence in the UV, visible and Near IR wavelengths. Fluorescence and phosphorescence are characterized by different radiation lifetimes. Radiation lifetime is also significantly influenced by environmental and physical conditions, such as temperature, pressure, solvent, crystal structure, and material state (solid, liquid or gas). These conditions also dictate the efficiency of radiationless relaxation processes.

The above-mentioned conditions also influence the IR fluorescence emission, which is primarily a function of temperature and population of vibrational states. This emission is measured in the IR region, which is suitable for measuring typical energy differences between molecular vibrational states.

In other instances, the Luminescence spectrum emitted is a function of the background material upon which the sample being tested is placed. One example of this is known as quenching, where a background material is provided which exhibits its own Luminescence spectrum. This background Luminescence spectrum is then quenched or masked by the controlled substance. Thus, in this instance, the controlled substance is identified by the change in the Luminescence spectrum. In another example, a background material is provided which generates an enhanced Luminescence spectrum when controlled substances are placed upon it. This enhancement is referred to as Additive Material Enhanced Luminescence.

Raman Spectroscopy

The interaction of a material and radiation from a laser or light source may also cause scattering of light without absorption of a photon and result in the photon being scattered by a molecule of the material, in an elastic or inelastic process. Raman scattering, when used throughout the description of the present invention, refers to this spectroscopic phenomenon where the molecule is excited to above the vibrational ground state and the photon is scattered by the molecule, resulting in an energy difference in the photon equal to the energy difference between molecular vibrational states. The scattered radiation can be analyzed to generate a spectrum, measuring the signal as a function of wavelength. Raman spectrum is usually measured as energy shift relative to the excitation wavelength, where energy shift is defined in $cm^{-1}$ units. The spectroscopic characteristics are dictated by molecular structure and vibrational energy levels and are therefore correlated to the IR spectrum of the molecule. Raman scattering is classified as a "two wave mixing" process, i.e. one wavelength radiation is converted to a second wavelength radiation upon interaction with a material. The influence of the tested material is increased by orders of magnitude when the excitation wavelength is close to resonance with the absorbing wavelength. This increase is referred to as Resonance Raman Enhancement. In some instances, Raman enhancement is also achieved by the influence of a surface on adsorbed material. This enhancement is referred to as Surface Enhanced Raman, the best known examples of which are silver and gold surface enhancement.

Second Harmonic Scattering

The interaction of material with radiation from a laser or light source may also cause scattering of the light without absorption of a photon and result in the photon being scattered by a molecule of the material in an elastic process without changing the energetic state of the molecule. Second Harmonic Scattering, when used throughout the description of the present invention, refers to a photon being scattered in a wavelength that is half of the original radiation wavelength, i.e. two photons combining into a single photon carrying the energy of both photons. Second Harmonic Scattering is classified as a "three wave mixing" process, i.e. two photons of incoming radiation interacting with a material to produce a third photon. Second harmonic generation is used to produce a laser beam with more energetic photons. This is achieved by using crystals with optical non-linear properties, the interaction of radiation in the bulk of material resulting in a directed laser beam. Second harmonic generation also occurs as a surface phenomenon and is used to monitor surface physical and chemical properties by measuring second harmonic scattering with spectroscopic means.

Laser-Induced Breakdown Spectroscopy (LIBS)

When irradiating material using a laser or light source focused on a small spot, a high-temperature, high electron density micro-plasma is formed and the sample material is broken down, vaporized and ionized to a very high temperature, measured in thousands of degrees. As this plasma cools to a point when neutral atoms in excited states are formed, the excited species—ionized atoms and neutral atoms—relax and emit optical energy at characteristic wavelengths. Laser-induced breakdown spectroscopy (LIBS) refers to spectrally resolving these optical energy emissions to identify, based on the presence of the characteristic spectral lines, the elemental species that are present in the sample.

Time-resolved Laser-induced Spectroscopy

Conventionally used steady state or continuous-wave (CW) luminescence, Raman and laser-induced breakdown spectroscopy is a process where the excitation sources pump the sample at constant intensity over the time necessary to perform the measurement. The end result is an emission spectrum, which can serve as a fingerprint of various controlled substances, such as explosives and drugs. Nevertheless, in many cases steady-state spectroscopy is inadequate as the discriminatory power of the emission spectra is limited. For example, large molecules, such as energetic materials, are difficult to detect spectroscopically because they posses weak transitions or broad and poorly defined spectral luminescence features. Raman spectra often are not satisfactory for identification because of high ambient light background and long-lived fluorescence. In laser-induced breakdown spectroscopy, as electrons interact and recombine with ions in the early stages of plasma thermalization, energy is released over a broad spectral range, resulting in an intense continuum emission which masks characteristic lines needed for identification.

To overcome these deficiencies, the present invention uses laser-induced time-resolved spectroscopy. This technique utilizes the luminescence lifetime or decay time that is the exponential fall time for the luminescence emission employing an impulse of excitation. Decay time is a measure of the transition probability from the emitting level, which is determined by a combination of radiation and radiationless events. Fluorescence can be observed over time ranges from femtoseconds to milliseconds and provides a characteristic and unique property of each material, such that it is not possible to find two materials with exactly the same temporal and spectral characteristics. The method of the present invention involves recording the intensity in a specific time "window" at a given delay after the excitation pulse where both delay and gate width are carefully chosen based on decay of controlled substances, such as explosives and drugs, and background. This method, when combined with the energetic selectivity of a laser beam, enables the present invention to combine time-resolved spectroscopy with individual excitation. Thus, a tunable laser source is preferred to find the optimal spectral window where emission properties of the substance being detected and background are most different.

Methodology

The present invention employs a fast detection step applying laser excitation and collecting optics combined with spectral filters and time-gated signal measuring. SH, LE or RS signals are used to detect and/or identify suspected controlled substances, such as explosives or drugs, on an object, such as a suitcase, an article of clothing or any other personally handled object, or a body portion. Spectral measurements are applied by operating at least one laser beam to induce luminescence or Raman scattering in order to chemically identify the detected material and verify detection. The laser source or sources are operated with suitable parameters to ensure power density, wavelength, pulsewidth, repetition-rate and measurement time (or number of pulses) to fulfill requirements of signal to noise ratio and above threshold for detection and of signal and spectral identification. The measurements are operated in a way to be non-destructive. When appropriate, the present invention also provides enhanced identification, by applying greater power density to activate micro-detonation of molecular fragments and atomic species, and measuring the emissions therefrom using laser-induced breakdown spectroscopy. Verification of detected controlled substances includes chemical identification of microscopic traces of explosive compounds, which are in particulate form. It has been shown that even the most fastidious clean-up might leave behind one solid particle, often with mass on the order of a few micrograms, which adheres to a surface that has, directly or indirectly, come into contact with an explosive material.

According to the present invention, the spectroscopic measurements can be operated using the same basic equipment with the following light parameters:

Pulse energy: 0.1 microJoule $\leqslant$ 100 milliJoule

Wavelength: 180 nm $\leqslant$ 10 μm

Pulse width: 10 fsec–100 msec

Pulsing: From single pulse up to a repetition rate of 100 kHz.

Q-switched pulse

Unfocused or focused

Power density range: $10^{14}$–1 W/cm$^2$

These parameters have been defined experimentally. The applicant found that several explosives, such as TNT, PETN and RDX, are characterized by scattering second harmonic of 1064 nm laser line of Nd-YAG. A first detection step scans for a strong characteristic line at 532 nm in the same time as laser excitation. Similar methods are used to detect LE and RS signals. Image analyses enable the detection of microparticles characterized by SH, LE or RS as suspected or defined as explosives with some probability.

In a second verification step, the present invention chemically identifies the detected material by applying a combination of spectral measurements with different laser excitation powers (EP):

Minimal EP of time-resolved luminescence spectroscopy is used when the suspected material is TATP, RDX or RDX based explosives, such as C4 and Semtex, which have mostly characteristic luminescence properties.

Intermediate EP of time-resolved Raman spectroscopy is used when the suspected material is RDX, C4, TNT, CompB, Urea Nitrate or TATP, which have the strongest Raman signals.

High EP based on time-resolved LIBS analyses may be used to provide origin identification of the explosive materials, based on impurity contents on the levels of ppm and ppb, which are characteristic of raw materials and may give an indication of the origin of the explosives.

Additionally, the applicant has found that several explosives, such as TNT and CompB, are characterized by a scattering of the second harmonic of a laser, which is strong enough to be detected even from microscopic traces of the substance, typically as small as a microgram or less, on the background of human skin. Similarly, several explosives, such as RDX, Semtex and C4, are characterized by characteristic LE, which is strong enough to be detected even from microscopic traces of the substance, typically as small as a microgram or less, on the background of human skin. Similarly, several explosives, such as RDX, TNT, PETN, Semtex, C4, TENN, TATP and Urea Nitrate, are characterized by RS signals, which are strong enough to be detected even from microscopic traces of the substance, typically as small as a microgram, on the background of human skin.

It is well known in the art that illegal drugs, such as heroin and cocaine, also exhibit characteristic RS signals, which can be detected, even from microscopic traces, and used to identify these illegal drugs.

Reference is now made to FIG. 1A, which is a simplified pictorial illustration of a non-imagewise system for detecting explosives on objects constructed and operative in accordance with a preferred embodiment of the present invention and employing second harmonic detection. In the illustrated embodiment, a baggage screening system is shown, it being appreciated that the present invention is not limited to baggage screening applications, but rather may be employed in any other suitable object inspection environment.

In the embodiment of FIG. 1A, baggage, such as suitcases 10, is transported by a conveyor 12 past an inspection station 14 at which the suitcases 10 are inspected. In accordance with a preferred embodiment of the present invention, the inspection station 14 employs a laser 16, preferably a Nd:YAG pulsed laser emitting with a peak wavelength at 1064 nm. It is appreciated that wavelengths in the range of 400 nm to 10 microns may be employed. An output beam of laser 16 impinges on a scanning element 18, such as a mirror, which is driven in rotational motion by a motor 20 in synchronization with the pulsed output of laser 16 in response to synchronization signals provided by a computer 22.

The output beam of laser 16 is thus scanned over suitcases 10, inducing second harmonic scattering of the output beam by certain materials, including a number of explosives, should those materials be present on the scanned surfaces of the suitcases 10. The scattered second harmonic of the laser beam is detected via collecting optics 24 and a narrow band spectral filter 26 having a peak wavelength of 532 nm preferably by a gated detector 28, such as a photodiode, photomultiplier or CCD. Alternatively, the detector need not be gated, although this is not preferred.

If more than a threshold amount of scattered second harmonic illumination at wavelength 532 is received by gated detector 28 within a time window defined to be during each laser pulse, an alarm indication is provided by computer 22, typically at a display 30. This alarm indication indicates that an explosive material having certain second harmonic scattering characteristics may be present on a surface of the suitcase 10.

Reference is now made to FIG. 1B, which is a simplified pictorial illustration of an imagewise system for detecting explosives on objects constructed and operative in accordance with a preferred embodiment of the present invention and employing second harmonic detection. In the illustrated embodiment, a baggage screening system is shown, it being appreciated that the present invention is not limited to baggage screening applications, but rather may be employed in any other suitable object inspection environment.

In the embodiment of FIG. 1B, baggage, such as suitcases 40, is transported by a conveyor 42 past an inspection station 44 at which the suitcases 40 are inspected. In accordance with a preferred embodiment of the present invention, the inspection station 44 employs a laser 46, preferably a Nd:YAG pulsed laser emitting with a peak wavelength at 1064 nm. It is appreciated that wavelengths in the range of 400 nm to 10 microns may be employed. An output beam of laser 46 impinges on a scanning assembly 48, typically comprising first and second scanning elements 49, such as mirrors, which are driven in rotational motion by motors 50 in synchronization with the pulsed output of laser 46 in response to synchronization signals provided by a computer 52.

The output beam of laser 46 is thus scanned in two dimensions over suitcases 40, inducing second harmonic scattering of the output beam by certain materials, including a number of explosives, should those materials be present on the scanned surfaces of the suitcases 40. The scattered second harmonic of the laser beam is detected via imaging optics 54 and a narrow band spectral filter 56 having a peak wavelength of 532 nm preferably by a gated detector array 58, such as a CCD or CMOS array. Alternatively, the detector array need not be gated, although this is not preferred. Alternatively, the use of imaging optics may be obviated by synchronizing the location of the detection with the location of the scanned laser beam.

If more than a threshold amount of scattered second harmonic illumination at wavelength 532 nm is received by gated detector array 58 within a predetermined time window during each laser pulse, an alarm indication is provided by computer 52, typically at a display 60. The alarm indication indicates that an explosive material having certain second harmonic scattering characteristics may be present on a surface of the suitcase 40. Display 60 preferably also visually indicates the location of the detected suspect material on the suitcase 40, here indicated on display 60 at reference numeral 62 and on the suitcase 40 at reference numeral 64.

Reference is now made to FIG. 1C, which is a simplified pictorial illustration of an imagewise system for detecting explosives constructed and operative in accordance with another preferred embodiment of the present invention and employing second harmonic detection. In the illustrated embodiment, a vehicle screening system is shown, it being appreciated that the present invention is not limited to vehicle screening applications, but rather may be employed in any other suitable remote object inspection environment.

In the embodiment of FIG. 1C, an inspection assembly 70, which may be portable or stationary, employs a laser 76, preferably a Nd:YAG pulsed laser emitting with a peak wavelength at 1064 nm. It is appreciated that wavelengths in the range of 400 nm to 10 microns may be employed. An output beam of laser 76 impinges on a scanning assembly 78, typically comprising first and second scanning elements (not shown) such as mirrors, which are driven in rotational motion by motors (not shown) in synchronization with the pulsed output of laser 76 in response to synchronization signals provided by a computer 79. The scanned laser beam output of scanning assembly 78 is projected onto a vehicle or other suitable remote object, preferably by a telescope 80.

The output beam of laser 76 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 84 and a narrow band spectral filter 86 having a peak wavelength of 532 nm preferably by a gated detector array 88, such as a CCD or CMOS array. Alternatively, the detector array need not be gated, although this is not preferred.

If more than a threshold amount of scattered second harmonic illumination at wavelength 532 nm is received by gated detector array 88 within a predetermined time window during each laser pulse, an alarm indication is provided by computer 79, typically at a display 90. The alarm indication indicates that an explosive material having certain second harmonic scattering characteristics may be present on a surface of the vehicle. Display 90 preferably also visually indicates the location of the detected suspect material on the vehicle, here indicated on display 90 at reference numeral 92 and on the vehicle at reference numeral 94.

Figure 1D:
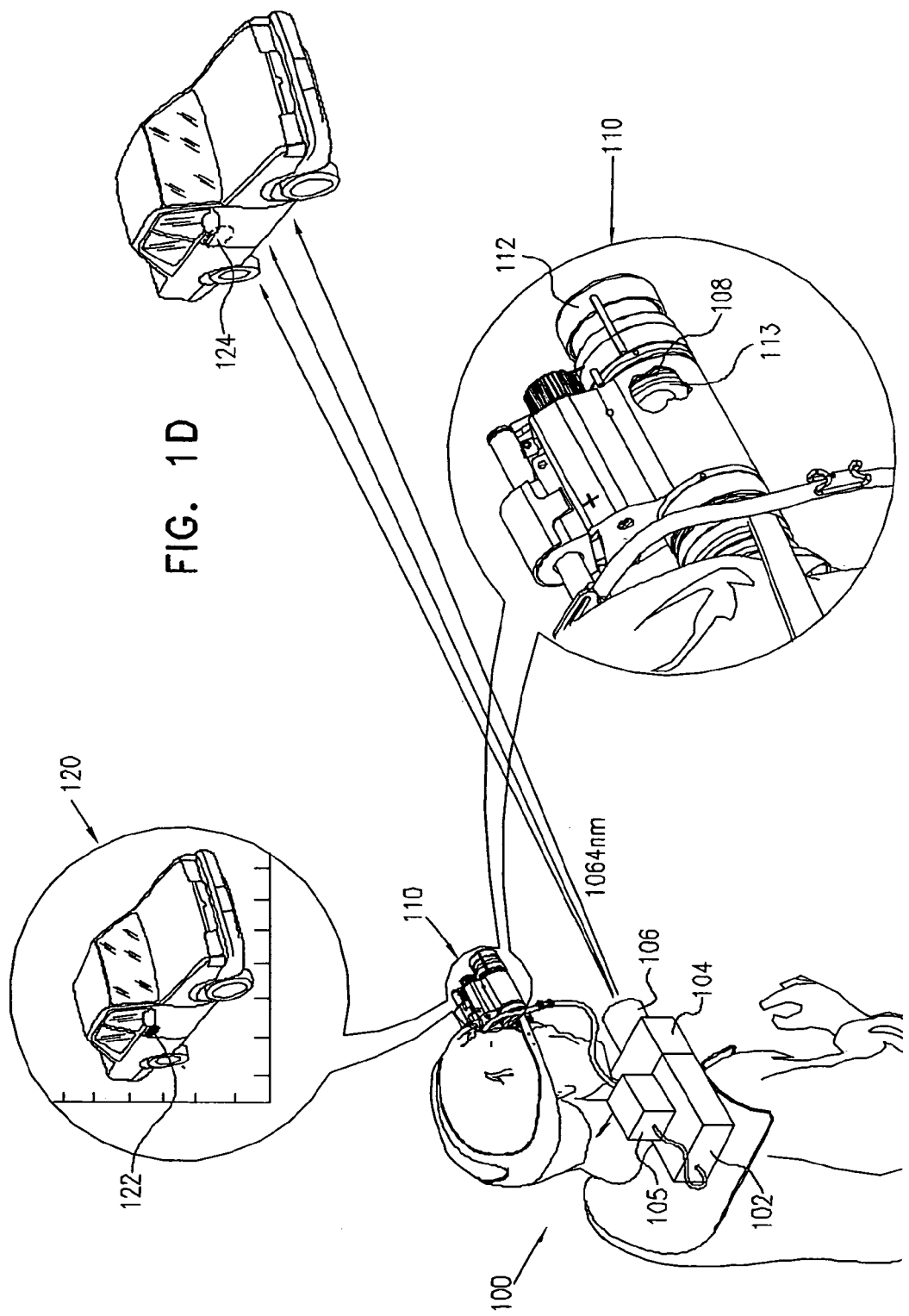
FIG. 1D is a simplified pictorial illustration of an imagewise system for detecting explosives constructed and operative in accordance with yet another preferred embodiment of the present invention and employing laser induced second harmonic detection.

Reference is now made to FIG. 1D, which is a simplified pictorial illustration of an imagewise system for detecting explosives constructed and operative in accordance with yet another preferred embodiment of the present invention and employing laser induced second harmonic detection. In the illustrated embodiment, a vehicle screening system is shown, it being appreciated that the present invention is not limited to vehicle screening applications, but rather may be employed in any other suitable remote object inspection environment.

In the embodiment of FIG. 1D, an inspection assembly 100, which is preferably portable, employs a laser 102, preferably a Nd:YAG pulsed laser emitting with a peak wavelength at 1064 nm. It is appreciated that wavelengths in the range of 400 nm to 10 microns may be employed. An output beam of laser 102 impinges on a scanning assembly 104, typically comprising first and second scanning elements (not shown) such as mirrors, which are driven in rotational motion by motors (not shown) in synchronization with the pulsed output of laser 102 in response to synchronization signals provided by a computer 105. The scanned laser beam output of scanning assembly 104 is projected onto a vehicle or other suitable remote object, preferably by a telescope 106.

The output beam of laser 102 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 108 forming part of a head-mounted viewing assembly 110, a narrow band spectral filter 112 having a peak wavelength of 532 nm and an image intensifier 113, all forming part of the head-mounted viewing assembly 110.

In accordance with a preferred embodiment of the present invention the image intensifier 113 is gated by control signals from computer 105 so as to be synchronized with the pulsed output of laser 102. Filter 112 is operative to eliminate transmission of reflected laser radiation at 1064 nm, to attenuate the ambient radiation and to fully transmit the second harmonic scattered radiation at 532 nm. Thus, an operator using the head-mounted viewing assembly 110 sees a scene such as that designated by reference numeral 120, wherein the location on the vehicle of a suspected explosive is highlighted over an ambient background image of the vehicle. The location of the suspected explosive is indicated on scene 120 at reference numeral 122 and on the vehicle at reference numeral 124.

Reference is now made to FIG. 2A, which is a simplified pictorial illustration of a non-imagewise system for detecting explosives on objects constructed and operative in accordance with a preferred embodiment of the present invention and employing time-resolved luminescence detection. In the illustrated embodiment, a baggage screening system is shown, it being appreciated that the present invention is not limited to baggage screening applications, but rather may be employed in any other suitable object inspection environment.

In the embodiment of FIG. 2A, baggage, such as suitcases 210, is transported by a conveyor 212 past an inspection station 214 at which the suitcases 210 are inspected. In accordance with a preferred embodiment of the present invention, the inspection station 214 employs a laser 216, preferably a Nd:YAG pulsed laser emitting a third or fourth harmonic having respective peak wavelengths at 355 and 266 nm. It is appreciated that wavelengths in the range of 180 nm to 10 microns may be employed. An output beam of laser 216 impinges on a scanning element 218, such as a mirror, which is driven in rotational motion by a motor 220 in synchronization with the pulsed output of laser 216 in response to synchronization signals provided by a computer 222.

The output beam of laser 216 is thus scanned over suitcases 210, inducing luminescence by certain materials, including a number of explosives, should those materials be present on the scanned surfaces of the suitcases 210. The luminescence is detected by a plurality of detector assemblies 224, each preferably including collecting optics 225, a spectral filter 226 and a gated detector 228, such as a photodiode, photomultiplier or CCD. Alternatively, the detector need not be gated, although this is not preferred.

Preferably, the spectral range of each spectral filter 226 of each detector assembly 224 differs from the spectral range of each other such filter. The following spectral ranges are preferably provided, each by a different spectral filter 226 and corresponding to the following gate intervals:

400–430 nm—10 microseconds

450–540 nm—50 nanoseconds

670–700 nm—100 microseconds.

If more than a threshold amount of luminescence is received by any one or more gated detector 228 within its time window and its spectral range, an alarm indication is provided by computer 222, typically at a display 230. This alarm indication indicates that an explosive material having certain luminescence characteristics may be present on a surface of the suitcase 210.

Figure 2B:
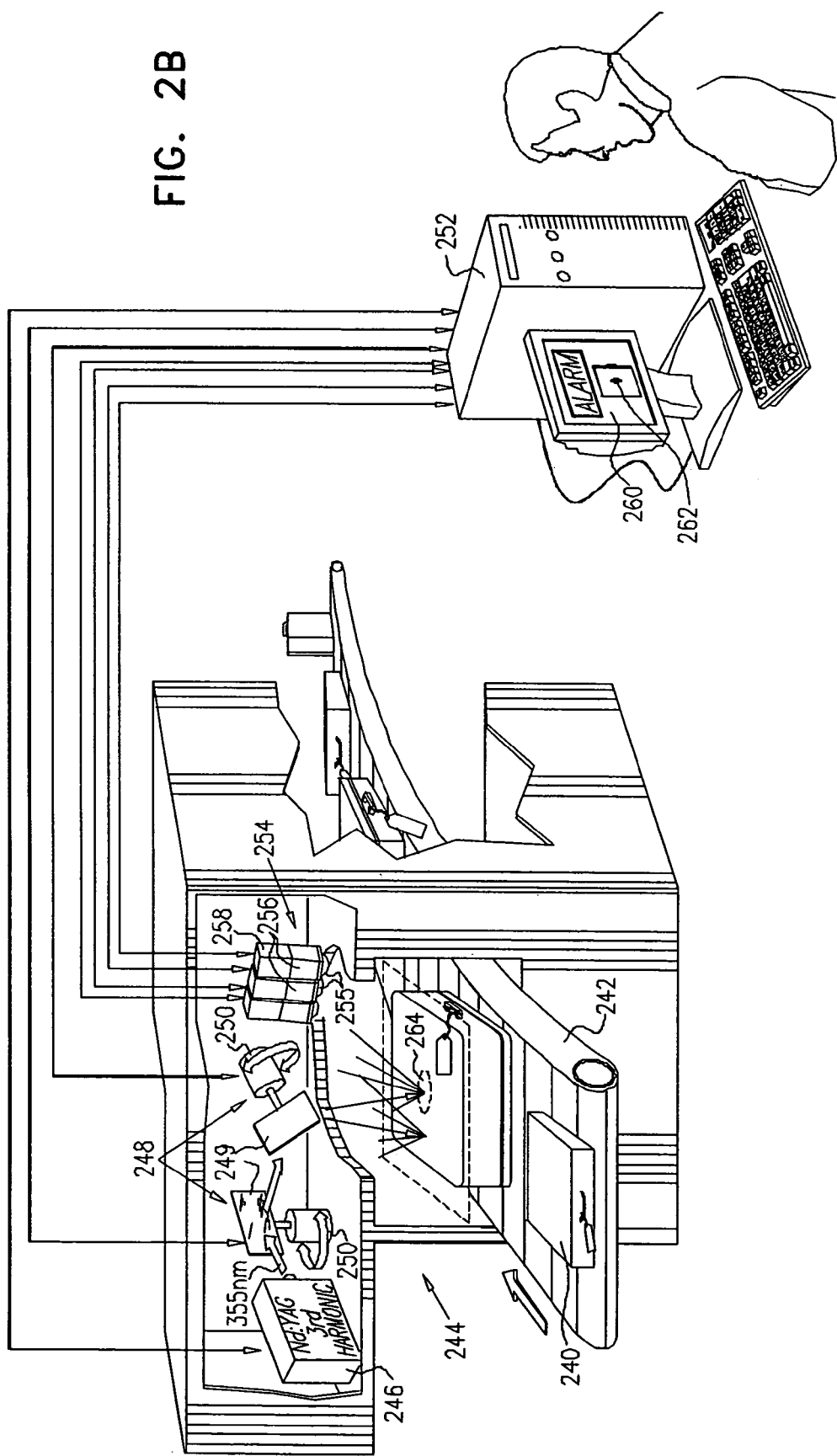
FIG. 2B is a simplified pictorial illustration of an imagewise system for detecting explosives on objects constructed and operative in accordance with a preferred embodiment of the present invention and employing laser induced time-resolved luminescence detection.

Reference is now made to FIG. 2B, which is a simplified pictorial illustration of an imagewise system for detecting explosives on objects constructed and operative in accordance with a preferred embodiment of the present invention and employing time-resolved luminescence detection. In the illustrated embodiment, a baggage screening system is shown, it being appreciated that the present invention is not limited to baggage screening applications, but rather may be employed in any other suitable object inspection environment.

In the embodiment of FIG. 2B, baggage, such as suitcases 240, is transported by a conveyor 242 past an inspection station 244 at which the suitcases 240 are inspected. In accordance with a preferred embodiment of the present invention, the inspection station 244 employs a laser 246, preferably a Nd:YAG pulsed laser emitting a third or fourth harmonic having respective peak wavelengths at 355 and 266 nm. It is appreciated that wavelengths in the range of 180 nm to 10 microns may be employed. An output beam of laser 246 impinges on a scanning assembly 248, typically comprising first and second scanning elements 249, such as mirrors, which are driven in rotational motion by motors 250 in synchronization with the pulsed output of laser 246 in response to synchronization signals provided by a computer 252.

The output beam of laser 246 is thus scanned in two dimensions over suitcases 240, inducing luminescence by certain materials, including a number of explosives, should those materials be present on the scanned surfaces of the suitcases 240. The luminescence induced by the laser beam is detected preferably by a plurality of detector assemblies 254, each preferably including imaging optics 255, a spectral filter 256 and a gated detector array 258, such as a CCD or CMOS array. Alternatively, the plurality of detector assemblies 254 may be replaced by a single broadband detector assembly, although this is not preferred. Alternatively, the detector array need not be gated, although this is not preferred.

Preferably, the spectral range of each spectral filter 256 of each detector assembly 254 differs from the spectral range of each other such filter. The following spectral ranges are preferably provided, each by a different spectral filter 256 and corresponding to the following gate intervals:

400–430 nm—10 microseconds
450–540 nm—50 nanoseconds
670–700 nm—100 microseconds.

If more than a threshold amount of luminescence is received by any one or more gated detector 258 within its time window and its spectral range, an alarm indication is provided by computer 252, typically at a display 260. This alarm indication indicates that an explosive material having certain luminescence characteristics may be present on a surface of the suitcase 240. Display 260 preferably also visually indicates the location of the detected suspect material on the suitcase 240, here indicated on display 260 at reference numeral 262 and on the suitcase 240 at reference numeral 264.

Figure 2C:
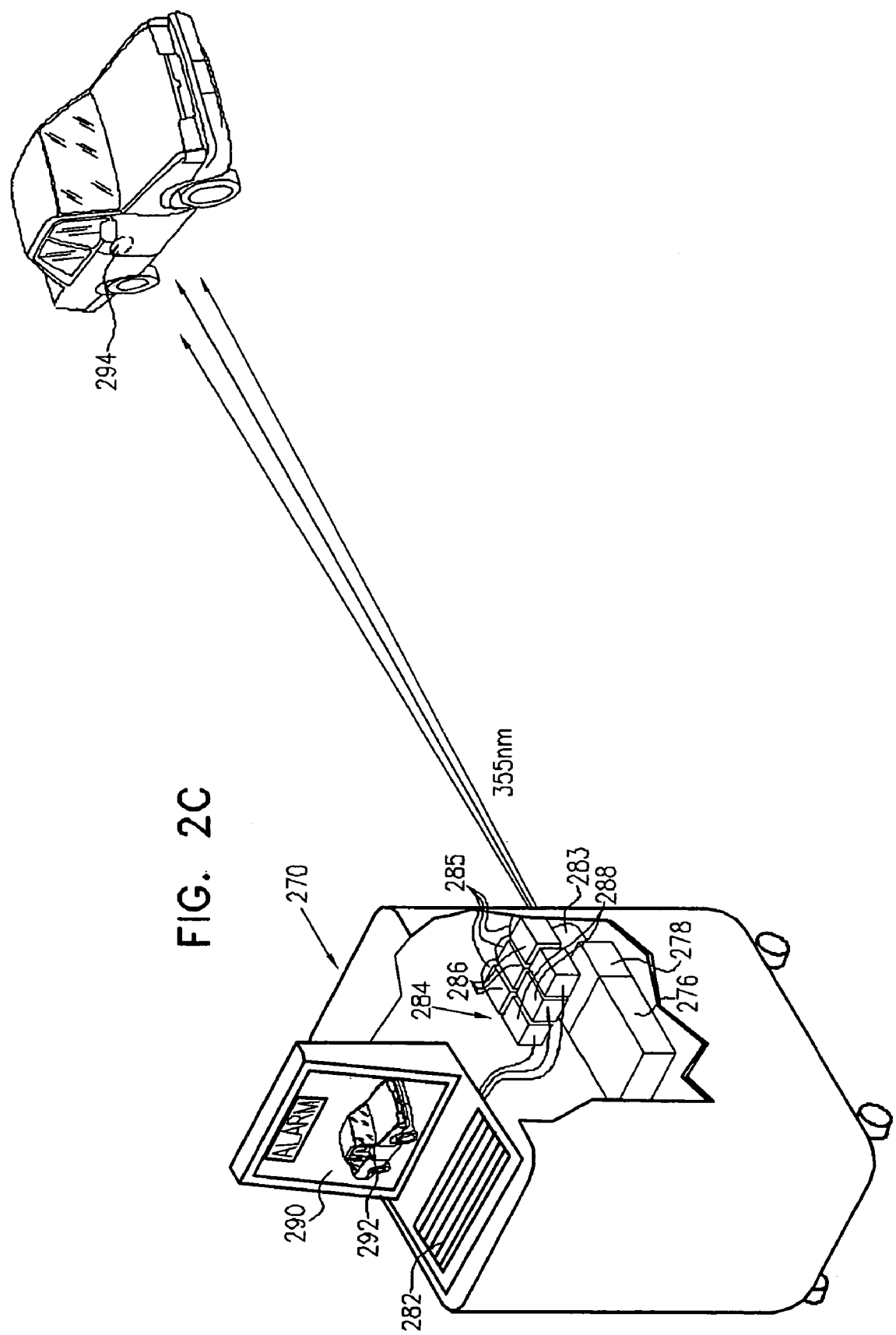
FIG. 2C is a simplified pictorial illustration of an imagewise system for detecting explosives constructed and operative in accordance with another preferred embodiment of the present invention and employing laser induced time-resolved luminescence detection.

Reference is now made to FIG. 2C, which is a simplified pictorial illustration of an imagewise system for detecting explosives constructed and operative in accordance with another preferred embodiment of the present invention and employing laser induced luminescence. In the illustrated embodiment, a vehicle screening system is shown, it being appreciated that the present invention is not limited to vehicle screening applications, but rather may be employed in any other suitable remote object inspection environment.

In the embodiment of FIG. 2C, an inspection assembly 270, which may be portable or stationary, employs a laser 276, preferably a Nd:YAG pulsed laser emitting a third or fourth harmonic having respective peak wavelengths at 355 and 266 nm. It is appreciated that wavelengths in the range of 180 nm to 10 microns may be employed. An output beam of laser 276 impinges on a scanning assembly 278, typically comprising first and second scanning elements (not shown), such as mirrors, which are driven in rotational motion by motors (not shown) in synchronization with the pulsed output of laser 276 in response to synchronization signals provided by a computer 282. The scanned laser beam output of scanning assembly 278 is projected onto a vehicle or other suitable remote object, preferably by a telescope 283.

The output beam of laser 276 is thus scanned in two dimensions over a vehicle, inducing luminescence by certain materials, including a number of explosives, should those materials be present on the scanned surfaces of the vehicle. The luminescence induced by the laser beam is detected preferably by a plurality of detector assemblies 284, each preferably including imaging optics 285, a spectral filter 286 and a gated detector array 288, such as a CCD or CMOS array. Alternatively, the plurality of detector assemblies 284 may be replaced by a single broadband detector assembly, although this is not preferred. Alternatively, the detector array need not be gated, although this is not preferred.

Preferably, the spectral range of each spectral filter 286 of each detector assembly 284 differs from the spectral range of each other such filter. The following spectral ranges are preferably provided, each by a different spectral filter 286 and corresponding to the following gate intervals:

400–430 nm—10 microseconds
450–540 nm—50 nanoseconds
670–700 nm—100 microseconds.

If more than a threshold amount of luminescence is received by any one or more gated detector 288 within its time window and its spectral range, an alarm indication is provided by computer 282, typically at a display 290. This alarm indication indicates that an explosive material having certain luminescence characteristics may be present on a surface of the vehicle. Display 290 preferably also visually indicates the location of the detected suspect material on the vehicle, here indicated on display 290 at reference numeral 292 and on the vehicle at reference numeral 294.

Reference is now made to FIG. 2D, which is a simplified pictorial illustration of an imagewise system for detecting explosives constructed and operative in accordance with yet another preferred embodiment of the present invention and employing laser induced luminescence. In the illustrated embodiment, a vehicle screening system is shown, it being appreciated that the present invention is not limited to vehicle screening applications, but rather may be employed in any other suitable remote object inspection environment.

In the embodiment of FIG. 2D, an inspection assembly 295, which is preferably portable, employs a laser 296, preferably a Nd:YAG pulsed laser emitting a third or fourth harmonic having respective peak wavelengths at 355 and 266 nm. It is appreciated that wavelengths in the range of 180 nm to 10 microns may be employed. An output beam of laser 296 impinges on a scanning assembly 298, typically comprising first and second scanning elements (not shown), such as mirrors, which are driven in rotational motion by motors (not shown) in synchronization with the pulsed output of laser 296 in response to synchronization signals provided by a computer 302. The scanned laser beam output of scanning assembly 298 is projected onto a vehicle or other suitable remote object, preferably by a telescope 303.

The output beam of laser 296 is thus scanned in two dimensions over a vehicle, inducing luminescence by certain materials, including a number of explosives, should those materials be present on the scanned surfaces of the vehicle. The luminescence induced by the laser beam is detected via imaging optics 308 forming part of a head-mounted viewing assembly 310, at least one and preferably a plurality of individually selectable and interchangeable narrow band spectral filters 312 and an image intensifier 314, all forming part of the head-mounted viewing assembly 310.

Preferably, the spectral range of each spectral filter 312 differs from the spectral range of each other such filter. The following spectral ranges are preferably provided, each by a different spectral filter 312 and corresponding to the following gate intervals:

400–430 nm—10 microseconds
450–540 nm—50 nanoseconds
670–700 nm—100 microseconds.

In accordance with a preferred embodiment of the present invention the image intensifier 314 is gated by control signals from computer 302 so as to be synchronized with the pulsed output of laser 296. Filters 312 are operative to eliminate transmission of reflected laser radiation at 355 nm and 266 nm, to attenuate the ambient radiation and to fully transmit the luminescence. Thus, an operator using the head-mounted viewing assembly 310 sees a scene such as that designated by reference numeral 316, wherein the location on the vehicle of a suspected explosive is highlighted over an ambient background image of the vehicle. The location of the suspected explosive is indicated on scene 316 at reference numeral 317 and on the vehicle at reference numeral 318.

Figure 3A:
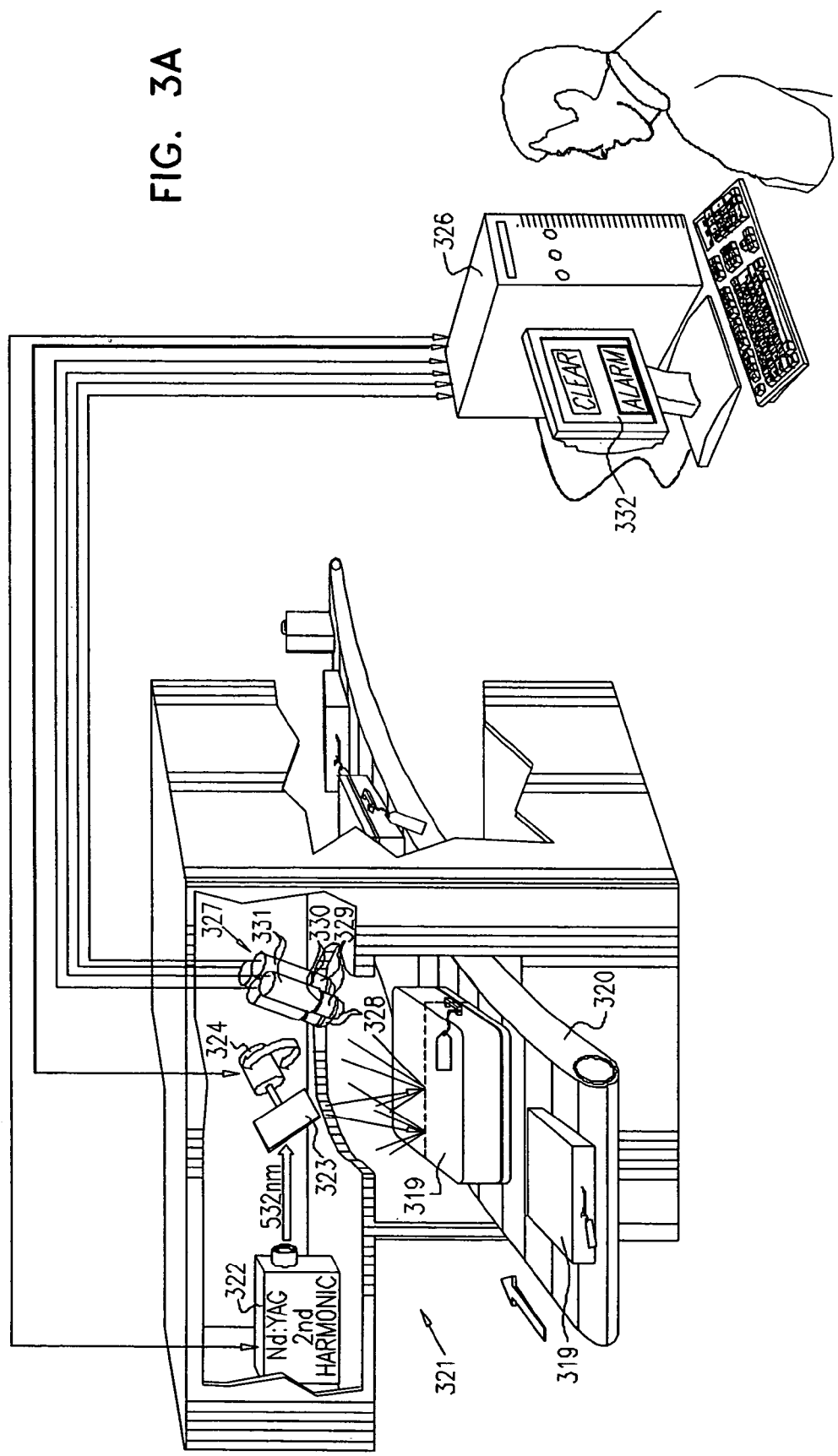
FIG. 3A is a simplified pictorial illustration of a non-imagewise system for detecting explosives on objects constructed and operative in accordance with a preferred embodiment of the present invention and employing laser induced time-resolved Raman scattering detection.

Reference is now made to FIG. 3A, which is a simplified pictorial illustration of a non-imagewise system for detecting explosives on objects constructed and operative in accordance with a preferred embodiment of the present invention and employing time-resolved Raman scattering detection. In the illustrated embodiment, a baggage screening system is shown, it being appreciated that the present invention is not limited to baggage screening applications, but rather may be employed in any other suitable object inspection environment.

In the embodiment of FIG. 3A, baggage, such as suitcases 319, is transported by a conveyor 320 past an inspection station 321 at which the suitcases 319 are inspected. In accordance with a preferred embodiment of the present invention, the inspection station 321 employs a laser 322, preferably a Nd:YAG pulsed laser emitting a second harmonic having a peak wavelength at 532 mm. It is appreciated that wavelengths in the range of 200 nm to 10 microns may be employed. An output beam of laser 322 impinges on a scanning element 323, such as a mirror, which is driven in rotational motion by a motor 324 in synchronization with the pulsed output of laser 322 in response to synchronization signals provided by a computer 326.

The output beam of laser 322 is thus scanned over suitcases 319, inducing Raman scattering by certain materials, including explosives, should those materials be present on the scanned surfaces of the suitcases 319. The Raman scattering is detected by a plurality of detector assemblies 327, each preferably including collecting optics 328, a spectral filter 329, a notch filter 330 and a gated detector 331, such as a photodiode, photomultiplier or CCD. Alternatively, the plurality of detector assemblies 327 may be replaced by a single broadband detector assembly, although this is not preferred. Alternatively, the detector need not be gated, although this is not preferred.

Preferably, the spectral range of each spectral filter 329 of each detector assembly 327 differs from the spectral range of each other such filter. The following Raman shifts relative to the laser excitation wavelength are preferably provided, each by a different spectral filter 329:

880–885 cm (−1)
1360–1365 cm (−1)
1270–1290 cm (−1)
2980–3000 cm (−1).

If more than a threshold amount of Raman scattering is received by any one or more gated detector 331 during the time interval of the laser excitation pulse and its spectral range, an alarm indication is provided by computer 326, typically at a display 332. This alarm indication indicates that an explosive material having certain Raman scattering characteristics may be present on a surface of the suitcase 319.

Figure 3B:
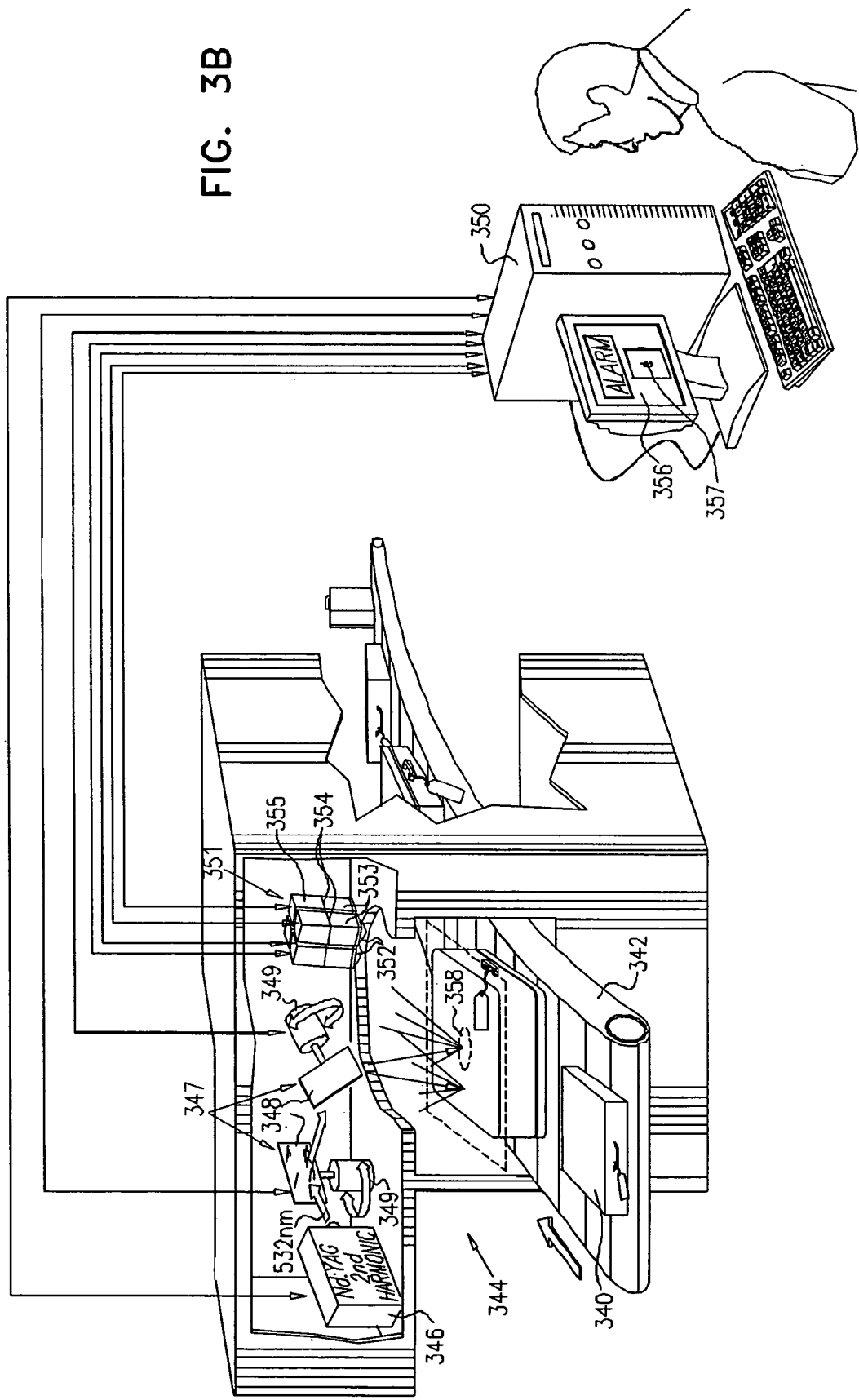
FIG. 3B is a simplified pictorial illustration of an imagewise system for detecting explosives on objects constructed and operative in accordance with a preferred embodiment of the present invention and employing laser induced time-resolved Raman scattering detection.

Reference is now made to FIG. 3B, which is a simplified pictorial illustration of an imagewise system for detecting explosives on objects constructed and operative in accordance with a preferred embodiment of the present invention and employing time-resolved Raman scattering detection. In the illustrated embodiment, a baggage screening system is shown, it being appreciated that the present invention is not limited to baggage screening applications, but rather may be employed in any other suitable object inspection environment.

In the embodiment of FIG. 3B, baggage, such as suitcases 340, is transported by a conveyor 342 past an inspection station 344 at which the suitcases 340 are inspected. In accordance with a preferred embodiment of the present invention, the inspection station 344 employs a laser 346, preferably a Nd:YAG pulsed laser emitting a second harmonic having a peak wavelength at 532 nm. It is appreciated that wavelengths in the range of 200 nm to 10 microns may be employed. An output beam of laser 346 impinges on a scanning assembly 347, typically comprising first and second scanning elements 348, such as mirrors, which are driven in rotational motion by motors 349 in synchronization with the pulsed output of laser 346 in response to synchronization signals provided by a computer 350.

The output beam of laser 346 is thus scanned over suitcases 340, inducing Raman scattering by certain materials, including explosives, should those materials be present on the scanned surfaces of the suitcases 340. The Raman scattering is detected by a plurality of detector assemblies 351, each preferably including imaging optics 352, a spectral filter 353, a notch filter 354 and a gated detector array 355, such as a CCD or CMOS array. Alternatively, the plurality of detector assemblies 351 may be replaced by a single broadband detector assembly, although this is not preferred. Alternatively, the detector array need not be gated, although this is not preferred.

Preferably, the spectral range of each spectral filter 353 of each detector assembly 351 differs from the spectral range of each other such filter. The following Raman shifts relative to the laser excitation wavelength are preferably provided, each by a different spectral filter 353:

880–885 cm (−1)
1360–1365 cm (−1)
1270–1290 cm (−1)
2980–3000 cm (−1).

If more than a threshold amount of Raman scattering is received by any one or more gated detector 355 during the time interval of the laser excitation pulse and its spectral range, an alarm indication is provided by computer 350, typically at a display 356. This alarm indication indicates that an explosive material having certain Raman scattering characteristics may be present on a surface of the suitcase 340. Display 356 preferably also visually indicates the location of the detected suspect material on the suitcase 340, here indicated on display 356 at reference numeral 357 and on the suitcase 340 at reference numeral 358.

Figure 3C:
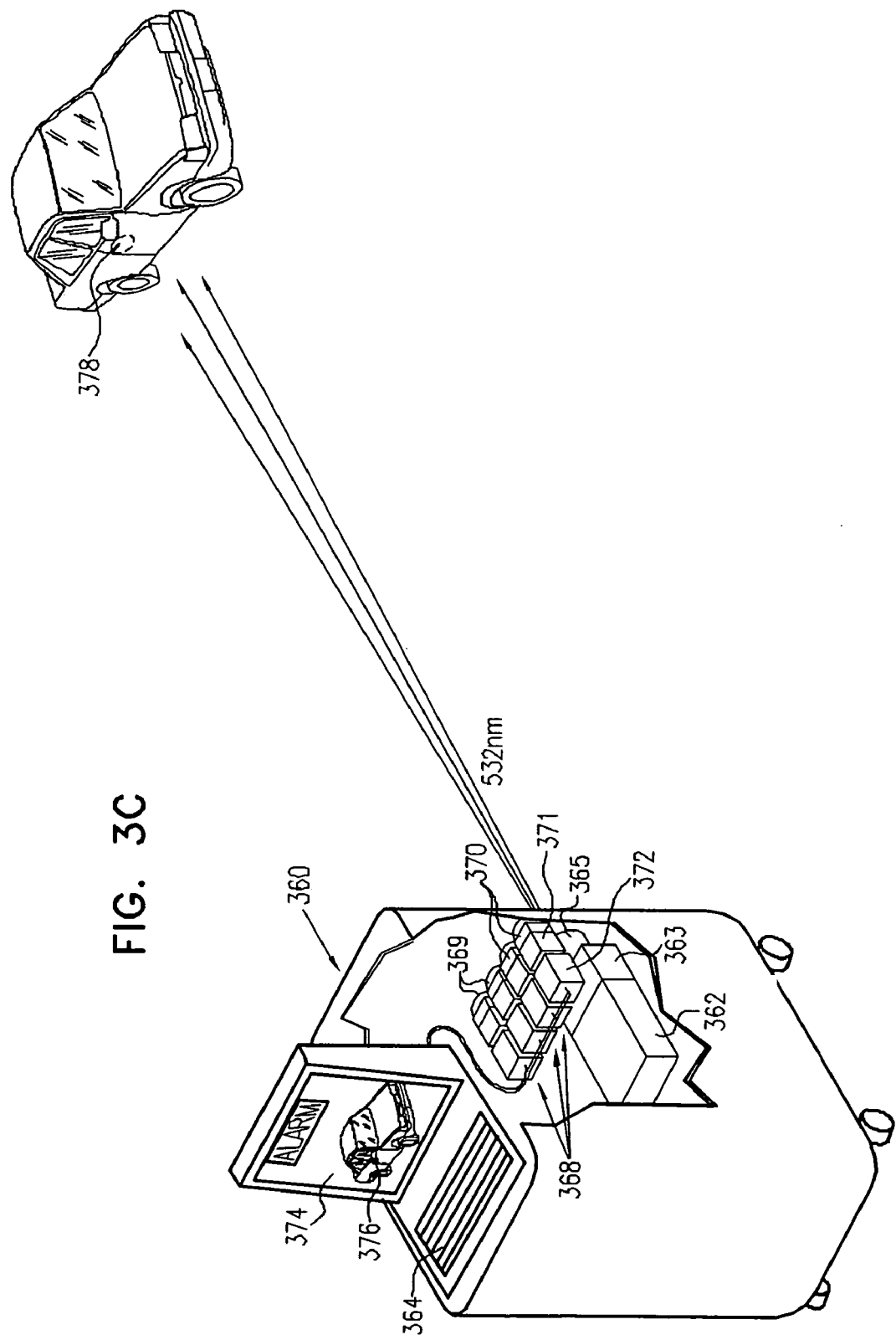
FIG. 3C is a simplified pictorial illustration of an imagewise system for detecting explosives constructed and operative in accordance with another preferred embodiment of the present invention and employing laser induced time-resolved Raman scattering detection.

Reference is now made to FIG. 3C, which is a simplified pictorial illustration of an imagewise system for detecting explosives constructed and operative in accordance with another preferred embodiment of the present invention and employing laser induced Raman scattering. In the illustrated embodiment, a vehicle screening system is shown, it being appreciated that the present invention is not limited to vehicle screening applications, but rather may be employed in any other suitable remote object inspection environment.

In the embodiment of FIG. 3C, an inspection assembly 360, which may be portable or stationary, employs a laser 362, preferably a Nd:YAG pulsed laser emitting a second harmonic having a peak wavelength at 532 nm. It is appreciated that wavelengths in the range of 200 nm to 10 microns may be employed. An output beam of laser 362 impinges on a scanning assembly 363, typically comprising first and second scanning elements (not shown), such as mirrors, which are driven in rotational motion by motors (not shown) in synchronization with the pulsed output of laser 362 in response to synchronization signals provided by a computer 364. The scanned laser beam output of scanning assembly 363 is projected onto a vehicle or other suitable remote object, preferably by a telescope 365.

The output beam of laser 362 is thus scanned in two dimensions over a vehicle, inducing Raman scattering by certain materials, including explosives, should those materials be present on the scanned surfaces of the vehicle. The Raman scattering is detected by a plurality of detector assemblies 368, each preferably including imaging optics 369, a spectral filter 370, a notch filter 371 and a gated detector array 372, such as a CCD or CMOS array. Alternatively, the plurality of detector assemblies 368 may be replaced by a single broadband detector assembly, although this is not preferred. Alternatively, the detector array need not be gated, although this is not preferred.

Preferably, the spectral range of each spectral filter 370 of each detector assembly 368 differs from the spectral range of each other such filter. The following Raman shifts relative to the laser excitation wavelength are preferably provided, each by a different spectral filter 370:

880–885 cm (−1)
  1360–1365 cm (−1)
  1270–1290 cm (−1)
  2980–3000 cm (−1).

If more than a threshold amount of Raman scattering is received by any one or more gated detector 372 during the time interval of the laser excitation pulse and its spectral range, an alarm indication is provided by computer 364, typically at a display 374. This alarm indication indicates that an explosive material having certain Raman scattering characteristics may be present on a surface of the vehicle. Display 374 preferably also visually indicates the location of the detected suspect material on the vehicle, here indicated on display 374 at reference numeral 376 and on the vehicle at reference numeral 378.

Figure 3D:
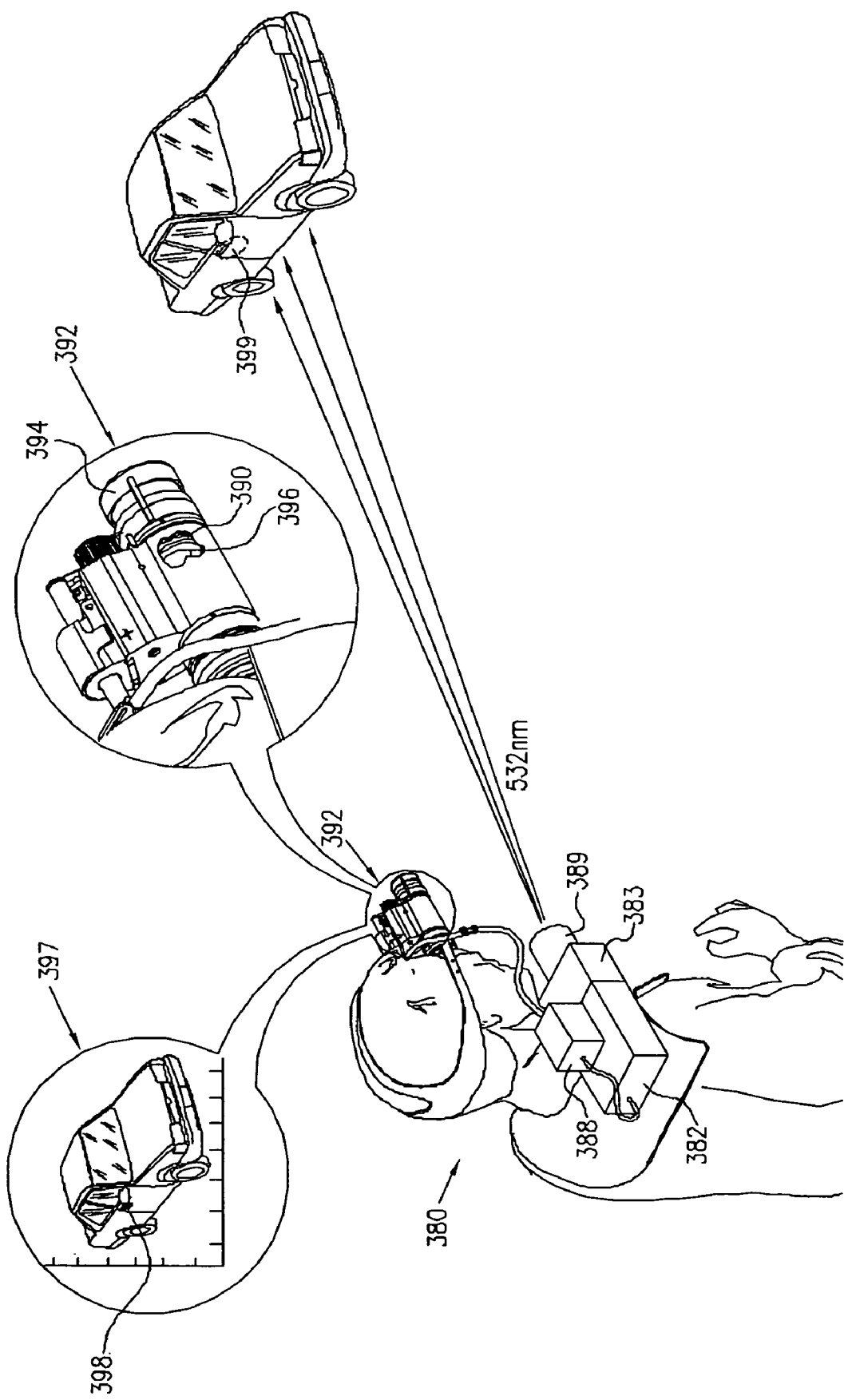
FIG. 3D is a simplified pictorial illustration of an imagewise system for detecting explosives constructed and operative in accordance with yet another preferred embodiment of the present invention and employing laser induced time-resolved Raman scattering detection.

Reference is now made to FIG. 3D, which is a simplified pictorial illustration of an imagewise system for detecting explosives constructed and operative in accordance with yet another preferred embodiment of the present invention and employing laser induced Raman scattering. In the illustrated embodiment, a vehicle screening system is shown, it being appreciated that the present invention is not limited to vehicle screening applications, but rather may be employed in any other suitable remote object inspection environment.

In the embodiment of FIG. 3D, an inspection assembly 380, which is preferably portable, employs a laser 382, preferably a Nd:YAG pulsed laser emitting a second harmonic having a peak wavelength at 532 nm. It is appreciated that wavelengths in the range of 200 nm to 10 microns may be employed. An output beam of laser 382 impinges on a scanning assembly 383, typically comprising first and second scanning elements (not shown), such as mirrors, which are driven in rotational motion by motors (not shown) in synchronization with the pulsed output of laser 382 in response to synchronization signals provided by a computer 388. The scanned laser beam output of scanning assembly 383 is projected onto a vehicle or other suitable remote object, preferably by a telescope 389.

The output beam of laser 382 is thus scanned in two dimensions over a vehicle, inducing Raman scattering by certain materials, including explosives, should those materials be present on the scanned surfaces of the vehicle. The Raman scattering induced by the laser beam is detected via imaging optics 390 forming part of a head-mounted viewing assembly 392, at least one and preferably a plurality of narrow band spectral filters 394 and an image intensifier 396, all forming part of the head-mounted viewing assembly 392.

Preferably, the spectral range of each spectral filter 394 differs from the spectral range of each other such filter. The following Raman shifts relative to the laser excitation wavelength are preferably provided, each by a different spectral filter 370:

880–885 cm (−1)
  1360–1365 cm (−1)
  1270–1290 cm (−1)
  2980–3000 cm (−1).

In accordance with a preferred embodiment of the present invention the image intensifier 396 is gated by control signals from computer 388 to operate during the time interval of the laser excitation pulse. Thus, an operator using the head-mounted viewing assembly 392 sees a scene such as that designated by reference numeral 397, wherein the location on the vehicle of a suspected explosive is highlighted over an ambient background image of the vehicle. The location of the suspected explosive is indicated on scene 397 at reference numeral 398 and on the vehicle at reference numeral 399.

Figure 4A:
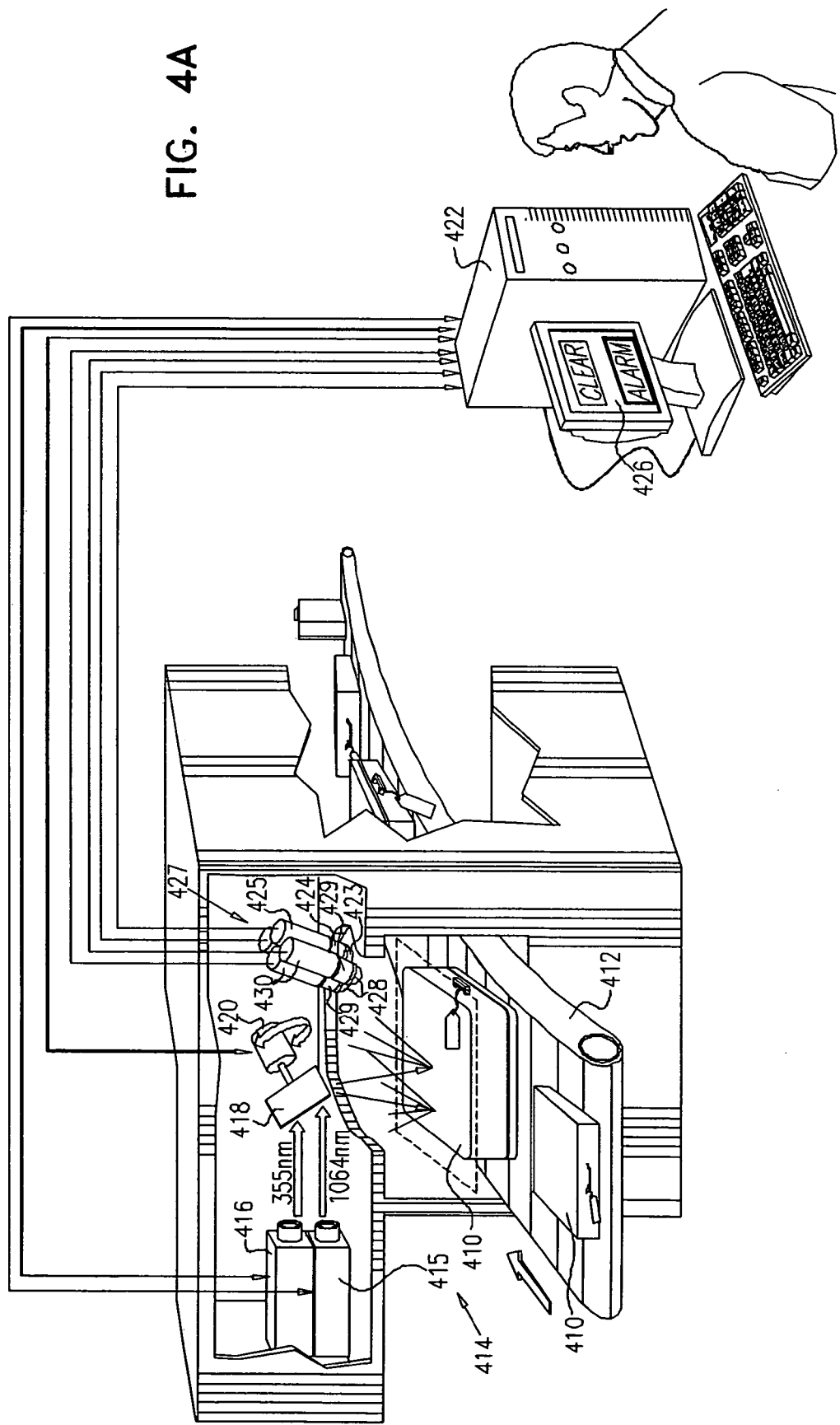
FIG. 4A is a simplified pictorial illustration of a non-imagewise system for detecting explosives on objects constructed and operative in accordance with a preferred embodiment of the present invention and employing laser induced second harmonic and time-resolved luminescence detection.

Reference is now made to FIG. 4A, which is a simplified pictorial illustration of a non-imagewise system for detecting explosives on objects constructed and operative in accordance with a preferred embodiment of the present invention and employing second harmonic and time-resolved luminescence detection. In the illustrated embodiment, a baggage screening system is shown, it being appreciated that the present invention is not limited to baggage screening applications, but rather may be employed in any other suitable object inspection environment.

In the embodiment of FIG. 4A, baggage, such as suitcases 410, is transported by a conveyor 412 past an inspection station 414 at which the suitcases 410 are inspected. In accordance with a preferred embodiment of the present invention, the inspection station 414 employs a first laser 415, preferably a Nd:YAG pulsed laser emitting with a peak wavelength at 1064 nm. It is appreciated that wavelengths in the range of 400 nm to 10 microns may be employed. The inspection station 414 preferably also employs a second laser 416, preferably a Nd:YAG pulsed laser emitting a third or fourth harmonic having respective peak wavelengths at 355 and 266 nm. It is appreciated that wavelengths in the range of 180 nm to 10 microns may be employed by this laser. Alternatively, a single laser may be used rather than two lasers.

Output beams of lasers 415 and 416 impinge on a scanning element 418, such as a mirror, which is driven in rotational motion by a motor 420 in synchronization with the pulsed outputs of lasers 415 and 416 in response to synchronization signals provided by a computer 422.

The output beam of laser 415 is thus scanned over suitcases 410, inducing second harmonic scattering of the output beam by certain materials, including a number of explosives, should those materials be present on the scanned surfaces of the suitcases 410. The scattered second harmonic of the laser beam from laser 415 is detected via collecting optics 423 and a narrow band spectral filter 424 having a peak wavelength of 532 nm preferably by a gated detector 425, such as a photodiode, photomultiplier or CCD. Alternatively, the detector need not be gated, although this is not preferred.

If more than a threshold amount of scattered second harmonic illumination at wavelength 532 is received by gated detector 425 within a time window defined to be during each laser pulse, an alarm indication is provided by computer 422, typically at a display 426. This alarm indication indicates that an explosive material having certain second harmonic scattering characteristics may be present on a surface of the suitcase 410.

The output beam of laser 416 is also scanned over suitcases 410, inducing luminescence by certain materials, including a number of explosives, should those materials be present on the scanned surfaces of the suitcases 410. The luminescence is detected by a plurality of detector assemblies 427, each preferably including collecting optics 428, a spectral filter 429 and a gated detector 430, such as a photodiode, photomultiplier or CCD. Alternatively, the plurality of detector assemblies 427 may be replaced by a single broadband detector assembly, although this is not preferred. Alternatively, the detector need not be gated, although this is not preferred.

Preferably, the spectral range of each spectral filter 429 of each detector assembly 427 differs from the spectral range of each other such filter. The following spectral ranges are preferably provided, each by a different spectral filter 429 and corresponding to the following gate intervals:

400–430 nm—10 microseconds
450–540 nm—50 nanoseconds
670–700 nm—100 microseconds.

If more than a threshold amount of luminescence is received by any one or more gated detector 430 within its time window and its spectral range, an alarm indication is provided by computer 422, typically at display 426. This alarm indication indicates that an explosive material having certain luminescence characteristics may be present on a surface of the suitcase 410.

Figure 4B:
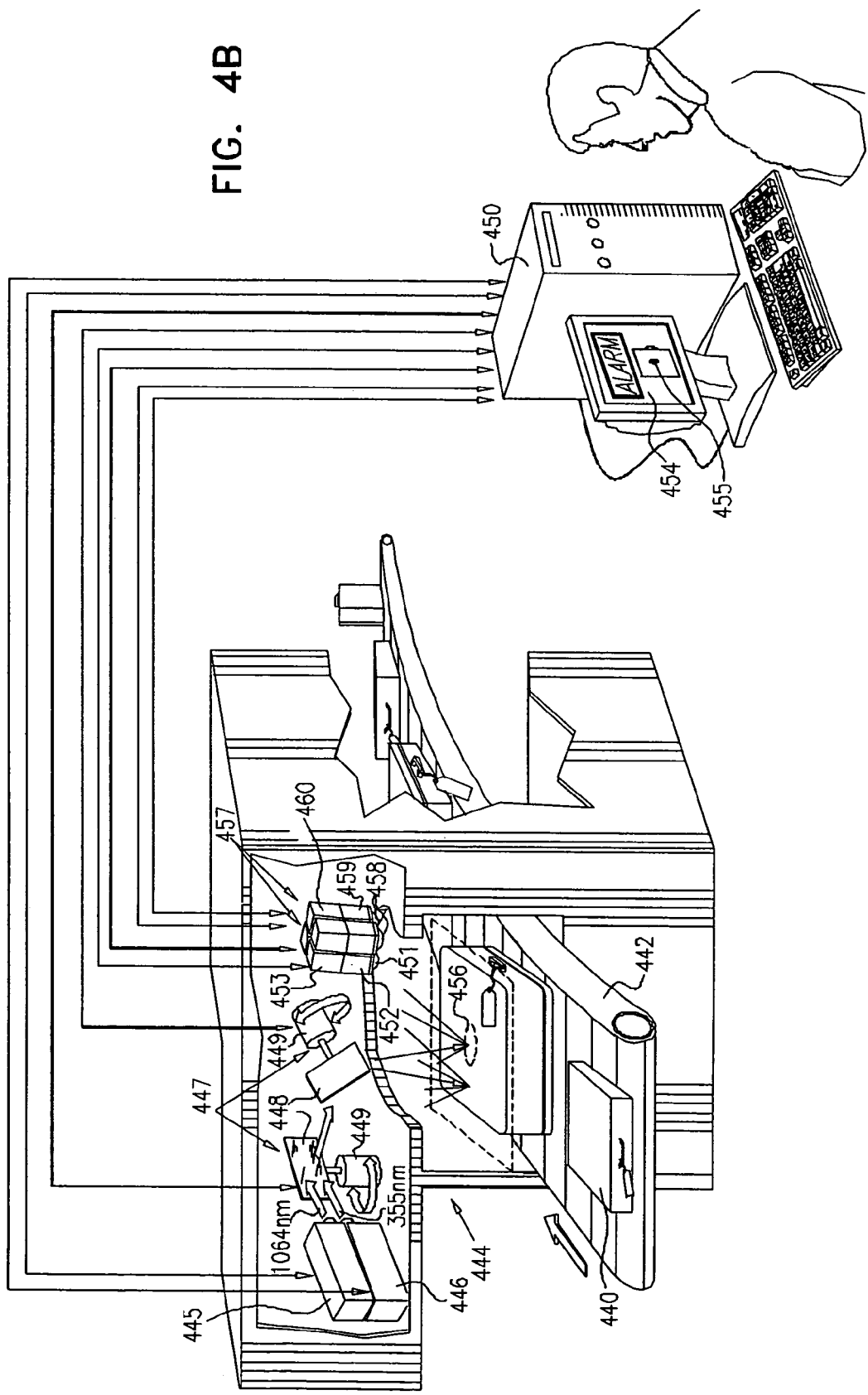
FIG. 4B is a simplified pictorial illustration of an imagewise system for detecting explosives on objects constructed and operative in accordance with a preferred embodiment of the present invention and employing laser induced second harmonic and time-resolved luminescence detection.

Reference is now made to FIG. 4B, which is a simplified pictorial illustration of an imagewise system for detecting explosives on objects constructed and operative in accordance with a preferred embodiment of the present invention and employing second harmonic detection and time-resolved luminescence. In the illustrated embodiment, a baggage screening system is shown, it being appreciated that the present invention is not limited to baggage screening applications, but rather may be employed in any other suitable object inspection environment.

In the embodiment of FIG. 4B, baggage, such as suitcases 440, is transported by a conveyor 442 past an inspection station 444 at which the suitcases 440 are inspected. In accordance with a preferred embodiment of the present invention, the inspection station 444 employs a first laser 445, preferably a Nd:YAG pulsed laser emitting with a peak wavelength at 1064 nm. It is appreciated that wavelengths in the range of 400 nm to 10 microns may be employed. The inspection station 444 preferably also employs a second laser 446, preferably a Nd:YAG pulsed laser emitting a third or fourth harmonic having respective peak wavelengths at 355 and 266 nm. It is appreciated that wavelengths in the range of 180 nm to 10 microns may be employed. Alternatively, a single laser may be used rather than two lasers.

The output beams of lasers 445 and 446 impinge on a scanning assembly 447, typically comprising first and second scanning elements 448, such as mirrors, which are driven in rotational motion by motors 449 in synchronization with the pulsed outputs of lasers 445 and 446 in response to synchronization signals provided by a computer 450.

The output beam of laser 445 is thus scanned in two dimensions over suitcases 440, inducing second harmonic scattering of the output beam by certain materials, including a number of explosives, should those materials be present on the scanned surfaces of the suitcases 440. The scattered second harmonic of the laser beam is detected via imaging optics 451 and a narrow band spectral filter 452 having a peak wavelength of 532 nm preferably by a gated detector array 453, such as a CCD or CMOS array. Alternatively, the detector array need not be gated, although this is not preferred.

If more than a threshold amount of scattered second harmonic illumination at wavelength 532 nm is received by gated detector array 453 within a predetermined time window during each laser pulse, an alarm indication is provided by computer 450, typically at a display 454. The alarm indication indicates that an explosive material having certain second harmonic scattering characteristics may be present on a surface of the suitcase 440. Display 454 preferably also visually indicates on location of the detected suspect material on the suitcase 440, here indicated on display 454 at reference numeral 455 and on the suitcase 440 at reference numeral 456.

The output beam of second laser 446 is also scanned in two dimensions over suitcases 440, inducing luminescence by certain materials, including a number of explosives, should those materials be present on the scanned surfaces of the suitcases 440. The luminescence induced by the laser beam is detected preferably by a plurality of detector assemblies 457, each preferably including imaging optics 458, a spectral filter 459 and a gated detector array 460, such as a CCD or CMOS array. Alternatively, the plurality of detector assemblies 457 may be replaced by a single broadband detector assembly, although this is not preferred. Alternatively, the detector array need not be gated, although this is not preferred.

Preferably, the spectral range of each spectral filter 459 of each detector assembly 457 differs from the spectral range of each other such filter. The following spectral ranges are preferably provided, each by a different spectral filter 459 and cnorresponding to the following gate intervals:

400–430 nm—10 microseconds
450–540 nm—50 nanoseconds
670–700 nm—100 microseconds.

If more than a threshold amount of luminescence is received by any one or more gated detector in gated detector array 460 within its time window and its spectral range, an alarm indication is provided by computer 450, typically at a display 454. This alarm indication indicates that an explosive material having certain luminescence characteristics may be present on a surface of the suitcase 440. Preferably computer 450 is operative to analyze and indicate detection of suspect materials on the suitcase 440 produced in response to excitation by the first and second lasers 445 and 446 and the resulting second harmonic scattering and luminescence detection resulting therefrom. Display 454 preferably also visually indicates, at location 455 on the display 454, the location 456 on the suitcase 440 of the detected suspect material.

Preferably computer 450 and display 454 are operative to superimpose and indicate the spatial relationship between the locations of the detected suspect materials on the suitcase 440 produced in response to excitation by the first and second lasers 445 and 446 and the second harmonic scattering and luminescence detection resulting therefrom.

Figure 4C:
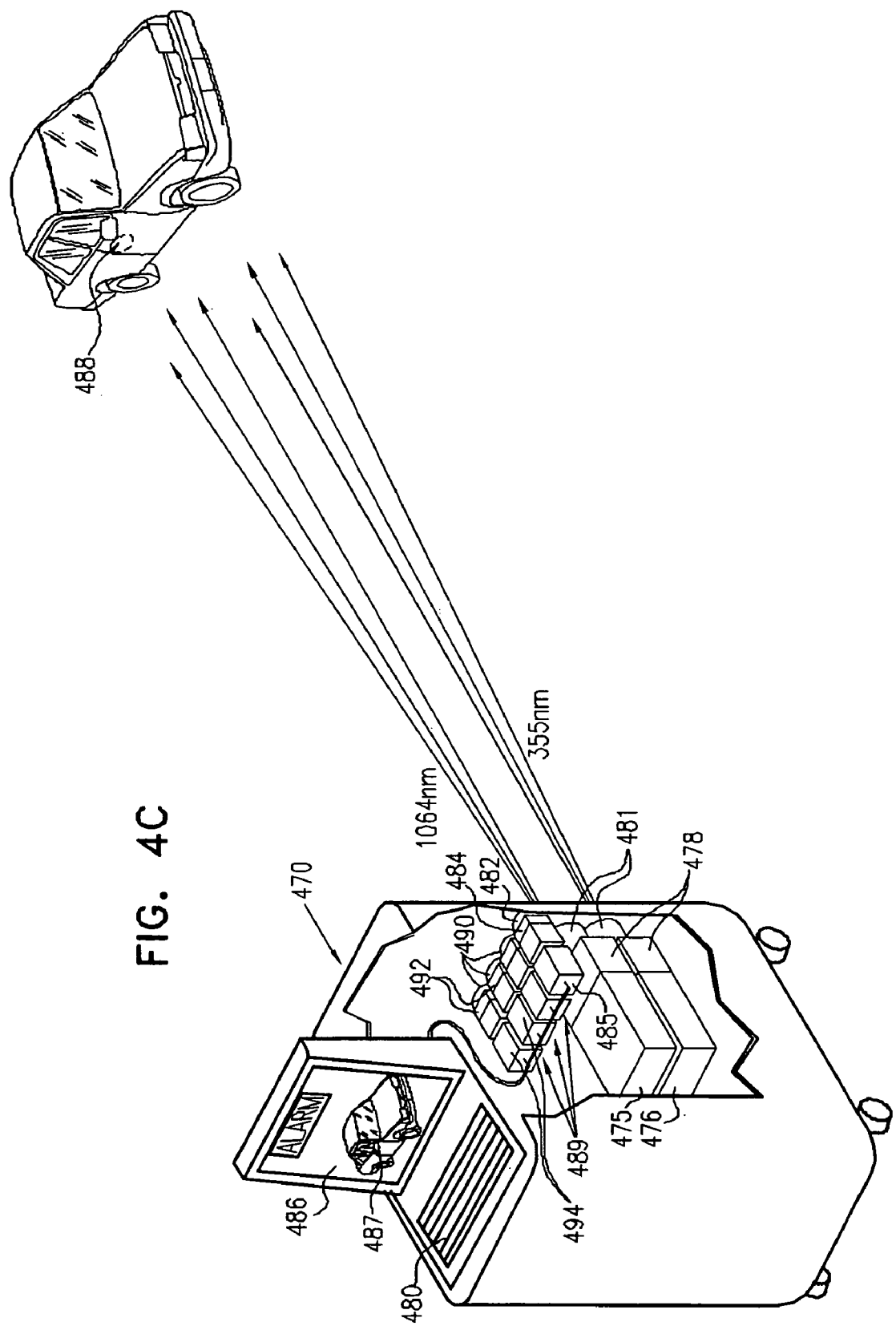
FIG. 4C is a simplified pictorial illustration of an imagewise system for detecting explosives constructed and operative in accordance with another preferred embodiment of the present invention and employing laser induced second harmonic and time-resolved luminescence detection.

Reference is now made to FIG. 4C, which is a simplified pictorial illustration of an imagewise system for detecting explosives constructed and operative in accordance with another preferred embodiment of the present invention and employing second harmonic detection and time-resolved luminescence. In the illustrated embodiment, a vehicle screening system is shown, it being appreciated that the present invention is not limited to vehicle screening applications, but rather may be employed in any other suitable remote object inspection environment.

In the embodiment of FIG. 4C, an inspection assembly 470, which may be portable or stationary, employs a first laser 475, preferably a Nd:YAG pulsed laser emitting with a peak wavelength at 1064 nm. It is appreciated that wavelengths in the range of 400 nm to 10 microns may be employed. Inspection assembly 470 preferably also employs a second laser 476, preferably a Nd:YAG pulsed laser emitting a third or fourth harmonic having respective peak wavelengths at 355 and 266 nm. It is appreciated that wavelengths in the range of 180 nm to 10 microns may be employed. Alternatively, a single laser may be used rather than two lasers.

Output beams of lasers 475 and 476 impinge on scanning assemblies 478, typically comprising first and second scanning elements (not shown) such as mirrors, which are driven in rotational motion by motors (not shown) in synchronization with the pulsed outputs of lasers 475 and 476 in response to synchronization signals provided by a computer 480. The scanned laser beam outputs of scanning assemblies 478 are projected onto a vehicle or other suitable remote object, preferably by a pair of telescopes 481.

The output beam of laser 475 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 482 and a narrow band spectral filter 484 having a peak wavelength of 532 nm, preferably by a gated detector array 485, such as a CCD or CMOS array. Alternatively, the detector array need not be gated, although this is not preferred.

If more than a threshold amount of scattered second harmonic illumination at wavelength 532 nm is received by gated detector array 485 within a predetermined time window during each laser pulse, an alarm indication is provided by computer 480, typically at a display 486. The alarm indication indicates that an explosive material having certain second harmonic scattering characteristics may be present on a surface of the vehicle. Display 486 preferably also visually indicates the location of the detected suspect material on the vehicle, here indicated on display 486 at reference numeral 487 and on the vehicle at reference numeral 488.

The output beam of second laser 476 is thus also scanned in two dimensions over the vehicle, inducing luminescence by certain materials, including a number of explosives, should those materials be present on the scanned surfaces of the vehicle. The luminescence induced by the laser beam is detected preferably by a plurality of detector assemblies 489, each preferably including imaging optics 490, a spectral filter 492 and a gated detector array 494, such as a CCD or CMOS array. Alternatively, the plurality of detector assemblies 489 may be replaced by a single broadband detector assembly, although this is not preferred. Alternatively, the detector array need not be gated, although this is not preferred.

Preferably, the spectral range of each spectral filter 492 of each detector assembly 489 differs from the spectral range of each other such filter. The following spectral ranges are preferably provided, each by a different spectral filter 492 and corresponding to the following gate intervals:

400–430 nm—10 microseconds
450–540 nm—50 nanoseconds
670–700 nm—100 microseconds.

If more than a threshold amount of luminescence is received by any one or more gated detector in array 494 within its time window and its spectral range, an alarm indication is provided by computer 480, typically at display 486. This alarm indication indicates that an explosive material having certain luminescence characteristics may be present on a surface of the vehicle. Preferably computer 480 is operative to analyze and indicate detection of suspect materials on the vehicle produced in response to excitation by the first and second lasers 475 and 476 and the resulting second harmonic scattering and luminescence detection resulting therefrom. Display 486 preferably also visually indicates, at location 487 on the display 486, the location 488 on the vehicle of the detected suspect material.

Preferably computer 480 and display 486 are operative to superimpose and indicate the spatial relationship between the locations of the detected suspect materials on the vehicle produced in response to excitation by the first and second lasers 475 and 476 and the second harmonic scattering and luminescence detection resulting therefrom.

Figure 5A:
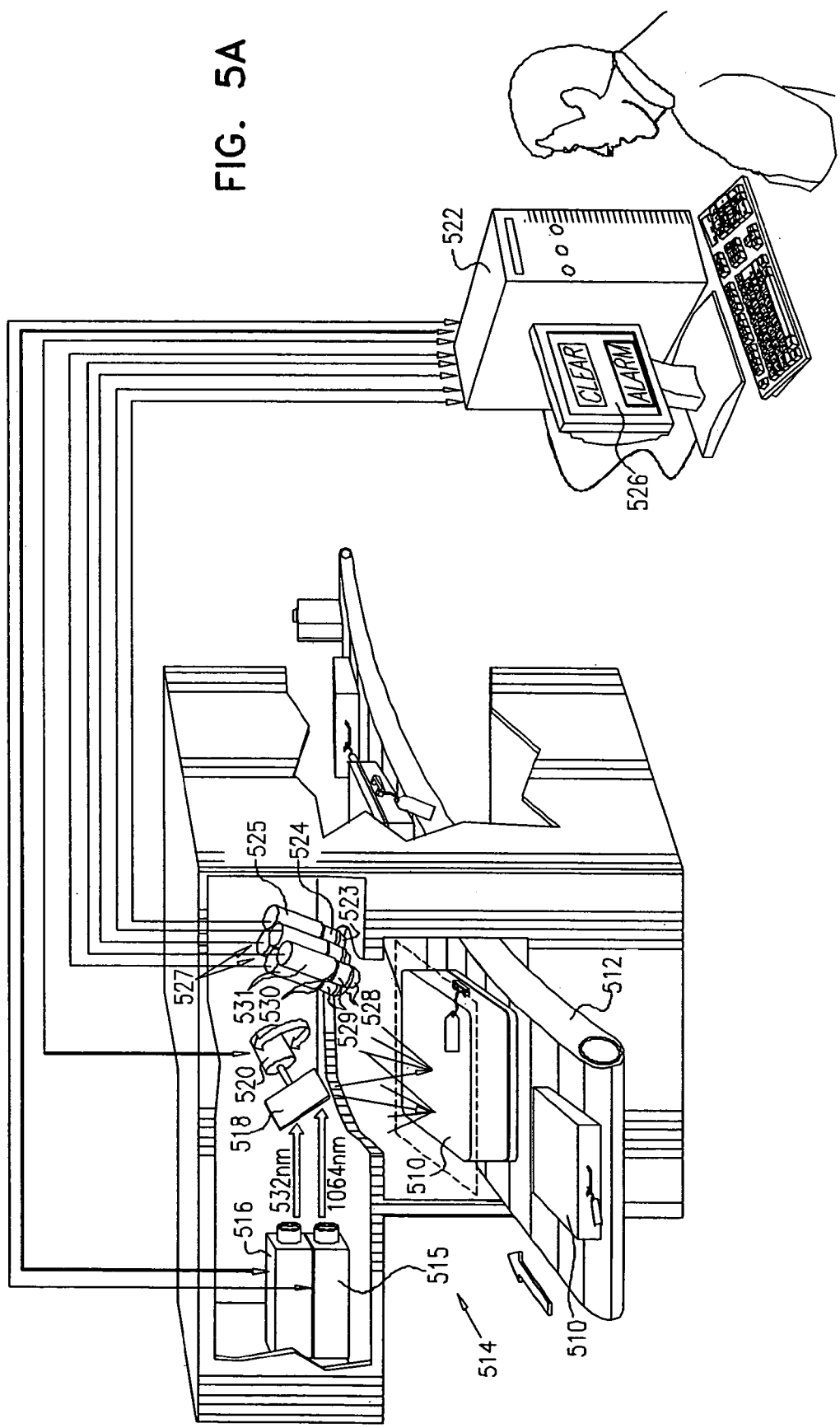
FIG. 5A is a simplified pictorial illustration of a non-imagewise system for detecting explosives on objects constructed and operative in accordance with a preferred embodiment of the present invention and employing laser induced second harmonic and time-resolved Raman scattering detection.

Reference is now made to FIG. 5A, which is a simplified pictorial illustration of a non-imagewise system for detecting explosives on objects constructed and operative in accordance with a preferred embodiment of the present invention and employing second harmonic and time-resolved Raman scattering detection. In the illustrated embodiment, a baggage screening system is shown, it being appreciated that the present invention is not limited to baggage screening applications, but rather may be employed in any other suitable object inspection environment.

In the embodiment of FIG. 5A, baggage, such as suitcases 510, is transported by a conveyor 512 past an inspection station 514 at which the suitcases 510 are inspected. In accordance with a preferred embodiment of the present invention, the inspection station 514 employs a first laser 515, preferably a Nd:YAG pulsed laser emitting with a peak wavelength at 1064 nm. It is appreciated that wavelengths in the range of 400 nm to 10 microns may be employed. The inspection station 514 preferably also employs a second laser 516, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

Output beams of lasers 515 and 516 impinge on a scanning element 518, such as a mirror, which is driven in rotational motion by a motor 520 in synchronization with the pulsed outputs of lasers 515 and 516 in response to synchronization signals provided by a computer 522.

The output beam of laser 515 is thus scanned over suitcases 510, inducing second harmonic scattering of the output beam by certain materials, including a number of explosives, should those materials be present on the scanned surfaces of the suitcases 510. The scattered second harmonic of the laser beam from laser 515 is detected via collecting optics 523 and a narrow band spectral filter 524 having a peak wavelength of 532 nm preferably by a gated detector 525, such as a photodiode, photomultiplier or CCD. Alternatively, the detector need not be gated, although this is not preferred.

If more than a threshold amount of scattered second harmonic illumination at wavelength 532 is received by gated detector 525 within a time window defined to be during each laser pulse, an alarm indication is provided by computer 522, typically at a display 526. This alarm indication indicates that an explosive material having certain second harmonic scattering characteristics may be present on a surface of the suitcase 510.

The output beam of laser 516 is also scanned over suitcases 510, inducing Raman scattering by certain materials, including explosives, should those materials be present on the scanned surfaces of the suitcases 510. The Raman scattering is detected by a plurality of detector assemblies 527, each preferably including collecting optics 528, a spectral filter 529, a notch filter 530 and a gated detector 531, such as a photodiode, photomultiplier or CCD. Alternatively, the plurality of detector assemblies 527 may be replaced by a single broadband detector assembly, although this is not preferred. Alternatively, the detector need not be gated, although this is not preferred.

Preferably, the spectral range of each spectral filter 529 of each detector assembly 527 differs from the spectral range of each other such filter. The following Raman shifts relative to the laser excitation wavelength are preferably provided, each by a different spectral filter 529:

880–885 cm (−1)
1360–1365 cm (−1)
1270–1290 cm (−1)
2980–3000 cm (−1).

If more than a threshold amount of Raman scattering is received by any one or more gated detector 531 during the time interval of the laser excitation pulse and its spectral range, an alarm indication is provided by computer 522, typically at display 526. This alarm indication indicates that an explosive material having certain Raman scattering characteristics may be present on a surface of the suitcase 510.

Figure 5B:
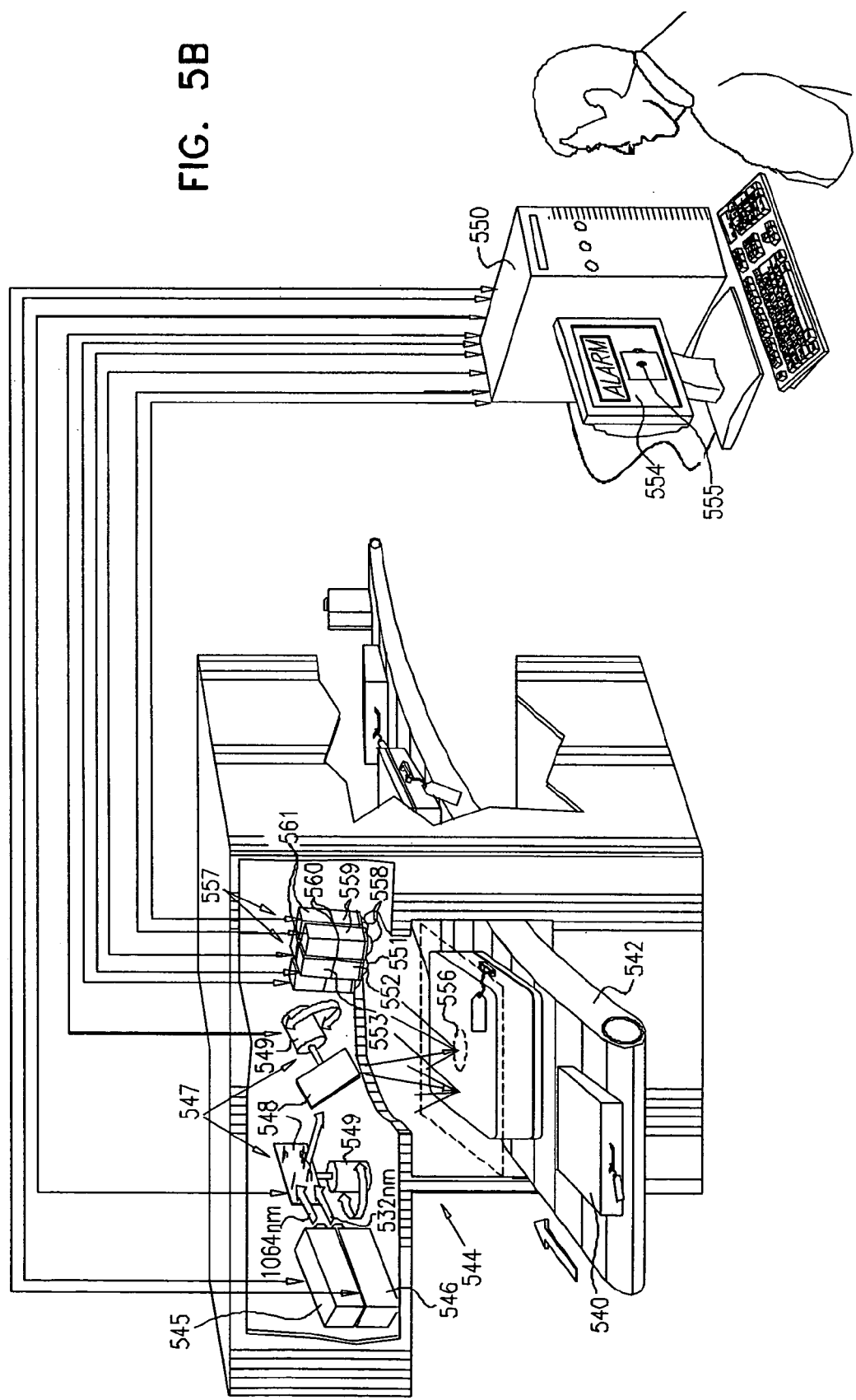
FIG. 5B is a simplified pictorial illustration of an imagewise system for detecting explosives on objects constructed and operative in accordance with a preferred embodiment of the present invention and employing laser induced second harmonic and time-resolved Raman scattering detection.

Reference is now made to FIG. 5B, which is a simplified pictorial illustration of an imagewise system for detecting explosives on objects constructed and operative in accordance with a preferred embodiment of the present invention and employing second harmonic detection and time-resolved luminescence. In the illustrated embodiment, a baggage screening system is shown, it being appreciated that the present invention is not limited to baggage screening applications, but rather may be employed in any other suitable object inspection environment.

In the embodiment of FIG. 5B, baggage, such as suitcases 540, is transported by a conveyor 542 past an inspection station 544 at which the suitcases 540 are inspected. In accordance with a preferred embodiment of the present invention, the inspection station 544 employs a first laser 545, preferably a Nd:YAG pulsed laser emitting with a peak wavelength at 1064 nm. It is appreciated that wavelengths in the range of 400 nm to 10 microns may be employed. The inspection station 544 preferably also employs a second laser 546, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

The output beams of lasers 545 and 546 impinge on a scanning assembly 547, typically comprising first and second scanning elements 548, such as mirrors, which are driven in rotational motion by motors 549 in synchronization with the pulsed outputs of lasers 545 and 546 in response to synchronization signals provided by a computer 550.

The output beam of laser 545 is thus scanned in two dimensions over suitcases 540, inducing second harmonic scattering of the output beam by certain materials, including a number of explosives, should those materials be present on the scanned surfaces of the suitcases 540. The scattered second harmonic of the laser beam is detected via imaging optics 551 and a narrow band spectral filter 552 having a peak wavelength of 532 nm preferably by a gated detector array 553, such as a CCD or CMOS array. Alternatively, the detector array need not be gated, although this is not preferred.

If more than a threshold amount of scattered second harmonic illumination at wavelength 532 nm is received by gated detector array 553 within a predetermined time window during each laser pulse, an alarm indication is provided by computer 550, typically at a display 554. The alarm indication indicates that an explosive material having certain second harmonic scattering characteristics may be present on a surface of the suitcase 540. Display 554 preferably also visually indicates the location of the detected suspect material on the suitcase 540, here indicated on display 554 at reference numeral 555 and on the suitcase 540 at reference numeral 556.

The output beam of second laser 546 is also scanned in two dimensions over suitcases 540, inducing Raman scattering by certain materials, including explosives, should those materials be present on the scanned surfaces of the suitcases 540. The Raman scattering is detected by a plurality of detector assemblies 557, each preferably including imaging optics 558, a spectral filter 559, a notch filter 560 and a gated detector array 561, such as a CCD or CMOS array. Alternatively, the plurality of detector assemblies 557 may be replaced by a single broadband detector assembly, although this is not preferred. Alternatively, the detector array need not be gated, although this is not preferred.

Preferably, the spectral range of each spectral filter 559 of each detector assembly 557 differs from the spectral range of each other such filter. The following Raman shifts relative to the laser excitation wavelength are preferably provided, each by a different spectral filter 559:

880–885 cm (−1)
1360–1365 cm (−1)
1270–1290 cm (−1)
2980–3000 cm (−1).

If more than a threshold amount of Raman scattering is received by any one or more gated detector in array 561 during the time interval of the laser excitation pulse and its spectral range, an alarm indication is provided by computer 550, typically at display 554. This alarm indication indicates that an explosive material having certain Raman scattering characteristics may be present on a surface of the suitcase 540. Display 554 preferably also visually indicates, at location 555 on the display 554, the location 556 on the suitcase 540 of the detected suspect material.

Preferably computer 550 and display 554 are operative to superimpose and indicate the spatial relationship between the locations of the detected suspect materials on the suitcase 540 produced in response to excitation by the first and second lasers 545 and 546 and the second harmonic scattering and luminescence detection resulting therefrom.

Reference is now made to FIG. 5C, which is a simplified pictorial illustration of an imagewise system for detecting explosives constructed and operative in accordance with another preferred embodiment of the present invention and employing second harmonic detection and time-resolved luminescence. In the illustrated embodiment, a vehicle screening system is shown, it being appreciated that the present invention is not limited to vehicle screening applications, but rather may be employed in any other suitable remote object inspection environment.

In the embodiment of FIG. 5C, an inspection assembly 570, which may be portable or stationary, employs a first laser 575, preferably a Nd:YAG pulsed laser emitting with a peak wavelength at 1064 nm. It is appreciated that wavelengths in the range of 400 nm to 10 microns may be employed. Inspection assembly 570 preferably also employs a second laser 576, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

Output beams of lasers 575 and 576 impinge on scanning assemblies 578, typically comprising first and second scanning elements (not shown) such as mirrors, which are driven in rotational motion by motors (not shown) in synchronization with the pulsed outputs of lasers 575 and 576 in response to synchronization signals provided by a computer 580. The scanned laser beam outputs of scanning assemblies 578 are projected onto a vehicle or other suitable remote object, preferably by a pair of telescopes 581.

The output beam of laser 575 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 582 and a narrow band spectral filter 584 having a peak wavelength of 532 nm, preferably by a gated detector array 585 such as a CCD or CMOS array. Alternatively, the detector array need not be gated, although this is not preferred.

If more than a threshold amount of scattered second harmonic illumination at wavelength 532 nm is received by gated detector array 585 within a predetermined time window during each laser pulse, an alarm indication is provided by computer 580, typically at a display 586. The alarm indication indicates that an explosive material having certain second harmonic scattering characteristics may be present on a surface of the vehicle. Display 586 preferably also visually indicates the location of the detected suspect material on the vehicle, here indicated on display 586 at reference numeral 587 and on the vehicle at reference numeral 588.

The output beam of second laser 576 is also scanned in two dimensions over the vehicle, inducing Raman scattering by certain materials, including explosives, should those materials be present on the scanned surfaces of the vehicle. The Raman scattering is detected by a plurality of detector assemblies 589, each preferably including imaging optics 590, a spectral filter 591, a notch filter 592 and a gated detector array 593, such as a CCD or CMOS array. Alternatively, the plurality of detector assemblies 589 may be replaced by a single broadband detector assembly, although this is not preferred. Alternatively, the detector array need not be gated, although this is not preferred.

Preferably, the spectral range of each spectral filter 591 of each detector assembly 589 differs from the spectral range of each other such filter. The following Raman shifts relative to the laser excitation wavelength are preferably provided, each by a different spectral filter 591:

880–885 cm (−1)
1360–1365 cm (−1)
1270–1290 cm (−1)
2980–3000 cm (−1).

If more than a threshold amount of Raman scattering is received by any one or more gated detector of array 593 during the time interval of the laser excitation pulse and its spectral range, an alarm indication is provided by computer 580, typically at display 586. This alarm indication indicates that an explosive material having certain Raman scattering characteristics may be present on a surface of the vehicle. Display 586 preferably also visually indicates, at location 587 on the display 586, the location 588 on the vehicle of the detected suspect material.

Preferably computer 580 is operative to analyze and indicate detection of suspect materials on the vehicle produced in response to excitation by the first and second lasers 575 and 576 and the resulting second harmonic scattering and Raman scattering detection resulting therefrom.

Preferably computer 580 and display 586 are operative to superimpose and indicate the spatial relationship between the locations of the detected suspect materials on the vehicle produced in response to excitation by the first and second lasers 575 and 576 and the second harmonic scattering and Raman scattering detection resulting therefrom.

Figure 6A:
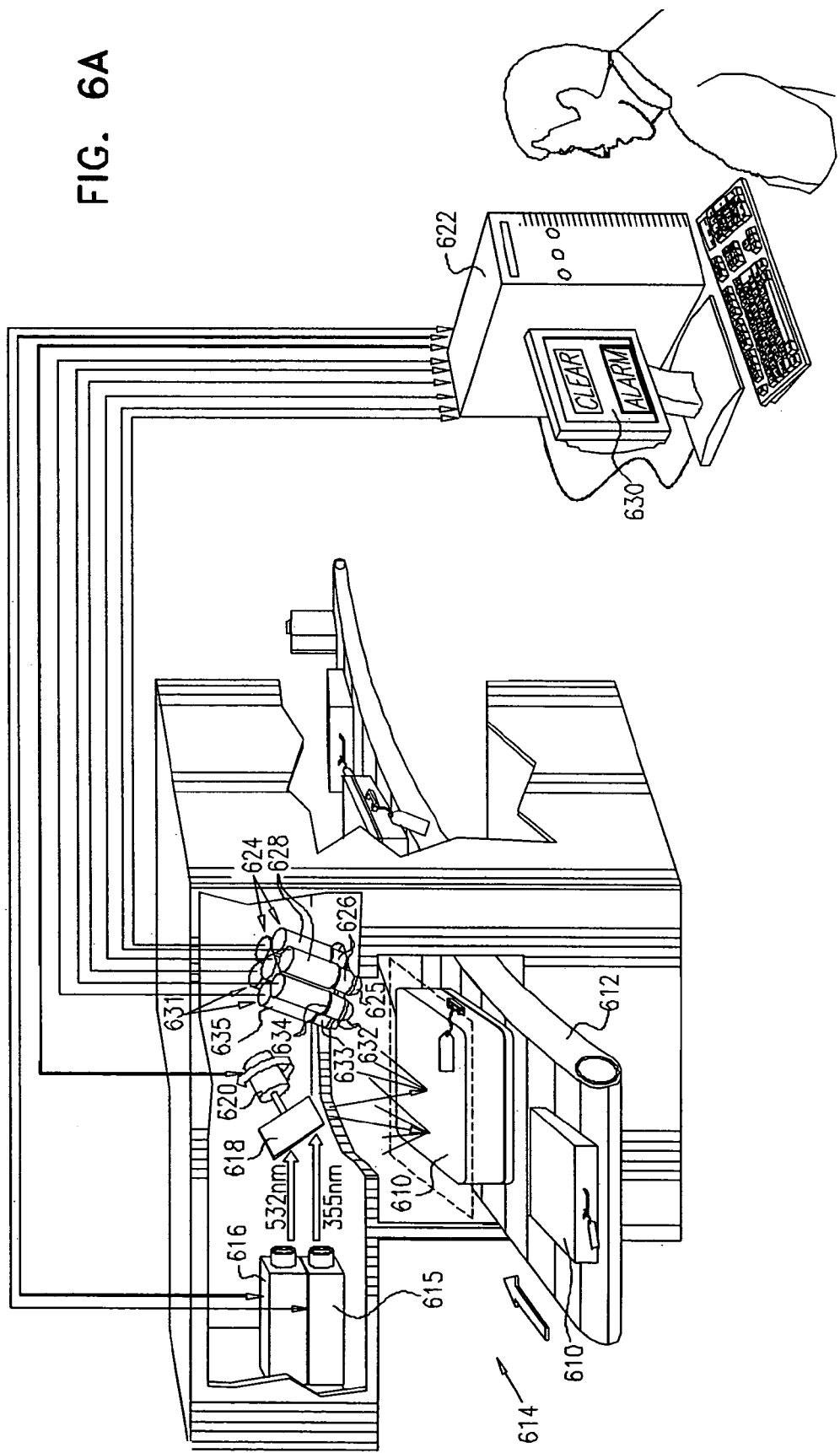
FIG. 6A is a simplified pictorial illustration of a non-imagewise system for detecting explosives on objects constructed and operative in accordance with a preferred embodiment of the present invention and employing laser induced time-resolved luminescence and time-resolved Raman scattering detection.

Reference is now made to FIG. 6A, which is a simplified pictorial illustration of a non-imagewise system for detecting explosives on objects constructed and operative in accordance with a preferred embodiment of the present invention and employing time-resolved luminescence and time-resolved Raman scattering detection. In the illustrated embodiment, a baggage screening system is shown, it being appreciated that the present invention is not limited to baggage screening applications, but rather may be employed in any other suitable object inspection environment.

In the embodiment of FIG. 6A, baggage, such as suitcases 610, is transported by a conveyor 612 past an inspection station 614 at which the suitcases 610 are inspected. In accordance with a preferred embodiment of the present invention, the inspection station 614 employs a first laser 615, preferably a Nd:YAG pulsed laser emitting a third or fourth harmonic having respective peak wavelengths at 355 and 266 nm. It is appreciated that wavelengths in the range of 180 nm to 10 microns may be employed. The inspection station 614 preferably also employs a second laser 616, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

Output beams of lasers 615 and 616 impinge on a scanning element 618, such as a mirror, which is driven in rotational motion by a motor 620 in synchronization with the pulsed outputs of lasers 615 and 616 in response to synchronization signals provided by a computer 622.

The output beam of laser 615 is thus scanned over suitcases 610, inducing luminescence by certain materials, including a number of explosives, should those materials be present on the scanned surfaces of the suitcases 610. The luminescence is detected by a plurality of detector assemblies 624, each preferably including collecting optics 625, a spectral filter 626 and a gated detector 628, such as a photodiode, photomultiplier or CCD. Alternatively, the plurality of detector assemblies 624 may be replaced by a single broadband detector assembly, although this is not preferred. Alternatively, the detector need not be gated, although this is not preferred.

Preferably, the spectral range of each spectral filter 626 of each detector assembly 624 differs from the spectral range of each other such filter. The following spectral ranges are preferably provided, each by a different spectral filter 626 and corresponding to the following gate intervals:

400–430 nm—10 microseconds
450–540 nm—50 nanoseconds
670–700 nm—100 microseconds.

If more than a threshold amount of luminescence is received by any one or more gated detector 628 within its time window and its spectral range, an alarm indication is provided by computer 622, typically at a display 630. This alarm indication indicates that an explosive material having certain luminescence characteristics may be present on a surface of the suitcase 610.

The output beam of laser 616 is also scanned over suitcases 610, inducing Raman scattering by certain materials, including explosives, should those materials be present on the scanned surfaces of the suitcases 610. The Raman scattering is detected by a plurality of detector assemblies 631, each preferably including collecting optics 632, a spectral filter 633, a notch filter 634 and a gated detector 635, such as a photodiode, photomultiplier or CCD. Alternatively, the plurality of detector assemblies 631 may be replaced by a single broadband detector assembly, although this is not preferred. Alternatively, the detector need not be gated, although this is not preferred.

Preferably, the spectral range of each spectral filter 633 of each detector assembly 631 differs from the spectral range of each other such filter. The following Raman shifts relative to the laser excitation wavelength are preferably provided, each by a different spectral filter 633:

880–885 cm (−1)
1360–1365 cm (−1)
1270–1290 cm (−1)
2980–3000 cm (−1).

If more than a threshold amount of Raman scattering is received by any one or more gated detector 635 during the time interval of the laser excitation pulse and its spectral range, an alarm indication is provided by computer 622, typically at display 630. This alarm indication indicates that an explosive material having certain Raman scattering characteristics may be present on a surface of the suitcase 610.

Figure 6B:
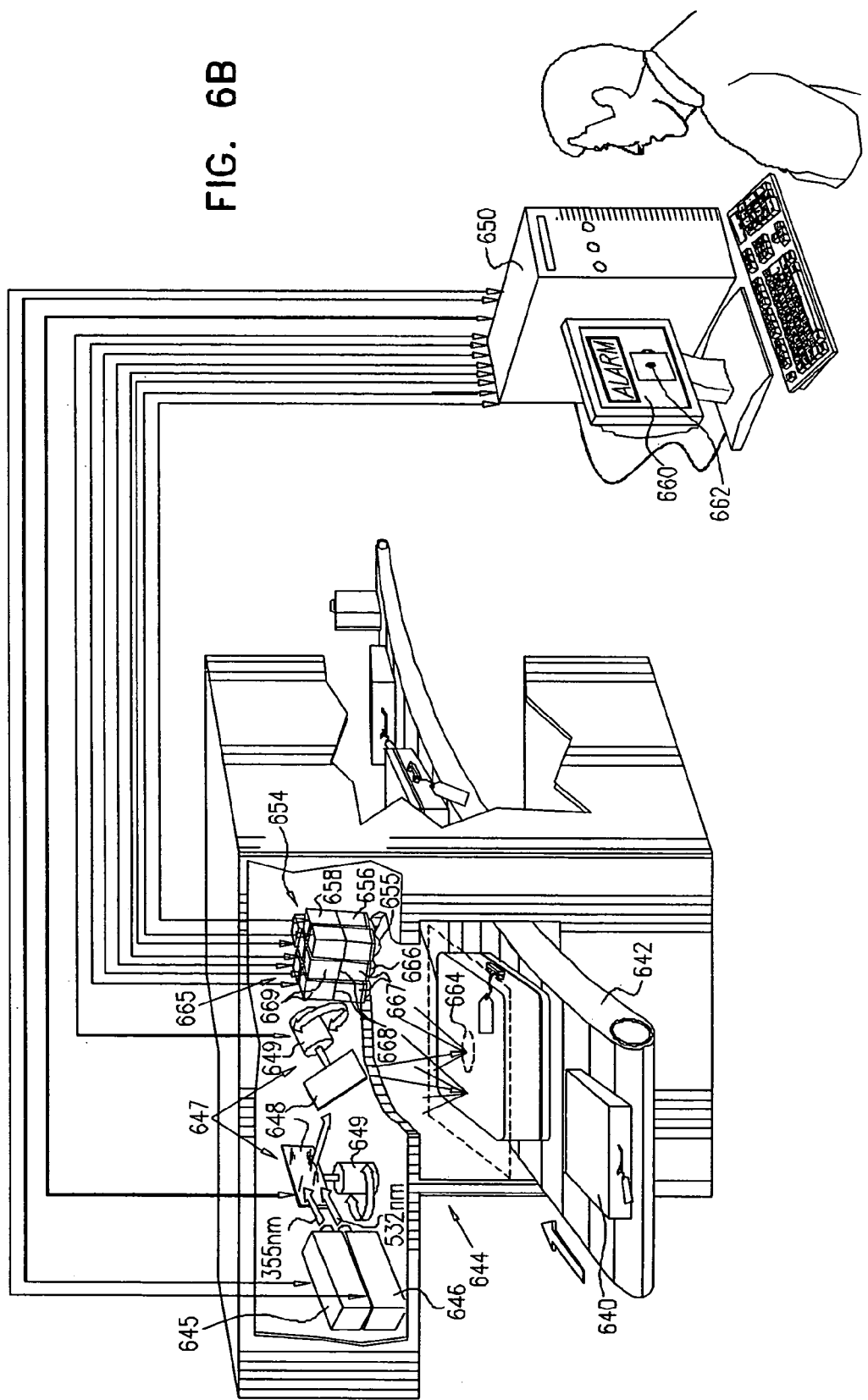
FIG. 6B is a simplified pictorial illustration of an imagewise system for detecting explosives on objects constructed and operative in accordance with a preferred embodiment of the present invention and employing laser induced time-resolved luminescence and time-resolved Raman scattering detection.

Reference is now made to FIG. 6B, which is a simplified pictorial illustration of an imagewise system for detecting explosives on objects constructed and operative in accordance with a preferred embodiment of the present invention and employing second harmonic detection and time-resolved luminescence. In the illustrated embodiment, a baggage screening system is shown, it being appreciated that the present invention is not limited to baggage screening applications, but rather may be employed in any other suitable object inspection environment.

In the embodiment of FIG. 6B, baggage, such as suitcases 640, is transported by a conveyor 642 past an inspection station 644 at which the suitcases 640 are inspected. In accordance with a preferred embodiment of the present invention, the inspection station 644 employs a first laser 645, preferably a Nd:YAG pulsed laser emitting a third or fourth harmonic having respective peak wavelengths at 355 and 266 nm. It is appreciated that wavelengths in the range of 180 nm to 10 microns may be employed. The inspection station 644 preferably also employs a second laser 646, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

The output beams of lasers 645 and 646 impinge on a scanning assembly 647, typically comprising first and second scanning elements 648, such as mirrors, which are driven in rotational motion by motors 649 in synchronization with the pulsed outputs of lasers 645 and 646 in response to synchronization signals provided by a computer 650.

The output beam of laser 645 is thus scanned in two dimensions over suitcases 640, inducing luminescence by certain materials, including a number of explosives, should those materials be present on the scanned surfaces of the suitcases 640. The luminescence induced by the laser beam is detected preferably by a plurality of detector assemblies 654, each preferably including imaging optics 655, a spectral filter 656 and a gated detector array 658, such as a CCD or CMOS array. Alternatively, the plurality of detector assemblies 654 may be replaced by a single broadband detector assembly, although this is not preferred. Alternatively, the detector array need not be gated, although this is not preferred.

Preferably, the spectral range of each spectral filter 656 of each detector assembly 654 differs from the spectral range of each other such filter. The following spectral ranges are preferably provided, each by a different spectral filter 656 and corresponding to the following gate intervals:

400–430 nm—10 microseconds
450–540 nm—50 nanoseconds
670–700 nm—100 microseconds.

If more than a threshold amount of luminescence is received by any one or more gated detector 658 within its time window and its spectral range, an alarm indication is provided by computer 650, typically at a display 660. This alarm indication indicates that an explosive material having certain luminescence characteristics may be present on a surface of the suitcase 640. Display 660 preferably also visually indicates the location of the detected suspect material on the suitcase 640, here indicated on display 660 at reference numeral 662 and on the suitcase 640 at reference numeral 664.

The output beam of second laser 646 is also scanned in two dimensions over suitcases 640, inducing Raman scattering by certain materials, including explosives, should those materials be present on the scanned surfaces of the suitcases 640. The Raman scattering is detected by a plurality of detector assemblies 665 each preferably including imaging optics 666, a spectral filter 667, a notch filter 668 and a gated detector array 669, such as a CCD or CMOS array. Alternatively, the plurality of detector assemblies 665 may be replaced by a single broadband detector assembly, although this is not preferred. Alternatively, the detector array need not be gated, although this is not preferred.

Preferably, the spectral range of each spectral filter 667 of each detector assembly 665 differs from the spectral range of each other such filter. The following Raman shifts relative to the laser excitation wavelength are preferably provided, each by a different spectral filter 667:

880–885 cm (–1)
1360–1365 cm (–1)
1270–1290 cm (–1)
2980–3000 cm (–1).

If more than a threshold amount of Raman scattering is received by any one or more gated detector in array 669 during the time interval of the laser excitation pulse and its spectral range, an alarm indication is provided by computer 650, typically at display 660. This alarm indication indicates that an explosive material having certain Raman scattering characteristics may be present on a surface of the suitcase 640. Display 660 preferably also visually indicates, at location 662 on the display 660, the location 664 on the suitcase 640 of the detected suspect material.

Preferably computer 650 and display 660 are operative to superimpose and indicate the spatial relationship between the locations of the detected suspect materials on the suitcase 640 produced in response to excitation by the first and second lasers 645 and 646 and the time-resolved luminescence and time-resolved Raman scattering detection resulting therefrom.

Reference is now made to FIG. 6C, which is a simplified pictorial illustration of an imagewise system for detecting explosives constructed and operative in accordance with another preferred embodiment of the present invention and employing time-resolved luminescence and time-resolved Raman scattering detection. In the illustrated embodiment, a vehicle screening system is shown, it being appreciated that the present invention is not limited to vehicle screening applications, but rather may be employed in any other suitable remote object inspection environment.

In the embodiment of FIG. 6C, an inspection assembly 672, which may be portable or stationary, employs a first laser 675, preferably a Nd:YAG pulsed laser emitting a third or fourth harmonic having respective peak wavelengths at 355 and 266 nm. It is appreciated that wavelengths in the range of 180 nm to 10 microns may be employed. Inspection assembly 672 preferably also employs a second laser 676, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

Output beams of lasers 675 and 676 impinge on scanning assemblies 678, typically comprising first and second scanning elements (not shown) such as mirrors, which are driven in rotational motion by motors (not shown) in synchronization with the pulsed outputs of lasers 675 and 676 in response to synchronization signals provided by a computer 680. The scanned laser beam outputs of scanning assemblies 678 are projected onto a vehicle or other suitable remote object, preferably by a pair of telescopes 681.

The output beam of laser 675 is thus scanned in two dimensions over a vehicle, inducing luminescence by certain materials, including a number of explosives, should those materials be present on the scanned surfaces of the vehicle. The luminescence induced by the laser beam is detected preferably by a plurality of detector assemblies 684, each preferably including imaging optics 685, a spectral filter 686 and a gated detector array 688, such as a CCD or CMOS array. Alternatively, the plurality of detector assemblies 684 may be replaced by a single broadband detector assembly, although this is not preferred. Alternatively, the detector array need not be gated, although this is not preferred.

Preferably, the spectral range of each spectral filter 686 of each detector assembly 684 differs from the spectral range of each other such filter. The following spectral ranges are preferably provided, each by a different spectral filter 686 and corresponding to the following gate intervals:

400–430 nm—10 microseconds
450–540 nm—50 nanoseconds
670–700 nm—100 microseconds.

If more than a threshold amount of luminescence is received by any one or more gated detector 688 within its time window and its spectral range, an alarm indication is provided by computer 680 typically at a display 690. This alarm indication indicates that an explosive material having certain luminescence characteristics may be present on a surface of the vehicle. Display 690 preferably also visually indicates the location of the detected suspect material on the vehicle, here indicated on display 690 at reference numeral 691 and on the vehicle at reference numeral 692.

The output beam of second laser 676 is thus also scanned in two dimensions over the vehicle, inducing Raman scattering by certain materials, including explosives, should those materials be present on the scanned surfaces of the vehicle. The Raman scattering is detected by a plurality of detector assemblies 693, each preferably including imaging optics 694, a spectral filter 695, a notch filter 696 and a gated detector array 697 such as a CCD or CMOS array. Alternatively, the plurality of detector assemblies 693 may be replaced by a single broadband detector assembly, although this is not preferred. Alternatively, the detector array need not be gated, although this is not preferred.

Preferably, the spectral range of each spectral filter 695 of each detector assembly 693 differs from the spectral range of each other such filter. The following Raman shifts relative to the laser excitation wavelength are preferably provided, each by a different spectral filter 695:

880–885 cm (–1)
1360–1365 cm (–1)
1270–1290 cm (–1)
2980–3000 cm (–1).

If more than a threshold amount of Raman scattering is received by any one or more gated detector of array 697 during the time interval of the laser excitation pulse and its spectral range, an alarm indication is provided by computer 680, typically at display 690. This alarm indication indicates that an explosive material having certain Raman scattering characteristics may be present on a surface of the vehicle. Display 690 preferably also visually indicates, at location 691 on the display 690, the location 692 on the vehicle of the detected suspect material.

Preferably computer 680 is operative to analyze and indicate detection of suspect materials on the vehicle produced in response to excitation by the first and second lasers 675 and 676 and the time-resolved luminescence and time-resolved Raman scattering detection resulting therefrom.

Preferably computer 680 and display 690 are operative to superimpose and indicate the spatial relationship between the locations of the detected suspect materials on the vehicle produced in response to excitation by the first and second lasers 675 and 676 and the time-resolved luminescence and time-resolved Raman scattering detection resulting therefrom.

Figure 7A:
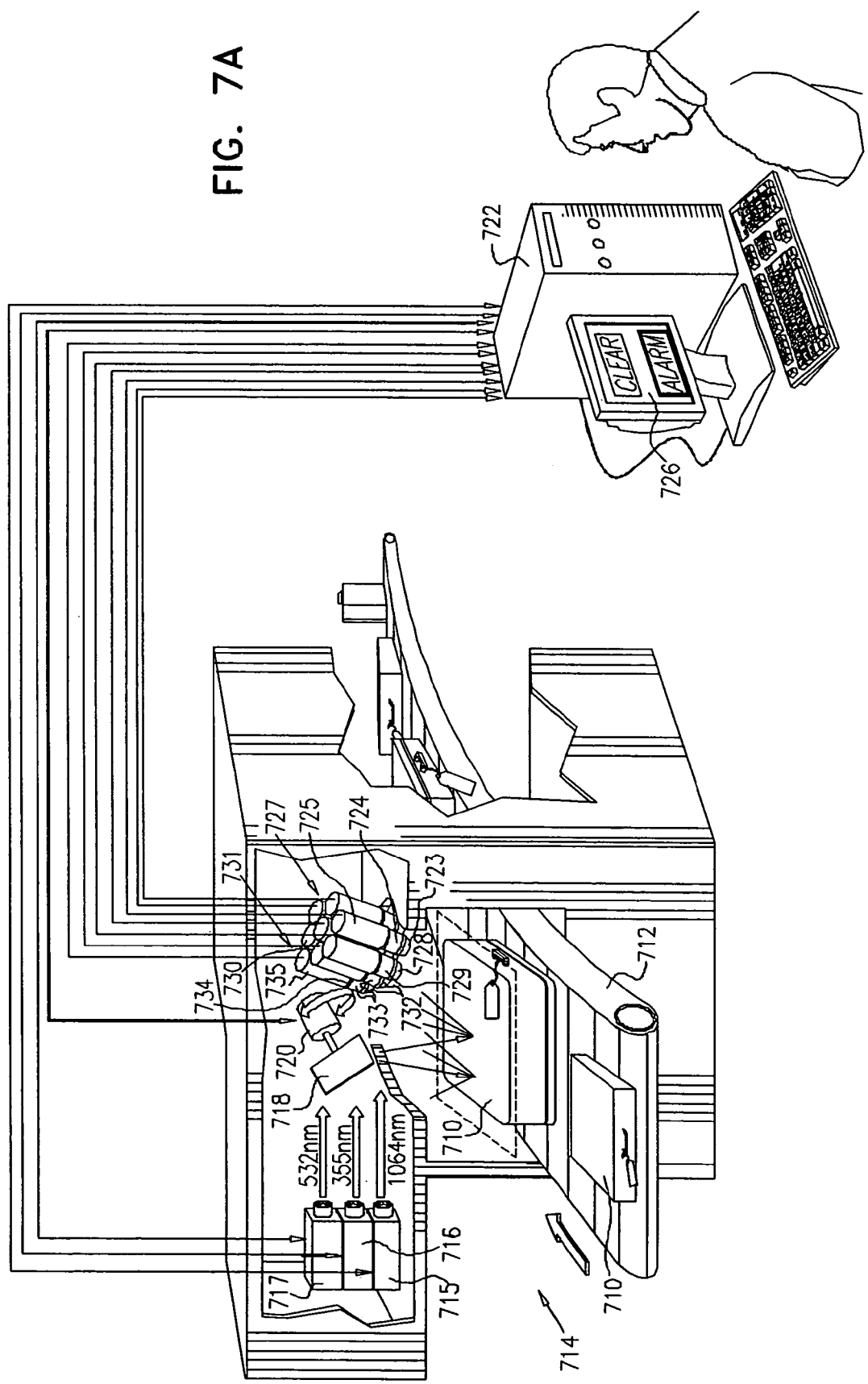
FIG. 7A is a simplified pictorial illustration of a non-imagewise system for detecting explosives on objects constructed and operative in accordance with a preferred embodiment of the present invention and employing laser induced second harmonic, time-resolved luminescence and time-resolved Raman scattering detection.

Reference is now made to FIG. 7A, which is a simplified pictorial illustration of a non-imagewise system for detecting explosives on objects constructed and operative in accordance with a preferred embodiment of the present invention and employing second harmonic, time-resolved luminescence and time-resolved Raman scattering detection. In the illustrated embodiment, a baggage screening system is shown, it being appreciated that the present invention is not limited to baggage screening applications, but rather may be employed in any other suitable object inspection environment.

In the embodiment of FIG. 7A, baggage, such as suitcases 710, is transported by a conveyor 712 past an inspection station 714 at which the suitcases 710 are inspected. In accordance with a preferred embodiment of the present invention, the inspection station 714 employs a first laser 715, preferably a Nd:YAG pulsed laser emitting with a peak wavelength at 1064 nm. It is appreciated that wavelengths in the range of 400 nm to 10 microns may be employed. The inspection station 714 preferably also employs a second laser 716, preferably a Nd:YAG pulsed laser emitting a third or fourth harmonic having respective peak wavelengths at 355 and 266 nm. It is appreciated that wavelengths in the range of 180 nm to 10 microns may be employed by this laser. The inspection station 714 preferably also employs a third laser 717, preferably a Nd:YAG pulsed laser emitting a second harmonic having a peak wavelength at 532 nm. It is appreciated that wavelengths in the range of 200 nm to 10 microns may be employed by this laser. Alternatively, a single laser or two lasers may be used rather than three lasers.

Output beams of lasers 715, 716 and 717 impinge on a scanning element 718, such as a mirror, which is driven in rotational motion by a motor 720 in synchronization with the pulsed outputs of lasers 715, 716 and 717 in response to synchronization signals provided by a computer 722.

The output beam of laser 715 is thus scanned over suitcases 710, inducing second harmonic scattering of the output beam by certain materials, including a number of explosives, should those materials be present on the scanned surfaces of the suitcases 710. The scattered second harmonic of the laser beam from laser 715 is detected via collecting optics 723 and a narrow band spectral filter 724 having a peak wavelength of 532 nm preferably by a gated detector 725, such as a photodiode, photomultiplier or CCD. Alternatively, the detector need not be gated, although this is not preferred.

If more than a threshold amount of scattered second harmonic illumination at wavelength 532 is received by gated detector 725 within a time window defined to be during each laser pulse, an alarm indication is provided by computer 722, typically at a display 726. This alarm indication indicates that an explosive material having certain second harmonic scattering characteristics may be present on a surface of the suitcase 710.

The output beam of laser 716 is also scanned over suitcases 710, inducing luminescence by certain materials, including a number of explosives, should those materials be present on the scanned surfaces of the suitcases 710. The luminescence is detected by a plurality of detector assemblies 727, each preferably including collecting optics 728, a spectral filter 729 and a gated detector 730, such as a photodiode, photomultiplier or CCD. Alternatively, the plurality of detector assemblies 727 may be replaced by a single broadband detector assembly, although this is not preferred. Alternatively, the detector need not be gated, although this is not preferred.

Preferably, the spectral range of each spectral filter 729 of each detector assembly 727 differs from the spectral range of each other such filter. The following spectral ranges are preferably provided, each by a different spectral filter 729 and corresponding to the following gate intervals:

400–430 nm—10 microseconds
450–540 nm—50 nanoseconds
670–700 nm—100 microseconds.

If more than a threshold amount of luminescence is received by any one or more gated detector 730 within its time window and its spectral range, an alarm indication is provided by computer 722, typically at display 726. This alarm indication indicates that an explosive material having certain luminescence characteristics may be present on a surface of the suitcase 710.

The output beam of laser 717 is also scanned over suitcases 710, inducing Raman scattering by certain materials, including explosives, should those materials be present on the scanned surfaces of the suitcases 710. The Raman scattering is detected by a plurality of detector assemblies 731, each preferably including collecting optics 732, a spectral filter 733, a notch filter 734 and a gated detector 735, such as a photodiode, photomultiplier or CCD. Alternatively, the plurality of detector assemblies 731 may be replaced by a single broadband detector assembly, although this is not preferred. Alternatively, the detector need not be gated, although this is not preferred.

Preferably, the spectral range of each spectral filter 733 of each detector assembly 731 differs from the spectral range of each other such filter. The following Raman shifts relative to the laser excitation wavelength are preferably provided, each by a different spectral filter 733:

880–885 cm (−1)
1360–1365 cm (−1)
1270–1290 cm (−1)
2980–3000 cm (−1).

If more than a threshold amount of Raman scattering is received by any one or more gated detector 735 during the time interval of the laser excitation pulse and its spectral range, an alarm indication is provided by computer 722, typically at display 726. This alarm indication indicates that an explosive material having certain Raman scattering characteristics may be present on a surface of the suitcase 710.

Figure 7B:
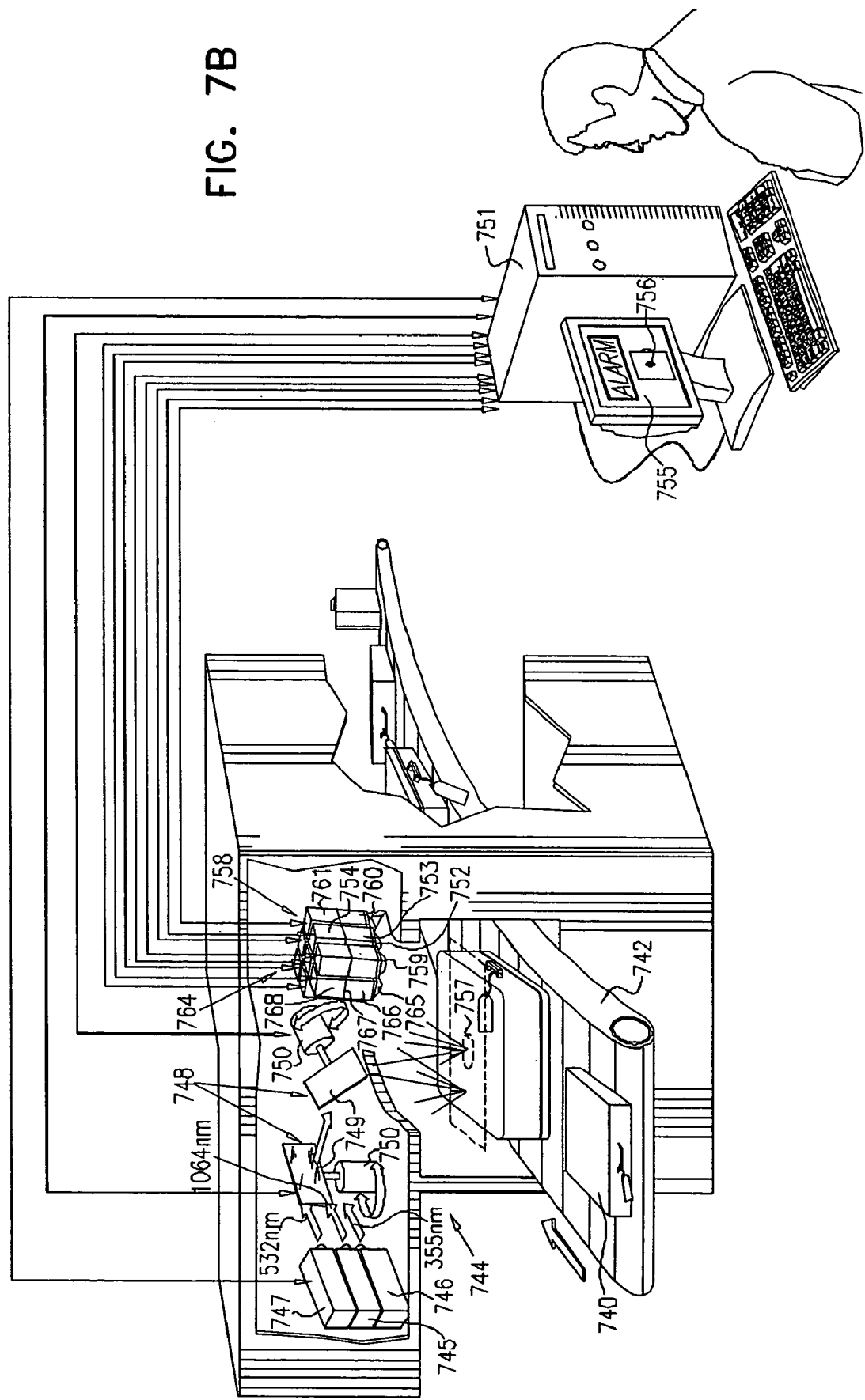
FIG. 7B is a simplified pictorial illustration of an imagewise system for detecting explosives on objects constructed and operative in accordance with a preferred embodiment of the present invention and employing laser induced second harmonic, time-resolved luminescence and time-resolved Raman scattering detection.

Reference is now made to FIG. 7B, which is a simplified pictorial illustration of an imagewise system for detecting explosives on objects constructed and operative in accordance with a preferred embodiment of the present invention and employing second harmonic detection and time-resolved luminescence. In the illustrated embodiment, a baggage screening system is shown, it being appreciated that the present invention is not limited to baggage screening applications, but rather may be employed in any other suitable object inspection environment.

In the embodiment of FIG. 7B, baggage, such as suitcases 740, is transported by a conveyor 742 past an inspection station 744 at which the suitcases 740 are inspected. In accordance with a preferred embodiment of the present invention, the inspection station 744 employs a first laser 745, preferably a Nd:YAG pulsed laser emitting with a peak wavelength at 1064 nm. It is appreciated that wavelengths in the range of 400 nm to 10 microns may be employed. The inspection station 744 preferably also employs a second laser 746, preferably a Nd:YAG pulsed laser emitting a third or fourth harmonic having respective peak wavelengths at 355 and 266 nm. It is appreciated that wavelengths in the range of 180 nm to 10 microns may be employed. The inspection station 744 preferably also employs a third laser 747, preferably a Nd:YAG pulsed laser emitting a second harmonic having a peak wavelength at 532 nm. It is appreciated that wavelengths in the range of 200 nm to 10 microns may be employed by this laser. Alternatively, a single laser or two lasers may be used rather than three lasers.

The output beams of lasers 745, 746 and 747 impinge on a scanning assembly 748, typically comprising first and second scanning elements 749, such as mirrors, which are driven in rotational motion by motors 750 in synchronization with the pulsed outputs of lasers 745, 746 and 747 in response to synchronization signals provided by a computer 751.

The output beam of laser 745 is thus scanned in two dimensions over suitcases 740, inducing second harmonic scattering of the output beam by certain materials, including a number of explosives, should those materials be present on the scanned surfaces of the suitcases 740. The scattered second harmonic of the laser beam is detected via imaging optics 752 and a narrow band spectral filter 753 having a peak wavelength of 532 nm preferably by a gated detector array 754, such as a CCD or CMOS array. Alternatively, the detector array need not be gated, although this is not preferred.

If more than a threshold amount of scattered second harmonic illumination at wavelength 532 nm is received by gated detector array 754 within a predetermined time window during each laser pulse, an alarm indication is provided by computer 751, typically at a display 755. The alarm indication indicates that an explosive material having certain second harmonic scattering characteristics may be present on a surface of the suitcase 740. Display 755 preferably also visually indicates the location of the detected suspect material on the suitcase 740, here indicated on display 755 at reference numeral 756 and on the suitcase 740 at reference numeral 757.

The output beam of second laser 746 is also scanned in two dimensions over suitcases 740, inducing luminescence by certain materials, including a number of explosives, should those materials be present on the scanned surfaces of the suitcases 740. The luminescence induced by the laser beam is detected preferably by a plurality of detector assemblies 758, each preferably including imaging optics 759, a spectral filter 760 and a gated detector array 761, such as a CCD or CMOS array. Alternatively, the plurality of detector assemblies 758 may be replaced by a single broadband detector assembly, although this is not preferred. Alternatively, the detector array need not be gated, although this is not preferred.

Preferably, the spectral range of each spectral filter 760 of each detector assembly 758 differs from the spectral range of each other such filter. The following spectral ranges are preferably provided, each by a different spectral filter 760 and corresponding to the following gate intervals:

400–430 nm—10 microseconds
450–540 nm—50 nanoseconds
670–700 nm—100 microseconds.

If more than a threshold amount of luminescence is received by any one or more gated detector in gated detector array 761 within its time window and its spectral range, an alarm indication is provided by computer 751, typically at display 755. This alarm indication indicates that an explosive material having certain luminescence characteristics may be present on a surface of the suitcase 740. Display 755 preferably also visually indicates, at location 756 on the display 755, the location 757 on the suitcase 740 of the detected suspect material.

The output beam of third laser 747 is also scanned in two dimensions over suitcases 740, inducing Raman scattering by certain materials, including explosives, should those materials be present on the scanned surfaces of the suitcases 740. The Raman scattering is detected by a plurality of detector assemblies 764, each preferably including imaging optics 765, a spectral filter 766, a notch filter 767 and a gated detector array 768, such as a CCD or CMOS array. Alternatively, the plurality of detector assemblies 764 may be replaced by a single broadband detector assembly, although this is not preferred. Alternatively, the detector array need not be gated, although this is not preferred.

Preferably, the spectral range of each spectral filter 766 of each detector assembly 764 differs from the spectral range of each other such filter. The following Raman shifts relative to the laser excitation wavelength are preferably provided, each by a different spectral filter 766:

880–885 cm (−1)
1360–1365 cm (−1)
1270–1290 cm (−1)
2980–3000 cm (−1).

If more than a threshold amount of Raman scattering is received by any one or more gated detector in array 768 during the time interval of the laser excitation pulse and its spectral range, an alarm indication is provided by computer 751, typically at display 755. This alarm indication indicates that an explosive material having certain Raman scattering characteristics may be present on a surface of the suitcase 740. Display 755 preferably also visually indicates, at location 756 on the display 755, the location 757 on the suitcase 740 of the detected suspect material.

Preferably computer 751 and display 755 are operative to superimpose and indicate the spatial relationship between the locations of the detected suspect materials on the suitcase 740 produced in response to excitation by the first, second and third lasers 745, 746 and 747 and the second harmonic scattering, time-resolved luminescence and time-resolved Raman scattering detection resulting therefrom.

Reference is now made to FIG. 7C, which is a simplified pictorial illustration of an imagewise system for detecting explosives constructed and operative in accordance with another preferred embodiment of the present invention and employing second harmonic detection and time-resolved luminescence. In the illustrated embodiment, a vehicle screening system is shown, it being appreciated that the present invention is not limited to vehicle screening applications, but rather may be employed in any other suitable remote object inspection environment.

In the embodiment of FIG. 7C, an inspection assembly 771, which may be portable or stationary, employs a first laser 775, preferably a Nd:YAG pulsed laser emitting with a peak wavelength at 1064 nm. It is appreciated that wavelengths in the range of 400 nm to 10 microns may be employed. Inspection assembly 771 preferably also employs a second laser 776, preferably a Nd:YAG pulsed laser emitting a third or fourth harmonic having respective peak wavelengths at 355 and 266 nm. It is appreciated that wavelengths in the range of 180 nm to 10 microns may be employed. The inspection assembly 771 preferably also employs a third laser 777, preferably a Nd:YAG pulsed laser emitting a second harmonic having a peak wavelength at 532 nm. It is appreciated that wavelengths in the range of 200 nm to 10 microns may be employed by this laser. Alternatively, a single laser or two lasers may be used rather than three lasers.

Output beams of lasers 775, 776 and 777 impinge on scanning assemblies 778, typically comprising first and second scanning elements (not shown) such as mirrors, which are driven in rotational motion by motors (not shown) in synchronization with the pulsed outputs of lasers 775, 776 and 777 in response to synchronization signals provided by a computer 780. The scanned laser beam outputs of scanning assemblies 778 are projected onto a vehicle or other suitable remote object, preferably by telescopes 781.

The output beam of laser 775 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 782 and a narrow band spectral filter 783 having a peak wavelength of 532 nm, preferably by a gated detector array 784, such as a CCD or CMOS array. Alternatively, the detector array need not be gated, although this is not preferred.

If more than a threshold amount of scattered second harmonic illumination at wavelength 532 nm is received by gated detector array 784 within a predetermined time window during each laser pulse, an alarm indication is provided by computer 780, typically at a display 785. The alarm indication indicates that an explosive material having certain second harmonic scattering characteristics may be present on a surface of the vehicle. Display 785 preferably also visually indicates the location of the detected suspect material on the vehicle, here indicated on display 785 at reference numeral 786 and on the vehicle at reference numeral 787.

The output beam of second laser 776 is thus also scanned in two dimensions over the vehicle, inducing luminescence by certain materials, including a number of explosives, should those materials be present on the scanned surfaces of the vehicle. The luminescence induced by the laser beam is detected preferably by a plurality of detector assemblies 789, each preferably including imaging optics 790, a spectral filter 792 and a gated detector array 793, such as a CCD or CMOS array. Alternatively, the plurality of detector assemblies 789 may be replaced by a single broadband detector assembly, although this is not preferred. Alternatively, the detector array need not be gated, although this is not preferred.

Preferably, the spectral range of each spectral filter 792 of each detector assembly 789 differs from the spectral range of each other such filter. The following spectral ranges are preferably provided, each by a different spectral filter 792 and corresponding to the following gate intervals:

400–430 nm—10 microseconds
450–540 nm—50 nanoseconds
670–700 nm—100 microseconds.

If more than a threshold amount of luminescence is received by any one or more gated detector in array 793 within its time window and its spectral range, an alarm indication is provided by computer 780, typically at display 785. This alarm indication indicates that an explosive material having certain luminescence characteristics may be present on a surface of the vehicle. Preferably computer 780 is operative to analyze and indicate detection of suspect materials on the vehicle produced in response to excitation by the first and second lasers 775 and 776 and the resulting second harmonic scattering and luminescence detection resulting therefrom. Display 785 preferably also visually indicates, at location 786 on the display 785, the location 787 on the vehicle of the detected suspect material.

The output beam of third laser 777 is thus also scanned in two dimensions over the vehicle, inducing Raman scattering by certain materials, including explosives, should those materials be present on the scanned surfaces of the vehicle. The Raman scattering is detected by a plurality of detector assemblies 794, each preferably including imaging optics 795, a spectral filter 796, a notch filter 797 and a gated detector array 798, such as a CCD or CMOS array. Alternatively, the plurality of detector assemblies 794 may be replaced by a single broadband detector assembly, although this is not preferred. Alternatively, the detector array need not be gated, although this is not preferred.

Preferably, the spectral range of each spectral filter 796 of each detector assembly 794 differs from the spectral range of each other such filter. The following Raman shifts relative to the laser excitation wavelength are preferably provided, each by a different spectral filter 796:

880–885 cm (−1)
1360–1365 cm (−1)
1270–1290 cm (−1)
2980–3000 cm (−1).

If more than a threshold amount of Raman scattering is received by any one or more gated detector of array 798 during the time interval of the laser excitation pulse and its spectral range, an alarm indication is provided by computer 780, typically at display 785. This alarm indication indicates that an explosive material having certain Raman scattering characteristics may be present on a surface of the vehicle. Display 785 preferably also visually indicates, at location 786 on the display 785, the location 787 on the vehicle of the detected suspect material.

Preferably computer 780 is operative to analyze and indicate detection of suspect materials on the vehicle produced in response to excitation by the first, second and third lasers 775, 776 and 777 and the second harmonic scattering, time-resolved luminescence and time-resolved Raman scattering detection resulting therefrom.

Preferably computer 780 and display 785 are operative to superimpose and indicate the spatial relationship between the locations of the detected suspect materials on the vehicle produced in response to excitation by the first, second and third lasers 775, 776 and 777 and the second harmonic scattering, time resolved luminescence and time-resolved Raman scattering detection resulting therefrom.

Figure 8A:
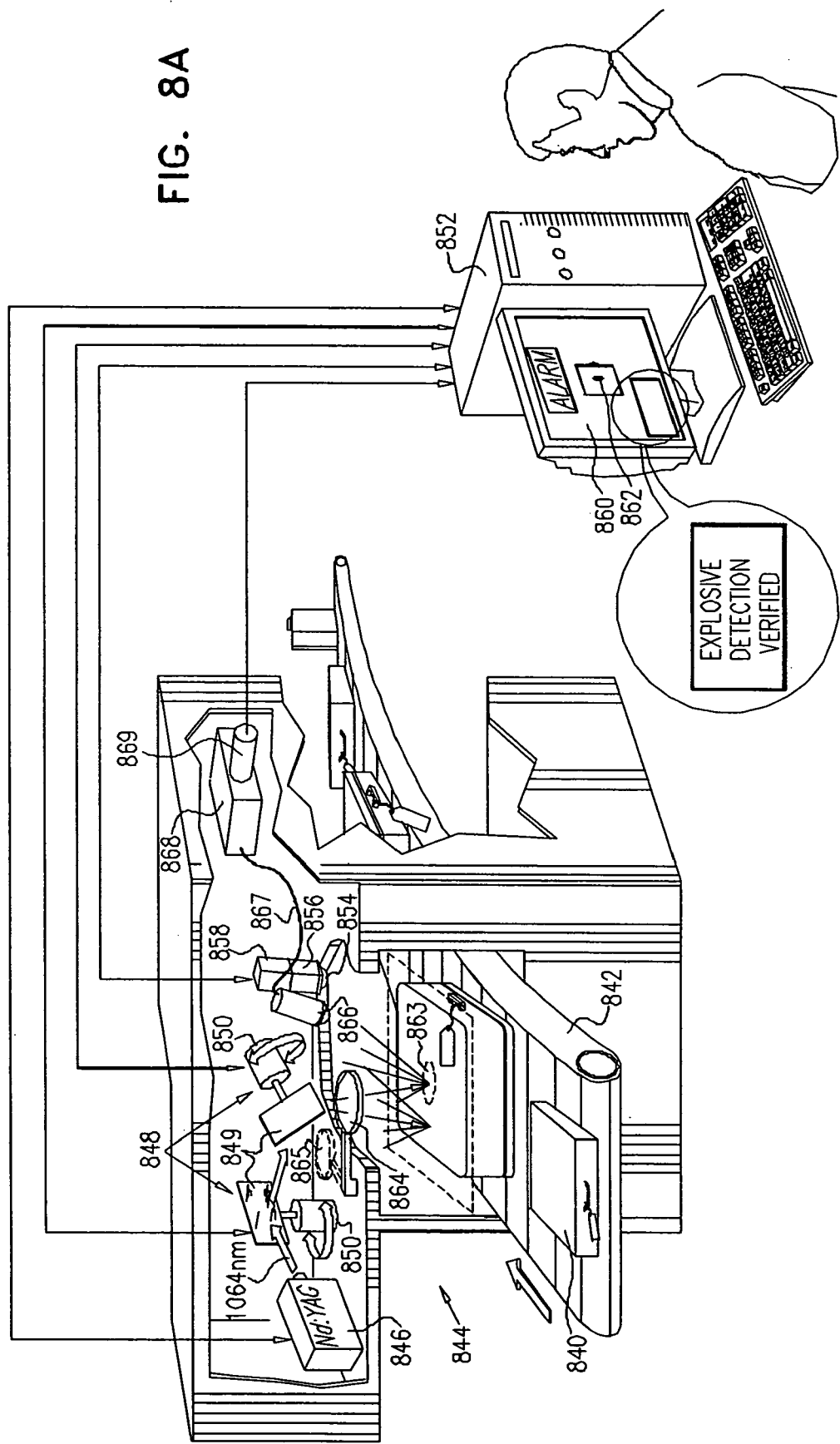
FIGS. 8A, 8B and 8C are simplified pictorial illustrations of imagewise systems for detecting and verifying the presence of explosives on objects constructed and operative in accordance with preferred embodiments of the present invention and employing second harmonic detection and time-resolved laser induced breakdown spectroscopy verification.

Reference is now made to FIG. 8A, which is a simplified pictorial illustration of an imagewise system for detecting and verifying the presence of explosives on objects constructed and operative in accordance with another preferred embodiment of the present invention and employing second harmonic detection and time-resolved laser induced breakdown spectroscopy verification. In the illustrated embodiment, a baggage screening system is shown, it being appreciated that the present invention is not limited to baggage screening applications, but rather may be employed in any other suitable object inspection environment.

In the embodiment of FIG. 8A, baggage, such as suitcases 840, is transported by a conveyor 842 past an inspection station 844 at which the suitcases 840 are inspected. In accordance with a preferred embodiment of the present invention, the inspection station 844 employs a laser 846, preferably a Nd:YAG pulsed laser emitting with a peak wavelength at 1064 nm. It is appreciated that wavelengths in the range of 400 nm to 10 microns may be employed. An output beam of laser 846 impinges on a scanning assembly 848, typically comprising first and second scanning elements 849, such as mirrors, which are driven in rotational motion by motors 850 in synchronization with the pulsed output of laser 846 in response to synchronization signals provided by a computer 852.

The output beam of laser 846 is thus scanned in two dimensions over suitcases 840, inducing second harmonic scattering of the output beam by certain materials, including a number of explosives, should those materials be present on the scanned surfaces of the suitcases 840. The scattered second harmonic of the laser beam is detected via imaging optics 854 and a narrow band spectral filter 856 having a peak wavelength of 532 nm preferably by a gated detector array 858, such as a CCD or CMOS array. Alternatively, the detector array need not be gated, although this is not preferred.

If more than a threshold amount of scattered second harmonic illumination at wavelength 532 nm is received by gated detector array 858 within a predetermined time window during each laser pulse, an alarm indication is provided by computer 852, typically at a display 860. The alarm indication indicates that an explosive material having certain second harmonic scattering characteristics may be present on a surface of the suitcase 840. Display 860 preferably also visually indicates the location of the detected suspect material on the suitcase, here indicated on display 860 at reference numeral 862 and on the suitcase 840 at reference numeral 863.

In accordance with a preferred embodiment of the present invention the system of FIG. 8A also provides verification of detection of an explosive on an object. This verification is preferably provided by employing a selectably positionable lens 864 intermediate the scanning assembly 848 and the suitcase 840. Lens 864 is normally positioned in an inoperative position, indicated in dashed lines at reference numeral 865, during detection, as opposed to verification, operation of the system.

During verification, verification collecting optics 866 are employed for receiving laser induced breakdown emissions from the location or locations of the detected suspect material on the suitcase 840. Lens 864 is operative to concentrate the output beam of the laser 846 on such locations. The output of verification collecting optics 866 is preferably supplied via a fiberoptic link 867 to a polychromator 868, which produces dispersion of the emission spectrum. The output from the polychromator 868 is supplied to a gated detector assembly 869, preferably employing a CCD array. Alternatively, the detector assembly need not be gated, although this is not preferred.

The output of gated detector assembly 869 is analyzed by computer 852 to compare the spectrum represented thereby with reference spectra characteristic of known explosives, in order to provide a verified output indication of the existence of an explosive on the suitcase 840.

Figure 8B:
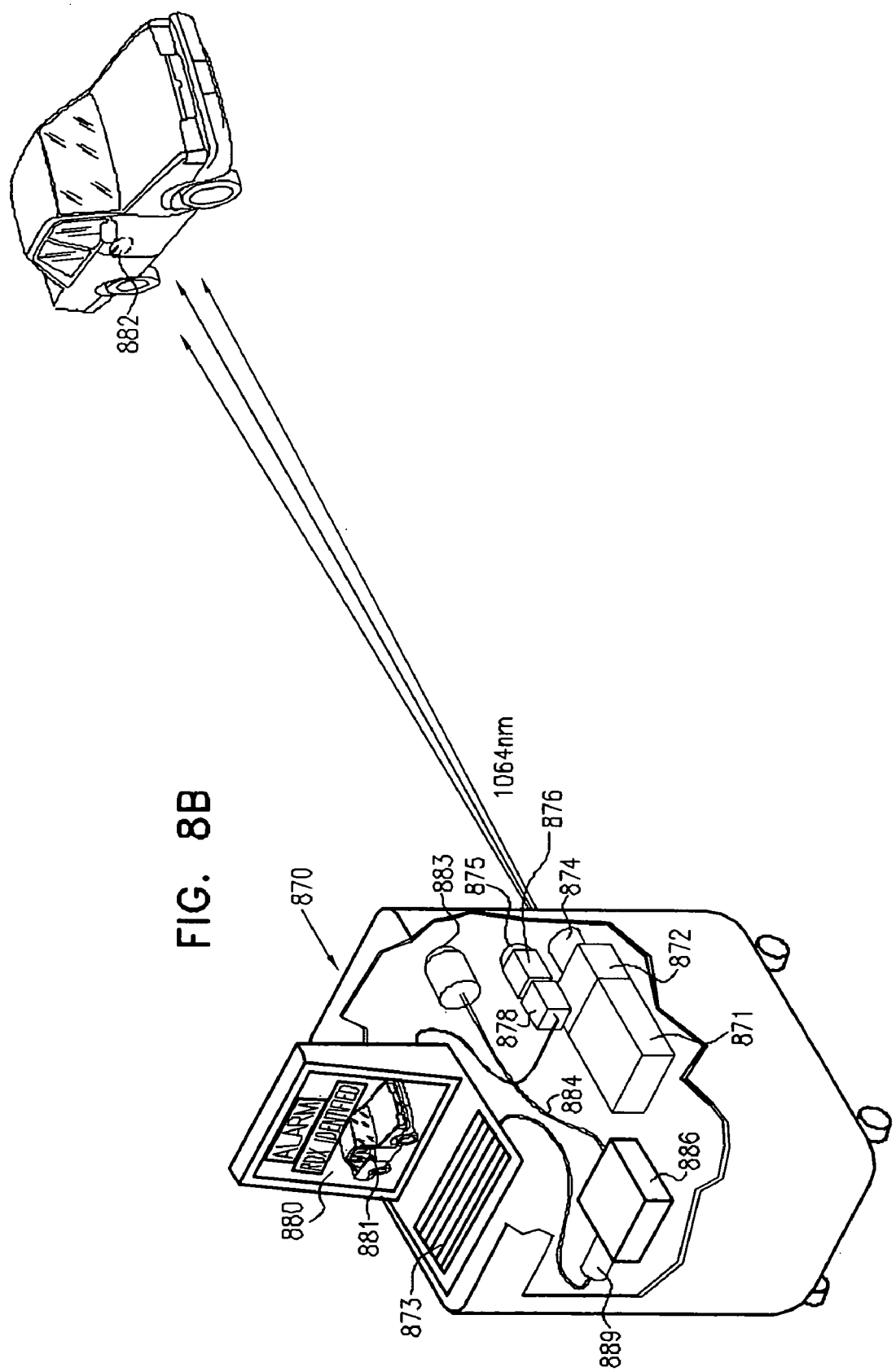

Reference is now made to FIG. 8B, which is a simplified pictorial illustration of an imagewise system for detecting and verifying the presence of explosives on objects constructed and operative in accordance with another preferred embodiment of the present invention and employing second harmonic detection and time-resolved laser induced breakdown spectroscopy verification. In the illustrated embodiment, a vehicle screening system is shown, it being appreciated that the present invention is not limited to vehicle screening applications, but rather may be employed in any other suitable remote object inspection environment.

In the embodiment of FIG. 8B, an inspection assembly 870, which may be portable or stationary, employs a laser 871, preferably a Nd:YAG pulsed laser emitting with a peak wavelength at 1064 nm. It is appreciated that wavelengths in the range of 400 nm to 10 microns may be employed. An output beam of laser 871 impinges on a scanning assembly 872, typically comprising first and second scanning elements (not shown) such as mirrors, which are driven in rotational motion by motors (not shown) in synchronization with the pulsed output of laser 871 in response to synchronization signals provided by a computer 873. The scanned laser beam output of scanning assembly 872 is projected onto a vehicle or other suitable remote object, preferably by a telescope 874.

The output beam of laser 871 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 875 and a narrow band spectral filter 876 having a peak wavelength of 532 nm preferably by a gated detector array 878, such as a CCD or CMOS array. Alternatively, the detector array need not be gated, although this is not preferred.

If more than a threshold amount of scattered second harmonic illumination at wavelength 532 nm is received by gated detector array 878 within a predetermined time window during each laser pulse, an alarm indication is provided by computer 873, typically at a display 880. The alarm indication indicates that an explosive material having certain second harmonic scattering characteristics may be present on a surface of the vehicle. Display 880 preferably also visually indicates the location of the detected suspect material on the vehicle, here indicated on display 880 at reference numeral 881 and on the vehicle at reference numeral 882.

In accordance with a preferred embodiment of the present invention the system of FIG. 8B also provides verification of detection of an explosive on an object. This verification is preferably provided by employing a selectably positionable lens (not shown) that is associated with telescope 874. This lens is normally positioned in an inoperative position during detection, as opposed to verification, operation of the system.

During verification, verification collecting optics 883 are employed for receiving laser induced breakdown emissions from the location or locations of the detected suspect material on the vehicle. The output of verification collecting optics 883 is preferably supplied via a fiberoptic link 884 to a polychromator 886, which produces dispersion of the emission spectrum. The output from the polychromator 886 is supplied to a gated detector assembly 889, preferably employing a CCD array. Alternatively, the detector assembly need not be gated, although this is not preferred.

The output of gated detector assembly 889 is analyzed by computer 873 to compare the spectrum represented thereby with reference spectra characteristic of known explosives, in order to provide a verified output indication of the existence of an explosive on the vehicle.

Figure 8C:
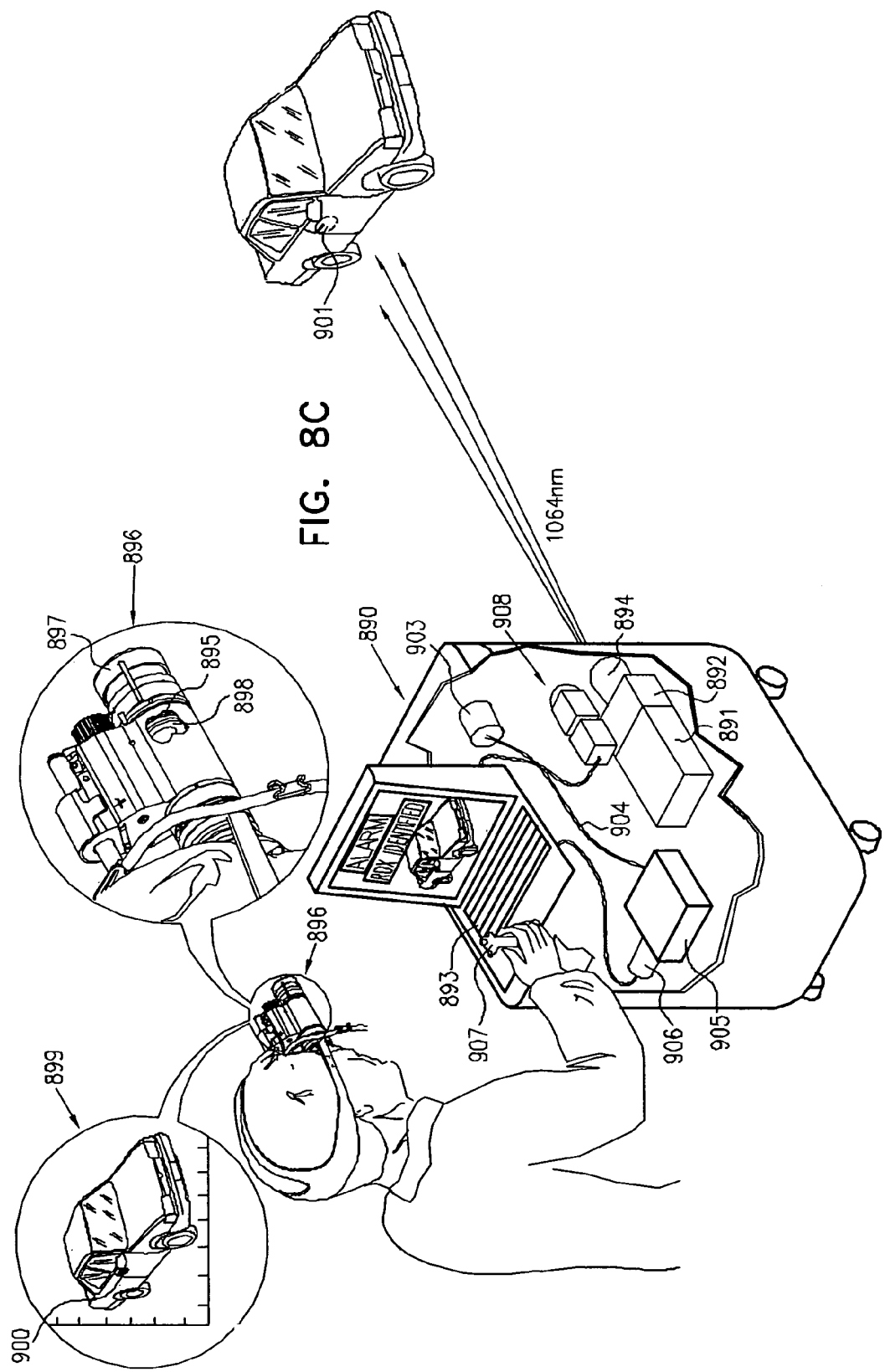

Reference is now made to FIG. 8C, which is a simplified pictorial illustration of an imagewise system for detecting and verifying the presence of explosives on objects constructed and operative in accordance with yet another preferred embodiment of the present invention and employing second harmonic detection and time-resolved laser induced breakdown spectroscopy verification. In the illustrated embodiment, a vehicle screening system is shown, it being appreciated that the present invention is not limited to vehicle screening applications, but rather may be employed in any other suitable remote object inspection environment.

In the embodiment of FIG. 8C, an inspection assembly 890, which is preferably portable, employs a laser 891, preferably a Nd:YAG pulsed laser emitting with a peak wavelength at 1064 nm. It is appreciated that wavelengths in the range of 400 nm to 10 microns may be employed. An output beam of laser 891 impinges on a scanning assembly 892, typically comprising first and second scanning elements (not shown) such as mirrors, which are driven in rotational motion by motors (not shown) in synchronization with the pulsed output of laser 891 in response to synchronization signals provided by a computer 893. The scanned laser beam output of scanning assembly 892 is projected onto a vehicle or other suitable remote object, preferably by a telescope 894.

The output beam of laser 891 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 895 forming part of a head-mounted viewing assembly 896, a narrow band spectral filter 897 having a peak wavelength of 532 nm and an image intensifier 898, all forming part of the head-mounted viewing assembly 896.

In accordance with a preferred embodiment of the present invention the image intensifier 898 is gated by control signals from computer 893 so as to be synchronized with the pulsed output of laser 891. Filter 897 is operative to eliminate transmission of reflected laser radiation at 1064 nm, to attenuate the ambient radiation and to fully transmit the second harmonic scattered radiation at 532 nm. Thus, an operator using the head-mounted viewing assembly 896 sees a scene such as that designated by reference numeral 899, wherein the location on the vehicle of a suspected explosive is highlighted over an ambient background image of the vehicle. The location of the suspected explosive is indicated on scene 899 at reference numeral 900 and on the vehicle at reference numeral 901.

In accordance with a preferred embodiment of the present invention the system of FIG. 8C also provides verification of detection of an explosive on an object. This verification is preferably provided by employing a selectably positionable lens (not shown) that is associated with telescope 894. This lens is normally positioned in an inoperative position during detection, as opposed to verification, operation of the system.

During verification, verification collecting optics 903 are employed for receiving laser induced breakdown emissions from the location or locations of the detected suspect material on the vehicle. The output of verification collecting optics 903 is preferably supplied via a fiberoptic link 904 to a polychromator 905, which produces dispersion of the emission spectrum. The output from the polychromator 905 is supplied to a gated detector assembly 906, preferably employing a CCD array. Alternatively, the detector assembly need not be gated, although this is not preferred.

The verification collecting optics 903 are preferably aimed by an operator at the location of the suspected explosive typically using a joystick 907 and a viewing camera 908 or marker which is visible through the image intensifier 898.

The output of gated detector assembly 906 is analyzed by computer 893 to compare the spectrum represented thereby with reference spectra characteristic of known explosives, in order to provide a verified output indication of the existence of an explosive on the vehicle.

Figure 9A:
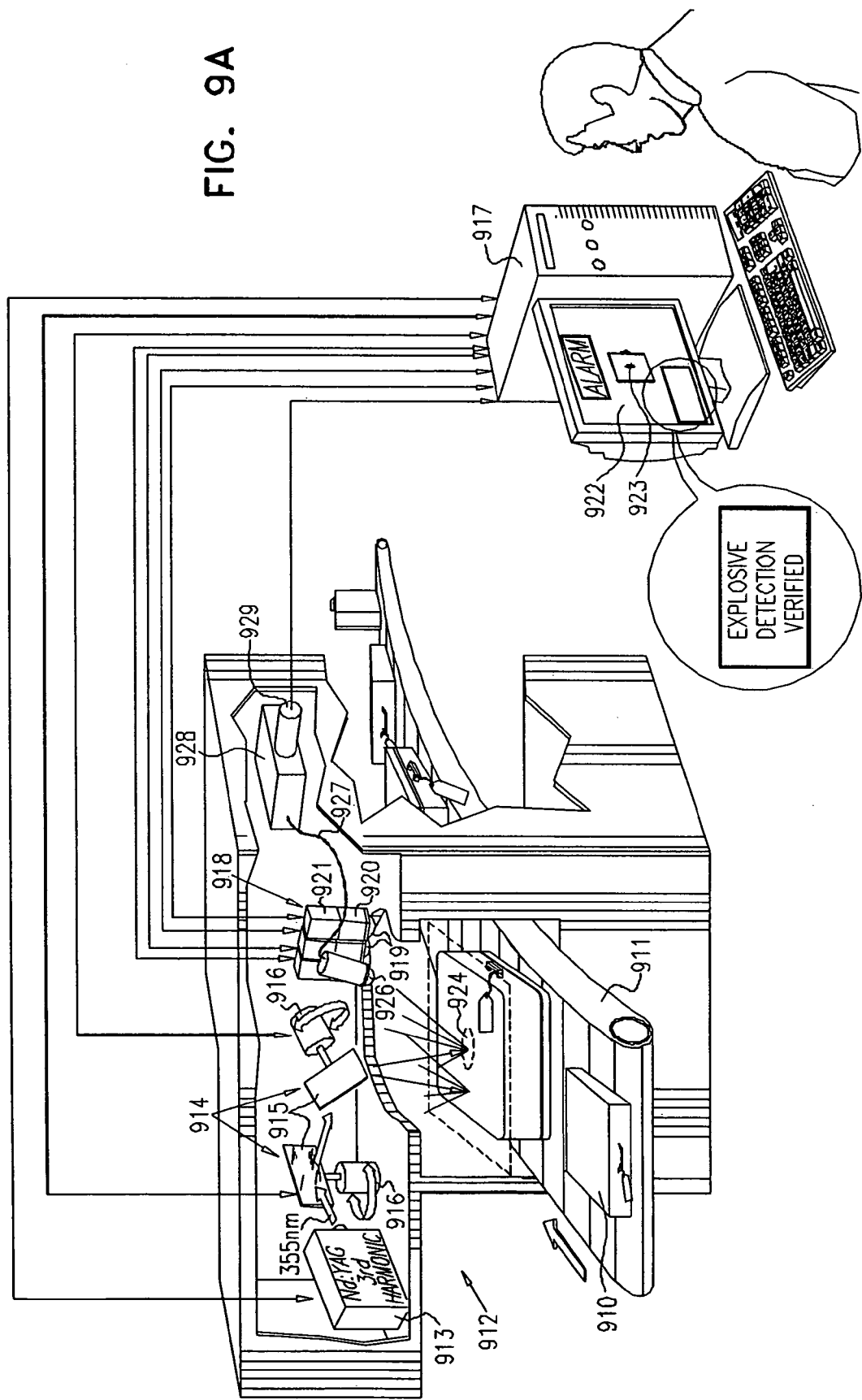

Reference is now made to FIG. 9A, which is a simplified pictorial illustration of an imagewise system for detecting and identifying explosives on objects constructed and operative in accordance with a preferred embodiment of the present invention and employing time-resolved luminescence detection and identification. In the illustrated embodiment, a baggage screening system is shown, it being appreciated that the present invention is not limited to baggage screening applications, but rather may be employed in any other suitable object inspection environment.

In the embodiment of FIG. 9A, baggage, such as suitcases 910, is transported by a conveyor 911 past an inspection station 912 at which the suitcases 910 are inspected. In accordance with a preferred embodiment of the present invention, the inspection station 912 employs a laser 913, preferably a Nd:YAG pulsed laser emitting a third or fourth harmonic having respective peak wavelengths at 355 and 266 nm. It is appreciated that wavelengths in the range of 180 nm to 10 microns may be employed. An output beam of laser 913 impinges on a scanning assembly 914, typically comprising first and second scanning elements 915, such as mirrors, which are driven in rotational motion by motors 916 in synchronization with the pulsed output of laser 913 in response to synchronization signals provided by a computer 917.

The output beam of laser 913 is thus scanned in two dimensions over suitcases 910, inducing luminescence by certain materials, including a number of explosives, should those materials be present on the scanned surfaces of the suitcases 910. The luminescence induced by the laser beam is detected preferably by a plurality of detector assemblies 918, each preferably including imaging optics 919, a spectral filter 920 and a gated detector array 921, such as a CCD or CMOS array. Alternatively, the plurality of detector assemblies 918 may be replaced by a single broadband detector assembly, although this is not preferred. Alternatively, the detector array need not be gated, although this is not preferred.

Preferably, the spectral range of each spectral filter 920 of each detector assembly 918 differs from the spectral range of each other such filter. The following spectral ranges are preferably provided, each by a different spectral filter 920 and corresponding to the following gate intervals:

400–430 nm—10 microseconds

450–540 nm—50 nanoseconds

670–700 nm—100 microseconds.

If more than a threshold amount of luminescence is received by any one or more gated detector 921 within its time window and its spectral range, an alarm indication is provided by computer 917, typically at a display 922. This alarm indication indicates that an explosive material having certain luminescence characteristics may be present on a surface of the suitcase 910. Display 922 preferably also visually indicates the location of the detected suspect material on the suitcase 910, here indicated on display 922 at reference numeral 923 and on the suitcase 910 at reference numeral 924.

In accordance with a preferred embodiment of the present invention the system of FIG. 9A also provides identification of an explosive on an object.

During identification, identification collecting optics 926 are employed for receiving time-resolved luminescence from the location or locations of the detected suspect material on the suitcase 910. During identification, the output beam of laser 913 is thus scanned in two dimensions at the previously determined location or locations 924 of suspect material on suitcases 910.

The output of identification collecting optics 926 is preferably supplied via a fiberoptic link 927 to a polychromator 928, which produces dispersion of the luminescence spectrum. The output from the polychromator 928 is supplied to a gated detector assembly 929, preferably employing a CCD array. Alternatively, the detector assembly need not be gated, although this is not preferred.

The output of gated detector assembly 929 is analyzed by computer 917 to compare the spectrum represented thereby with reference spectra characteristic of known explosives, in order to provide identification of an explosive on the suitcase 910.

Figure 9B:
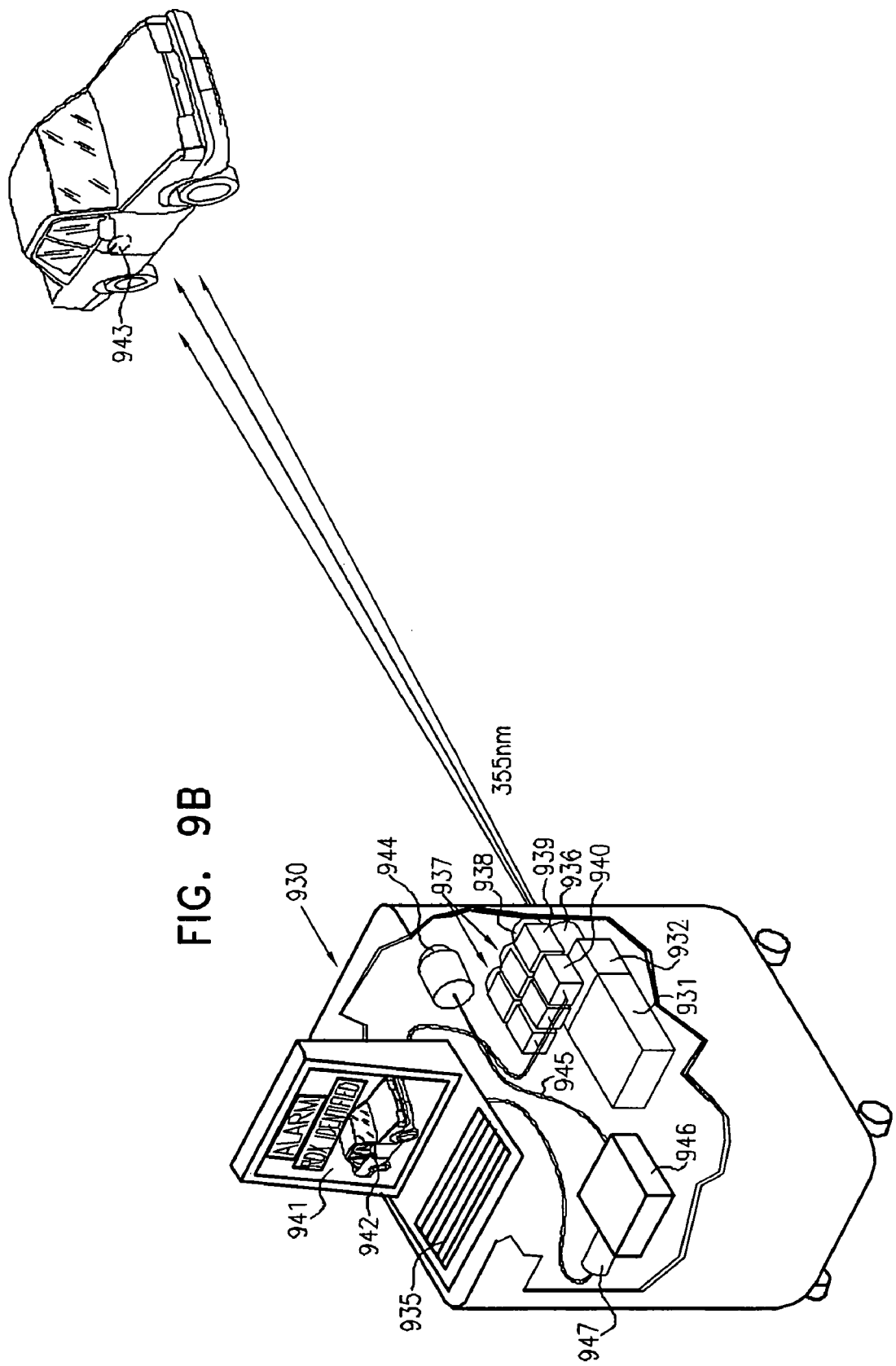

Reference is now made to FIG. 9B, which is a simplified pictorial illustration of an imagewise system for detecting and identifying explosives on objects constructed and operative in accordance with another preferred embodiment of the present invention and employing time-resolved luminescence detection and identification. In the illustrated embodiment, a vehicle screening system is shown, it being appreciated that the present invention is not limited to vehicle screening applications, but rather may be employed in any other suitable remote object inspection environment.

In the embodiment of FIG. 9B, an inspection assembly 930, which may be portable or stationary, employs a laser 931, preferably a Nd:YAG pulsed laser emitting a third or fourth harmonic having respective peak wavelengths at 355 and 266 nm. It is appreciated that wavelengths in the range of 180 nm to 10 microns may be employed. An output beam of laser 931 impinges on a scanning assembly 932, typically comprising first and second scanning elements (not shown), which operate in synchronization with the pulsed output of laser 931 in response to synchronization signals provided by a computer 935. The scanned laser beam output of scanning assembly 932 is projected onto a vehicle or other suitable remote object, preferably by a telescope 936.

The output beam of laser 931 is thus scanned in two dimensions over a vehicle, inducing luminescence by certain materials, including a number of explosives, should those materials be present on the scanned surfaces of the vehicle. The luminescence induced by the laser beam is detected preferably by a plurality of detector assemblies 937, each preferably including imaging optics 938, a spectral filter 939 and a gated detector array 940, such as a CCD or CMOS array. Alternatively, the plurality of detector assemblies 937 may be replaced by a single broadband detector assembly, although this is not preferred. Alternatively, the detector array need not be gated, although this is not preferred.

Preferably, the spectral range of each spectral filter 939 of each detector assembly 937 differs from the spectral range of each other such filter. The following spectral ranges are preferably provided, each by a different spectral filter 939 and corresponding to the following gate intervals:

400–430 nm—10 microseconds
450–540 nm—50 nanoseconds
670–700 nm—100 microseconds.

If more than a threshold amount of luminescence is received by any one or more gated detector in array 940 within its time window and its spectral range, an alarm indication is provided by computer 935, typically at a display 941. This alarm indication indicates that an explosive material having certain luminescence characteristics may be present on a surface of the vehicle. Display 941 preferably also visually indicates the location of the detected suspect material on the vehicle, here indicated on display 941 at reference numeral 942 and on the vehicle at reference numeral 943.

In accordance with a preferred embodiment of the present invention the system of FIG. 9B also provides identification of an explosive on an object.

During identification, identification collecting optics 944 are employed for receiving time-resolved luminescence from the location or locations of the detected suspect material on the vehicle. During identification, the output beam of laser 931 is thus scanned in two dimensions at the previously determined location or locations 943 of suspect material on a vehicle.

The output of identification collecting optics 944 is preferably supplied via a fiberoptic link 945 to a polychromator 946, which produces dispersion of the luminescence spectrum. The output from the polychromator 946 is supplied to a gated detector assembly 947, preferably employing a CCD array. Alternatively, the detector assembly need not be gated, although this is not preferred.

The output of gated detector assembly 947 is analyzed by computer 935 to compare the spectrum represented thereby with reference spectra characteristic of known explosives, in order to provide identification of an explosive on the vehicle.

Reference is now made to FIG. 9C, which is a simplified pictorial illustration of an imagewise system for detecting and identifying explosives on objects constructed and operative in accordance with yet another preferred embodiment of the present invention and employing time-resolved luminescence detection and identification. In the illustrated embodiment, a vehicle screening system is shown, it being appreciated that the present invention is not limited to vehicle screening applications, but rather may be employed in any other suitable remote object inspection environment.

In the embodiment of FIG. 9C, an inspection assembly 955, which is preferably portable, employs a laser 956, preferably a Nd:YAG pulsed laser emitting a third or fourth harmonic having respective peak wavelengths at 355 and 266 nm. It is appreciated that wavelengths in the range of 180 nm to 10 microns may be employed. An output beam of laser 956 impinges on a scanning assembly 957, typically comprising first and second scanning elements (not shown) which are operated in synchronization with the pulsed output of laser 956 in response to synchronization signals provided by a computer 958.

The scanned laser beam output of scanning assembly 957 is projected onto a vehicle or other suitable remote object, preferably by a telescope 959.

The output beam of laser 956 is thus scanned in two dimensions over a vehicle, inducing luminescence by certain materials, including a number of explosives, should those materials be present on the scanned surfaces of the vehicle. The luminescence induced by the laser beam is detected via imaging optics 960 forming part of a head-mounted viewing assembly 961, including at least one and preferably a plurality of individually selectable and interchangeable narrow band spectral filters 962 and an image intensifier 963, all forming part of the head-mounted viewing assembly 961.

Preferably, the spectral range of each spectral filter 962 differs from the spectral range of each other such filter. The following spectral ranges are preferably provided, each by a different spectral filter 962 and corresponding to the following gate intervals:

400–430 nm—10 microseconds
450–540 nm—50 nanoseconds
670–700 nm—100 microseconds.

In accordance with a preferred embodiment of the present invention the image intensifier 963 is gated by control signals from computer 958 so as to be synchronized with the pulsed output of laser 956. Filters 962 are operative to eliminate transmission of reflected laser radiation at 355 nm and 266 nm, to attenuate the ambient radiation and to fully transmit the luminescence. Thus, an operator using the head-mounted viewing assembly 961 sees a scene such as that designated by reference numeral 964, wherein the location on the vehicle of a suspected explosive is highlighted over an ambient background image of the vehicle.

The location of the suspected explosive is indicated on scene 964 at reference numeral 965 and on the vehicle at reference numeral 966.

In accordance with a preferred embodiment of the present invention the system of FIG. 9C also provides identification of an explosive on an object.

During identification, identification collecting optics 967 are employed for receiving time-resolved luminescence from the location or locations of the detected suspect material on the vehicle. During identification, the output beam of laser 956 is thus scanned in two dimensions at the previously determined location or locations 966 of suspect material on a vehicle.

The identification collecting optics 967 are preferably aimed by an operator at the location of the suspected explosive typically using a joystick 968 and a viewing camera 969 or marker which is visible through the image intensifier 963.

The output of identification collecting optics 967 is preferably supplied via a fiberoptic link 970 to a polychromator 972, which produces dispersion of the luminescence spectrum. The output from the polychromator 972 is supplied to a gated detector assembly 974, preferably employing a CCD array. Alternatively, the detector assembly need not be gated, although this is not preferred.

The output of gated detector assembly 974 is analyzed by computer 958 to compare the spectrum represented thereby with reference spectra characteristic of known explosives, in order to provide identification of an explosive on the vehicle.

Figure 10A:
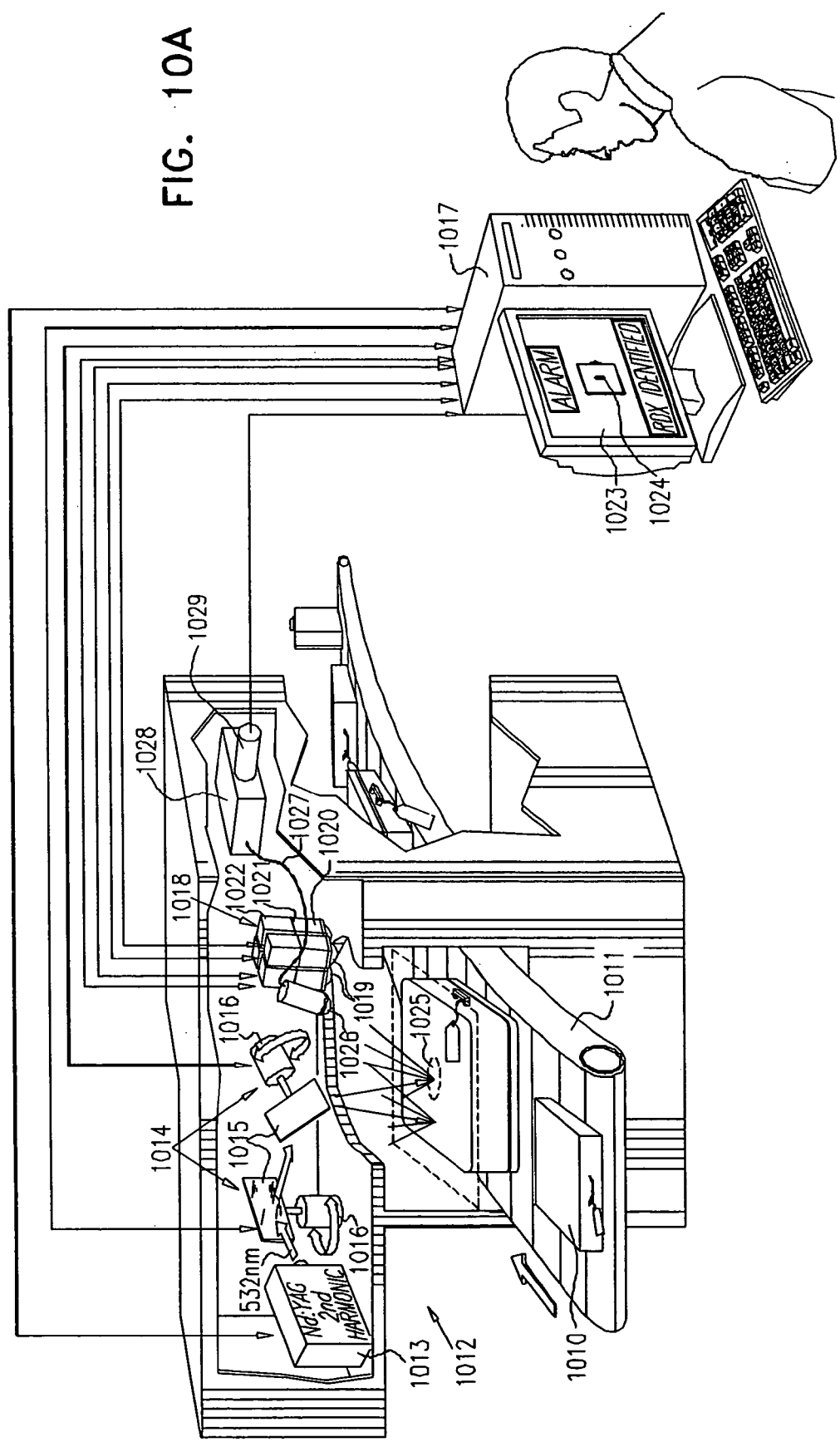

Reference is now made to FIG. 10A, which is a simplified pictorial illustration of an imagewise system for detecting and identifying explosives on objects constructed and operative in accordance with a preferred embodiment of the present invention and employing time-resolved Raman scattering detection and identification. In the illustrated embodiment, a baggage screening system is shown, it being appreciated that the present invention is not limited to baggage screening applications, but rather may be employed in any other suitable object inspection environment.

In the embodiment of FIG. 10A, baggage, such as suitcases 1010, is transported by a conveyor 1011 past an inspection station 1012 at which the suitcases 1010 are inspected. In accordance with a preferred embodiment of the present invention, the inspection station 1012 employs a laser 1013, preferably a Nd:YAG pulsed laser emitting a second harmonic having a peak wavelength at 532 nm. It is appreciated that wavelengths in the range of 200 nm to 10 microns may be employed.

An output beam of laser 1013 impinges on a scanning assembly 1014, typically comprising first and second scanning elements 1015, such as mirrors, which are driven in rotational motion by motors 1016 in synchronization with the pulsed output of laser 1013 in response to synchronization signals provided by a computer 1017.

The output beam of laser 1013 is thus scanned in two dimensions over suitcases 1010, inducing Raman scattering by certain materials, including a number of explosives, should those materials be present on the scanned surfaces of the suitcases 1010. The Raman scattering induced by the laser beam is detected preferably by a plurality of detector assemblies 1018, each preferably including imaging optics 1019, a spectral filter 1020, a notch filter 1021 and a gated detector array 1022, such as a CCD or CMOS array. Alternatively, the plurality of detector assemblies 1018 may be replaced by a single broadband detector assembly, although this is not preferred. Alternatively, the detector array need not be gated, although this is not preferred.

Preferably, the spectral range of each spectral filter 1020 of each detector assembly 1018 differs from the spectral range of each other such filter. The following Raman shifts relative to the laser excitation wavelength are preferably provided, each by a different spectral filter 1020:

880–885 cm (−1)
1360–1365 cm (−1)
1270–1290 cm (−1)
2980–3000 cm (−1).

If more than a threshold amount of Raman scattering is received by any one or more gated detector 1022 within its time window and its spectral range, an alarm indication is provided by computer 1017, typically at a display 1023. This alarm indication indicates that an explosive material having certain Raman scattering characteristics may be present on a surface of the suitcase 1010. Display 1023 preferably also visually indicates the location of the detected suspect material on the suitcase 1010, here indicated on display 1023 at reference numeral 1024 and on the suitcase 1010 at reference numeral 1025.

In accordance with a preferred embodiment of the present invention the system of FIG. 10A also provides identification of an explosive on an object.

During identification, identification collecting optics 1026 are employed for receiving time-resolved Raman scattering from the location or locations of the detected suspect material on the suitcase 1010. During identification, the output beam of laser 1013 is thus scanned in two dimensions at the previously determined location or locations 1025 of suspect material on suitcases 1010.

The output of identification collecting optics 1026 is preferably supplied via a fiberoptic link 1027 to a polychromator 1028, which produces dispersion of the Raman scattering spectrum. The output from the polychromator 1028 is supplied to a gated detector assembly 1029, preferably employing a CCD array. Alternatively, the detector assembly need not be gated, although this is not preferred.

The output of gated detector assembly 1029 is analyzed by computer 1017 to compare the spectrum represented thereby with reference spectra characteristic of known explosives, in order to provide identification of an explosive on the suitcase 1010.

Figure 10B:
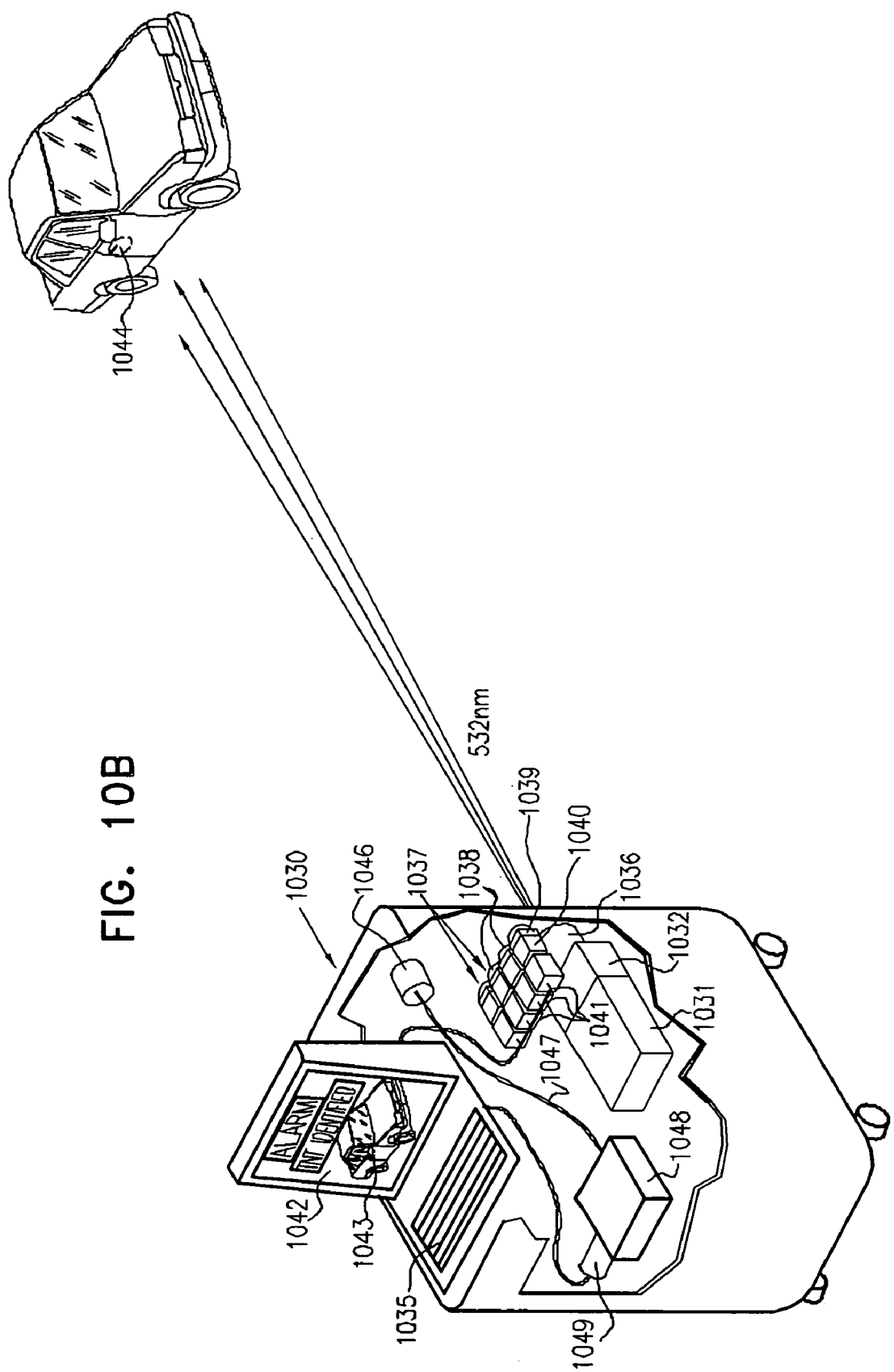

Reference is now made to FIG. 10B, which is a simplified pictorial illustration of an imagewise system for detecting and identifying explosives on objects constructed and operative in accordance with another preferred embodiment of the present invention and employing time-resolved Raman scattering detection and identification. In the illustrated embodiment, a vehicle screening system is shown, it being appreciated that the present invention is not limited to vehicle screening applications, but rather may be employed in any other suitable remote object inspection environment.

In the embodiment of FIG. 10B, an inspection assembly 1030, which may be portable or stationary, employs a laser 1031, preferably a Nd:YAG pulsed laser emitting a second harmonic having a peak wavelength at 532 nm. It is appreciated that wavelengths in the range of 200 nm to 10 microns may be employed. An output beam of laser 1031 impinges on a scanning assembly 1032, typically comprising first and second scanning elements (not shown), which operate in synchronization with the pulsed output of laser 1031 in response to synchronization signals provided by a computer 1035. The scanned laser beam output of scanning assembly 1032 is projected onto a vehicle or other suitable remote object, preferably by a telescope 1036.

The output beam of laser 1031 is thus scanned in two dimensions over a vehicle, inducing Raman scattering by certain materials, including a number of explosives, should those materials be present on the scanned surfaces of the vehicle. The Raman scattering induced by the laser beam is detected preferably by a plurality of detector assemblies 1037, each preferably including imaging optics 1038, a spectral filter 1039, a notch filter 1040 and a gated detector array 1041, such as a CCD or CMOS array. Alternatively, the plurality of detector assemblies 1037 may be replaced by a single broadband detector assembly, although this is not preferred. Alternatively, the detector array need not be gated, although this is not preferred.

Preferably, the spectral range of each spectral filter 1039 of each detector assembly 1037 differs from the spectral range of each other such filter. The following Raman shifts relative to the laser excitation wavelength are preferably provided, each by a different spectral filter 1039:

880–885 cm (−1)
1360–1365 cm (−1)
1270–1290 cm (−1)
2980–3000 cm (−1).

If more than a threshold amount of Raman scattering is received by any one or more gated detector in array 1041 within its time window and its spectral range, an alarm indication is provided by computer 1035, typically at a display 1042. This alarm indication indicates that an explosive material having certain Raman scattering characteristics may be present on a surface of the vehicle. Display 1042 preferably also visually indicates the location of the detected suspect material on the vehicle, here indicated on display 1042 at reference numeral 1043 and on the vehicle at reference numeral 1044.

In accordance with a preferred embodiment of the present invention the system of FIG. 10B also provides identification of an explosive on an object.

During identification, identification collecting optics 1046 are employed for receiving time-resolved Raman scattering from the location or locations of the detected suspect material on the vehicle. During identification, the output beam of laser 1031 is thus scanned in two dimensions at the previously determined location or locations 1044 of suspect material on a vehicle.

The output of identification collecting optics 1046 is preferably supplied via a fiberoptic link 1047 to a polychromator 1048, which produces dispersion of the Raman scattering spectrum. The output from the polychromator 1048 is supplied to a gated detector assembly 1049, preferably employing a CCD array. Alternatively, the detector array need not be gated, although this is not preferred.

The output of gated detector assembly 1049 is analyzed by computer 1035 to compare the spectrum represented thereby with reference spectra characteristic of known explosives, in order to provide identification of an explosive on the vehicle.

Reference is now made to FIG. 10C, which is a simplified pictorial illustration of an imagewise system for detecting and identifying explosives on objects constructed and operative in accordance with yet another preferred embodiment of the present invention and employing time-resolved Raman scattering detection and identification. In the illustrated embodiment, a vehicle screening system is shown, it being appreciated that the present invention is not limited to vehicle screening applications, but rather may be employed in any other suitable remote object inspection environment.

In the embodiment of FIG. 10C, an inspection assembly 1055, which is preferably portable, employs a laser 1056, preferably a Nd:YAG pulsed laser emitting a second harmonic having a peak wavelength at 532 nm. It is appreciated that wavelengths in the range of 200 nm to 10 microns may be employed.

An output beam of laser 1056 impinges on a scanning assembly 1057, typically comprising first and second scanning elements (not shown) which are operated in synchronization with the pulsed output of laser 1056 in response to synchronization signals provided by a computer 1058.

The scanned laser beam output of scanning assembly 1057 is projected onto a vehicle or other suitable remote object, preferably by a telescope 1059.

The output beam of laser 1056 is thus scanned in two dimensions over a vehicle, inducing Raman scattering by certain materials, including a number of explosives, should those materials be present on the scanned surfaces of the vehicle. The Raman scattering induced by the laser beam is detected via imaging optics 1060 forming part of a head-mounted viewing assembly 1061, including at least one and preferably a plurality of individually selectable and interchangeable narrow band spectral filters 1062 and an image intensifier 1064, all forming part of the head-mounted viewing assembly 1061.

Preferably, the spectral range of each spectral filter 1062 of each viewing assembly 1061 differs from the spectral range of each other such filter. The following Raman shifts relative to the laser excitation wavelength are preferably provided, each by a different spectral filter 1062:

880–885 cm (−1)
1360–1365 cm (−1)
1270–1290 cm (−1)
2980–3000 cm (−1).

In accordance with a preferred embodiment of the present invention the image intensifier 1064 is gated by control signals from computer 1058 so as to be synchronized with the pulsed output of laser 1056. Filters 1062 and 1063 are operative to eliminate transmission of reflected laser radiation at 532 nm to attenuate the ambient radiation and to fully transmit the Raman scattering. Thus, an operator using the head-mounted viewing assembly 1061 sees a scene such as that designated by reference numeral 1065, wherein the location on the vehicle of a suspected explosive is highlighted over an ambient background image of the vehicle. The location of the suspected explosive is indicated on scene 1065 at reference numeral 1066 and on the vehicle at reference numeral 1067.

In accordance with a preferred embodiment of the present invention the system of FIG. 10C also provides identification of an explosive on an object.

During identification, identification collecting optics 1080 are employed for receiving time-resolved Raman scattering from the location or locations of the detected suspect material on the vehicle. During identification, the output beam of laser 1056 is thus scanned in two dimensions at the previously determined location or locations 1067 of suspect material on a vehicle.

The identification collecting optics 1080 are preferably aimed by an operator at the location of the suspected explosive typically using a joystick 1081 and a viewing camera 1082 or marker which is visible through the image intensifier 1064.

The output of identification collecting optics 1080 is preferably supplied via a fiberoptic link 1085 to a polychromator 1086, which produces dispersion of the Raman scattering spectrum. The output from the polychromator 1086 is supplied to a gated detector assembly 1087, preferably employing a CCD array. Alternatively, the detector assembly need not be gated, although this is not preferred.

The output of gated detector assembly 1087 is analyzed by computer 1058 to compare the spectrum represented thereby with reference spectra characteristic of known explosives, in order to provide identification of an explosive on the vehicle.

Figure 11A:
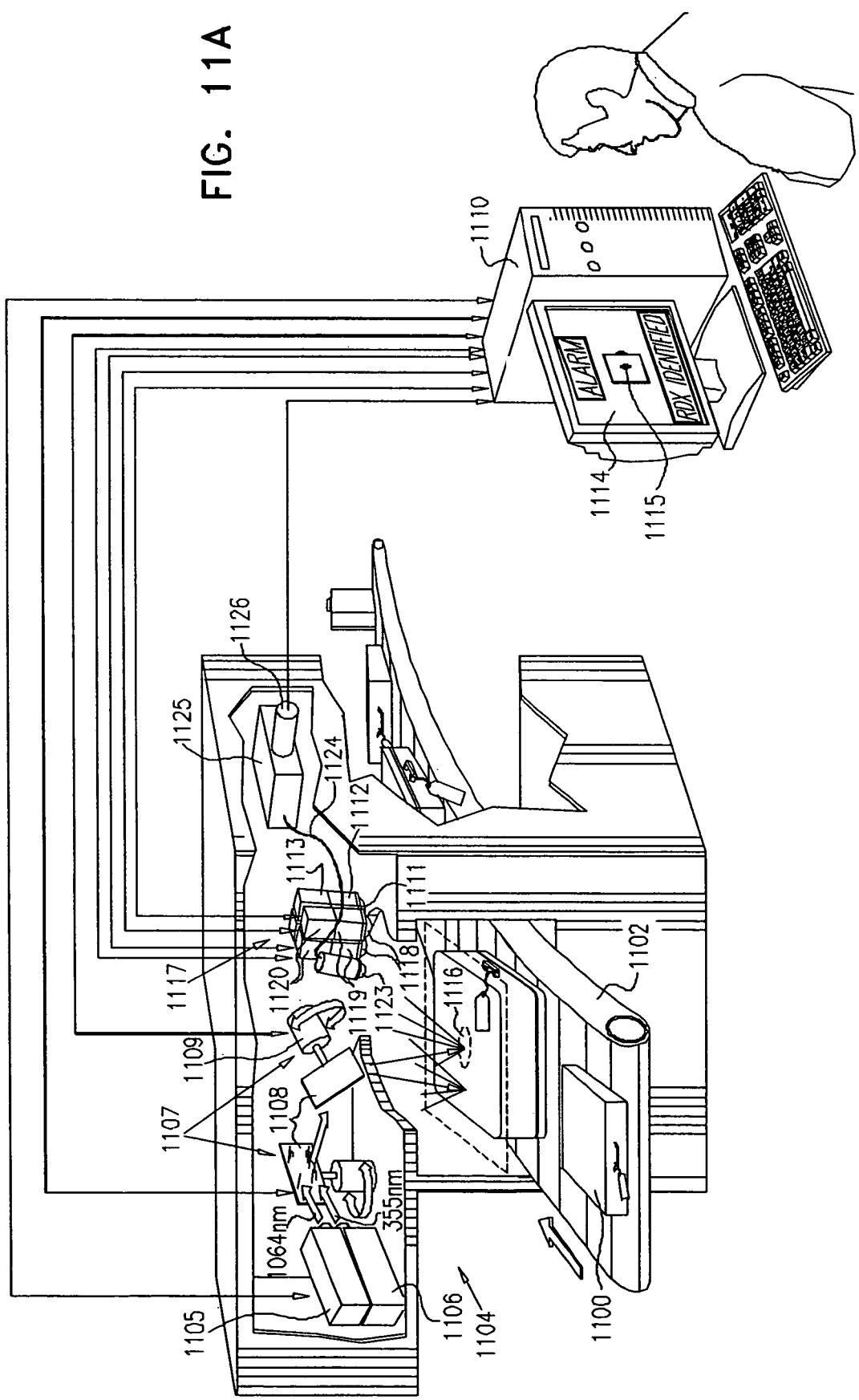

Reference is now made to FIG. 11A, which is a simplified pictorial illustration of an imagewise system for detecting and identifying explosives on objects constructed and operative in accordance with a preferred embodiment of the present invention and employing second harmonic and time-resolved luminescence detection and time-resolved luminescence identification. In the illustrated embodiment, a baggage screening system is shown, it being appreciated that the present invention is not limited to baggage screening applications, but rather may be employed in any other suitable object inspection environment.

In the embodiment of FIG. 1A, baggage, such as suitcases 1100, is transported by a conveyor 1102 past an inspection station 1104 at which the suitcases 1100 are inspected. In accordance with a preferred embodiment of the present invention, the inspection station 1104 employs a first laser 1105, preferably a Nd:YAG pulsed laser emitting with a peak wavelength at 1064 nm. It is appreciated that wavelengths in the range of 400 nm to 10 microns may be employed. The inspection station 1104 preferably also employs a second laser 1106, preferably a Nd:YAG pulsed laser emitting a third or fourth harmonic having respective peak wavelengths at 355 and 266 nm. It is appreciated that wavelengths in the range of 180 nm to 10 microns may be employed. Alternatively, a single laser may be used rather than two lasers.

The output beams of lasers 1105 and 1106 impinge on a scanning assembly 1107, typically comprising first and second scanning elements 1108, such as mirrors, which are driven in rotational motion by motors 1109 in synchronization with the pulsed outputs of lasers 1105 and 1106 in response to synchronization signals provided by a computer 1110.

The output beam of laser 1105 is thus scanned in two dimensions over suitcases 1100, inducing second harmonic scattering of the output beam by certain materials, including a number of explosives, should those materials be present on the scanned surfaces of the suitcases 1100. The scattered second harmonic of the laser beam is detected via imaging optics 1111 and a narrow band spectral filter 1112 having a peak wavelength of 532 nm preferably by a gated detector array 1113, such as a CCD or CMOS array. Alternatively, the detector array need not be gated, although this is not preferred.

If more than a threshold amount of scattered second harmonic illumination at wavelength 532 nm is received by gated detector array 1113 within a predetermined time window during each laser pulse, an alarm indication is provided by computer 1110, typically at a display 1114. The alarm indication indicates that an explosive material having certain second harmonic scattering characteristics may be present on a surface of the suitcase 1100. Display 1114 preferably also visually indicates the location of the detected suspect material on the suitcase 1100, here indicated on display 1114 at reference numeral 1115 and on the suitcase 1100 at reference numeral 1116.

The output beam of second laser 1106 is also scanned in two dimensions over suitcases 1100, inducing luminescence by certain materials, including a number of explosives, should those materials be present on the scanned surfaces of the suitcases 1100. The luminescence induced by the laser beam is detected preferably by a plurality of detector assemblies 1117, each preferably including imaging optics 1118, a spectral filter 1119 and a gated detector array 1120, such as a CCD or CMOS array. Alternatively, the plurality of detector assemblies 1117 may be replaced by a single broadband detector assembly, although this is not preferred. Alternatively, the detector array need not be gated, although this is not preferred.

Preferably, the spectral range of each spectral filter 1119 of each detector assembly 1117 differs from the spectral range of each other such filter. The following spectral ranges are preferably provided, each by a different spectral filter 1119 and corresponding to the following gate intervals:

400–430 nm—10 microseconds
    450–540 nm—50 nanoseconds
    670–700 nm—100 microseconds.

If more than a threshold amount of luminescence is received by any one or more gated detector in gated detector array 1120 within its time window and its spectral range, an alarm indication is provided by computer 1110, typically at display 1114. This alarm indication indicates that an explosive material having certain luminescence characteristics may be present on a surface of the suitcase 1100. Display 1114 preferably also visually indicates, at location 1115 on the display 1114, the location 1116 on the suitcase 1100 of the detected suspect material.

Preferably computer 1110 is operative to analyze and indicate detection of suspect materials on the suitcase 1100 produced in response to excitation by the first and second lasers 1105 and 1106 and the resulting second harmonic scattering and luminescence detection resulting therefrom.

Preferably computer 1110 and display 1114 are operative to superimpose and indicate the spatial relationship between the locations of the detected suspect materials on the suitcase 1100 produced in response to excitation by the first and second lasers 1105 and 1106 and the second harmonic scattering and luminescence detection resulting therefrom.

In accordance with a preferred embodiment of the present invention the system of FIG. 11A also provides identification of an explosive on an object.

During identification, identification collecting optics 1123 are employed for receiving time-resolved luminescence from the location or locations of the detected suspect material on the suitcase 1100. During identification, the output beam of laser 1106 is thus scanned in two dimensions at the previously determined location or locations 1116 of suspect material on suitcases 1100.

The output of identification collecting optics 1123 is preferably supplied via a fiberoptic link 1124 to a polychromator 1125, which produces dispersion of the luminescence spectrum. The output from the polychromator 1125 is supplied to a gated detector assembly 1126, preferably employing a CCD array. Alternatively, the detector assembly need not be gated, although this is not preferred.

The output of gated detector assembly 1126 is analyzed by computer 1110 to compare the spectrum represented thereby with reference spectra characteristic of known explosives, in order to provide identification of an explosive on the suitcase 1100.

Figure 11B:
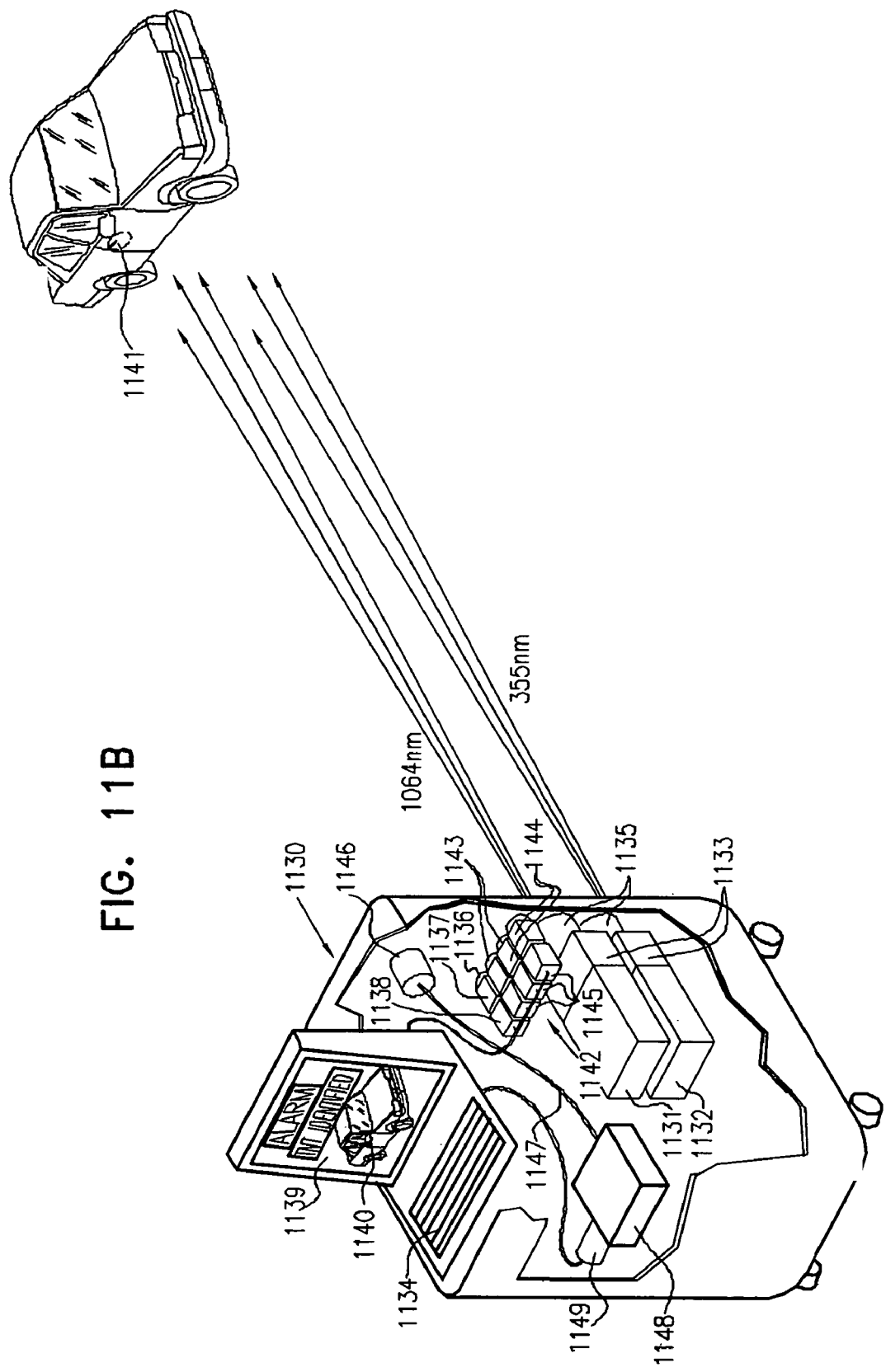

Reference is now made to FIG. 11B, which is a simplified pictorial illustration of an imagewise system for detecting and identifying explosives on objects constructed and operative in accordance with another preferred embodiment of the present invention and employing second harmonic and time-resolved luminescence detection and time-resolved luminescence identification. In the illustrated embodiment, a vehicle screening system is shown, it being appreciated that the present invention is not limited to vehicle screening applications, but rather may be employed in any other suitable remote object inspection environment.

In the embodiment of FIG. 11B, an inspection assembly 1130, which may be portable or stationary, employs a first laser 1131, preferably a Nd:YAG pulsed laser emitting with a peak wavelength at 1064 nm. It is appreciated that wavelengths in the range of 400 nm to 10 microns may be employed. Inspection assembly 1130 preferably also employs a second laser 1132, preferably a Nd:YAG pulsed laser emitting a third or fourth harmonic having respective peak wavelengths at 355 and 266 nm. It is appreciated that wavelengths in the range of 180 nm to 10 microns may be employed. Alternatively, a single laser may be used rather than two lasers.

Output beams of lasers 1131 and 1132 impinge on scanning assemblies 1133, typically comprising first and second scanning elements (not shown) such as mirrors, which are driven in rotational motion by motors (not shown) in synchronization with the pulsed outputs of lasers 1131 and 1132 in response to synchronization signals provided by a computer 1134. The scanned laser beam outputs of scanning assemblies 1133 are projected onto a vehicle or other suitable remote object, preferably by a pair of telescopes 1135.

The output beam of laser 1131 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 1136 and a narrow band spectral filter 1137 having a peak wavelength of 532 nm, preferably by a gated detector array 1138, such as a CCD or CMOS array. Alternatively, the detector array need not be gated, although this is not preferred.

If more than a threshold amount of scattered second harmonic illumination at wavelength 532 nm is received by a detector in gated detector array 1138 within a predetermined time window during each laser pulse, an alarm indication is provided by computer 1134, typically at a display 1139. The alarm indication indicates that an explosive material having certain second harmonic scattering characteristics may be present on a surface of the vehicle. Display 1139 preferably also visually indicates the location of the detected suspect material on the vehicle, here indicated on display 1139 at reference numeral 1140 and on the vehicle at reference numeral 1141.

The output beam of second laser 1132 is thus also scanned in two dimensions over the vehicle, inducing luminescence by certain materials, including a number of explosives, should those materials be present on the scanned surfaces of the vehicle. The luminescence induced by the laser beam is detected preferably by a plurality of detector assemblies 1142, each preferably including imaging optics 1143, a spectral filter 1144 and a gated detector array 1145, such as a CCD or CMOS array. Alternatively, the plurality of detector assemblies 1142 may be replaced by a single broadband detector assembly, although this is not preferred.

Preferably, the spectral range of each spectral filter 1144 of each detector assembly 1142 differs from the spectral range of each other such filter. The following spectral ranges are preferably provided, each by a different spectral filter 1144 and corresponding to the following gate intervals:

400–430 nm—10 microseconds
450–540 nm—50 nanoseconds
670–700 nm—100 microseconds.

If more than a threshold amount of luminescence is received by any one or more gated detector in array 1145 within its time window and its spectral range, an alarm indication is provided by computer 1134, typically at display 1139. This alarm indication indicates that an explosive material having certain luminescence characteristics may be present on a surface of the vehicle. Preferably computer 1134 is operative to analyze and indicate detection of suspect materials on the vehicle produced in response to excitation by the first and second lasers 1131 and 1132 and the resulting second harmonic scattering and luminescence detection resulting therefrom. Display 1139 preferably also visually indicates, at location 1140 on the display 1139, the location 1141 on the vehicle of the detected suspect material.

Preferably computer 1134 and display 1139 are operative to superimpose and indicate the spatial relationship between the locations of the detected suspect materials on the vehicle produced in response to excitation by the first and second lasers 1131 and 1132 and the second harmonic scattering and luminescence detection resulting therefrom.

In accordance with a preferred embodiment of the present invention the system of FIG. 11B also provides identification of an explosive on an object.

During identification, identification collecting optics 1146 are employed for receiving time-resolved luminescence from the location or locations 1141 of the detected suspect material on the vehicle. During identification, the output beam of laser 1132 is thus scanned in two dimensions at the previously determined location or locations 1141 of suspect material on a vehicle.

The output of identification collecting optics 1146 is preferably supplied via a fiberoptic link 1147 to a polychromator 1148, which produces dispersion of the luminescence spectrum. The output from the polychromator 1148 is supplied to a gated detector assembly 1149, preferably employing a CCD array. Alternatively, the detector assembly need not be gated, although this is not preferred.

The output of gated detector assembly 1149 is analyzed by computer 1134 to compare the spectrum represented thereby with reference spectra characteristic of known explosives, in order to provide identification of an explosive on the vehicle.

Reference is now made to FIG. 11C, which is a simplified pictorial illustration of an imagewise system for detecting and identifying explosives on objects constructed and operative in accordance with yet another preferred embodiment of the present invention and employing second harmonic detection and time-resolved luminescence identification. In the illustrated embodiment, a vehicle screening system is shown, it being appreciated that the present invention is not limited to vehicle screening applications, but rather may be employed in any other suitable remote object inspection environment.

In the embodiment of FIG. 11C, an inspection assembly 1150, which is preferably portable, employs a first laser 1151, preferably a Nd:YAG pulsed laser emitting with a peak wavelength at 1064 nm. It is appreciated that wavelengths in the range of 400 nm to 10 microns may be employed. Inspection assembly 1150 preferably also employs a second laser 1152, preferably a Nd:YAG pulsed laser emitting a third or fourth harmonic having respective peak wavelengths at 355 and 266 nm. It is appreciated that wavelengths in the range of 180 nm to 10 microns may be employed. Alternatively, a single laser may be used rather than two lasers.

Output beams of lasers 1151 and 1152 impinge on scanning assemblies 1153, typically comprising first and second scanning elements (not shown) such as mirrors, which are driven in rotational motion by motors (not shown) in synchronization with the pulsed outputs of lasers 1151 and 1152 in response to synchronization signals provided by a computer 1154. The scanned laser beam outputs of scanning assemblies 1153 are projected onto a vehicle or other suitable remote object, preferably by a pair of telescopes 1155.

The output beam of laser 1151 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 1156 forming part of a head-mounted viewing assembly 1157, a narrow band spectral filter 1158 having a peak wavelength of 532 nm and an image intensifier 1159, all forming part of the head-mounted viewing assembly 1157.

In accordance with a preferred embodiment of the present invention the image intensifier 1159 is gated by control signals from computer 1154 so as to be synchronized with the pulsed output of laser 1151. Filter 1158 is operative to eliminate transmission of reflected laser radiation at 1064 nm, to attenuate the ambient radiation and to fully transmit the second harmonic scattered radiation at 532 nm. Thus, an operator using the head-mounted viewing assembly 1157 sees a scene such as that designated by reference numeral 1160, wherein the location on the vehicle of a suspected explosive is highlighted over an ambient background image of the vehicle. The location of the suspected explosive is indicated on scene 1160 at reference numeral 1161 and on the vehicle at reference numeral 1162.

The output beam of laser 1152 is also scanned in two dimensions over the vehicle, inducing luminescence by certain materials, including a number of explosives, should those materials be present on the scanned surfaces of the vehicle. The luminescence induced by the laser beam is detected via imaging optics 1156 forming part of head-mounted viewing assembly 1157, including at least one and preferably a plurality of individually selectable and interchangeable narrow band spectral filters 1158 and image intensifier 1159, all forming part of the head-mounted viewing assembly 1157.

Preferably, the spectral range of each spectral filter 1158 differs from the spectral range of each other such filter. The following spectral ranges are preferably provided, each by a different spectral filter 1158 and corresponding to the following gate intervals:

400–430 nm—10 microseconds
450–540 nm—50 nanoseconds
670–700 nm—100 microseconds.

In accordance with a preferred embodiment of the present invention the image intensifier 1159 is gated by control signals from computer 1154 so as to be synchronized with the pulsed output of laser 1152. Filters 1158 are operative to eliminate transmission of reflected laser radiation at 355 nm and 266 nm, to attenuate the ambient radiation and to fully transmit the luminescence. Thus, an operator using the head-mounted viewing assembly 1157 sees a scene such as scene 1160, wherein location 1162 of a suspected explosive on the vehicle is highlighted on the scene 1160 at location 1161 over an ambient background image of the vehicle.

In accordance with a preferred embodiment of the present invention the system of FIG. 11C also provides identification of an explosive on an object.

During identification, identification collecting optics 1180 are employed for receiving time-resolved luminescence from the location or locations of the detected suspect material on the vehicle. During identification, the output beam of second laser 1152 is scanned in two dimensions at the previously determined location or locations 1162 of suspect material on a vehicle. The identification collecting optics 1180 are preferably aimed by an operator at the location of the suspected explosive typically using a joystick 1181 and a viewing camera 1182 or marker which is visible through the image intensifier 1159.

The output of identification collecting optics 1180 is preferably supplied via a fiberoptic link 1185 to a polychromator 1186, which produces dispersion of the luminescence spectrum. The output from the polychromator 1186 is supplied to a gated detector assembly 1187, preferably employing a CCD array. Alternatively, the detector assembly need not be gated, although this is not preferred.

The output of gated detector assembly 1187 is analyzed by computer 1154 to compare the spectrum represented thereby with reference spectra characteristic of known explosives, in order to provide identification of an explosive on the vehicle.

Figure 12A:
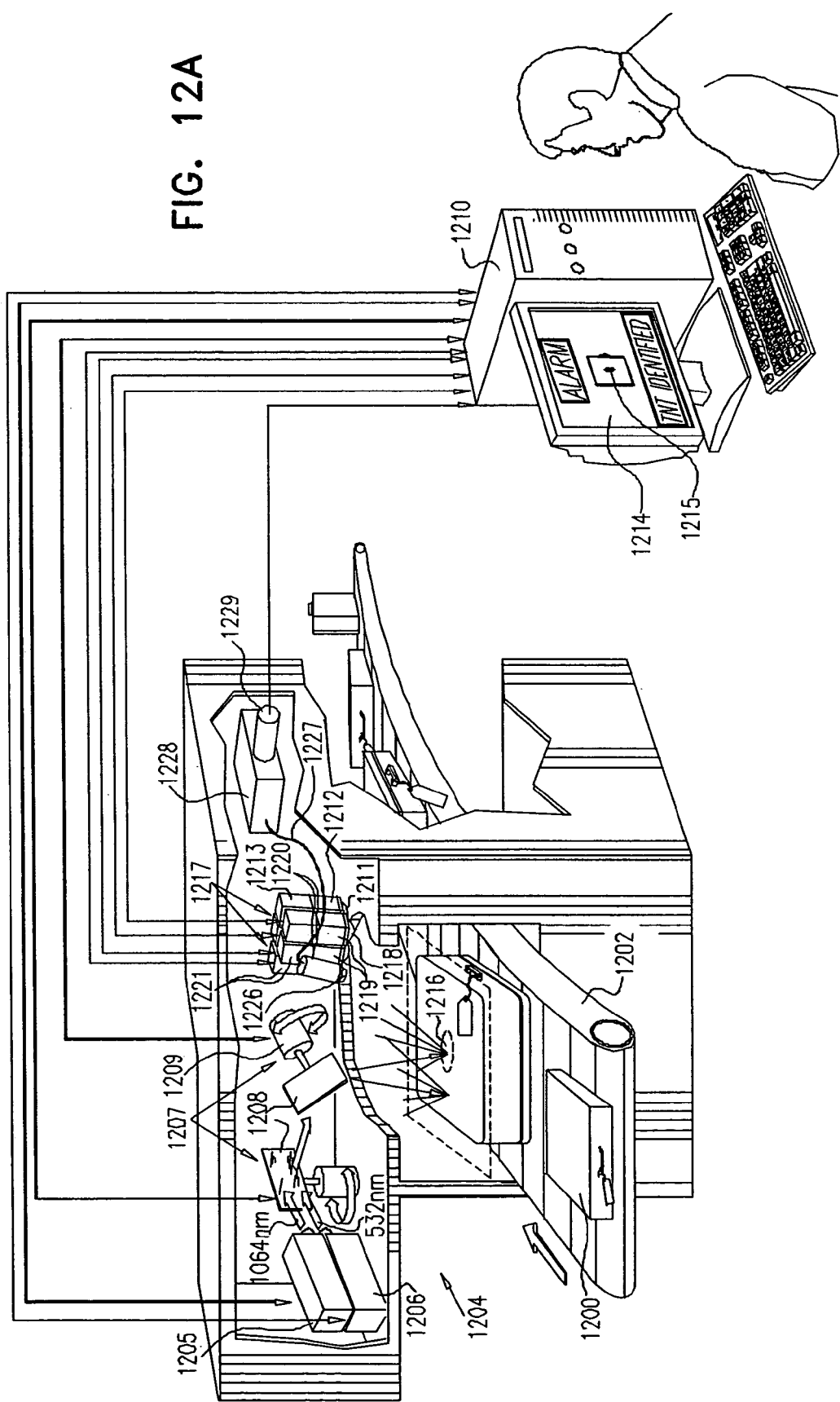

Reference is now made to FIG. 12A, which is a simplified pictorial illustration of an imagewise system for detecting and identifying explosives on objects constructed and operative in accordance with a preferred embodiment of the present invention and employing second harmonic and time-resolved Raman scattering detection and time-resolved Raman scattering identification. In the illustrated embodiment, a baggage screening system is shown, it being appreciated that the present invention is not limited to baggage screening applications, but rather may be employed in any other suitable object inspection environment.

In the embodiment of FIG. 12A, baggage, such as suitcases 1200, is transported by a conveyor 1202 past an inspection station 1204 at which the suitcases 1200 are inspected. In accordance with a preferred embodiment of the present invention, the inspection station 1204 employs a first laser 1205, preferably a Nd:YAG pulsed laser emitting with a peak wavelength at 1064 nm. It is appreciated that wavelengths in the range of 400 nm to 10 microns may be employed. The inspection station 1204 preferably also employs a second laser 1206, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

The output beams of lasers 1205 and 1206 impinge on a scanning assembly 1207, typically comprising first and second scanning elements 1208, such as mirrors, which are driven in rotational motion by motors 1209 in synchronization with the pulsed outputs of lasers 1205 and 1206 in response to synchronization signals provided by a computer 1210.

The output beam of laser 1205 is thus scanned in two dimensions over suitcases 1200, inducing second harmonic scattering of the output beam by certain materials, including a number of explosives, should those materials be present on the scanned surfaces of the suitcases 1200. The scattered second harmonic of the laser beam is detected via imaging optics 1211 and a narrow band spectral filter 1212 having a peak wavelength of 532 nm preferably by a gated detector array 1213, such as a CCD or CMOS array. Alternatively, the detector array need not be gated, although this is not preferred.

If more than a threshold amount of scattered second harmonic illumination at wavelength 532 nm is received by gated detector array 1213 within a predetermined time window during each laser pulse, an alarm indication is provided by computer 1210, typically at a display 1214. The alarm indication indicates that an explosive material having certain second harmonic scattering characteristics may be present on a surface of the suitcase 1200. Display 1214 preferably also visually indicates the location of the detected suspect material on the suitcase 1200, here indicated on display 1214 at reference numeral 1215 and on the suitcase 1200 at reference numeral 1216.

The output beam of second laser 1206 is also scanned in two dimensions over suitcases 1200, inducing Raman scattering by certain materials, including explosives, should those materials be present on the scanned surfaces of the suitcases 1200. The Raman scattering is detected by a plurality of detector assemblies 1217, each preferably including imaging optics 1218, a spectral filter 1219, a notch filter 1220 and a gated detector array 1221, such as a CCD or CMOS array. Alternatively, the plurality of detector assemblies 1217 may be replaced by a single broadband detector assembly, although this is not preferred. Alternatively, the detector array need not be gated, although this is not preferred.

Preferably, the spectral range of each spectral filter 1219 of each detector assembly 1217 differs from the spectral range of each other such filter. The following Raman shifts relative to the laser excitation wavelength are preferably provided, each by a different spectral filter 1219:

880–885 cm (−1)
1360–1365 cm (−1)
1270–1290 cm (−1)
2980–3000 cm (−1).

If more than a threshold amount of Raman scattering is received by any one or more gated detector in array 1221 during the time interval of the laser excitation pulse and its spectral range, an alarm indication is provided by computer 1210, typically at display 1214. This alarm indication indicates that an explosive material having certain Raman scattering characteristics may be present on a surface of the suitcase 1200. Display 1214 preferably also visually indicates, at location 1215 on the display 1214, the location 1216 on the suitcase 1200 of the detected suspect material.

Preferably computer 1210 and display 1214 are operative to superimpose and indicate the spatial relationship between the locations of the detected suspect materials on the suitcase 1200 produced in response to excitation by the first and second lasers 1205 and 1206 and the second harmonic scattering and luminescence detection resulting therefrom.

In accordance with a preferred embodiment of the present invention the system of FIG. 12A also provides identification of an explosive on an object.

During identification, identification collecting optics 1226 are employed for receiving time-resolved Raman scattering from the location or locations of the detected suspect material on the suitcase 1200. During identification, the output beam of laser 1206 is thus scanned in two dimensions at the previously determined location or locations 1216 of suspect material on suitcases 1200.

The output of identification collecting optics 1226 is preferably supplied via a fiberoptic link 1227 to a polychromator 1228, which produces dispersion of the Raman scattering spectrum. The output from the polychromator 1228 is supplied to a gated detector assembly 1229, preferably employing a CCD array. Alternatively, the detector assembly need not be gated, although this is not preferred.

The output of gated detector assembly 1229 is analyzed by computer 1210 to compare the spectrum represented thereby with reference spectra characteristic of known explosives, in order to provide identification of an explosive on the suitcase 1200.

Reference is now made to FIG. 12B, which is a simplified pictorial illustration of an imagewise system for detecting and identifying explosives on objects constructed and operative in accordance with another preferred embodiment of the present invention and employing second harmonic and time-resolved Raman scattering detection and time-resolved Raman scattering identification. In the illustrated embodiment, a vehicle screening system is shown, it being appreciated that the present invention is not limited to vehicle screening applications, but rather may be employed in any other suitable remote object inspection environment.

In the embodiment of FIG. 12B, an inspection assembly 1230, which may be portable or stationary, employs a first laser 1231, preferably a Nd:YAG pulsed laser emitting with a peak wavelength at 1064 nm. It is appreciated that wavelengths in the range of 400 nm to 10 microns may be employed. Inspection assembly 1230 preferably also employs a second laser 1232, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

Output beams of lasers 1231 and 1232 impinge on scanning assemblies 1233, typically comprising first and second scanning elements (not shown) such as mirrors, which are driven in rotational motion by motors (not shown) in synchronization with the pulsed outputs of lasers 1231 and 1232 in response to synchronization signals provided by a computer 1234. The scanned laser beam outputs of scanning assemblies 1233 are projected onto a vehicle or other suitable remote object, preferably by a pair of telescopes 1235.

The output beam of laser 1231 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 1236 and a narrow band spectral filter 1237 having a peak wavelength of 532 nm, preferably by a gated detector array 1238, such as a CCD or CMOS array. Alternatively, the detector array need not be gated, although this is not preferred.

If more than a threshold amount of scattered second harmonic illumination at wavelength 532 nm is received by gated detector array 1238 within a predetermined time window during each laser pulse, an alarm indication is provided by computer 1234, typically at a display 1239. The alarm indication indicates that an explosive material having certain second harmonic scattering characteristics may be present on a surface of the vehicle. Display 1239 preferably also visually indicates the location of the detected suspect material on the vehicle, here indicated on display 1239 at reference numeral 1240 and on the vehicle at reference numeral 1241.

The output beam of second laser 1232 is thus also scanned in two dimensions over the vehicle, inducing Raman scattering by certain materials, including explosives, should those materials be present on the scanned surfaces of the vehicle. The Raman scattering is detected by a plurality of detector assemblies 1242, each preferably including imaging optics 1243, a spectral filter 1244, a notch filter 1245 and a gated detector array 1246, such as a CCD or CMOS array.

Alternatively, the plurality of detector assemblies 1242 may be replaced by a single broadband detector assembly, although this is not preferred. Alternatively, the detector array need not be gated, although this is not preferred.

Preferably, the spectral range of each spectral filter 1244 of each detector assembly 1242 differs from the spectral range of each other such filter. The following Raman shifts relative to the laser excitation wavelength are preferably provided, each by a different spectral filter 1244:

880–885 cm (−1)
1360–1365 cm (−1)
1270–1290 cm (−1)
2980–3000 cm (−1).

If more than a threshold amount of Raman scattering is received by any one or more gated detector of array 1246 during the time interval of the laser excitation pulse and its spectral range, an alarm indication is provided by computer 1234, typically at display 1239. This alarm indication indicates that an explosive material having certain Raman scattering characteristics may be present on a surface of the vehicle. Display 1239 preferably also visually indicates, at location 1240 on the display 1239, the location 1241 on the vehicle of the detected suspect material.

Preferably computer 1234 is operative to analyze and indicate detection of suspect materials on the vehicle produced in response to excitation by the first and second lasers 1231 and 1232 and the resulting second harmonic scattering and Raman scattering detection resulting therefrom.

Preferably computer 1234 and display 1239 are operative to superimpose and indicate the spatial relationship between the locations of the detected suspect materials on the vehicle produced in response to excitation by the first and second lasers 1231 and 1232 and the second harmonic scattering and Raman scattering detection resulting therefrom.

In accordance with a preferred embodiment of the present invention the system of FIG. 12B also provides identification of an explosive on an object.

During identification, identification collecting optics 1247 are employed for receiving time-resolved Raman scattering from the location or locations 1241 of the detected suspect material on the vehicle. During identification, the output beam of laser 1232 is thus scanned in two dimensions at the previously determined location or locations 1241 of suspect material on a vehicle.

The output of identification collecting optics 1247 is preferably supplied via a fiberoptic link 1248 to a polychromator 1249, which produces dispersion of the Raman scattering spectrum. The output from the polychromator 1249 is supplied to a gated detector assembly 1250, preferably employing a CCD array. Alternatively, the detector assembly need not be gated, although this is not preferred.

The output of gated detector assembly 1250 is analyzed by computer 1234 to compare the spectrum represented thereby with reference spectra characteristic of known explosives, in order to provide identification of an explosive on the vehicle.

Reference is now made to FIG. 12C, which is a simplified pictorial illustration of an imagewise system for detecting and identifying explosives on objects constructed and operative in accordance with yet another preferred embodiment of the present invention and employing second harmonic and time-resolved Raman scattering detection and time-resolved Raman scattering identification. In the illustrated embodiment, a vehicle screening system is shown, it being appreciated that the present invention is not limited to vehicle screening applications, but rather may be employed in any other suitable remote object inspection environment.

In the embodiment of FIG. 12C, an inspection assembly 1251, which is preferably portable, employs a first laser 1252, preferably a Nd:YAG pulsed laser emitting with a peak wavelength at 1064 nm. It is appreciated that wavelengths in the range of 400 nm to 10 microns may be employed. Inspection assembly 1251 preferably also employs a second laser 1253, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

Output beams of lasers 1252 and 1253 impinge on scanning assemblies 1254, typically comprising first and second scanning elements (not shown) such as mirrors, which are driven in rotational motion by motors (not shown) in synchronization with the pulsed outputs of lasers 1252 and 1253 in response to synchronization signals provided by a computer 1255. The scanned laser beam outputs of scanning assemblies 1254 are projected onto a vehicle or other suitable remote object, preferably by a pair of telescopes 1256.

The output beam of laser 1252 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 1257 forming part of a head-mounted viewing assembly 1258, a narrow band spectral filter 1259 having a peak wavelength of 532 nm and an image intensifier 1260, all forming part of the head-mounted viewing assembly 1258.

In accordance with a preferred embodiment of the present invention the image intensifier 1260 is gated by control signals from computer 1255 so as to be synchronized with the pulsed output of laser 1252. Filter 1259 is operative to eliminate transmission of reflected laser radiation at 1064 nm, to attenuate the ambient radiation and to fully transmit the second harmonic scattered radiation at 532 nm. Thus, an operator using the head-mounted viewing assembly 1258 sees a scene such as that designated by reference numeral 1261, wherein the location on the vehicle of a suspected explosive is highlighted over an ambient background image of the vehicle. The location of the suspected explosive is indicated on scene 1261 at reference numeral 1262 and on the vehicle at reference numeral 1263.

The output beam of laser 1253 is also scanned in two dimensions over the vehicle, inducing Raman scattering by certain materials, including explosives, should those materials be present on the scanned surfaces of the vehicle. The Raman scattering induced by the laser beam is detected via imaging optics 1257 forming part of a head-mounted viewing assembly 1258, at least one and preferably a plurality of narrow band spectral filters 1259 and image intensifier 1260, all forming part of the head-mounted viewing assembly 1258.

Preferably, the spectral range of each spectral filter 1259 differs from the spectral range of each other such filter. The following Raman shifts relative to the laser excitation wavelength are preferably provided, each by a different spectral filter 1259:

880–885 cm (−1)
1360–1365 cm (−1)
1270–1290 cm (−1)
2980–3000 cm (−1).

In accordance with a preferred embodiment of the present invention the image intensifier 1260 is gated by control signals from computer 1255 to operate during the time interval of the laser excitation pulse. Thus, an operator using the head-mounted viewing assembly 1258 sees a scene such as scene 1261, wherein location 1263 of a suspected explosive on the vehicle is highlighted on the scene 1261 at location 1262 over an ambient background image of the vehicle.

In accordance with a preferred embodiment of the present invention the system of FIG. 12C also provides identification of an explosive on an object.

During identification, identification collecting optics 1280 are employed for receiving time-resolved Raman scattering from the location or locations of the detected suspect material on the vehicle. During identification, the output beam of laser 1253 is thus scanned in two dimensions at the previously determined location or locations 1263 of suspect material on a vehicle.

The identification collecting optics 1280 are preferably aimed by an operator at the location of the suspected explosive typically using a joystick 1281 and a viewing camera 1282 or marker which is visible through the image intensifier 1260.

The output of identification collecting optics 1280 is preferably supplied via a fiberoptic link 1285 to a polychromator 1286 which produces dispersion of the Raman scattering spectrum. The output from the polychromator 1286 is supplied to a gated detector assembly 1287, preferably employing a CCD array. Alternatively, the detector assembly need not be gated, although this is not preferred.

The output of gated detector assembly 1287 is analyzed by computer 1255 to compare the spectrum represented thereby with reference spectra characteristic of known explosives, in order to provide identification of an explosive on the vehicle.

Figure 13A:
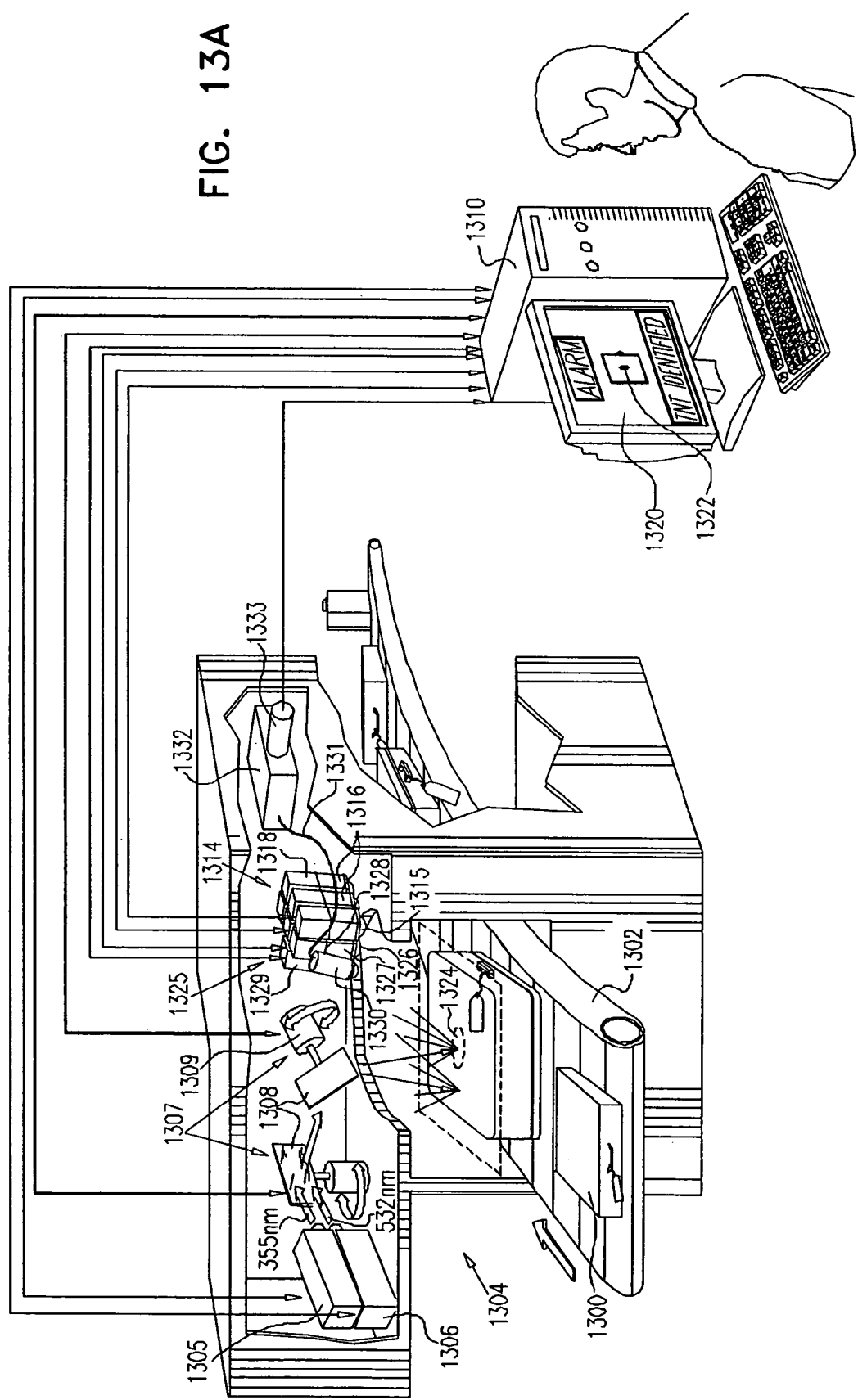
FIGS. 13A, 13B and 13C are simplified pictorial illustrations of dual mode systems for detecting and identifying explosives constructed and operative in accordance with preferred embodiments of the present invention and employing time-resolved luminescence and time-resolved Raman detection and employing time-resolved luminescence and time-resolved Raman identification.

Reference is now made to FIG. 13A, which is a simplified pictorial illustration of a dual mode system for detecting and identifying explosives constructed and operative in accordance with a preferred embodiment of the present invention and employing time-resolved luminescence and time-resolved Raman detection and employing time-resolved luminescence and time-resolved Raman identification. In the illustrated embodiment, a baggage screening system is shown, it being appreciated that the present invention is not limited to baggage screening applications, but rather may be employed in any other suitable object inspection environment.

In the embodiment of FIG. 13A, baggage, such as suitcases 1300, is transported by a conveyor 1302 past an inspection station 1304 at which the suitcases 1300 are inspected. In accordance with a preferred embodiment of the present invention, the inspection station 1304 employs a first laser 1305, preferably a Nd:YAG pulsed laser emitting a third or fourth harmonic having respective peak wavelengths at 355 and 266 nm. It is appreciated that wavelengths in the range of 180 nm to 10 microns may be employed. The inspection station 1304 preferably also employs a second laser 1306, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

The output beams of lasers 1305 and 1306 impinge on a scanning assembly 1307, typically comprising first and second scanning elements 1308, such as mirrors, which are driven in rotational motion by motors 1309 in synchronization with the pulsed outputs of lasers 1305 and 1306 in response to synchronization signals provided by a computer 1310.

The output beam of laser 1305 is thus scanned in two dimensions over suitcases 1300, inducing luminescence by certain materials, including a number of explosives, should those materials be present on the scanned surfaces of the suitcases 1300. The luminescence induced by the laser beam is detected preferably by a plurality of detector assemblies 1314, each preferably including imaging optics 1315, a spectral filter 1316 and a gated detector array 1318, such as a CCD or CMOS array. Alternatively, the plurality of detector assemblies 1314 may be replaced by a single broadband detector assembly, although this is not preferred. Alternatively, the detector array need not be gated, although this is not preferred.

Preferably, the spectral range of each spectral filter 1316 of each detector assembly 1314 differs from the spectral range of each other such filter. The following spectral ranges are preferably provided, each by a different spectral filter 1316 and corresponding to the following gate intervals:

400–430 nm—10 microseconds
450–540 nm—50 nanoseconds
670–700 nm—100 microseconds.

If more than a threshold amount of luminescence is received by any one or more gated detector 1318 within its time window and its spectral range, an alarm indication is provided by computer 1310, typically at a display 1320. This alarm indication indicates that an explosive material having certain luminescence characteristics may be present on a surface of the suitcase 1300. Display 1320 preferably also visually indicates the location of the detected suspect material on the suitcase 1300, here indicated on display 1320 at reference numeral 1322 and on the suitcase 1300 at reference numeral 1324.

The output beam of second laser 1306 is also scanned in two dimensions over suitcases 1300, inducing Raman scattering by certain materials, including explosives, should those materials be present on the scanned surfaces of the suitcases 1300. The Raman scattering is detected by a plurality of detector assemblies 1325 each preferably including imaging optics 1326, a spectral filter 1327, a notch filter 1328 and a gated detector array 1329, such as a CCD or CMOS array. Alternatively, the plurality of detector assemblies 1325 may be replaced by a single broadband detector assembly, although this is not preferred. Alternatively, the detector array need not be gated, although this is not preferred.

Preferably, the spectral range of each spectral filter 1327 of each detector assembly 1325 differs from the spectral range of each other such filter. The following Raman shifts relative to the laser excitation wavelength are preferably provided, each by a different spectral filter 1327:

880–885 cm (−1)
1360–1365 cm (−1)
1270–1290 cm (−1)
2980–3000 cm (−1).

If more than a threshold amount of Raman scattering is received by any one or more gated detector in array 1329 during the time interval of the laser excitation pulse and its spectral range, an alarm indication is provided by computer 1310, typically at display 1320. This alarm indication indicates that an explosive material having certain Raman scattering characteristics may be present on a surface of the suitcase 1300. Display 1320 preferably also visually indicates, at location 1322 on the display 1320, the location 1324 on the suitcase 1300 of the detected suspect material.

Preferably computer 1310 and display 1320 are operative to superimpose and indicate the spatial relationship between the locations of the detected suspect materials on the suitcase 1300 produced in response to excitation by the first and second lasers 1305 and 1306 and the time-resolved luminescence and time-resolved Raman scattering detection resulting therefrom.

In accordance with a preferred embodiment of the present invention, the system of FIG. 13A also provides identification of an explosive on an object.

During identification, identification collecting optics 1330 are employed for receiving time-resolved luminescence and time-resolved Raman scattering from the location or locations of the detected suspect material on the suitcase 1300. During identification, the output beams of lasers 1305 and 1306 are thus scanned in two dimensions at the previously determined location or locations 1324 of suspect material on suitcases 1300.

The output of identification collecting optics 1330 is preferably supplied via a fiberoptic link 1331 to a polychromator 1332, which produces dispersion of the luminescence and Raman spectra. The output from the polychromator 1332 is supplied to a gated detector assembly 1333, preferably employing a CCD array. Alternatively, the detector assembly need not be gated, although this is not preferred.

The output of gated detector assembly 1333 is analyzed by computer 1310 to compare the spectrum represented thereby with reference spectra characteristic of known explosives, in order to provide identification of an explosive on the suitcase 1300.

Figure 13B:
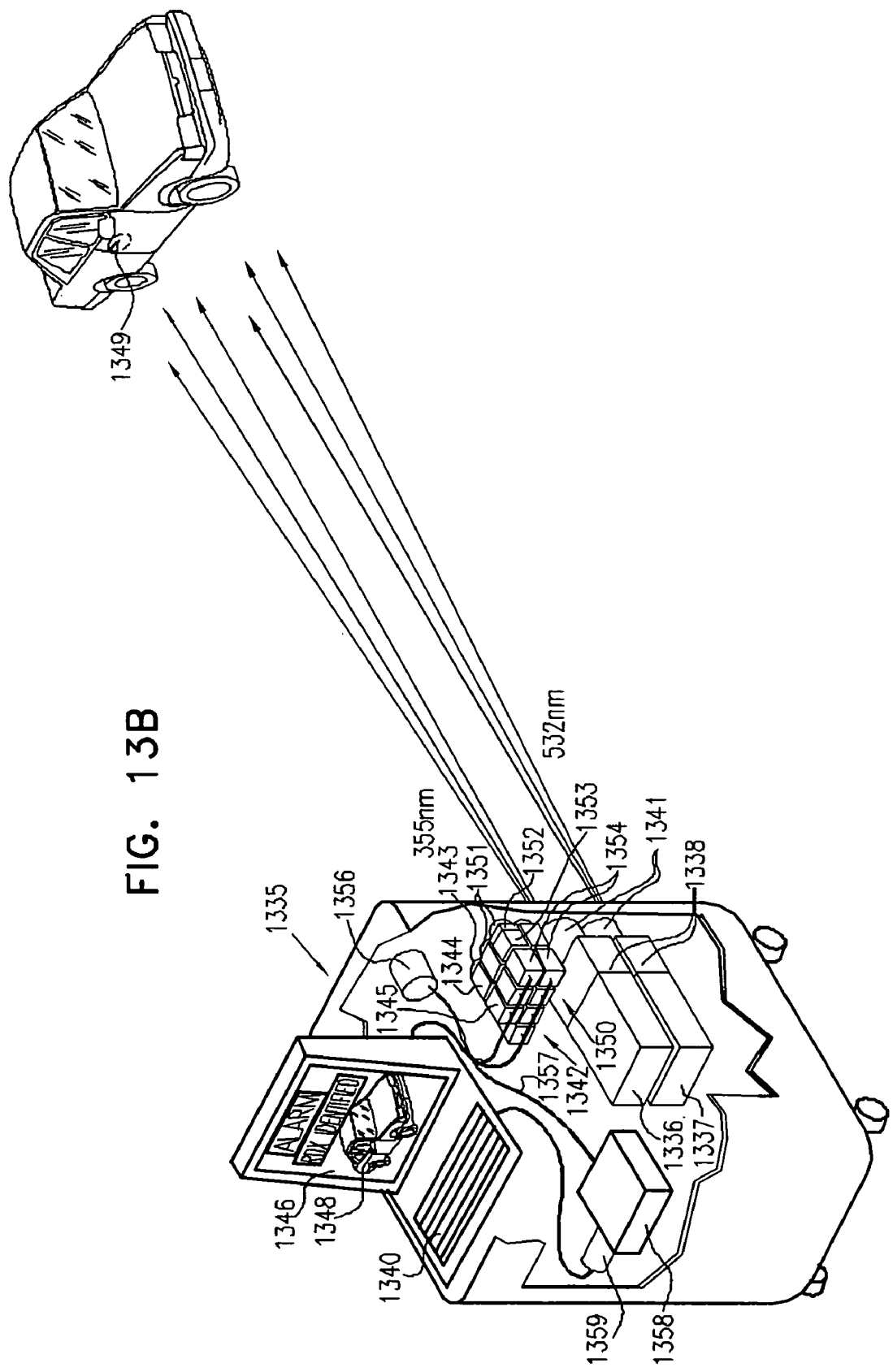

Reference is now made to FIG. 13B, which is a simplified pictorial illustration of a dual mode system for detecting and identifying explosives constructed and operative in accordance with another preferred embodiment of the present invention and employing time-resolved luminescence and time-resolved Raman detection and employing time-resolved luminescence and time-resolved Raman identification. In the illustrated embodiment, a vehicle screening system is shown, it being appreciated that the present invention is not limited to vehicle screening applications, but rather may be employed in any other suitable remote object inspection environment.

In the embodiment of FIG. 13B, an inspection assembly 1335, which may be portable or stationary, employs a first laser 1336, preferably a Nd:YAG pulsed laser emitting a third or fourth harmonic having respective peak wavelengths at 355 and 266 nm. It is appreciated that wavelengths in the range of 180 nm to 10 microns may be employed. Inspection assembly 1335 preferably also employs a second laser 1337, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

Output beams of lasers 1336 and 1337 impinge on scanning assemblies 1338, typically comprising first and second scanning elements (not shown) such as mirrors, which are driven in rotational motion by motors (not shown) in synchronization with the pulsed outputs of lasers 1336 and 1337 in response to synchronization signals provided by a computer 1340. The scanned laser beam outputs of scanning assemblies 1338 are projected onto a vehicle or other suitable remote object, preferably by a pair of telescopes 1341.

The output beam of laser 1336 is thus scanned in two dimensions over a vehicle, inducing luminescence by certain materials, including a number of explosives, should those materials be present on the scanned surfaces of the vehicle. The luminescence induced by the laser beam is detected preferably by a plurality of detector assemblies 1342, each preferably including imaging optics 1343, a spectral filter 1344 and a gated detector array 1345, such as a CCD or CMOS array. Alternatively, the plurality of detector assemblies 1342 may be replaced by a single broadband detector assembly, although this is not preferred. Alternatively, the detector array need not be gated, although this is not preferred.

Preferably, the spectral range of each spectral filter 1344 of each detector assembly 1342 differs from the spectral range of each other such filter. The following spectral ranges are preferably provided, each by a different spectral filter 1344 and corresponding to the following gate intervals:

400–430 nm—10 microseconds
450–540 nm—50 nanoseconds
670–700 nm—100 microseconds.

If more than a threshold amount of luminescence is received by any one or more gated detector 1345 within its time window and its spectral range, an alarm indication is provided by computer 1340, typically at a display 1346. This alarm indication indicates that an explosive material having certain luminescence characteristics may be present on a surface of the vehicle. Display 1346 preferably also visually indicates the location of the detected suspect material on the vehicle, here indicated on display 1346 at reference numeral 1348 and on the vehicle at reference numeral 1349.

The output beam of second laser 1337 is thus also scanned in two dimensions over the vehicle, inducing Raman scattering by certain materials, including explosives, should those materials be present on the scanned surfaces of the vehicle. The Raman scattering is detected by a plurality of detector assemblies 1350, each preferably including imaging optics 1351, a spectral filter 1352, a notch filter 1353 and a gated detector array 1354 such as a CCD or CMOS array. Alternatively, the plurality of detector assemblies 1350 may be replaced by a single broadband detector assembly, although this is not preferred. Alternatively, the detector array need not be gated, although this is not preferred.

Preferably, the spectral range of each spectral filter 1352 of each detector assembly 1350 differs from the spectral range of each other such filter. The following Raman shifts relative to the laser excitation wavelength are preferably provided, each by a different spectral filter 1352:

880–885 cm (−1)
1360–1365 cm (−1)
1270–1290 cm (−1)
2980–3000 cm (−1).

If more than a threshold amount of Raman scattering is received by any one or more gated detector of array 1354 during the time interval of the laser excitation pulse and its spectral range, an alarm indication is provided by computer 1340, typically at display 1346. This alarm indication indicates that an explosive material having certain Raman scattering characteristics may be present on a surface of the vehicle. Display 1346 preferably also visually indicates, at location 1348 on the display 1346, the location 1349 on the vehicle of the detected suspect material.

Preferably computer 1340 is operative to analyze and indicate detection of suspect materials on the vehicle produced in response to excitation by the first and second lasers 1336 and 1337 and the time-resolved luminescence and time-resolved Raman scattering detection resulting therefrom.

Preferably computer 1340 and display 1346 are operative to superimpose and indicate the spatial relationship between the locations of the detected suspect materials on the vehicle produced in response to excitation by the first and second lasers 1336 and 1337 and the time-resolved luminescence and time-resolved Raman scattering detection resulting therefrom.

In accordance with a preferred embodiment of the present invention the system of FIG. 13B also provides identification of an explosive on an object.

During identification, identification collecting optics 1356 are employed for receiving time-resolved luminescence and time-resolved Raman scattering from the location or locations 1349 of the detected suspect material on the vehicle. During identification, the output beams of lasers 1336 and 1337 are thus scanned in two dimensions at the previously determined location or locations 1349 of suspect material on a vehicle.

The output of identification collecting optics 1356 is preferably supplied via a fiberoptic link 1357 to a polychromator 1358, which produces dispersion of the luminescence and Raman spectra. The output from the polychromator 1358 is supplied to a gated detector assembly 1359, preferably employing a CCD array. Alternatively, the detector assembly need not be gated, although this is not preferred.

The output of gated detector assembly 1359 is analyzed by computer 1340 to compare the spectrum represented thereby with reference spectra characteristic of known explosives, in order to provide identification of an explosive on the vehicle.

Figure 13C:
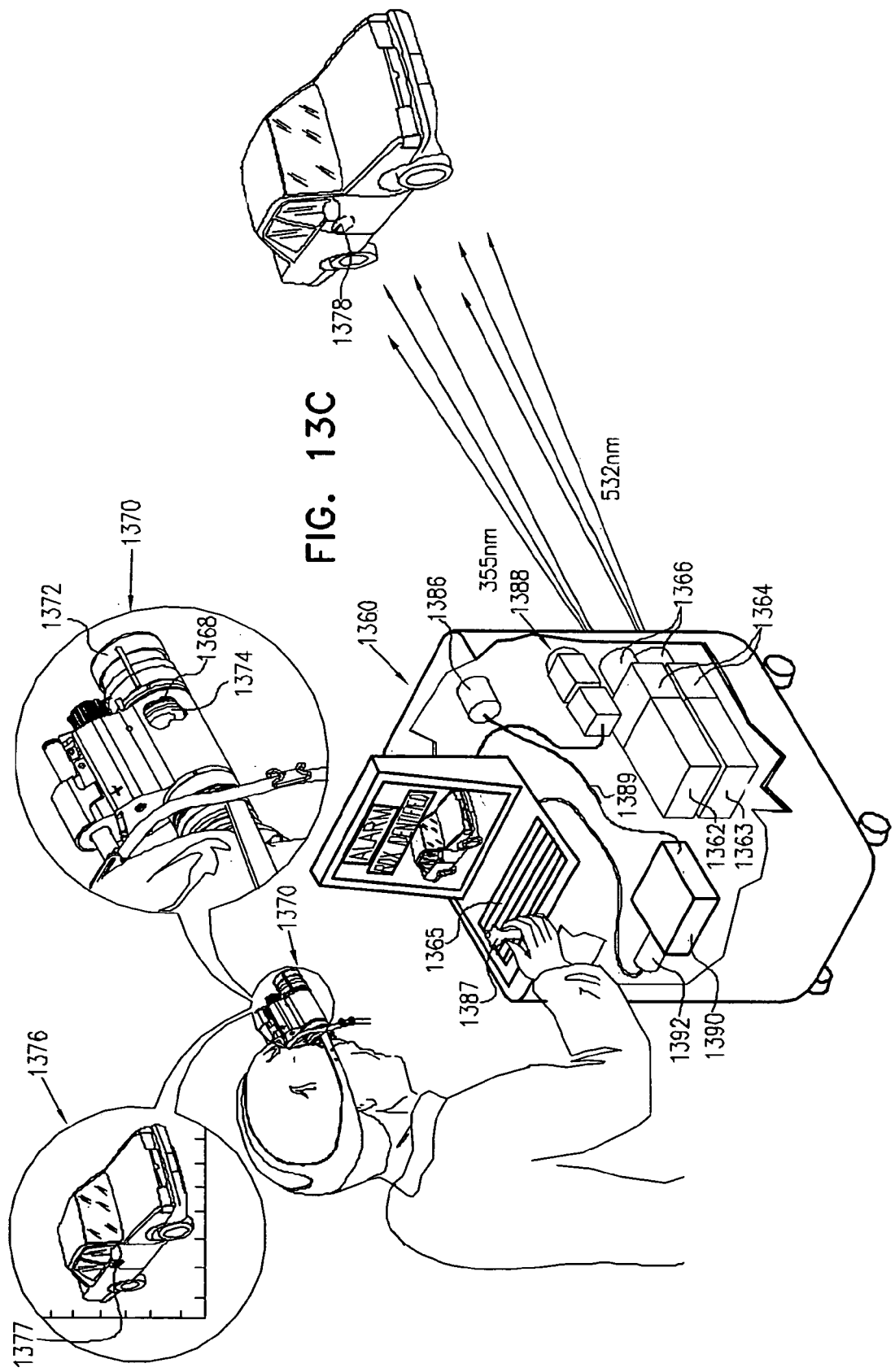

Reference is now made to FIG. 13C, which is a simplified pictorial illustration of a dual mode system for detecting and identifying explosives constructed and operative in accordance with a yet another preferred embodiment of the present invention and employing time-resolved luminescence and time-resolved Raman detection and employing time-resolved luminescence and time-resolved Raman identification. In the illustrated embodiment, a vehicle screening system is shown, it being appreciated that the present invention is not limited to vehicle screening applications, but rather may be employed in any other suitable remote object inspection environment.

In the embodiment of FIG. 13C, an inspection assembly 1360, which is preferably portable, employs a first laser 1362, preferably a Nd:YAG pulsed laser emitting a third or fourth harmonic having respective peak wavelengths at 355 and 266 nm. It is appreciated that wavelengths in the range of 180 nm to 10 microns may be employed. Inspection assembly 1360 preferably also employs a second laser 1363, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

Output beams of lasers 1362 and 1363 impinge on scanning assemblies 1364, typically comprising first and second scanning elements (not shown) such as mirrors, which are driven in rotational motion by motors (not shown) in synchronization with the pulsed outputs of lasers 1362 and 1363 in response to synchronization signals provided by a computer 1365. The scanned laser beam outputs of scanning assemblies 1364 are projected onto a vehicle or other suitable remote object, preferably by a pair of telescopes 1366.

The output beam of laser 1362 is thus scanned in two dimensions over a vehicle, inducing luminescence by certain materials, including a number of explosives, should those materials be present on the scanned surfaces of the vehicle. The luminescence induced by the laser beam is detected via imaging optics 1368 forming part of a head-mounted viewing assembly 1370, at least one and preferably a plurality of individually selectable and interchangeable narrow band spectral filters 1372 and an image intensifier 1374, all forming part of the head-mounted viewing assembly 1370.

Preferably, the spectral range of each spectral filter 1372 differs from the spectral range of each other such filter. The following spectral ranges are preferably provided, each by a different spectral filter 1372 and corresponding to the following gate intervals:

400–430 nm—10 microseconds
450–540 nm—50 nanoseconds
670–700 nm—100 microseconds.

In accordance with a preferred embodiment of the present invention the image intensifier 1374 is gated by control signals from computer 1365 so as to be synchronized with the pulsed output of laser 1362. Filters 1372 are operative to eliminate transmission of reflected laser radiation at 355 nm and 266 nm, to attenuate the ambient radiation and to fully transmit the luminescence. Thus, an operator using the head-mounted viewing assembly 1370 sees a scene such as that designated by reference numeral 1376, wherein the location on the vehicle of a suspected explosive is highlighted over an ambient background image of the vehicle. The location of the suspected explosive is indicated on scene 1376 at reference numeral 1377 and on the vehicle at reference numeral 1378.

The output beam of laser 1363 is also scanned in two dimensions over the vehicle, inducing Raman scattering by certain materials, including explosives, should those materials be present on the scanned surfaces of the vehicle. The Raman scattering induced by the laser beam is detected via imaging optics 1368 forming part of head-mounted viewing assembly 1370, at least one and preferably a plurality of narrow band spectral filters 1372 and image intensifier 1374, all forming part of the head-mounted viewing assembly 1370.

Preferably, the spectral range of each spectral filter 1372 differs from the spectral range of each other such filter. The following Raman shifts relative to the laser excitation wavelength are preferably provided, each by a different spectral filter 1372:

880–885 cm (−1)
1360–1365 cm (−1)
1270–1290 cm (−1)
2980–3000 cm (−1).

In accordance with a preferred embodiment of the present invention the image intensifier 1374 is gated by control signals from computer 1365 to operate during the time interval of the laser excitation pulse. Thus, an operator using the head-mounted viewing assembly 1370 sees a scene such as scene 1376, wherein location 1378 of a suspected explosive on the vehicle is highlighted on the scene 1376 at location 1377 over an ambient background image of the vehicle.

In accordance with a preferred embodiment of the present invention the system of FIG. 13C also provides identification of an explosive on an object.

During identification, identification collecting optics 1386 are employed for receiving time-resolved luminescence and time-resolved Raman scattering from the location or locations of the detected suspect material on the vehicle. During identification, the output beams of lasers 1362 and 1363 are scanned in two dimensions at the previously determined location or locations 1378 of suspect material on a vehicle.

The identification collecting optics 1386 are preferably aimed by an operator at the location of the suspected explosive typically using a joystick 1387 and a viewing camera 1388 or marker which is visible through the image intensifier 1374.

The output of identification collecting optics 1386 is preferably supplied via a fiberoptic link 1389 to a polychromator 1390, which produces dispersion of the luminescence and Raman spectra. The output from the polychromator 1390 is supplied to a gated detector assembly 1392, preferably employing a CCD array. Alternatively, the detector assembly need not be gated, although this is not preferred.

The output of gated detector assembly 1392 is analyzed by computer 1365 to compare the spectrum represented thereby with reference spectra characteristic of known explosives, in order to provide identification of an explosive on the vehicle.

Reference is now made to FIG. 14A, which is a simplified pictorial illustration of a dual mode system for detecting and identifying explosives constructed and operative in accordance with a preferred embodiment of the present invention and employing time-resolved luminescence detection and employing time-resolved luminescence and time-resolved laser induced breakdown spectroscopy for enhanced identification. In the illustrated embodiment, a baggage screening system is shown, it being appreciated that the present invention is not limited to baggage screening applications, but rather may be employed in any other suitable object inspection environment.

In the embodiment of FIG. 14A, baggage, such as suitcases 1400, is transported by a conveyor 1402 past an inspection station 1404 at which the suitcases 1400 are inspected. In accordance with a preferred embodiment of the present invention, the inspection station 1404 employs a laser 1406, preferably a Nd:YAG pulsed laser emitting a third or fourth harmonic having respective peak wavelengths at 355 and 266 nm. It is appreciated that wavelengths in the range of 180 nm to 10 microns may be employed. An output beam of laser 1406 impinges on a scanning assembly 1407, typically comprising first and second scanning elements 1408, such as mirrors, which are driven in rotational motion by motors 1409 in synchronization with the pulsed output of laser 1406 in response to synchronization signals provided by a computer 1410.

The output beam of laser 1406 is thus scanned in two dimensions over suitcases 1400, inducing luminescence by certain materials, including a number of explosives, should those materials be present on the scanned surfaces of the suitcases 1400. The luminescence induced by the laser beam is detected preferably by a plurality of detector assemblies 1414, each preferably including imaging optics 1415, a spectral filter 1416 and a gated detector array 1418, such as a CCD or CMOS array. Alternatively, the plurality of detector assemblies 1414 may be replaced by a single broadband detector assembly, although this is not preferred. Alternatively, the detector array need not be gated, although this is not preferred.

Preferably, the spectral range of each spectral filter 1416 of each detector assembly 1414 differs from the spectral range of each other such filter. The following spectral ranges are preferably provided, each by a different spectral filter 1416 and corresponding to the following gate intervals:

400–430 nm—10 microseconds
450–540 nm—50 nanoseconds
670–700 nm—100 microseconds.

If more than a threshold amount of luminescence is received by any one or more gated detector 1418 within its time window and its spectral range, an alarm indication is provided by computer 1410, typically at a display 1420. This alarm indication indicates that an explosive material having certain luminescence characteristics may be present on a surface of the suitcase 1400. Display 1420 preferably also visually indicates the location of the detected suspect material on the suitcase 1400, here indicated on display 1420 at reference numeral 1422 and on the suitcase 1400 at reference numeral 1424.

In accordance with a preferred embodiment of the present invention the system of FIG. 14A also provides identification of an explosive on an object.

During identification, identification collecting optics 1426 are employed for receiving time-resolved luminescence from the location or locations of the detected suspect material on the suitcase 1400. During identification, the output beam of laser 1406 is thus scanned in two dimensions at the previously determined location or locations 1424 of suspect material on suitcases 1400.

The output of identification collecting optics 1426 is preferably supplied via a fiberoptic link 1427 to a polychromator 1428, which produces dispersion of the luminescence spectrum. The output from the polychromator 1428 is supplied to a gated detector assembly 1429, preferably employing a CCD array. Alternatively, the detector assembly need not be gated, although this is not preferred.

The output of gated detector assembly 1429 is analyzed by computer 1410 to compare the spectrum represented thereby with reference spectra characteristic of known explosives, in order to provide identification of an explosive on the suitcase 1400.

In accordance with a preferred embodiment of the present invention the system of FIG. 14A also provides enhanced identification of an explosive on an object. This enhanced identification is preferably provided by employing a selectably positionable lens 1430 intermediate the scanning assembly 1407 and the suitcase 1400. Lens 1430 is normally positioned in an inoperative position, indicated in dashed lines at reference numeral 1431, during detection, as opposed to during enhanced identification, operation of the system.

During enhanced identification, identification collecting optics 1426 are employed for receiving laser induced breakdown emissions from the location or locations of the detected suspect material on the suitcase 1400. Lens 1430 is operative to concentrate the output beam of the laser 1406 on such locations. The output of identification collecting optics 1426 is preferably supplied via fiberoptic link 1427 to polychromator 1428, which produces dispersion of the emission spectrum. The output from the polychromator 1428 is supplied to gated detector assembly 1429.

The output of gated detector assembly 1429 is analyzed by computer 1410 to compare the spectrum represented thereby with reference spectra characteristic of known explosives, in order to provide an enhanced output indication of the existence of an explosive on the suitcase 1400.

Figure 14B:
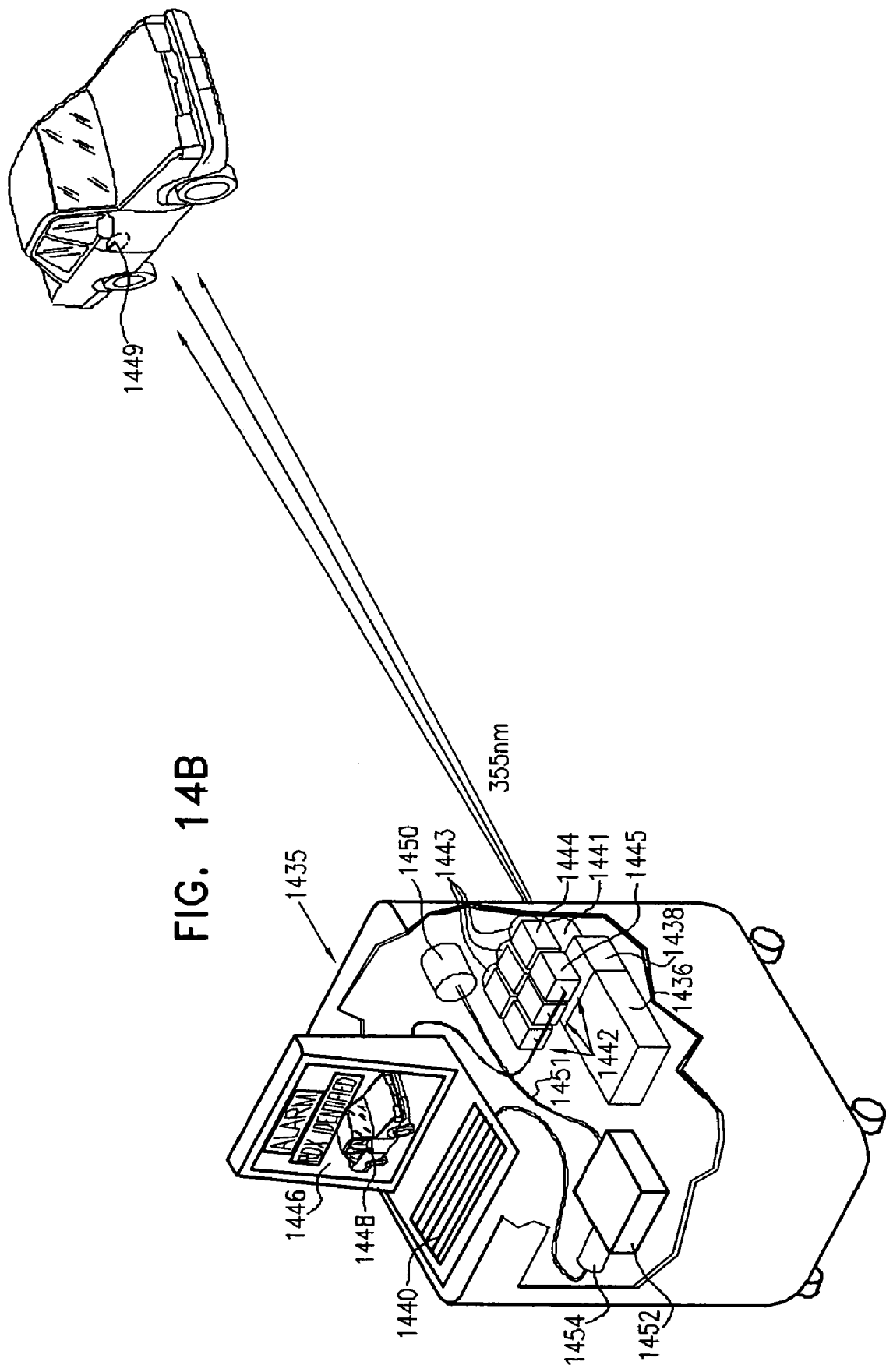

Reference is now made to FIG. 14B, which is a simplified pictorial illustration of a dual mode system for detecting and identifying explosives constructed and operative in accordance with another preferred embodiment of the present invention and employing time-resolved luminescence detection and employing time-resolved luminescence and time-resolved laser induced breakdown spectroscopy for enhanced identification. In the illustrated embodiment, a vehicle screening system is shown, it being appreciated that the present invention is not limited to vehicle screening applications, but rather may be employed in any other suitable remote object inspection environment.

In the embodiment of FIG. 14B, an inspection assembly 1435, which may be portable or stationary, employs a laser 1436, preferably a Nd:YAG pulsed laser emitting a third or fourth harmonic having respective peak wavelengths at 355 and 266 nm. It is appreciated that wavelengths in the range of 180 nm to 10 microns may be employed. An output beam of laser 1436 impinges on a scanning assembly 1438, typically comprising first and second scanning elements (not shown), such as mirrors, which are driven in rotational motion by motors (not shown) in synchronization with the pulsed output of laser 1436 in response to synchronization signals provided by a computer 1440. The scanned laser beam output of scanning assembly 1438 is projected onto a vehicle or other suitable remote object, preferably by a telescope 1441.

The output beam of laser 1436 is thus scanned in two dimensions over a vehicle, inducing luminescence by certain materials, including a number of explosives, should those materials be present on the scanned surfaces of the vehicle. The luminescence induced by the laser beam is detected preferably by a plurality of detector assemblies 1442, each preferably including imaging optics 1443, a spectral filter 1444 and a gated detector array 1445, such as a CCD or CMOS array. Alternatively, the plurality of detector assemblies 1442 may be replaced by a single broadband detector assembly, although this is not preferred. Alternatively, the detector array need not be gated, although this is not preferred.

Preferably, the spectral range of each spectral filter 1444 of each detector assembly 1442 differs from the spectral range of each other such filter. The following spectral ranges are preferably provided, each by a different spectral filter 1444 and corresponding to the following gate intervals:

400–430 nm—10 microseconds
450–540 nm—50 nanoseconds
670–700 nm—100 microseconds.

If more than a threshold amount of luminescence is received by any one or more gated detector 1445 within its time window and its spectral range, an alarm indication is provided by computer 1440, typically at a display 1446. This alarm indication indicates that an explosive material having certain luminescence characteristics may be present on a surface of the vehicle. Display 1446 preferably also visually indicates the location of the detected suspect material on the vehicle, here indicated on display 1446 at reference numeral 1448 and on the vehicle at reference numeral 1449.

In accordance with a preferred embodiment of the present invention the system of FIG. 14B also provides identification of an explosive on an object.

During identification, identification collecting optics 1450 are employed for receiving time-resolved luminescence from the location or locations of the detected suspect material on the vehicle. During identification, the output beam of laser 1436 is thus scanned in two dimensions at the previously determined location or locations 1449 of suspect material on a vehicle.

The output of identification collecting optics 1450 is preferably supplied via a fiberoptic link 1451 to a polychromator 1452, which produces dispersion of the luminescence spectrum. The output from the polychromator 1452 is supplied to a gated detector assembly 1454, preferably employing a CCD array. Alternatively, the detector assembly need not be gated, although this is not preferred.

The output of gated detector assembly 1454 is analyzed by computer 1440 to compare the spectrum represented thereby with reference spectra characteristic of known explosives, in order to provide identification of an explosive on the vehicle.

In accordance with a preferred embodiment of the present invention the system of FIG. 14B also provides enhanced identification of detection of an explosive on an object. This enhanced identification is preferably provided by employing a selectably positionable lens (not shown) that is associated with telescope 1441. This lens is normally positioned in an inoperative position during detection, as opposed to enhanced identification, operation of the system.

During enhanced identification, identification collecting optics 1450 are employed for receiving laser induced breakdown emissions from the location or locations of the detected suspect material on the vehicle. The output of identification collecting optics 1450 is preferably supplied via fiberoptic link 1451 to polychromator 1452, which produces dispersion of the emission spectrum. The output from the polychromator 1452 is supplied to gated detector assembly 1454.

The output of gated detector assembly 1454 is analyzed by computer 1440 to compare the spectrum represented thereby with reference spectra characteristic of known explosives, in order to provide an enhanced output indication of the existence of an explosive on the vehicle.

Figure 14C:
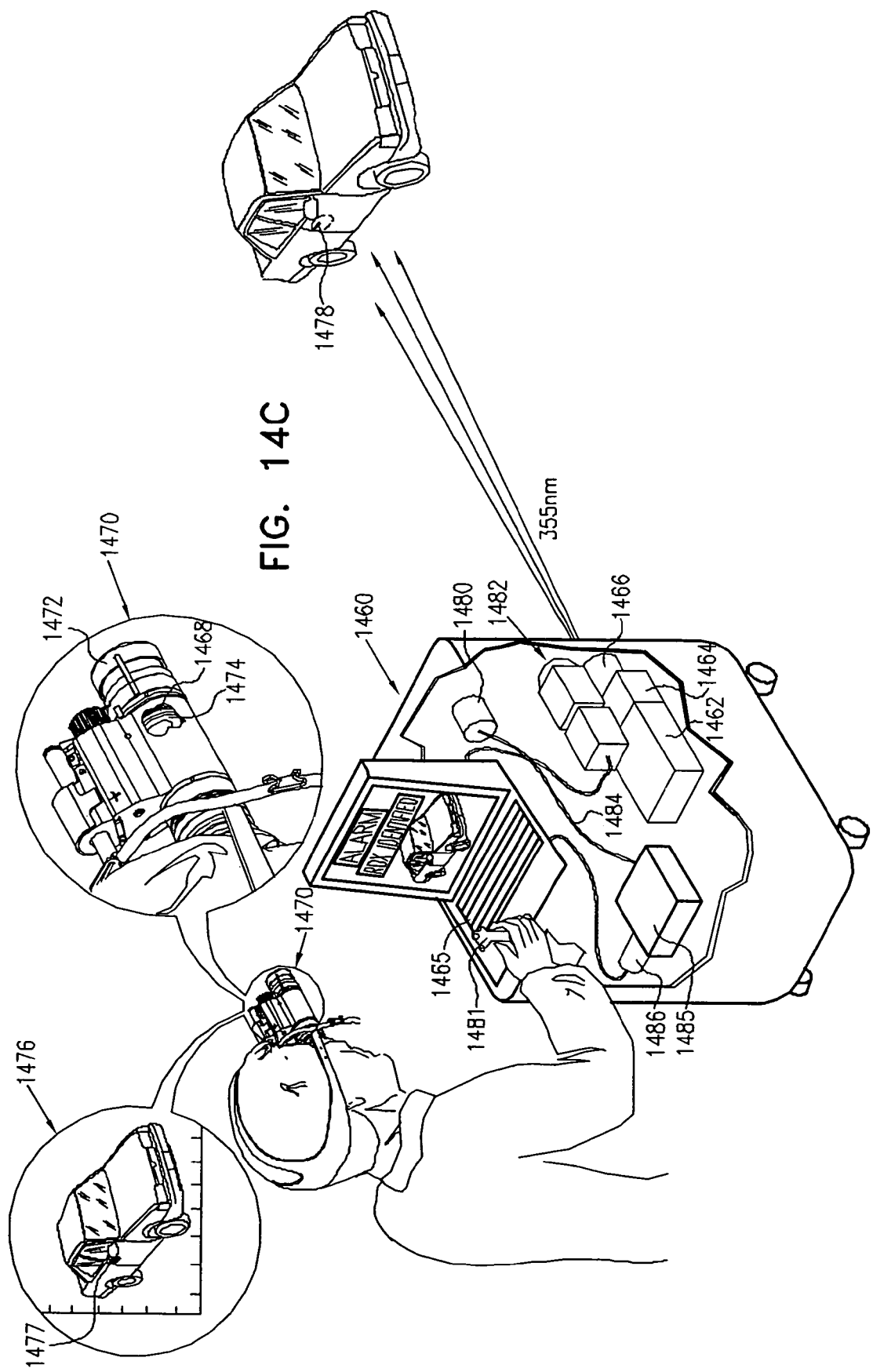

Reference is now made to FIG. 14C, which is a simplified pictorial illustration of a dual mode system for detecting and identifying explosives constructed and operative in accordance with yet another preferred embodiment of the present invention and employing time-resolved luminescence detection and employing time-resolved luminescence and time-resolved laser induced breakdown spectroscopy for enhanced identification. In the illustrated embodiment, a vehicle screening system is shown, it being appreciated that the present invention is not limited to vehicle screening applications, but rather may be employed in any other suitable remote object inspection environment.

In the embodiment of FIG. 14C, an inspection assembly 1460, which is preferably portable, employs a laser 1462, preferably a Nd:YAG pulsed laser emitting a third or fourth harmonic having respective peak wavelengths at 355 and 266 nm. It is appreciated that wavelengths in the range of 180 nm to 10 microns may be employed. An output beam of laser 1462 impinges on a scanning assembly 1464, typically comprising first and second scanning elements (not shown), such as mirrors, which are driven in rotational motion by motors (not shown) in synchronization with the pulsed output of laser 1462 in response to synchronization signals provided by a computer 1465. The scanned laser beam output of scanning assembly 1464 is projected onto a vehicle or other suitable remote object, preferably by a telescope 1466.

The output beam of laser 1464 is thus scanned in two dimensions over a vehicle, inducing luminescence by certain materials, including a number of explosives, should those materials be present on the scanned surfaces of the vehicle. The luminescence induced by the laser beam is detected via imaging optics 1468 forming part of a head-mounted viewing assembly 1470, at least one and preferably a plurality of individually selectable and interchangeable narrow band spectral filters 1472 and an image intensifier 1474, all forming part of the head-mounted viewing assembly 1470.

Preferably, the spectral range of each spectral filter 1472 differs from the spectral range of each other such filter. The following spectral ranges are preferably provided, each by a different spectral filter 1472 and corresponding to the following gate intervals:

400–430 nm—10 microseconds
450–540 nm—50 nanoseconds
670–700 nm—100 microseconds.

In accordance with a preferred embodiment of the present invention the image intensifier 1474 is gated by control signals from computer 1465 so as to be synchronized with the pulsed output of laser 1462. Filters 1472 are operative to eliminate transmission of reflected laser radiation at 355 nm and 266 nm, to attenuate the ambient radiation and to fully transmit the luminescence. Thus, an operator using the head-mounted viewing assembly 1470 sees a scene such as that designated by reference numeral 1476, wherein the location on the vehicle of a suspected explosive is highlighted over an ambient background image of the vehicle. The location of the suspected explosive is indicated on scene 1476 at reference numeral 1477 and on the vehicle at reference numeral 1478.

In accordance with a preferred embodiment of the present invention the system of FIG. 14C also provides identification of an explosive on an object.

During identification, identification collecting optics 1480 are employed for receiving time-resolved luminescence from the location or locations of the detected suspect material on the vehicle. During identification, the output beam of laser 1462 is thus scanned in two dimensions at the previously determined location or locations 1478 of suspect material on a vehicle.

The identification collecting optics 1480 are preferably aimed by an operator at the location of the suspected explosive typically using a joystick 1481 and a viewing camera 1482 or marker which is visible through the image intensifier 1474.

The output of identification collecting optics 1480 is preferably supplied via a fiberoptic link 1484 to a polychromator 1485, which produces dispersion of the luminescence spectrum. The output from the polychromator 1485 is supplied to a gated detector assembly 1486, preferably employing a CCD array. Alternatively, the detector assembly need not be gated, although this is not preferred.

The output of gated detector assembly 1486 is analyzed by computer 1465 to compare the spectrum represented thereby with reference spectra characteristic of known explosives, in order to provide identification of an explosive on the vehicle.

In accordance with a preferred embodiment of the present invention the system of FIG. 14C also provides enhanced identification of detection of an explosive on an object. This enhanced identification is preferably provided by employing a selectably positionable lens (not shown) that is associated with telescope 1466. This lens is normally positioned in an inoperative position during detection, as opposed to during enhanced identification, operation of the system.

During enhanced identification, identification collecting optics 1480 are employed for receiving laser induced breakdown emissions from the location or locations of the detected suspect material on the vehicle. The output of identification collecting optics 1480 is preferably supplied via fiberoptic link 1484 to polychromator 1485, which produces dispersion of the emission spectrum. The output from the polychromator 1485 is supplied to gated detector assembly 1486.

The identification collecting optics 1480 are preferably aimed by an operator at the location of the suspected explosive typically using a joystick 1481 and a viewing camera 1482 or marker which is visible through the image intensifier 1483.

The output of gated detector assembly 1486 is analyzed by computer 1465 to compare the spectrum represented thereby with reference spectra characteristic of known explosives, in order to provide an enhanced output indication of the existence of an explosive on the vehicle.

Figure 15A:
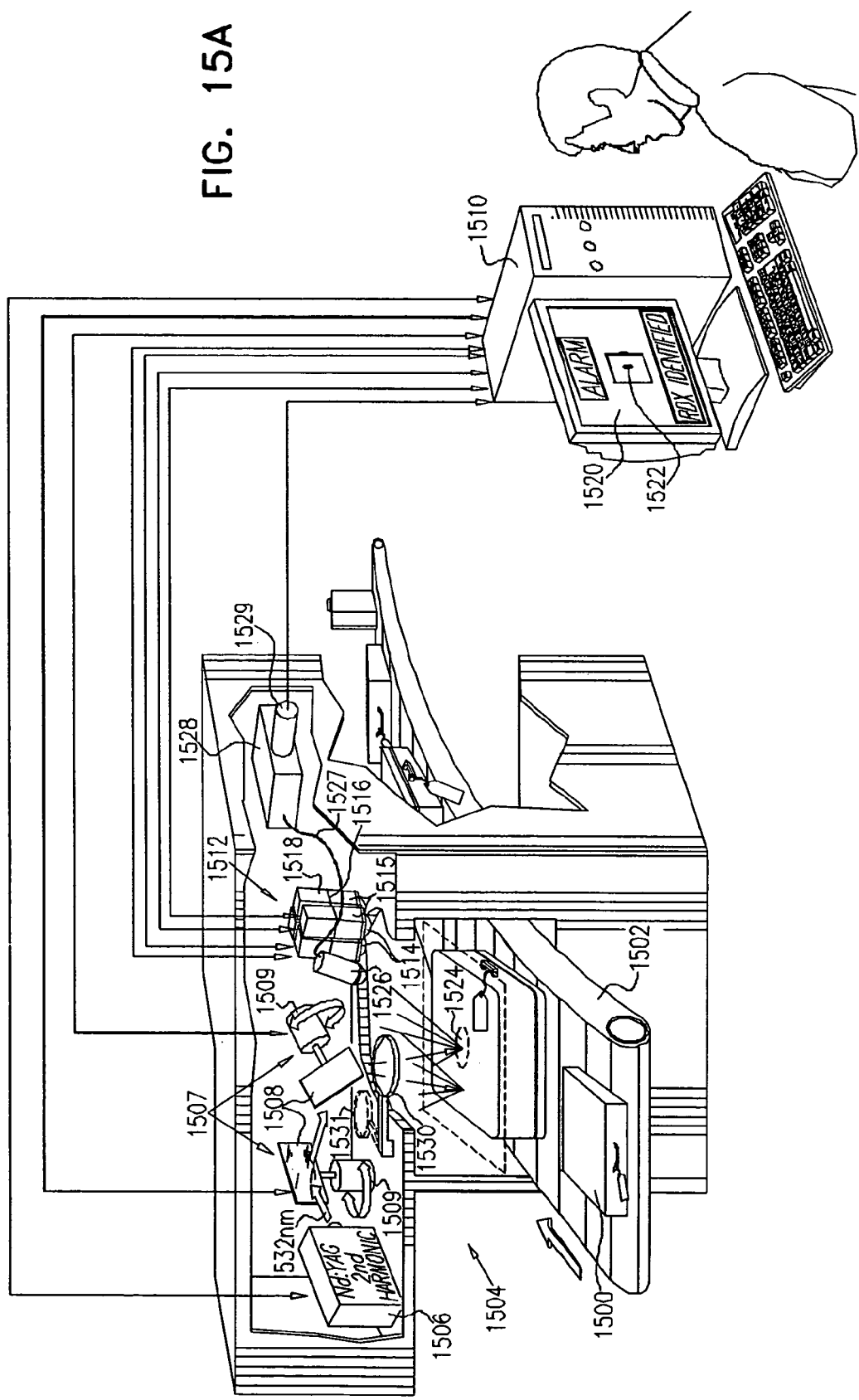

Reference is now made to FIG. 15A, which is a simplified pictorial illustration of a dual mode system for detecting and identifying explosives constructed and operative in accordance with a preferred embodiment of the present invention and employing time-resolved Raman scattering detection and employing time-resolved Raman scattering and time-resolved laser induced breakdown spectroscopy for enhanced identification. In the illustrated embodiment, a baggage screening system is shown, it being appreciated that the present invention is not limited to baggage screening applications, but rather may be employed in any other suitable object inspection environment.

In the embodiment of FIG. 15A, baggage, such as suitcases 1500, is transported by a conveyor 1502 past an inspection station 1504 at which the suitcases 1500 are inspected. In accordance with a preferred embodiment of the present invention, the inspection station 1504 employs a laser 1506, preferably a Nd:YAG pulsed laser emitting a second harmonic having a peak wavelength at 532 nm. It is appreciated that wavelengths in the range of 200 nm to 10 microns may be employed. An output beam of laser 1506 impinges on a scanning assembly 1507, typically comprising first and second scanning elements 1508, such as mirrors, which are driven in rotational motion by motors 1509 in synchronization with the pulsed output of laser 1506 in response to synchronization signals provided by a computer 1510.

The output beam of laser 1506 is thus scanned over suitcases 1500, inducing Raman scattering by certain materials, including explosives, should those materials be present on the scanned surfaces of the suitcases 1500. The Raman scattering is detected by a plurality of detector assemblies 1512, each preferably including imaging optics 1514, a spectral filter 1515, a notch filter 1516 and a gated detector array 1518, such as a CCD or CMOS array. Alternatively, the plurality of detector assemblies 1512 may be replaced by a single broadband detector assembly, although this is not preferred. Alternatively, the detector array need not be gated, although this is not preferred.

Preferably, the spectral range of each spectral filter 1515 of each detector assembly 1512 differs from the spectral range of each other such filter. The following Raman shifts relative to the laser excitation wavelength are preferably provided, each by a different spectral filter 1515:

880–885 cm (−1)
1360–1365 cm (−1)
1270–1290 cm (−1)
2980–3000 cm (−1).

If more than a threshold amount of Raman scattering is received by anyone or more gated detector 1518 during the time interval of the laser excitation pulse and its spectral range, an alarm indication is provided by computer 1510, typically at a display 1520. This alarm indication indicates that an explosive material having certain Raman scattering characteristics may be present on a surface of the suitcase 1500. Display 1520 preferably also visually indicates the location of the detected suspect material on the suitcase 1500, here indicated on display 1520 at reference numeral 1522 and on the suitcase 1500 at reference numeral 1524.

In accordance with a preferred embodiment of the present invention the system of FIG. 15A also provides identification of an explosive on an object.

During identification, identification collecting optics 1526 are employed for receiving time-resolved Raman scattering from the location or locations of the detected suspect material on the suitcase 1500. During identification, the output beam of laser 1506 is thus scanned in two dimensions at the previously determined location or locations 1524 of suspect material on suitcases 1500.

The output of identification collecting optics 1526 is preferably supplied via a fiberoptic link 1527 to a polychromator 1528, which produces dispersion of the Raman scattering spectrum. The output from the polychromator 1528 is supplied to a gated detector assembly 1529, preferably employing a CCD array. Alternatively, the detector array need not be gated, although this is not preferred.

The output of gated detector assembly 1529 is analyzed by computer 1510 to compare the spectrum represented thereby with reference spectra characteristic of known explosives, in order to provide identification of an explosive on the suitcase 1500.

In accordance with a preferred embodiment of the present invention the system of FIG. 15A also provides enhanced identification of an explosive on an object. This enhanced identification is preferably provided by employing a selectably positionable lens 1530 intermediate the scanning assembly 1507 and the suitcase 1500. Lens 1530 is normally positioned in an inoperative position, indicated in dashed lines at reference numeral 1531, during detection, as opposed to during enhanced identification, operation of the system.

During enhanced identification, identification collecting optics 1526 are employed for receiving laser induced breakdown emissions from the location or locations of the detected suspect material on the suitcase 1500. Lens 1530 is operative to concentrate the output beam of the laser 1506 on such locations. The output of identification collecting optics 1526 is preferably supplied via fiberoptic link 1527 to polychromator 1528, which produces dispersion of the emission spectrum. The output from the polychromator 1528 is supplied to gated detector assembly 1529.

The output of gated detector assembly 1529 is analyzed by computer 1510 to compare the spectrum represented thereby with reference spectra characteristic of known explosives, in order to provide an enhanced output indication of the existence of an explosive on the suitcase 1500.

Figure 15B:
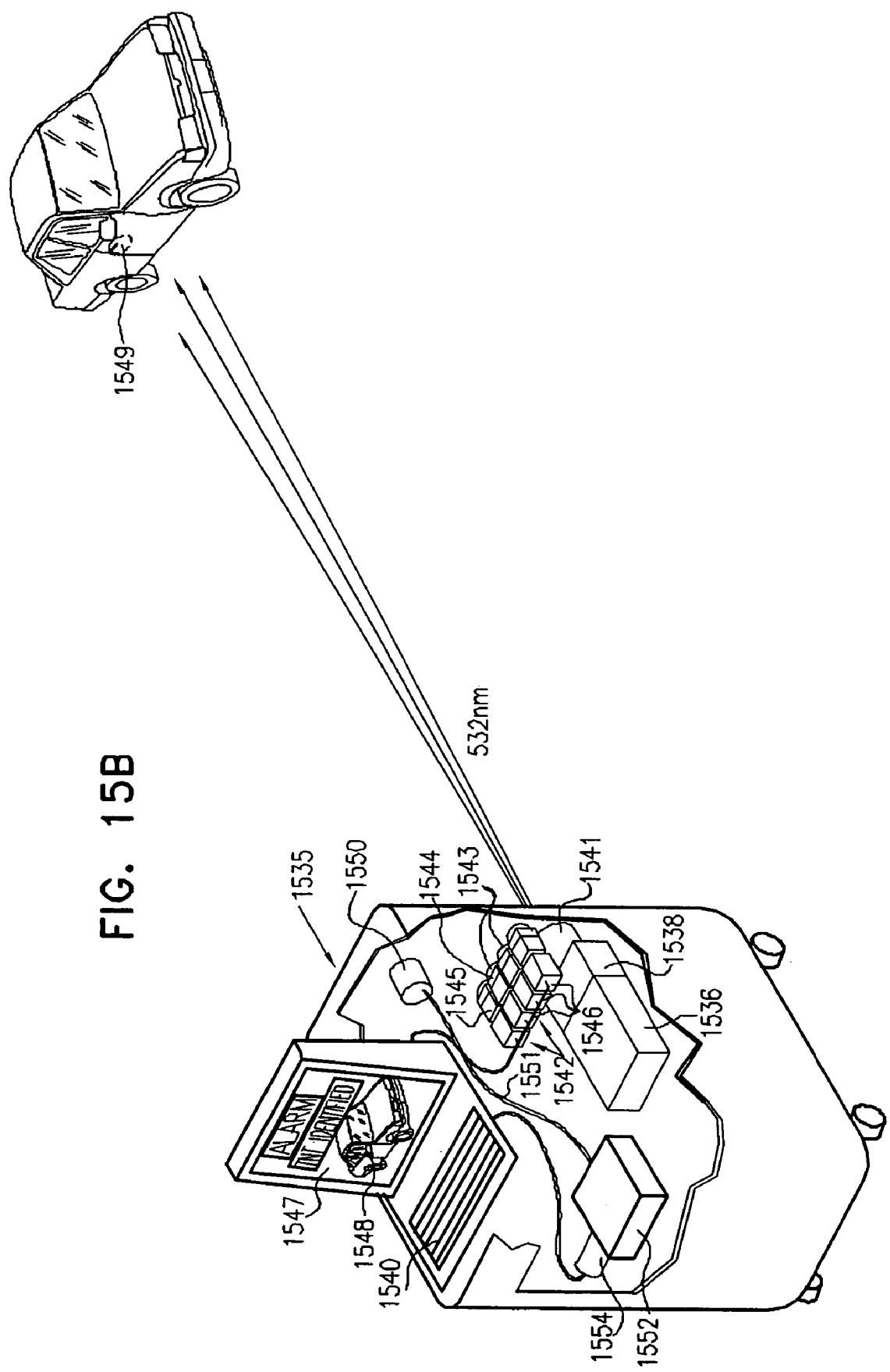

Reference is now made to FIG. 15B, which is a simplified pictorial illustration of a dual mode system for detecting and identifying explosives constructed and operative in accordance with another preferred embodiment of the present invention and employing time-resolved Raman scattering detection and employing time-resolved Raman scattering and time-resolved laser induced breakdown spectroscopy for enhanced identification. In the illustrated embodiment, a vehicle screening system is shown, it being appreciated that the present invention is not limited to vehicle screening applications, but rather may be employed in any other suitable remote object inspection environment.

In the embodiment of FIG. 15B, an inspection assembly 1535, which may be portable or stationary, employs a laser 1536, preferably a Nd:YAG pulsed laser emitting a second harmonic having a peak wavelength at 532 nm. It is appreciated that wavelengths in the range of 200 nm to 10 microns may be employed. An output beam of laser 1536 impinges on a scanning assembly 1538, typically comprising first and second scanning elements (not shown), such as mirrors, which are driven in rotational motion by motors (not shown) in synchronization with the pulsed output of laser 1536 in response to synchronization signals provided by a computer 1540. The scanned laser beam output of scanning assembly 1538 is projected onto a vehicle or other suitable remote object, preferably by a telescope 1541.

The output beam of laser 1536 is thus scanned in two dimensions over a vehicle, inducing Raman scattering by certain materials, including explosives, should those materials be present on the scanned surfaces of the vehicle. The Raman scattering is detected by a plurality of detector assemblies 1542, each preferably including imaging optics 1543, a spectral filter 1544, a notch filter 1545 and a gated detector array 1546, such as a CCD or CMOS array. Alternatively, the plurality of detector assemblies 1542 may be replaced by a single broadband detector assembly, although this is not preferred. Alternatively, the detector array need not be gated, although this is not preferred.

Preferably, the spectral range of each spectral filter 1544 of each detector assembly 1542 differs from the spectral range of each other such filter. The following Raman shifts relative to the laser excitation wavelength are preferably provided, each by a different spectral filter 1544:

880–885 cm (−1)
1360–1365 cm (−1)
1270–1290 cm (−1)
2980–3000 cm (−1).

If more than a threshold amount of Raman scattering is received by any one or more gated detector 1546 during the time interval of the laser excitation pulse and its spectral range, an alarm indication is provided by computer 1540, typically at a display 1547. This alarm indication indicates that an explosive material having certain Raman scattering characteristics may be present on a surface of the vehicle. Display 1547 preferably also visually indicates the location of the detected suspect material on the vehicle, here indicated on display 1547 at reference numeral 1548 and on the vehicle at reference numeral 1549.

In accordance with a preferred embodiment of the present invention the system of FIG. 15B also provides identification of an explosive on an object.

During identification, identification collecting optics 1550 are employed for receiving time-resolved Raman scattering from the location or locations of the detected suspect material on the vehicle. During identification, the output beam of laser 1536 is thus scanned in two dimensions at the previously determined location or locations 1549 of suspect material on a vehicle.

The output of identification collecting optics 1550 is preferably supplied via a fiberoptic link 1551 to a polychromator 1552, which produces dispersion of the Raman scattering spectrum. The output from the polychromator 1552 is supplied to a gated detector assembly 1554, preferably employing a CCD array. Alternatively, the detector assembly need not be gated, although this is not preferred.

The output of gated detector assembly 1554 is analyzed by computer 1540 to compare the spectrum represented thereby with reference spectra characteristic of known explosives, in order to provide identification of an explosive on the vehicle.

In accordance with a preferred embodiment of the present invention the system of FIG. 15B also provides enhanced identification of detection of an explosive on an object. This enhanced identification is preferably provided by employing a selectably positionable lens (not shown) that is associated with telescope 1541. This lens is normally positioned in an inoperative position during detection, as opposed to enhanced identification, operation of the system.

During enhanced identification, identification collecting optics 1550 are employed for receiving laser induced breakdown emissions from the location or locations of the detected suspect material on the vehicle. The output of identification collecting optics 1550 is preferably supplied via fiberoptic link 1551 to polychromator 1552, which produces dispersion of the emission spectrum. The output from the polychromator 1552 is supplied to gated detector assembly 1554.

The output of gated detector assembly 1554 is analyzed by computer 1540 to compare the spectrum represented thereby with reference spectra characteristic of known explosives, in order to provide an enhanced output indication of the existence of an explosive on the vehicle.

Reference is now made to FIG. 15C, which is a simplified pictorial illustration of a dual mode system for detecting and identifying explosives constructed and operative in accordance with yet another preferred embodiment of the present invention and employing time-resolved Raman scattering detection and employing time-resolved Raman scattering and time-resolved laser induced breakdown spectroscopy for enhanced identification. In the illustrated embodiment, a vehicle screening system is shown, it being appreciated that the present invention is not limited to vehicle screening applications, but rather may be employed in any other suitable remote object inspection environment.

In the embodiment of FIG. 15C, an inspection assembly 1560, which is preferably portable, employs a laser 1562, preferably a Nd:YAG pulsed laser emitting a second harmonic having a peak wavelength at 532 nm. It is appreciated that wavelengths in the range of 200 nm to 10 microns may be employed. An output beam of laser 1562 impinges on a scanning assembly 1564, typically comprising first and second scanning elements (not shown), such as mirrors, which are driven in rotational motion by motors (not shown) in synchronization with the pulsed output of laser 1562 in response to synchronization signals provided by a computer 1565. The scanned laser beam output of scanning assembly 1564 is projected onto a vehicle or other suitable remote object, preferably by a telescope 1566.

The output beam of laser 1562 is thus scanned in two dimensions over a vehicle, inducing Raman scattering by certain materials, including explosives, should those materials be present on the scanned surfaces of the vehicle. The Raman scattering induced by the laser beam is detected via imaging optics 1568 forming part of a head-mounted viewing assembly 1570, at least one and preferably a plurality of narrow band spectral filters 1572 and an image intensifier 1574, all forming part of the head-mounted viewing assembly 1570.

Preferably, the spectral range of each spectral filter 1572 differs from the spectral range of each other such filter. The following Raman shifts relative to the laser excitation wavelength are preferably provided, each by a different spectral filter 1572:

880–885 cm (−1)

1360–1365 cm (−1)

1270–1290 cm (−1)

2980–3000 cm (−1).

In accordance with a preferred embodiment of the present invention the image intensifier 1574 is gated by control signals from computer 1565 to operate during the time interval of the laser excitation pulse. Thus, an operator using the head-mounted viewing assembly 1570 sees a scene such as that designated by reference numeral 1576, wherein the location on the vehicle of a suspected explosive is highlighted over an ambient background image of the vehicle.

The location of the suspected explosive is indicated on scene 1576 at reference numeral 1577 and on the vehicle at reference numeral 1578.

In accordance with a preferred embodiment of the present invention the system of FIG. 15C also provides identification of an explosive on an object.

During identification, identification collecting optics 1580 are employed for receiving time-resolved Raman scattering from the location or locations of the detected suspect material on the vehicle. During identification, the output beam of laser 1562 is thus scanned in two dimensions at the previously determined location or locations 1578 of suspect material on a vehicle.

The identification collecting optics 1580 are preferably aimed by an operator at the location of the suspected explosive typically using a joystick 1581 and a viewing camera 1582 or marker which is visible through the image intensifier 1583.

The output of identification collecting optics 1580 is preferably supplied via a fiberoptic link 1584 to a polychromator 1585, which produces dispersion of the Raman scattering spectrum. The output from the polychromator 1585 is supplied to a gated detector assembly 1586, preferably employing a CCD array. Alternatively, the detector assembly need not be gated, although this is not preferred.

The output of gated detector assembly 1586 is analyzed by computer 1565 to compare the spectrum represented thereby with reference spectra characteristic of known explosives, in order to provide identification of an explosive on the vehicle.

In accordance with a preferred embodiment of the present invention the system of FIG. 15C also provides enhanced identification of detection of an explosive on an object. This enhanced identification is preferably provided by employing a selectably positionable lens (not shown) that is associated with telescope 1566. This lens is normally positioned in an inoperative position during detection, as opposed to during enhanced identification, operation of the system.

During enhanced identification, identification collecting optics 1580 are employed for receiving laser induced breakdown emissions from the location or locations of the detected suspect material on the vehicle. The output of identification collecting optics 1580 is preferably supplied via fiberoptic link 1584 to polychromator 1585, which produces dispersion of the emission spectrum. The output from the polychromator 1585 is supplied to gated detector assembly 1586.

The identification collecting optics 1580 are preferably aimed by an operator at the location of the suspected explosive typically using a joystick 1581 and a viewing camera 1582 or marker which is visible through the image intensifier 1583.

The output of gated detector assembly 1586 is analyzed by computer 1565 to compare the spectrum represented thereby with reference spectra characteristic of known explosives, in order to provide an enhanced output indication of the existence of an explosive on the vehicle.

Figure 16A:
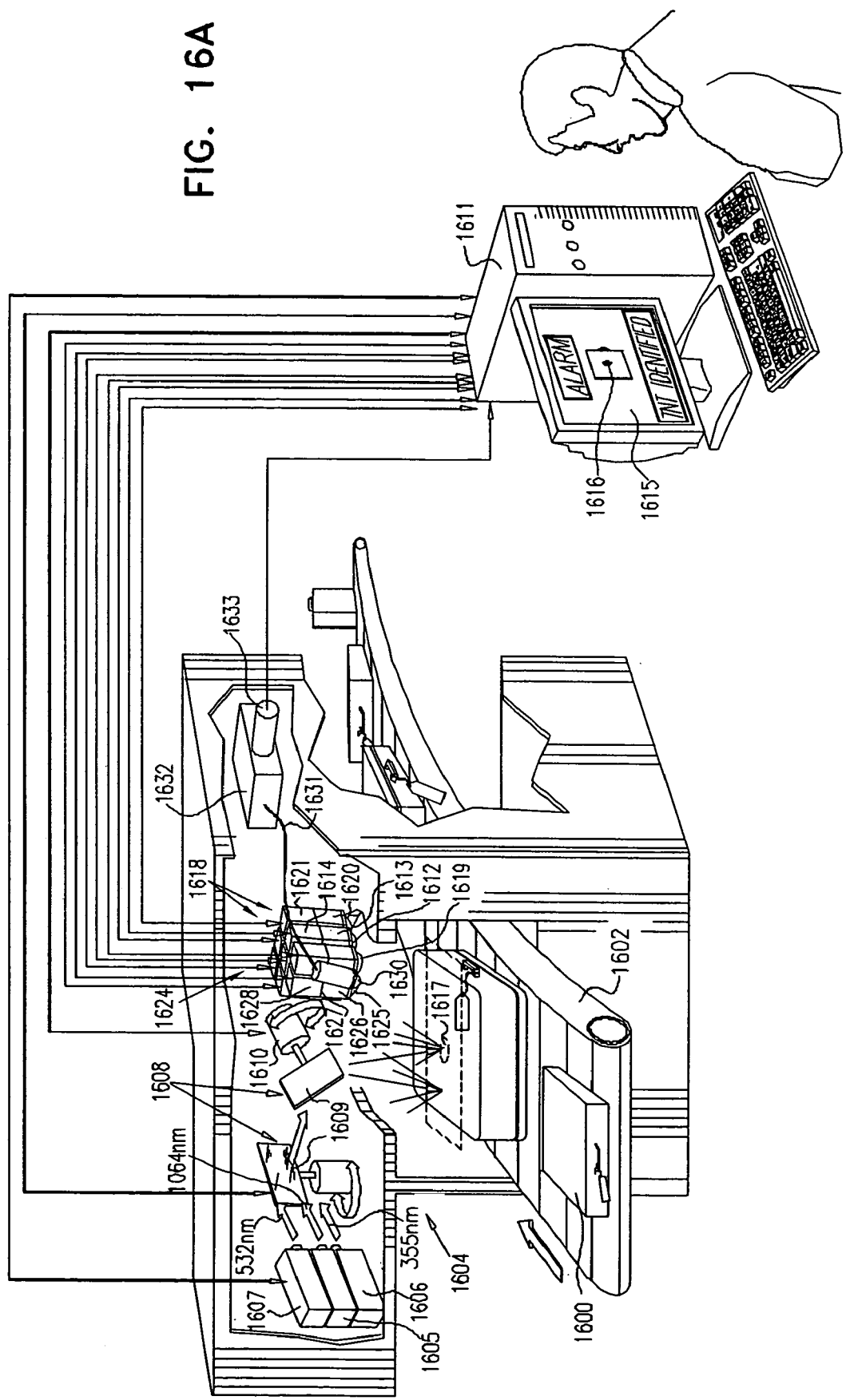
FIGS. 16A, 16B and 16C are simplified pictorial illustration of triple mode systems for detecting and identifying explosives constructed and operative in accordance with preferred embodiments of the present invention and employing second harmonic, time-resolved luminescence and time-resolved Raman scattering detection and time-resolved luminescence and time-resolved Raman scattering identification.

Reference is now made to FIG. 16A, which is a simplified pictorial illustration of a triple mode system for detecting and identifying explosives constructed and operative in accordance with a preferred embodiment of the present invention and employing second harmonic, time-resolved luminescence and time-resolved Raman scattering detection and time-resolved luminescence and time-resolved Raman scattering identification. In the illustrated embodiment, a baggage screening system is shown, it being appreciated that the present invention is not limited to baggage screening applications, but rather may be employed in any other suitable object inspection environment.

In the embodiment of FIG. 16A, baggage, such as suitcases 1600, is transported by a conveyor 1602 past an inspection station 1604 at which the suitcases 1600 are inspected. In accordance with a preferred embodiment of the present invention, the inspection station 1604 employs a first laser 1605, preferably a Nd:YAG pulsed laser emitting with a peak wavelength at 1064 nm. It is appreciated that wavelengths in the range of 400 nm to 10 microns may be employed. The inspection station 1604 preferably also employs a second laser 1606, preferably a Nd:YAG pulsed laser emitting a third or fourth harmonic having respective peak wavelengths at 355 and 266 nm. It is appreciated that wavelengths in the range of 180 nm to 10 microns may be employed. The inspection station 1604 preferably also employs a third laser 1607, preferably a Nd:YAG pulsed laser emitting a second harmonic having a peak wavelength at 532 nm. It is appreciated that wavelengths in the range of 200 nm to 10 microns may be employed by this laser. Alternatively, a single laser or two lasers may be used rather than three lasers.

The output beams of lasers 1605, 1606 and 1607 impinge on scanning assembly 1608, typically comprising first and second scanning elements 1609, such as mirrors, which are driven in rotational motion by motors 1610 in synchronization with the pulsed outputs of lasers 1605, 1606 and 1607 in response to synchronization signals provided by a computer 1611.

The output beam of laser 1605 is thus scanned in two dimensions over suitcases 1600, inducing second harmonic scattering of the output beam by certain materials, including a number of explosives, should those materials be present on the scanned surfaces of the suitcases 1600. The scattered second harmonic of the laser beam is detected via imaging optics 1612 and a narrow band spectral filter 1613 having a peak wavelength of 532 nm preferably by a gated detector array 1614, such as a CCD or CMOS array. Alternatively, the detector array need not be gated, although this is not preferred.

If more than a threshold amount of scattered second harmonic illumination at wavelength 532 nm is received by gated detector array 1614 within a predetermined time window during each laser pulse, an alarm indication is provided by computer 1611, typically at a display 1615. The alarm indication indicates that an explosive material having certain second harmonic scattering characteristics may be present on a surface of the suitcase 1600. Display 1615 preferably also visually indicates the location of the detected suspect material on the suitcase 1600, here indicated on display 1615 at reference numeral 1616 and on the suitcase 1600 at reference numeral 1617.

The output beam of second laser 1606 is also scanned in two dimensions over suitcases 1600, inducing luminescence by certain materials, including a number of explosives, should those materials be present on the scanned surfaces of the suitcases 1600. The luminescence induced by the laser beam is detected preferably by a plurality of detector assemblies 1618, each preferably including imaging optics 1619, a spectral filter 1620 and a gated detector array 1621, such as a CCD or CMOS array. Alternatively, the plurality of detector assemblies 1618 may be replaced by a single broadband detector assembly, although this is not preferred. Alternatively, the detector array need not be gated, although this is not preferred.

Preferably, the spectral range of each spectral filter 1620 of each detector assembly 1618 differs from the spectral range of each other such filter. The following spectral ranges are preferably provided, each by a different spectral filter 1620 and corresponding to the following gate intervals:

400–430 nm—10 microseconds
450–540 nm—50 nanoseconds
670–700 nm—100 microseconds.

If more than a threshold amount of luminescence is received by any one or more gated detector in gated detector array 1621 within its time window and its spectral range, an alarm indication is provided by computer 1611, typically at display 1615. This alarm indication indicates that an explosive material having certain luminescence characteristics may be present on a surface of the suitcase 1600. Display 1615 preferably also visually indicates, at location 1616 on the display 1615, the location 1617 on the suitcase 1600 of the detected suspect material.

The output beam of third laser 1607 is also scanned in two dimensions over suitcases 1600, inducing Raman scattering by certain materials, including explosives, should those materials be present on the scanned surfaces of the suitcases 1600. The Raman scattering is detected by a plurality of detector assemblies 1624, each preferably including imaging optics 1625, a spectral filter 1626, a notch filter 1627 and a gated detector array 1628, such as a CCD or CMOS array. Alternatively, the plurality of detector assemblies 1624 may be replaced by a single broadband detector assembly, although this is not preferred. Alternatively, the detector array need not be gated, although this is not preferred.

Preferably, the spectral range of each spectral filter 1626 of each detector assembly 1624 differs from the spectral range of each other such filter. The following Raman shifts relative to the laser excitation wavelength are preferably provided, each by a different spectral filter 1626:

880–885 cm (−1)
1360–1365 cm (−1)
1270–1290 cm (−1)
2980–3000 cm (−1).

If more than a threshold amount of Raman scattering is received by any one or more gated detector in array 1628 during the time interval of the laser excitation pulse and its spectral range, an alarm indication is provided by computer 1611, typically at display 1615. This alarm indication indicates that an explosive material having certain Raman scattering characteristics may be present on a surface of the suitcase 1600. Display 1615 preferably also visually indicates, at location 1616 on the display 1615, the location 1617 on the suitcase 1600 of the detected suspect material.

Preferably computer 1611 and display 1615 are operative to superimpose and indicate the spatial relationship between the locations of the detected suspect materials on the suitcase 1600 produced in response to excitation by the first, second and third lasers 1605, 1606 and 1607 and the second harmonic scattering, time-resolved luminescence and time-resolved Raman scattering detection resulting therefrom.

In accordance with a preferred embodiment of the present invention the system of FIG. 16A also provides identification of an explosive on an object.

During identification, identification collecting optics 1630 are employed for receiving time-resolved luminescence and time-resolved Raman scattering from the location or locations of the detected suspect material on the suitcase 1600. During identification, the output beam of lasers 1606 and 1607 are thus scanned in two dimensions at the previously determined location or locations 1617 of suspect material on suitcases 1600.

The output of identification collecting optics 1630 is preferably supplied via a fiberoptic link 1631 to a polychromator 1632, which produces dispersion of the luminescence and Raman spectra. The output from the polychromator 1632 is supplied to a gated detector assembly 1633, preferably employing a CCD array. Alternatively, the detector assembly need not be gated, although this is not preferred.

The output of gated detector assembly 1633 is analyzed by computer 1611 to compare the spectrum represented thereby with reference spectra characteristic of known explosives, in order to provide identification of an explosive on the suitcase 1600.

Figure 16B:
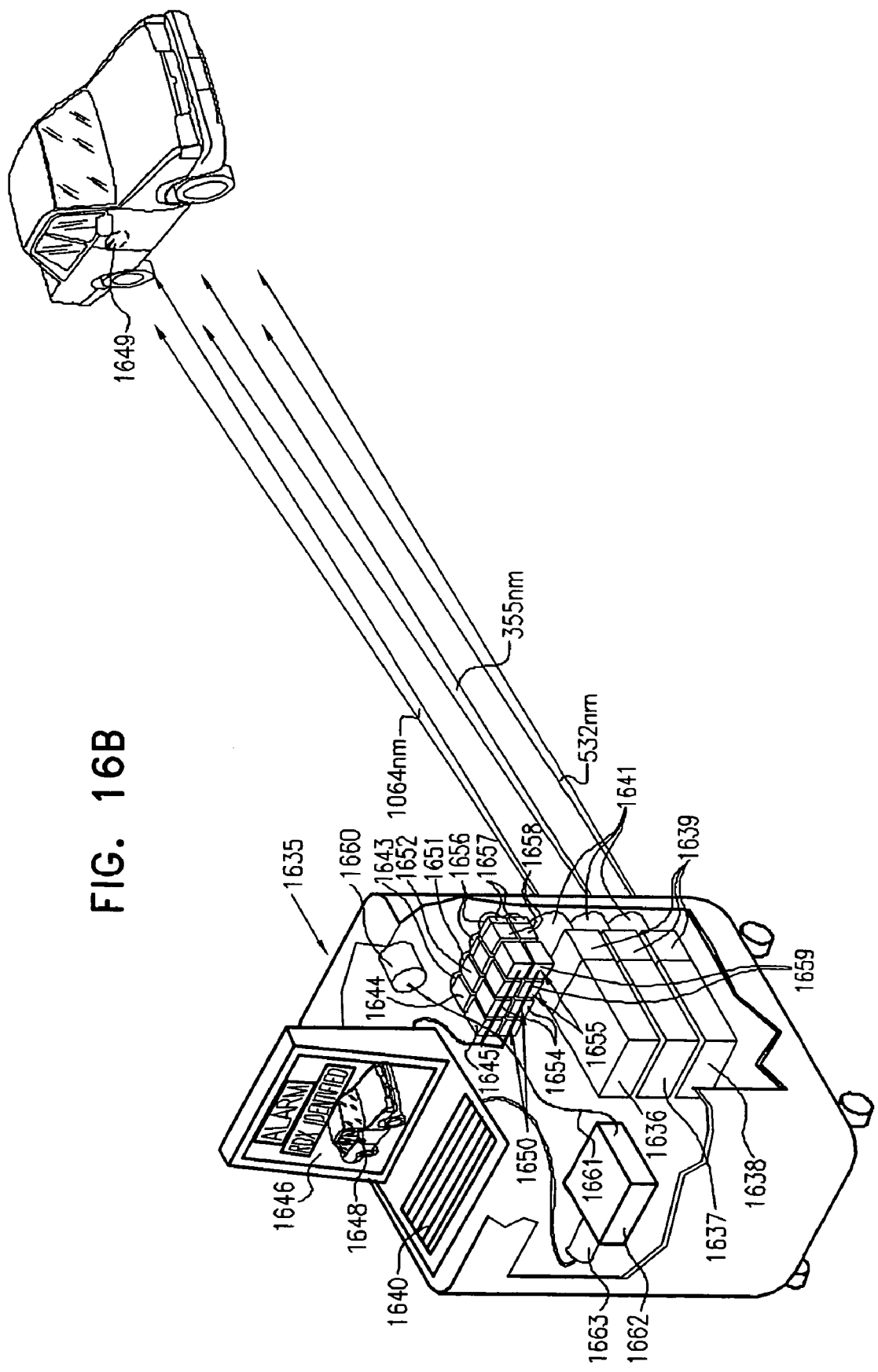

Reference is now made to FIG. 16B, which is a simplified pictorial illustration of a triple mode system for detecting and identifying explosives constructed and operative in accordance with another preferred embodiment of the present invention and employing second harmonic, time-resolved luminescence and time-resolved Raman scattering detection and time-resolved luminescence and time-resolved Raman scattering identification. In the illustrated embodiment, a vehicle screening system is shown, it being appreciated that the present invention is not limited to vehicle screening applications, but rather may be employed in any other suitable remote object inspection environment.

In the embodiment of FIG. 16B, an inspection assembly 1635, which may be portable or stationary, employs a first laser 1636, preferably a Nd:YAG pulsed laser emitting with a peak wavelength at 1064 nm. It is appreciated that wavelengths in the range of 400 nm to 10 microns may be employed. Inspection assembly 1635 preferably also employs a second laser 1637, preferably a Nd:YAG pulsed laser emitting a third or fourth harmonic having respective peak wavelengths at 355 and 266 nm. It is appreciated that wavelengths in the range of 180 nm to 10 microns may be employed. The inspection assembly 1635 preferably also employs a third laser 1638, preferably a Nd:YAG pulsed laser emitting a second harmonic having a peak wavelength at 532 nm. It is appreciated that wavelengths in the range of 200 nm to 10 microns may be employed by this laser. Alternatively, a single laser or two lasers may be used rather than three lasers.

Output beams of lasers 1636, 1637 and 1638 impinge on scanning assemblies 1639, typically comprising first and second scanning elements (not shown) such as mirrors, which are driven in rotational motion by motors (not shown) in synchronization with the pulsed outputs of lasers 1636, 1637 and 1638 in response to synchronization signals provided by a computer 1640. The scanned laser beam outputs of scanning assemblies 1639 are projected onto a vehicle or other suitable remote object, preferably by telescopes 1641.

The output beam of laser 1636 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 1643 and a narrow band spectral filter 1644 having a peak wavelength of 532 nm, preferably by a gated detector array 1645, such as a CCD or CMOS array. Alternatively, the detector array need not be gated, although this is not preferred.

If more than a threshold amount of scattered second harmonic illumination at wavelength 532 nm is received by gated detector array 1645 within a predetermined time window during each laser pulse, an alarm indication is provided by computer 1640, typically at a display 1646. The alarm indication indicates that an explosive material having certain second harmonic scattering characteristics may be present on a surface of the vehicle. Display 1646 preferably also visually indicates the location of the detected suspect material on the vehicle, here indicated on display 1646 at reference numeral 1648 and on the vehicle at reference numeral 1649.

The output beam of second laser 1637 is also scanned in two dimensions over the vehicle, inducing luminescence by certain materials, including a number of explosives, should those materials be present on the scanned surfaces of the vehicle. The luminescence induced by the laser beam is detected preferably by a plurality of detector assemblies 1650, each preferably including imaging optics 1651, a spectral filter 1652 and a gated detector array 1654, such as a CCD or CMOS array. Alternatively, the plurality of detector assemblies 1654 may be replaced by a single broadband detector assembly, although this is not preferred. Alternatively, the detector array need not be gated, although this is not preferred.

Preferably, the spectral range of each spectral filter 1652 of each detector assembly 1650 differs from the spectral range of each other such filter. The following spectral ranges are preferably provided, each by a different spectral filter 1652 and corresponding to the following gate intervals:

400–430 nm—10 microseconds
450–540 nm—50 nanoseconds
670–700 nm—100 microseconds.

If more than a threshold amount of luminescence is received by any one or more gated detector in array 1654 within its time window and its spectral range, an alarm indication is provided by computer 1640, typically at display 1646. This alarm indication indicates that an explosive material having certain luminescence characteristics may be present on a surface of the vehicle. Preferably computer 1640 is operative to analyze and indicate detection of suspect materials on the vehicle produced in response to excitation by the first and second lasers 1636 and 1637 and the resulting second harmonic scattering and luminescence detection resulting therefrom. Display 1646 preferably also visually indicates, at location 1648 on the display 1646, the location 1649 on the vehicle of the detected suspect material.

The output beam of third laser 1638 is also scanned in two dimensions over the vehicle, inducing Raman scattering by certain materials, including explosives, should those materials be present on the scanned surfaces of the vehicle. The Raman scattering is detected by a plurality of detector assemblies 1655, each preferably including imaging optics 1656, a spectral filter 1657, a notch filter 1658 and a gated detector array 1659, such as a CCD or CMOS array. Alternatively, the plurality of detector assemblies 1655 may be replaced by a single broadband detector assembly, although this is not preferred. Alternatively, the detector array need not be gated, although this is not preferred.

Preferably, the spectral range of each spectral filter 1657 of each detector assembly 1655 differs from the spectral range of each other such filter. The following Raman shifts relative to the laser excitation wavelength are preferably provided, each by a different spectral filter 1657:

880–885 cm (−1)
1360–1365 cm (−1)
1270–1290 cm (−1)
2980–3000 cm (−1).

If more than a threshold amount of Raman scattering is received by any one or more gated detector of array 1659 during the time interval of the laser excitation pulse and its spectral range, an alarm indication is provided by computer 1640, typically at display 1646. This alarm indication indicates that an explosive material having certain Raman scattering characteristics may be present on a surface of the vehicle. Display 1646 preferably also visually indicates, at location 1648 on the display 1646, the location 1649 on the vehicle of the detected suspect material.

Preferably computer 1640 is operative to analyze and indicate detection of suspect materials on the vehicle produced in response to excitation by the first, second and third lasers 1636, 1637 and 1638 and the second harmonic scattering, time-resolved luminescence and time-resolved Raman scattering detection resulting therefrom.

Preferably computer 1640 and display 1646 are operative to superimpose and indicate the spatial relationship between the locations of the detected suspect materials on the vehicle produced in response to excitation by the first, second and third lasers 1636, 1637 and 1638 and the second harmonic scattering, time resolved luminescence and time-resolved Raman scattering detection resulting therefrom.

In accordance with a preferred embodiment of the present invention the system of FIG. 16B also provides identification of an explosive on an object.

During identification, identification collecting optics 1660 are employed for receiving time-resolved luminescence and time-resolved Raman scattering from the location or locations 1649 of the detected suspect material on the vehicle. During identification, the output beams of lasers 1636 and 1637 are thus scanned in two dimensions at the previously determined location or locations 1649 of suspect material on a vehicle.

The output of identification collecting optics 1660 is preferably supplied via a fiberoptic link 1661 to a polychromator 1662, which produces dispersion of the luminescence and Raman spectra. The output from the polychromator 1662 is supplied to a gated detector assembly 1663, preferably employing a CCD array. Alternatively, the detector assembly need not be gated, although this is not preferred.

The output of gated detector assembly 1663 is analyzed by computer 1640 to compare the spectrum represented thereby with reference spectra characteristic of known explosives, in order to provide identification of an explosive on the vehicle.

Figure 16C:
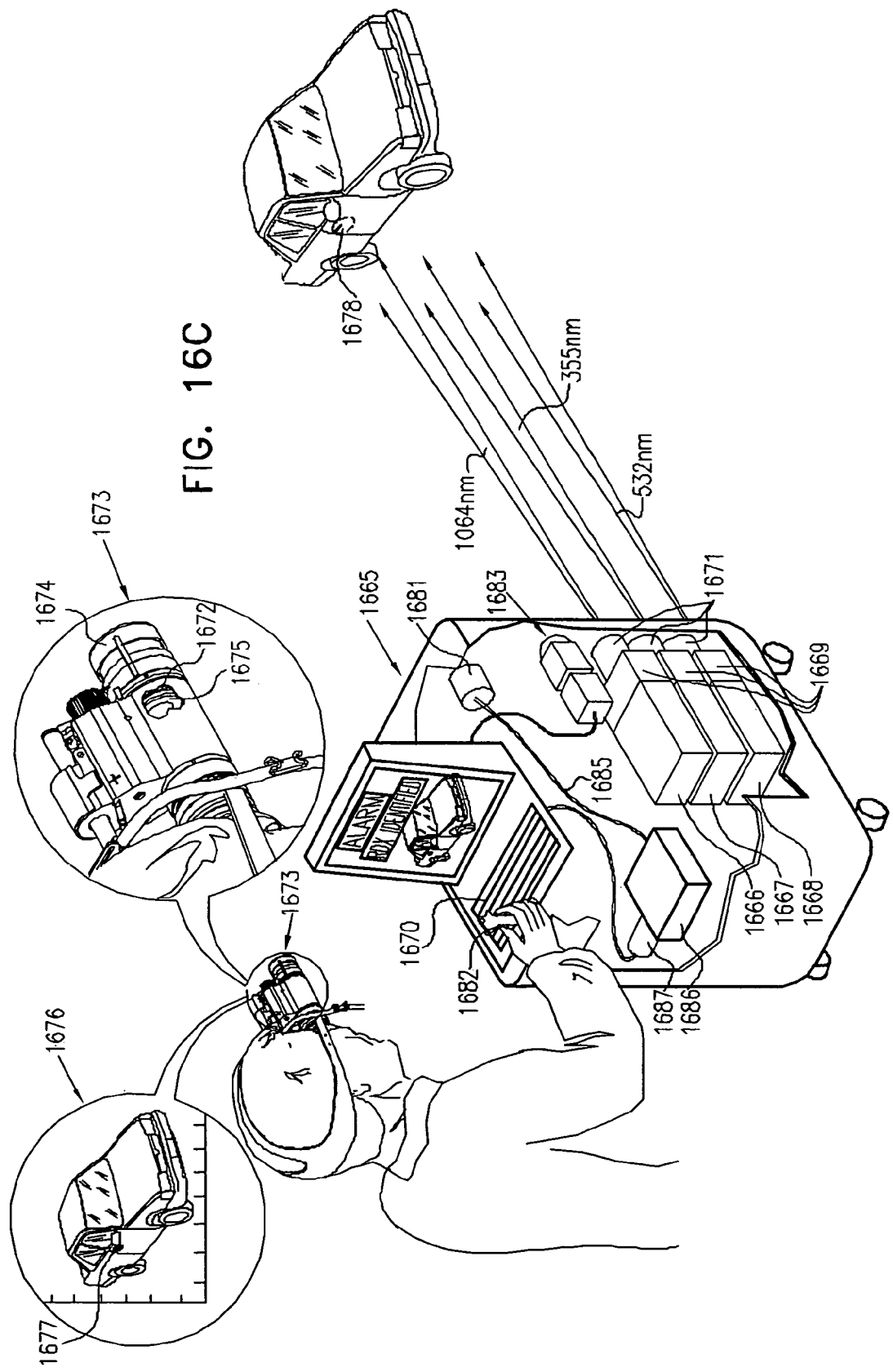

Reference is now made to FIG. 16C, which is a simplified pictorial illustration of a triple mode system for detecting and identifying explosives constructed and operative in accordance with yet another preferred embodiment of the present invention and employing second harmonic, time-resolved luminescence and time-resolved Raman scattering detection and time-resolved luminescence and time-resolved Raman scattering identification. In the illustrated embodiment, a vehicle screening system is shown, it being appreciated that the present invention is not limited to vehicle screening applications, but rather may be employed in any other suitable remote object inspection environment.

In the embodiment of FIG. 16C, an inspection assembly 1665, which is preferably portable, employs a first laser 1666, preferably a Nd:YAG pulsed laser emitting with a peak wavelength at 1064 nm. It is appreciated that wavelengths in the range of 400 nm to 10 microns may be employed. The inspection assembly 1665 preferably also employs a second laser 1667, preferably a Nd:YAG pulsed laser emitting a third or fourth harmonic having respective peak wavelengths at 355 and 266 nm. It is appreciated that wavelengths in the range of 180 nm to 10 microns may be employed. Inspection assembly 1665 preferably also employs a third laser 1668, preferably a Nd:YAG pulsed laser emitting a second harmonic having a peak wavelength at 532 nm. It is appreciated that wavelengths in the range of 200 nm to 10 microns may be employed by this laser. Alternatively, a single laser or two lasers may be used rather than three lasers.

The output beams of lasers 1666, 1667 and 1668 impinge on scanning assemblies 1669, typically comprising first and second scanning elements (not shown) such as mirrors, which are driven in rotational motion by motors (not shown) in synchronization with the pulsed output of lasers 1666, 1667 and 1668 in response to synchronization signals provided by a computer 1670. The scanned laser beam outputs of scanning assemblies 1669 are projected onto a vehicle or other suitable remote object, preferably by telescopes 1671.

The output beam of laser 1666 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 1672 forming part of a head-mounted viewing assembly 1673, a narrow band spectral filter 1674 having a peak wavelength of 532 nm and an image intensifier 1675, all forming part of the head-mounted viewing assembly 1673.

In accordance with a preferred embodiment of the present invention the image intensifier 1675 is gated by control signals from computer 1670 so as to be synchronized with the pulsed output of laser 1666. Filter 1674 is operative to eliminate transmission of reflected laser radiation at 1064 nm, to attenuate the ambient radiation and to fully transmit the second harmonic scattered radiation at 532 nm. Thus, an operator using the head-mounted viewing assembly 1673 sees a scene such as that designated by reference numeral 1676, wherein the location on the vehicle of a suspected explosive is highlighted over an ambient background image of the vehicle. The location of the suspected explosive is indicated on scene 1676 at reference numeral 1677 and on the vehicle at reference numeral 1678.

The output beam of laser 1667 is also scanned in two dimensions over a vehicle, inducing luminescence by certain materials, including a number of explosives, should those materials be present on the scanned surfaces of the vehicle. The luminescence induced by the laser beam is detected via imaging optics 1672 forming part of a head-mounted viewing assembly 1673, at least one and preferably a plurality of individually selectable and interchangeable narrow band spectral filters 1674 and an image intensifier 1675, all forming part of the head-mounted viewing assembly 1675.

Preferably, the spectral range of each spectral filter 1674 differs from the spectral range of each other such filter. The following spectral ranges are preferably provided, each by a different spectral filter 1674 and corresponding to the following gate intervals:

400–430 nm—10 microseconds
  450–540 nm—50 nanoseconds
  670–700 nm—100 microseconds.

In accordance with a preferred embodiment of the present invention the image intensifier 1675 is gated by control signals from computer 1670 so as to be synchronized with the pulsed output of laser 1667. Filters 1674 are operative to eliminate transmission of reflected laser radiation at 355 nm and 266 nm, to attenuate the ambient radiation and to fully transmit the luminescence. Thus, an operator using the head-mounted viewing assembly 1673 sees a scene such as scene 1676, wherein location 1678 of a suspected explosive on the vehicle is highlighted on the scene 1676 at location 1677 over an ambient background image of the vehicle.

The output beam of laser 1668 is also scanned in two dimensions over the vehicle, inducing Raman scattering by certain materials, including explosives, should those materials be present on the scanned surfaces of the vehicle. The Raman scattering induced by the laser beam is detected via imaging optics 1672 forming part of a head-mounted viewing assembly 1673, at least one and preferably a plurality of narrow band spectral filters 1674 and image intensifier 1675, all forming part of the head-mounted viewing assembly 1673.

Preferably, the spectral range of each spectral filter 1674 differs from the spectral range of each other such filter. The following Raman shifts relative to the laser excitation wavelength are preferably provided, each by a different spectral filter 1674:

880–885 cm (−1)
1360–1365 cm (−1)
1270–1290 cm (−1)
2980–3000 cm (−1).

In accordance with a preferred embodiment of the present invention the image intensifier 1675 is gated by control signals from computer 1670 to operate during the time interval of the laser excitation pulse. Thus, an operator using the head-mounted viewing assembly 1673 sees a scene such as scene 1676, wherein location 1678 of a suspected explosive on the vehicle is highlighted on the scene 1676 at location 1677 over an ambient background image of the vehicle.

In accordance with a preferred embodiment of the present invention the system of FIG. 16C also provides identification of an explosive on an object.

During identification, identification collecting optics 1681 are employed for receiving time-resolved luminescence and time-resolved Raman scattering from the location or locations of the detected suspect material on the vehicle. During identification, the output beam of first laser 1666 is scanned in two dimensions at the previously determined location or locations 1678 of suspect material on a vehicle. During identification, the output beam of second laser 1667 is also scanned in two dimensions at the previously determined location or locations 1678 of suspect material on a vehicle.

The identification collecting optics 1681 are preferably aimed by an operator at the location of the suspected explosive typically using a joystick 1682 and a viewing camera 1683 or marker which is visible through the image intensifier 1675.

The output of identification collecting optics 1681 is preferably supplied via a fiberoptic link 1685 to a polychromator 1686, which produces dispersion of the luminescence and Raman spectra. The output from the polychromator 1686 is supplied to a gated detector assembly 1687, preferably employing a CCD array. Alternatively, the detector assembly need not be gated, although this is not preferred.

The output of gated detector assembly 1687 is analyzed by computer 1670 to compare the spectrum represented thereby with reference spectra characteristic of known explosives, in order to provide identification of an explosive on the vehicle.

Figure 17A:
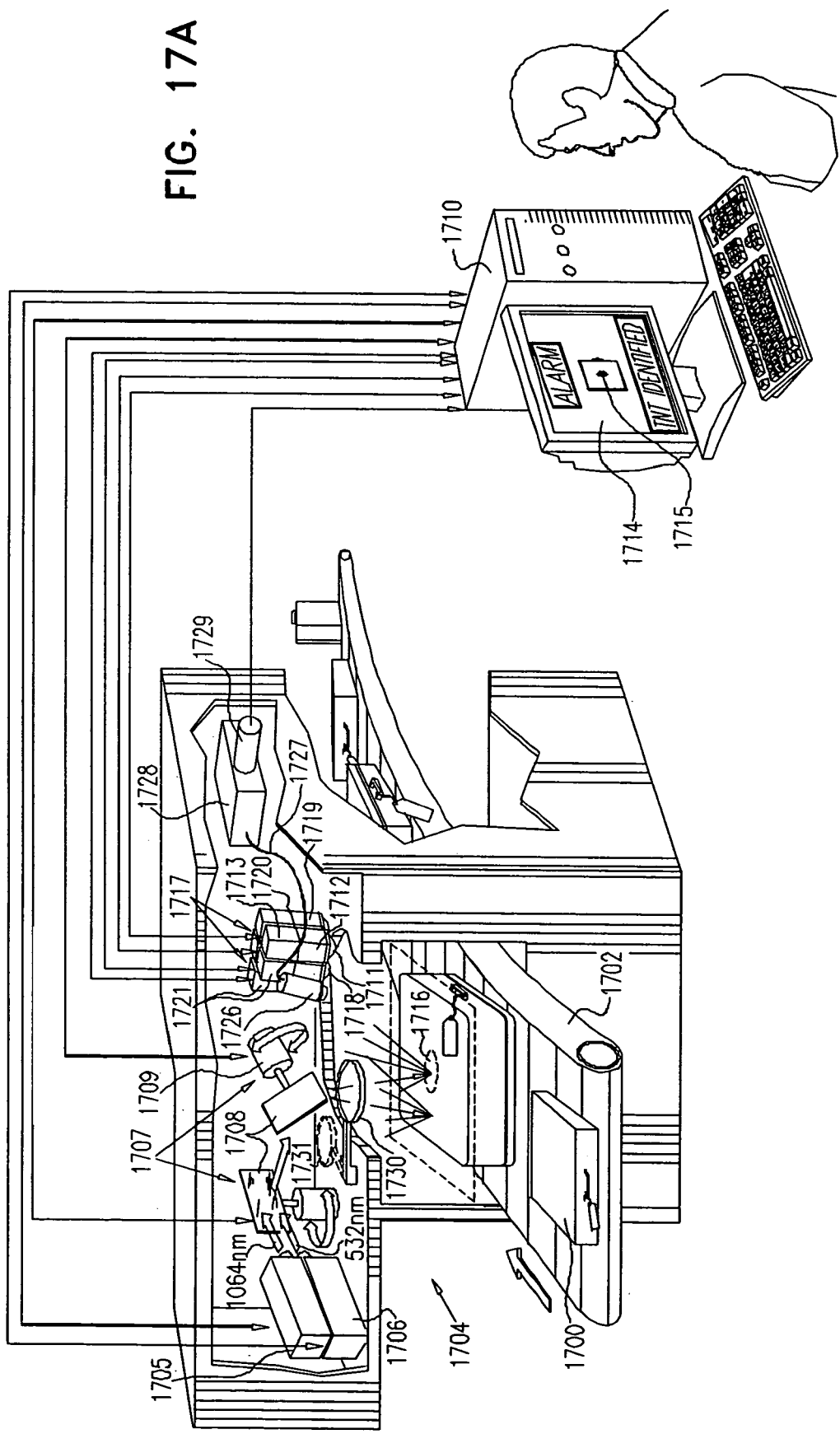
FIGS. 17A, 17B and 17C are simplified pictorial illustrations of triple mode systems for detecting and identifying explosives constructed and operative in accordance with preferred embodiments of the present invention and employing second harmonic and time-resolved Raman scattering detection and employing time-resolved Raman scattering and time-resolved laser induced breakdown spectroscopy for enhanced identification.

Reference is now made to FIG. 17A, which is a simplified pictorial illustration of a triple mode system for detecting and identifying explosives constructed and operative in accordance with a preferred embodiment of the present invention and employing second harmonic and time-resolved Raman scattering detection and employing time-resolved Raman scattering and time-resolved laser induced breakdown spectroscopy for enhanced identification. In the illustrated embodiment, a baggage screening system is shown, it being appreciated that the present invention is not limited to baggage screening applications, but rather may be employed in any other suitable object inspection environment.

In the embodiment of FIG. 17A, baggage, such as suitcases 1700, is transported by a conveyor 1702 past an inspection station 1704 at which the suitcases 1700 are inspected. In accordance with a preferred embodiment of the present invention, the inspection station 1704 employs a first laser 1705, preferably a Nd:YAG pulsed laser emitting with a peak wavelength at 1064 nm. It is appreciated that wavelengths in the range of 400 nm to 10 microns may be employed. The inspection station 1704 preferably also employs a second laser 1706, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

The output beams of lasers 1705 and 1706 impinge on a scanning assembly 1707, typically comprising first and second scanning elements 1708, such as mirrors, which are driven in rotational motion by motors 1709 in synchronization with the pulsed outputs of lasers 1705 and 1706 in response to synchronization signals provided by a computer 1710.

The output beam of laser 1705 is thus scanned in two dimensions over suitcases 1700, inducing second harmonic scattering of the output beam by certain materials, including a number of explosives, should those materials be present on the scanned surfaces of the suitcases 1700. The scattered second harmonic of the laser beam is detected via imaging optics 1711 and a narrow band spectral filter 1712 having a peak wavelength of 532 nm preferably by a gated detector array 1713, such as a CCD or CMOS array. Alternatively, the detector array need not be gated, although this is not preferred.

If more than a threshold amount of scattered second harmonic illumination at wavelength 532 nm is received by gated detector array 1713 within a predetermined time window during each laser pulse, an alarm indication is provided by computer 1710, typically at a display 1714. The alarm indication indicates that an explosive material having certain second harmonic scattering characteristics may be present on a surface of the suitcase 1700. Display 1714 preferably also visually indicates the location of the detected suspect material on the suitcase 1700, here indicated on display 1714 at reference numeral 1715 and on the suitcase 1700 at reference numeral 1716.

The output beam of second laser 1706 is also scanned in two dimensions over suitcases 1700, inducing Raman scattering by certain materials, including explosives, should those materials be present on the scanned surfaces of the suitcases 1700. The Raman scattering is detected by a plurality of detector assemblies 1717, each preferably including imaging optics 1718, a spectral filter 1719, a notch filter 1720 and a gated detector array 1721, such as a CCD or CMOS array. Alternatively, the plurality of detector assemblies 1717 may be replaced by a single broadband detector assembly, although this is not preferred. Alternatively, the detector array need not be gated, although this is not preferred.

Preferably, the spectral range of each spectral filter 1719 of each detector assembly 1717 differs from the spectral range of each other such filter. The following Raman shifts relative to the laser excitation wavelength are preferably provided, each by a different spectral filter 1719:

880–885 cm (−1)
1360–1365 cm (−1)
1270–1290 cm (−1)
2980–3000 cm (−1).

If more than a threshold amount of Raman scattering is received by any one or more gated detector in array 1721 during the time interval of the laser excitation pulse and its spectral range, an alarm indication is provided by computer 1710, typically at display 1714. This alarm indication indicates that an explosive material having certain Raman scattering characteristics may be present on a surface of the suitcase 1700. Display 1714 preferably also visually indicates, at location 1715 on the display 1714, the location 1716 on the suitcase 1700 of the detected suspect material.

Preferably computer 1710 and display 1714 are operative to superimpose and indicate the spatial relationship between the locations of the detected suspect materials on the suitcase 1700 produced in response to excitation by the first and second lasers 1705 and 1706 and the second harmonic scattering and luminescence detection resulting therefrom.

In accordance with a preferred embodiment of the present invention the system of FIG. 17A also provides identification of an explosive on an object.

During identification, identification collecting optics 1726 are employed for receiving time-resolved Raman scattering from the location or locations of the detected suspect material on the suitcase 1700. During identification, the output beam of laser 1706 is thus scanned in two dimensions at the previously determined location or locations 1716 of suspect material on suitcases 1700.

The output of identification collecting optics 1726 is preferably supplied via a fiberoptic link 1727 to a polychromator 1728, which produces dispersion of the Raman scattering spectrum. The output from the polychromator 1728 is supplied to a gated detector assembly 1729, preferably employing a CCD array. Alternatively, the detector assembly need not be gated, although this is not preferred.

The output of gated detector assembly 1729 is analyzed by computer 1710 to compare the spectrum represented thereby with reference spectra characteristic of known explosives, in order to provide identification of an explosive on the suitcase 1700.

In accordance with a preferred embodiment of the present invention the system of FIG. 17A also provides enhanced identification of an explosive on an object. This enhanced identification is preferably provided by employing a selectably positionable lens 1730 intermediate the scanning assembly 1707 and the suitcase 1700. Lens 1730 is normally positioned in an inoperative position, indicated in dashed lines at reference numeral 1731, during detection, as opposed to during enhanced identification, operation of the system.

During enhanced identification, identification collecting optics 1726 are employed for receiving laser induced breakdown emissions from the location or locations of the detected suspect material on the suitcase 1700. Lens 1730 is operative to concentrate the output beam of the laser 1705 on such locations. The output of identification collecting optics 1726 is preferably supplied via fiberoptic link 1727 to polychromator 1728, which produces dispersion of the emission spectrum. The output from the polychromator 1728 is supplied to gated detector assembly 1729.

The output of gated detector assembly 1729 is analyzed by computer 1710 to compare the spectrum represented thereby with reference spectra characteristic of known explosives, in order to provide an enhanced output indication of the existence of an explosive on the suitcase 1700.

Figure 17B:
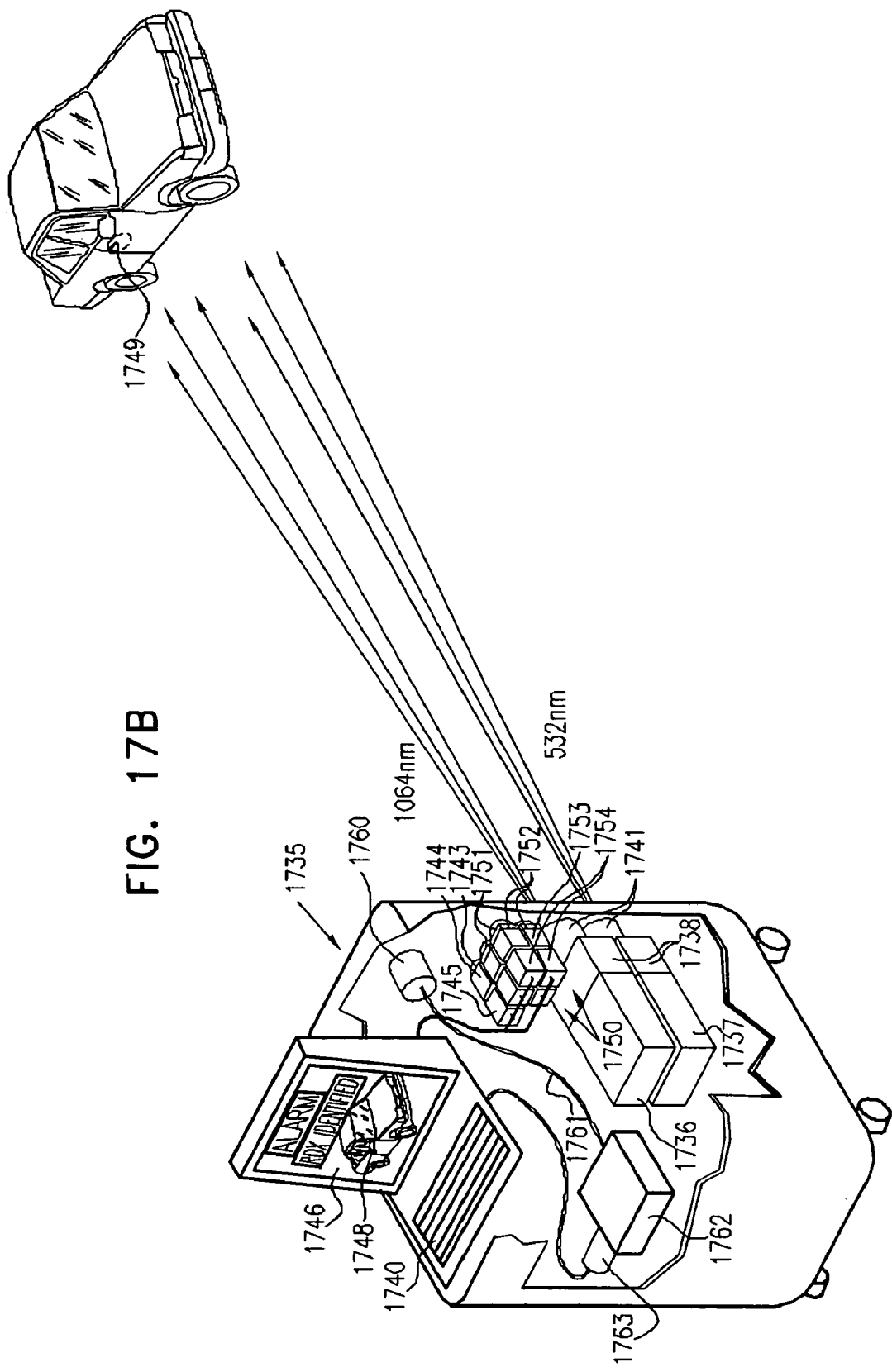

Reference is now made to FIG. 17B, which is a simplified pictorial illustration of a triple mode system for detecting and identifying explosives constructed and operative in accordance with another preferred embodiment of the present invention and employing second harmonic and time-resolved Raman scattering detection and employing time-resolved Raman scattering and time-resolved laser induced breakdown spectroscopy for enhanced identification. In the illustrated embodiment, a vehicle screening system is shown, it being appreciated that the present invention is not limited to vehicle screening applications, but rather may be employed in any other suitable remote object inspection environment.

In the embodiment of FIG. 17B, an inspection assembly 1735, which may be portable or stationary, employs a first laser 1736, preferably a Nd:YAG pulsed laser emitting with a peak wavelength at 1064 nm. It is appreciated that wavelengths in the range of 400 nm to 10 microns may be employed. Inspection assembly 1735 preferably also employs a second laser 1737, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

Output beams of lasers 1736 and 1737 impinge on scanning assemblies 1738, typically comprising first and second scanning elements (not shown) such as mirrors, which are driven in rotational motion by motors (not shown) in synchronization with the pulsed outputs of lasers 1736 and 1737 in response to synchronization signals provided by a computer 1740. The scanned laser beam outputs of scanning assemblies 1738 are projected onto a vehicle or other suitable remote object, preferably by a pair of telescopes 1741.

The output beam of laser 1736 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 1743 and a narrow band spectral filter 1744 having a peak wavelength of 532 nm, preferably by a gated detector array 1745, such as a CCD or CMOS array. Alternatively, the detector array need not be gated, although this is not preferred.

If more than a threshold amount of scattered second harmonic illumination at wavelength 532 nm is received by gated detector array 1745 within a predetermined time window during each laser pulse, an alarm indication is provided by computer 1740, typically at a display 1746. The alarm indication indicates that an explosive material having certain second harmonic scattering characteristics may be present on a surface of the vehicle. Display 1746 preferably also visually indicates the location of the detected suspect material on the vehicle, here indicated on display 1746 at reference numeral 1748 and on the vehicle at reference numeral 1749.

The output beam of second laser 1737 is thus also scanned in two dimensions over the vehicle, inducing Raman scattering by certain materials, including explosives, should those materials be present on the scanned surfaces of the vehicle. The Raman scattering is detected by a plurality of detector assemblies 1750, each preferably including imaging optics 1751, a spectral filter 1752, a notch filter 1753 and a gated detector array 1754, such as a CCD or CMOS array. Alternatively, the plurality of detector assemblies 1750 may be replaced by a single broadband detector assembly, although this is not preferred. Alternatively, the detector array need not be gated, although this is not preferred.

Preferably, the spectral range of each spectral filter 1752 of each detector assembly 1750 differs from the spectral range of each other such filter. The following Raman shifts relative to the laser excitation wavelength are preferably provided, each by a different spectral filter 1752:

880–885 cm (−1)
1360–1365 cm (−1)
1270–1290 cm (−1)
2980–3000 cm (−1).

If more than a threshold amount of Raman scattering is received by any one or more gated detector of array 1754 during the time interval of the laser excitation pulse and its spectral range, an alarm indication is provided by computer 1740, typically at display 1746. This alarm indication indicates that an explosive material having certain Raman scattering characteristics may be present on a surface of the vehicle. Display 1746 preferably also visually indicates, at location 1748 on the display 1746, the location 1749 on the vehicle of the detected suspect material.

Preferably computer 1740 is operative to analyze and indicate detection of suspect materials on the vehicle produced in response to excitation by the first and second lasers 1736 and 1737 and the resulting second harmonic scattering and Raman scattering detection resulting therefrom.

Preferably computer 1740 and display 1746 are operative to superimpose and indicate the spatial relationship between the locations of the detected suspect materials on the vehicle produced in response to excitation by the first and second lasers 1736 and 1737 and the second harmonic scattering and Raman scattering detection resulting therefrom.

In accordance with a preferred embodiment of the present invention the system of FIG. 17B also provides identification of an explosive on an object.

During identification, identification collecting optics 1760 are employed for receiving time-resolved Raman scattering from the location or locations of the detected suspect material on the vehicle. During identification, the output beam of laser 1737 is thus scanned in two dimensions at the previously determined location or locations 1749 of suspect material on a vehicle.

The output of identification collecting optics 1760 is preferably supplied via a fiberoptic link 1761 to a polychromator 1762, which produces dispersion of the Raman scattering spectrum. The output from the polychromator 1762 is supplied to a gated detector assembly 1763, preferably employing a CCD array. Alternatively, the detector assembly need not be gated, although this is not preferred.

The output of gated detector assembly 1763 is analyzed by computer 1740 to compare the spectrum represented thereby with reference spectra characteristic of known explosives, in order to provide identification of an explosive on the vehicle.

In accordance with a preferred embodiment of the present invention the system of FIG. 17B also provides enhanced identification of detection of an explosive on an object. This enhanced identification is preferably provided by employing a selectably positionable lens (not shown) that is associated with telescope 1741. This lens is normally positioned in an inoperative position during detection, as opposed to enhanced identification, operation of the system.

During enhanced identification, identification collecting optics 1760 are employed for receiving laser induced breakdown emissions from the location or locations of the detected suspect material on the vehicle. The output of identification collecting optics 1760 is preferably supplied via fiberoptic link 1761 to polychromator 1762, which produces dispersion of the emission spectrum. The output from the polychromator 1762 is supplied to gated detector assembly 1763.

The output of gated detector assembly 1763 is analyzed by computer 1740 to compare the spectrum represented thereby with reference spectra characteristic of known explosives, in order to provide an enhanced output indication of the existence of an explosive on the vehicle.

Figure 17C:
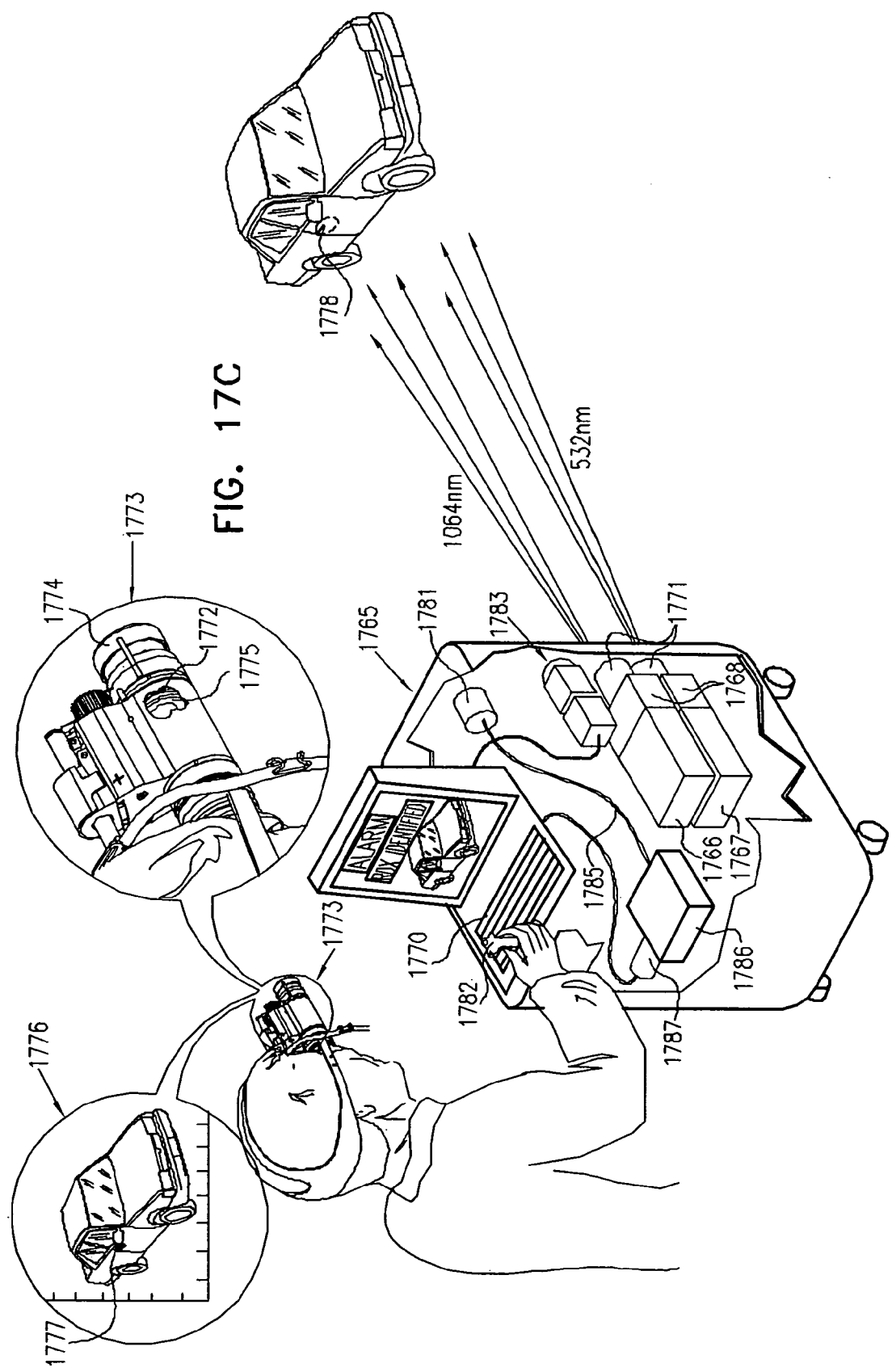

Reference is now made to FIG. 17C, which is a simplified pictorial illustration of a triple mode system for detecting and identifying explosives constructed and operative in accordance with yet another preferred embodiment of the present invention and employing second harmonic and time-resolved Raman scattering detection and employing time-resolved Raman scattering and time-resolved laser induced breakdown spectroscopy for enhanced identification. In the illustrated embodiment, a vehicle screening system is shown, it being appreciated that the present invention is not limited to vehicle screening applications, but rather may be employed in any other suitable remote object inspection environment.

In the embodiment of FIG. 17C, an inspection assembly 1765, which is preferably portable, employs a first laser 1766, preferably a Nd:YAG pulsed laser emitting with a peak wavelength at 1064 nm. It is appreciated that wavelengths in the range of 400 nm to 10 microns may be employed. Inspection assembly 1765 preferably also employs a second laser 1767, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

Output beams of lasers 1766 and 1767 impinge on scanning assemblies 1768, typically comprising first and second scanning elements (not shown) such as mirrors, which are driven in rotational motion by motors (not shown) in synchronization with the pulsed outputs of lasers 1766 and 1767 in response to synchronization signals provided by a computer 1770. The scanned laser beam outputs of scanning assemblies 1768 are projected onto a vehicle or other suitable remote object, preferably by a pair of telescopes 1771.

The output beam of laser 1766 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 1772 forming part of a head-mounted viewing assembly 1773, a narrow band spectral filter 1774 having a peak wavelength of 532 nm and an image intensifier 1775, all forming part of the head-mounted viewing assembly 1773.

In accordance with a preferred embodiment of the present invention the image intensifier 1775 is gated by control signals from computer 1770 so as to be synchronized with the pulsed output of laser 1766. Filter 1766 is operative to eliminate transmission of reflected laser radiation at 1064 nm, to attenuate the ambient radiation and to fully transmit the second harmonic scattered radiation at 532 nm. Thus, an operator using the head-mounted viewing assembly 1773 sees a scene such as that designated by reference numeral 1776, wherein the location on the vehicle of a suspected explosive is highlighted over an ambient background image of the vehicle. The location of the suspected explosive is indicated on scene 1776 at reference numeral 1777 and on the vehicle at reference numeral 1778.

The output beam of laser 1767 is also scanned in two dimensions over the vehicle, inducing Raman scattering by certain materials, including explosives, should those materials be present on the scanned surfaces of the vehicle. The Raman scattering induced by the laser beam is detected via imaging optics 1772 forming part of a head-mounted viewing assembly 1773, at least one and preferably a plurality of narrow band spectral filters 1774 and image intensifier 1775, all forming part of the head-mounted viewing assembly 1773.

Preferably, the spectral range of each spectral filter 1774 differs from the spectral range of each other such filter. The following Raman shifts relative to the laser excitation wavelength are preferably provided, each by a different spectral filter 1774:

880–885 cm (−1)
1360–1365 cm (−1)
1270–1290 cm (−1)
2980–3000 cm (−1).

In accordance with a preferred embodiment of the present invention the image intensifier 1775 is gated by control signals from computer 1770 to operate during the time interval of the laser excitation pulse. Thus, an operator using the head-mounted viewing assembly 1773 sees a scene such as scene 1776, wherein location 1778 of a suspected explosive on the vehicle is highlighted on the scene 1776 at location 1777 over an ambient background image of the vehicle.

In accordance with a preferred embodiment of the present invention the system of FIG. 17C also provides identification of an explosive on an object.

During identification, identification collecting optics 1781 are employed for receiving time-resolved Raman scattering from the location or locations of the detected suspect material on the vehicle. During identification, the output beam of laser 1767 is thus scanned in two dimensions at the previously determined location or locations 1778 of suspect material on a vehicle.

The identification collecting optics 1781 are preferably aimed by an operator at the location of the suspected explosive typically using a joystick 1782 and a viewing camera 1783 or marker which is visible through the image intensifier 1775.

The output of identification collecting optics 1781 is preferably supplied via a fiberoptic link 1785 to a polychromator 1786, which produces dispersion of the Raman scattering spectrum. The output from the polychromator 1786 is supplied to a gated detector assembly 1787, preferably employing a CCD array. Alternatively, the detector assembly need not be gated, although this is not preferred.

The output of gated detector assembly 1787 is analyzed by computer 1770 to compare the spectrum represented thereby with reference spectra characteristic of known explosives, in order to provide identification of an explosive on the vehicle.

In accordance with a preferred embodiment of the present invention the system of FIG. 17C also provides enhanced identification of detection of an explosive on an object. This enhanced identification is preferably provided by employing a selectably positionable lens (not shown) that is associated with telescope 1771. This lens is normally positioned in an inoperative position during detection, as opposed to during enhanced identification, operation of the system.

During enhanced identification, identification collecting optics 1781 are employed for receiving laser induced breakdown emissions from the location or locations of the detected suspect material on the vehicle. The output of identification collecting optics 1781 is preferably supplied via fiberoptic link 1785 to polychromator 1786, which produces dispersion of the emission spectrum. The output from the polychromator 1786 is supplied to gated detector assembly 1787.

The identification collecting optics 1781 are preferably aimed by an operator at the location of the suspected explosive typically using a joystick 1782 and a viewing camera 1783 or marker which is visible through the image intensifier 1775.

The output of gated detector assembly 1787 is analyzed by computer 1770 to compare the spectrum represented thereby with reference spectra characteristic of known explosives, in order to provide an enhanced output indication of the existence of an explosive on the vehicle.

Figure 18A:
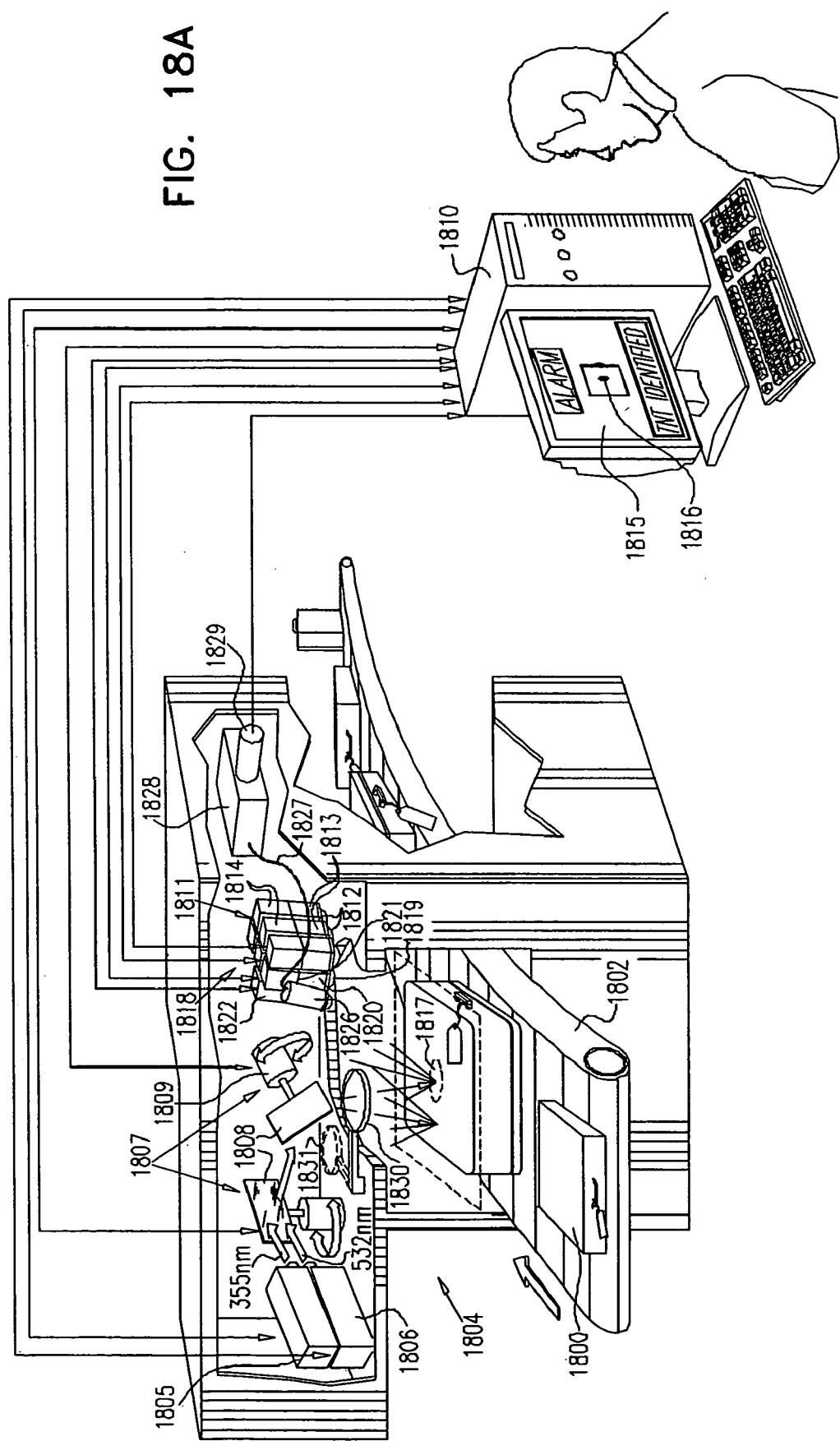

Reference is now made to FIG. 18A, which is a simplified pictorial illustration of a triple mode system for detecting and identifying explosives constructed and operative in accordance with a preferred embodiment of the present invention and employing time-resolved luminescence and time-resolved Raman scattering detection and employing time-resolved luminescence, time-resolved Raman scattering and time-resolved laser induced breakdown spectroscopy for enhanced identification. In the illustrated embodiment, a baggage screening system is shown, it being appreciated that the present invention is not limited to baggage screening applications, but rather may be employed in any other suitable object inspection environment.

In the embodiment of FIG. 18A, baggage, such as suitcases 1800, is transported by a conveyor 1802 past an inspection station 1804 at which the suitcases 1800 are inspected. In accordance with a preferred embodiment of the present invention, the inspection station 1804 employs a first laser 1805, preferably a Nd:YAG pulsed laser emitting a third or fourth harmonic having respective peak wavelengths at 355 and 266 nm. It is appreciated that wavelengths in the range of 180 nm to 10 microns may be employed. The inspection station 1804 preferably also employs a second laser 1806, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

The output beams of lasers 1805 and 1806 impinge on a scanning assembly 1807, typically comprising first and second scanning elements 1808, such as mirrors, which are driven in rotational motion by motors 1809 in synchronization with the pulsed outputs of lasers 1805 and 1806 in response to synchronization signals provided by a computer 1810.

The output beam of laser 1805 is thus scanned in two dimensions over suitcases 1800, inducing luminescence by certain materials, including a number of explosives, should those materials be present on the scanned surfaces of the suitcases 1800. The luminescence induced by the laser beam is detected preferably by a plurality of detector assemblies 1811, each preferably including imaging optics 1812, a spectral filter 1813 and a gated detector array 1814, such as a CCD or CMOS array. Alternatively, the plurality of detector assemblies 1811 may be replaced by a single broadband detector assembly, although this is not preferred. Alternatively, the detector array need not be gated, although this is not preferred.

Preferably, the spectral range of each spectral filter 1813 of each detector assembly 1811 differs from the spectral range of each other such filter. The following spectral ranges are preferably provided, each by a different spectral filter 1813 and corresponding to the following gate intervals:

400–430 nm—10 microseconds
450–540 nm—50 nanoseconds
670–700 nm—100 microseconds.

If more than a threshold amount of luminescence is received by any one or more gated detector 1814 within its time window and its spectral range, an alarm indication is provided by computer 1810, typically at a display 1815. This alarm indication indicates that an explosive material having certain luminescence characteristics may be present on a surface of the suitcase 1800. Display 1815 preferably also visually indicates the location of the detected suspect material on the suitcase 1800, here indicated on display 1815 at reference numeral 1816 and on the suitcase 1800 at reference numeral 1817.

The output beam of second laser 1806 is also scanned in two dimensions over suitcases 1800, inducing Raman scattering by certain materials, including explosives, should those materials be present on the scanned surfaces of the suitcases 1800. The Raman scattering is detected by a plurality of detector assemblies 1818 each preferably including imaging optics 1819, a spectral filter 1820, a notch filter 1821 and a gated detector array 1822, such as a CCD or CMOS array. Alternatively, the plurality of detector assemblies 1818 may be replaced by a single broadband detector assembly, although this is not preferred. Alternatively, the detector array need not be gated, although this is not preferred.

Preferably, the spectral range of each spectral filter 1820 of each detector assembly 1818 differs from the spectral range of each other such filter. The following Raman shifts relative to the laser excitation wavelength are preferably provided, each by a different spectral filter 1820:

880–885 cm (−1)
1360–1365 cm (−1)
1270–1290 cm (−1)
2980–3000 cm (−1).

If more than a threshold amount of Raman scattering is received by any one or more gated detector in array 1822 during the time interval of the laser excitation pulse and its spectral range, an alarm indication is provided by computer 1810, typically at display 1815. This alarm indication indicates that an explosive material having certain Raman scattering characteristics may be present on a surface of the suitcase 1800. Display 1815 preferably also visually indicates, at location 1816 on the display 1815, the location 1817 on the suitcase 1800 of the detected suspect material.

Preferably computer 1810 and display 1815 are operative to superimpose and indicate the spatial relationship between the locations of the detected suspect materials on the suitcase 1800 produced in response to excitation by the first and second lasers 1805 and 1806 and the time-resolved luminescence and time-resolved Raman scattering detection resulting therefrom.

In accordance with a preferred embodiment of the present invention the system of FIG. 18A also provides identification of an explosive on an object.

During identification, identification collecting optics 1826 are employed for receiving time-resolved luminescence and time-resolved Raman scattering from the location or locations of the detected suspect material on the suitcase 1800. During identification, the output beams of lasers 1805 and 1806 are thus scanned in two dimensions at the previously determined location or locations 1817 of suspect material on suitcases 1800.

The output of identification collecting optics 1826 is preferably supplied via a fiberoptic link 1827 to a polychromator 1828, which produces dispersion of the luminescence and Raman spectra. The output from the polychromator 1828 is supplied to a gated detector assembly 1829, preferably employing a CCD array. Alternatively, the detector assembly need not be gated, although this is not preferred.

The output of gated detector assembly 1829 is analyzed by computer 1810 to compare the spectrum represented thereby with reference spectra characteristic of known explosives, in order to provide identification of an explosive on the suitcase 1800.

In accordance with a preferred embodiment of the present invention the system of FIG. 18A also provides enhanced identification of an explosive on an object. This enhanced identification is preferably provided by employing a selectably positionable lens 1830 intermediate the scanning assembly 1807 and the suitcase 1800. Lens 1830 is normally positioned in an inoperative position, indicated in dashed lines at reference numeral 1831, during detection, as opposed to during enhanced identification, operation of the system.

During enhanced identification, identification collecting optics 1826 are employed for receiving laser induced breakdown emissions from the location or locations of the detected suspect material on the suitcase 1800. Lens 1830 is operative to concentrate the output beam of the laser 1806 on such locations. The output of identification collecting optics 1826 is preferably supplied via fiberoptic link 1827 to polychromator 1828, which produces dispersion of the emission spectrum. The output from the polychromator 1828 is supplied to gated detector assembly 1829.

The output of gated detector assembly 1829 is analyzed by computer 1810 to compare the spectrum represented thereby with reference spectra characteristic of known explosives, in order to provide an enhanced output indication of the existence of an explosive on the suitcase 1800.

Reference is now made to FIG. 18B, which is a simplified pictorial illustration of a triple mode system for detecting and identifying explosives constructed and operative in accordance with another preferred embodiment of the present invention and employing time-resolved luminescence and time-resolved Raman scattering detection and employing time-resolved luminescence, time-resolved Raman scattering and time-resolved laser induced breakdown spectroscopy for enhanced identification. In the illustrated embodiment, a vehicle screening system is shown, it being appreciated that the present invention is not limited to vehicle screening applications, but rather may be employed in any other suitable remote object inspection environment.

In the embodiment of FIG. 18B, an inspection assembly 1835, which may be portable or stationary, employs a first laser 1836, preferably a Nd:YAG pulsed laser emitting a third or fourth harmonic having respective peak wavelengths at 355 and 266 nm. It is appreciated that wavelengths in the range of 180 nm to 10 microns may be employed. Inspection assembly 1835 preferably also employs a second laser 1837, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

Output beams of lasers 1836 and 1837 impinge on scanning assemblies 1838, typically comprising first and second scanning elements (not shown) such as mirrors, which are driven in rotational motion by motors (not shown) in synchronization with the pulsed outputs of lasers 1836 and 1837 in response to synchronization signals provided by a computer 1840. The scanned laser beam outputs of scanning assemblies 1838 are projected onto a vehicle or other suitable remote object, preferably by a pair of telescopes 1841.

The output beam of laser 1836 is thus scanned in two dimensions over a vehicle, inducing luminescence by certain materials, including a number of explosives, should those materials be present on the scanned surfaces of the vehicle. The luminescence induced by the laser beam is detected preferably by a plurality of detector assemblies 1842, each preferably including imaging optics 1843, a spectral filter 1844 and a gated detector array 1845, such as a CCD or CMOS array. Alternatively, the plurality of detector assemblies 1842 may be replaced by a single broadband detector assembly, although this is not preferred. Alternatively, the detector array need not be gated, although this is not preferred.

Preferably, the spectral range of each spectral filter 1844 of each detector assembly 1842 differs from the spectral range of each other such filter. The following spectral ranges are preferably provided, each by a different spectral filter 1844 and corresponding to the following gate intervals:
- 400–430 nm—10 microseconds
- 450–540 nm—50 nanoseconds
- 670–700 nm—100 microseconds.

If more than a threshold amount of luminescence is received by any one or more gated detector 1845 within its time window and its spectral range, an alarm indication is provided by computer 1840, typically at a display 1846. This alarm indication indicates that an explosive material having certain luminescence characteristics may be present on a surface of the vehicle. Display 1846 preferably also visually indicates the location of the detected suspect material on the vehicle, here indicated on display 1846 at reference numeral 1848 and on the vehicle at reference numeral 1849.

The output beam of second laser 1837 is also scanned in two dimensions over the vehicle, inducing Raman scattering by certain materials, including explosives, should those materials be present on the scanned surfaces of the vehicle. The Raman scattering is detected by a plurality of detector assemblies 1850, each preferably including imaging optics 1851, a spectral filter 1852, a notch filter 1853 and a gated detector array 1854 such as a CCD or CMOS array. Alternatively, the plurality of detector assemblies 1850 may be replaced by a single broadband detector assembly, although this is not preferred. Alternatively, the detector array need not be gated, although this is not preferred.

Preferably, the spectral range of each spectral filter 1852 of each detector assembly 1850 differs from the spectral range of each other such filter. The following Raman shifts relative to the laser excitation wavelength are preferably provided, each by a different spectral filter 1852:
- 880–885 cm (−1)
- 1360–1365 cm (−1)
- 1270–1290 cm (−1)
- 2980–3000 cm (−1).

If more than a threshold amount of Raman scattering is received by any one or more gated detector of array 1854 during the time interval of the laser excitation pulse and its spectral range, an alarm indication is provided by computer 1840, typically at display 1846. This alarm indication indicates that an explosive material having certain Raman scattering characteristics may be present on a surface of the vehicle. Display 1846 preferably also visually indicates, at location 1848 on the display 1846, the location 1849 on the vehicle of the detected suspect material.

Preferably computer 1840 is operative to analyze and indicate detection of suspect materials on the vehicle produced in response to excitation by the first and second lasers 1836 and 1837 and the time-resolved luminescence and time-resolved Raman scattering detection resulting therefrom.

Preferably computer 1840 and display 1846 are operative to superimpose and indicate the spatial relationship between the locations of the detected suspect materials on the vehicle produced in response to excitation by the first and second lasers 1836 and 1837 and the time-resolved luminescence and time-resolved Raman scattering detection resulting therefrom.

In accordance with a preferred embodiment of the present invention the system of FIG. 18B also provides identification of an explosive on an object.

During identification, identification collecting optics 1856 are employed for receiving time-resolved luminescence and time-resolved Raman scattering from the location or locations 1849 of the detected suspect material on the vehicle. During identification, the output beams of lasers 1836 and 1837 are thus scanned in two dimensions at the previously determined location or locations 1849 of suspect material on a vehicle.

The output of identification collecting optics 1856 is preferably supplied via a fiberoptic link 1857 to a polychromator 1858, which produces dispersion of the luminescence and Raman spectra. The output from the polychromator 1858 is supplied to a gated detector assembly 1859, preferably employing a CCD array. Alternatively, the detector assembly need not be gated, although this is not preferred.

The output of gated detector assembly 1859 is analyzed by computer 1840 to compare the spectrum represented thereby with reference spectra characteristic of known explosives, in order to provide identification of an explosive on the vehicle.

In accordance with a preferred embodiment of the present invention the system of FIG. 18B also provides enhanced identification of detection of an explosive on an object. This enhanced identification is preferably provided by employing a selectably positionable lens (not shown) that is associated with telescope 1841. This lens is normally positioned in an inoperative position during detection, as opposed to enhanced identification, operation of the system.

During enhanced identification, identification collecting optics 1856 are employed for receiving laser induced breakdown emissions from the location or locations of the detected suspect material on the vehicle. The output of identification collecting optics 1856 is preferably supplied via fiberoptic link 1857 to polychromator 1858, which produces dispersion of the emission spectrum. The output from the polychromator 1858 is supplied to gated detector assembly 1859.

The output of gated detector assembly 1859 is analyzed by computer 1840 to compare the spectrum represented thereby with reference spectra characteristic of known explosives, in order to provide an enhanced output indication of the existence of an explosive on the vehicle.

Reference is now made to FIG. 18C, which is a simplified pictorial illustration of a triple mode system for detecting and identifying explosives constructed and operative in accordance with yet another preferred embodiment of the present invention and employing time-resolved luminescence and time-resolved Raman scattering detection and employing time-resolved luminescence, time-resolved Raman scattering and time-resolved laser induced breakdown spectroscopy for enhanced identification. In the illustrated embodiment, a vehicle screening system is shown, it being appreciated that the present invention is not limited to vehicle screening applications, but rather may be employed in any other suitable remote object inspection environment.

In the embodiment of FIG. 18C, an inspection assembly 1865, which is preferably portable, employs a first laser 1866, preferably a Nd:YAG pulsed laser emitting a third or fourth harmonic having respective peak wavelengths at 355 and 266 nm. It is appreciated that wavelengths in the range of 180 nm to 10 microns may be employed. Inspection assembly 1865 preferably also employs a second laser 1867, preferably a Nd:YAG pulsed laser emitting a second harmonic having a peak wavelength at 532 nm. It is appreciated that wavelengths in the range of 200 nm to 10 microns may be employed by this laser. Alternatively, a single laser may be used rather than two lasers.

Output beams of lasers 1866 and 1867 impinge on scanning assemblies 1868, typically comprising first and second scanning elements (not shown) such as mirrors, which are driven in rotational motion by motors (not shown) in synchronization with the pulsed outputs of lasers 1866 and 1867 in response to synchronization signals provided by a computer 1870. The scanned laser beam outputs of scanning assemblies 1868 are projected onto a vehicle or other suitable remote object, preferably by a pair of telescopes 1871.

The output beam of laser 1866 is thus scanned in two dimensions over a vehicle, inducing luminescence by certain materials, including a number of explosives, should those materials be present on the scanned surfaces of the vehicle. The luminescence induced by the laser beam is detected via imaging optics 1872 forming part of a head-mounted viewing assembly 1873, at least one and preferably a plurality of individually selectable and interchangeable narrow band spectral filters 1874 and an image intensifier 1875, all forming part of the head-mounted viewing assembly 1873.

Preferably, the spectral range of each spectral filter 1874 differs from the spectral range of each other such filter. The following spectral ranges are preferably provided, each by a different spectral filter 1874 and corresponding to the following gate intervals:

400–430 nm—10 microseconds
450–540 nm—50 nanoseconds
670–700 nm—100 microseconds.

In accordance with a preferred embodiment of the present invention the image intensifier 1875 is gated by control signals from computer 1870 so as to be synchronized with the pulsed output of laser 1866. Filters 1874 are operative to eliminate transmission of reflected laser radiation at 355 nm and 266 nm, to attenuate the ambient radiation and to fully transmit the luminescence. Thus, an operator using the head-mounted viewing assembly 1873 sees a scene such as that designated by reference numeral 1876, wherein the location on the vehicle of a suspected explosive is highlighted over an ambient background image of the vehicle. The location of the suspected explosive is indicated on scene 1876 at reference numeral 1877 and on the vehicle at reference numeral 1878.

The output beam of laser 1867 is also scanned in two dimensions over the vehicle, inducing Raman scattering by certain materials, including explosives, should those materials be present on the scanned surfaces of the vehicle. The Raman scattering induced by the laser beam is detected via imaging optics 1872 forming part of a head-mounted viewing assembly 1873, at least one and preferably a plurality of narrow band spectral filters 1874 and image intensifier 1875, all forming part of the head-mounted viewing assembly 1873.

Preferably, the spectral range of each spectral filter 1874 differs from the spectral range of each other such filter. The following Raman shifts relative to the laser excitation wavelength are preferably provided, each by a different spectral filter 1874:

880–885 cm (−1)
1360–1365 cm (−1)
1270–1290 cm (−1)
2980–3000 cm (−1).

In accordance with a preferred embodiment of the present invention the image intensifier 1875 is gated by control signals from computer 1870 to operate during the time interval of the laser excitation pulse. Thus, an operator using the head-mounted viewing assembly 1873 sees a scene such as scene 1876, wherein location 1878 of a suspected explosive on the vehicle is highlighted on the scene 1876 at location 1877 over an ambient background image of the vehicle.

In accordance with a preferred embodiment of the present invention the system of FIG. 18C also provides identification of an explosive on an object.

During identification, identification collecting optics 1881 are employed for receiving time-resolved luminescence and time-resolved Raman scattering from the location or locations of the detected suspect material on the vehicle. During identification, the output beams of lasers 1866 and 1867 are scanned in two dimensions at the previously determined location or locations 1878 of suspect material on a vehicle.

The identification collecting optics 1881 are preferably aimed by an operator at the location of the suspected explosive typically using a joystick 1882 and a viewing camera 1883 or marker which is visible through the image intensifier 1875.

The output of identification collecting optics 1881 is preferably supplied via a fiberoptic link 1885 to a polychromator 1886, which produces dispersion of the luminescence and Raman spectra. The output from the polychromator 1886 is supplied to a gated detector assembly 1887, preferably employing a CCD array. Alternatively, the detector assembly need not be gated, although this is not preferred.

The output of gated detector assembly 1887 is analyzed by computer 1870 to compare the spectrum represented thereby with reference spectra characteristic of known explosives, in order to provide identification of an explosive on the vehicle.

In accordance with a preferred embodiment of the present invention the system of FIG. 18C also provides enhanced identification of detection of an explosive on an object. This enhanced identification is preferably provided by employing a selectably positionable lens (not shown) that is associated with telescope 1871. This lens is normally positioned in an inoperative position during detection, as opposed to during enhanced identification, operation of the system.

During enhanced identification, identification collecting optics 1881 are employed for receiving laser induced breakdown emissions from the location or locations of the detected suspect material on the vehicle. The output of identification collecting optics 1881 is preferably supplied via fiberoptic link 1885 to polychromator 1886, which produces dispersion of the emission spectrum. The output from the polychromator 1886 is supplied to gated detector assembly 1887.

The identification collecting optics 1881 are preferably aimed by an operator at the location of the suspected explosive typically using a joystick 1882 and a viewing camera 1883 or marker which is visible through the image intensifier 1875.

The output of gated detector assembly 1887 is analyzed by computer 1870 to compare the spectrum represented thereby with reference spectra characteristic of known explosives, in order to provide an enhanced output indication of the existence of an explosive on the vehicle.

Reference is now made to FIG. 19A, which is a simplified pictorial illustration of a triple mode system for detecting and identifying explosives constructed and operative in accordance with a preferred embodiment of the present invention and employing second harmonic and time-resolved luminescence detection and employing time-resolved luminescence and time-resolved laser induced breakdown spectroscopy for enhanced identification. In the illustrated embodiment, a baggage screening system is shown, it being appreciated that the present invention is not limited to baggage screening applications, but rather may be employed in any other suitable object inspection environment.

In the embodiment of FIG. 19A, baggage, such as suitcases 1900, is transported by a conveyor 1902 past an inspection station 1904 at which the suitcases 1900 are inspected. In accordance with a preferred embodiment of the present invention, the inspection station 1904 employs a first laser 1905, preferably a Nd:YAG pulsed laser emitting with a peak wavelength at 1064 nm. It is appreciated that wavelengths in the range of 400 nm to 10 microns may be employed. The inspection station 1904 preferably also employs a second laser 1906, preferably a Nd:YAG pulsed laser emitting a third or fourth harmonic having respective peak wavelengths at 355 and 266 nm. It is appreciated that wavelengths in the range of 180 nm to 10 microns may be employed. Alternatively, a single laser may be used rather than two lasers.

The output beams of lasers 1905 and 1906 impinge on a scanning assembly 1907, typically comprising first and second scanning elements 1908, such as mirrors, which are driven in rotational motion by motors 1909 in synchronization with the pulsed outputs of lasers 1905 and 1906 in response to synchronization signals provided by a computer 1910.

The output beam of laser 1905 is thus scanned in two dimensions over suitcases 1900, inducing second harmonic scattering of the output beam by certain materials, including a number of explosives, should those materials be present on the scanned surfaces of the suitcases 1900. The scattered second harmonic of the laser beam is detected via imaging optics 1911 and a narrow band spectral filter 1912 having a peak wavelength of 532 nm preferably by a gated detector array 1913, such as a CCD or CMOS array. Alternatively, the detector array need not be gated, although this is not preferred.

If more than a threshold amount of scattered second harmonic illumination at wavelength 532 nm is received by gated detector array 1913 within a predetermined time window during each laser pulse, an alarm indication is provided by computer 1910, typically at a display 1914. The alarm indication indicates that an explosive material having certain second harmonic scattering characteristics may be present on a surface of the suitcase 1900. Display 1914 preferably also visually indicates the location of the detected suspect material on the suitcase 1900, here indicated on display 1914 at reference numeral 1915 and on the suitcase 1900 at reference numeral 1916.

The output beam of second laser 1906 is also scanned in two dimensions over suitcases 1900, inducing luminescence by certain materials, including a number of explosives, should those materials be present on the scanned surfaces of the suitcases 1900. The luminescence induced by the laser beam is detected preferably by a plurality of detector assemblies 1917, each preferably including imaging optics 1918, a spectral filter 1919 and a gated detector array 1920, such as a CCD or CMOS array. Alternatively, the plurality of detector assemblies 1917 may be replaced by a single broadband detector assembly, although this is not preferred. Alternatively, the detector array need not be gated, although this is not preferred.

Preferably, the spectral range of each spectral filter 1919 of each detector assembly 1917 differs from the spectral range of each other such filter. The following spectral ranges are preferably provided, each by a different spectral filter 1919 and corresponding to the following gate intervals:

400–430 nm—10 microseconds
450–540 nm—50 nanoseconds
670–700 nm—100 microseconds.

If more than a threshold amount of luminescence is received by any one or more gated detector in gated detector array 1920 within its time window and its spectral range, an alarm indication is provided by computer 1910, typically at display 1914. This alarm indication indicates that an explosive material having certain luminescence characteristics may be present on a surface of the suitcase 1900. Display 1914 preferably also visually indicates, at location 1915 on the display 1914, the location 1916 on the suitcase 1900 of the detected suspect material.

Preferably computer 1910 is operative to analyze and indicate detection of suspect materials on the suitcase 1900 produced in response to excitation by the first and second lasers 1905 and 1906 and the resulting second harmonic scattering and luminescence detection resulting therefrom.

Preferably computer 1910 and display 1914 are operative to superimpose and indicate the spatial relationship between the locations of the detected suspect materials on the suitcase 1900 produced in response to excitation by the first and second lasers 1905 and 1906 and the second harmonic scattering and luminescence detection resulting therefrom.

In accordance with a preferred embodiment of the present invention the system of FIG. 19A also provides identification of an explosive on an object.

During identification, identification collecting optics 1926 are employed for receiving time-resolved luminescence from the location or locations of the detected suspect material on the suitcase 1900. During identification, the output beam of laser 1906 is thus scanned in two dimensions at the previously determined location or locations 1924 of suspect material on suitcases 1900.

The output of identification collecting optics 1926 is preferably supplied via a fiberoptic link 1927 to a polychromator 1928, which produces dispersion of the luminescence spectrum. The output from the polychromator 1928 is supplied to a gated detector assembly 1929, preferably employing a CCD array. Alternatively, the detector assembly need not be gated, although this is not preferred.

The output of gated detector assembly 1929 is analyzed by computer 1910 to compare the spectrum represented thereby with reference spectra characteristic of known explosives, in order to provide identification of an explosive on the suitcase 1900.

In accordance with a preferred embodiment of the present invention the system of FIG. 19A also provides enhanced identification of an explosive on an object. This enhanced identification is preferably provided by employing a selectably positionable lens 1930 intermediate the scanning assembly 1907 and the suitcase 1900. Lens 1930 is normally positioned in an inoperative position, indicated in dashed lines at reference numeral 1931, during detection, as opposed to during enhanced identification, operation of the system.

During enhanced identification, identification collecting optics 1926 are employed for receiving laser induced breakdown emissions from the location or locations of the detected suspect material on the suitcase 1900. Lens 1930 is operative to concentrate the output beam of the laser 1905 on such locations. The output of identification collecting optics 1926 is preferably supplied via fiberoptic link 1927 to polychromator 1928, which produces dispersion of the emission spectrum. The output from the polychromator 1928 is supplied to gated detector assembly 1929.

The output of gated detector assembly 1929 is analyzed by computer 1910 to compare the spectrum represented thereby with reference spectra characteristic of known explosives, in order to provide an enhanced output indication of the existence of an explosive on the suitcase 1900.

Figure 19B:
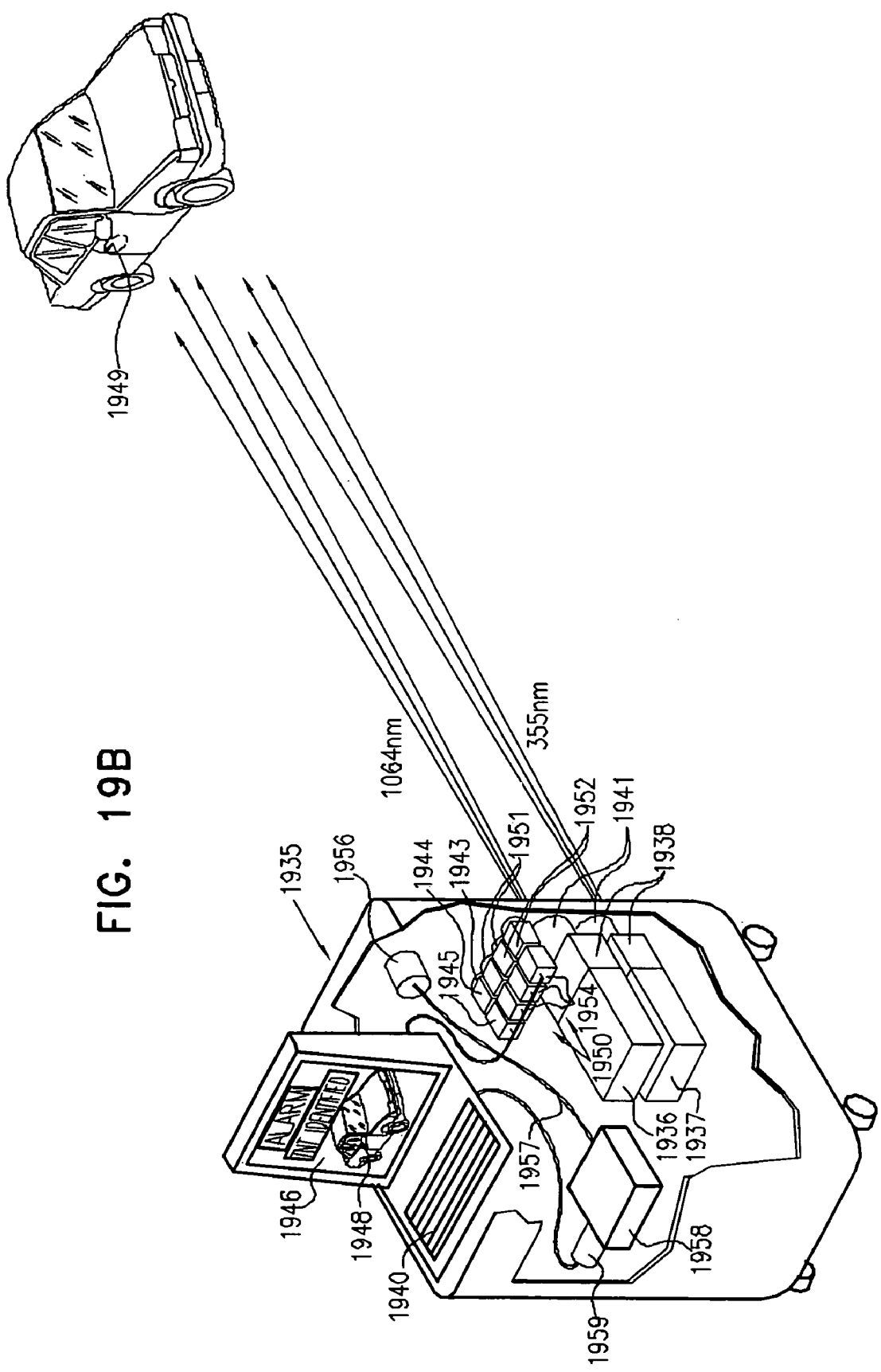

Reference is now made to FIG. 19B, which is a simplified pictorial illustration of a triple mode system for detecting and identifying explosives constructed and operative in accordance with another preferred embodiment of the present invention and employing second harmonic and time-resolved luminescence detection and employing time-resolved luminescence and time-resolved laser induced breakdown spectroscopy for enhanced identification. In the illustrated embodiment, a vehicle screening system is shown, it being appreciated that the present invention is not limited to vehicle screening applications, but rather may be employed in any other suitable remote object inspection environment.

In the embodiment of FIG. 19B, an inspection assembly 1935, which may be portable or stationary, employs a first laser 1936, preferably a Nd:YAG pulsed laser emitting with a peak wavelength at 1064 nm. It is appreciated that wavelengths in the range of 400 nm to 10 microns may be employed. Inspection assembly 1935 preferably also employs a second laser 1937, preferably a Nd:YAG pulsed laser emitting a third or fourth harmonic having respective peak wavelengths at 355 and 266 nm. It is appreciated that wavelengths in the range of 180 nm to 10 microns may be employed. Alternatively, a single laser may be used rather than two lasers.

Output beams of lasers 1936 and 1937 impinge on scanning assemblies 1938, typically comprising first and second scanning elements (not shown) such as mirrors, which are driven in rotational motion by motors (not shown) in synchronization with the pulsed outputs of lasers 1936 and 1937 in response to synchronization signals provided by a computer 1940. The scanned laser beam outputs of scanning assemblies 1938 are projected onto a vehicle or other suitable remote object, preferably by a pair of telescopes 1941.

The output beam of laser 1936 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 1943 and a narrow band spectral filter 1944 having a peak wavelength of 532 nm, preferably by a gated detector array 1945, such as a CCD or CMOS array. Alternatively, the detector array need not be gated, although this is not preferred.

If more than a threshold amount of scattered second harmonic illumination at wavelength 532 nm is received by a detector in gated detector array 1945 within a predetermined time window during each laser pulse, an alarm indication is provided by computer 1940, typically at a display 1946. The alarm indication indicates that an explosive material having certain second harmonic scattering characteristics may be present on a surface of the vehicle. Display 1946 preferably also visually indicates the location of the detected suspect material on the vehicle, here indicated on display 1946 at reference numeral 1948 and on the vehicle at reference numeral 1949.

The output beam of second laser 1937 is also scanned in two dimensions over the vehicle, inducing luminescence by certain materials, including a number of explosives, should those materials be present on the scanned surfaces of the vehicle. The luminescence induced by the laser beam is detected preferably by a plurality of detector assemblies 1950, each preferably including imaging optics 1951, a spectral filter 1952 and a gated detector array 1954, such as a CCD or CMOS array. Alternatively, the plurality of detector assemblies 1950 may be replaced by a single broadband detector assembly, although this is not preferred. Alternatively, the detector array need not be gated, although this is not preferred.

Preferably, the spectral range of each spectral filter 1952 of each detector assembly 1950 differs from the spectral range of each other such filter. The following spectral ranges are preferably provided, each by a different spectral filter 1952 and corresponding to the following gate intervals:

400–430 nm—10 microseconds
450–540 nm—50 nanoseconds
670–700 nm—100 microseconds.

If more than a threshold amount of luminescence is received by any one or more gated detector in array 1954 within its time window and its spectral range, an alarm indication is provided by computer 1940, typically at display 1946. This alarm indication indicates that an explosive material having certain luminescence characteristics may be present on a surface of the vehicle. Display 1946 preferably also visually indicates, at location 1948 on the display 1946, the location 1949 on the vehicle of the detected suspect material.

Preferably computer 1940 is operative to analyze and indicate detection of suspect materials on the vehicle produced in response to excitation by the first and second lasers 1936 and 1937 and the resulting second harmonic scattering and luminescence detection resulting therefrom.

Preferably computer 1940 and display 1946 are operative to superimpose and indicate the spatial relationship between the locations of the detected suspect materials on the vehicle produced in response to excitation by the first and second lasers 1936 and 1937 and the second harmonic scattering and luminescence detection resulting therefrom.

In accordance with a preferred embodiment of the present invention the system of FIG. 19B also provides identification of an explosive on an object.

During identification, identification collecting optics 1956 are employed for receiving time-resolved luminescence from the location or locations of the detected suspect material on the vehicle. During identification, the output beam of laser 1937 is thus scanned in two dimensions at the previously determined location or locations 1949 of suspect material on a vehicle.

The output of identification collecting optics 1956 is preferably supplied via a fiberoptic link 1957 to a polychromator 1958, which produces dispersion of the luminescence spectrum. The output from the polychromator 1958 is supplied to a gated detector assembly 1959, preferably employing a CCD array. Alternatively, the detector assembly need not be gated, although this is not preferred.

The output of gated detector assembly 1959 is analyzed by computer 1940 to compare the spectrum represented thereby with reference spectra characteristic of known explosives, in order to provide identification of an explosive on the vehicle.

In accordance with a preferred embodiment of the present invention the system of FIG. 19B also provides enhanced identification of detection of an explosive on an object. This enhanced identification is preferably provided by employing a selectably positionable lens (not shown) that is associated with telescope 1941. This lens is normally positioned in an inoperative position during detection, as opposed to enhanced identification, operation of the system.

During enhanced identification, identification collecting optics 1956 are employed for receiving laser induced breakdown emissions from the location or locations of the detected suspect material on the vehicle. The output of identification collecting optics 1956 is preferably supplied via fiberoptic link 1957 to polychromator 1958, which produces dispersion of the emission spectrum. The output from the polychromator 1958 is supplied to gated detector assembly 1959.

The output of gated detector assembly 1959 is analyzed by computer 1940 to compare the spectrum represented thereby with reference spectra characteristic of known explosives, in order to provide an enhanced output indication of the existence of an explosive on the vehicle.

Figure 19C:
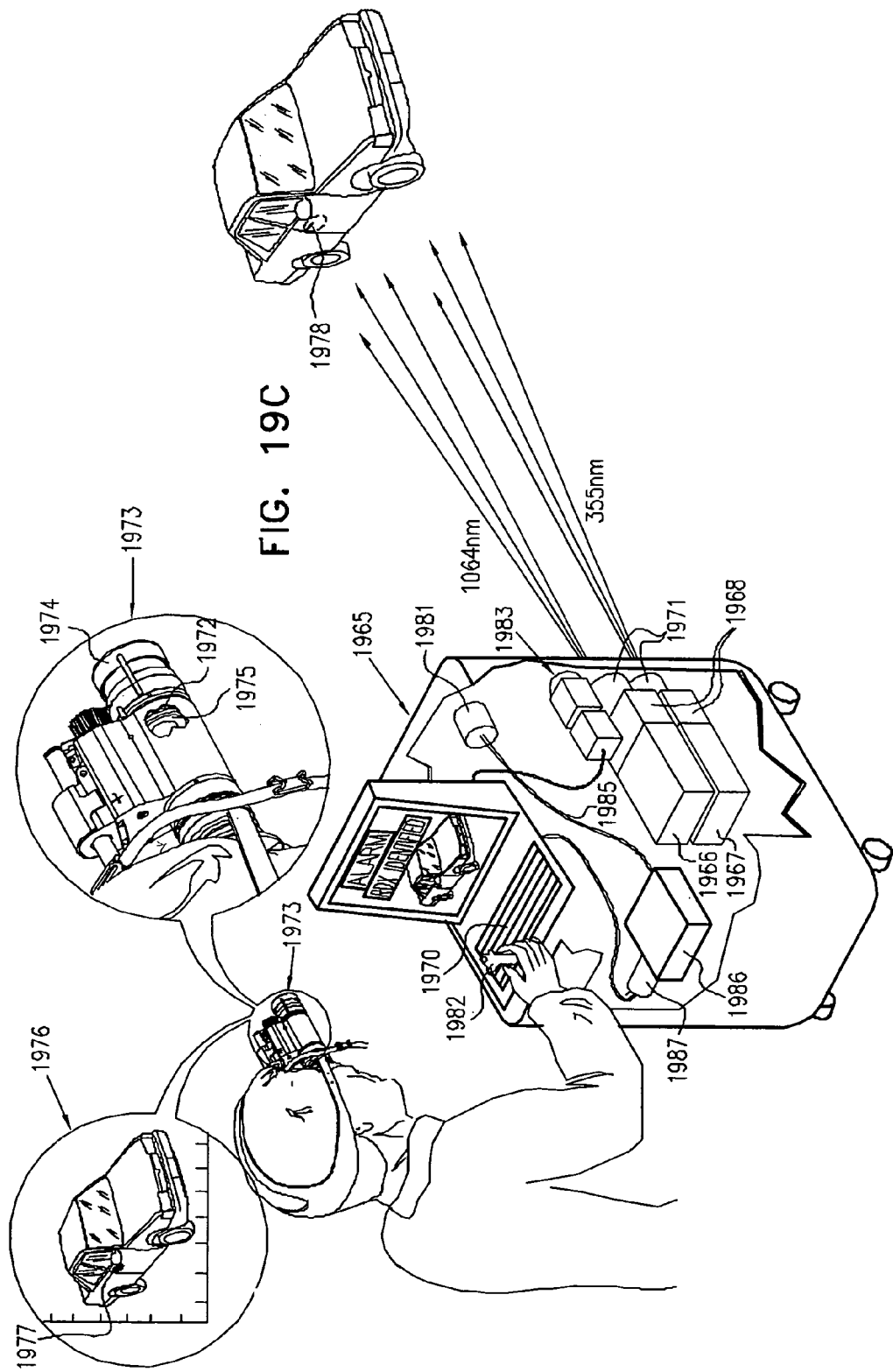

Reference is now made to FIG. 19C, which is a simplified pictorial illustration of a triple mode system for detecting and identifying explosives constructed and operative in accordance with yet another preferred embodiment of the present invention and employing second harmonic and time-resolved luminescence detection and employing time-resolved luminescence and time-resolved laser induced breakdown spectroscopy for enhanced identification. In the illustrated embodiment, a vehicle screening system is shown, it being appreciated that the present invention is not limited to vehicle screening applications, but rather may be employed in any other suitable remote object inspection environment.

In the embodiment of FIG. 19C, an inspection assembly 1965, which is preferably portable, employs a first laser 1966, preferably a Nd:YAG pulsed laser emitting with a peak wavelength at 1064 nm. It is appreciated that wavelengths in the range of 400 nm to 10 microns may be employed. Inspection assembly 1965 preferably also employs a second laser 1967, preferably a Nd:YAG pulsed laser emitting a third or fourth harmonic having respective peak wavelengths at 355 and 266 nm. It is appreciated that wavelengths in the range of 180 nm to 10 microns may be employed. Alternatively, a single laser may be used rather than two lasers.

Output beams of lasers 1966 and 1967 impinge on scanning assemblies 1968, typically comprising first and second scanning elements (not shown) such as mirrors, which are driven in rotational motion by motors (not shown) in synchronization with the pulsed outputs of lasers 1966 and 1967 in response to synchronization signals provided by a computer 1970. The scanned laser beam outputs of scanning assemblies 1968 are projected onto a vehicle or other suitable remote object, preferably by a pair of telescopes 1971.

The output beam of laser 1966 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 1972 forming part of a head-mounted viewing assembly 1973, a narrow band spectral filter 1974 having a peak wavelength of 532 nm and an image intensifier 1975, all forming part of the head-mounted viewing assembly 1973.

In accordance with a preferred embodiment of the present invention the image intensifier 1973 is gated by control signals from computer 1970 so as to be synchronized with the pulsed output of laser 1966. Filter 1974 is operative to eliminate transmission of reflected laser radiation at 1064 nm, to attenuate the ambient radiation and to fully transmit the second harmonic scattered radiation at 532 nm. Thus, an operator using the head-mounted viewing assembly 1973 sees a scene such as that designated by reference numeral 1976, wherein the location on the vehicle of a suspected explosive is highlighted over an ambient background image of the vehicle. The location of the suspected explosive is indicated on scene 1976 at reference numeral 1977 and on the vehicle at reference numeral 1978.

The output beam of laser 1967 is also scanned in two dimensions over the vehicle, inducing luminescence by certain materials, including a number of explosives, should those materials be present on the scanned surfaces of the vehicle. The luminescence induced by the laser beam is detected via imaging optics 1972 forming part of head-mounted viewing assembly 1973, including at least one and preferably a plurality of individually selectable and interchangeable narrow band spectral filters 1974 and image intensifier 1975, all forming part of the head-mounted viewing assembly 1973.

Preferably, the spectral range of each spectral filter 1974 differs from the spectral range of each other such filter. The following spectral ranges are preferably provided, each by a different spectral filter 1974 and corresponding to the following gate intervals:

400–430 nm—10 microseconds
450–540 nm—50 nanoseconds
670–700 nm—100 microseconds.

In accordance with a preferred embodiment of the present invention the image intensifier 1975 is gated by control signals from computer 1970 so as to be synchronized with the pulsed output of laser 1967. Filters 1974 are operative to eliminate transmission of reflected laser radiation at 355 nm and 266 nm, to attenuate the ambient radiation and to fully transmit the luminescence. Thus, an operator using the head-mounted viewing assembly 1973 sees a scene such as scene 1976, wherein location 1978 of a suspected explosive on the vehicle is highlighted on the scene 1976 at location 1977 over an ambient background image of the vehicle.

In accordance with a preferred embodiment of the present invention the system of FIG. 19C also provides identification of an explosive on an object.

During identification, identification collecting optics 1981 are employed for receiving time-resolved luminescence from the location or locations of the detected suspect material on the vehicle. During identification, the output beam of laser 1967 is thus scanned in two dimensions at the previously determined location or locations 1978 of suspect material on a vehicle.

The identification collecting optics 1981 are preferably aimed by an operator at the location of the suspected explosive typically using a joystick 1982 and a viewing camera 1983 or marker which is visible through the image intensifier 1975.

The output of identification collecting optics 1981 is preferably supplied via a fiberoptic link 1985 to a polychromator 1986, which produces dispersion of the luminescence spectrum. The output from the polychromator 1986 is supplied to a gated detector assembly 1987, preferably employing a CCD array. Alternatively, the detector assembly need not be gated, although this is not preferred.

The output of gated detector assembly 1987 is analyzed by computer 1970 to compare the spectrum represented thereby with reference spectra characteristic of known explosives, in order to provide identification of an explosive on the vehicle.

In accordance with a preferred embodiment of the present invention the system of FIG. 19C also provides enhanced identification of detection of an explosive on an object. This enhanced identification is preferably provided by employing a selectably positionable lens (not shown) that is associated with telescope 1971. This lens is normally positioned in an inoperative position during detection, as opposed to during enhanced identification, operation of the system.

During enhanced identification, identification collecting optics 1981 are employed for receiving laser induced breakdown emissions from the location or locations of the detected suspect material on the vehicle. The output of identification collecting optics 1981 is preferably supplied via fiberoptic link 1985 to polychromator 1986, which produces dispersion of the emission spectrum. The output from the polychromator 1986 is supplied to gated detector assembly 1987.

The identification collecting optics 1981 are preferably aimed by an operator at the location of the suspected explosive typically using joystick 1982 and viewing camera 1983 or marker which is visible through the image intensifier 1975.

The output of gated detector assembly 1987 is analyzed by computer 1970 to compare the spectrum represented thereby with reference spectra characteristic of known explosives, in order to provide an enhanced output indication of the existence of an explosive on the vehicle.

Figure 20A:
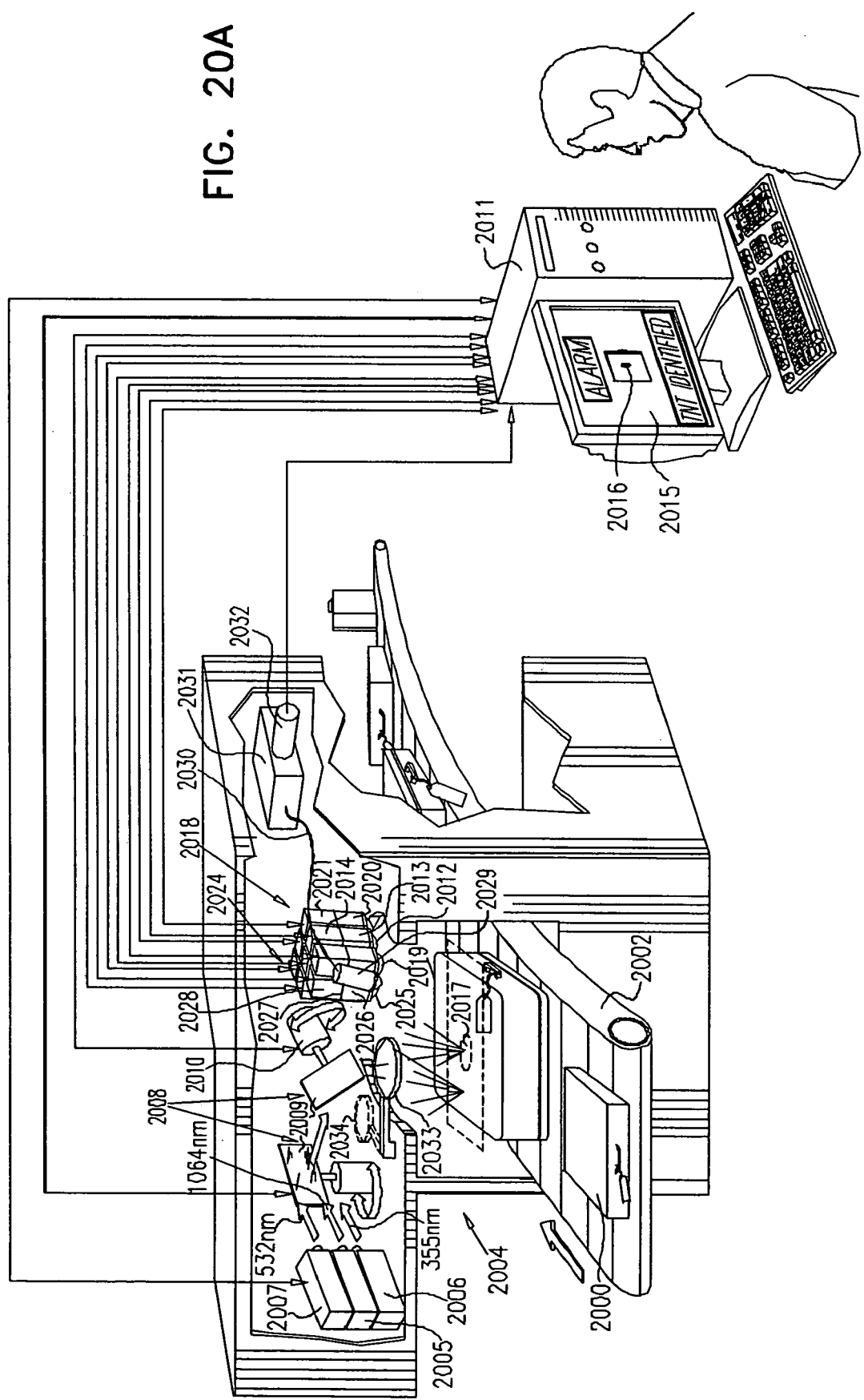
FIGS. 20A, 20B and 20C are simplified pictorial illustrations of quadruple mode systems for detecting and identifying explosives constructed and operative in accordance with preferred embodiments of the present invention and employing second harmonic, time-resolved luminescence and time-resolved Raman scattering detection and time-resolved luminescence, time-resolved Raman scattering and time-resolved laser induced breakdown spectroscopy for enhanced identification.

Reference is now made to FIG. 20A, which is a simplified pictorial illustration of a quadruple mode system for detecting and identifying explosives constructed and operative in accordance with a preferred embodiment of the present invention and employing second harmonic, time-resolved luminescence and time-resolved Raman scattering detection and time-resolved luminescence, time-resolved Raman scattering and time-resolved laser induced breakdown spectroscopy for enhanced identification. In the illustrated embodiment, a baggage screening system is shown, it being appreciated that the present invention is not limited to baggage screening applications, but rather may be employed in any other suitable object inspection environment.

In the embodiment of FIG. 20A, baggage, such as suitcases 2000, is transported by a conveyor 2002 past an inspection station 2004 at which the suitcases 2000 are inspected. In accordance with a preferred embodiment of the present invention, the inspection station 2004 employs a first laser 2005, preferably a Nd:YAG pulsed laser emitting with a peak wavelength at 1064 nm. It is appreciated that wavelengths in the range of 400 nm to 10 microns may be employed. The inspection station 2004 preferably also employs a second laser 2006, preferably a Nd:YAG pulsed laser emitting a third or fourth harmonic having respective peak wavelengths at 355 and 266 nm. It is appreciated that wavelengths in the range of 180 nm to 10 microns may be employed. The inspection station 2004 preferably also employs a third laser 2007, preferably a Nd:YAG pulsed laser emitting a second harmonic having a peak wavelength at 532 nm. It is appreciated that wavelengths in the range of 200 nm to 10 microns may be employed by this laser. Alternatively, a single laser or two lasers may be used rather than three lasers.

The output beams of lasers 2005, 2006 and 2007 impinge on a scanning assembly 2008, typically comprising first and second scanning elements 2009, such as mirrors, which are driven in rotational motion by motors 2010 in synchronization with the pulsed outputs of lasers 2005, 2006 and 2007 in response to synchronization signals provided by a computer 2011.

The output beam of laser 2005 is thus scanned in two dimensions over suitcases 2000, inducing second harmonic scattering of the output beam by certain materials, including a number of explosives, should those materials be present on the scanned surfaces of the suitcases 2000. The scattered second harmonic of the laser beam is detected via imaging optics 2012 and a narrow band spectral filter 2013 having a peak wavelength of 532 nm preferably by a gated detector array 2014, such as a CCD or CMOS array. Alternatively, the detector array need not be gated, although this is not preferred.

If more than a threshold amount of scattered second harmonic illumination at wavelength 532 nm is received by gated detector array 2014 within a predetermined time window during each laser pulse, an alarm indication is provided by computer 2011, typically at a display 2015. The alarm indication indicates that an explosive material having certain second harmonic scattering characteristics may be present on a surface of the suitcase 2000. Display 2015 preferably also visually indicates the location of the detected suspect material on the suitcase 2000, here indicated on display 2015 at reference numeral 2016 and on the suitcase 2000 at reference numeral 2017.

The output beam of second laser 2006 is also scanned in two dimensions over suitcases 2000, inducing luminescence by certain materials, including a number of explosives, should those materials be present on the scanned surfaces of the suitcases 2000. The luminescence induced by the laser beam is detected preferably by a plurality of detector assemblies 2018, each preferably including imaging optics 2019, a spectral filter 2020 and a gated detector array 2021, such as a CCD or CMOS array. Alternatively, the plurality of detector assemblies 2018 may be replaced by a single broadband detector assembly, although this is not preferred. Alternatively, the detector array need not be gated, although this is not preferred.

Preferably, the spectral range of each spectral filter 2020 of each detector assembly 2018 differs from the spectral range of each other such filter. The following spectral ranges are preferably provided, each by a different spectral filter 2020 and corresponding to the following gate intervals:
  400–430 nm—10 microseconds
  450–540 nm—50 nanoseconds
  670–700 nm—100 microseconds.

If more than a threshold amount of luminescence is received by any one or more gated detector in gated detector array 2021 within its time window and its spectral range, an alarm indication is provided by computer 2011, typically at display 2015. This alarm indication indicates that an explosive material having certain luminescence characteristics may be present on a surface of the suitcase 2000. Display 2015 preferably also visually indicates, at location 2016 on the display 2015, the location 2017 on the suitcase 2000 of the detected suspect material.

The output beam of third laser 2007 is also scanned in two dimensions over suitcases 2000, inducing Raman scattering by certain materials, including explosives, should those materials be present on the scanned surfaces of the suitcases 2000. The Raman scattering is detected by a plurality of detector assemblies 2024, each preferably including imaging optics 2025, a spectral filter 2026, a notch filter 2027 and a gated detector array 2028, such as a CCD or CMOS array. Alternatively, the plurality of detector assemblies 2024 may be replaced by a single broadband detector assembly, although this is not preferred. Alternatively, the detector array need not be gated, although this is not preferred.

Preferably, the spectral range of each spectral filter 2026 of each detector assembly 2024 differs from the spectral range of each other such filter. The following Raman shifts relative to the laser excitation wavelength are preferably provided, each by a different spectral filter 2026:

880–885 cm (−1)
1360–1365 cm (−1)
1270–1290 cm (−1)
2980–3000 cm (−1).

If more than a threshold amount of Raman scattering is received by any one or more gated detector in array 2028 during the time interval of the laser excitation pulse and its spectral range, an alarm indication is provided by computer 2011, typically at display 2015. This alarm indication indicates that an explosive material having certain Raman scattering characteristics may be present on a surface of the suitcase 2000. Display 2015 preferably also visually indicates, at location 2016 on the display 2015, the location 2017 on the suitcase 2000 of the detected suspect material.

Preferably computer 2011 and display 2015 are operative to superimpose and indicate the spatial relationship between the locations of the detected suspect materials on the suitcase 2000 produced in response to excitation by the first, second and third lasers 2005, 2006 and 2007 and the second harmonic scattering, time-resolved luminescence and time-resolved Raman scattering detection resulting therefrom.

In accordance with a preferred embodiment of the present invention the system of FIG. 20A also provides identification of an explosive on an object.

During identification, identification collecting optics 2029 are employed for receiving time-resolved luminescence and time-resolved Raman scattering from the location or locations of the detected suspect material on the suitcase 2000. During identification, the output beam of lasers 2006 and 2007 are thus scanned in two dimensions at the previously determined location or locations 2017 of suspect material on suitcases 2000.

The output of identification collecting optics 2029 is preferably supplied via a fiberoptic link 2030 to a polychromator 2031, which produces dispersion of the luminescence and Raman spectra. The output from the polychromator 2031 is supplied to a gated detector assembly 2032, preferably employing a CCD array. Alternatively, the detector assembly need not be gated, although this is not preferred.

The output of gated detector assembly 2032 is analyzed by computer 2011 to compare the spectrum represented thereby with reference spectra characteristic of known explosives, in order to provide identification of an explosive on the suitcase 2000.

In accordance with a preferred embodiment of the present invention the system of FIG. 20A also provides enhanced identification of an explosive on an object. This enhanced identification is preferably provided by employing a selectably positionable lens 2033 intermediate the scanning assembly 2008 and the suitcase 2000. Lens 2033 is normally positioned in an inoperative position, indicated in dashed lines at reference numeral 2034, during detection, as opposed to during enhanced identification, operation of the system.

During enhanced identification, identification collecting optics 2029 are employed for receiving laser induced breakdown emissions from the location or locations of the detected suspect material on the suitcase 2000. Lens 2033 is operative to concentrate the output beam of the laser 2005 on such locations. The output of identification collecting optics 2029 is preferably supplied via fiberoptic link 2030 to polychromator 2031, which produces dispersion of the emission spectrum. The output from the polychromator 2031 is supplied to gated detector assembly 2032.

The output of gated detector assembly 2032 is analyzed by computer 2011 to compare the spectrum represented thereby with reference spectra characteristic of known explosives, in order to provide an enhanced output indication of the existence of an explosive on the suitcase 2000.

Figure 20B:
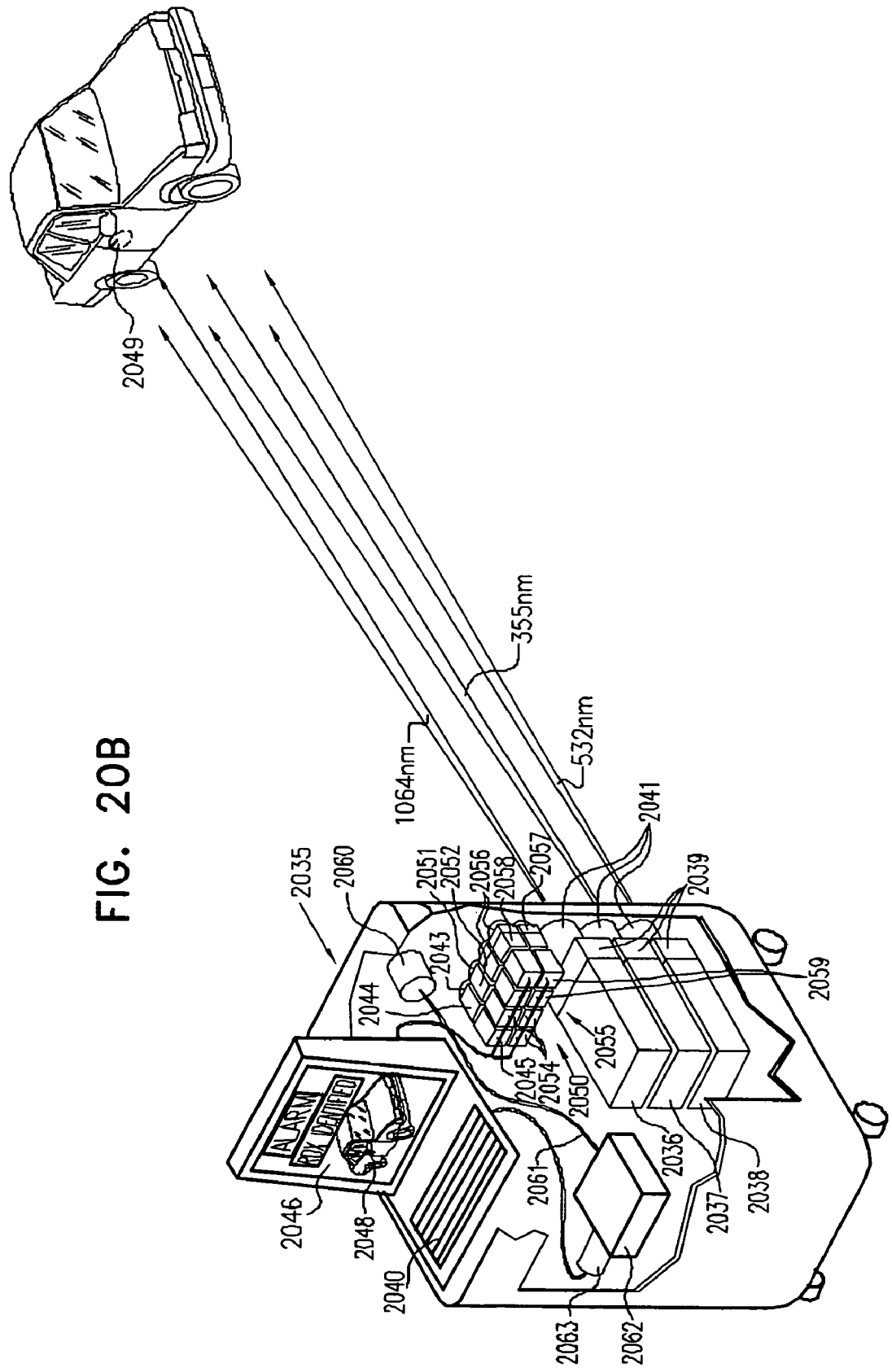

Reference is now made to FIG. 20B, which is a simplified pictorial illustration of a quadruple mode system for detecting and identifying explosives constructed and operative in accordance with another preferred embodiment of the present invention and employing second harmonic, time-resolved luminescence and time-resolved Raman scattering detection and time-resolved luminescence, time-resolved Raman scattering and time-resolved laser induced breakdown spectroscopy for enhanced identification.

In the illustrated embodiment, a vehicle screening system is shown, it being appreciated that the present invention is not limited to vehicle screening applications, but rather may be employed in any other suitable remote object inspection environment.

In the embodiment of FIG. 20B, an inspection assembly 2035, which may be portable or stationary, employs a first laser 2036, preferably a Nd:YAG pulsed laser emitting with a peak wavelength at 1064 nm. It is appreciated that wavelengths in the range of 400 nm to 10 microns may be employed. Inspection assembly 2035 preferably also employs a second laser 2037, preferably a Nd:YAG pulsed laser emitting a third or fourth harmonic having respective peak wavelengths at 355 and 266 nm. It is appreciated that wavelengths in the range of 180 nm to 10 microns may be employed. The inspection assembly 2035 preferably also employs a third laser 2038, preferably a Nd:YAG pulsed laser emitting a second harmonic having a peak wavelength at 532 nm. It is appreciated that wavelengths in the range of 200 nm to 10 microns may be employed by this laser. Alternatively, a single laser or two lasers may be used rather than three lasers.

Output beams of lasers 2036, 2037 and 2038 impinge on scanning assemblies 2039, each typically comprising first and second scanning elements (not shown) such as mirrors, which are driven in rotational motion by motors (not shown) in synchronization with the pulsed outputs of lasers 2036, 2037 and 2038 in response to synchronization signals provided by a computer 2040. The scanned laser beam outputs of scanning assemblies 2039 are projected onto a vehicle or other suitable remote object, preferably by telescopes 2041.

The output beam of laser 2036 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 2043 and a narrow band spectral filter 2044 having a peak wavelength of 532 nm, preferably by a gated detector array 2045, such as a CCD or CMOS array. Alternatively, the detector array need not be gated, although this is not preferred.

If more than a threshold amount of scattered second harmonic illumination at wavelength 532 nm is received by gated detector array 2045 within a predetermined time window during each laser pulse, an alarm indication is provided by computer 2040, typically at a display 2046. The alarm indication indicates that an explosive material having certain second harmonic scattering characteristics may be present on a surface of the vehicle. Display 2046 preferably also visually indicates the location of the detected suspect material on the vehicle, here indicated on display 2046 at reference numeral 2048 and on the vehicle at reference numeral 2049.

The output beam of second laser 2037 is also scanned in two dimensions over the vehicle, inducing luminescence by certain materials, including a number of explosives, should those materials be present on the scanned surfaces of the vehicle. The luminescence induced by the laser beam is detected preferably by a plurality of detector assemblies 2050, each preferably including imaging optics 2051, a spectral filter 2052 and a gated detector array 2054, such as a CCD or CMOS array. Alternatively, the plurality of detector assemblies 2054 may be replaced by a single broadband detector assembly, although this is not preferred. Alternatively, the detector array need not be gated, although this is not preferred.

Preferably, the spectral range of each spectral filter 2052 of each detector assembly 2050 differs from the spectral range of each other such filter. The following spectral ranges are preferably provided, each by a different spectral filter 2052 and corresponding to the following gate intervals:
  400–430 nm—10 microseconds
  450–540 nm—50 nanoseconds
  670–700 nm—100 microseconds.

If more than a threshold amount of luminescence is received by any one or more gated detector in array 2054 within its time window and its spectral range, an alarm indication is provided by computer 2040, typically at display 2046. This alarm indication indicates that an explosive material having certain luminescence characteristics may be present on a surface of the vehicle. Display 2046 preferably also visually indicates, at location 2048 on the display 2046, the location 2049 on the vehicle of the detected suspect material.

Preferably computer 2040 is operative to analyze and indicate detection of suspect materials on the vehicle produced in response to excitation by the first and second lasers 2036 and 2037 and the resulting second harmonic scattering and luminescence detection resulting therefrom.

The output beam of third laser 2038 is also scanned in two dimensions over the vehicle, inducing Raman scattering by certain materials, including explosives, should those materials be present on the scanned surfaces of the vehicle. The Raman scattering is detected by a plurality of detector assemblies 2055, each preferably including imaging optics 2056, a spectral filter 2057, a notch filter 2058 and a gated detector array 2059, such as a CCD or CMOS array. Alternatively, the plurality of detector assemblies 2055 may be replaced by a single broadband detector assembly, although this is not preferred. Alternatively, the detector array need not be gated, although this is not preferred.

Preferably, the spectral range of each spectral filter 2057 of each detector assembly 2055 differs from the spectral range of each other such filter. The following Raman shifts relative to the laser excitation wavelength are preferably provided, each by a different spectral filter 2057:
  880–885 cm (−1)
  1360–1365 cm (−1)
  1270–1290 cm (−1)
  2980–3000 cm (−1).

If more than a threshold amount of Raman scattering is received by any one or more gated detector of array 2059 during the time interval of the laser excitation pulse and its spectral range, an alarm indication is provided by computer 2040, typically at display 2046. This alarm indication indicates that an explosive material having certain Raman scattering characteristics may be present on a surface of the vehicle. Display 2046 preferably also visually indicates, at location 2048 on the display 2046, the location 2049 on the vehicle of the detected suspect material.

Preferably computer 2040 is operative to analyze and indicate detection of suspect materials on the vehicle produced in response to excitation by the first, second and third lasers 2036, 2037 and 2038 and the second harmonic scattering, time-resolved luminescence and time-resolved Raman scattering detection resulting therefrom.

Preferably computer 2040 and display 2046 are operative to superimpose and indicate the spatial relationship between the locations of the detected suspect materials on the vehicle produced in response to excitation by the first, second and third lasers 2036, 2037 and 2038 and the second harmonic scattering, time resolved luminescence and time-resolved Raman scattering detection resulting therefrom.

In accordance with a preferred embodiment of the present invention the system of FIG. 20B also provides identification of an explosive on an object.

During identification, identification collecting optics 2060 are employed for receiving time-resolved luminescence and time-resolved Raman scattering from the location or locations 2049 of the detected suspect material on the vehicle. During identification, the output beams of lasers 2037 and 2038 are thus scanned in two dimensions at the previously determined location or locations 2049 of suspect material on a vehicle.

The output of identification collecting optics 2060 is preferably supplied via a fiberoptic link 2061 to a polychromator 2062, which produces dispersion of the luminescence and Raman spectra. The output from the polychromator 2062 is supplied to a gated detector assembly 2063, preferably employing a CCD array. Alternatively, the detector assembly need not be gated, although this is not preferred.

The output of gated detector assembly 2063 is analyzed by computer 2040 to compare the spectrum represented thereby with reference spectra characteristic of known explosives, in order to provide identification of an explosive on the vehicle.

In accordance with a preferred embodiment of the present invention the system of FIG. 20B also provides enhanced identification of detection of an explosive on an object. This enhanced identification is preferably provided by employing a selectably positionable lens (not shown) that is associated with telescope 2041. This lens is normally positioned in an inoperative position during detection, as opposed to enhanced identification, operation of the system.

During enhanced identification, identification collecting optics 2060 are employed for receiving laser induced breakdown emissions from the location or locations of the detected suspect material on the vehicle. The output of identification collecting optics 2060 is preferably supplied via fiberoptic link 2061 to polychromator 2062, which produces dispersion of the emission spectrum. The output from the polychromator 2062 is supplied to gated detector assembly 2063.

The output of gated detector assembly 2063 is analyzed by computer 2040 to compare the spectrum represented thereby with reference spectra characteristic of known explosives, in order to provide an enhanced output indication of the existence of an explosive on the vehicle.

Figure 20C:
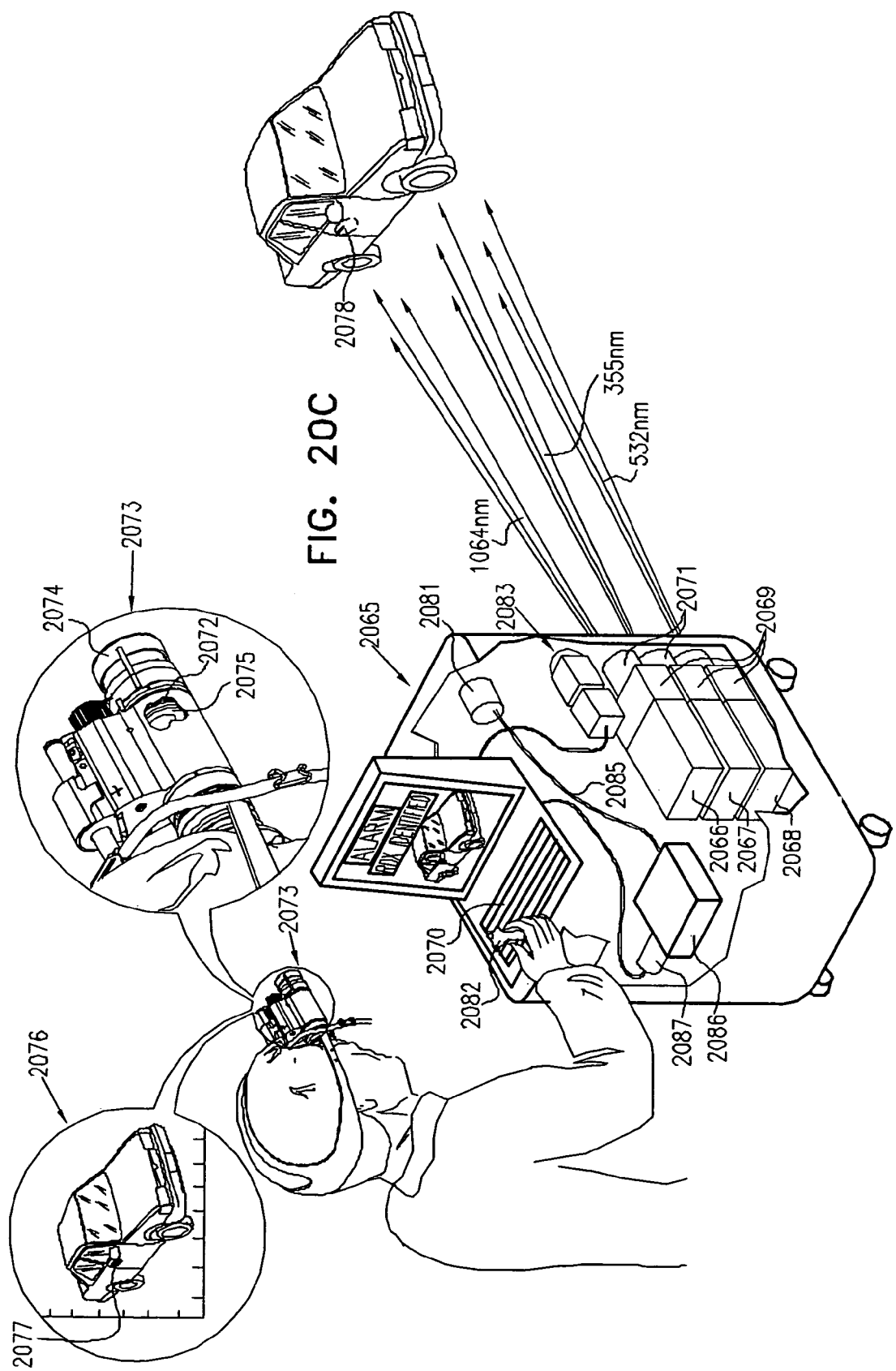

Reference is now made to FIG. 20C, which is a simplified pictorial illustration of a quadruple mode system for detecting and identifying explosives constructed and operative in accordance with yet another preferred embodiment of the present invention and employing second harmonic, time-resolved luminescence and time-resolved Raman scattering detection and time-resolved luminescence, time-resolved Raman scattering and time-resolved laser induced breakdown spectroscopy for enhanced identification.

In the illustrated embodiment, a vehicle screening system is shown, it being appreciated that the present invention is not limited to vehicle screening applications, but rather may be employed in any other suitable remote object inspection environment.

In the embodiment of FIG. 20C, an inspection assembly 2065, which is preferably portable, employs a first laser 2066, preferably a Nd:YAG pulsed laser emitting with a peak wavelength at 1064 nm. It is appreciated that wavelengths in the range of 400 nm to 10 microns may be employed. The inspection assembly 2065 preferably also employs a second laser 2067, preferably a Nd:YAG pulsed laser emitting a third or fourth harmonic having respective peak wavelengths at 355 and 266 nm. It is appreciated that wavelengths in the range of 180 nm to 10 microns may be employed. Inspection assembly 2065 preferably also employs a third laser 2068, preferably a Nd:YAG pulsed laser emitting a second harmonic having a peak wavelength at 532 nm. It is appreciated that wavelengths in the range of 200 nm to 10 microns may be employed by this laser. Alternatively, a single laser or two lasers may be used rather than three lasers.

The output beams of lasers 2066, 2067 and 2068 impinge on scanning assemblies 2069, typically comprising first and second scanning elements (not shown) such as mirrors, which are driven in rotational motion by motors (not shown) in synchronization with the pulsed output of lasers 2066, 2067 and 2068 in response to synchronization signals provided by a computer 2070. The scanned laser beam outputs of scanning assemblies 2069 are projected onto a vehicle or other suitable remote object, preferably by telescopes 2071.

The output beam of laser 2066 is thus scanned in two dimensions over a vehicle, inducing second harmonic scattering of the output beam by certain materials, including a number of explosives, should those materials be present on the scanned surfaces of the vehicle. The scattered second harmonic of the laser beam is detected via imaging optics 2072 forming part of a head-mounted viewing assembly 2073, a narrow band spectral filter 2074 having a peak wavelength of 532 nm and an image intensifier 2075, all forming part of the head-mounted viewing assembly 2073.

In accordance with a preferred embodiment of the present invention the image intensifier 2075 is gated by control signals from computer 2070 so as to be synchronized with the pulsed output of laser 2066. Filter 2074 is operative to eliminate transmission of reflected laser radiation at 1064 nm, to attenuate the ambient radiation and to fully transmit the second harmonic scattered radiation at 532 nm. Thus, an operator using the head-mounted viewing assembly 2073 sees a scene such as that designated by reference numeral 2076, wherein the location on the vehicle of a suspected explosive is highlighted over an ambient background image of the vehicle. The location of the suspected explosive is indicated on scene 2076 at reference numeral 2077 and on the vehicle at reference numeral 2078.

The output beam of laser 2067 is also scanned in two dimensions over a vehicle, inducing luminescence by certain materials, including a number of explosives, should those materials be present on the scanned surfaces of the vehicle. The luminescence induced by the laser beam is detected via imaging optics 2072 forming part of a head-mounted viewing assembly 2073, at least one and preferably a plurality of individually selectable and interchangeable narrow band spectral filters 2074 and an image intensifier 2075, all forming part of the head-mounted viewing assembly 2075.

Preferably, the spectral range of each spectral filter 2074 differs from the spectral range of each other such filter. The following spectral ranges are preferably provided, each by a different spectral filter 2074 and corresponding to the following gate intervals:

400–430 nm—10 microseconds
450–540 nm—50 nanoseconds
670–700 nm—100 microseconds.

In accordance with a preferred embodiment of the present invention the image intensifier 2075 is gated by control signals from computer 2070 so as to be synchronized with the pulsed output of laser 2067. Filters 2074 are operative to eliminate transmission of reflected laser radiation at 355 nm and 266 nm, to attenuate the ambient radiation and to fully transmit the luminescence. Thus, an operator using the head-mounted viewing assembly 2073 sees a scene such as scene 2076, wherein location 2078 of a suspected explosive on the vehicle is highlighted on the scene 2076 at location 2077 over an ambient background image of the vehicle.

The output beam of laser 2068 is also scanned in two dimensions over the vehicle, inducing Raman scattering by certain materials, including explosives, should those materials be present on the scanned surfaces of the vehicle. The Raman scattering induced by the laser beam is detected via imaging optics 2072 forming part of a head-mounted viewing assembly 2073, at least one and preferably a plurality of narrow band spectral filters 2074 and image intensifier 2075, all forming part of the head-mounted viewing assembly 2073.

Preferably, the spectral range of each spectral filter 2074 differs from the spectral range of each other such filter. The following Raman shifts relative to the laser excitation wavelength are preferably provided, each by a different spectral filter 2074:

880–885 cm (−1)
1360–1365 cm (−1)
1270–1290 cm (−1)
2980–3000 cm (−1).

In accordance with a preferred embodiment of the present invention the image intensifier 2075 is gated by control signals from computer 2070 to operate during the time interval of the laser excitation pulse. Thus, an operator using the head-mounted viewing assembly 2073 sees a scene such as scene 2076, wherein location 2078 of a suspected explosive on the vehicle is highlighted on the scene 2076 at location 2077 over an ambient background image of the vehicle.

In accordance with a preferred embodiment of the present invention the system of FIG. 20C also provides identification of an explosive on an object.

During identification, identification collecting optics 2081 are employed for receiving time-resolved luminescence and time-resolved Raman scattering from the location or locations of the detected suspect material on the vehicle. During identification, the output beam of first laser 2066 is scanned in two dimensions at the previously determined location or locations 2078 of suspect material on a vehicle. During identification, the output beam of second laser 2067 is also scanned in two dimensions at the previously determined location or locations 2078 of suspect material on a vehicle.

The identification collecting optics 2081 are preferably aimed by an operator at the location of the suspected explosive typically using a joystick 2082 and a viewing camera 2083 or marker which is visible through the image intensifier 2075.

The output of identification collecting optics 2081 is preferably supplied via a fiberoptic link 2085 to a polychromator 2086, which produces dispersion of the luminescence and Raman spectra. The output from the polychromator 2086 is supplied to a gated detector assembly 2087, preferably employing a CCD array. Alternatively, the detector assembly need not be gated, although this is not preferred.

The output of gated detector assembly 2087 is analyzed by computer 2070 to compare the spectrum represented thereby with reference spectra characteristic of known explosives, in order to provide identification of an explosive on the vehicle.

In accordance with a preferred embodiment of the present invention the system of FIG. 20C also provides enhanced identification of detection of an explosive on an object. This enhanced identification is preferably provided by employing a selectably positionable lens (not shown) that is associated with telescope 2071. This lens is normally positioned in an inoperative position during detection, as opposed to during enhanced identification, operation of the system.

During enhanced identification, identification collecting optics 2081 are employed for receiving laser induced breakdown emissions from the location or locations of the detected suspect material on the vehicle. The output of identification collecting optics 2081 is preferably supplied via fiberoptic link 2085 to polychromator 2086, which produces dispersion of the emission spectrum. The output from the polychromator 2086 is supplied to gated detector assembly 2087.

The identification collecting optics 2081 are preferably aimed by an operator at the location of the suspected explosive typically using joystick 2082 and viewing camera 2083 or marker which is visible through the image intensifier 2075.

The output of gated detector assembly 2087 is analyzed by computer 2070 to compare the spectrum represented thereby with reference spectra characteristic of known explosives, in order to provide an enhanced output indication of the existence of an explosive on the vehicle.

It is appreciated that in the systems described hereinabove in reference to FIGS. 8A–20C, that provide both detection and identification, the detection is preferably performed in a relatively fast mode, while the identification of suspected materials may be carried out thereafter in a relatively slower mode.

It is noted that, even though the illustrated embodiments described hereinabove show the detection portion of the systems including detector assemblies including imaging optics, filters and gated detector assemblies, any suitable configuration of components, such as incorporating a fiberoptic link for remote detection, may be used for collecting and analyzing the scattered output from the laser.

It is further noted that, even though the illustrated embodiments described hereinabove show the identification portion of the systems including collecting optics linked to a polychromator via a fiberoptic link, any suitable configuration of components, such as directly connecting the polychromator to the collecting optics without using a fiberoptic link, may be used for collecting and analyzing the scattered output from the laser.

It is also appreciated that, even though the illustrated embodiments described hereinabove show the use of single or multiple lasers, that any appropriate light source may be substituted for the laser or lasers.

It is noted that, in the systems described hereinabove in reference to FIGS. 8A–20C, a monochromator or any other suitable spectral device may be substituted for the polychromator.

It is further appreciated that in the systems described hereinabove the use of imaging optics may be obviated by synchronizing the location of the detection with the location of the scanned laser beam.

In another preferred embodiment of the second harmonic detection, luminescence detection and Raman scattering detection systems described hereinabove, the system may be operative to generate multiple excitation wavelengths to find optimal wavelengths which will minimize interfering spectra of background or other non-explosive material. These multiple wavelengths may be provided using an optical parameter oscillator (OPO) source or any other suitable light source.

It is appreciated that, even though the illustrated embodiments show suspected material being detected at a single location, there may be multiple locations at which suspected material is detected using each detection method.

It is further appreciated that locations of the suspected material detected may not be identical for the detection methods illustrated. In many cases the various locations may completely or partially overlap.

It is also noted that in the systems described hereinabove, which use multiple different types of filters in the head-mounted viewing assembly, these filters may be mounted and removed manually by the operator. Alternatively, an automatic mechanism may be provided for cycling the different filters.

It is further noted that in the systems described hereinabove the scanning for materials on the surface of the object scanned also includes scanning in the vicinity of the object for particles which may be present due to evaporation or other physical phenomena.

Figure 21:
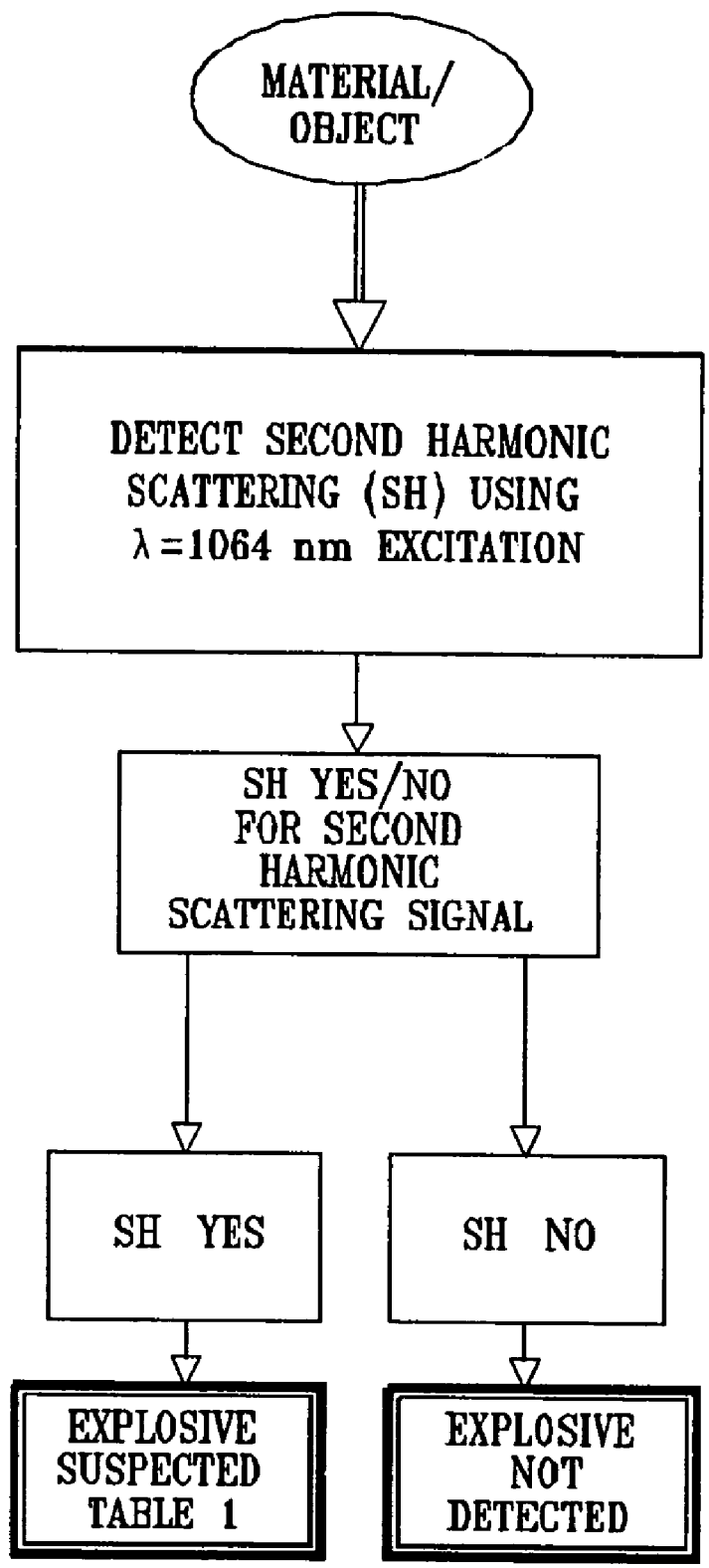
FIG. 21 is a simplified flowchart illustrating operation of the embodiments of FIGS. 1A–1D.

Reference is now made to FIG. 21, which is a simplified flowchart illustrating operation of the embodiments of FIGS. 1A–1D. An object, such as, for example, a suitcase or a vehicle, which is sought to be examined for the possible presence of explosives thereon, is illuminated by laser radiation, as described in FIGS. 1A–1D, and is subject to detection of second harmonic scattering. If second harmonic scattering is detected, it is concluded that one or more of the explosives listed in Table 1 may be present on the object.

TABLE 1

| | Substance | Comments |
|---|---|---|
| 1. | TNT | Flakes |
| 2. | Ch6 | |
| 3. | CompB | |
| 4. | RDX | Crystals |
| 5. | RDX | Mixture1 |
| 6. | RDX | Mixture2 |
| 7. | C4 | |

TABLE 1-continued

| | Substance | Comments |
|---|---|---|
| 8. | A5 | (RDX) |
| 9. | TENN | |

Figure 22:
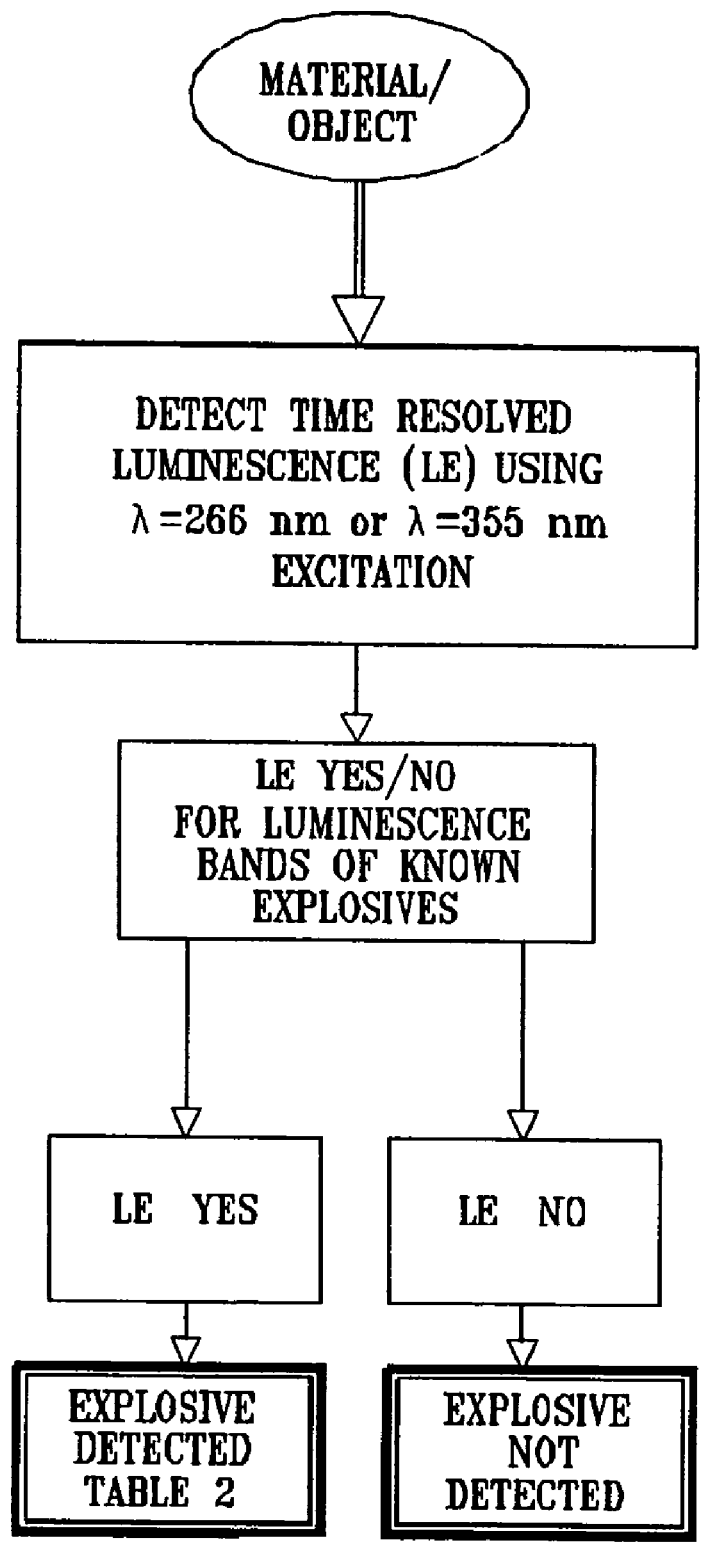
FIG. 22 is a simplified flowchart illustrating operation of the embodiments of FIGS. 2A–2D.

Reference is now made to FIG. 22, which is a simplified flowchart illustrating operation of the embodiments of FIGS. 2A–2D. An object, such as, for example, a suitcase or a vehicle, which is sought to be examined for the possible presence of explosives thereon, is illuminated by laser radiation, as described in FIGS. 2A–2D, and is subject to time-resolved detection of luminescence. If luminescence within the luminescence bands of known explosives in Table 2 is detected, it is concluded that one or more of the explosives listed in Table 2 is present on the object. If luminescence within the luminescence bands of known explosives in Table 2 is not detected, it is concluded that the explosives listed in Table 2 are not present on the object.

TABLE 2

| | Substance | Comments |
|---|---|---|
| 1. | RDX | Crystals |
| 2. | RDX | Mixture1 |
| 3. | RDX | Mixture2 |
| 4. | C4 | |
| 5. | Semtex | |
| 6. | PETN | Mixture |
| 7. | TATP | Crystals |
| 8. | BP | |
| 9. | UN | Crystals |

Figure 23:
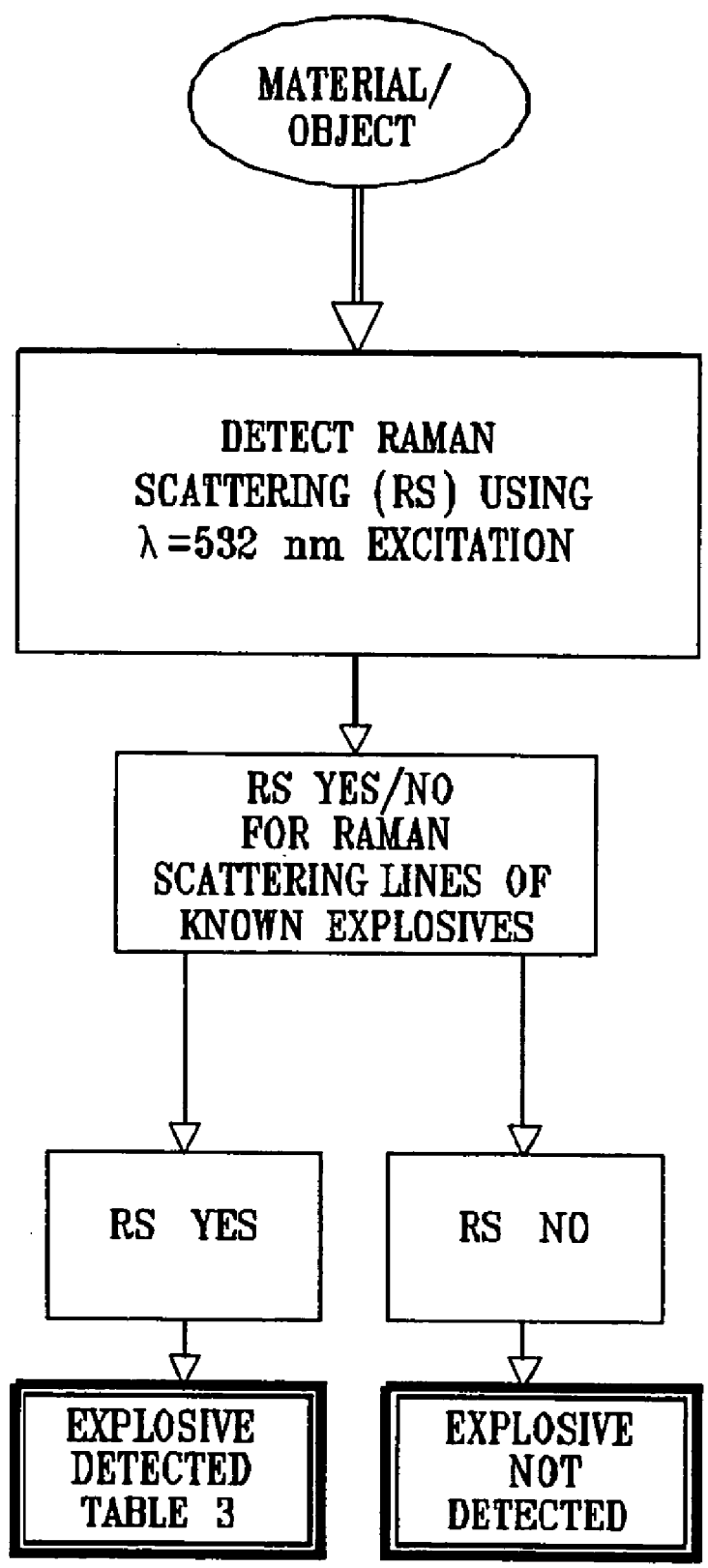
FIG. 23 is a simplified flowchart illustrating operation of the embodiments of FIGS. 3A–3D.

Reference is now made to FIG. 23, which is a simplified flowchart illustrating operation of the embodiments of FIGS. 3A–3D. An object, such as, for example, a suitcase or a vehicle, which is sought to be examined for the possible presence of explosives thereon, is illuminated by laser radiation, as described in FIGS. 3A–3D, and is subject to time-resolved detection of Raman scattering. If Raman scattering having Raman scattering lines of known explosives listed in Table 3 is detected, it is concluded that one or more of the explosives listed in Table 3 is present on the object. If Raman scattering having Raman scattering lines of known explosives listed in Table 3 is not detected, it is concluded that one or more of the explosives listed in Table 3 is probably not present on the object.

TABLE 3

| | Substance | Comments |
|---|---|---|
| 1. | TNT | Flakes |
| 2. | Ch6 | |
| 3. | CompB | |
| 4. | RDX | Crystals |
| 5. | RDX | Mixture1 |
| 6. | RDX | Mixture2 |
| 7. | C4 | |
| 8. | A5 | (RDX) |
| 9. | PETN | Crystals |
| 10. | TENN | |
| 11. | TATP | Crystals |
| 12. | UN | Crystals |

Figure 24A:
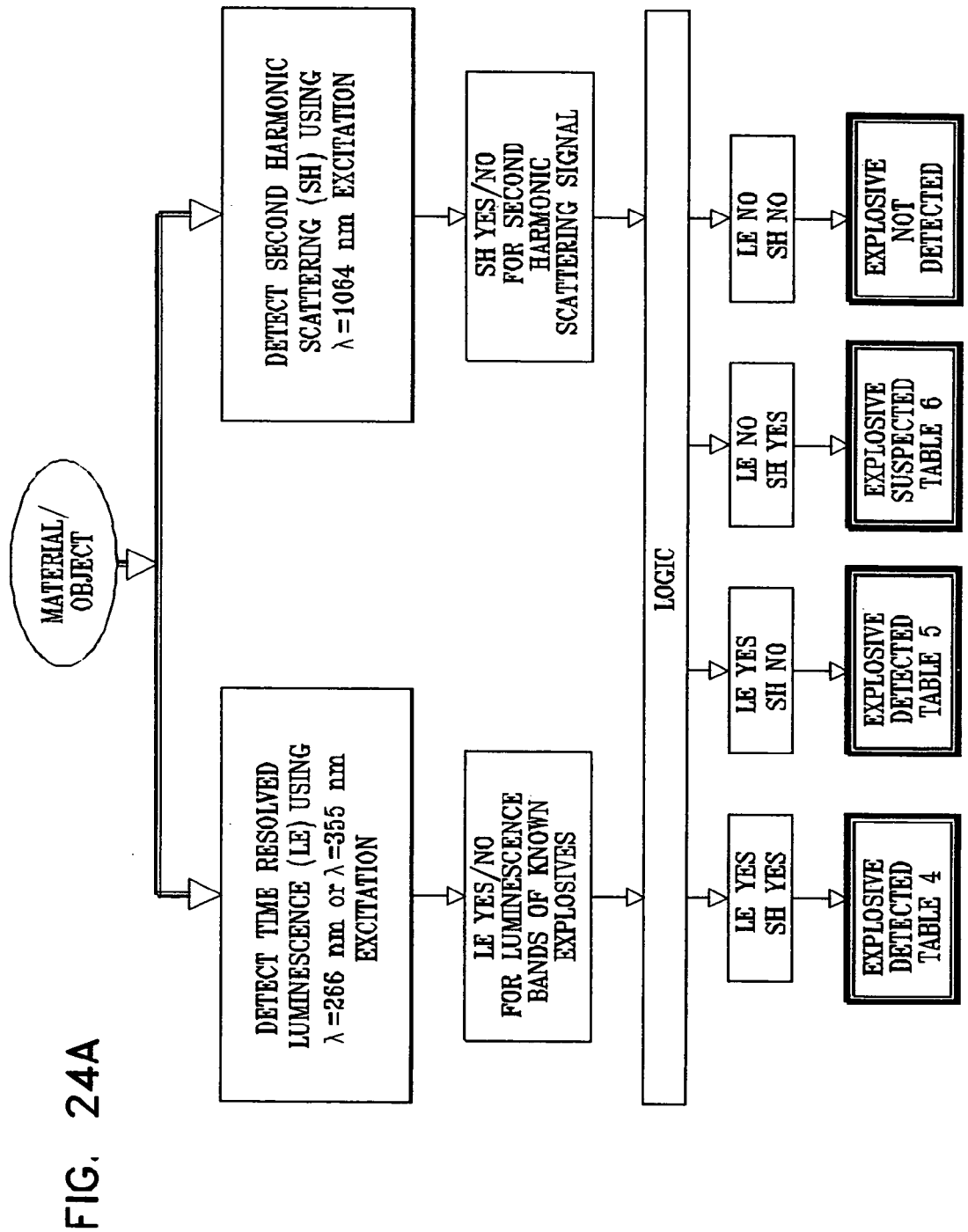
FIG. 24A is a simplified flowchart illustrating operation of the embodiment of FIG. 4A.

Reference is now made to FIG. 24A, which is a simplified flowchart illustrating operation of the embodiment of FIG. 4A. An object, such as, for example, a suitcase, which is sought to be examined for the possible presence of explosives thereon, is illuminated by laser radiation, as described in FIG. 4A, and is subject to detection of second harmonic scattering and to time-resolved detection of luminescence. If luminescence within the luminescence bands of known explosives in Table 2 is detected and second harmonic scattering is detected, it is concluded that one or more of the explosives listed in Table 4 is present on the object.

TABLE 4

| | Substance | Comments |
|---|---|---|
| 1. | TNT | Flakes |
| 2. | Ch6 | |
| 3. | CompB | |
| 4. | RDX | Crystals |
| 5. | RDX | Mixture1 |
| 6. | RDX | Mixture2 |
| 7. | C4 | |
| 8. | A5 | (RDX) |
| 9. | Semtex | |
| 10. | PETN | Mixture |
| 11. | TENN | |
| 12. | TATP | Crystals |
| 13. | BP | |
| 14. | UN | Crystals |

If luminescence within the luminescence bands of known explosives in Table 2 is detected and second harmonic scattering is not detected, it is concluded that one or more of the explosives listed in Table 5 is present on the object.

TABLE 5

| | Substance | Comments |
|---|---|---|
| 1. | Semtex | |
| 2. | PETN | Mixture |
| 3. | TATP | Crystals |
| 4. | BP | |
| 5. | UN | Crystals |

If luminescence within the luminescence bands of known explosives in Table 2 is not detected and second harmonic scattering is detected, it is concluded that the explosives listed in Table 6 are suspected to be present on the object.

TABLE 6

| | Substance | Comments |
|---|---|---|
| 1. | TNT | Flakes |
| 2. | Ch6 | |
| 3. | CompB | |
| 4. | A5 | (RDX) |
| 5. | TENN | |

If luminescence within the luminescence bands of known explosives in any of Table 2 is not detected and second harmonic scattering is not detected, it is concluded that the explosives listed in Table 4 are not present on the object.

Figure 24B:
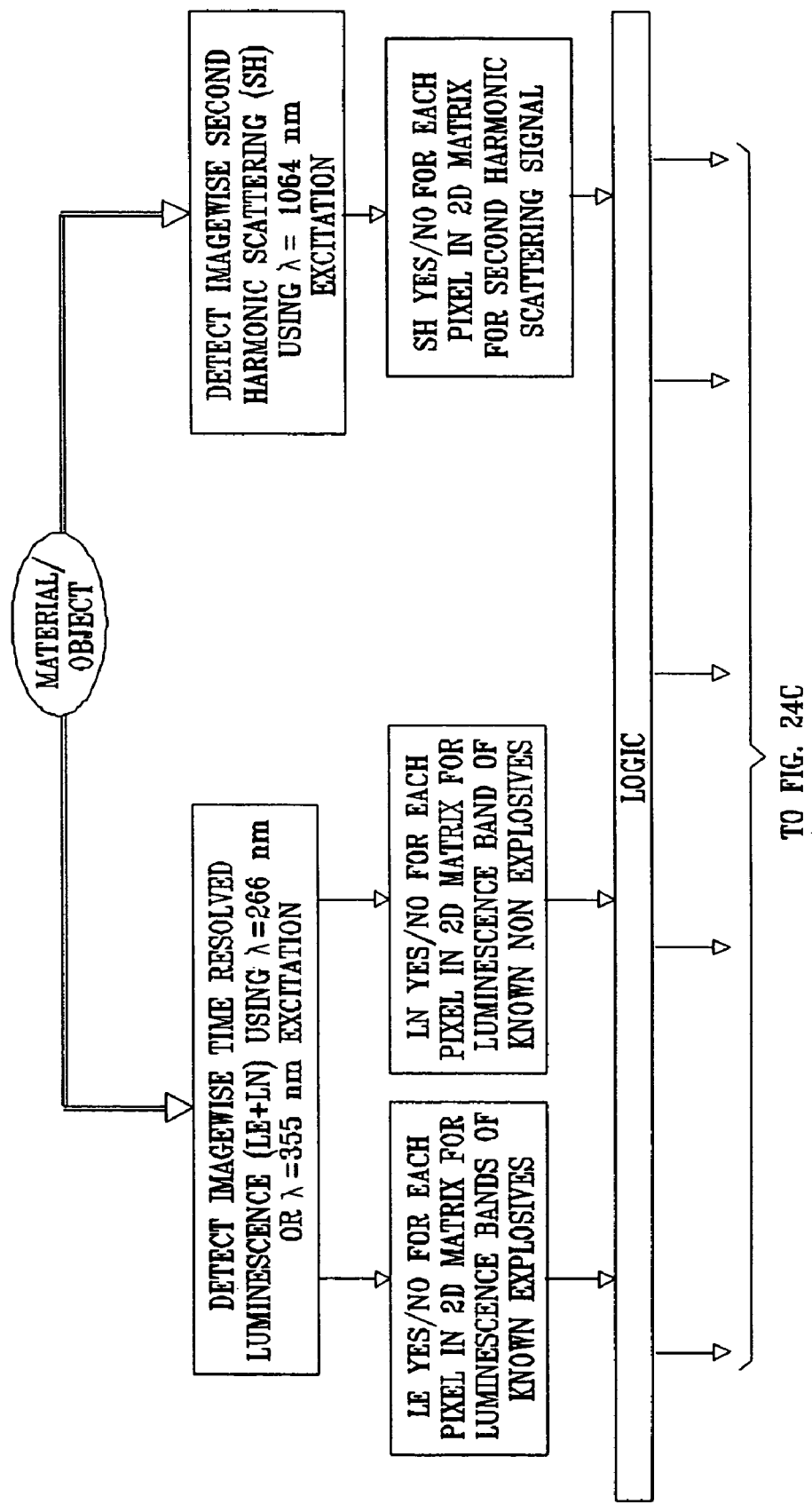
FIGS. 24B and 24C, taken together, are a simplified flowchart illustrating operation of the embodiments of FIGS. 4B & 4C.
Figure 24C:
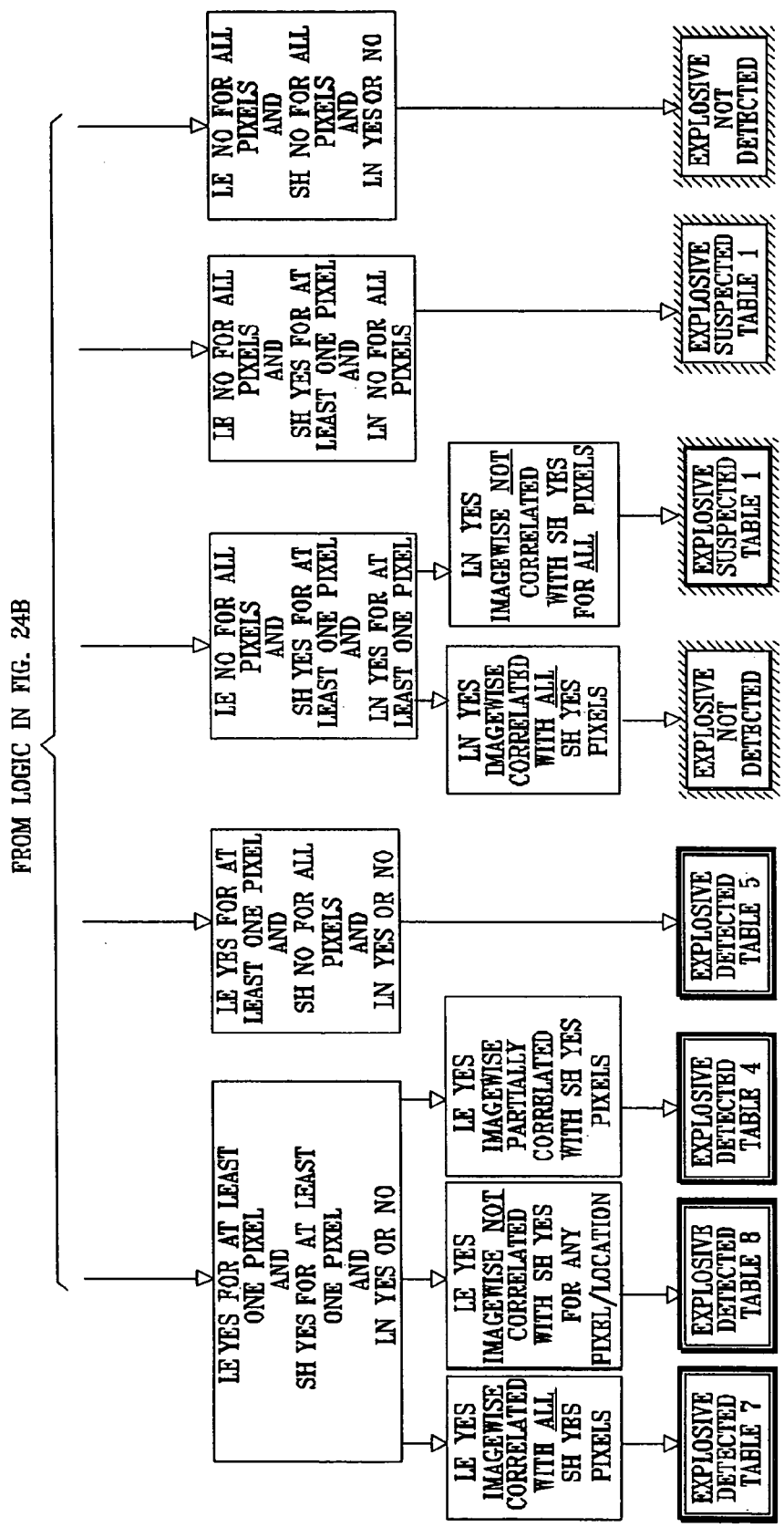

Reference is now made to FIGS. 24B and 24C, which, taken together, are a simplified flowchart illustrating operation of the embodiment of FIGS. 4B & 4C. An object, such as, for example, a suitcase or a vehicle, which is sought to be examined for the possible presence of explosives thereon, is illuminated by laser radiation, as described in FIG. 4B or 4C, and is subject to imagewise detection of second harmonic scattering and to imagewise time-resolved detection of luminescence.

If luminescence within the luminescence bands of known explosives in Table 2 is detected for given pixels and second harmonic scattering is detected only for all of the same pixels, it is concluded that one or more of the explosives listed in Table 7 is present on the object at the locations of the given pixels.

TABLE 7

|     | Substance | Comments |
| --- | --------- | -------- |
| 1.  | RDX       | Crystals |
| 2.  | RDX       | Mixture1 |
| 3.  | RDX       | Mixture2 |
| 4.  | C4        |          |

If luminescence within the luminescence bands of known explosives in Table 2 is detected for given pixels and second harmonic scattering is detected, if at all, only for different pixels, it is concluded that one or more of the explosives listed in Table 8 is present on the object.

TABLE 8

|     | Substance | Comments |
| --- | --------- | -------- |
| 1.  | TNT       | Flakes   |
| 2.  | Ch6       |          |
| 3.  | CompB     |          |
| 4.  | A5        | (RDX)    |
| 5.  | Semtex    |          |
| 6.  | PETN      | Mixture  |
| 7.  | TENN      |          |
| 8.  | TATP      | Crystals |
| 9.  | BP        |          |
| 10. | UN        | Crystals |

If luminescence within the luminescence bands of known explosives in Table 2 is detected for given pixels and second harmonic scattering is detected, for some of the same pixels as well as for different pixels, it is concluded that one or more of the explosives listed in Table 4 is present on the object.

If luminescence within the luminescence bands of known explosives in Table 2 is detected in at least one pixel and second harmonic scattering is not detected, it is concluded that one or more of the explosives listed in Table 5 is present on the object at the locations of the at least one pixel.

If luminescence within the luminescence bands of known non-explosives, such as fabrics or metals, is detected for given pixels and second harmonic scattering is detected for the same pixels, it is concluded that none of the explosives listed in Table 4 is present on the object at the locations of the relevant pixels.

If luminescence within the luminescence bands of known non-explosives is detected for given pixels and second harmonic scattering is detected, if at all, only for different pixels, it is concluded that one or more of the explosives listed in Table 1 may be present on the object at the locations of the pixels where second harmonic scattering is detected.

If luminescence within the luminescence bands of known explosives in Table 2 and within the luminescence bands of known non-explosives is not detected and second harmonic scattering is detected for at least one pixel, it is concluded that one or more of the explosives listed in Table 1 may be present on the object at the location of the at least one pixel.

If luminescence within the luminescence bands of known explosives in Table 2 is not detected and second harmonic scattering is not detected for any pixels, it is concluded that none of the explosives listed in Table 4 is present on the object.

Reference is now made to FIG. 25A, which is a simplified flowchart illustrating operation of the embodiment of FIG. 5A. An object, such as, for example, a suitcase, which is sought to be examined for the possible presence of explosives thereon, is illuminated by laser radiation, as described in FIG. 5A, and is subject to detection of second harmonic scattering and to time-resolved detection of Raman scattering. If Raman scattering at the lines of the known explosives in Table 3 is detected and second harmonic scattering is detected, it is concluded that one or more of the explosives listed in Table 3 is present on the object. If Raman scattering at the lines of the known explosives in Table 3 is detected and second harmonic scattering is not detected, it is concluded that one or more of the explosives listed in Table 9 is present on the object.

TABLE 9

|     | Substance | Comments |
| --- | --------- | -------- |
| 1.  | PETN      | Crystals |
| 2.  | TATP      | Crystals |
| 3.  | UN        | Crystals |

If Raman scattering at the lines of the known explosives in Table 3 is not detected and second harmonic scattering is detected, it is concluded that one or more of the explosives listed in Table 1 are suspected to be present on the object. If Raman scattering at the lines of the known explosives in Table 3 is not detected and second harmonic scattering is also not detected, it is concluded that the explosives listed in Table 3 are not present on the object.

Figure 25B:
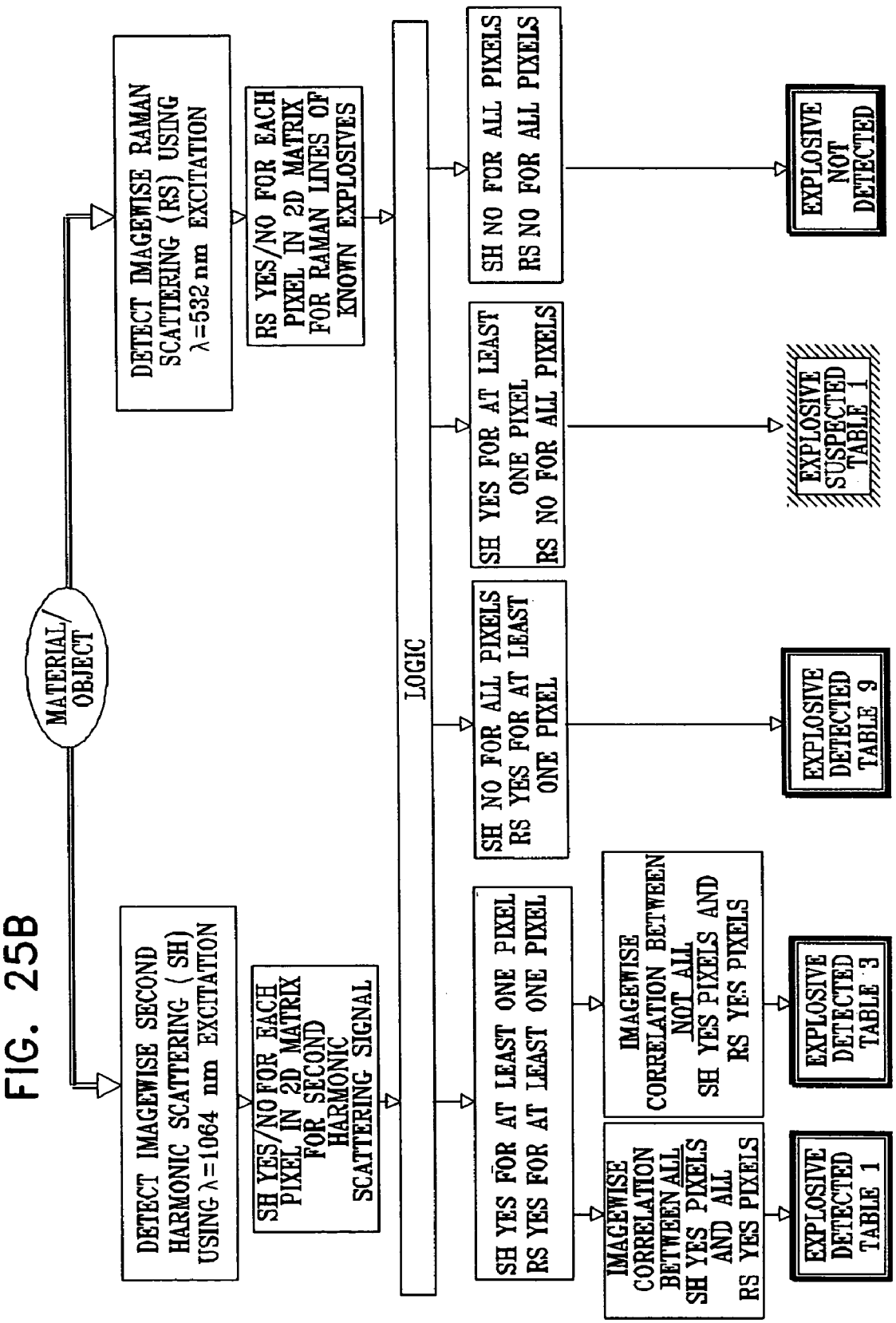
FIG. 25B is a simplified flowchart illustrating operation of the embodiments of FIGS. 5B & 5C.

Reference is now made to FIG. 25B, which is a simplified flowchart illustrating operation of the embodiment of FIGS. 5B & 5C. An object, such as, for example, a suitcase or a vehicle, which is sought to be examined for the possible presence of explosives thereon, is illuminated by laser radiation, as described in FIG. 5B or 5C, and is subject to imagewise detection of second harmonic scattering and to imagewise time-resolved detection of Raman scattering.

If Raman scattering at the lines of known explosives in Table 3 is detected for given pixels and second harmonic scattering is detected only for all of the same pixels, it is concluded that one or more of the explosives listed in Table 1 is present on the object at the locations of the given pixels.

If Raman scattering at the lines of known explosives in Table 3 is detected for given pixels and second harmonic scattering is detected, at at least some different pixels, it is concluded that one or more of the explosives listed in Table 3 is present on the object.

If Raman scattering at the lines of known explosives in Table 3 is detected in at least one pixel and second harmonic scattering is not detected, it is concluded that one or more of the explosives listed in Table 9 is present on the object at the locations of the at least one pixel.

If Raman scattering at the lines of known explosives in Table 3 is not detected and second harmonic scattering is detected for at least one pixel, it is concluded that at least one of the explosives listed in Table 1 may be present on the object at the location of the at least one pixel.

If Raman scattering at the lines of known explosives in Table 3 is not detected and second harmonic scattering is not detected for any pixels, it is concluded that none of the explosives listed in Table 3 is present on the object.

Figure 26A:
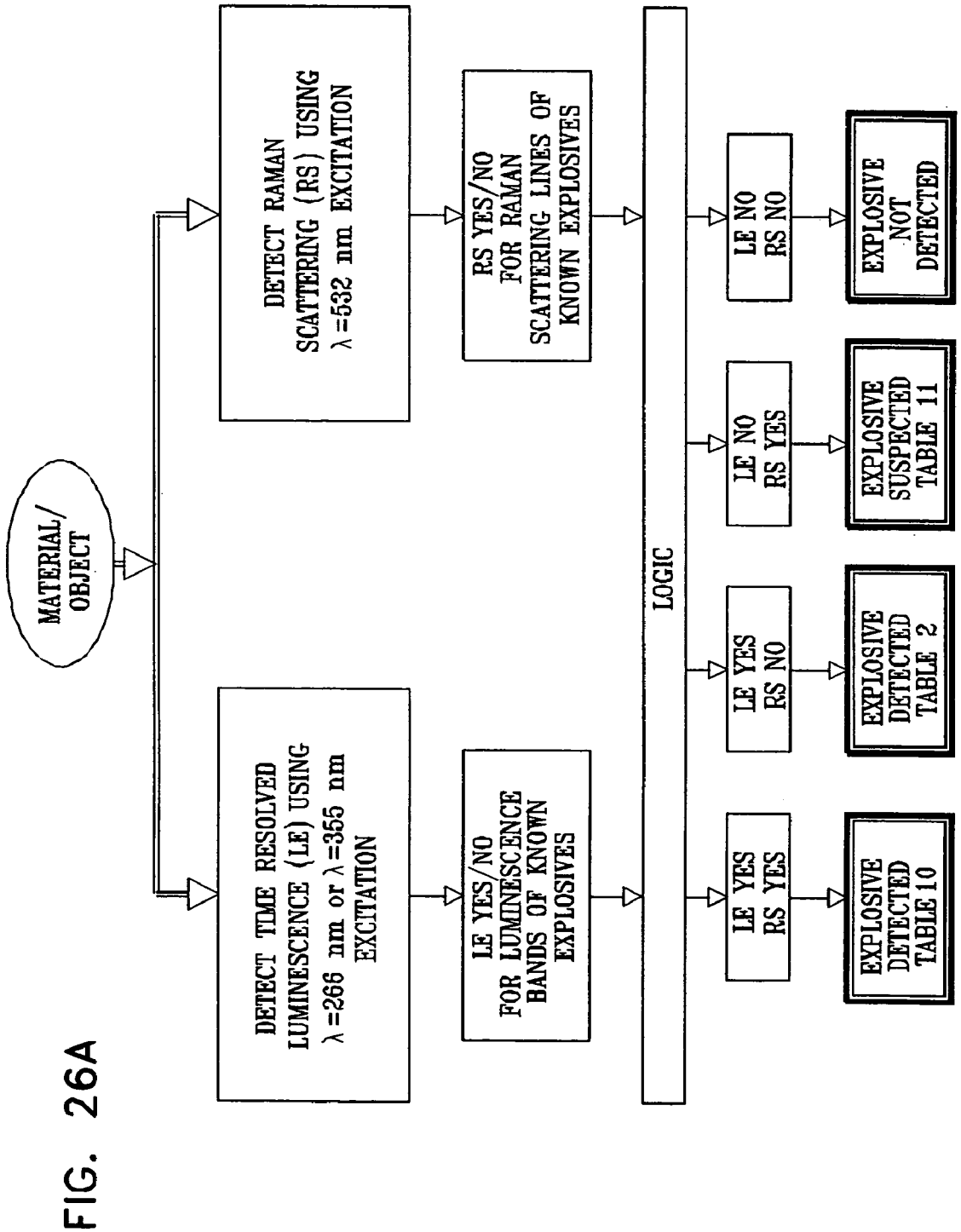
FIG. 26A is a simplified flowchart illustrating operation of the embodiment of FIG. 6A.

Reference is now made to FIG. 26A, which is a simplified flowchart illustrating operation of the embodiment of FIG. 6A. An object, such as, for example, a suitcase, which is sought to be examined for the possible presence of explosives thereon, is illuminated by laser radiation, as described in FIG. 6A, and is subject to time-resolved detection of luminescence and of Raman scattering. If luminescence within the luminescence bands of known explosives in Table 2 and Raman scattering at the lines of the known explosives in Table 3 is detected, it is concluded that one or more of the explosives listed in Table 10 is present on the object.

TABLE 10

|   | Substance | Comments |
|---|---|---|
| 1. | TNT | Flakes |
| 2. | Ch6 | |
| 3. | CompB | |
| 4. | RDX | Crystals |
| 5. | RDX | Mixture1 |
| 6. | RDX | Mixture2 |
| 7. | C4 | |
| 8. | A5 | (RDX) |
| 9. | Semtex | |
| 10. | PETN | Mixture |
| 11. | PETN | Crystals |
| 12. | TENN | |
| 13. | TATP | Crystals |
| 14. | BP | |
| 15. | UN | Crystals |

If luminescence within the luminescence bands of known explosives in Table 2 is detected and Raman scattering at the lines of the known explosives in Table 3 is not detected, it is concluded that one or more of the explosives listed in Table 2 is present on the object. If luminescence within the luminescence bands of known explosives in Table 2 is not detected and Raman scattering at the lines of the known explosives in Table 3 is detected, it is concluded that at least one of the explosives listed in Table 11 is present on the object.

TABLE 11

|   | Substance | Comments |
|---|---|---|
| 1. | TNT | Flakes |
| 2. | Ch6 | |
| 3. | CompB | |
| 4. | A5 | (RDX) |
| 5. | PETN | Crystals |
| 6. | TENN | |

If luminescence within the luminescence bands of known explosives in Table 2 is not detected and Raman scattering at the lines of the known explosives in Table 3 is not detected, it is concluded that the explosives listed in Table 10 are not present on the object.

Figure 26B:
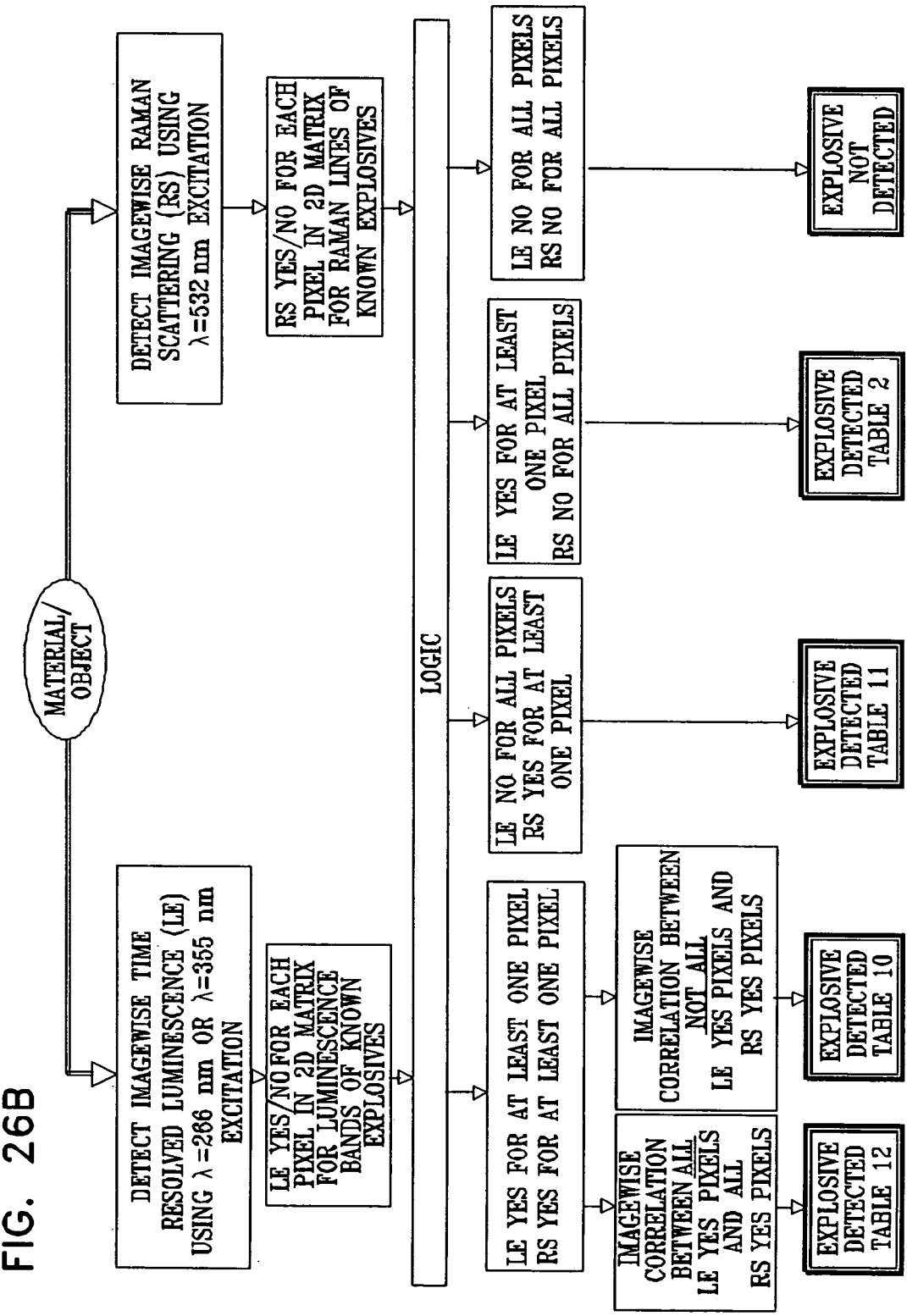
FIG. 26B is a simplified flowchart illustrating operation of the embodiments of FIGS. 6B & 6C.

Reference is now made to FIG. 26B, which is a simplified flowchart illustrating operation of the embodiment of FIGS. 6B & 6C. An object, such as, for example, a suitcase or a vehicle, which is sought to be examined for the possible presence of explosives thereon, is illuminated by laser radiation, as described in FIG. 6B or 6C, and is subject to imagewise detection of luminescence and to imagewise time-resolved detection of Raman scattering.

If luminescence within the luminescence bands of known explosives in Table 2 is detected for given pixels and Raman scattering at the lines of known explosives in Table 3 is detected only for all of the same pixels, it is concluded that one or more of the explosives listed in Table 12 is present on the object at the locations of the given pixels.

TABLE 12

|   | Substance | Comments |
|---|---|---|
| 1. | RDX | Crystals |
| 2. | RDX | Mixture1 |
| 3. | RDX | Mixture2 |
| 4. | C4 | |
| 5. | TATP | Crystals |
| 6. | UN | Crystals |

If luminescence within the luminescence bands of known explosives in Table 2 is detected for given pixels and Raman scattering at the lines of known explosives in Table 3 is detected for at least some different pixels, it is concluded that one or more of the explosives listed in Table 10 is present on the object.

If luminescence within the luminescence bands of known explosives in Table 2 is not detected for any pixels and Raman scattering at the lines of known explosives in Table 3 is detected in at least one pixel, it is concluded that one or more of the explosives listed in Table 11 is present on the object at the locations of the at least one pixel.

If luminescence within the luminescence bands of known explosives in Table 2 is detected for at least one pixel and Raman scattering at the lines of known explosives in Table 3 is not detected, it is concluded that at least one of the explosives listed in Table 2 is present on the object at the location of the at least one pixel.

If Raman scattering at the lines of known explosives in Table 3 is not detected and luminescence within the luminescence bands of known explosives in Table 2 is not detected for any pixels, it is concluded that none of the explosives listed in Table 10 is present on the object.

Figure 27A:
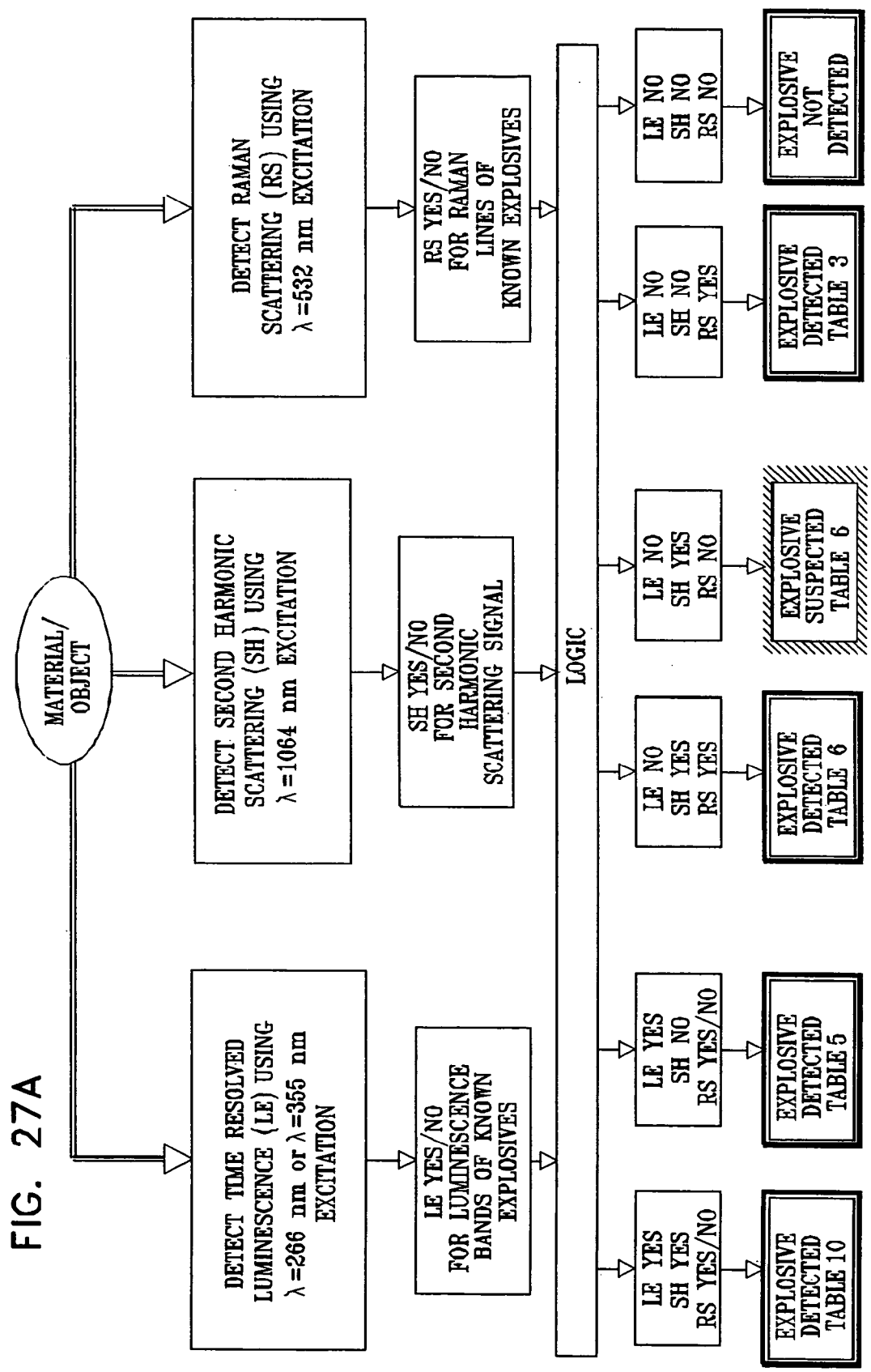
FIG. 27A is a simplified flowchart illustrating operation of the embodiment of FIG. 7A.

Reference is now made to FIG. 27A, which is a simplified flowchart illustrating operation of the embodiment of FIG. 7A. An object, such as, for example, a suitcase, which is sought to be examined for the possible presence of explosives thereon, is illuminated by laser radiation, as described in FIG. 7A, and is subject to detection of second harmonic scattering, time-resolved detection of luminescence and time-resolved detection of Raman scattering.

If luminescence within the luminescence bands of known explosives in Table 2 is detected and second harmonic scattering is detected, it is concluded that one or more of the explosives listed in Table 10 is present on the object.

If luminescence within the luminescence bands of known explosives in Table 2 is detected and second harmonic scattering is not detected, it is concluded that one or more of the explosives listed in Table 5 is present on the object.

If luminescence within the luminescence bands of known explosives in Table 2 is not detected, second harmonic scattering is detected and Raman scattering at the lines of known explosives in Table 3 is detected, it is concluded that one or more of the explosives listed in Table 6 are present on the object.

If luminescence within the luminescence bands of known explosives in Table 2 is not detected, second harmonic scattering is detected and Raman scattering at the lines of known explosives in Table 3 is not detected, it is concluded that one or more of the explosives listed in Table 6 are suspected to be present on the object.

If luminescence within the luminescence bands of known explosives in Table 2 is not detected, second harmonic scattering is not detected and Raman scattering at the lines of known explosives in Table 3 is detected, it is concluded that one or more of the explosives listed in Table 11 are present on the object.

If luminescence within the luminescence bands of known explosives in Table 2 is not detected, second harmonic scattering is not detected and Raman scattering at the lines of known explosives in Table 3 is not detected, it is concluded that the explosives listed in Table 10 are not present on the object.

Figure 27B:
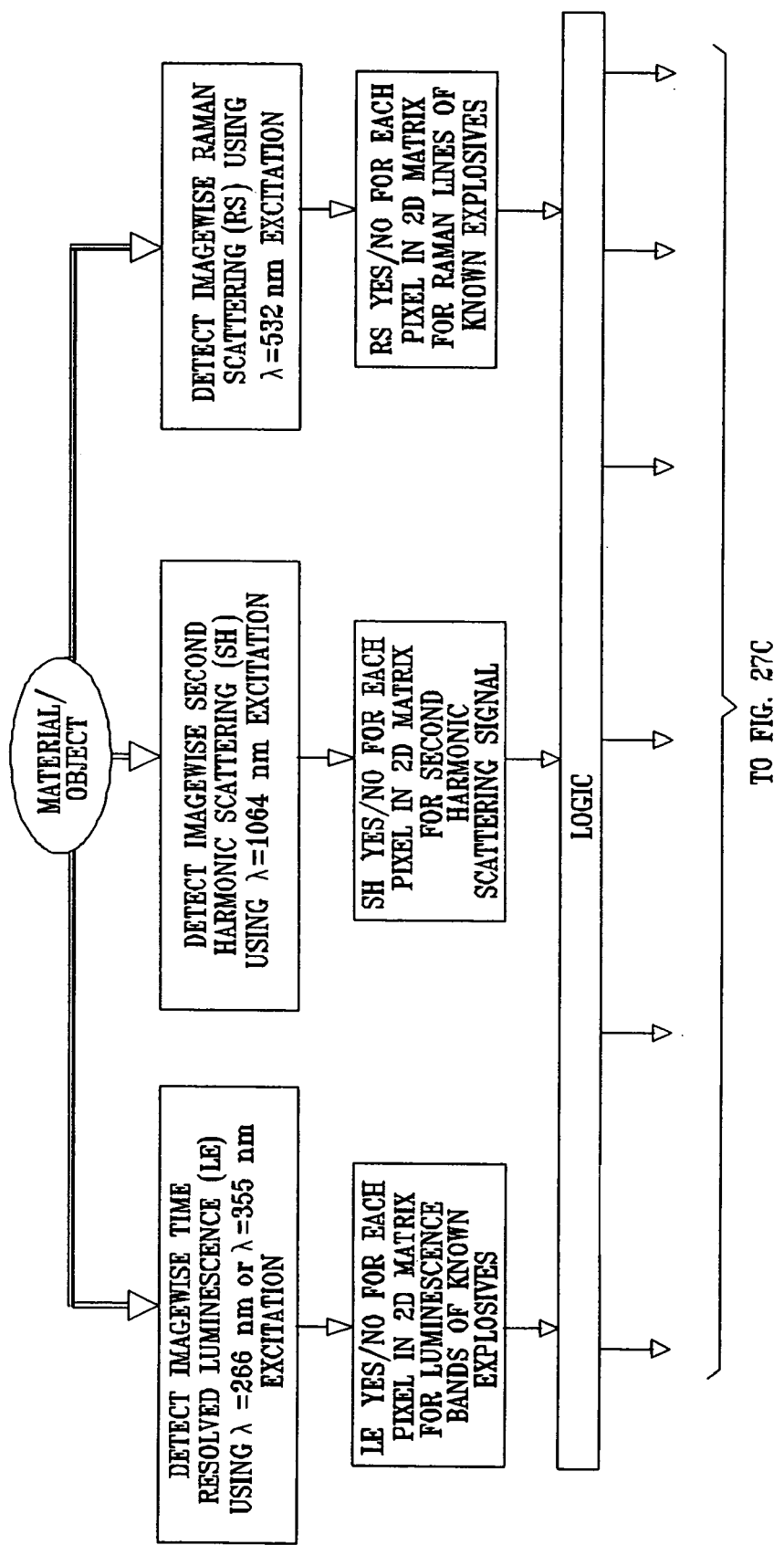
FIGS. 27B and 27C, taken together, are a simplified flowchart illustrating operation of the embodiments of FIGS. 7B & 7C.
Figure 27C:
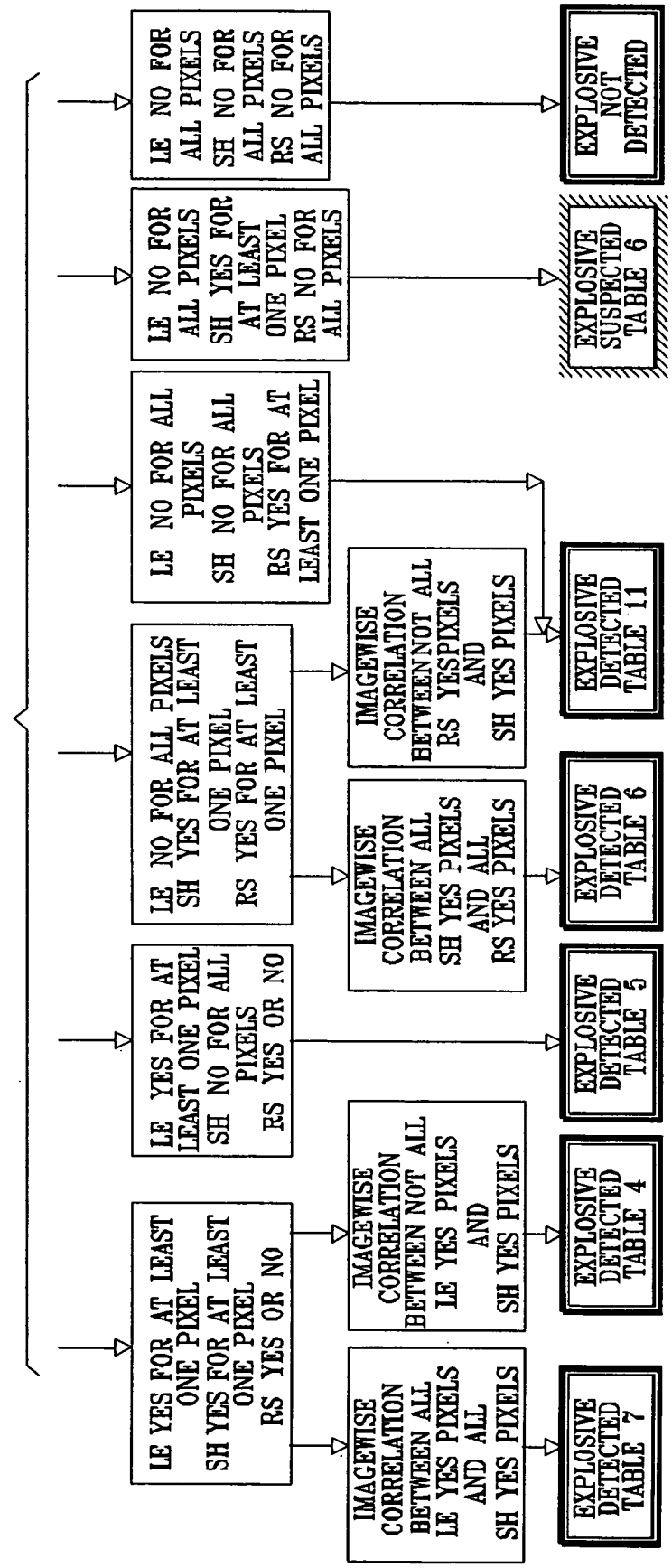

Reference is now made to FIGS. 27B and 27C, which, taken together, are a simplified flowchart illustrating operation of the embodiment of FIGS. 7B & 7C. An object, such as, for example, a suitcase or a vehicle, which is sought to be examined for the possible presence of explosives thereon, is illuminated by laser radiation, as described in FIG. 7B or 7C, and is subject to imagewise detection of second harmonic scattering, imagewise time-resolved detection of luminescence and imagewise time-resolved detection of Raman scattering.

If luminescence within the luminescence bands of known explosives in Table 2 is detected for given pixels and second harmonic scattering is detected only for at least one of the same pixels, it is concluded that one or more of the explosives listed in Table 7 is present on the object at the locations of the given pixels.

If luminescence within the luminescence bands of known explosives in Table 2 is detected for given pixels and second harmonic scattering is detected, if at all, only for different pixels, it is concluded that one or more of the explosives listed in Table 4 is present on the object.

If luminescence within the luminescence bands of known explosives in Table 2 is detected in at least one pixel and second harmonic scattering is not detected, it is concluded that one or more of the explosives listed in Table 5 is present on the object at the locations of the at least one pixel.

If luminescence within the luminescence bands of known explosives in Table 2 is not detected and Raman scattering at the lines of known explosives in Table 3 is detected for at least one pixel and second harmonic scattering is detected for at least the same pixel, it is concluded that one or more of the explosives listed in Table 6 is present on the object at the locations of the at least one pixel.

If luminescence within the luminescence bands of known explosives in Table 2 is not detected and Raman scattering at the lines of known explosives in Table 3 is detected for at least one pixel and second harmonic scattering is detected, for at least one different pixel, it is concluded that one or more of the explosives listed in Table 11 is present on the object at the locations of the at least one pixel.

If luminescence within the luminescence bands of known explosives in Table 2 and second harmonic scattering are not detected and Raman scattering at the lines of known explosives in Table 3 is detected for at least one pixel, it is concluded that one or more of the explosives listed in Table 11 is present on the object at the locations of the at least one pixel.

If luminescence within the luminescence bands of known explosives in Table 2 and Raman scattering at the lines of known explosives in Table 3 are not detected and second harmonic scattering is detected for at least one pixel, it is suspected that one or more of the explosives listed in Table 6 is present on the object at the locations of the at least one pixel.

If luminescence within the luminescence bands of known explosives in Table 2, Raman scattering at the lines of known explosives in Table. 3 and second harmonic scattering are not detected for any pixels, it is concluded that none of the explosives listed in Table 10 is present on the object.

Figure 28:
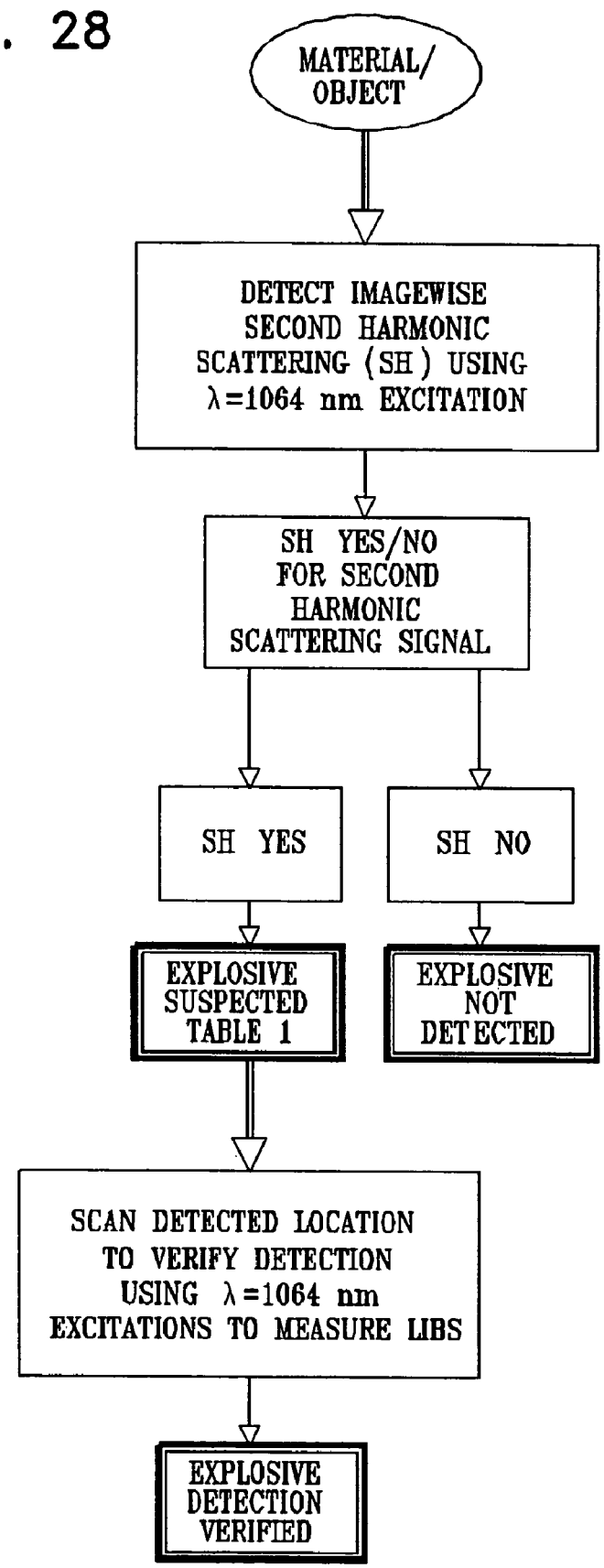
FIG. 28 is a simplified flowchart illustrating operation of the embodiments of FIGS. 8A–8C.

Reference is now made to FIG. 28, which is a simplified flowchart illustrating operation of the embodiment of FIGS. 8A–8C. An object, such as, for example, a suitcase or a vehicle, which is sought to be examined for the possible presence of explosives thereon, is illuminated by laser radiation, as described in FIGS. 8A–8C, and is subject to imagewise detection of second harmonic scattering and verification of explosive detection using time-resolved laser induced breakdown spectroscopy.

If second harmonic scattering is detected at at least one pixel, it is concluded that one or more of the explosives listed in Table 1 may be present at the pixel location on the object. If laser induced breakdown spectroscopy, at the pixel location where second harmonic scattering was detected, finds a spectral match to the laser induced breakdown spectroscopy spectral graphs, such as, for example, those seen in FIGS. 48A–53D, of one or more of the known explosives in Table 1, it is concluded that one or more of the explosives listed in Table 1 is indeed present at the pixel location on the object.

Figure 29:
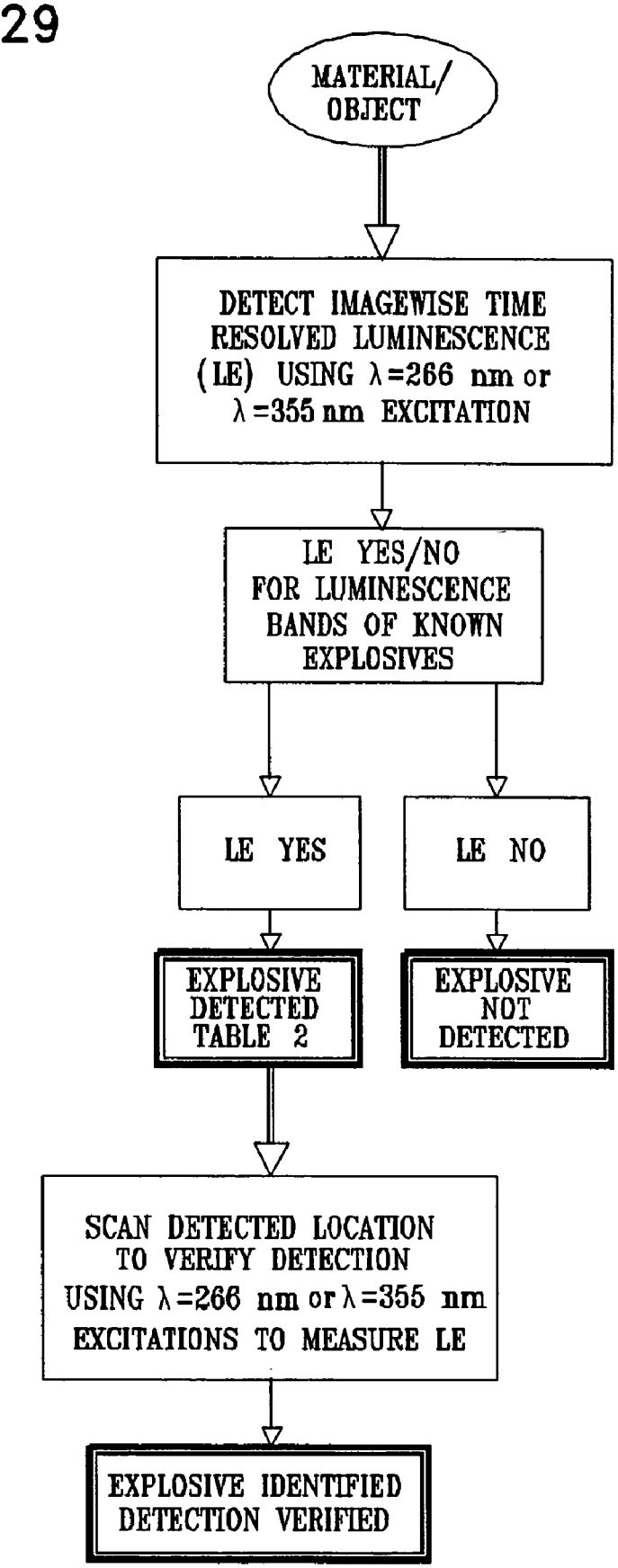
FIG. 29 is a simplified flowchart illustrating operation of the embodiments of FIGS. 9A–9C.

Reference is now made to FIG. 29, which is a simplified flowchart illustrating operation of the embodiment of FIGS. 9A–9C. An object, such as, for example, a suitcase or a vehicle, which is sought to be examined for the possible presence of explosives thereon, is illuminated by laser radiation, as described in FIGS. 9A–9C, and is subject to imagewise time-resolved detection of luminescence within the luminescence bands of known explosives and identification of detected explosives using time-resolved measurements of luminescence.

If luminescence within the luminescence bands of known explosives in Table 2 is detected at at least one pixel, it is concluded that one or more of the explosives listed in Table 2 is present at the pixel location on the object. If spectral patterns matching the luminescence spectral graphs of known explosives, such as, for example, those seen in FIGS. 42A–H, are detected, it is concluded that the explosive whose spectral pattern is matched is present on the object at the location of the at least one pixel.

If luminescence within the luminescence bands of known explosives in Table 2 is not detected, it is concluded that the explosives listed in Table 2 are not present on the object.

Figure 30:
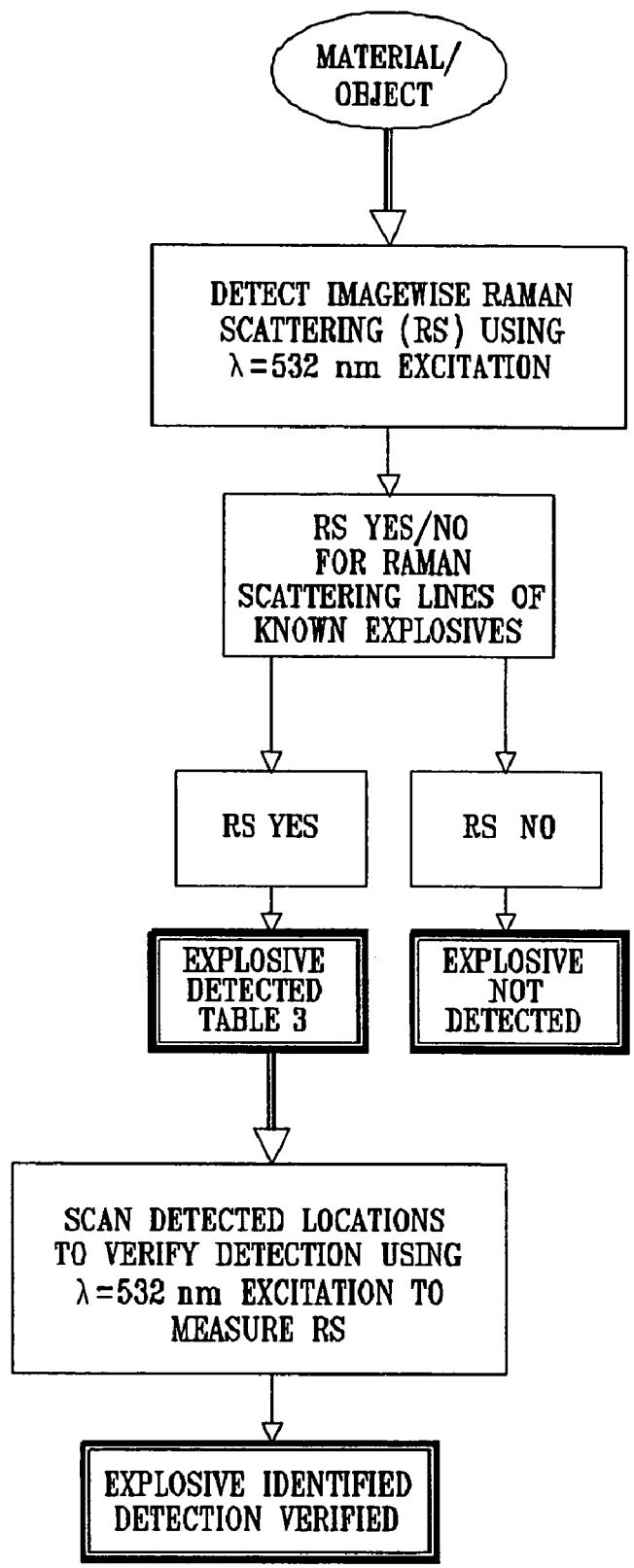
FIG. 30 is a simplified flowchart illustrating operation of the embodiments of FIGS. 10A–10C.

Reference is now made to FIG. 30, which is a simplified flowchart illustrating operation of the embodiment of FIGS. 10A–10C. An object, such as, for example, a suitcase or a vehicle, which is sought to be examined for the possible presence of explosives thereon, is illuminated by laser radiation, as described in FIGS. 10A–10C, and is subject to imagewise time-resolved detection of Raman scattering at the lines of known explosives and identification of detected explosives using time-resolved measurements of Raman scattering.

If Raman scattering at the lines of known explosives in Table 3 is detected at at least one pixel, it is concluded that one or more of the explosives listed in Table 3 is present at the pixel location on the object. If spectral patterns matching the Raman scattering spectral graphs of known explosives, such as, for example, those seen in FIGS. 45A–47C, are detected, it is concluded that the explosive whose spectral pattern is matched is present on the object at the location of the at least one pixel.

If Raman scattering having Raman scattering lines of known explosives listed in Table 3 is not detected, it is concluded that one or more of the explosives listed in Table 3 is probably not present on the object.

Figure 31A:
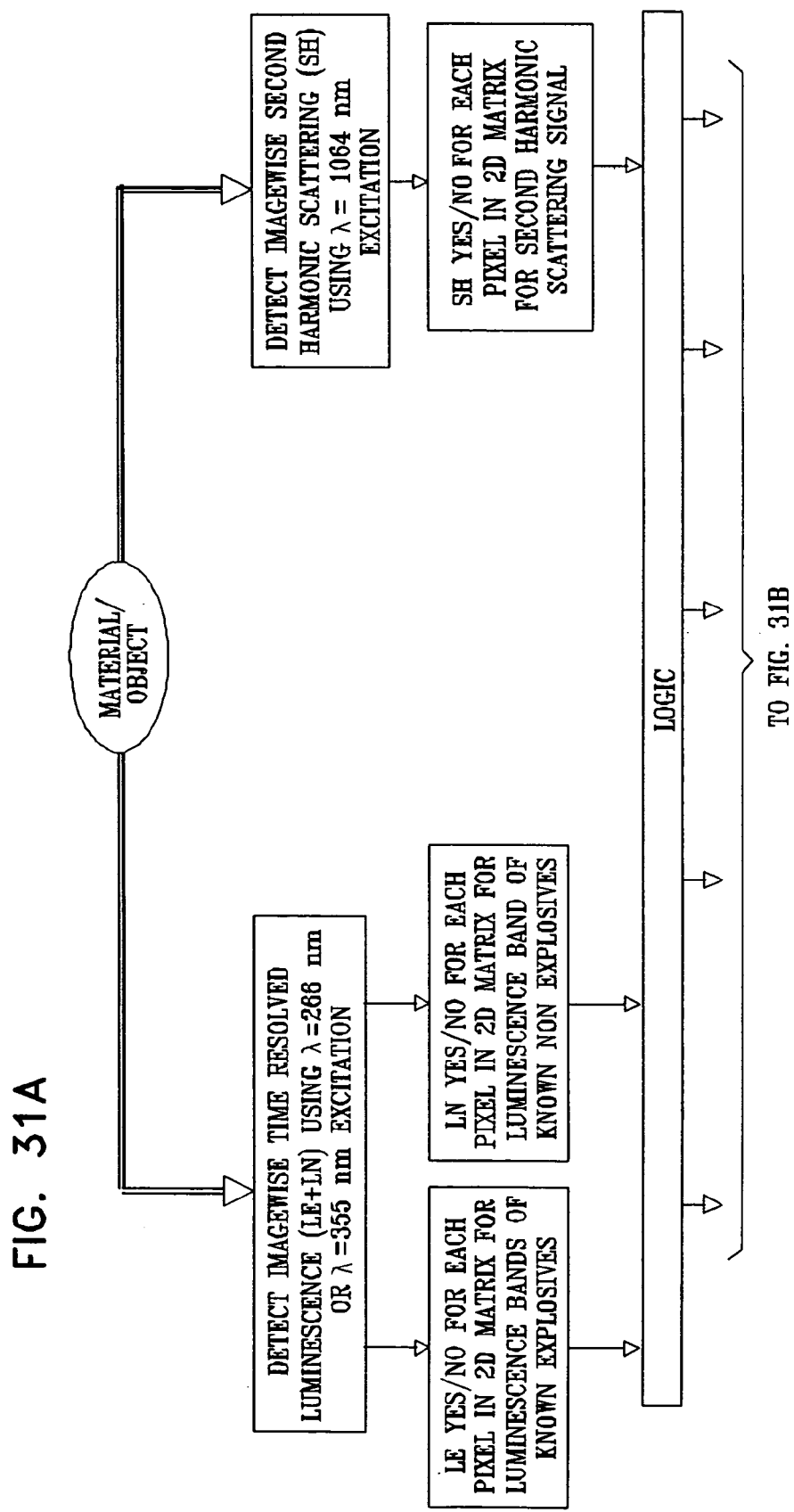
FIGS. 31A and 31B, taken together, are a simplified flowchart illustrating operation of the embodiments of FIGS. 11A–11C.
Figure 31B:
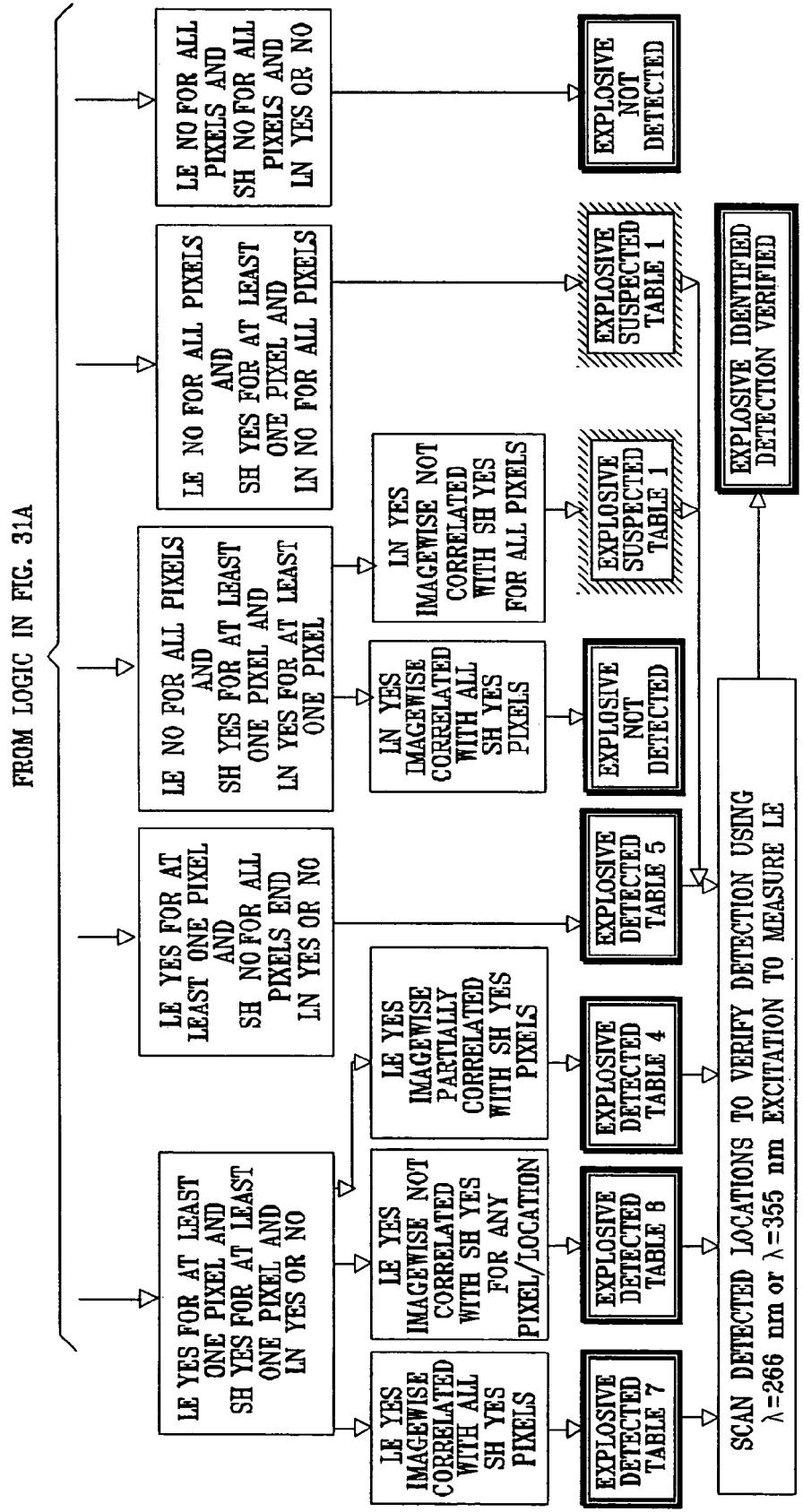

Reference is now made to FIGS. 31A and 31B, which, taken together, are a simplified flowchart illustrating operation of the embodiment of FIGS. 11A–11C. An object, such as, for example, a suitcase or a vehicle, which is sought to be examined for the possible presence of explosives thereon, is illuminated by laser radiation, as described in FIGS. 11A–11C, and is subject to imagewise detection of second harmonic scattering and to imagewise time-resolved detection of luminescence as well as to identification of detected explosives using time-resolved measurements of luminescence.

If luminescence within the luminescence bands of known explosives in Table 2 is detected for given pixels and second harmonic scattering is detected only for all of the same pixels, it is concluded that one or more of the explosives listed in Table 7 is present on the object at the locations of the given pixels.

If luminescence within the luminescence bands of known explosives in Table 2 is detected for given pixels and second harmonic scattering is detected, if at all, only for different pixels, it is concluded that one or more of the explosives listed in Table 8 is present on the object.

If luminescence within the luminescence bands of known explosives in Table 2 is detected for given pixels and second harmonic scattering is detected, for some of the same pixels as well as for different pixels, it is concluded that one or more of the explosives listed in Table 4 is present on the object.

If luminescence within the luminescence bands of known explosives in Table 2 is detected in at least one pixel and second harmonic scattering is not detected, it is concluded that one or more of the explosives listed in Table 5 is present on the object at the locations of the at least one pixel.

If luminescence within the luminescence bands of known non-explosives, such as fabrics or metals, is detected for given pixels and second harmonic scattering is detected for the same pixels, it is concluded that none of the explosives listed in Table 4 is present on the object at the locations of the relevant pixels.

If luminescence within the luminescence bands of known non-explosives is detected for given pixels and second harmonic scattering is detected, if at all, only for different pixels, it is concluded that one or more of the explosives listed in Table 1 may be present on the object at the locations of the pixels where second harmonic scattering is detected.

If luminescence within the luminescence bands of known explosives in Table 2 and within the luminescence bands of known non-explosives is not detected and second harmonic scattering is detected for at least one pixel, it is concluded that one or more of the explosives listed in Table 1 may be present on the object at the location of the at least one pixel.

If luminescence within the luminescence bands of known explosives in Table 2 is not detected and second harmonic scattering is not detected for any pixels, it is concluded that none of the explosives listed in Table 4 is present on the object.

Following detection of explosives, as described hereinabove, the explosives are identified, at locations where the presence of an explosive has been detected, by using time-resolved luminescence. If spectral patterns matching the luminescence spectral graphs of known explosives, such as, for example, those seen in FIGS. 42A–H, are detected, it is concluded that the explosive whose spectral pattern is matched is present on the object at the location of the at least one pixel.

Figure 32:
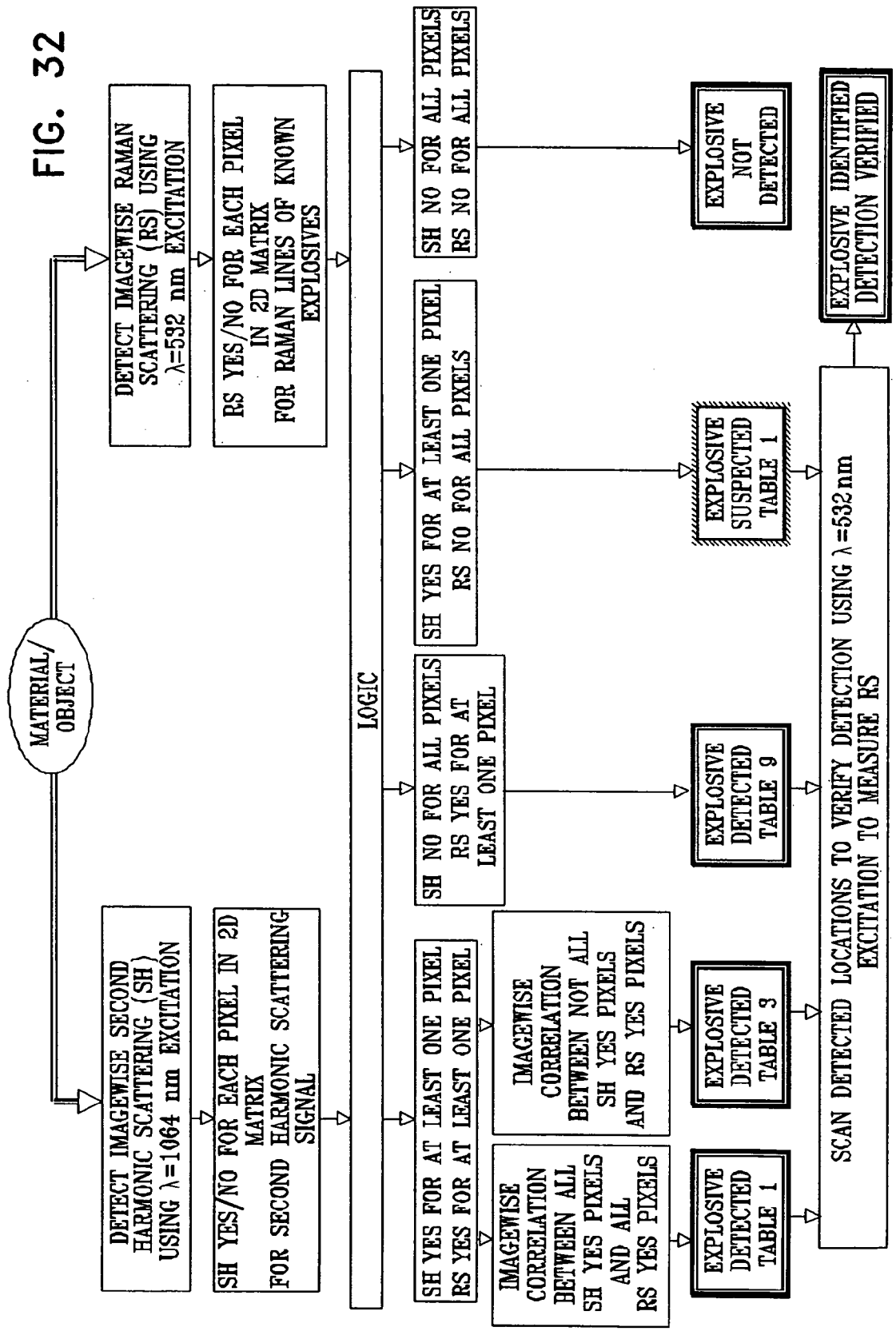
FIG. 32 is a simplified flowchart illustrating operation of the embodiments of FIGS. 12A–12C.

Reference is now made to FIG. 32, which is a simplified flowchart illustrating operation of the embodiment of FIGS. 12A–12C. An object, such as, for example, a suitcase or a vehicle, which is sought to be examined for the possible presence of explosives thereon, is illuminated by laser radiation, as described in FIGS. 12A–12C, and is subject to imagewise detection of second harmonic scattering and to imagewise time-resolved detection of Raman scattering as well as to identification of detected explosives using time-resolved measurements of Raman scattering.

If Raman scattering at the lines of known explosives in Table 3 is detected for given pixels and second harmonic scattering is detected only for all of the same pixels, it is concluded that one or more of the explosives listed in Table 1 is present on the object at the locations of the given pixels.

If Raman scattering at the lines of known explosives in Table 3 is detected for given pixels and second harmonic scattering is detected, at at least some different pixels, it is concluded that one or more of the explosives listed in Table 3 is present on the object.

If Raman scattering at the lines of known explosives in Table 3 is detected in at least one pixel and second harmonic scattering is not detected, it is concluded that one or more of the explosives listed in Table 9 is present on the object at the locations of the at least one pixel.

If Raman scattering at the lines of known explosives in Table 3 is not detected and second harmonic scattering is detected for at least one pixel, it is concluded that at least one of the explosives listed in Table 1 may be present on the object at the location of the at least one pixel.

If Raman scattering at the lines of known explosives in Table 3 is not detected and second harmonic scattering is not detected for any pixels, it is concluded that none of the explosives listed in Table 3 is present on the object.

Following detection of explosives, as described hereinabove, the explosives are identified, at locations where the presence of an explosive has been detected, by using time-resolved Raman scattering. If spectral patterns matching the Raman scattering spectral graphs of known explosives, such as, for example, those seen in FIGS. 45A–47C, are detected, it is concluded that the explosive whose spectral pattern is matched is present on the object at the location of the at least one pixel.

Figure 33:
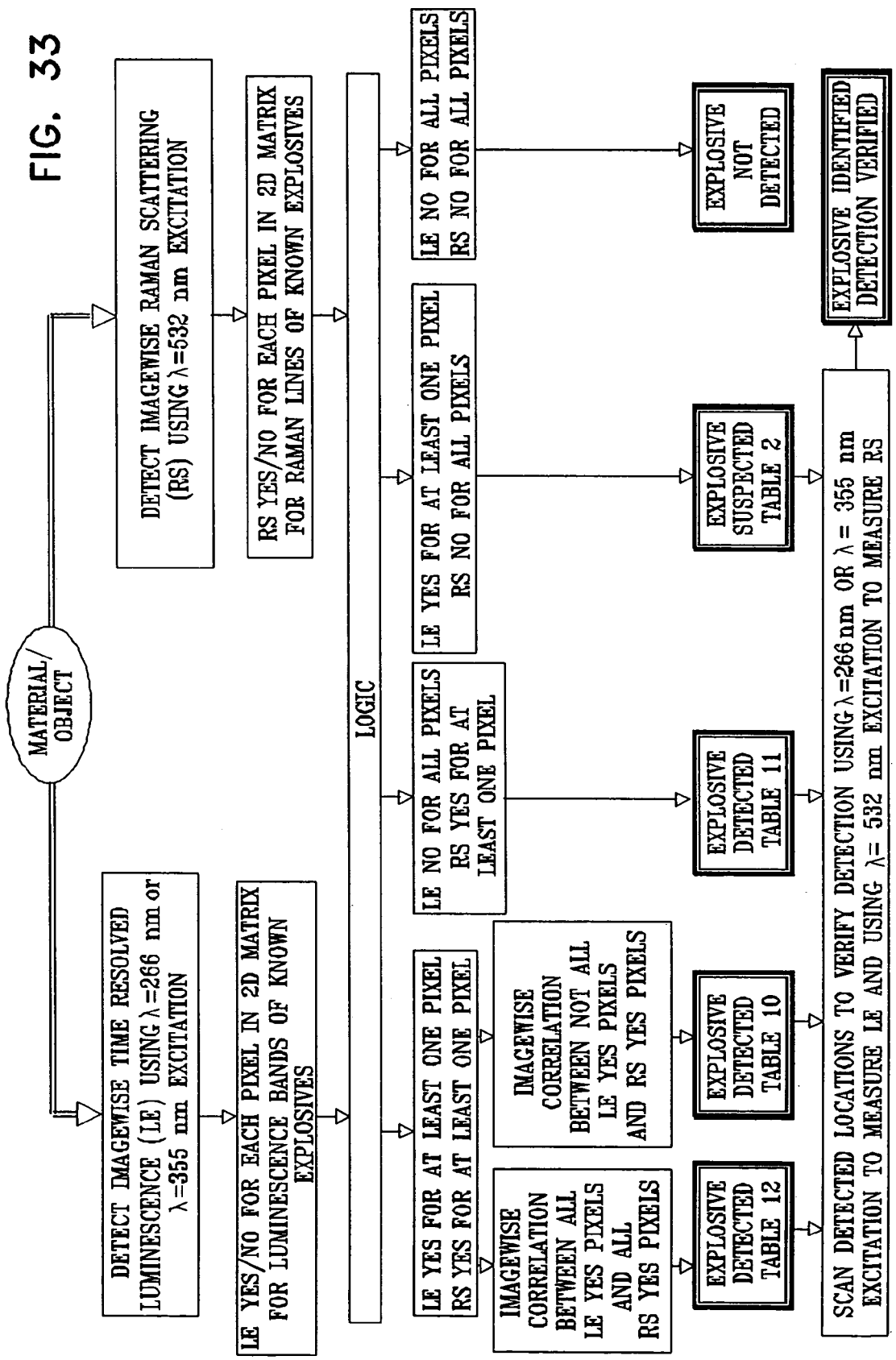
FIG. 33 is a simplified flowchart illustrating operation of the embodiments of FIGS. 13A–13C.

Reference is now made to FIG. 33, which is a simplified flowchart illustrating operation of the embodiment of FIGS. 13A–13C. An object, such as, for example, a suitcase or a vehicle, which is sought to be examined for the possible presence of explosives thereon, is illuminated by laser radiation, as described in FIGS. 13A–13C, and is subject to imagewise time-resolved detection of luminescence and to imagewise time-resolved detection of Raman scattering as well as to identification of detected explosives using time-resolved measurements of luminescence and of Raman scattering.

If luminescence within the luminescence bands of known explosives in Table 2 is detected for given pixels and Raman scattering at the lines of known explosives in Table 3 is detected only for all of the same pixels, it is concluded that one or more of the explosives listed in Table 12 is present on the object at the locations of the given pixels.

If luminescence within the luminescence bands of known explosives in Table 2 is detected for given pixels and Raman scattering at the lines of known explosives in Table 3 is detected for at least some different pixels, it is concluded that one or more of the explosives listed in Table 10 is present on the object.

If luminescence within the luminescence bands of known explosives in Table 2 is not detected for any pixels and Raman scattering at the lines of known explosives in Table 3 is detected in at least one pixel, it is concluded that one or more of the explosives listed in Table 11 is present on the object at the locations of the at least one pixel.

If luminescence within the luminescence bands of known explosives in Table 2 is detected for at least one pixel and Raman scattering at the lines of known explosives in Table 3 is not detected, it is concluded that at least one of the explosives listed in Table 2 is present on the object at the location of the at least one pixel.

If Raman scattering at the lines of known explosives in Table 3 is not detected and luminescence within the luminescence bands of known explosives in Table 2 is not detected for any pixels, it is concluded that none of the explosives listed in Table 10 is present on the object.

Following detection of explosives, as described hereinabove, the explosives are identified, at locations where the presence of an explosive has been detected, by using time-resolved luminescence and time-resolved Raman scattering. If spectral patterns matching the luminescence spectral graphs of known explosives, such as, for example, those seen in FIGS. 42A–H, are detected, it is concluded that the explosive whose spectral pattern is matched is present on the object at the location of the at least one pixel. If spectral patterns matching the Raman scattering spectral graphs of known explosives, such as, for example, those seen in FIGS. 45A–47C, are detected, it is concluded that the explosive whose spectral pattern is matched is present on the object at the location of the at least one pixel.

Figure 34:
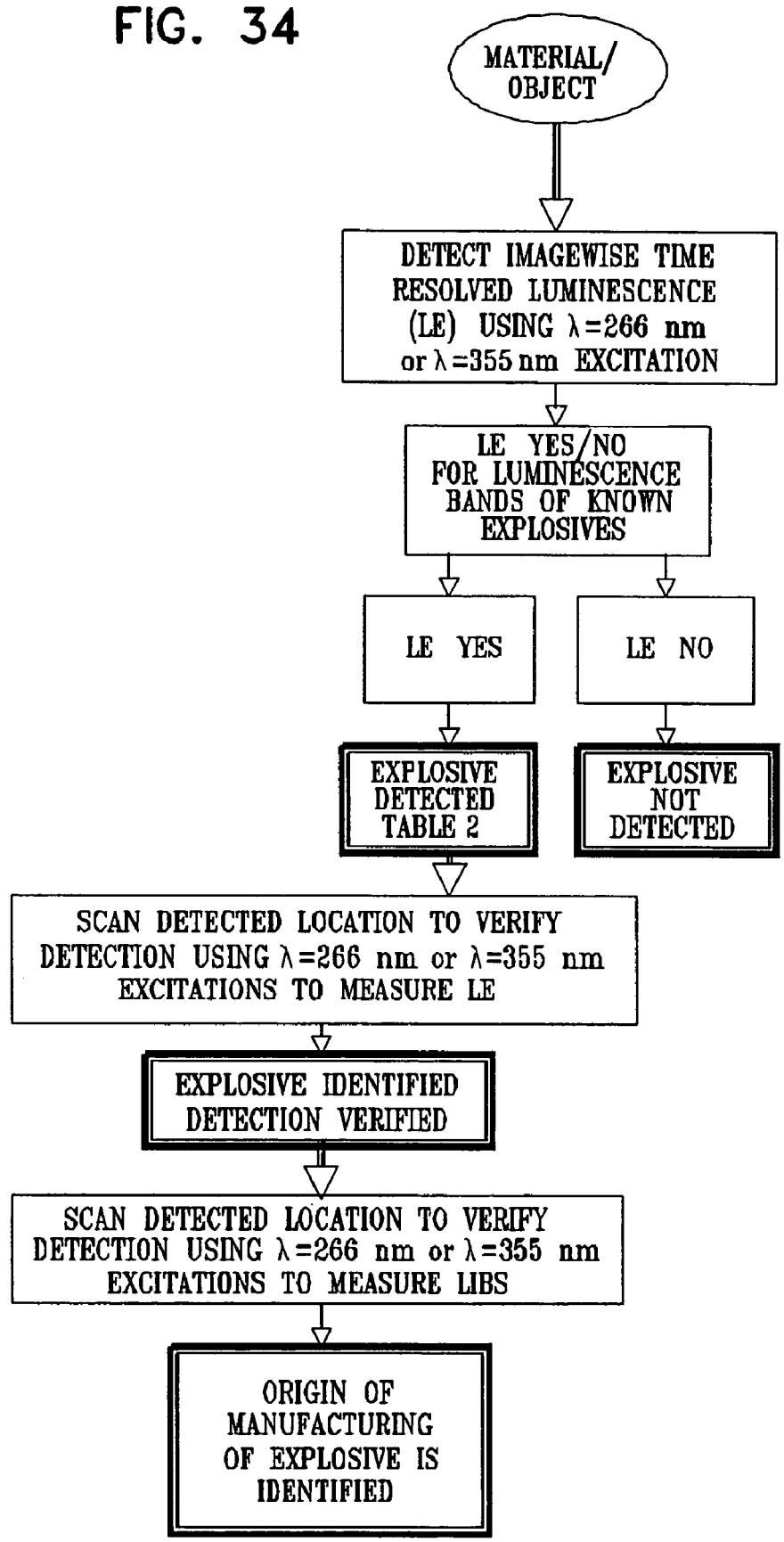
FIG. 34 is a simplified flowchart illustrating operation of the embodiments of FIGS. 14A–14C.

Reference is now made to FIG. 34, which is a simplified flowchart illustrating operation of the embodiment of FIGS. 14A–14C. An object, such as, for example, a suitcase or a vehicle, which is sought to be examined for the possible presence of explosives thereon, is illuminated by laser radiation, as described in FIGS. 14A–14C, and is subject to imagewise time-resolved detection of luminescence within the luminescence bands of known explosives, identification of detected explosives using time resolved measurements of luminescence and determination of the origin of manufacture of the explosive using time-resolved laser induced breakdown spectroscopy.

Figure 54A:
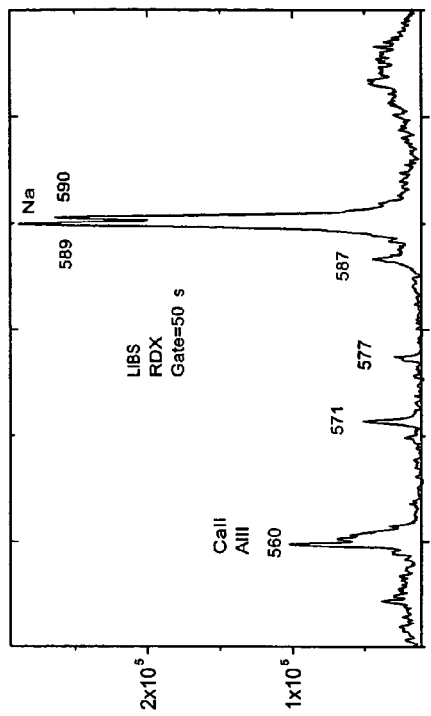
FIGS. 54A, 54B, 54C and 54D are graphs showing laser induced breakdown spectra of yet another explosive.
Figure 54B:
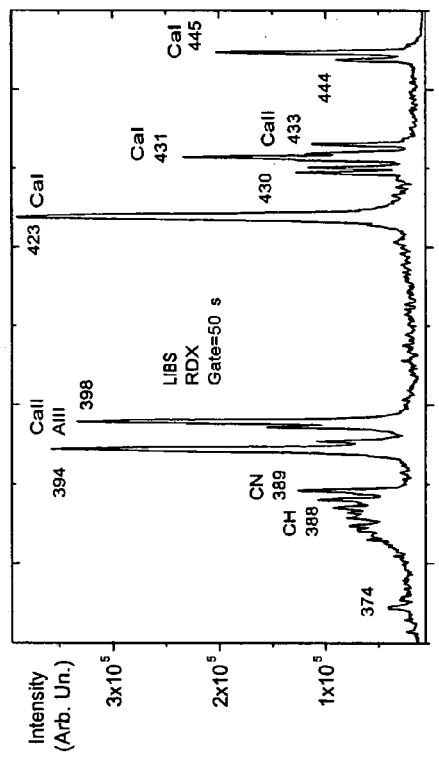
Figure 54C:
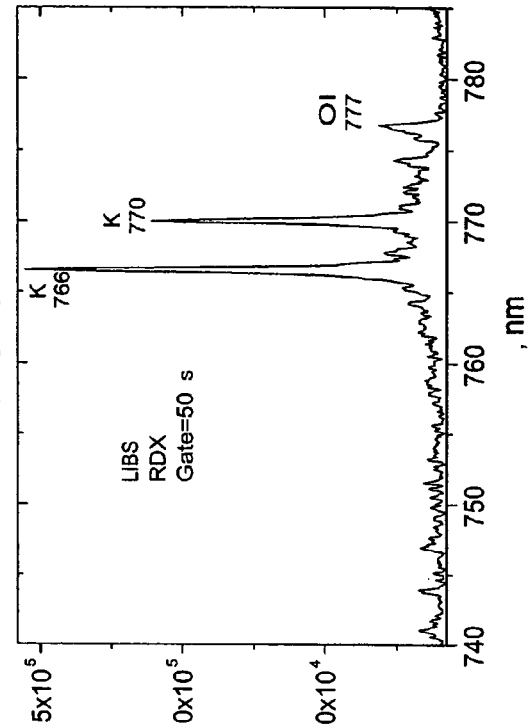
Figure 54D:
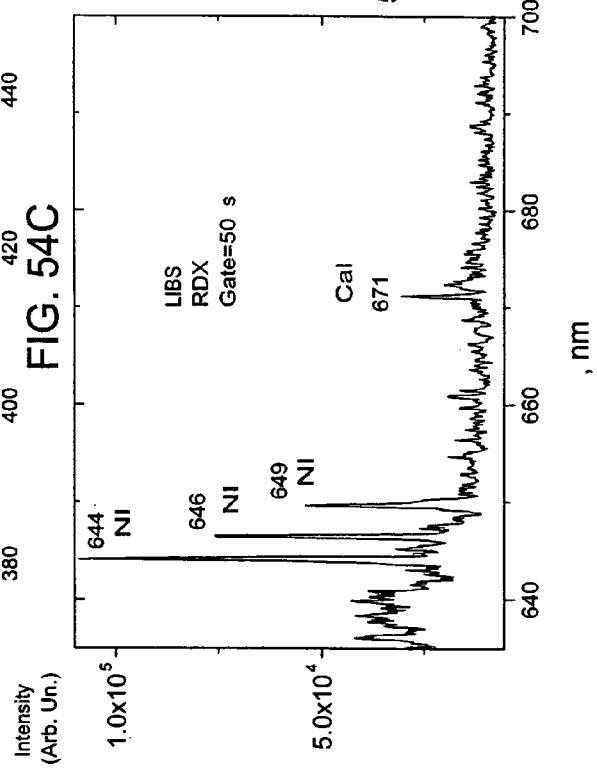

If luminescence within the luminescence bands of known explosives in Table 2 is detected at at least one pixel, it is concluded that one or more of the explosives listed in Table 2 is present at the pixel location on the object. If spectral patterns matching the luminescence spectral graphs of known explosives, such as, for example, those seen in FIGS. 42A–H, are detected, it is concluded that the explosive whose spectral pattern is matched is present on the object at the location of the at least one pixel. The origin of manufacture of the explosive is then determined using time-resolved laser induced breakdown spectroscopy to detect spectral patterns, such as, for example, those shown in FIGS. 54A–B, matching those of known manufacturers of the identified explosive.

If luminescence within the luminescence bands of known explosives in Table 2 is not detected, it is concluded that the explosives listed in Table 2 are not present on the object.

Figure 35:
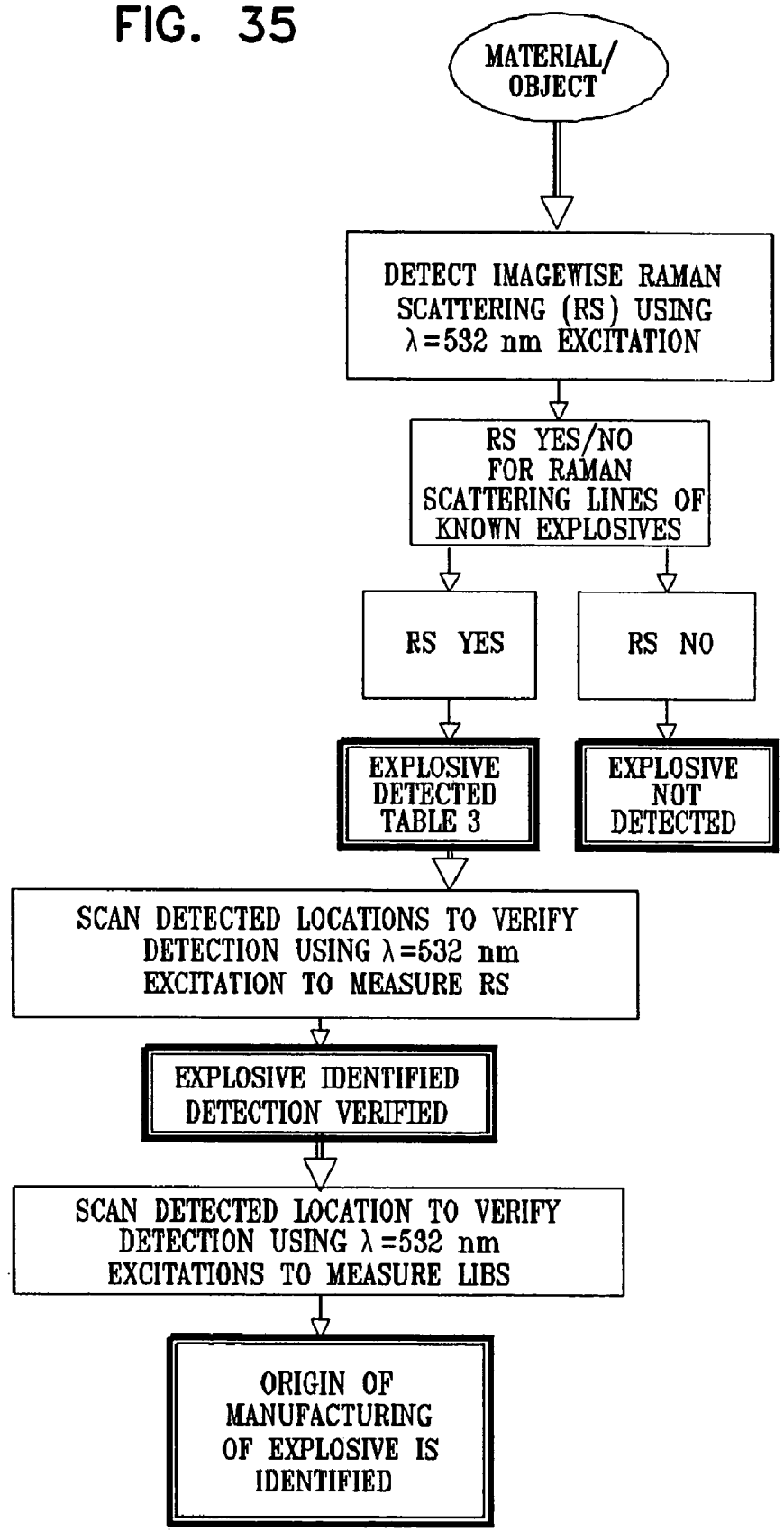
FIG. 35 is a simplified flowchart illustrating operation of the embodiments of FIGS. 15A–15C.

Reference is now made to FIG. 35, which is a simplified flowchart illustrating operation of the embodiment of FIGS. 15A–15C. An object, such as, for example, a suitcase or a vehicle, which is sought to be examined for the possible presence of explosives thereon, is illuminated by laser radiation, as described in FIGS. 15A–15C, and is subject to imagewise time-resolved detection of Raman scattering at the lines of known explosives, identification of detected explosives using time-resolved measurements of Raman scattering and determination of the origin of manufacture of the explosive using time-resolved laser induced breakdown spectroscopy.

If Raman scattering at the lines of known explosives in Table 3 is detected at at least one pixel, it is concluded that one or more of the explosives listed in Table 3 is present at the pixel location on the object. If spectral patterns matching the Raman scattering spectral graphs of known explosives, such as, for example, those seen in FIGS. 45A–47C, are detected, it is concluded that the explosive whose spectral pattern is matched is present on the object at the location of the at least one pixel. The origin of manufacture of the explosive is then determined using time-resolved laser induced breakdown spectroscopy to detect spectral patterns, such as, for example, those shown in FIGS. 54A–B, matching those of known manufacturers of the identified explosive.

If Raman scattering having Raman scattering lines of known explosives listed in Table 3 is not detected, it is concluded that one or more of the explosives listed in Table 3 is probably not present on the object.

Figure 36A:
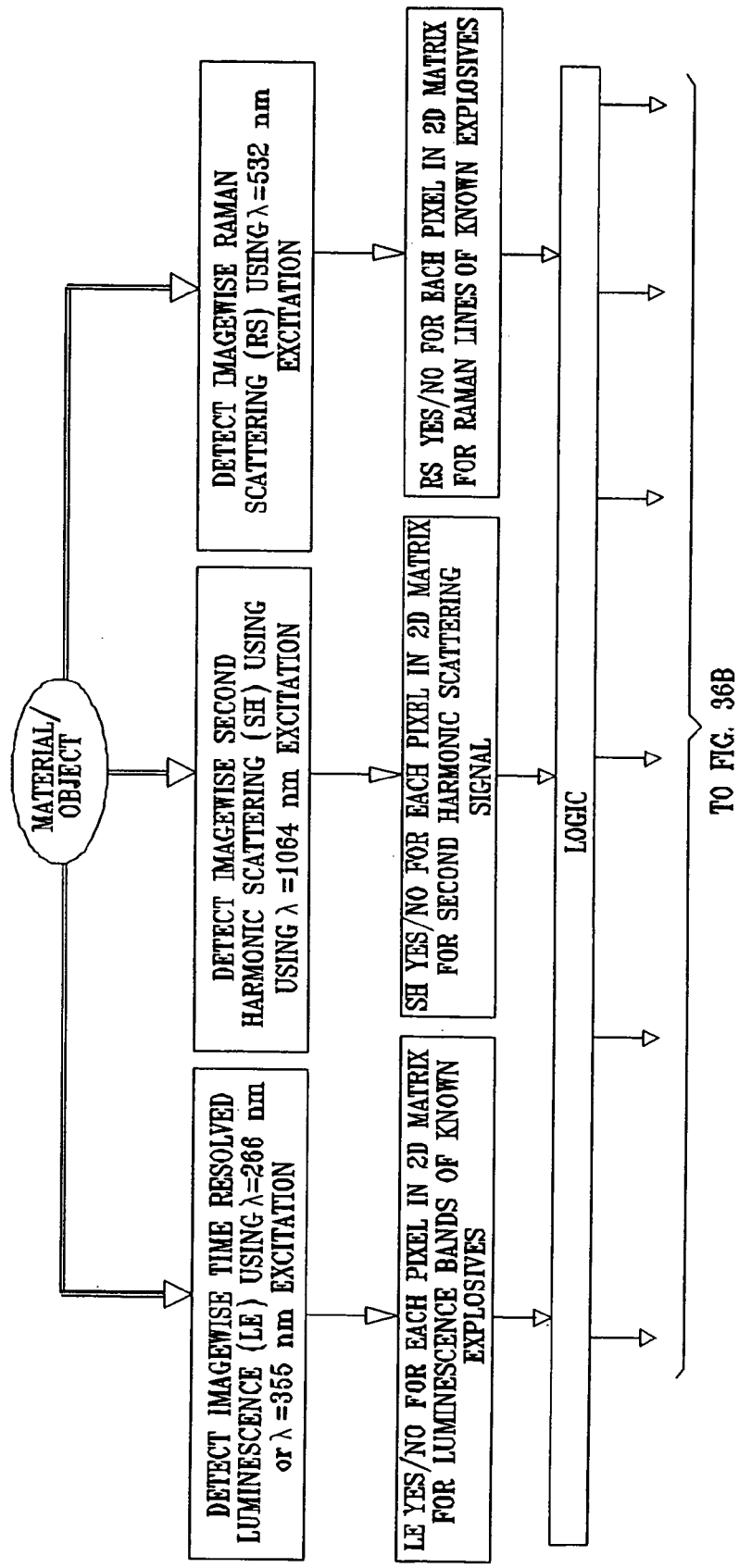
FIGS. 36A and 36B, taken together, are a simplified flowchart illustrating operation of the embodiments of FIGS. 16A–16C.
Figure 36B:
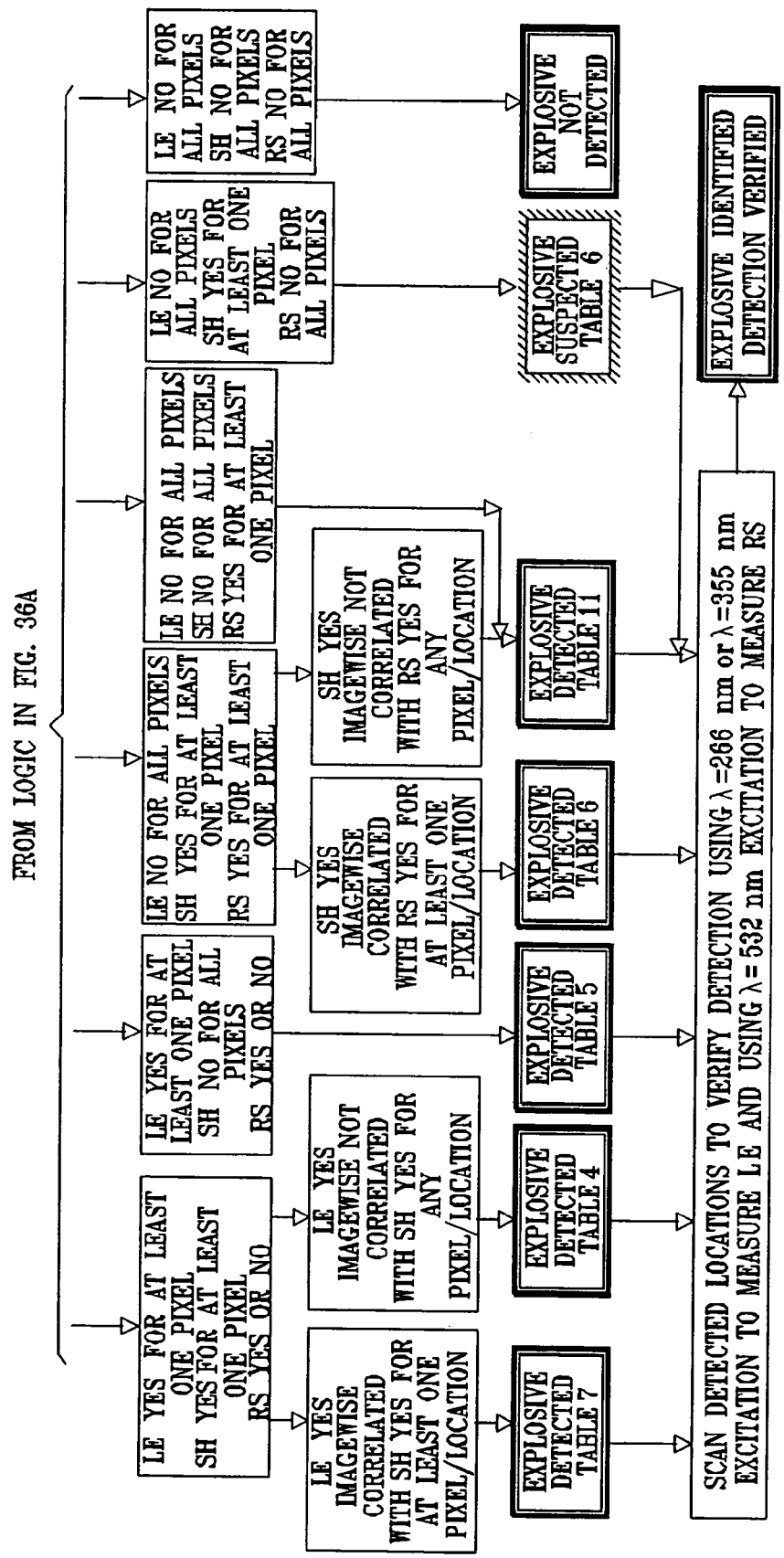

Reference is now made to FIGS. 36A and 36B, which, taken together, are a simplified flowchart illustrating operation of the embodiment of FIGS. 16A–16C. An object, such as, for example, a suitcase or a vehicle, which is sought to be examined for the possible presence of explosives thereon, is illuminated by laser radiation, as described in FIGS. 16A–16C, and is subject to imagewise detection of second harmonic scattering, imagewise time-resolved detection of luminescence and imagewise time-resolved detection of Raman scattering and explosive identification using time-resolved luminescence and time-resolved Raman scattering.

If luminescence within the luminescence bands of known explosives in Table 2 is detected for given pixels and second harmonic scattering is detected only for at least one of the same pixels, it is concluded that one or more of the explosives listed in Table 7 is present on the object at the locations of the given pixels.

If luminescence within the luminescence bands of known explosives in Table 2 is detected for given pixels and second harmonic scattering is detected, if at all, only for different pixels, it is concluded that one or more of the explosives listed in Table 4 is present on the object.

If luminescence within the luminescence bands of known explosives in Table 2 is detected in at least one pixel and second harmonic scattering is not detected, it is concluded that one or more of the explosives listed in Table 5 is present on the object at the locations of the at least one pixel.

If luminescence within the luminescence bands of known explosives in Table 2 is not detected and Raman scattering at the lines of known explosives in Table 3 is detected for at least one pixel and second harmonic scattering is detected for at least the same pixel, it is concluded that one or more of the explosives listed in Table 6 is present on the object at the locations of the at least one pixel.

If luminescence within the luminescence bands of known explosives in Table 2 is not detected and Raman scattering at the lines of known explosives in Table 3 is detected for at least one pixel and second harmonic scattering is detected, for at least one different pixel, it is concluded that one or more of the explosives listed in Table 11 is present on the object at the locations of the at least one pixel.

If luminescence within the luminescence bands of known explosives in Table 2 and second harmonic scattering are not detected and Raman scattering at the lines of known explosives in Table 3 is detected for at least one pixel, it is concluded that one or more of the explosives listed in Table 11 is present on the object at the locations of the at least one pixel.

If luminescence within the luminescence bands of known explosives in Table 2 and Raman scattering at the lines of known explosives in Table 3 are not detected and second harmonic scattering is detected for at least one pixel, it is suspected that one or more of the explosives listed in Table 6 is present on the object at the locations of the at least one pixel.

If luminescence within the luminescence bands of known explosives in Table 2, Raman scattering at the lines of known explosives in Table 3 and second harmonic scattering are not detected for any pixels, it is concluded that none of the explosives listed in Table 10 is present on the object.

Following detection of explosives, as described hereinabove, the explosives are identified, at locations where the presence of an explosive has been detected, by using time-resolved luminescence and time-resolved Raman scattering. If spectral patterns matching the luminescence spectral graphs of known explosives, such as, for example, those seen in FIGS. 42A–H, are detected, it is concluded that the explosive whose spectral pattern is matched is present on the object at the location of the at least one pixel. If spectral patterns matching the Raman scattering spectral graphs of known explosives, such as, for example, those seen in FIGS. 45A–47C, are detected, it is concluded that the explosive whose spectral pattern is matched is present on the object at the location of the at least one pixel.

Figure 37:
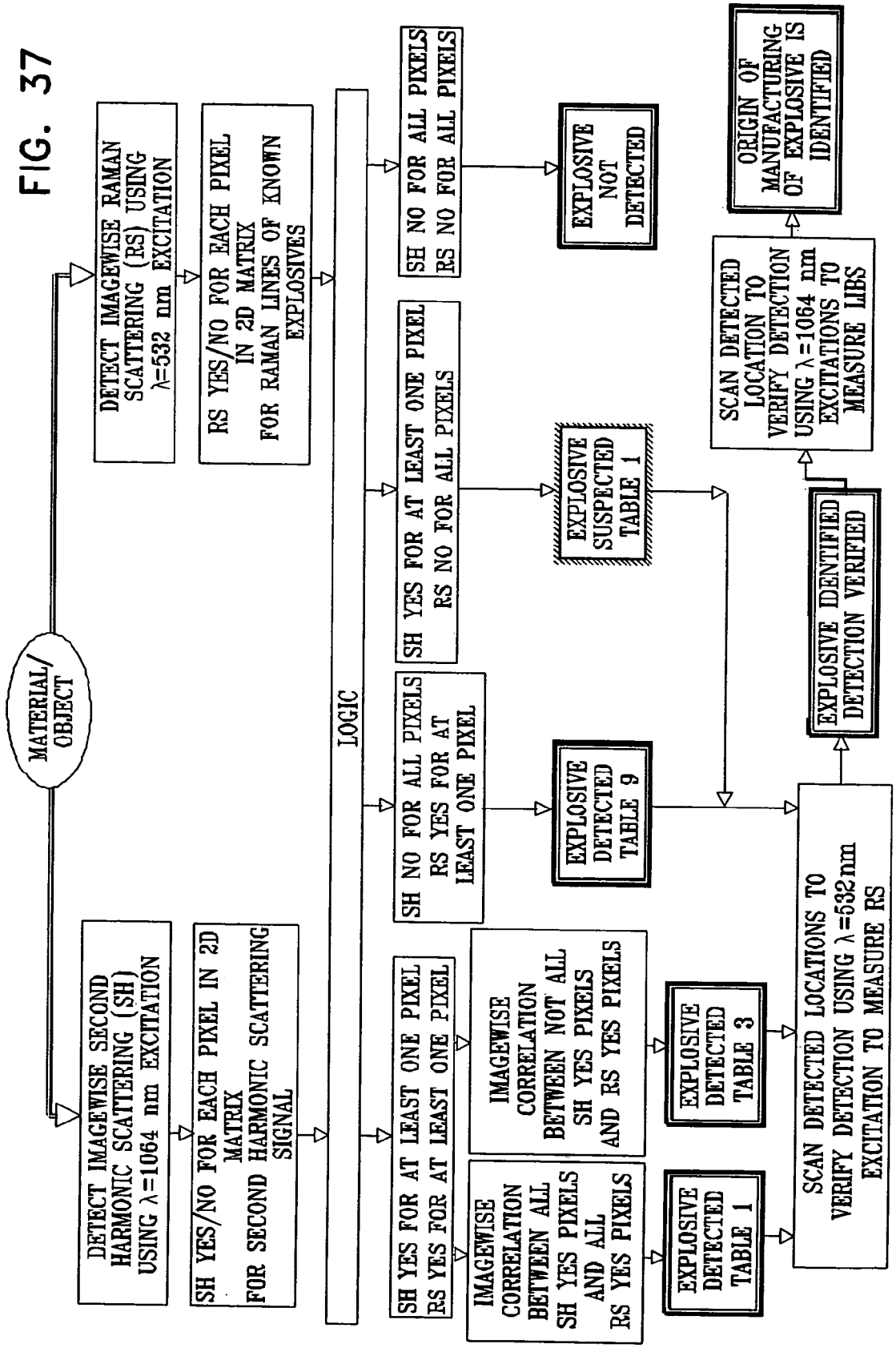
FIG. 37 is a simplified flowchart illustrating operation of the embodiments of FIGS. 17A–17C.

Reference is now made to FIG. 37, which is a simplified flowchart illustrating operation of the embodiment of FIGS. 17A–17C. An object, such as, for example, a suitcase or a vehicle, which is sought to be examined for the possible presence of explosives thereon, is illuminated by laser radiation, as described in FIGS. 17A–17C, and is subject to imagewise detection of second harmonic scattering and to imagewise time-resolved detection of Raman scattering as well as identification of detected explosives using time-resolved measurements of Raman scattering and determination of the origin of manufacture of the explosive using time-resolved laser induced breakdown spectroscopy.

If Raman scattering at the lines of known explosives in Table 3 is detected for given pixels and second harmonic scattering is detected only for all of the same pixels, it is concluded that one or more of the explosives listed in Table 1 is present on the object at the locations of the given pixels.

If Raman scattering at the lines of known explosives in Table 3 is detected for given pixels and second harmonic scattering is detected, at at least some different pixels, it is concluded that one or more of the explosives listed in Table 3 is present on the object.

If Raman scattering at the lines of known explosives in Table 3 is detected in at least one pixel and second harmonic scattering is not detected, it is concluded that one or more of the explosives listed in Table 9 is present on the object at the locations of the at least one pixel.

If Raman scattering at the lines of known explosives in Table 3 is not detected and second harmonic scattering is detected for at least one pixel, it is concluded that at least one of the explosives listed in Table 1 may be present on the object at the location of the at least one pixel.

If Raman scattering at the lines of known explosives in Table 3 is not detected and second harmonic scattering is not detected for any pixels, it is concluded that none of the explosives listed in Table 3 is present on the object.

Following detection of explosives, as described hereinabove, the explosives are identified, at locations where the presence of an explosive has been detected, by using time-resolved Raman scattering. If spectral patterns matching the Raman scattering spectral graphs of known explosives, such as, for example, those seen in FIGS. 45A–47C, are detected, it is concluded that the explosive whose spectral pattern is matched is present on the object at the location of the at least one pixel. The origin of manufacture of the explosive is then determined using time-resolved laser induced breakdown spectroscopy to detect spectral patterns, such as, for example, those shown in FIGS. 54A–B, matching those of known manufacturers of the identified explosive.

Figure 38:
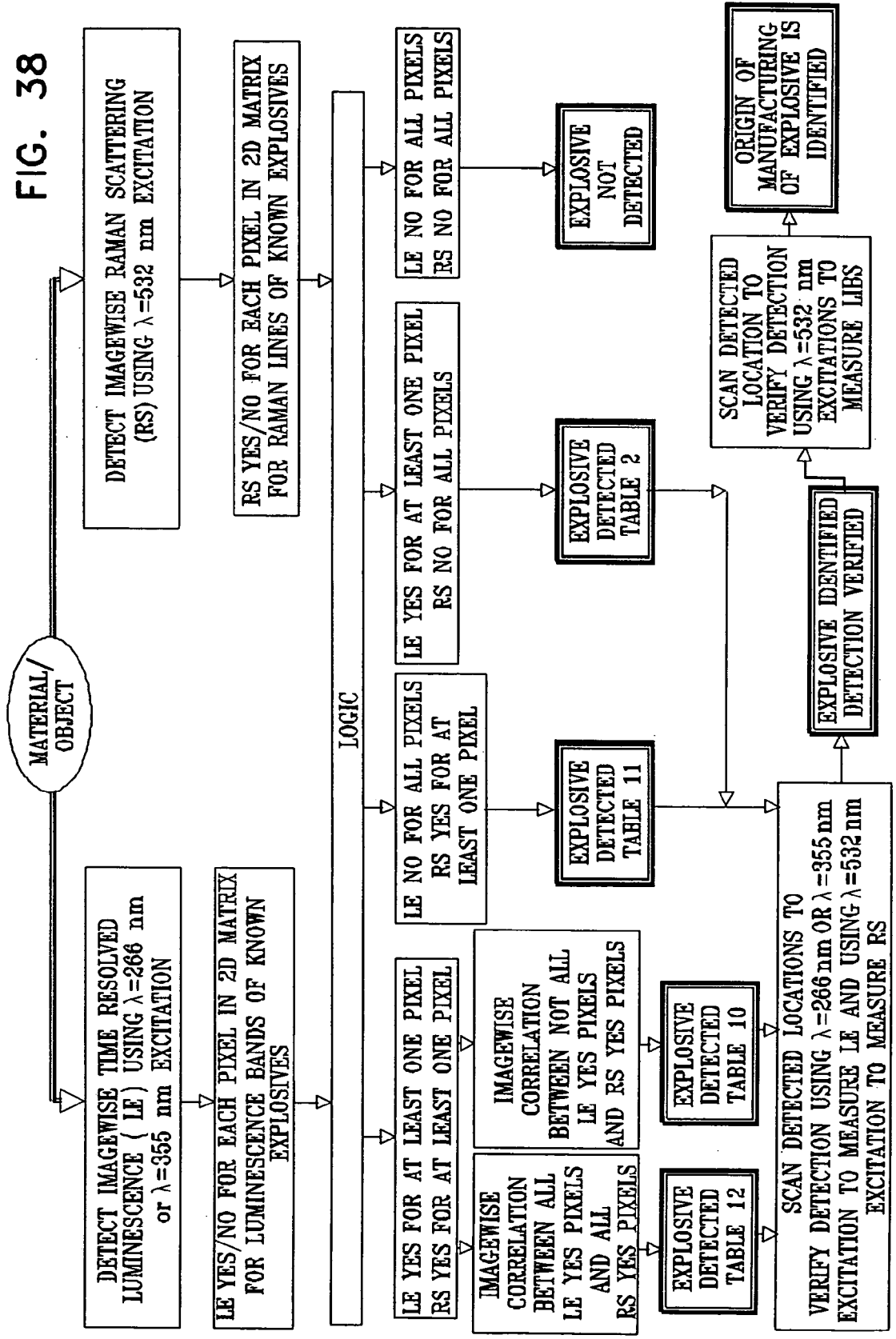
FIG. 38 is a simplified flowchart illustrating operation of the embodiments of FIGS. 18A–18C.

Reference is now made to FIG. 38, which is a simplified flowchart illustrating operation of the embodiment of FIGS. 18A–18C. An object, such as, for example, a suitcase or a vehicle, which is sought to be examined for the possible presence of explosives thereon, is illuminated by laser radiation, as described in FIGS. 18A–18C, and is subject to imagewise time-resolved detection of luminescence and to imagewise time-resolved detection of Raman scattering as well as to identification of detected explosives using time-resolved measurements of luminescence and of Raman scattering and determination of the origin of manufacture of the explosive using time-resolved laser induced breakdown spectroscopy.

If luminescence within the luminescence bands of known explosives in Table 2 is detected for given pixels and Raman scattering at the lines of known explosives in Table 3 is detected only for all of the same pixels, it is concluded that one or more of the explosives listed in Table 12 is present on the object at the locations of the given pixels.

If luminescence within the luminescence bands of known explosives in Table 2 is detected for given pixels and Raman scattering at the lines of known explosives in Table 3 is detected for at least some different pixels, it is concluded that one or more of the explosives listed in Table 10 is present on the object.

If luminescence within the luminescence bands of known explosives in Table 2 is not detected for any pixels and Raman scattering at the lines of known explosives in Table 3 is detected in at least one pixel, it is concluded that one or more of the explosives listed in Table 11 is present on the object at the locations of the at least one pixel.

If luminescence within the luminescence bands of known explosives in Table 2 is detected for at least one pixel and Raman scattering at the lines of known explosives in Table 3 is not detected, it is concluded that at least one of the explosives listed in Table 2 is present on the object at the location of the at least one pixel.

If Raman scattering at the lines of known explosives in Table 3 is not detected and luminescence within the luminescence bands of known explosives in Table 2 is not detected for any pixels, it is concluded that none of the explosives listed in Table 10 is present on the object.

Following detection of explosives, as described hereinabove, the explosives are identified, at locations where the presence of an explosive has been detected, by using time-resolved luminescence and time-resolved Raman scattering. If spectral patterns matching the luminescence spectral graphs of known explosives, such as, for example, those seen in FIGS. 42A–H, are detected, it is concluded that the explosive whose spectral pattern is matched is present on the object at the location of the at least one pixel. If spectral patterns matching the Raman scattering spectral graphs of known explosives, such as, for example, those seen in FIGS. 45A–47C, are detected, it is concluded that the explosive whose spectral pattern is matched is present on the object at the location of the at least one pixel. The origin of manufacture of the explosive is then determined using time-resolved laser induced breakdown spectroscopy to detect spectral patterns, such as, for example, those shown in FIGS. 54A–B, matching those of known manufacturers of the identified explosive.

Figure 39B:
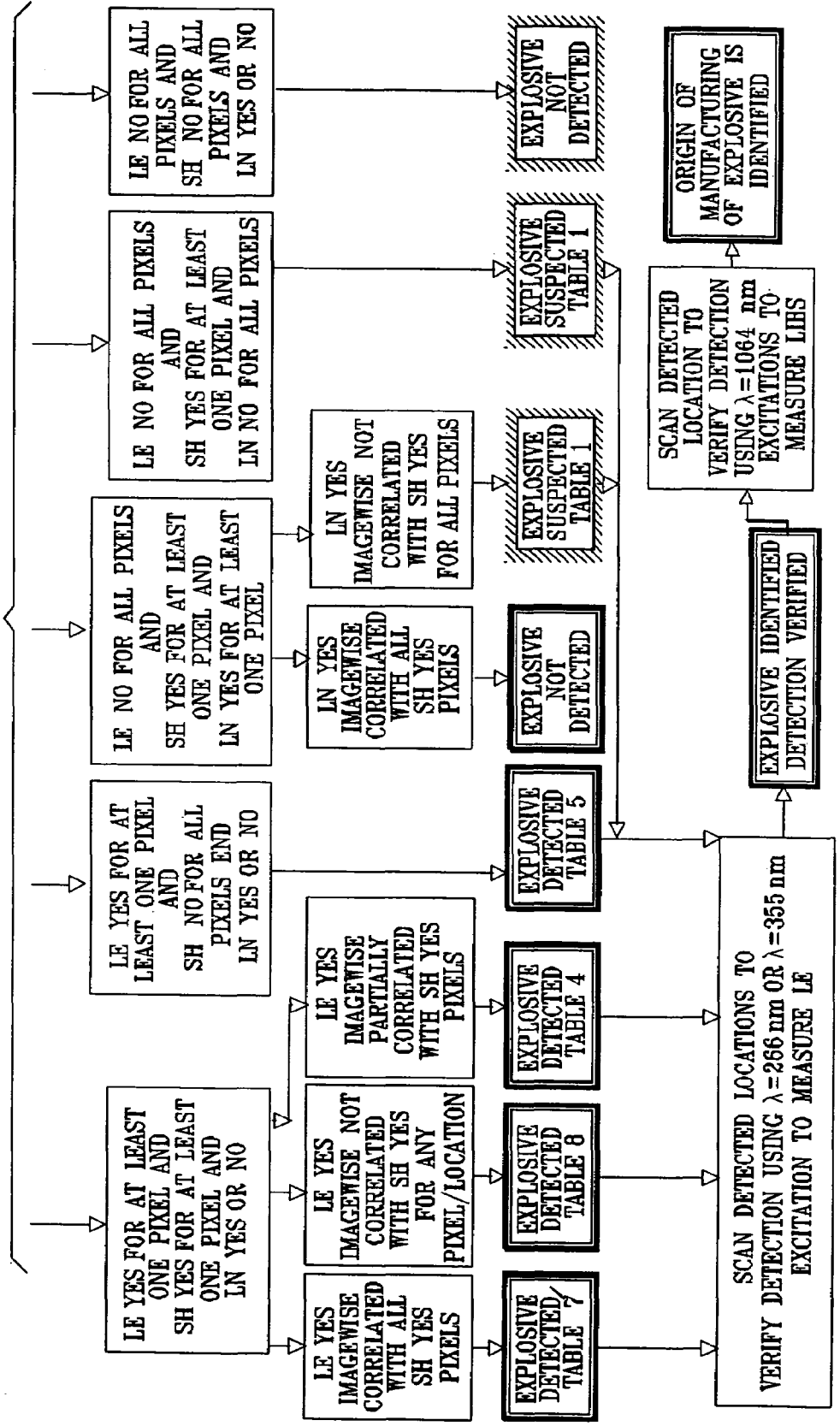

Reference is now made to FIGS. 39A and 39B, which, taken together, are a simplified flowchart illustrating operation of the embodiment of FIGS. 19A–19C. An object, such as, for example, a suitcase or a vehicle, which is sought to be examined for the possible presence of explosives thereon, is illuminated by laser radiation, as described in FIGS. 19A–19C, and is subject to imagewise detection of second harmonic scattering and to imagewise time-resolved detection of luminescence as well as to identification of detected explosives using time-resolved measurements of luminescence and determination of the origin of manufacture of the explosive using time-resolved laser induced breakdown spectroscopy.

If luminescence within the luminescence bands of known explosives in Table 2 is detected for given pixels and second harmonic scattering is detected only for all of the same pixels, it is concluded that one or more of the explosives listed in Table 7 is present on the object at the locations of the given pixels.

If luminescence within the luminescence bands of known explosives in Table 2 is detected for given pixels and second harmonic scattering is detected, if at all, only for different pixels, it is concluded that one or more of the explosives listed in Table 8 is present on the object.

If luminescence within the luminescence bands of known explosives in Table 2 is detected for given pixels and second harmonic scattering is detected, for some of the same pixels as well as for different pixels, it is concluded that one or more of the explosives listed in Table 4 is present on the object.

If luminescence within the luminescence bands of known explosives in Table 2 is detected in at least one pixel and second harmonic scattering is not detected, it is concluded that one or more of the explosives listed in Table 5 is present on the object at the locations of the at least one pixel.

If luminescence within the luminescence bands of known non-explosives, such as fabrics or metals, is detected for given pixels and second harmonic scattering is detected for the same pixels, it is concluded that none of the explosives listed in Table 4 is present on the object at the locations of the relevant pixels.

If luminescence within the luminescence bands of known non-explosives is detected for given pixels and second harmonic scattering is detected, if at all, only for different pixels, it is concluded that one or more of the explosives listed in Table 1 may be present on the object at the locations of the pixels where second harmonic scattering is detected.

If luminescence within the luminescence bands of known explosives in Table 2 and within the luminescence bands of known non-explosives is not detected and second harmonic scattering is detected for at least one pixel, it is concluded that one or more of the explosives listed in Table 1 may be present on the object at the location of the at least one pixel.

If luminescence within the luminescence bands of known explosives in Table 2 is not detected and second harmonic scattering is not detected for any pixels, it is concluded that none of the explosives listed in Table 4 is present on the object.

Following detection of explosives, as described hereinabove, the explosives are identified, at locations where the presence of an explosive has been detected, by using time-resolved luminescence. If spectral patterns matching the luminescence spectral graphs of known explosives, such as, for example, those seen in FIGS. 42A–H, are detected, it is concluded that the explosive whose spectral pattern is matched is present on the object at the location of the at least one pixel. The origin of manufacture of the explosive is then determined using time-resolved laser induced breakdown spectroscopy to detect spectral patterns, such as, for example, those shown in FIGS. 54A–B, matching those of known manufacturers of the identified explosive.

Figure 40A:
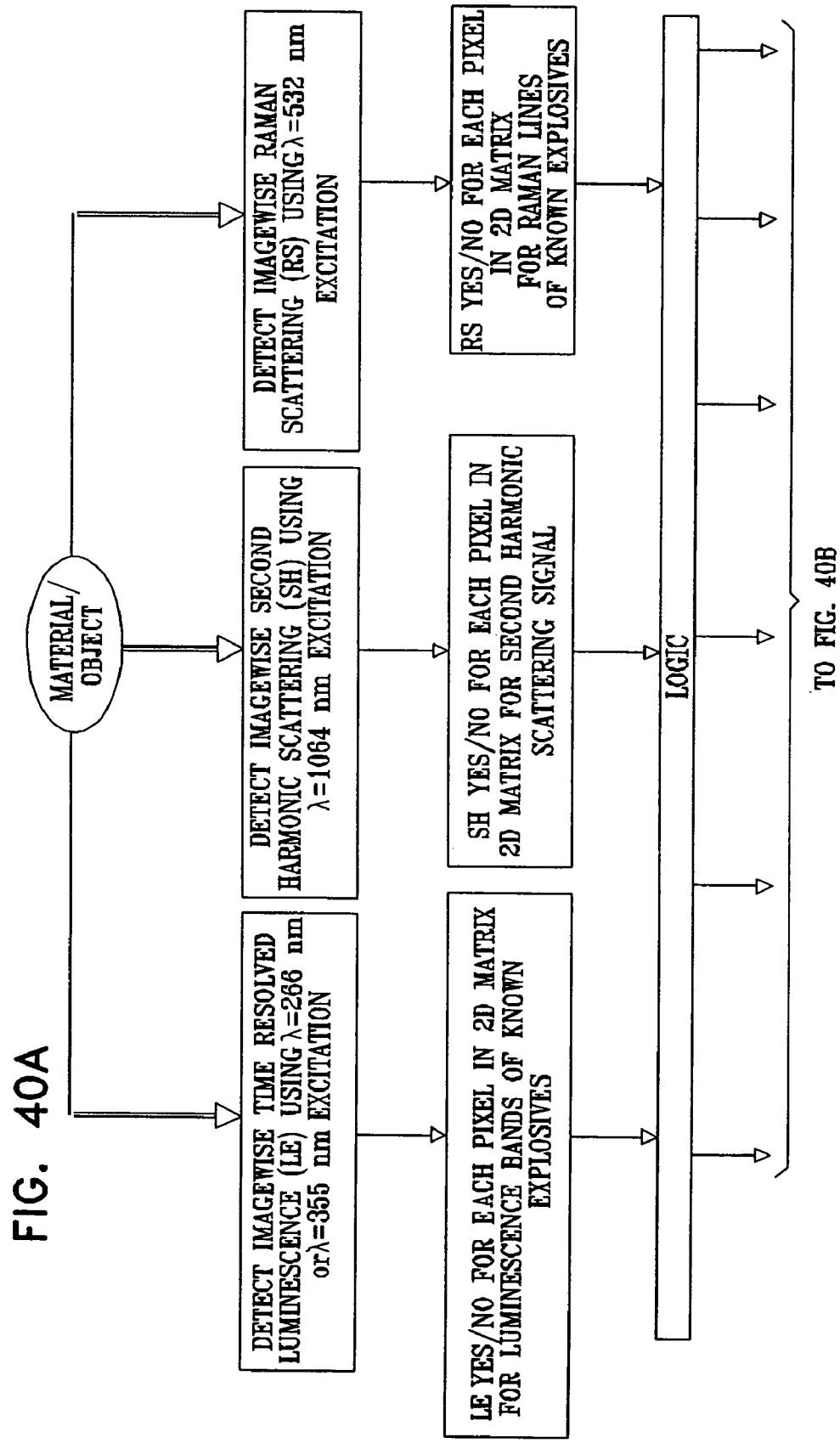
FIGS. 40A and 40B, taken together, are a simplified flowchart illustrating operation of the embodiments of FIGS. 20A–20C.
Figure 40B:
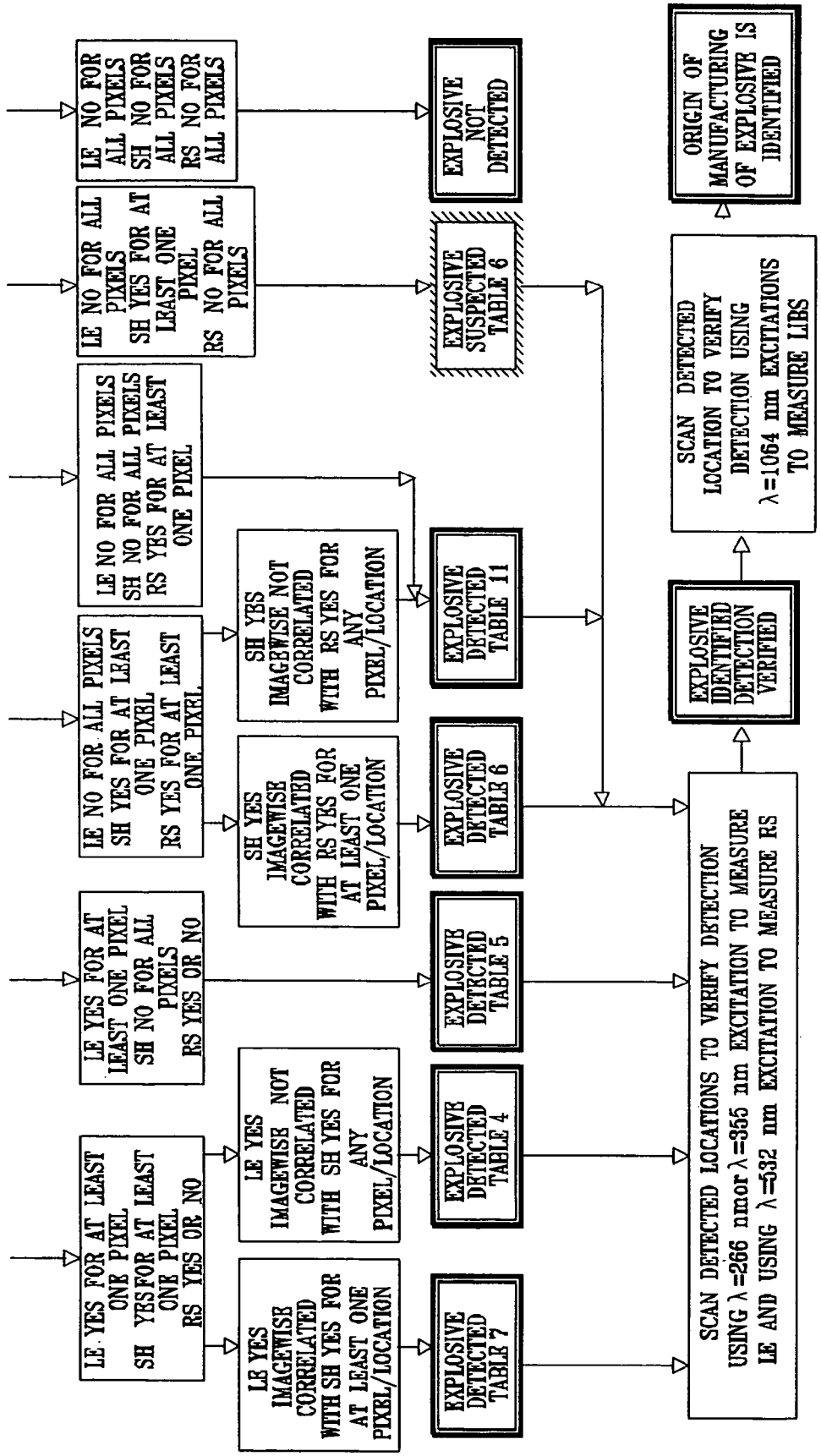

Reference is now made to FIGS. 40A and 40B, which, taken together, are a simplified flowchart illustrating operation of the embodiment of FIGS. 20A–20C. An object, such as, for example, a suitcase or a vehicle, which is sought to be examined for the possible presence of explosives thereon, is illuminated by laser radiation, as described in FIGS. 20A–20C, and is subject to imagewise detection of second harmonic scattering, imagewise time-resolved detection of luminescence and imagewise time-resolved detection of Raman scattering and explosive identification using time resolved luminescence and time-resolved Raman scattering and determination of the origin of manufacture of the explosive using time-resolved laser induced breakdown spectroscopy.

If luminescence within the luminescence bands of known explosives in Table 2 is detected for given pixels and second harmonic scattering is detected only for at least one of the same pixels, it is concluded that one or more of the explosives listed in Table 7 is present on the object at the locations of the given pixels.

If luminescence within the luminescence bands of known explosives in Table 2 is detected for given pixels and second harmonic scattering is detected, if at all, only for different pixels, it is concluded that one or more of the explosives listed in Table 4 is present on the object.

If luminescence within the luminescence bands of known explosives in Table 2 is detected in at least one pixel and second harmonic scattering is not detected, it is concluded that one or more of the explosives listed in Table 5 is present on the object at the locations of the at least one pixel.

If luminescence within the luminescence bands of known explosives in Table 2 is not detected and Raman scattering at the lines of known explosives in Table 3 is detected for at least one pixel and second harmonic scattering is detected for at least the same pixel, it is concluded that one or more of the explosives listed in Table 6 is present on the object at the locations of the at least one pixel.

If luminescence within the luminescence bands of known explosives in Table 2 is not detected and Raman scattering at the lines of known explosives in Table 3 is detected for at least one pixel and second harmonic scattering is detected, for at least one different pixel, it is concluded that one or more of the explosives listed in Table 11 is present on the object at the locations of the at least one pixel.

If luminescence within the luminescence bands of known explosives in Table 2 and second harmonic scattering are not detected and Raman scattering at the lines of known explosives in Table 3 is detected for at least one pixel, it is concluded that one or more of the explosives listed in Table 11 is present on the object at the locations of the at least one pixel.

If luminescence within the luminescence bands of known explosives in Table 2 and Raman scattering at the lines of known explosives in Table 3 are not detected and second harmonic scattering is detected for at least one pixel, it is suspected that one or more of the explosives listed in Table 6 is present on the object at the locations of the at least one pixel.

If luminescence within the luminescence bands of known explosives in Table 2, Raman scattering at the lines of known explosives in Table 3 and second harmonic scattering are not detected for any pixels, it is concluded that none of the explosives listed in Table 10 is present on the object.

Following detection of explosives, as described hereinabove, the explosives are identified, at locations where the presence of an explosive has been detected, by using time-resolved luminescence and time-resolved Raman scattering. If spectral patterns matching the luminescence spectral graphs of known explosives, such as, for example, those seen in FIGS. 42A–H, are detected, it is concluded that the explosive whose spectral pattern is matched is present on the object at the location of the at least one pixel. If spectral patterns matching the Raman scattering spectral graphs of known explosives, such as, for example, those seen in FIGS. 45A–47C, are detected, it is concluded that the explosive whose spectral pattern is matched is present on the object at the location of the at least one pixel. The origin of manufacture of the explosive is then determined using time-resolved laser induced breakdown spectroscopy to detect spectral patterns, such as, for example, those shown in FIGS. 54A–B, matching those of known manufacturers of the identified explosive.

It is appreciated that the lists of explosives contained in Tables 1–12 are not complete or exhaustive and that changes and additions to such tables are expected to occur over time as additional explosives are analyzed, developed and identified.

Figure 41:
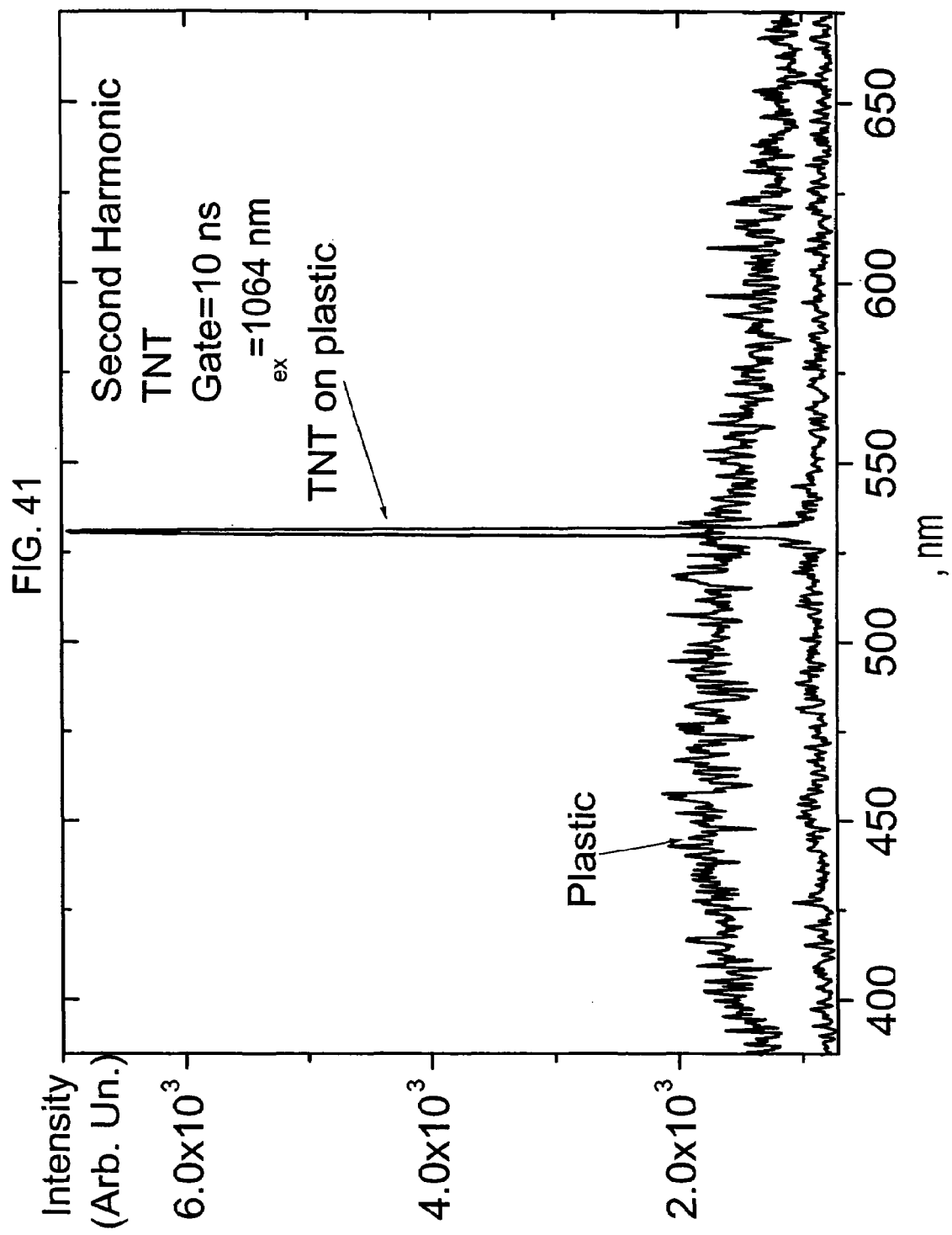
FIG. 41 is a graph showing second harmonic scattering spectral lines.
Figure 42A:
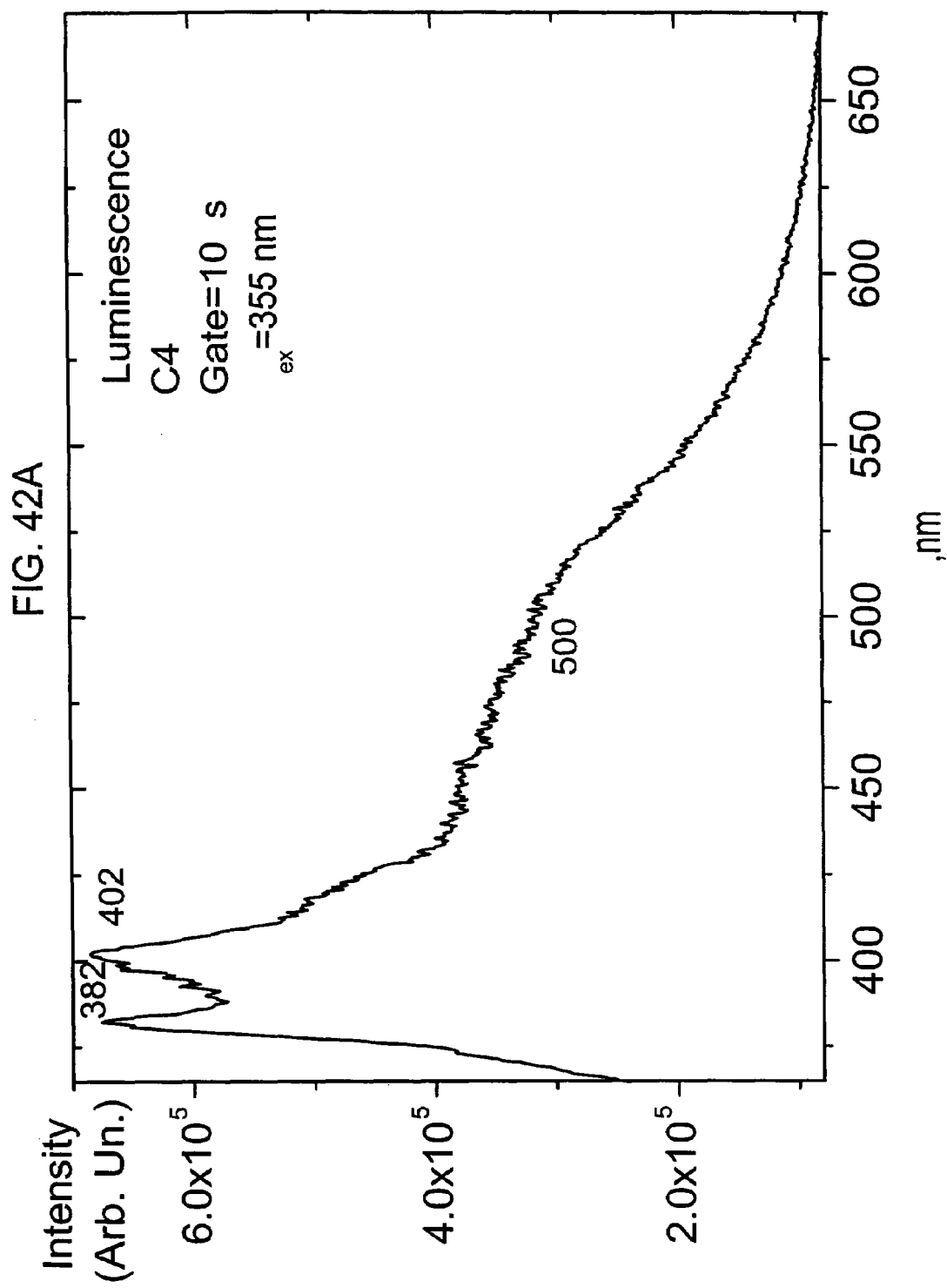
Figure 42C:
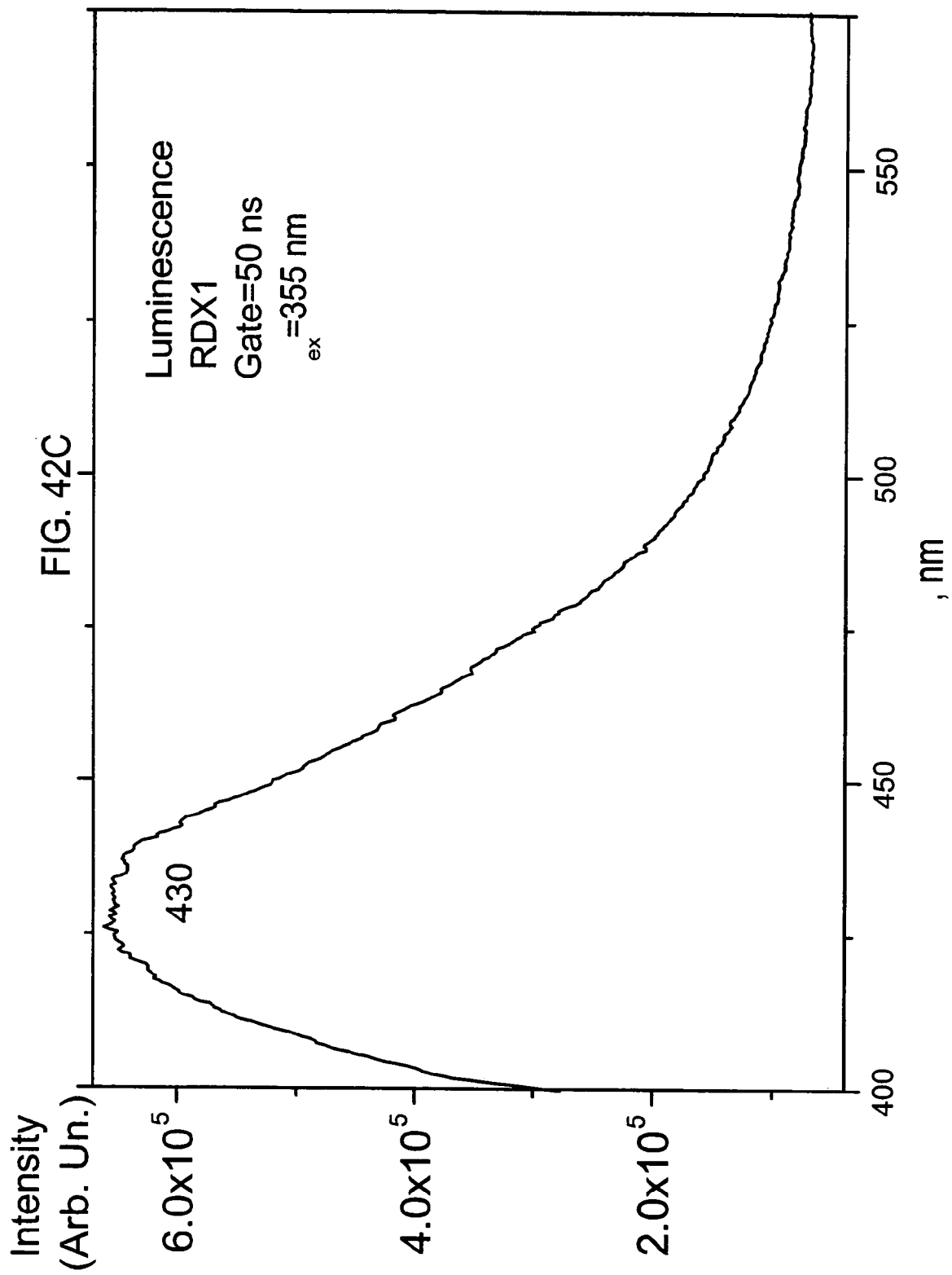
Figure 42G:
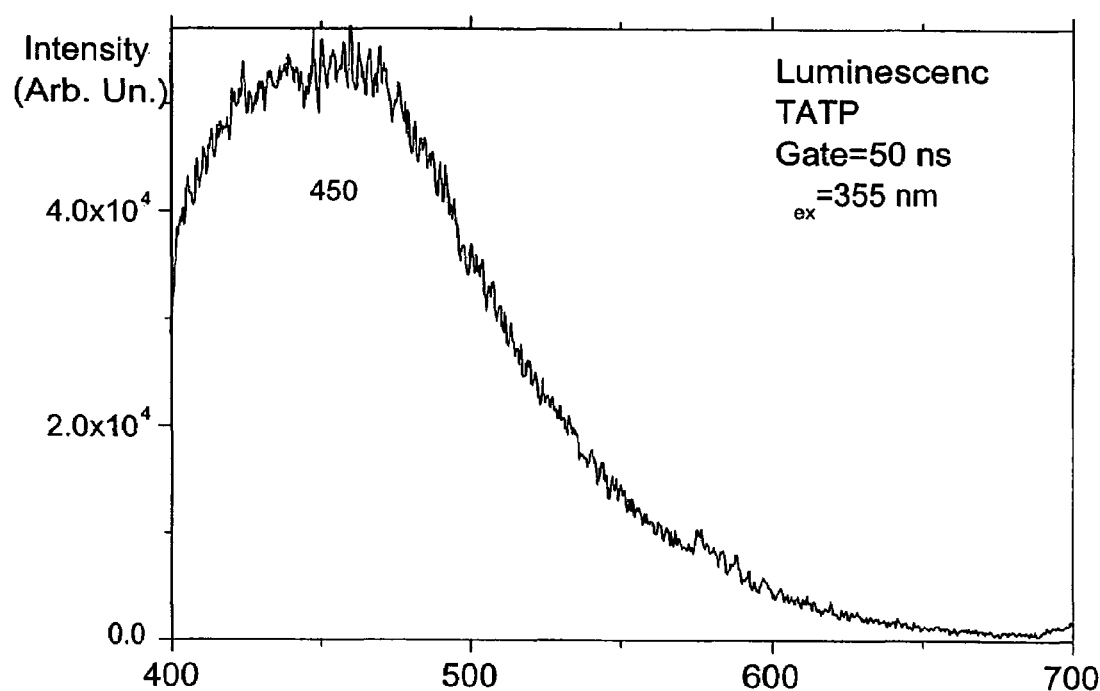
Figure 42H:
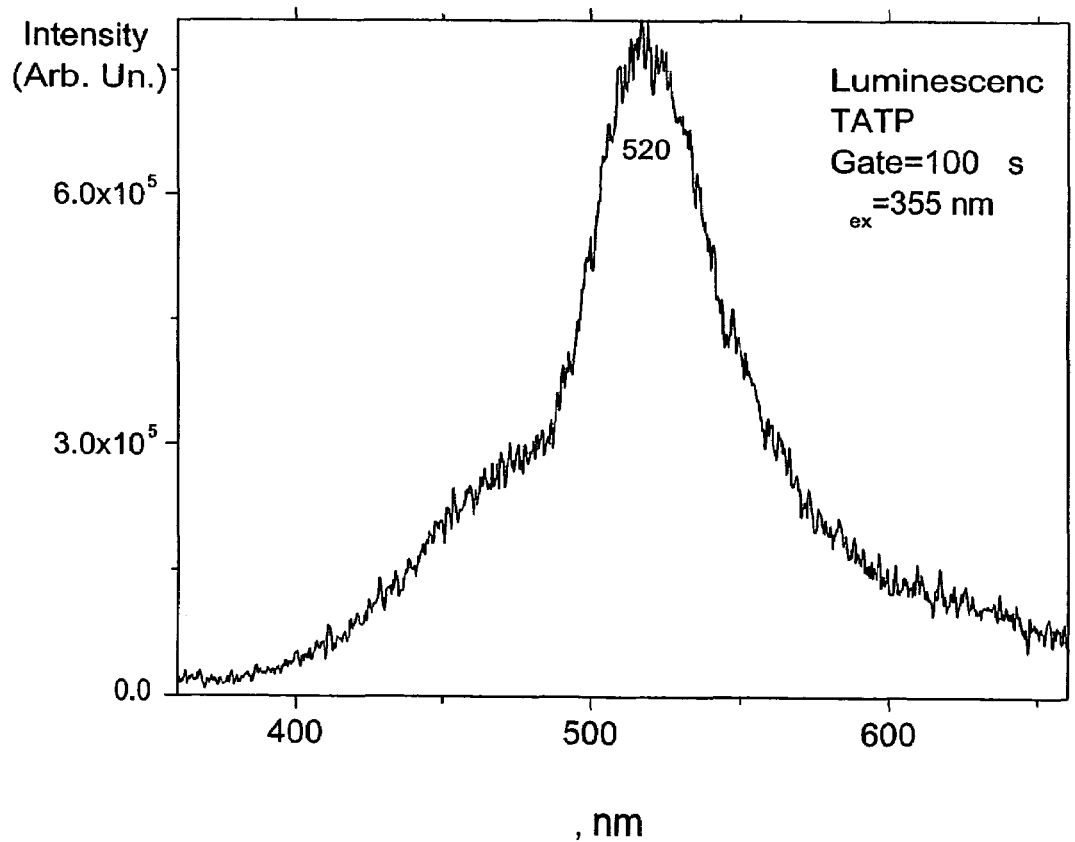

Reference is now made to FIG. 41, which is a graph showing time-resolved second harmonic scattering spectral lines. As seen in FIG. 41, there is a recognizable second harmonic line in the spectral graph when an explosive, such as TNT in the illustrated example, is scanned.

Figure 44A:
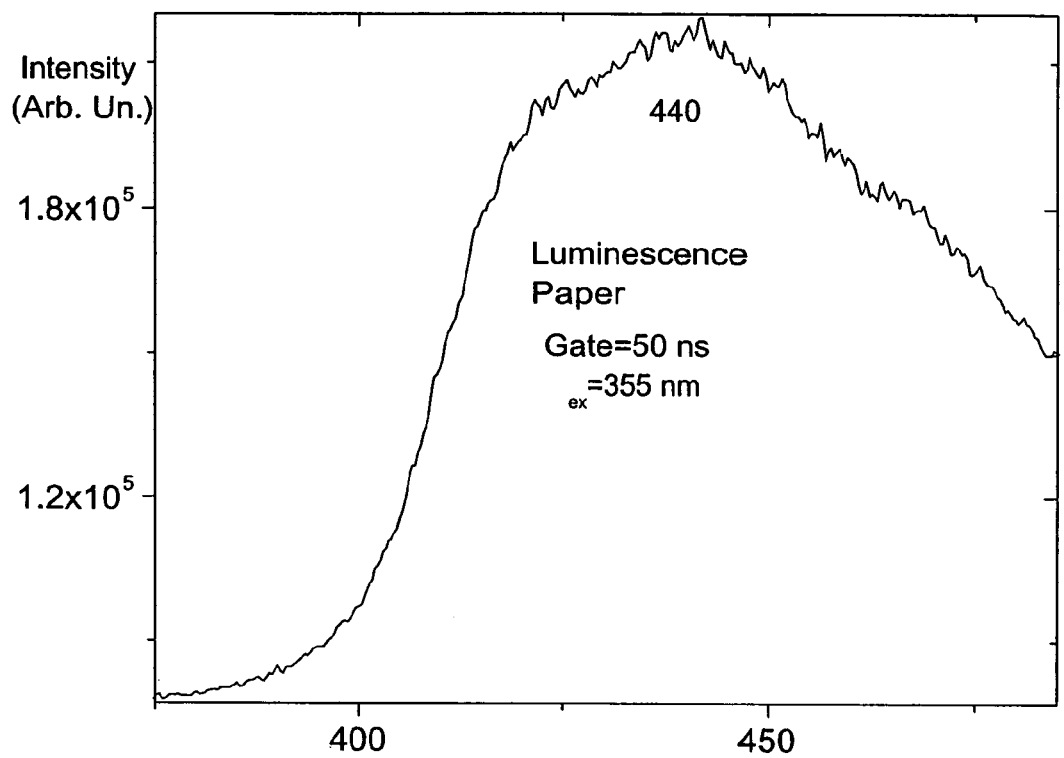
FIGS. 44A and 44B are graphs showing luminescence spectra of various non-explosives.
Figure 44B:
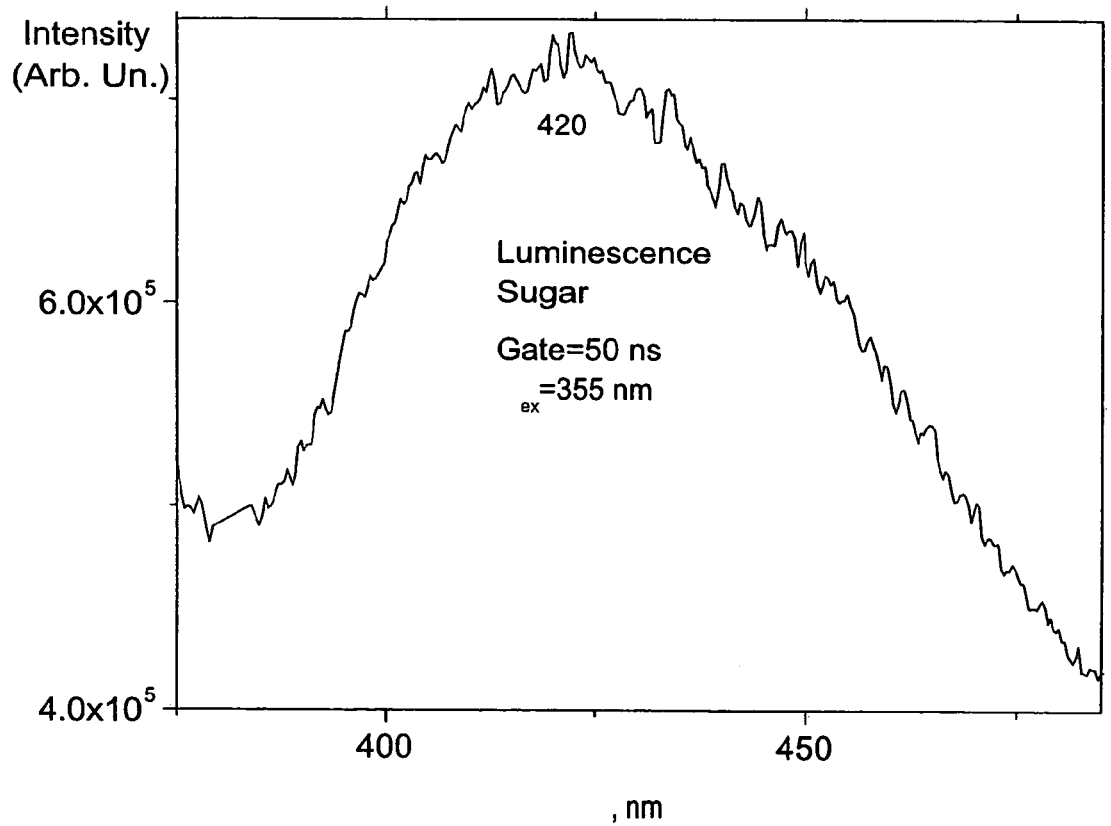
Figure 45A:
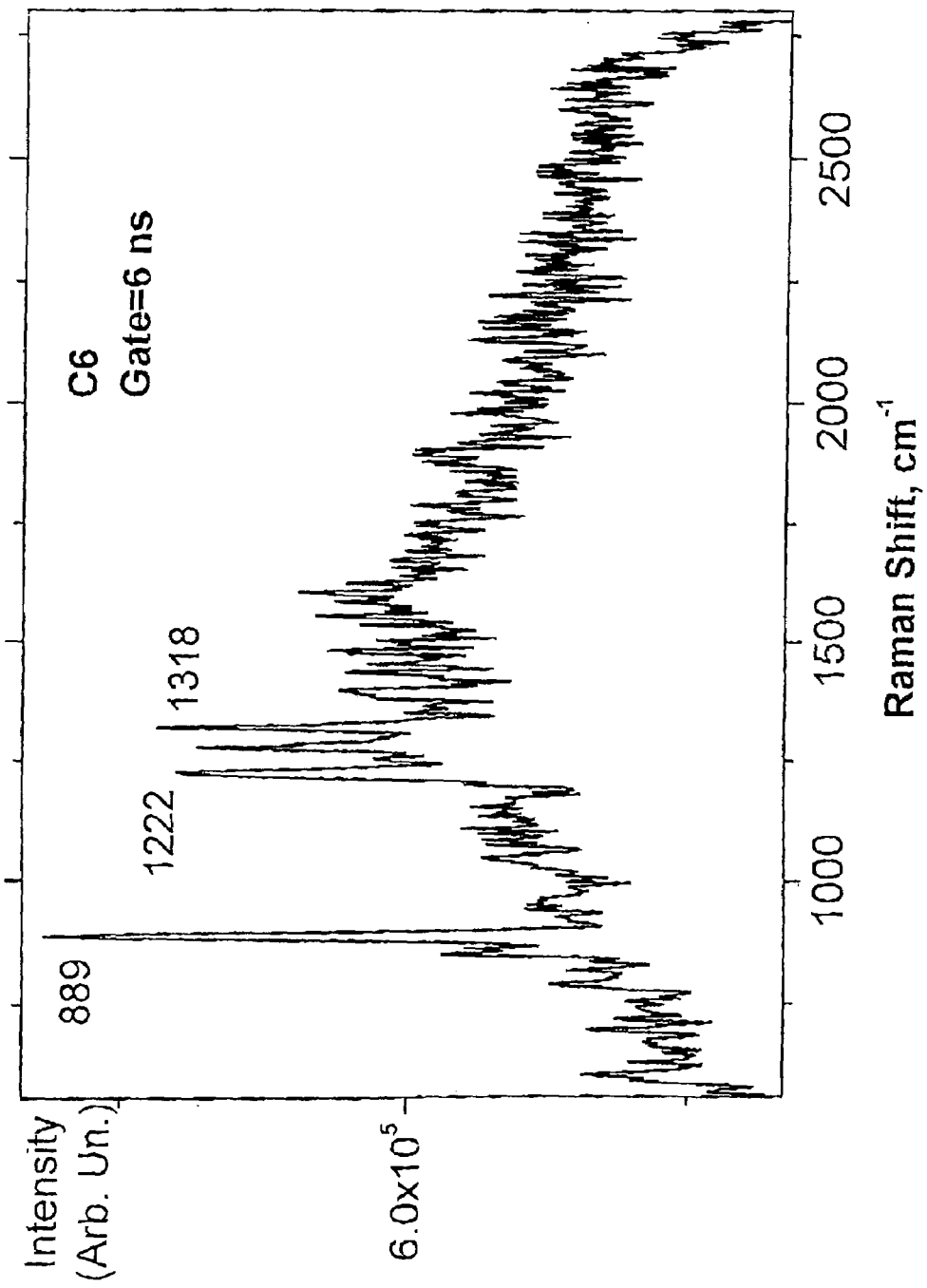
Figure 45B:
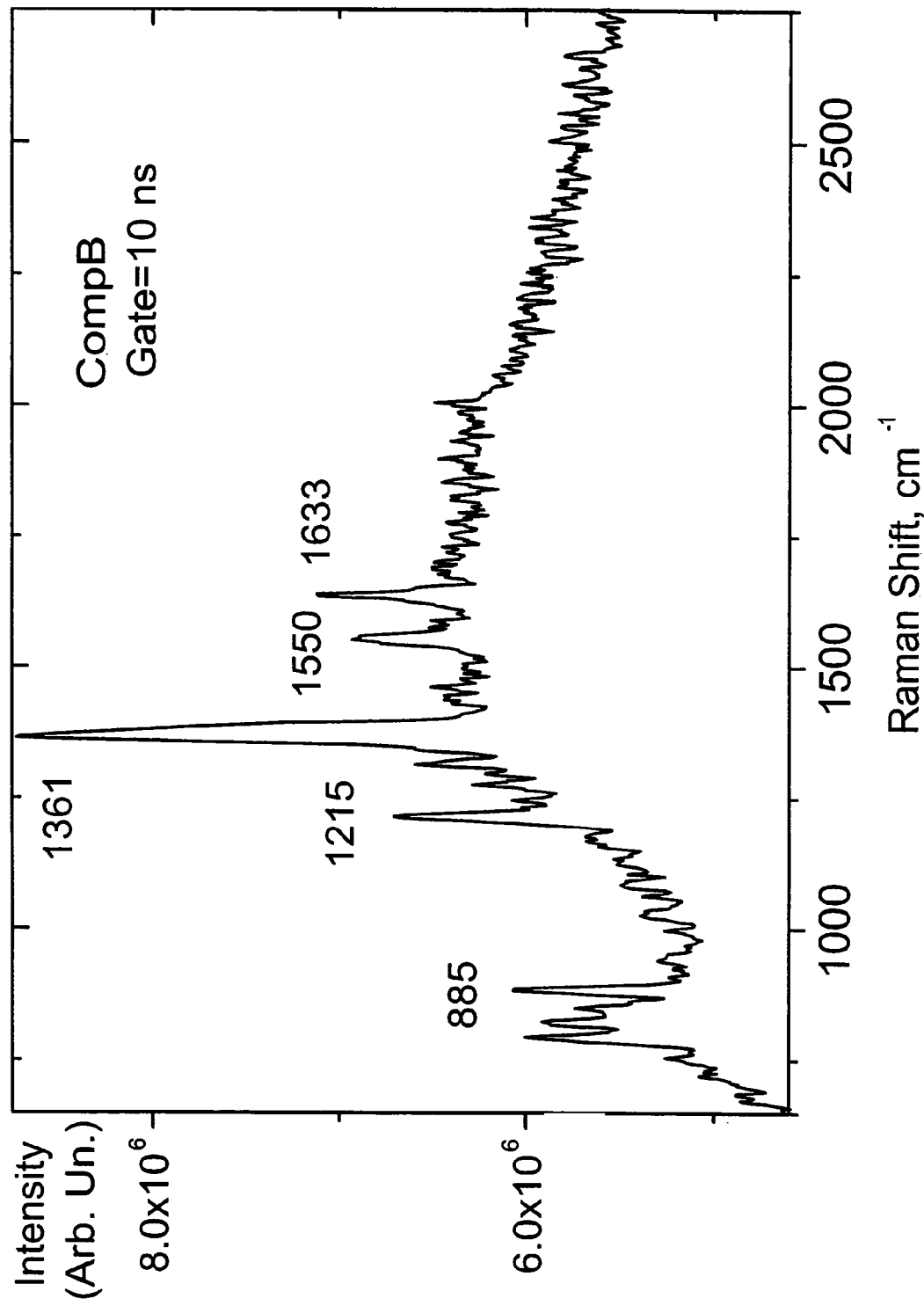
Figure 45C:
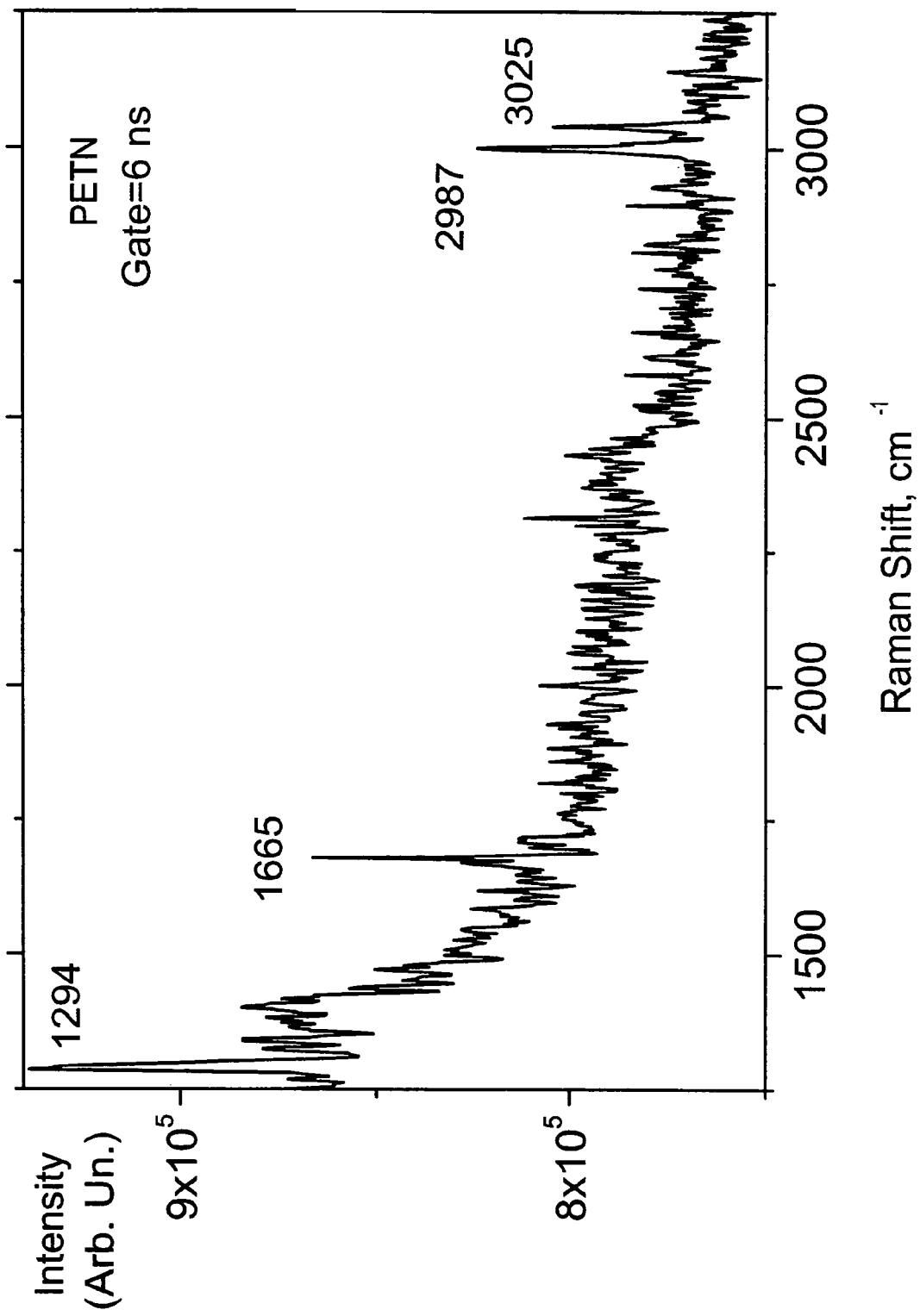
Figure 45F:
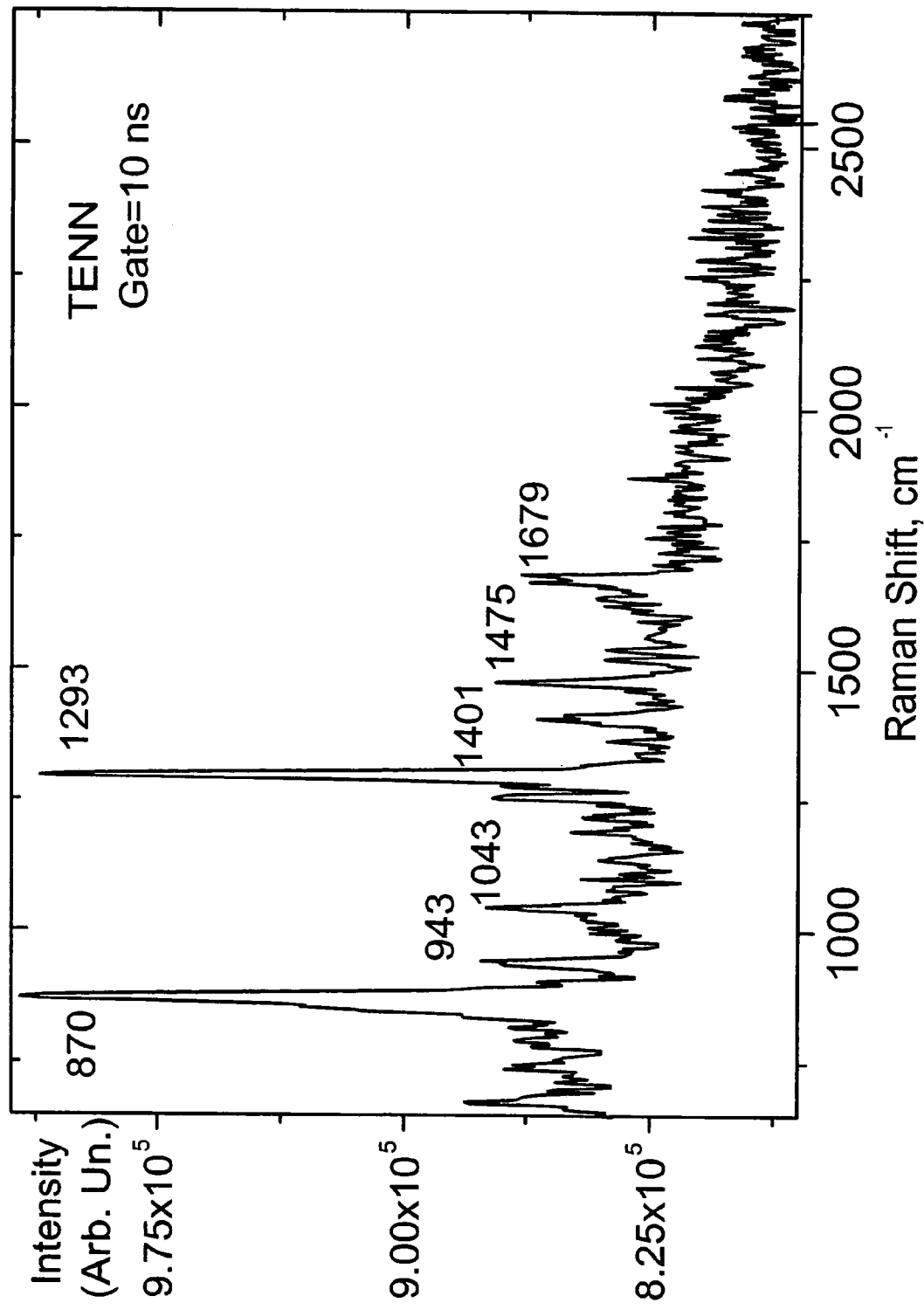
Figure 45G:
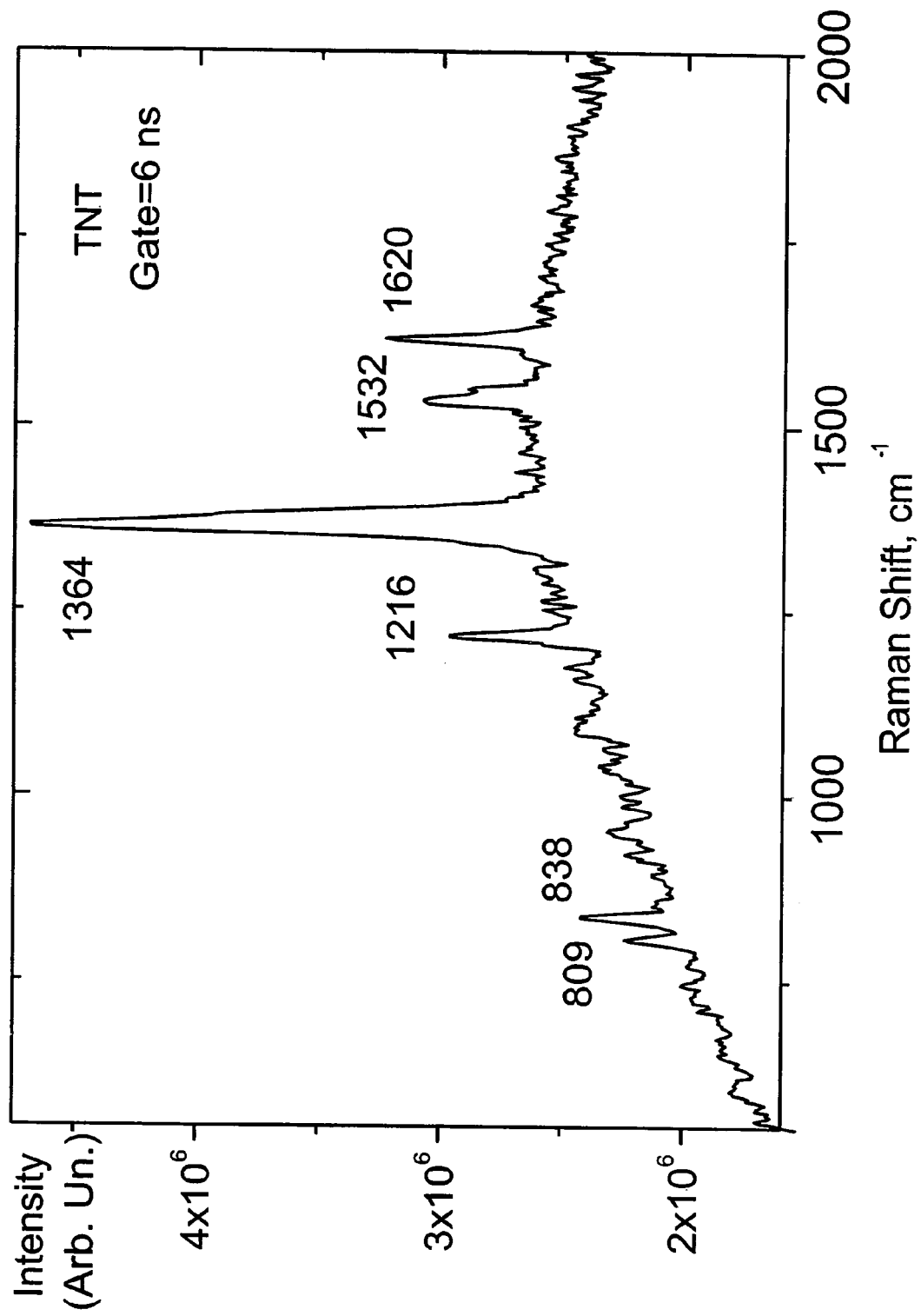

Reference is now made to FIGS. 42A, 42B, 42C, 42D, 42E, 42F, 42G, 42H, 43, 44A and 44B, which are graphs showing time-resolved luminescence spectra of various substances. As seen in FIGS. 42A–42H, explosives typically generate recognizable bands in the gated luminescence spectra in the ranges of 400–600 nm. FIG. 43 shows the recognizable nature of this band by comparing a luminescence spectrum generated by a sample explosive to a luminescence spectrum generated by a fabric. FIGS. 44A and 44B show luminescence spectra of sample non-explosive substances.

Figure 46A:
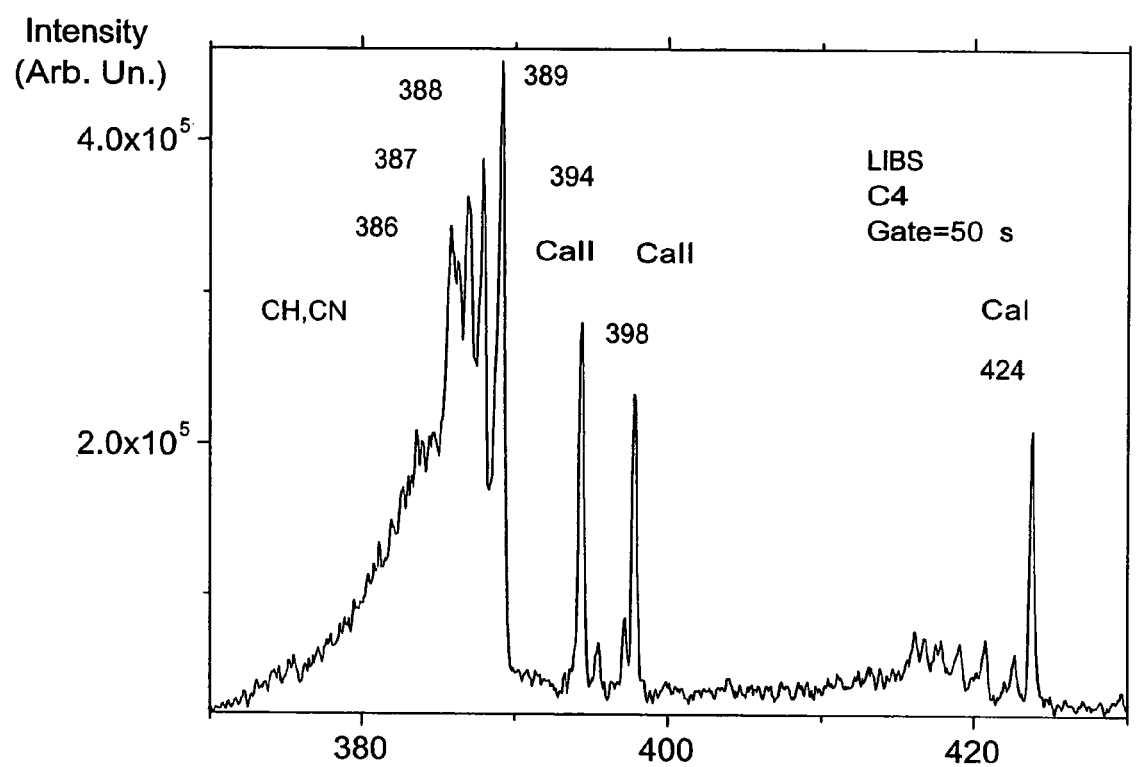
FIGS. 46A and 46B are graphs showing Raman spectra of a sample explosive with multiple spectral detection ranges.
Figure 46B:
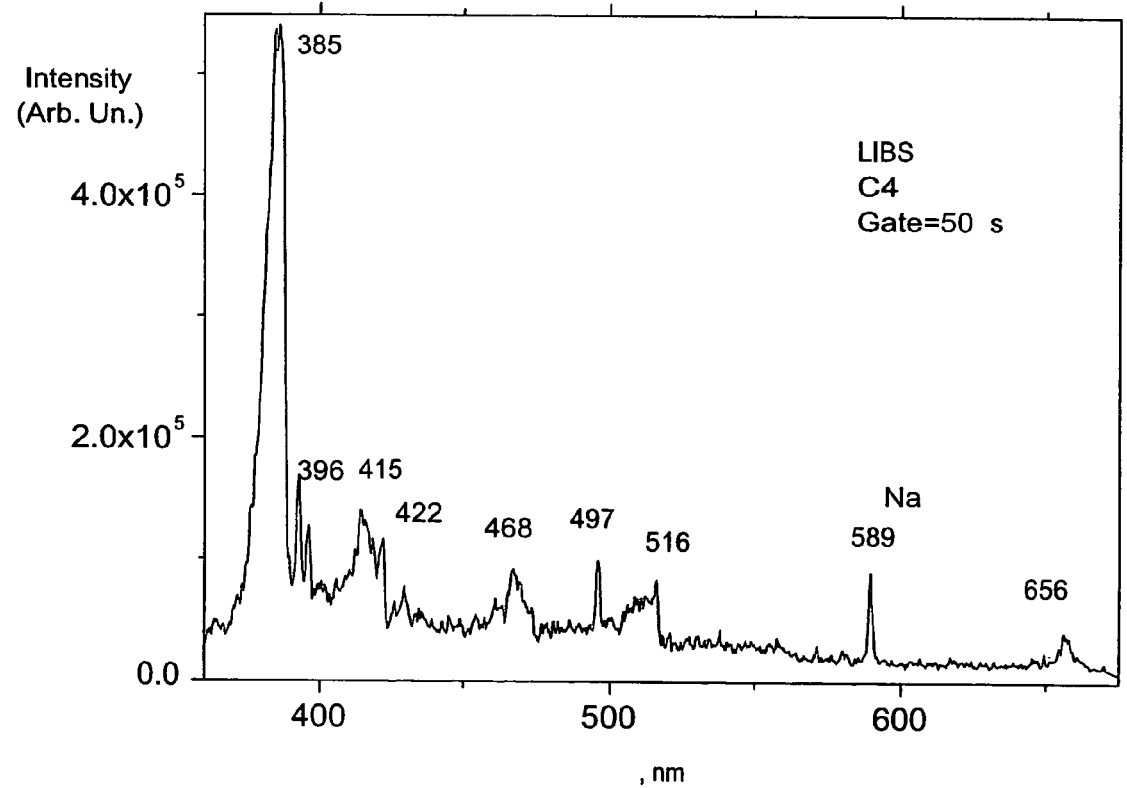
Figure 47A:
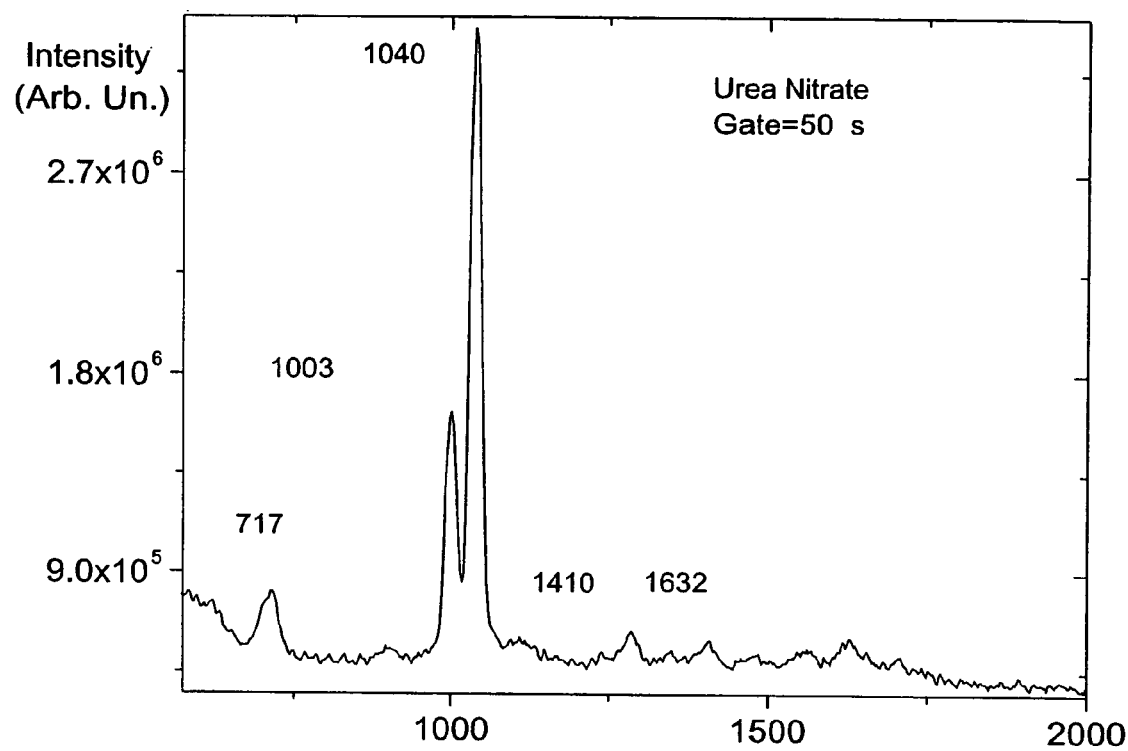
FIGS. 47A and 47B are graphs showing Raman spectra of another sample explosive with multiple spectral detection ranges.
Figure 47B:
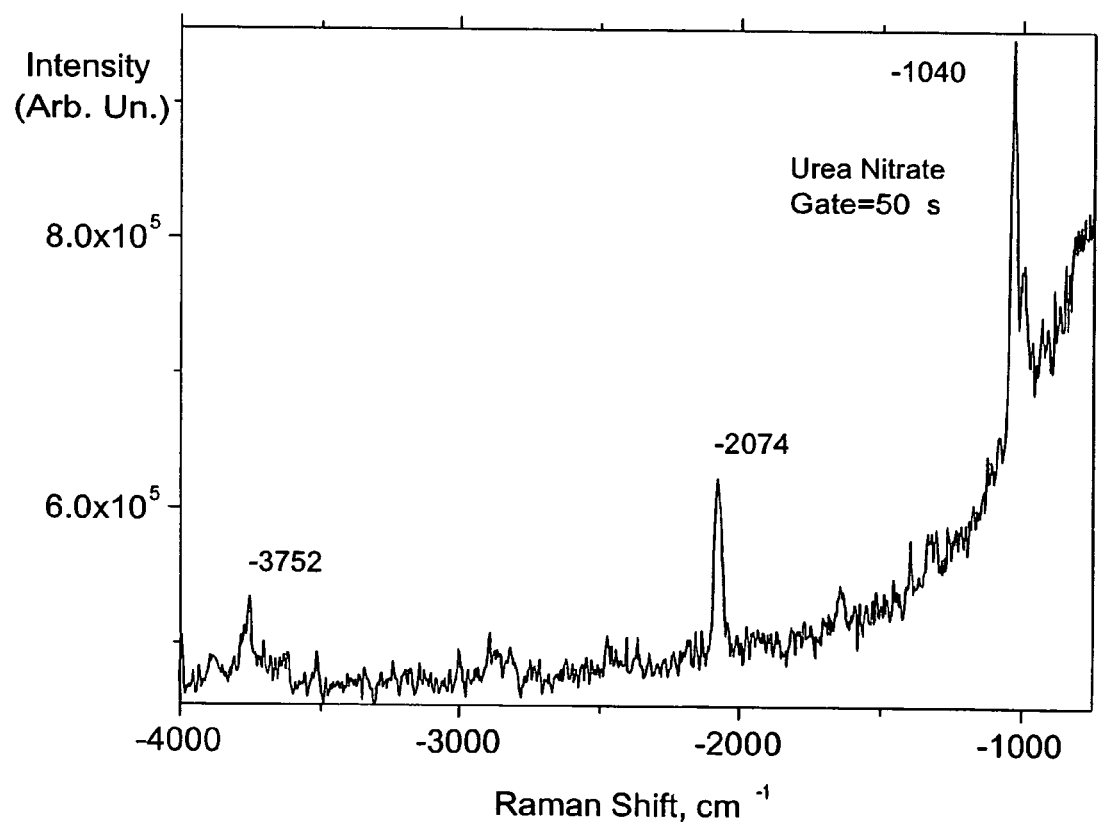
Figure 48A:
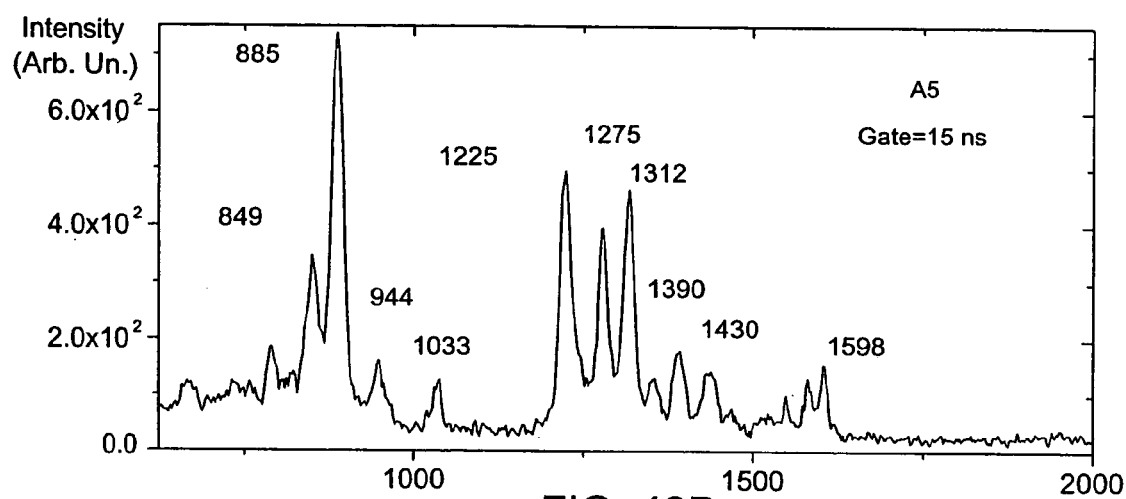
FIGS. 48A, 48B and 48C are graphs showing Raman spectra of yet another sample explosive with multiple spectral detection ranges.
Figure 48B:
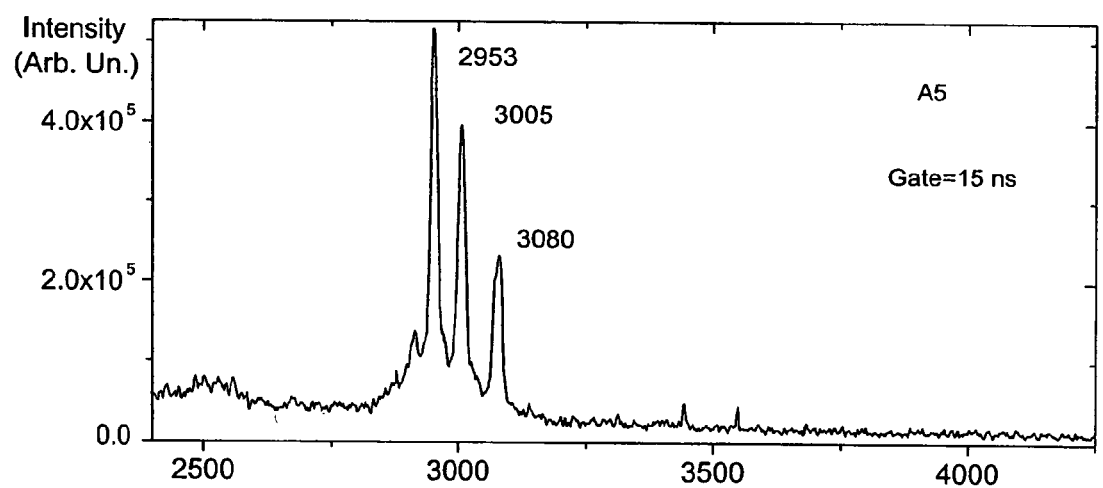
Figure 48C:
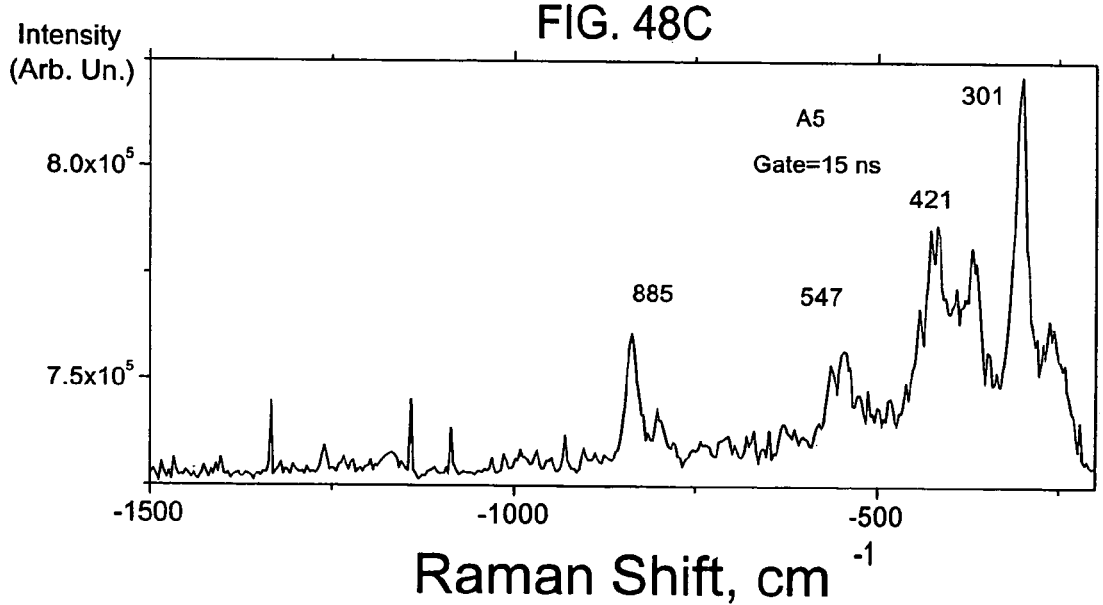
Figure 49A:
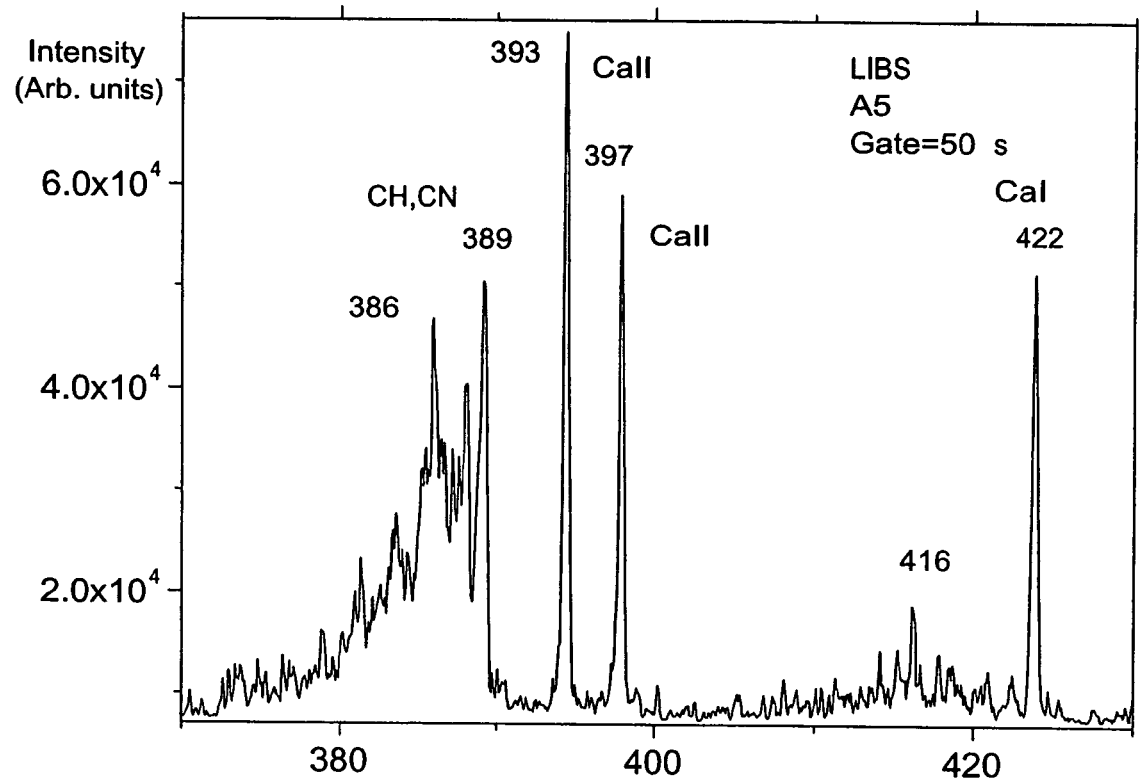
FIGS. 49A and 49B are graphs showing laser induced breakdown spectra of an explosive.
Figure 49B:
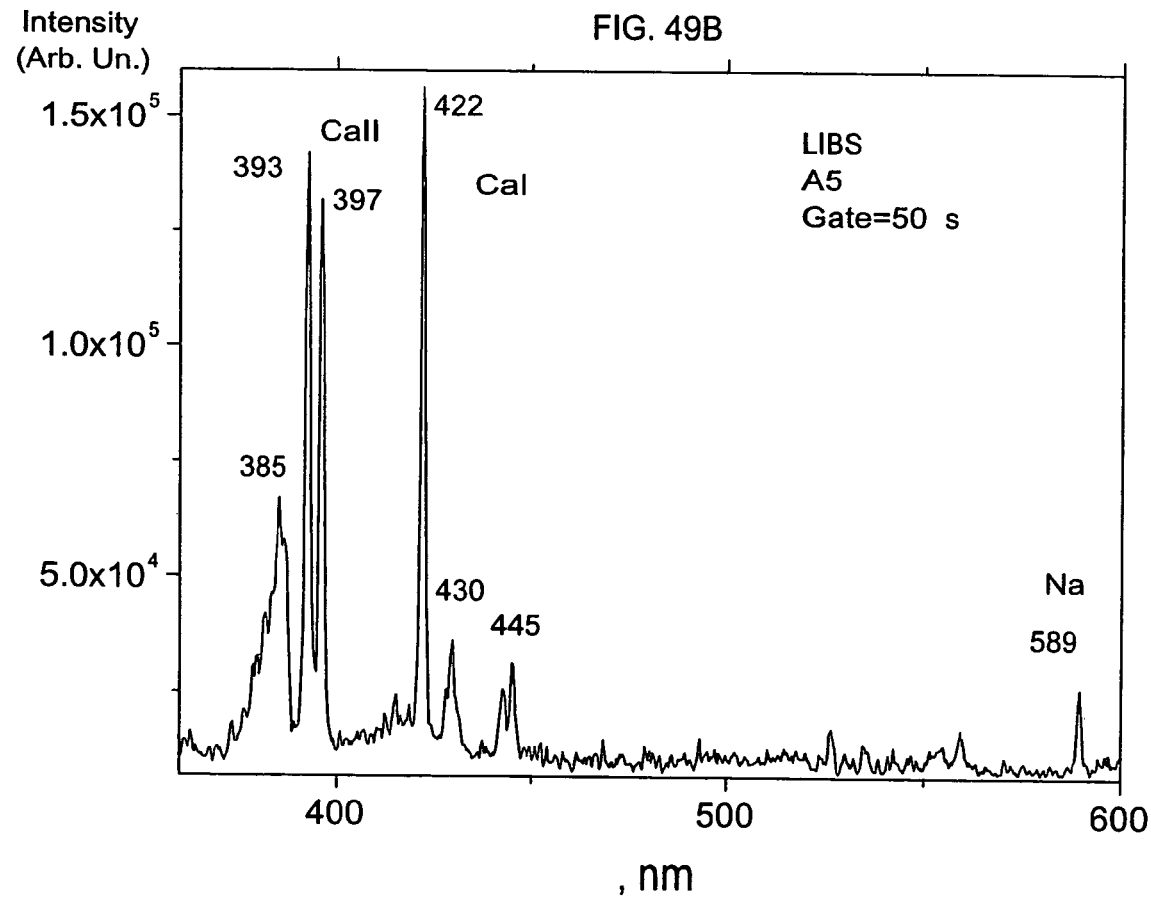
Figure 50A:
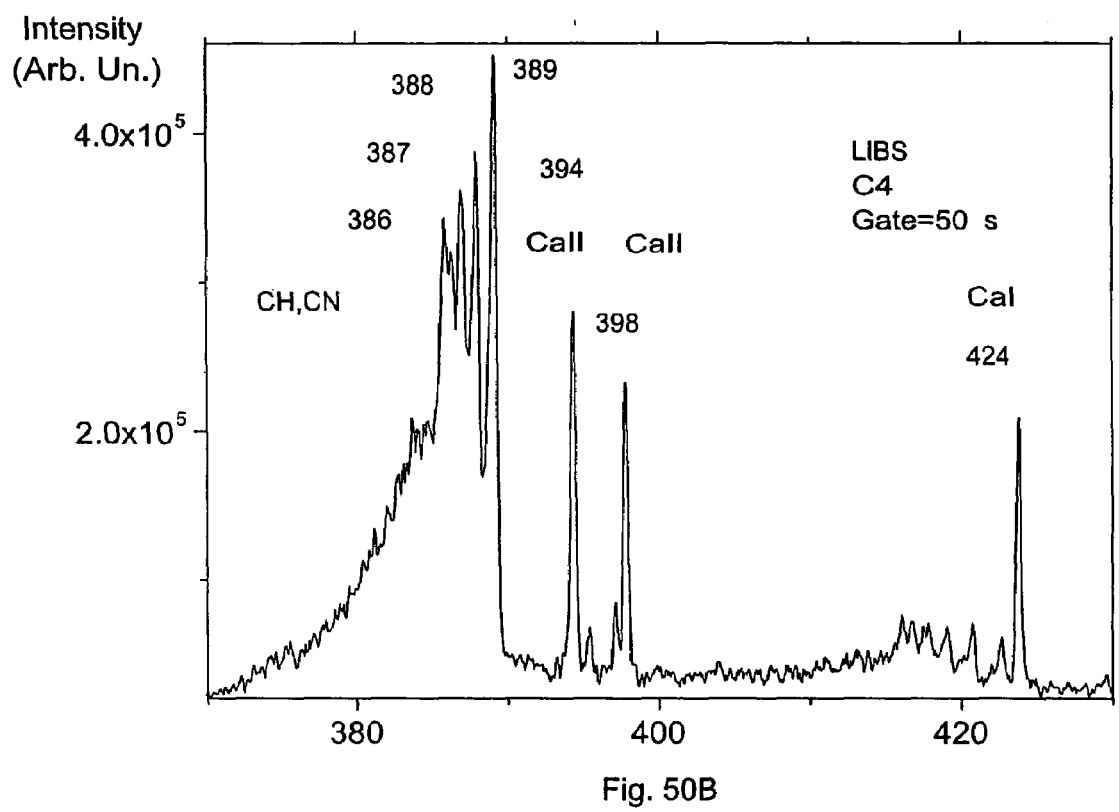
FIGS. 50A and 50B are graphs showing laser induced breakdown spectra of another explosive.
Figure 50B:
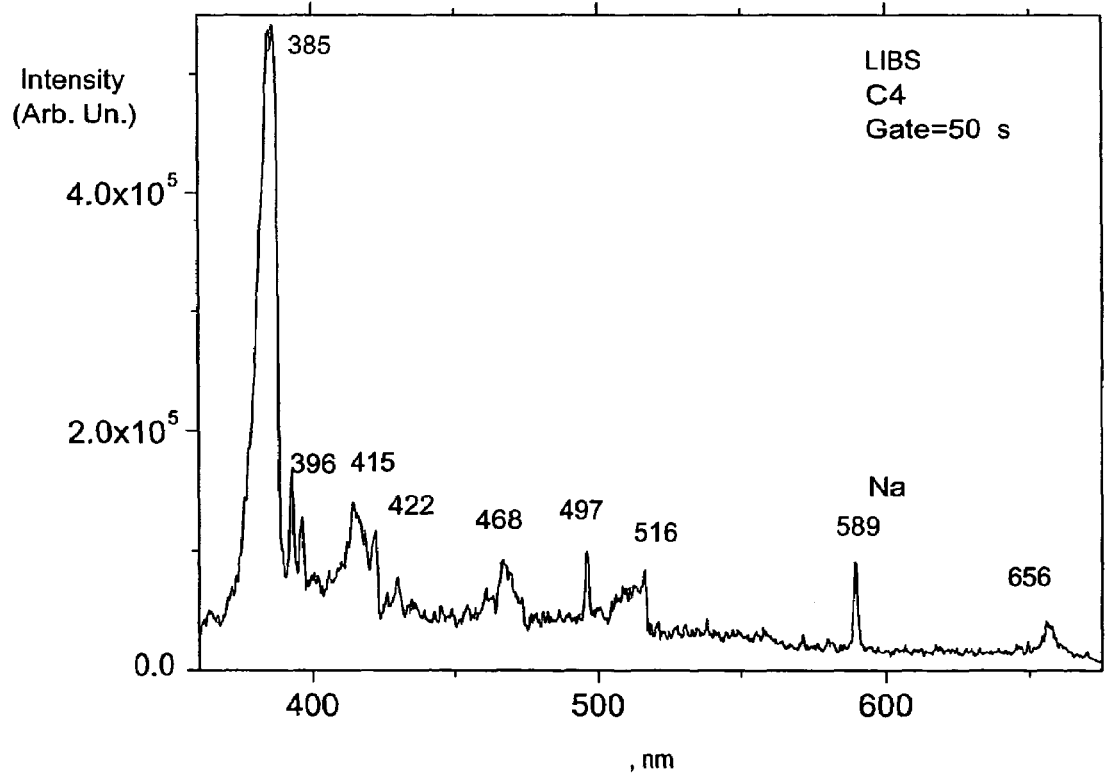
Figure 51A:
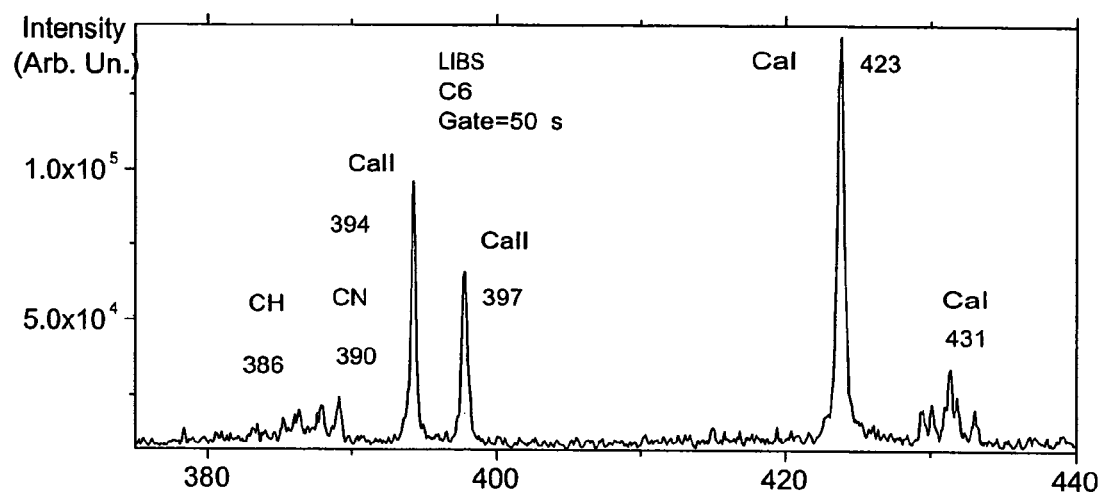
FIGS. 51A, 51B and 51C are graphs showing laser induced breakdown spectra of yet another explosive.
Figure 51B:
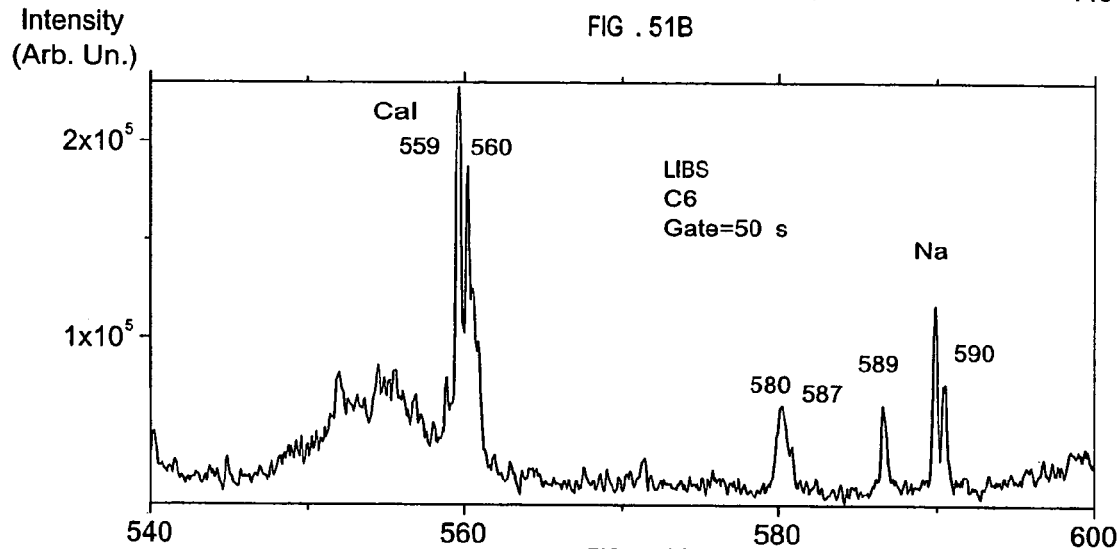
Figure 51C:
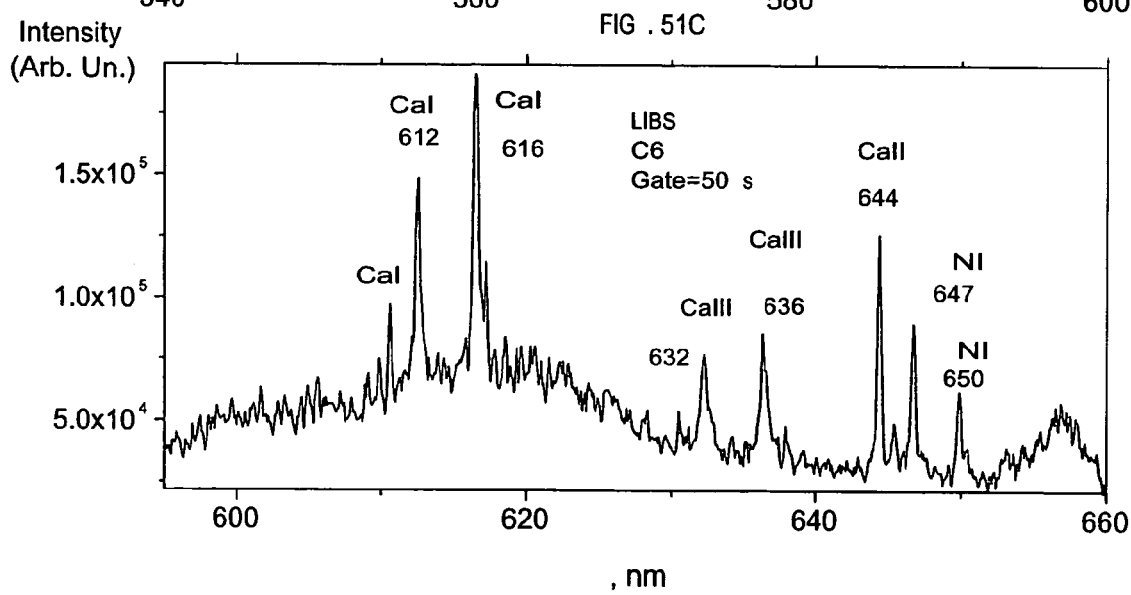
Figure 52A:
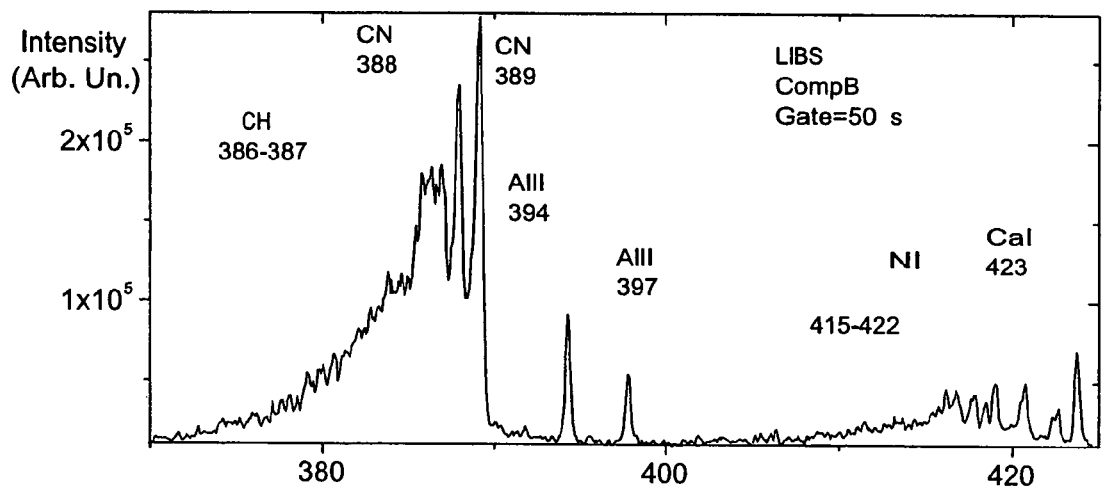
FIGS. 52A, 52B and 52C are graphs showing laser induced breakdown spectra of still another explosive.
Figure 52B:
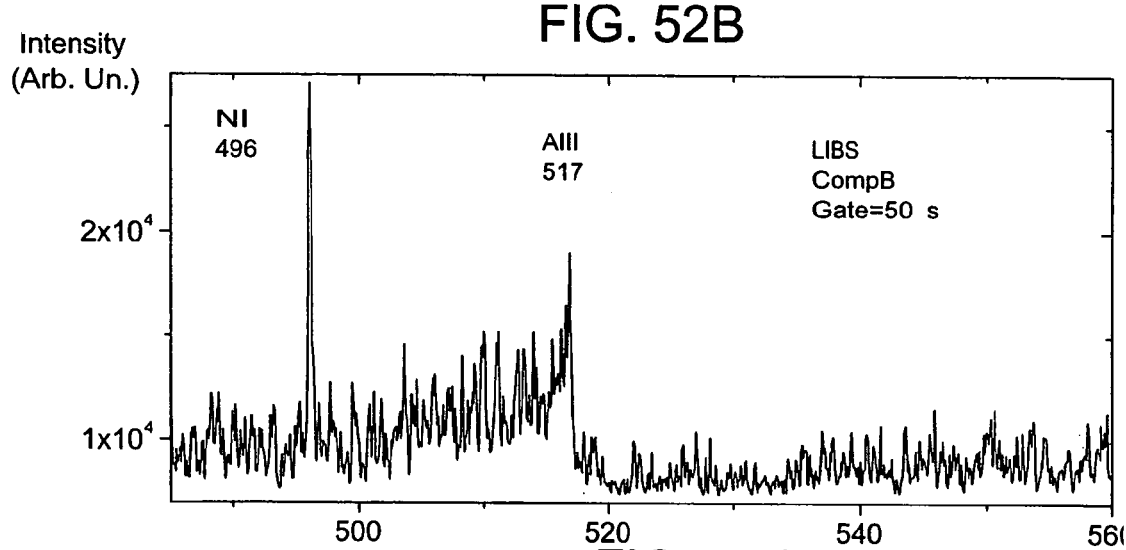
Figure 52C:
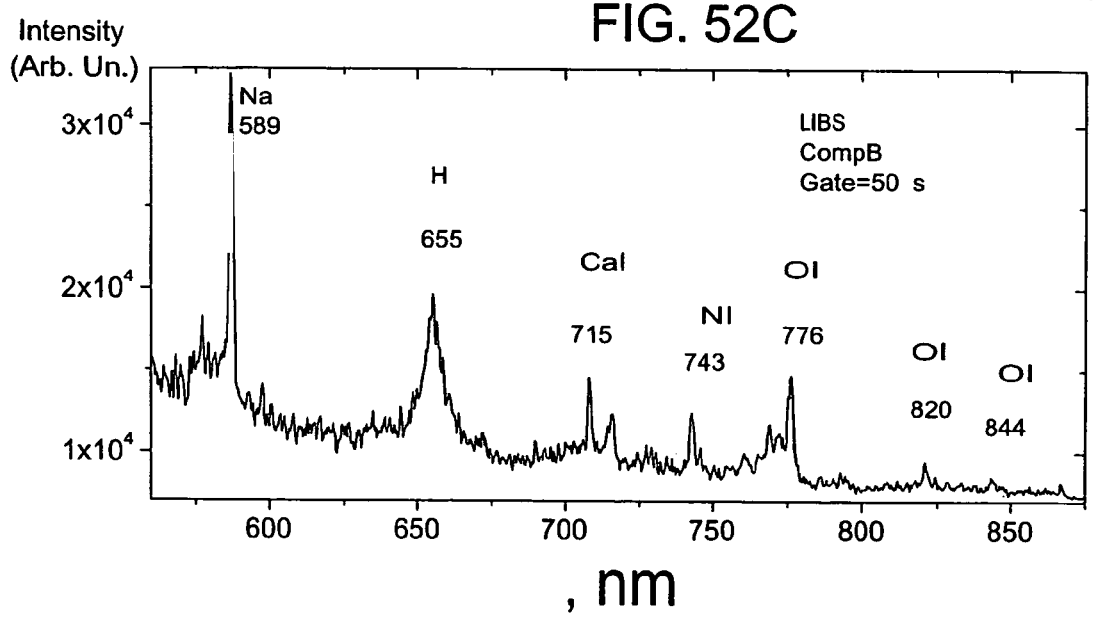
Figures 53A, 53B, 53C:
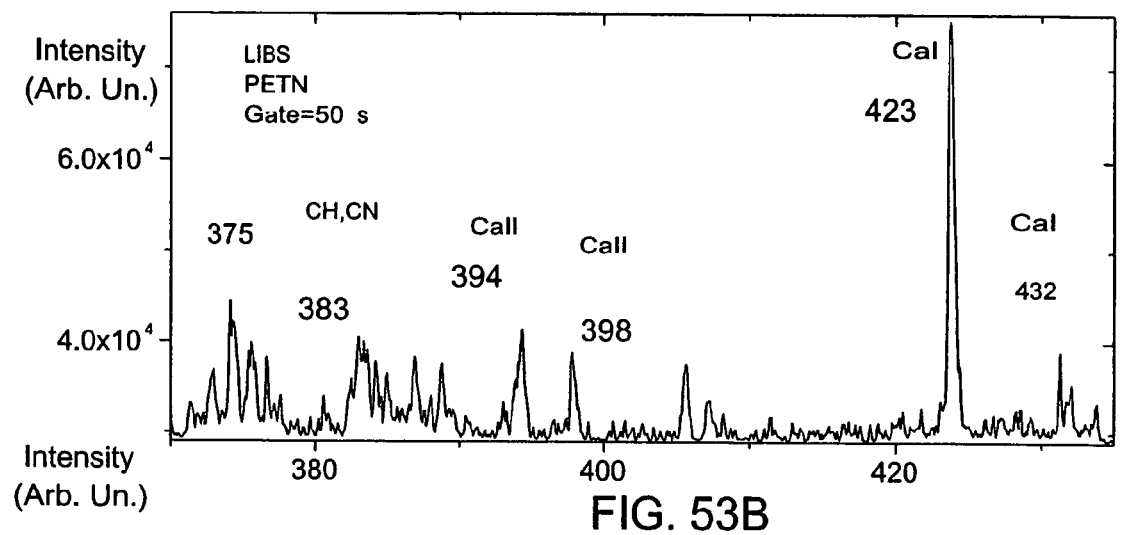
FIGS. 53A, 53B and 53C are graphs showing laser induced breakdown spectra of another explosive.

Reference is now made to FIGS. 45A, 45B, 45C, 45D, 45E, 45F, 45G, 46A, 46B, 47A, 47B, 48A, 48B and 48C, which are graphs showing time-resolved Raman spectra of various explosives. As seen in FIGS. 45A–45G, explosives typically generate recognizable spectral patterns in the Raman spectra. FIGS. 46A–48C are examples of substances with recognizable spectral patterns in multiple wavelength ranges. FIGS. 46A and 46B show sample explosive C4 in two different wavelength ranges and FIGS. 47A and 47B show sample explosive urea nitrate in two different wavelength ranges, while FIGS. 48A–48C show sample explosive A5 having recognizable spectral patterns in three different wavelength ranges. These recognizable spectral patterns in multiple wavelength ranges produce clearly defined spectra, which provide for positive identification of explosives, as described hereinabove.

Reference is now made to FIGS. 49A, 49B, 50A, 50B, 51A, 51B, 51C, 52A, 52B, 52C, 53A, 53B, 53C, 54A, 54B, 54C and 54D, which are graphs showing time-resolved laser induced breakdown spectra of various explosives. As seen in FIGS. 49A–54D, explosives typically generate recognizable spectral patterns in the laser induced breakdown spectra. These spectral patterns produce clearly defined spectra which provide for positive identification of explosives, as described hereinabove.

Figure 55A:
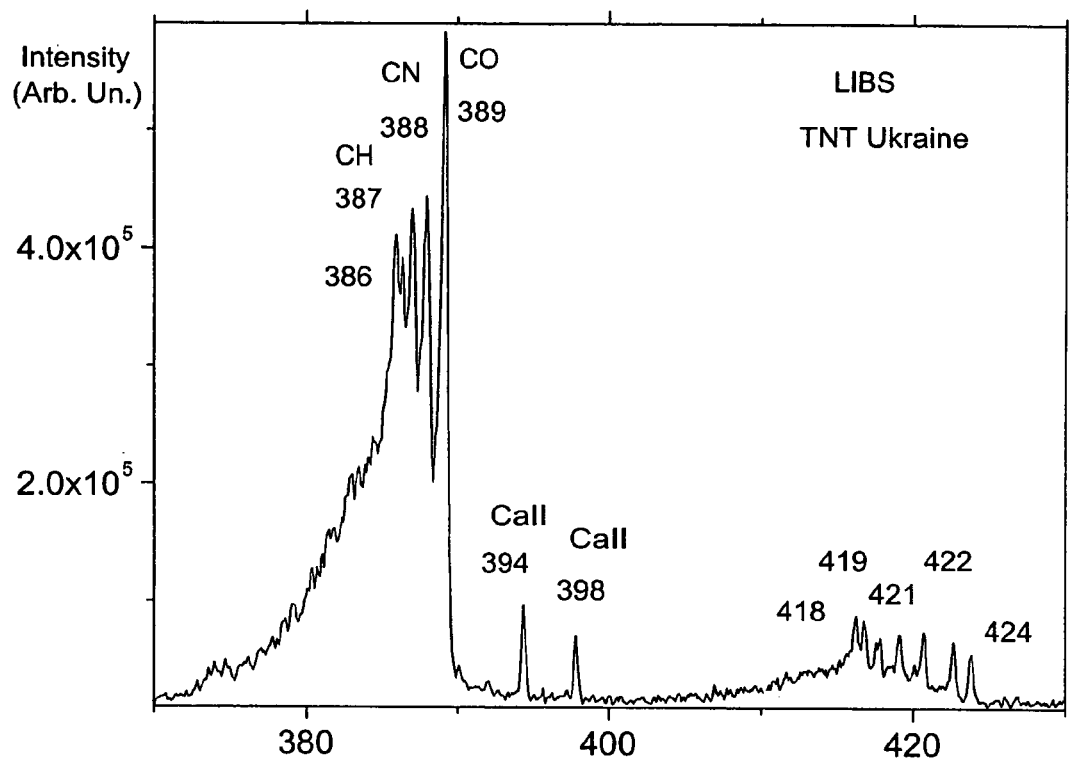
FIGS. 55A and 55B are graphs showing laser induced breakdown spectra of different varieties of the same explosive.
Figure 55B:
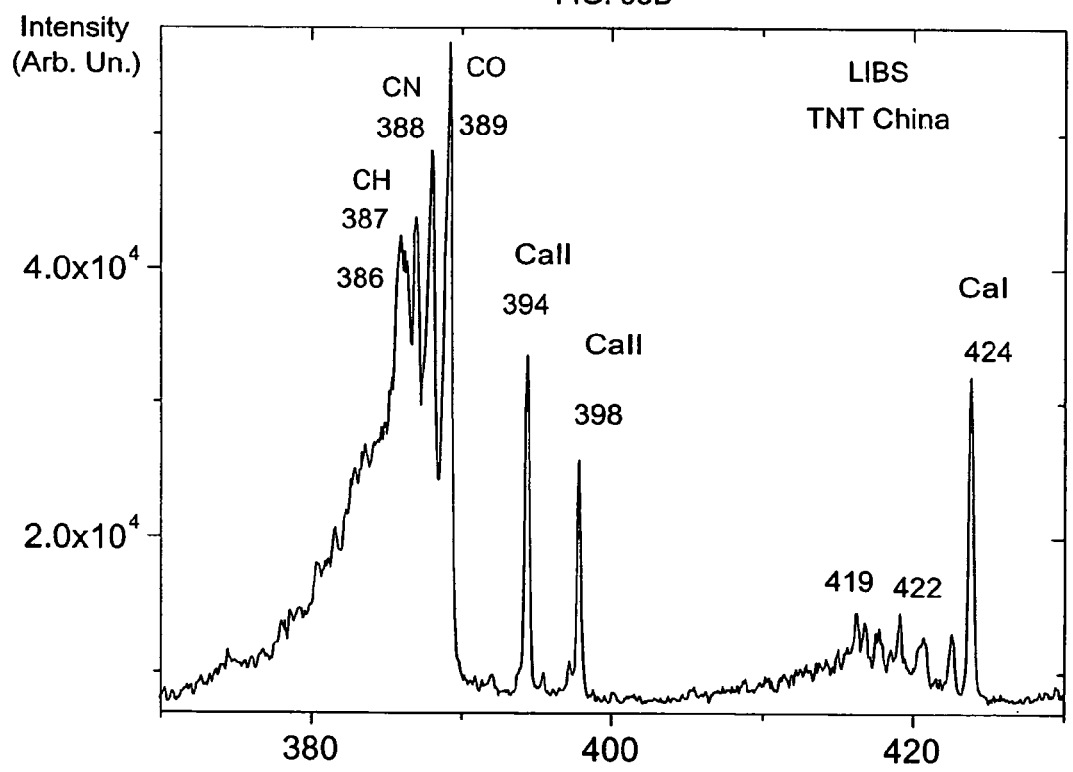

Reference is now made to FIGS. 55A and 55B, which are graphs showing laser induced breakdown spectra of different varieties of the same explosive. As seen in FIGS. 55A and 55B, the spectra of the two varieties are very similar, yet have an identifiable difference which provides for positive identification of the specific variety of explosives, as described hereinabove.

Figure 56A:
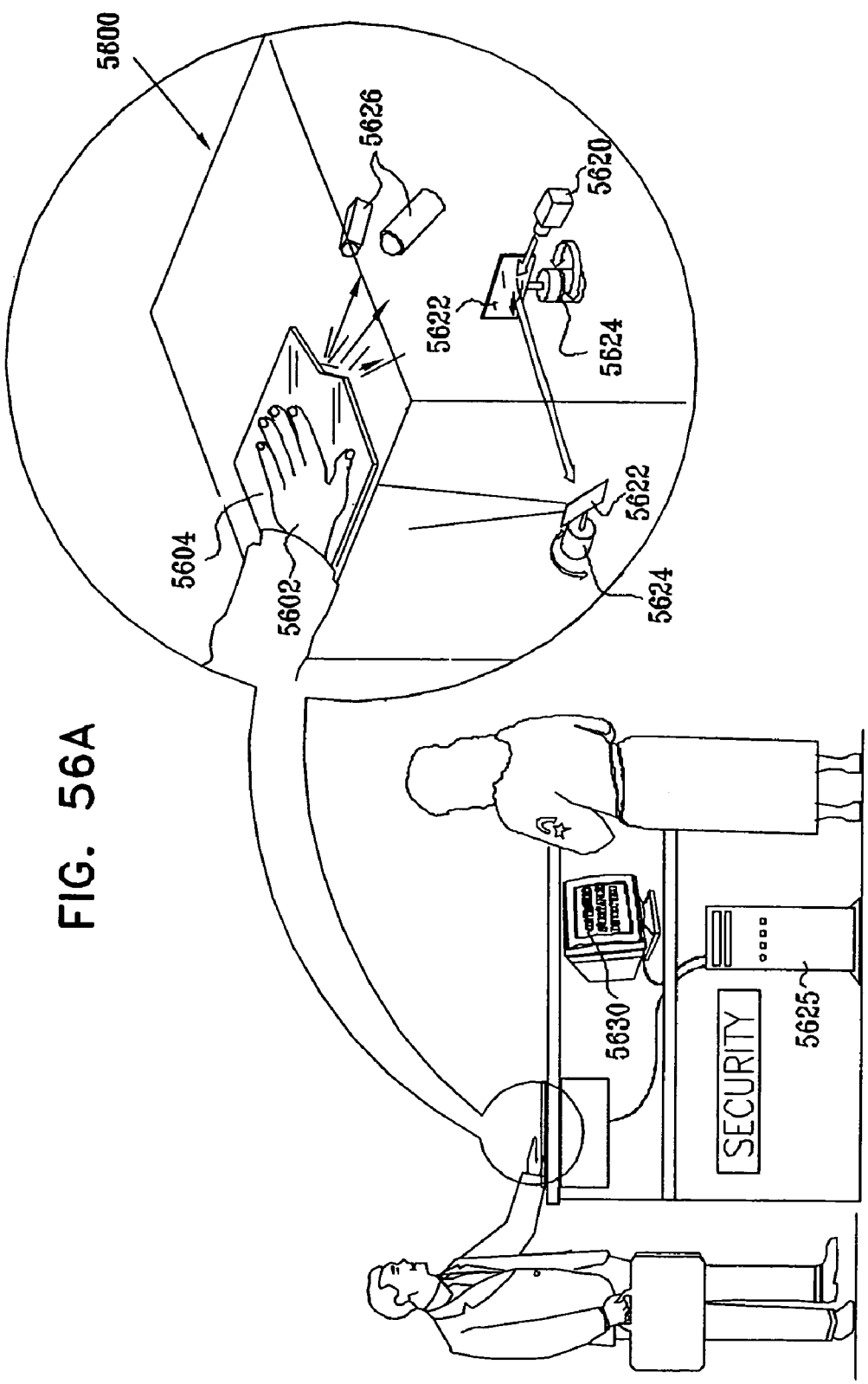
FIGS. 56A and 56B are simplified pictorial illustrations of systems for identifying controlled substances constructed and operative in accordance with preferred embodiments of the present invention.

Reference is now made to FIG. 56A, which is a simplified pictorial illustration of a controlled substance detection system, constructed and operative in accordance with a preferred embodiment of the present invention. In the illustrated embodiment of FIG. 56A a transportation check-in system is shown, it being appreciated that the present invention is not limited to the illustrated embodiment, but rather may be employed in any other suitable personal identification screening environment.

As seen in FIG. 56A, the controlled substance detection system includes a spectroscopic scanning system 5600, operative to spectroscopically scan a body portion 5602, such as a hand, for the possible presence of controlled substances, such as explosives or drugs, on the body portion 5602.

In accordance with a preferred embodiment of the present invention, the spectroscopic scanning system 5600 includes a transparent substrate 5604 upon which the scannable body portion 5602 is placed, and the spectroscopic identifications are recorded while body portion 5602 is resting on the transparent substrate 5604. Preferably, the transparent substrate 5604 is made of a material that does not exhibit characteristic SH, RS and LE under the parameters defined for use in identifying controlled substances. Even more preferably, the substrate 5604 is coated with a thin layer of a substance that may exhibit Surface Enhanced Raman Spectrum (SERS), such as silver, gold or copper, having a suitably roughened surface. With such an appropriate surface, molecules of controlled substances, such as explosives or drugs, may exhibit Surface Enhanced Raman Spectrum (SERS), which increases the visibility of the RS by a factor of 10 or more.

Additionally or alternatively, the transparent substrate 5604 includes a material that exhibits luminescence that is quenched by controlled substances or a material that provides additive material enhanced luminescence in the presence of controlled substances.

In the illustrated embodiment of FIG. 56A, the spectroscopic scanning system 5600 employs at least one light source, such as a laser 5620. An output beam of laser 5620 impinges on one or more scanning elements 5622, such as mirrors, which are driven in rotational motion by one or more motors 5624 in synchronization with the pulsed output of laser 5620 in response to synchronization signals, such as signals provided by a computer 5625.

In accordance with a preferred embodiment of the present invention, laser 5620 is preferably a Nd:YAG pulsed laser emitting first, second, third and forth harmonics having peak wavelengths at 1064, 532, 355 and 266 nm. Alternatively, multiple lasers, preferably Nd:YAG pulsed lasers, may be provided. It is appreciated that wavelengths in the range of 200 nm to 10 microns may be employed.

The output beam of laser 5620 is thus scanned over the body portion 5602, inducing SH, RS and LE by certain materials, including controlled substances, such as explosives and drugs, should those materials be present on the scanned surfaces of the body portion 5602. The emitted and scattered light is detected by one or more detector assemblies 5626, preferably including collecting optics, a notch filter, a spectral filter, a polychromator and a gated detector, such as a photodiode, photo multiplier, CCD or CMOS.

Preferably, a laser wavelength of 1064 nm is used for SH generation and the spectral filter, such as a filter having a narrow passband centered on 532 nm, is used for SH detection. Preferably, a laser wavelength of 532 nm is used for RS generation and the notch filter, such as a narrowband filter centered on 532 nm, is used for RS detection. The polychromator preferably has a spectral range from 360 to 900 nm.

Preferably, the gating interval for SH and RS detection coincides with duration of the laser pulse, while the interval for LE detection starts with the beginning of the laser pulse and continues beyond the end of the pulse for a time period based on the decay time of the luminescence emission. Alternatively, the detector need not be gated, although this is not preferred.

Alternatively, the polychromator may be replaced by a spectroscopic system employing several filters for RS and LE detection. The following Raman shifts relative to the laser excitation wavelength are preferably provided, each by a different spectral filter:

880–885 $cm^{-1}$
1360–1365 $cm^{-1}$
1270–1290 $cm^{-1}$
2980–3000 $cm^{-1}$.

The following spectral ranges are preferably provided for LE detection, each by a different spectral filter and corresponding to the following gate intervals:

400–430 nm—100 nanoseconds
450–540 nm—10 nanoseconds.

If more than threshold amounts of any of SH, RS and LE are received by any one or more gated detector during the corresponding time interval and in its spectral range, an alarm indication is provided by computer 5625, typically at a display 5630. Alternatively, for some controlled substances, the spectroscopic scanning system 5600 may require a positive response from at least two or more of the spectroscopic identifiers for an alarm indication to be provided. This alarm indication indicates that a controlled substance having certain spectroscopic characteristics may be present on the body portion 5602.

It is noted that, even though the embodiment described hereinabove describe the spectroscopic scanning system including detector assemblies, imaging optics, filters, polychromator, detector assemblies, any suitable configuration of components, such as incorporating a fiber optic link for remote detection, may be used for collecting and analyzing the scattered output from the laser.

It is appreciated that the operational parameters for the spectroscopic scanning system 5600 are preferably selected so as to provide optimal contrast between the substances being identified and the background.

It is further appreciated that, while in a preferred mode of the present invention the spectroscopic scanning system 5600 scans for SH, RS and LE, spectroscopic analysis of body portion 5602 may include any combination of one or more of these of other spectroscopic analysis methods.

Table 13 is a chart showing various substances that may be uniquely identified by the spectroscopic methodologies described hereinabove. It is appreciated that, while Table 13 was developed relating specifically to identification of explosives against the background of the hand, the spectroscopic scanning system 5600 may be operative to identify other controlled substances, such as drugs. As described hereinabove, a single positive identification, by any of the spectroscopic methods, of a potential controlled substance may result in an alarm indication being provided by computer 5625, typically at display 5630.

TABLE 13

| | CONTROLLED SUBSTANCE | Raman (RS) | Luminescence (LE) |
|---|---|---|---|
| 1 | AS (95% RDX) | Yes | — |
| 2 | C4 | Yes | Yes |
| 3 | CompB | Yes | — |
| 4 | RDX (with binder) | Yes | Yes |
| 5 | Semtex | Yes | Yes |
| 6 | TATP | Yes | — |
| 7 | TENN | Yes | — |
| 8 | TNT | Yes | — |
| 9 | Urea Nitrate | Yes | — |

It is appreciated that the list of controlled substances, for which body portion 5602 is spectroscopically scanned, contained in Table 13 is not complete or exhaustive and that changes and additions are expected to occur over time as additional controlled substances are analyzed, developed and identified.

It is further appreciated that the alarm indication provided at display 5630 may include an identification of the controlled substance or substances suspected.

Figure 56B:
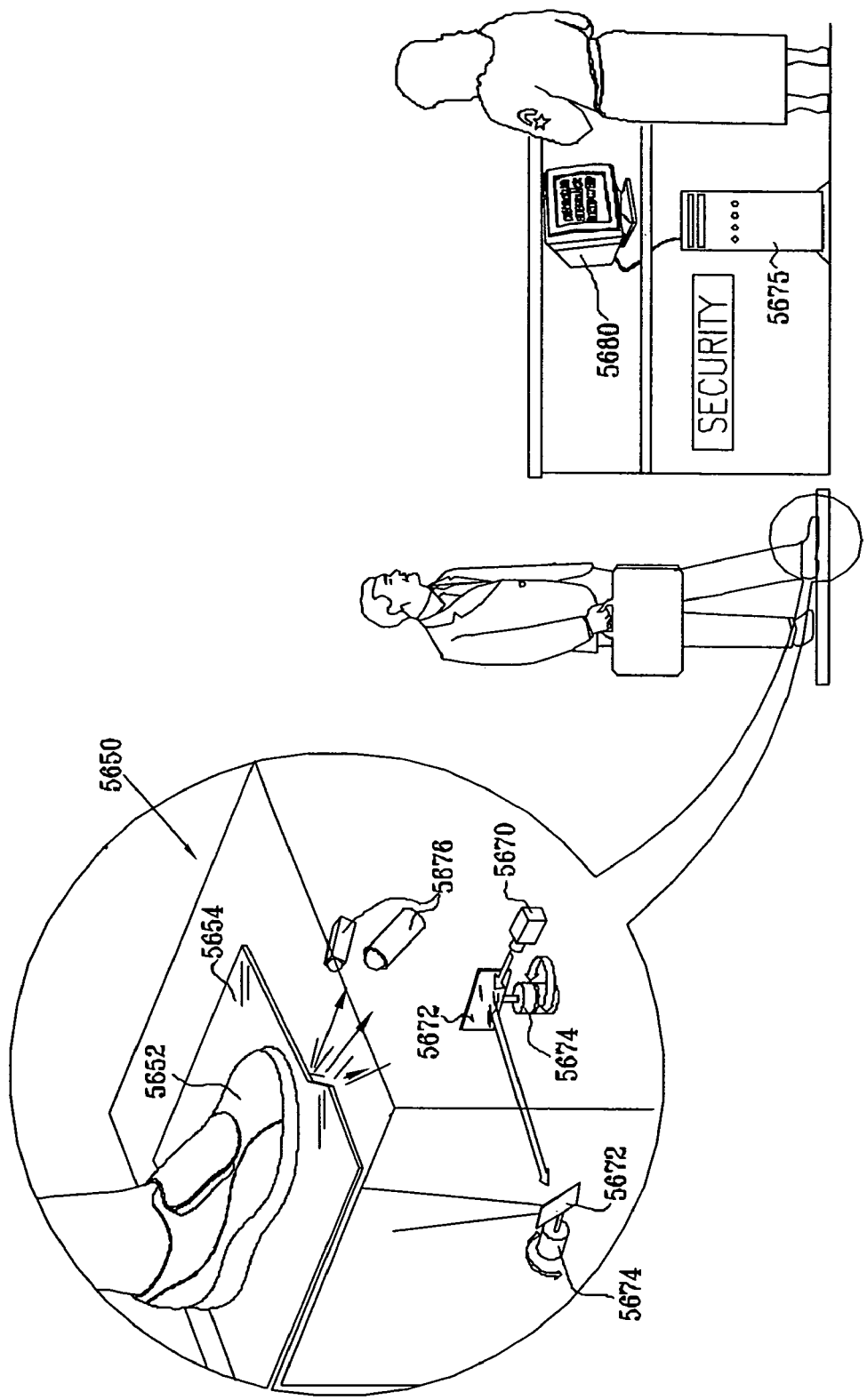

Reference is now made to FIG. 56B, which is a simplified pictorial illustration of a controlled substance identification system, constructed and operative in accordance with another preferred embodiment of the present invention. In the illustrated embodiment of FIG. 56B a transportation check-in system is shown, it being appreciated that the present invention is not limited to the illustrated embodiment, but rather may be employed in any other suitable personal identification screening environment.

As seen in FIG. 56B, the controlled substance identification system includes a spectroscopic scanning system 5650, operative to spectroscopically scan a section of an object, preferably a piece of clothing, such as a shoe 5652, for the possible presence of controlled substances, such as explosives or drugs, on the shoe 5652.

In accordance with a preferred embodiment of the present invention, the spectroscopic scanning system 5650 includes a transparent substrate 5654 upon which the shoe 5652 is placed, and the spectroscopic identifications are recorded while shoe 5652 is resting on the transparent substrate 5654. Preferably, the transparent substrate 5654 is made of a material that does not exhibit characteristic SH, RS and LE under the parameters defined for use in identifying controlled substances. Even more preferably, the substrate 5654 is coated with a thin layer of a substance that may exhibit Surface Enhanced Raman Spectrum (SERS), such as silver, gold or copper, having a suitably roughened surface. With such an appropriate surface, molecules of controlled substances, such as explosives or drugs, may exhibit Surface Enhanced Raman Spectrum (SERS), which increases the visibility of the RS by a factor of 10 or more.

Additionally or alternatively, the transparent substrate 5654 includes a material that exhibits luminescence that is quenched by controlled substances or a material that provides additive material enhanced luminescence in the presence of controlled substances.

In the illustrated embodiment of 56B, the spectroscopic scanning system 5650 employs at least one light source, such as a laser 5670. An output beam of laser 5670 impinges on one or more scanning elements 5672, such as mirrors, which are driven in rotational motion by one or more motors 5674 in synchronization with the pulsed output of laser 5670 in response to synchronization signals, such as signals provided by a computer 5675.

In accordance with a preferred embodiment of the present invention, laser 5670 is preferably a Nd:YAG pulsed laser emitting first, second, third and forth harmonics having peak wavelengths at 1064, 532, 355 and 266 nm. Alternatively, multiple lasers, preferably Nd:YAG pulsed lasers, may be provided. It is appreciated that wavelengths in the range of 200 nm to 10 microns may be employed.

The output beam of laser 5670 is thus scanned over shoe 5652, inducing SH, RS and LE by certain materials, including controlled substances, such as explosives and drugs, should those materials be present on the scanned surfaces of the shoe 5652. The emitted and scattered light is detected by one or more detector assemblies 5676, preferably including collecting optics, a notch filter, a spectral filter, a polychromator and a gated detector, such as a photodiode, photo multiplier, CCD or CMOS.

Preferably, a laser wavelength of 1064 nm is used for SH generation and the spectral filter, such as a filter having a narrow passband centered on 532 nm, is used for SH detection. Preferably, a laser wavelength of 532 nm is used for RS generation and the notch filter, such as a narrowband filter centered on 532 nm, is used for RS detection. The polychromator preferably has a spectral range from 360 to 900 nm.

Preferably, the gating interval for SH and RS detection coincides with duration of the laser pulse, while the interval for LE detection starts with the beginning of the laser pulse and continues beyond the end of the pulse for a time period based on the decay time of the luminescence emission. Alternatively, the detector need not be gated, although this is not preferred.

Alternatively, the polychromator may be replaced by a spectroscopic system employing several filters for RS and LE detection. The following Raman shifts relative to the laser excitation wavelength are preferably provided, each by a different spectral filter:

880–885 $cm^{-1}$
1360–1365 $cm^{-1}$
1270–1290 $cm^{-1}$
2980–3000 $cm^{-1}$.

The following spectral ranges are preferably provided for LE detection, each by a different spectral filter and corresponding to the following gate intervals:

400–430 nm—100 nanoseconds
450–540 nm—10 nanoseconds.

If more than threshold amounts of any of SH, RS and LE are received by any one or more gated detector during the corresponding time interval and in its spectral range, an alarm indication is provided by computer 5675, typically at a display 5680. Alternatively, for some controlled substances, the spectroscopic scanning system 5650 may require a positive response from at least two or more of the spectroscopic identifiers for an alarm indication to be provided. This alarm indication indicates that a controlled substance having certain spectroscopic characteristics may be present on the shoe 5652.

It is noted that, even though the embodiments described hereinabove describe the spectroscopic scanning system including detector assemblies, imaging optics, filters, polychromator, detector assemblies, any suitable configuration of components, such as incorporating a fiber optic link for remote detection, may be used for collecting and analyzing the scattered output from the laser.

It is appreciated that the operational parameters for the spectroscopic scanning system 5650 are preferably selected so as to provide optimal contrast between the substances being identified and the background.

It is further appreciated that, while in a preferred mode of the present invention the spectroscopic scanning system 5650 scans for SH, RS and LE, spectroscopic analysis of shoe 5652 may include any combination of one or more of these or other spectroscopic analysis methods.

Table 13 shows various substances that may be uniquely identified by the spectroscopic methodologies described hereinabove. It is appreciated that, while Table 13 was developed relating specifically to identification of explosives against the background of the hand, the spectroscopic scanning system 5650 may be operative to identify other controlled substances, such as drugs. As described hereinabove, a single positive identification, by any of the spectroscopic methods, of a potential controlled substance may result in an alarm indication being provided by computer 5675, typically at display 5680.

It is appreciated that the list of controlled substances, for which shoe 5652 is spectroscopically scanned, contained in Table 13 is not complete or exhaustive and that changes and additions are expected to occur over time as additional controlled substances are analyzed, developed and identified.

It is further appreciated that the alarm indication provided at display 5680 may include an identification of the controlled substance or substances suspected.

Figure 57:
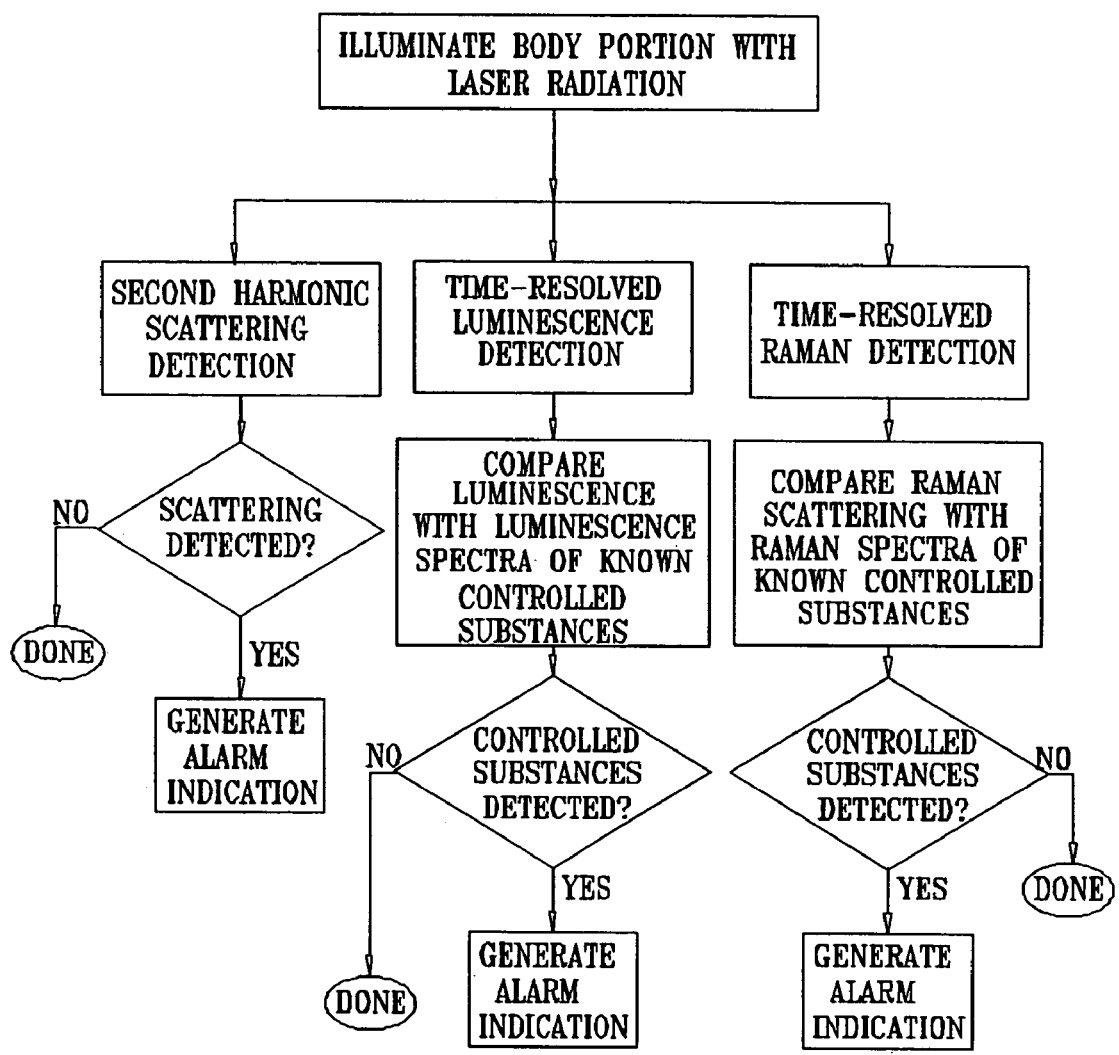
FIG. 57 is a simplified flowchart illustrating operation of the embodiments of FIGS. 56A and 56B.

Reference is now made to FIG. 57, which is a simplified flowchart illustrating operation of the spectroscopic scanning systems 5600 and 5650 shown in FIGS. 56A and 56B, in accordance with a preferred embodiment of the present invention. As shown in FIG. 57, a body portion, such as body portion 5602 of FIG. 56A, or a piece of clothing, such as shoe 5652 is examined for the possible presence of controlled substances, such as explosives or drugs, thereon. Body portion 5602 or shoe 5652 is illuminated by laser radiation, as described in FIGS. 56A and 56B, and is subject to detection of second harmonic scattering, time-resolved detection of luminescence and time-resolved detection of Raman scattering to provide identification of controlled substances.

Figure 58B:
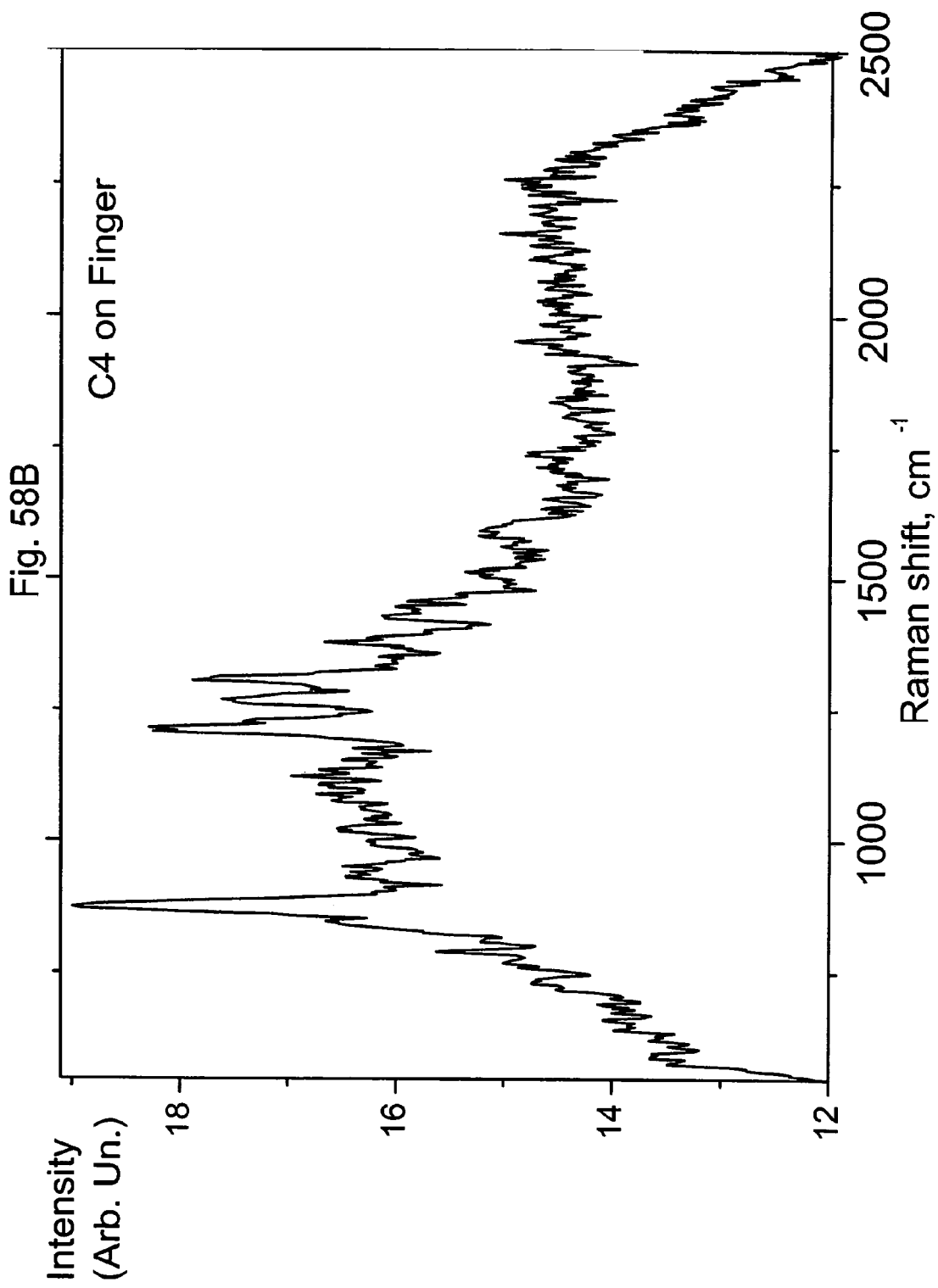
Figure 58C:
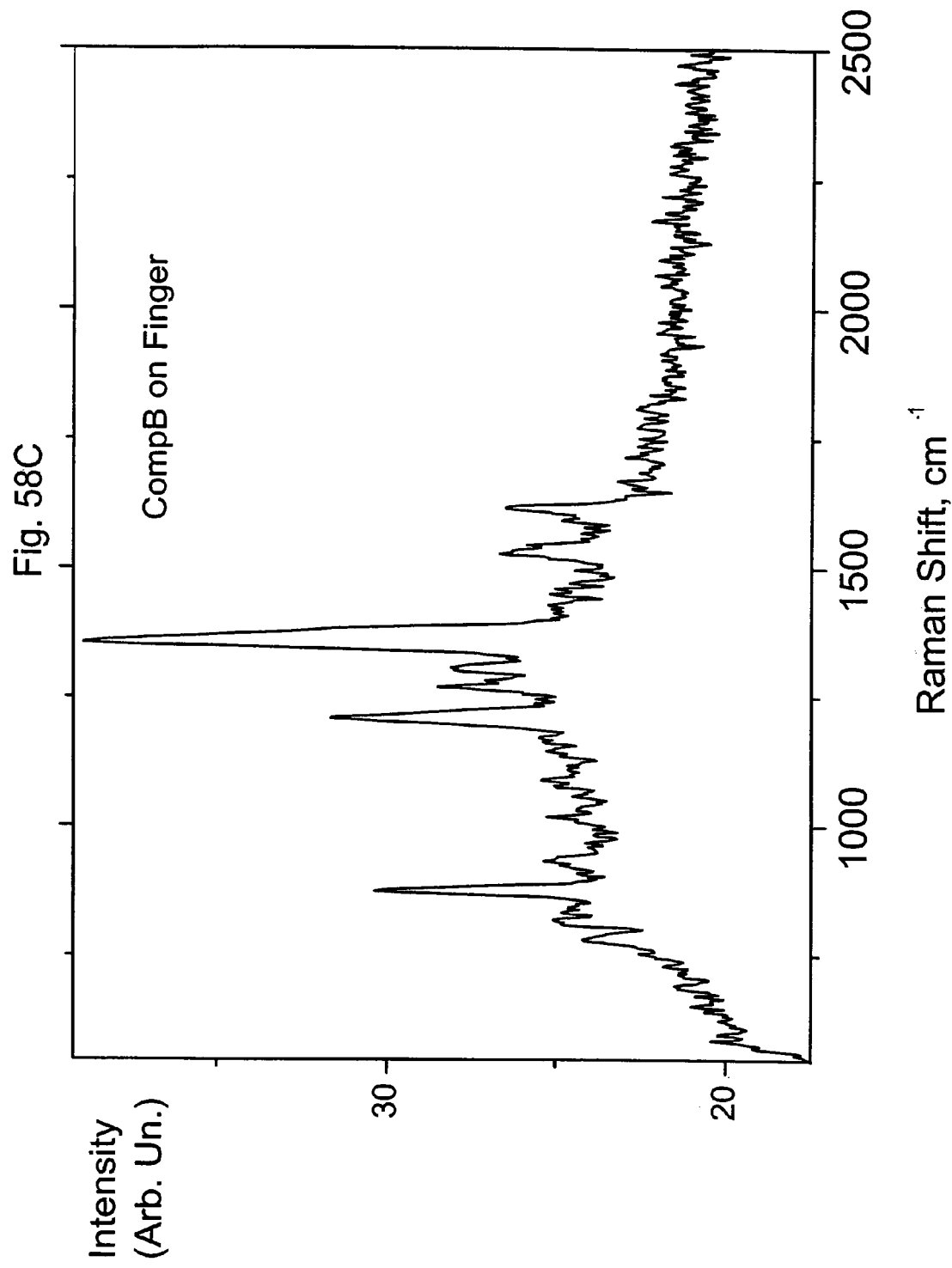
Figure 58D:
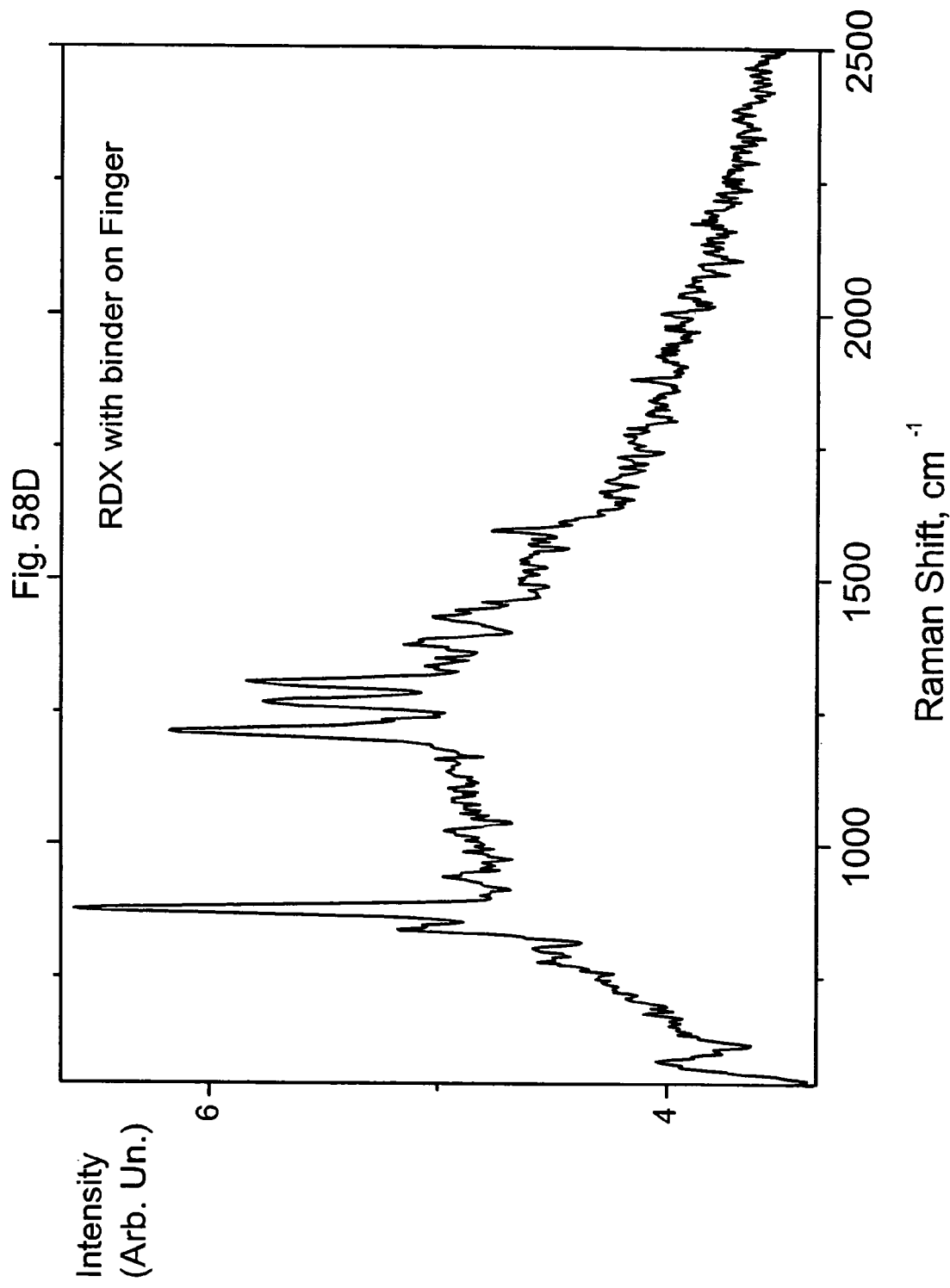
Figure 58E:
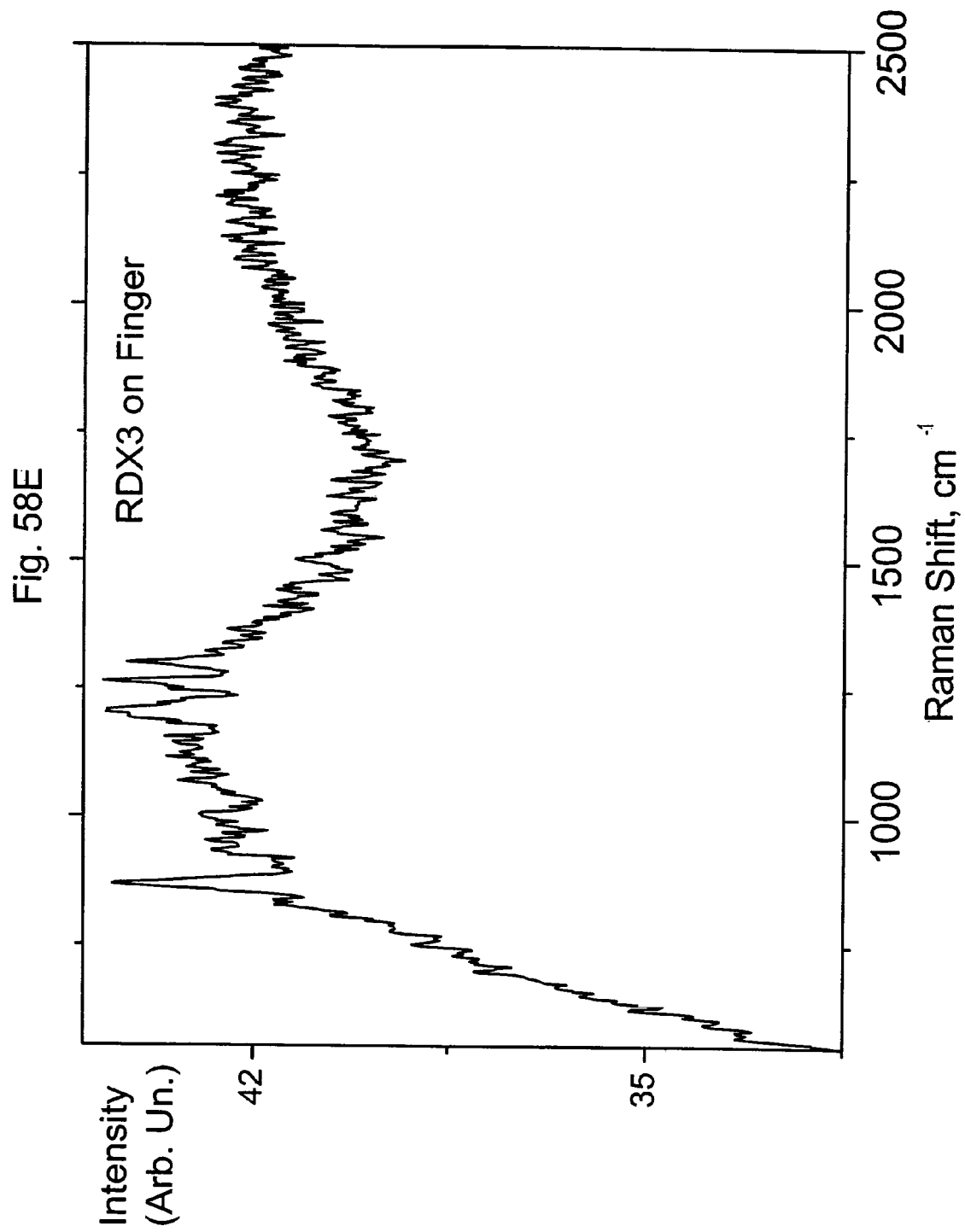
Figure 58F:
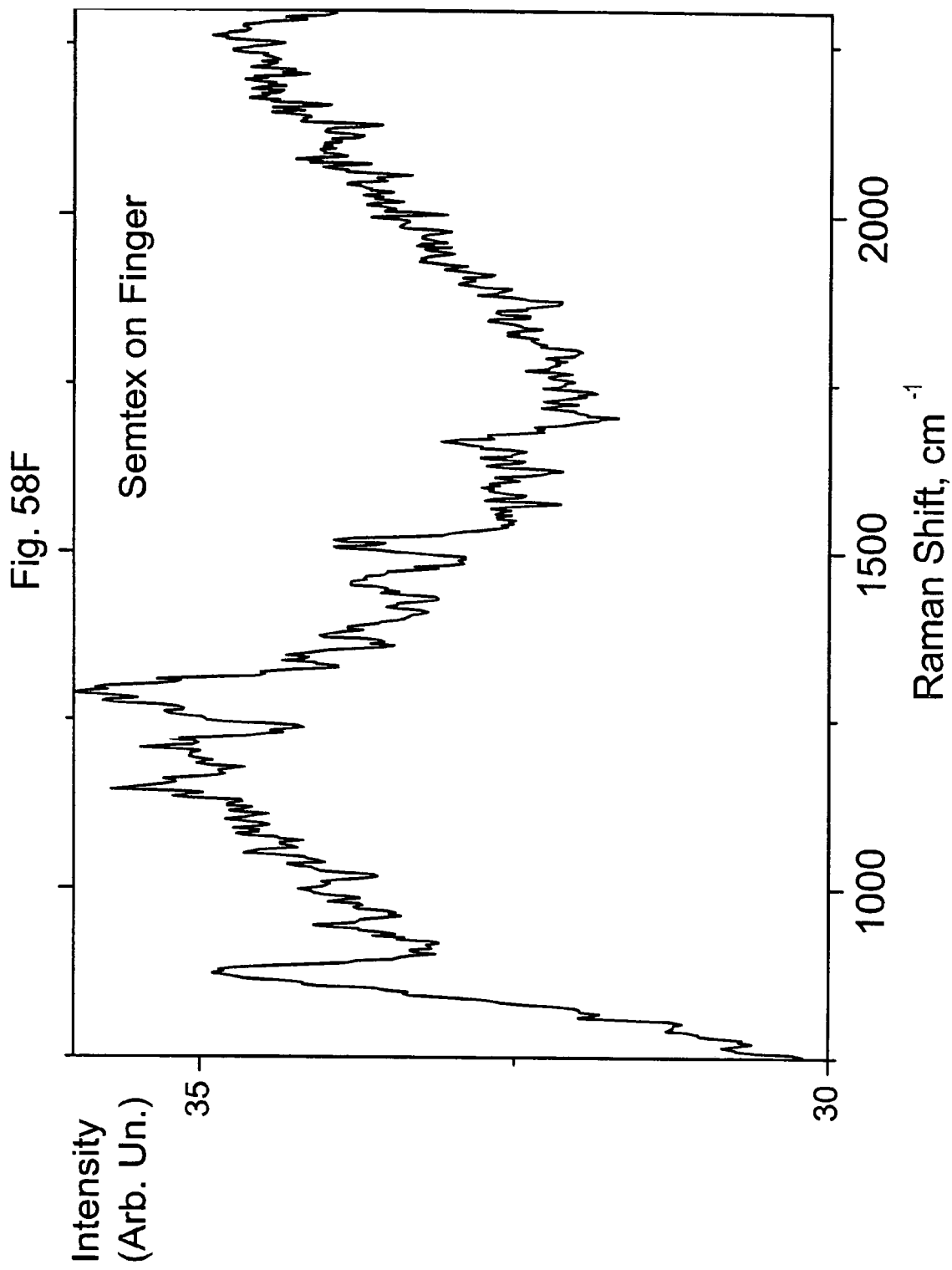
Figure 58G:
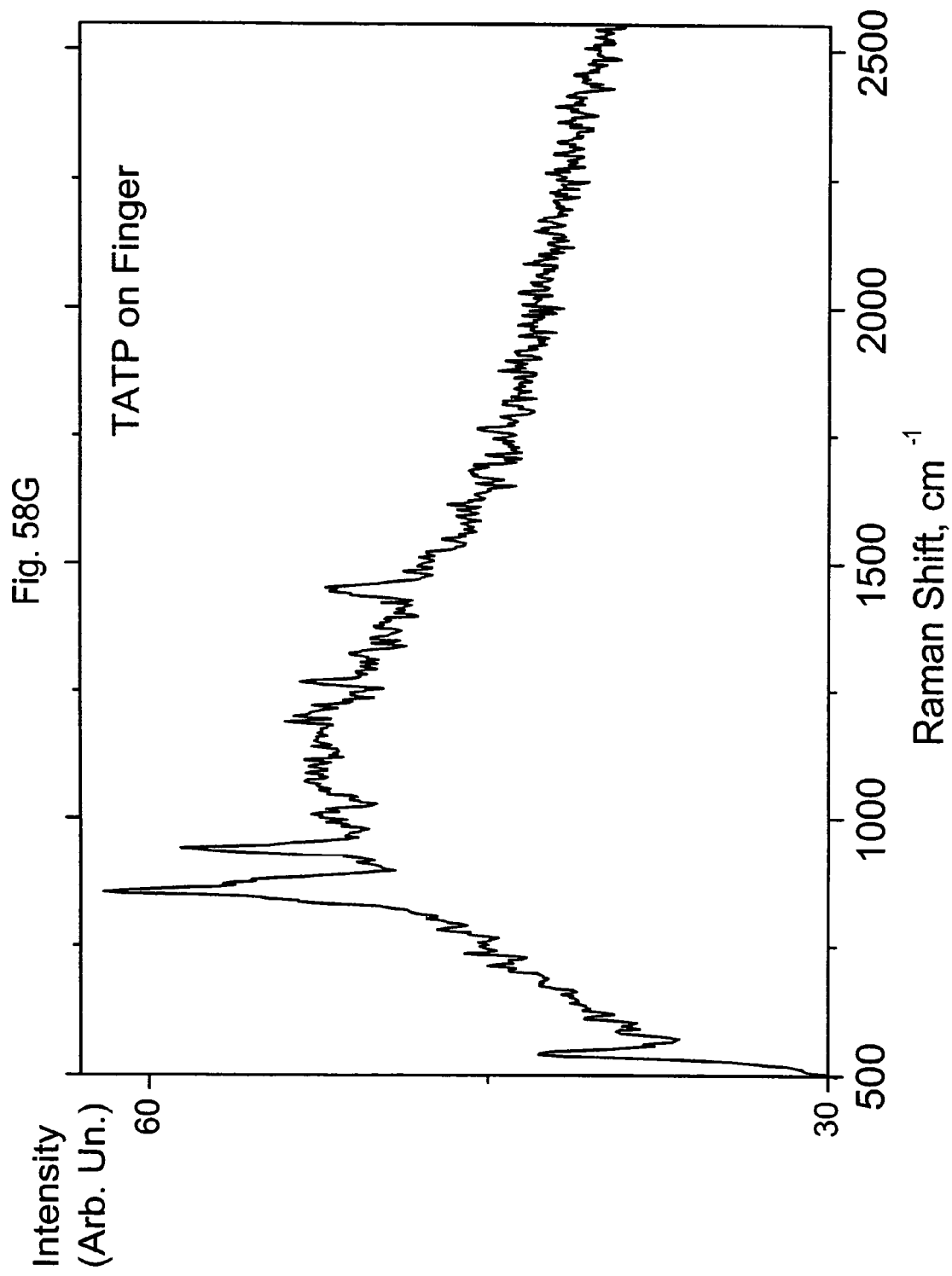
Figure 58H:
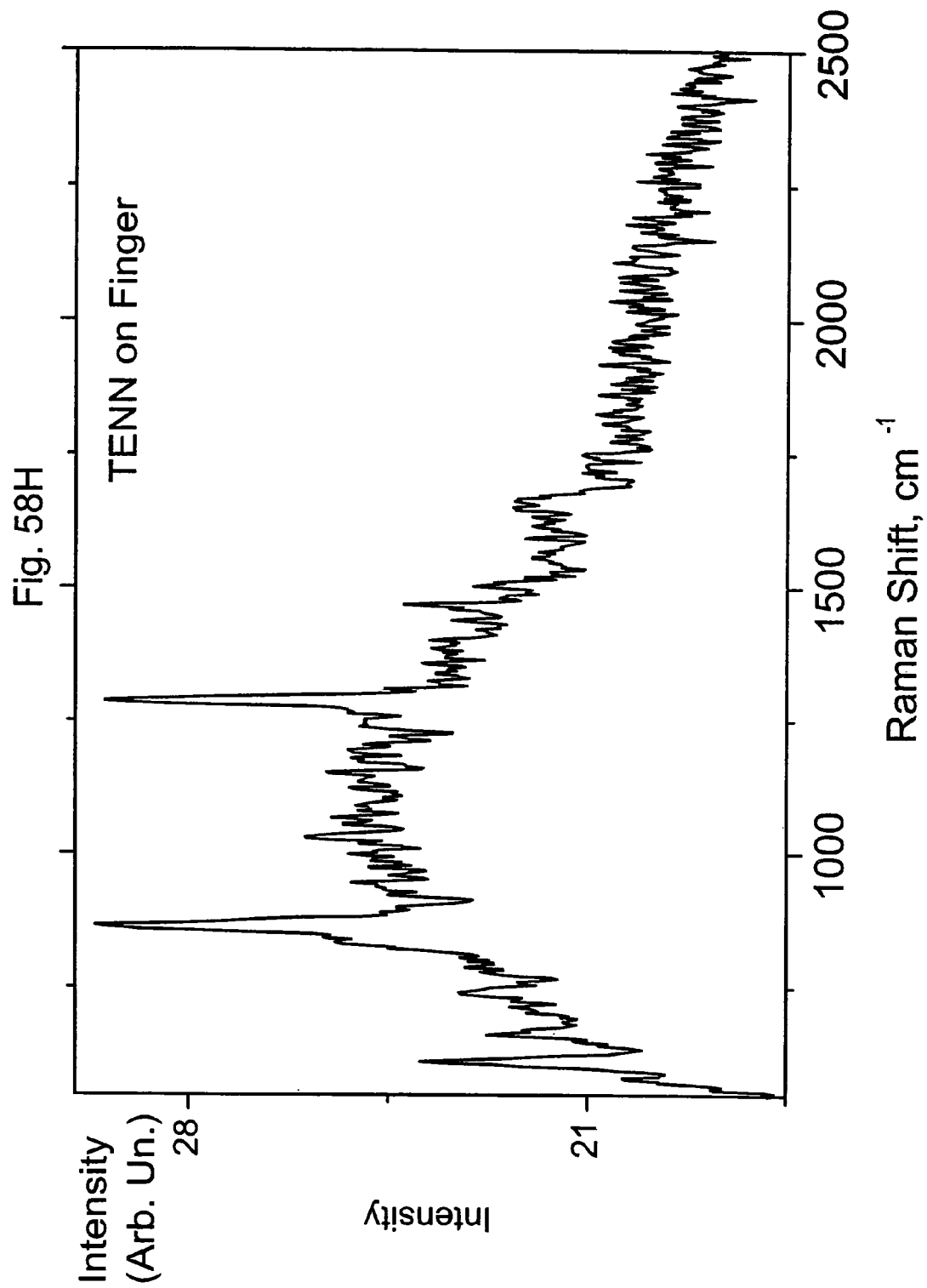
Figure 58I:
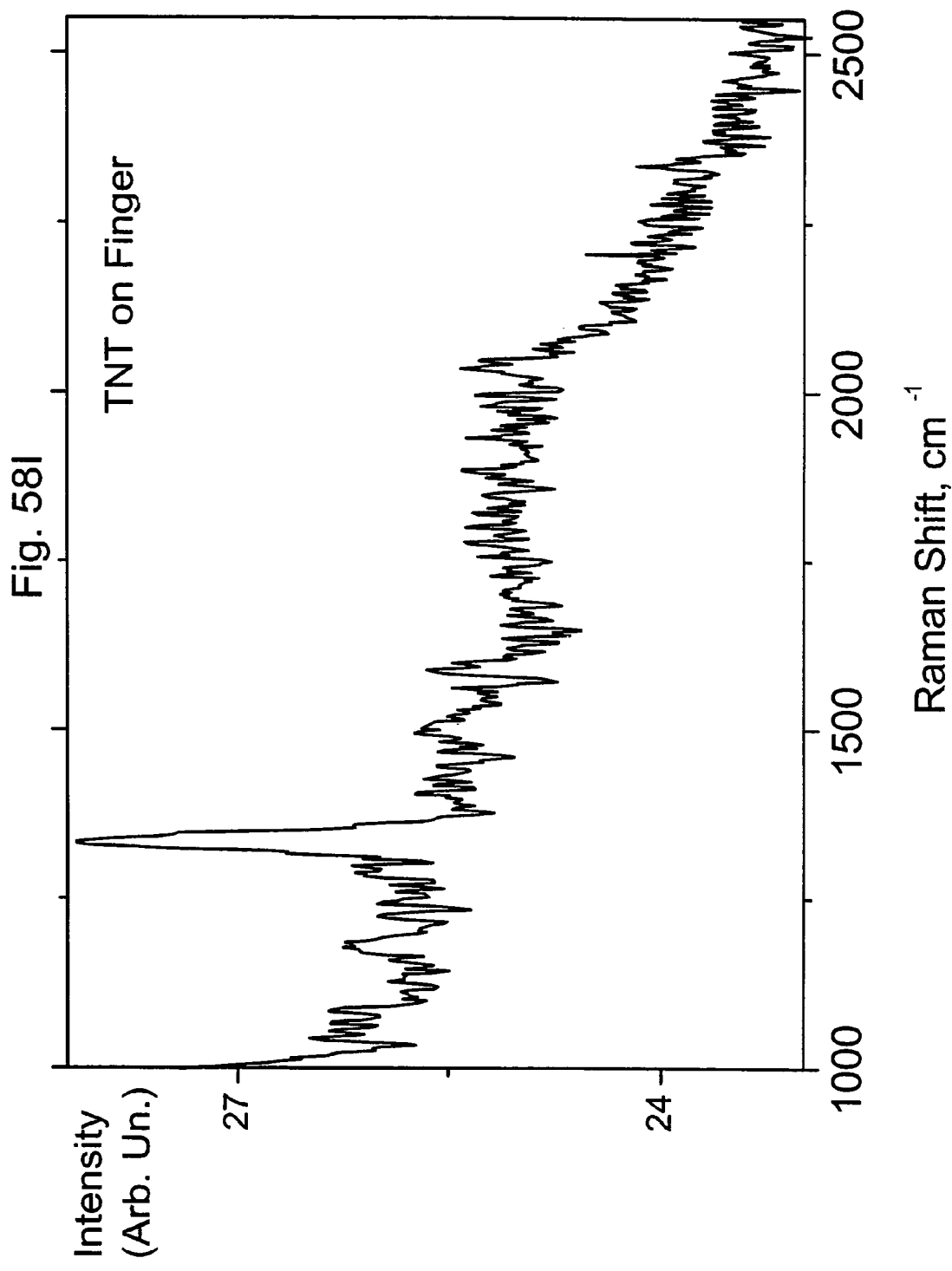

The controlled substances, such as those listed in Table 13 hereinabove, are preferably identified using time-resolved luminescence and time-resolved Raman scattering. If spectra matching the luminescence spectra of known controlled substances, such as, for example, those seen in FIGS. 60A-61, are detected, it is concluded that the controlled substance whose spectra is matched is present on the body portion 5602 or shoe 5652 and an alarm indication is provided, typically by computer 5625 or 5675. If spectra matching the Raman scattering spectra of known controlled substances, such as, for example, those seen in FIGS. 58A–59, are detected, it is concluded that the controlled substance whose spectra is matched is present on the body portion 5602 or shoe 5652 and an alarm indication is provided, typically by computer 5625 or 5675.

Alternatively, for some controlled substances, such as C4 and TNT, the spectroscopic scanning system 5600 or 5650 may require a positive response from at least two spectroscopic identifiers for an alarm indication to be provided. Table 13 shows the positive spectroscopic responses required for the alarm indication to be provided.

Reference is now made to FIGS. 58A, 58B, 58C, 58D, 58E, 58F, 58G, 58H, 58I and 58J, which are graphs showing time-resolved Raman spectra, at an excitation wavelength of 532 nm, of various explosives against the background of a human hand. As seen in FIGS. 58A–58J, these explosives typically generate spectra in the Raman spectra that are recognizable against the background of the human hand. These recognizable spectra provide for positive identification of these controlled substances listed in Table 13, as described hereinabove.

Figure 59:
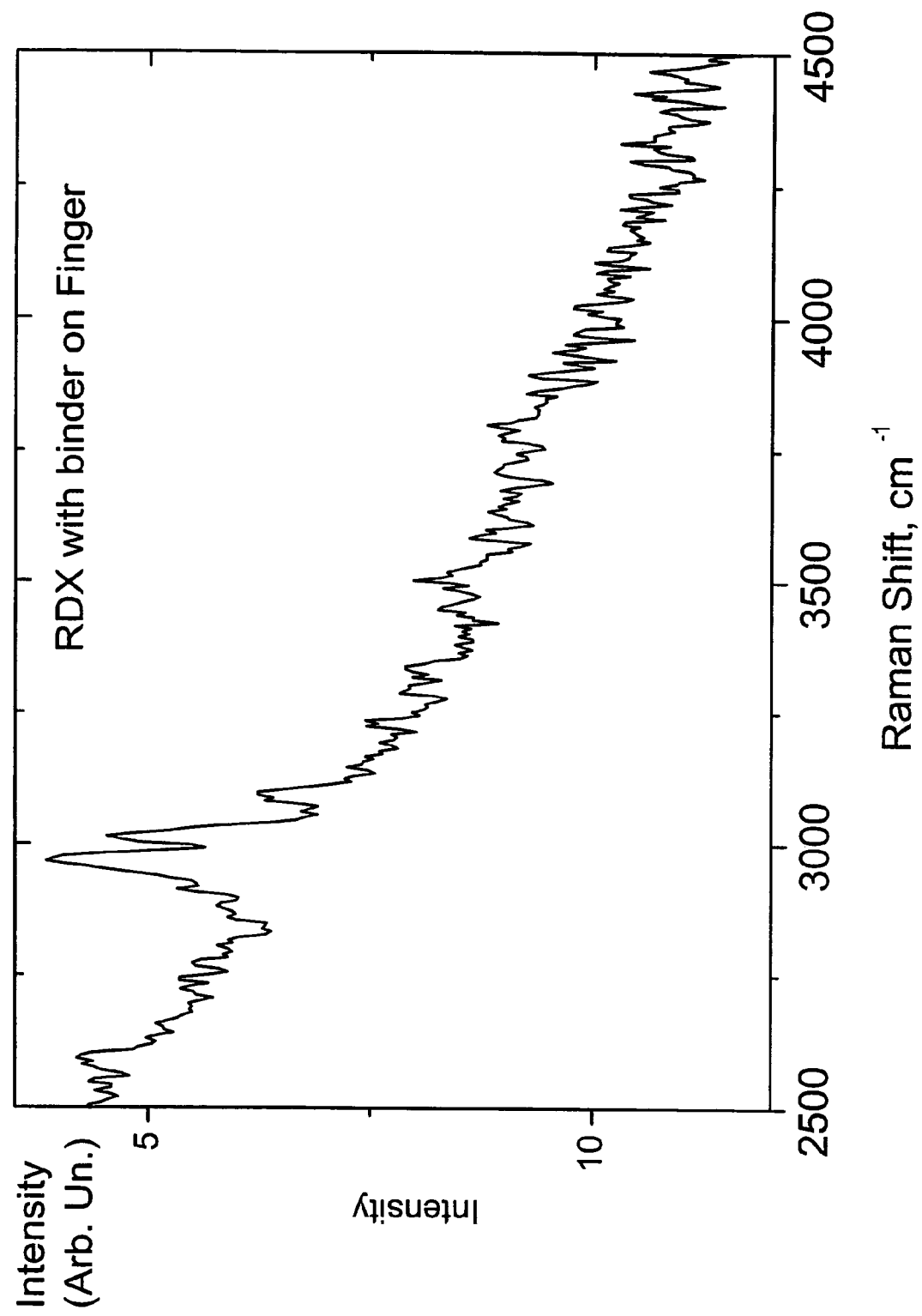

Reference is now made to FIG. 59, which is a graph showing time-resolved Raman spectrum, at an excitation wavelength of 355 nm, of RDX against the background of a human hand. As seen in FIG. 59, characteristic Raman spectrum can be seen against the background of a human hand at multiple excitation wavelengths. These recognizable spectra provide for positive identification, as described hereinabove.

Figure 60B:
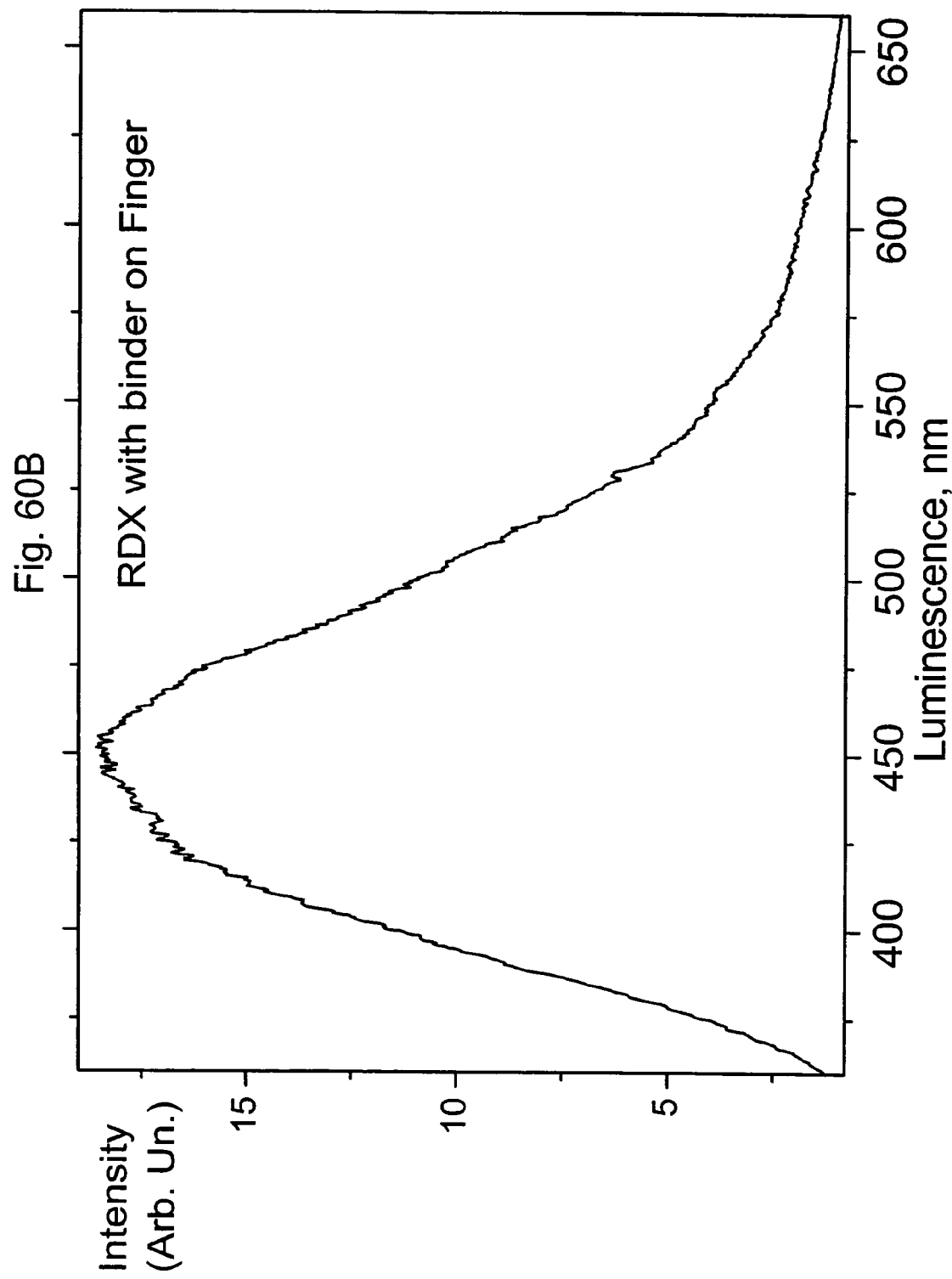
Figure 61:
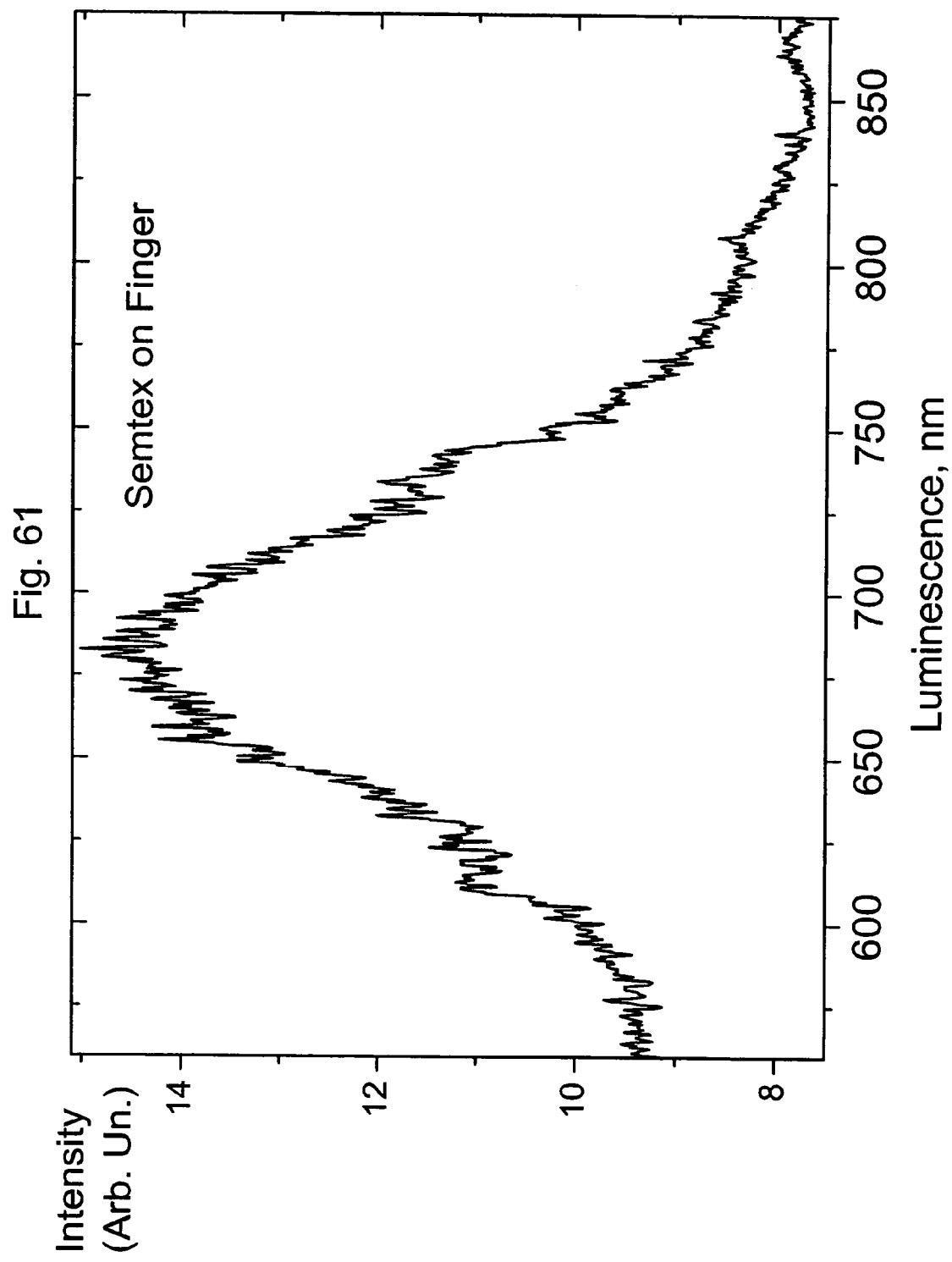

Reference is now made to FIGS. 60A, 60B and 60C, which are graphs showing time-resolved luminescence spectra, at an excitation wavelength of 355 nm, of various explosives against the background of a human hand. As seen in FIGS. 60A–60C, C4, RDX with binder and Semtex typically generate spectra in the time-resolved luminescence spectra that are recognizable against the background of the human hand. These recognizable spectra provide for positive identification, as described hereinabove.

Reference is now made to FIG. 61, which is a graph showing luminescence spectrum, at an excitation wavelength of 532 nm, of Semtex against the background of a human hand. As seen in FIG. 61, Semtex generates spectra in the time-resolved luminescence spectra that are recognizable against the background of the human hand. These recognizable spectra provide for positive identification, as described hereinabove.

Figure 62A:
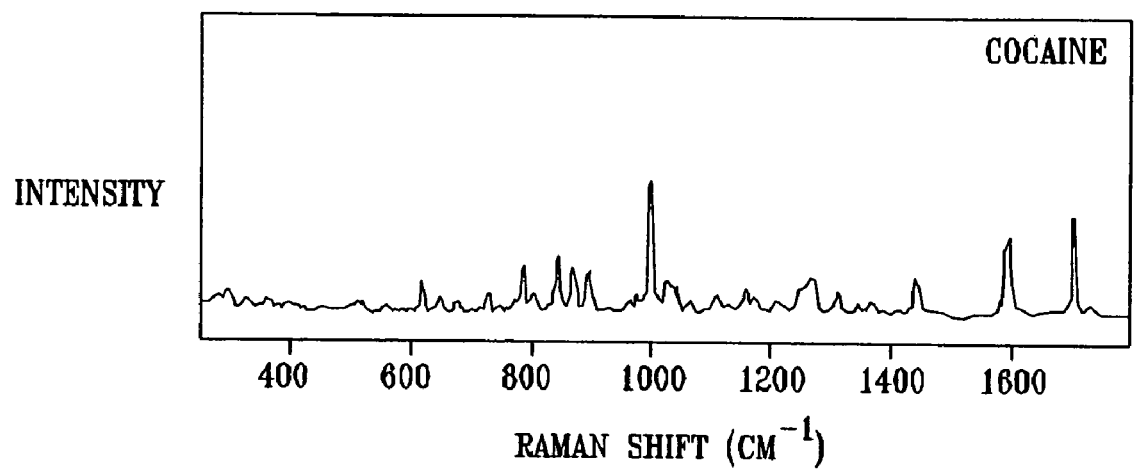
FIGS. 62A and 62B are graphs showing Raman spectra of other controlled substances.
Figure 62B:
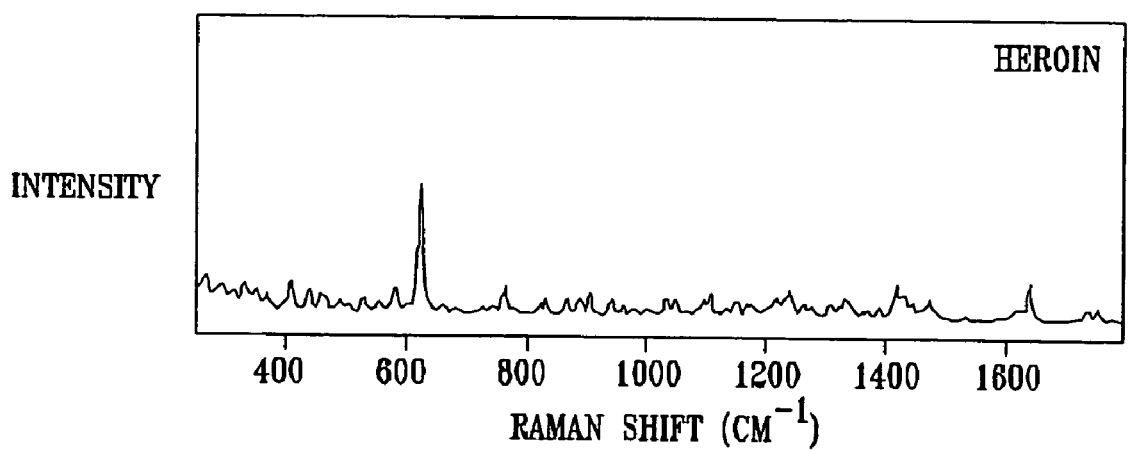

Reference is now made to FIGS. 62A and 62B, which are graphs showing Raman spectra of heroin and cocaine. As seen in FIGS. 62A and 62B, these drugs typically generate spectra in the Raman spectra that are recognizable. These recognizable spectra provide for positive identification, as described hereinabove.

It will be appreciated by persons skilled in the art that the present invention is not limited by what has been particularly shown and described hereinabove. Rather the scope of the present invention includes both combinations and subcombinations of the various features described hereinabove as well as variations and modifications which would occur to persons skilled in the art upon reading the specification and which are not in the prior art.

The invention claimed is:

1. A system for detecting controlled substances on an object comprising:
    at least one laser for illuminating at least part of an object with laser energy at a first wavelength;
    a second harmonic detector for detecting laser energy scattered from said object to detect scattered laser energy having a second wavelength which is a second harmonic of said first wavelength, wherein detection of scattered laser energy having a second wavelength which is a second harmonic of said first wavelength indicates that one or more controlled substances may be present on said object; and
    at least one additional controlled substance detector comprising at least one of a time-resolved luminescence controlled substance detector for detecting luminescence produced by impingement of said laser energy, wherein detection of luminescence indicates that one or more controlled substances may be present on said object, and a Raman scattering controlled substance detector, for detecting Raman scattering produced by impingement of said laser energy.

2. A system for detecting controlled substances on an object according to claim 1 and also comprising:
    logic operative in response to outputs of said second harmonic detector and said at least one additional controlled substance detector to provide an enhanced output indication of a possibility that one or more controlled substances may be present.

3. A system for detecting controlled substances on an object comprising:
    a laser for illuminating at least part of an object with laser energy at a wavelength of at least one of 355 nm and 266 nm; and
    a time-resolved luminescence controlled substance detector for detecting luminescence produced by impingement of said laser energy, wherein detection of luminescence indicates that one or more controlled substances may be present on said object.

4. A system for detecting controlled substances on an object comprising:
    a laser for illuminating at least part of an object with laser energy;
    a time-resolved luminescence controlled substance detector for detecting luminescence produced by impingement of said laser energy, wherein detection of luminescence indicates that one or more controlled substances may be present on said object; and
    a Raman scattering controlled substance detector for detecting Raman scattering produced by impingement of said laser energy.

5. A system for detecting controlled substances on an object according to claim 4 and also comprising:
    logic operative in response to outputs of said luminescence controlled substance detector and Raman scattering controlled substance detector to provide an enhanced output indication of a possibility that one or more controlled substances may be present.

6. A system for detecting controlled substances on an object comprising:
    at least one laser for illuminating at least part of an object with laser energy at a first wavelength; and
    a time-resolved second harmonic detector for detecting laser energy scattered from said object to detect scattered laser energy having a second wavelength which is a second harmonic of said first wavelength, wherein detection of scattered laser energy having a second wavelength which is a second harmonic of said first wavelength indicates that one or more controlled substances may be present on said object.

7. A system for detecting controlled substances on an object according to claim 1 and wherein said Raman scattering controlled substance detector is a time-resolved detector.

8. A system for detecting controlled substances on an object according to claim 4 and wherein said Raman scattering controlled substance detector is a time-resolved detector.

9. A system for detecting controlled substances on an object comprising:
    a laser for illuminating at least part of an object with laser energy; and
    a time-resolved luminescence controlled substance detector for detecting luminescence produced by impingement of said laser energy, wherein detection of luminescence indicates that one or more controlled substances may be present on said object,
    said system being an imagewise system.

10. A system for detecting controlled substances on an object comprising:
 a laser for illuminating at least part of an object with laser energy; and
 a time-resolved luminescence controlled substance detector for detecting luminescence produced by impingement of said laser energy, wherein detection of luminescence indicates that one or more controlled substances may be present on said object,
 said system being a non-imagewise system.

11. A system for detecting controlled substances on an object according to claim 1 and also comprising a controlled substance identifier.

12. A system for detecting controlled substances on an object comprising:
 a laser for illuminating at least part of an object with laser energy;
 a time-resolved luminescence controlled substance detector for detecting luminescence produced by impingement of said laser energy, wherein detection of luminescence indicates that one or more controlled substances may be present on said object; and
 a controlled substance identifier.

13. A system for detecting controlled substances on an object according to claim 4 and also comprising a controlled substance identifier.

14. A system for detecting controlled substances on an object according to claim 11 and wherein said controlled substances identifier employs at least one of time-resolved luminescence and time-resolved Raman scattering.

15. A system for detecting controlled substances on an object according to claim 13 and wherein said controlled substances identifier employs at least one of time-resolved luminescence and time-resolved Raman scattering.

16. A system for detecting controlled substances on an object according to claim 14 and wherein said controlled substances identifier also employs time-resolved laser induced breakdown spectroscopy for enhanced identification.

17. A system for detecting controlled substances on an object according to claim 15 and wherein said controlled substances identifier also employs time-resolved laser induced breakdown spectroscopy for enhanced identification.

18. A method for detecting controlled substances on an object comprising:
 illuminating at least part of an object with laser energy at a first wavelength; and
 detecting scattered laser energy from said object having a second wavelength which is a second harmonic of said first wavelength, wherein said detecting indicates that one or more controlled substances may be present on said object; and
 at least one of detecting, in a time-resolved manner, luminescence produced by impingement of said laser energy, wherein said detecting luminescence indicates that one or more controlled substances may be present on said object, and detecting Raman scattering produced by impingement of said laser energy.

19. A method for detecting controlled substances on an object according to claim 18 and also comprising:
 providing an enhanced output indication of a possibility that one or more controlled substances may be present in response to said detecting scattered laser energy having a second wavelength which is a second harmonic of said first wavelength and said detecting at least one of luminescence produced and Raman scattering produced.

20. A method for detecting controlled substances on an object comprising:
 illuminating at least part of an object with laser energy at a wavelength of at least one of 355 nm and 266 nm; and
 detecting, in a time-resolved manner, luminescence produced by impingement of said laser energy, wherein said detecting luminescence indicates that one or more controlled substances may be present on said object.

21. A method for detecting controlled substances on an object comprising:
 illuminating at least part of an object with laser energy;
 detecting, in a time-resolved manner, luminescence produced by impingement of said laser energy, wherein said detecting luminescence indicates that one or more controlled substances may be present on said object; and
 detecting Raman scattering produced by impingement of said laser energy.

22. A method for detecting controlled substances on an object according to claim 21 and also comprising:
 providing an enhanced output indication of a possibility that one or more controlled substances may be present in response to said detecting luminescence and said detecting Raman scattering.

23. A method for detecting controlled substances on an object comprising:
 illuminating at least part of an object with laser energy at a first wavelength; and
 detecting scattered laser energy from said object having a second wavelength which is a second harmonic of said first wavelength, wherein said detecting indicates that one or more controlled substances may be present on said object;
 said detecting scattered laser energy having a second wavelength which is a second harmonic comprising detecting in a time-resolved manner.

24. A method for detecting controlled substances on an, object according to claim 18 and wherein said detecting Raman scattering comprises detecting in a time-resolved manner.

25. A method for detecting controlled substances on an object according to claim 21 and wherein said detecting Raman scattering comprises detecting in a time-resolved manner.

26. A method for detecting controlled substances on an object comprising:
 illuminating at least part of an object with laser energy;
 detecting, in a time-resolved manner, luminescence produced by impingement of said laser energy, wherein said detecting luminescence indicates that one or more controlled substances may be present on said object;
 displaying an image of said object on a display; and
 visually indicating at least one location of said controlled substance on said display.

27. A method for detecting controlled substances on an object according to claim 18 and also comprising identifying said controlled substances.

28. A method for detecting controlled substances on an object comprising:
 illuminating at least part of an object with laser energy;
 detecting, in a time-resolved manner, luminescence produced by impingement of said laser energy, wherein said detecting luminescence indicates that one or more controlled substances may be present on said object; and identifying said controlled substances.

29. A method for detecting controlled substances on an object according to claim 21 and also comprising identifying said controlled substances.

30. A method for detecting controlled substances on an object according to claim 27 and wherein said identifying comprises employing at least one of time-resolved luminescence identification and time-resolved Raman scattering identification.

31. A method for detecting controlled substances on an object according to claim 29 and wherein said identifying comprises employing at least one of time-resolved luminescence identification and time-resolved Raman scattering identification.

32. A method for detecting controlled substances on an object according to claim 30 and wherein said identifying comprises employing time-resolved laser induced breakdown spectroscopy for enhanced identification.

33. A method for detecting controlled substances on an object according to claim 31 and wherein said identifying comprises employing time-resolved laser induced breakdown spectroscopy for enhanced identification.

* * * * *